United States Patent
Petit et al.

(10) Patent No.: US 11,897,927 B2
(45) Date of Patent: Feb. 13, 2024

(54) IMMUNOGENIC COMPOSITIONS TARGETING RECURRENT CANCER MUTATIONS AND METHODS OF USE THEREOF

(71) Applicant: Advaxis, Inc., Princeton, NJ (US)

(72) Inventors: Robert Petit, Newtown, PA (US); Michael F. Princiotta, Hightstown, NJ (US); Brandon Coder, Trenton, NJ (US); David Balli, Warrington, PA (US)

(73) Assignee: ADVAXIS, INC., Princeton, NJ (US)

( * ) Notice: Subject to any disclaimer, the term of this patent is extended or adjusted under 35 U.S.C. 154(b) by 462 days.

(21) Appl. No.: 16/348,274

(22) PCT Filed: Nov. 30, 2017

(86) PCT No.: PCT/US2017/064015
§ 371 (c)(1),
(2) Date: May 8, 2019

(87) PCT Pub. No.: WO2018/102584
PCT Pub. Date: Jun. 7, 2018

(65) Prior Publication Data
US 2019/0322714 A1   Oct. 24, 2019

Related U.S. Application Data

(60) Provisional application No. 62/583,292, filed on Nov. 8, 2017, provisional application No. 62/443,483, filed (Continued)

(51) Int. Cl.
*C07K 14/47* (2006.01)
*A61K 35/74* (2015.01)
(Continued)

(52) U.S. Cl.
CPC .......... *C07K 14/4748* (2013.01); *A61K 35/74* (2013.01); *A61K 39/0011* (2013.01); *A61K 39/00115* (2018.08); *A61K 39/001103* (2018.08); *A61K 39/001104* (2018.08); *A61K 39/001107* (2018.08); *A61K 39/001157* (2018.08); *A61K 39/001186* (2018.08); *A61K 39/001188* (2018.08); *A61K 39/001189* (2018.08); *A61K 39/001194* (2018.08); *A61K 39/001195* (2018.08); *C12N 15/74* (2013.01); *A61K 2039/523* (2013.01);
(Continued)

(58) Field of Classification Search
CPC .................... C07K 14/4748; A61K 39/001103
See application file for complete search history.

(56) References Cited

U.S. PATENT DOCUMENTS

| | | |
|---|---|---|
| 5,830,702 A | 11/1998 | Portnoy et al. |
| 6,051,237 A | 4/2000 | Paterson |
| 6,099,848 A | 8/2000 | Frankel et al. |
| 6,504,020 B1 | 1/2003 | Frankel et al. |
| 6,565,852 B1 | 5/2003 | Paterson |
| 6,635,749 B2 | 10/2003 | Frankel |
| 6,767,542 B2 | 7/2004 | Paterson et al. |
| 6,855,320 B2 | 2/2005 | Paterson |
| 7,135,188 B2 | 11/2006 | Paterson |
| 7,488,487 B2 | 2/2009 | Frankel et al. |
| 7,588,930 B2 | 9/2009 | Paterson et al. |
| 7,635,479 B2 | 12/2009 | Paterson et al. |

(Continued)

FOREIGN PATENT DOCUMENTS

| | | |
|---|---|---|
| CN | 106794235 A | 5/2017 |
| CN | 107073094 A | 8/2017 |

(Continued)

OTHER PUBLICATIONS

Prior et al (Cancer Research, 72(10):2457-2467, 2012).*
(Continued)

*Primary Examiner* — Brian Gangle
*Assistant Examiner* — Lakia J Jackson-Tongue
(74) *Attorney, Agent, or Firm* — Alston & Bird LLP

(57) ABSTRACT

Provided herein are recombinant fusion polypeptides comprising one or more antigenic peptides (e.g., fused to a PEST-containing peptide) from cancer-associated proteins. The antigenic peptides can comprise one or more or all of an antigenic peptide comprising a recurrent cancer mutation, an antigenic peptide comprising a heteroclitic mutation, or an antigenic peptide fused to a ubiquitin protein. For example, provided herein are recombinant fusion polypeptides comprising two or more antigenic peptides (e.g., fused to a PEST-containing peptide), wherein each antigenic peptide comprises a recurrent cancer mutation, and wherein at least two of the antigenic peptides are fragments of the same cancer-associated protein. Also provided are nucleic acids encoding such fusion polypeptides, recombinant bacteria or *Listeria* strains comprising such fusion polypeptides or such nucleic acids, and cell banks comprising such recombinant bacteria or *Listeria* strains. Also provided herein are methods of generating such fusion polypeptides, such nucleic acids, and such recombinant bacteria or *Listeria* strains. Also provided are immunogenic compositions, pharmaceutical compositions, and vaccines comprising such fusion polypeptides, such nucleic acids, or such recombinant bacteria or *Listeria* strains. Also provided are methods of inducing an anti-tumor-associated-antigen immune response in a subject, methods of inducing an anti-tumor or anti-cancer immune response in a subject, methods of treating a tumor or cancer in a subject, methods of preventing a tumor or cancer in a subject, and methods of protecting a subject against a tumor or cancer using such recombinant fusion polypeptides, nucleic acids, recombinant bacteria or *Listeria* strains, immunogenic compositions, pharmaceutical compositions, or vaccines.

74 Claims, 22 Drawing Sheets

Specification includes a Sequence Listing.

Related U.S. Application Data on Jan. 6, 2017, provisional application No. 62/428,515, filed on Nov. 30, 2016.

(51) Int. Cl.
  *A61K 39/00* (2006.01)
  *C12N 15/74* (2006.01)

(52) U.S. Cl.
  CPC .............. *A61K 2039/55544* (2013.01); *A61K 2039/55594* (2013.01); *A61K 2039/645* (2013.01); *C07K 2319/43* (2013.01); *C07K 2319/95* (2013.01)

(56) References Cited

U.S. PATENT DOCUMENTS

| | | | |
|---|---|---|---|
| 7,655,238 B2 | 2/2010 | Paterson et al. | |
| 7,662,396 B2 | 2/2010 | Paterson et al. | |
| 7,700,344 B2 | 4/2010 | Paterson et al. | |
| 7,794,729 B2 | 9/2010 | Paterson et al. | |
| 7,820,180 B2 | 10/2010 | Singh et al. | |
| 7,855,064 B2 | 12/2010 | Paterson et al. | |
| 7,858,097 B2 | 12/2010 | Paterson et al. | |
| 8,114,414 B2 | 2/2012 | Paterson et al. | |
| 8,241,636 B2 | 8/2012 | Paterson et al. | |
| 8,268,326 B2 | 9/2012 | Paterson et al. | |
| 8,337,861 B2 | 12/2012 | Paterson et al. | |
| 8,771,702 B2 | 7/2014 | Paterson et al. | |
| 8,778,329 B2 | 7/2014 | Seavey et al. | |
| 8,791,237 B2 | 7/2014 | Paterson et al. | |
| 8,906,664 B2 | 12/2014 | Paterson et al. | |
| 8,956,621 B2 | 2/2015 | Paterson et al. | |
| 9,012,141 B2 | 4/2015 | Paterson et al. | |
| 9,017,660 B2 | 4/2015 | Shahabi et al. | |
| 9,084,747 B2 | 7/2015 | Shahabi et al. | |
| 9,226,958 B2 | 1/2016 | Harn, Jr. et al. | |
| 9,408,898 B2 | 8/2016 | Seavey et al. | |
| 9,463,227 B2 | 10/2016 | Rothman et al. | |
| 9,492,527 B2 | 11/2016 | Paterson et al. | |
| 9,499,602 B2 | 11/2016 | Paterson et al. | |
| 9,549,973 B2 | 1/2017 | Paterson et al. | |
| 9,644,212 B2 | 5/2017 | Maciag et al. | |
| 9,650,639 B2 | 5/2017 | Maciag et al. | |
| 9,700,608 B2 | 7/2017 | Paterson et al. | |
| 9,919,038 B2 | 3/2018 | Seavey et al. | |
| 9,943,590 B2 | 4/2018 | Harn et al. | |
| 9,981,024 B2 | 5/2018 | Seavey et al. | |
| 10,010,593 B2 | 7/2018 | Paterson | |
| 10,016,617 B2 | 7/2018 | Mason et al. | |
| 10,058,599 B2 | 8/2018 | Singh et al. | |
| 10,064,898 B2 | 9/2018 | Rothman et al. | |
| 10,143,734 B2 | 12/2018 | Petit | |
| 10,166,276 B2 | 1/2019 | Paterson et al. | |
| 10,189,885 B2 | 1/2019 | Paterson et al. | |
| 10,258,679 B2 | 4/2019 | Wallecha et al. | |
| 10,900,044 B2 | 1/2021 | Petit et al. | |
| 11,179,339 B2 | 11/2021 | Fela et al. | |
| 11,446,369 B2 | 9/2022 | Paterson et al. | |
| 2002/0025323 A1 | 2/2002 | Paterson et al. | |
| 2002/0028206 A1 | 3/2002 | Paterson | |
| 2002/0136737 A1 | 9/2002 | Frankel | |
| 2003/0138808 A1 | 7/2003 | Simard et al. | |
| 2003/0202985 A1 | 10/2003 | Paterson | |
| 2004/0241177 A1 | 12/2004 | Frazer | |
| 2005/0048081 A1 | 3/2005 | Frankel et al. | |
| 2005/0118184 A1 | 6/2005 | Paterson et al. | |
| 2005/0129715 A1 | 6/2005 | Paterson et al. | |
| 2006/0093582 A1 | 5/2006 | Paterson et al. | |
| 2006/0094649 A1 | 5/2006 | Keogh et al. | |
| 2006/0104991 A1 | 5/2006 | Paterson et al. | |
| 2006/0204516 A1 | 9/2006 | Paterson et al. | |
| 2006/0205067 A1 | 9/2006 | Paterson et al. | |
| 2006/0210540 A1 | 9/2006 | Paterson et al. | |
| 2006/0233835 A1 | 10/2006 | Paterson et al. | |
| 2006/0269561 A1 | 11/2006 | Paterson et al. | |
| 2007/0003567 A1 | 1/2007 | Paterson et al. | |
| 2007/0055049 A1 | 3/2007 | Gray et al. | |
| 2007/0207170 A1 | 9/2007 | Dubensky et al. | |
| 2007/0253976 A1 | 11/2007 | Paterson et al. | |
| 2007/0264279 A1 | 11/2007 | Gravekamp et al. | |
| 2008/0020465 A1 | 1/2008 | Padidam | |
| 2008/0131456 A1 | 6/2008 | Paterson et al. | |
| 2009/0081248 A1 | 3/2009 | Paterson et al. | |
| 2009/0081250 A1 | 3/2009 | Paterson et al. | |
| 2009/0169574 A1 | 7/2009 | Shabnam et al. | |
| 2009/0186051 A1 | 7/2009 | Paterson et al. | |
| 2009/0202587 A1 | 8/2009 | Paterson et al. | |
| 2010/0016220 A1 | 1/2010 | Nakamura et al. | |
| 2010/0189739 A1 | 7/2010 | Paterson et al. | |
| 2010/0291140 A1 | 11/2010 | Paterson et al. | |
| 2011/0105343 A1 | 5/2011 | Puledran et al. | |
| 2011/0129499 A1 | 6/2011 | Maciag et al. | |
| 2011/0142791 A1 | 6/2011 | Shahabi | |
| 2011/0182926 A1 | 7/2011 | La Monica et al. | |
| 2011/0305724 A1 | 12/2011 | Paterson et al. | |
| 2012/0014984 A1 | 1/2012 | Shahabi | |
| 2012/0114685 A1 | 5/2012 | Seavey et al. | |
| 2012/0135033 A1 | 5/2012 | Wallecha | |
| 2012/0177678 A1 | 7/2012 | Paterson et al. | |
| 2013/0259891 A1 | 10/2013 | Harn, Jr. et al. | |
| 2014/0199258 A1 | 7/2014 | Rothman | |
| 2014/0234370 A1 | 8/2014 | Shahabi | |
| 2014/0248304 A1 | 9/2014 | Paterson et al. | |
| 2014/0314708 A1 | 10/2014 | Maciag et al. | |
| 2014/0335120 A1* | 11/2014 | Maciag | A61K 39/0011 424/190.1 |
| 2015/0079034 A1 | 3/2015 | Seavey et al. | |
| 2015/0098964 A1 | 4/2015 | Singh et al. | |
| 2015/0125480 A1 | 5/2015 | Paterson et al. | |
| 2015/0196628 A1 | 7/2015 | Mason et al. | |
| 2015/0238584 A1 | 8/2015 | Shahabi et al. | |
| 2015/0297702 A1 | 10/2015 | Shahabi et al. | |
| 2015/0335721 A1 | 11/2015 | Paterson et al. | |
| 2015/0343047 A1 | 12/2015 | Paterson et al. | |
| 2015/0366955 A9 | 12/2015 | Shahabi et al. | |
| 2016/0022814 A1 | 1/2016 | Petit et al. | |
| 2016/0024173 A1 | 1/2016 | Paterson et al. | |
| 2016/0158331 A1 | 6/2016 | Paterson et al. | |
| 2016/0206716 A1 | 7/2016 | Seavey et al. | |
| 2016/0220652 A1 | 8/2016 | Petit et al. | |
| 2016/0228530 A1 | 8/2016 | Paterson | |
| 2016/0256538 A1 | 9/2016 | Harn, Jr. et al. | |
| 2016/0324903 A1 | 11/2016 | Rothman et al. | |
| 2016/0361401 A1 | 12/2016 | Shahabi et al. | |
| 2016/0367650 A1 | 12/2016 | Paterson | |
| 2017/0028045 A1 | 2/2017 | Paterson et al. | |
| 2017/0042996 A1 | 2/2017 | Wallecha et al. | |
| 2017/0049867 A1 | 2/2017 | Seavey et al. | |
| 2017/0080064 A1 | 3/2017 | Petit et al. | |
| 2017/0100469 A1 | 4/2017 | Paterson et al. | |
| 2017/0106072 A1 | 4/2017 | Petit | |
| 2017/0204361 A1 | 7/2017 | Eapen et al. | |
| 2017/0246273 A1 | 8/2017 | Wallecha et al. | |
| 2017/0281691 A1 | 10/2017 | Paterson et al. | |
| 2017/0368157 A1 | 12/2017 | Khleif et al. | |
| 2018/0064765 A1 | 3/2018 | Petit et al. | |
| 2018/0265879 A1 | 3/2018 | Wallecha et al. | |
| 2018/0104284 A1 | 4/2018 | Wallecha et al. | |
| 2018/0280487 A1 | 4/2018 | Petit et al. | |
| 2018/0153974 A1 | 6/2018 | Petit et al. | |
| 2018/0305702 A1 | 10/2018 | Petit et al. | |
| 2018/0325964 A1 | 11/2018 | Eapen et al. | |
| 2018/0360940 A1 | 12/2018 | Petit et al. | |
| 2019/0002891 A1 | 1/2019 | Petit et al. | |
| 2019/0032064 A1 | 1/2019 | Petit et al. | |
| 2019/0240303 A1 | 8/2019 | Wallecha et al. | |
| 2019/0248856 A1 | 8/2019 | Princiotta et al. | |
| 2019/0322714 A1 | 10/2019 | Petit et al. | |
| 2020/0061167 A1 | 2/2020 | Hayes et al. | |
| 2020/0069785 A1 | 3/2020 | Paterson et al. | |
| 2020/0261369 A1 | 8/2020 | Fela et al. | |
| 2021/0003558 A1 | 1/2021 | Molli et al. | |
| 2021/0177955 A1 | 6/2021 | Petit et al. | |

(56) References Cited

U.S. PATENT DOCUMENTS

| | | | |
|---|---|---|---|
| 2021/0239681 A1 | 8/2021 | Wallecha et al. |
| 2021/0246457 A1 | 8/2021 | Petit et al. |
| 2022/0062181 A1 | 3/2022 | Gosse et al. |

FOREIGN PATENT DOCUMENTS

| | | | |
|---|---|---|---|
| JP | 2011-529684 A1 | 12/2011 | |
| KR | 1020140134695 A | 11/2014 | |
| WO | WO 1996/014087 A1 | 5/1996 | |
| WO | WO 1999/025376 A1 | 5/1999 | |
| WO | WO 2001/036452 A2 | 5/2001 | |
| WO | WO 2007/103261 A2 | 5/2001 | |
| WO | WO 2001/062776 A1 | 8/2001 | |
| WO | WO 2001/072329 A1 | 10/2001 | |
| WO | WO 2004/062597 A2 | 7/2004 | |
| WO | WO 2006/017856 A2 | 2/2006 | |
| WO | WO 2006/036550 A2 | 4/2006 | |
| WO | WO 2007/061848 | * | 5/2007 |
| WO | WO 2007/106476 A2 | 9/2007 | |
| WO | WO 2007/130455 A2 | 11/2007 | |
| WO | WO 2008/079172 A2 | 7/2008 | |
| WO | WO 2008/087102 A2 | 7/2008 | |
| WO | WO 2008/109155 A2 | 9/2008 | |
| WO | WO 2008/112927 A2 | 9/2008 | |
| WO | WO 2008/130551 A2 | 10/2008 | |
| WO | WO 2008/140812 A2 | 11/2008 | |
| WO | WO 2009/143167 A2 | 11/2009 | |
| WO | WO 2010/008782 A1 | 1/2010 | |
| WO | WO 2010/040135 A1 | 4/2010 | |
| WO | WO 2010/102140 A1 | 9/2010 | |
| WO | WO 2011/020604 A1 | 2/2011 | |
| WO | WO 2011/060260 A2 | 5/2011 | |
| WO | WO 2011/100754 A1 | 8/2011 | |
| WO | WO 2012/023033 A2 | 2/2012 | |
| WO | WO 2012/125551 A1 | 9/2012 | |
| WO | WO 2012/138377 A2 | 10/2012 | |
| WO | WO 2013/025925 A1 | 2/2013 | |
| WO | WO 2013/106834 A2 | 7/2013 | |
| WO | WO 2013/138337 A1 | 9/2013 | |
| WO | WO 2014/052707 A2 | 4/2014 | |
| WO | WO 2015/029056 A1 | 3/2015 | |
| WO | WO 2015/126921 | 8/2015 | |
| WO | WO 2015/130810 A2 | 9/2015 | |
| WO | WO 2015/134722 A2 | 9/2015 | |
| WO | WO 2015/164121 A1 | 10/2015 | |
| WO | WO 2015/167748 A1 | 11/2015 | |
| WO | WO 2016/011320 A1 | 1/2016 | |
| WO | WO 2016/011353 A1 | 1/2016 | |
| WO | WO 2016/011357 A1 | 1/2016 | |
| WO | WO 2016/011362 A1 | 1/2016 | |
| WO | WO 2016/049024 A2 | 3/2016 | |
| WO | WO 2016/061182 A1 | 4/2016 | |
| WO | WO 2016/061277 A1 | 4/2016 | |
| WO | WO 2016/100924 A1 | 6/2016 | |
| WO | WO 2016/100929 A1 | 6/2016 | |
| WO | WO 2016/126876 A2 | 8/2016 | |
| WO | WO 2016/126878 A2 | 8/2016 | |
| WO | WO 2016/141121 A1 | 9/2016 | |
| WO | WO 2016/154412 A2 | 9/2016 | |
| WO | WO 2016/183361 A1 | 11/2016 | |
| WO | WO 2016/191545 A1 | 12/2016 | |
| WO | WO 2016/207859 A1 | 12/2016 | |
| WO | WO 2017/048714 A1 | 3/2017 | |
| WO | WO 2017/048850 A1 | * | 3/2017 |
| WO | WO 2017/049218 A2 | 3/2017 | |
| WO | WO 2017/106754 A2 | 3/2017 | |
| WO | WO 2017/066706 A1 | 4/2017 | |
| WO | WO 2017/085691 A1 | 5/2017 | |
| WO | WO 2017/087857 A1 | 5/2017 | |
| WO | WO 2017/132547 A1 | 8/2017 | |
| WO | WO 2018/009461 A1 | 1/2018 | |
| WO | WO 2018/085854 A1 | 5/2018 | |
| WO | WO 2018/102584 A1 | 6/2018 | |
| WO | WO 2018/102585 A1 | 6/2018 | |
| WO | WO 2018/129306 A1 | 7/2018 | |
| WO | WO 2018/170313 A1 | 9/2018 | |
| WO | WO 2019/006401 A2 | 1/2019 | |
| WO | WO 2019/060115 A1 | 3/2019 | |
| WO | WO 2019/094607 A2 | 5/2019 | |
| WO | WO 2019/157098 A1 | 8/2019 | |
| WO | WO 2019/173684 A1 | 9/2019 | |
| WO | WO 2019/210034 A1 | 10/2019 | |

OTHER PUBLICATIONS

Hoppner, Horm Re. 2002, 58 Suppl. 3:7-15 (Year: 2002).*
Michalek, et al., "A role for the ubiquitin-dependent protolytic pathway in MHC class I-restricted antigen presentation," Nature, vol. 363, pp. 552-554, (Jun. 1993).
Paal, et al., "A novel Ecotin-Ubiquitin-Tag (ECUT) for efficient, soluble peptide production in the periplasm of *Escherichia coli*," Microbial Cell Factories, 8:7, pp. 1-9, (2009).
Rodriguez, et al., "DNA Immunization: Ubiquitination of a Viral Protein Enhances Cytotoxic T-Lymphocyte Inductin and Antiviral Protection but Abrogates Antibody Induction," Journal of Viroloogy, vol. 71, No. 11, pp. 8497-8503, (Nov. 1997).
Wolf, et al., "Viral band bacterial minigene products are presented by MHC class I molecules with similar efficiencies," Molecular Immunology, 48, 463-471, (2011).
Bei, et al., "TAA Polyepitope DNA-Based Vaccines: A Potential Tool for Cancer Therapy," Journal of Biomedicine and Biotechnology, vol. 2010, Art. ID 102758, (2010).
EP Application 17875504.7 Supplementary European Search Report dated Jul. 10, 2020.
WIPO Application No. PCT/US2018/059849, PCT International Preliminary Report on Patentability dated May 20, 2020.
Aurisicchio, et al., "Superior Immunologic and Therapeutic Efficacy of a Xenogeneic Genetic Cancer Vaccine Targeting Carcinoembryonic Human Antigen," Hum. Gene Ther., 26(6):386-398, (Apr. 13, 2015).
Hazama, et al., "A phase I study of combination vaccine treatment of five therapeutic epitope-peptides for metastatic colorectal cancer; safety, immunological response, and clinical outcome," J. Transl. Med., 12:63, (2014).
He, et al., "Engineering α-fetoprotein-based gene vaccines to prevent and treat hepatocellular carcinoma: review and future prospects," Immunotherapy, 6(6):725-736, (Jul. 21, 2014).
Kawada, et al., "Heteroclitic serological response in esophageal and prostate cancer patients after NY-ESO-1 protein vaccination," Int. J. Cancer, 130(3):584-592, (May 25, 2011).
Mateo, et al., "An HLA-A2 polyepitope vaccine for melanoma immunotherapy," J. Immunol., 163(7):4058-4063, (Oct. 1, 1999).
Sinnathamby, et al., "Priming and Activation of Human Ovarian and Breast Cancer-specific CD8+ T Cells by Polyvalent Listeria moocytogenes-based Vaccines," J. Immunother, 32(8):856-869, (Oct. 2009).
Wallecha, et al., "Construction and Characterization of an Attenuated Listeria monocytogenes Strain for Clinical Use in Cancer Immunotherapy," Clin. Vaccine Immunol., 16(1):96-103, (Jan. 2009).
Yang, et al., "Attenuated Listeria monocytogenes as a cancer vaccine vector for the delivery of CD24, a biomarker for hepatic cancer stem cells," Cell. Mol. Immunol., 11(2):184-196, (2014).
EP 18875375 Supplementary European Search Report dated Nov. 4, 2021.
EP 18875375 Supplementary Partial European Search Report dated Jul. 13, 2021.
SG 11202004107Y Search Report dated Nov. 16, 2021.
WIPO Application No. PCT/US2017/064015, PCT International Preliminary Report on Patentability dated Jun. 4, 2019.
WIPO Application No. PCT/US2018/059849, PCT International Search Report and Written Opinion of the International Searching Authority dated May 1, 2019.
Alves, et al., "STEAP, prostate tumor antigen, is a target of human CD8+ T cells," Cancer Immunol Immunother, 55: 1515-1523, (2006).
Anderson, et al., "HLA-A24 and survivin: possibilities in therapeutic vaccination against cancer," Journal of Translational Medicine, 4:38, (2006).

(56) References Cited

OTHER PUBLICATIONS

Biontech RNA Pharmaceuticals, IVAC®—Individualized Vaccines Against Cancer Platform, retrieved from http://biontech.de/wp-content/uploads/2016/03/IVAC.pdf> on Nov. 28, 2016.
Castle, et al., "Exploiting the Mutanome for Tumor Vaccination," Cancer Res, 72(5): 1081-1091 (2012).
Chang, et al., "Identifying recurrent mutations in cancer reveals widespread lineage diversity and mutational specificity," Nat Biotechnol, 34:(2), 155-163, (Feb. 2016).
Chinnasamy, et al., "A TCR Targeting the HLA-A*0201—Restricted Epitope of MAGE-A3 Recognizes Multiple Epitopes of the MAGE-A Antigen Superfamily in Several Types of Cancer," J Immunol, 186:685-696 (Dec. 13, 2010).
Editorial, Nature Biotechnology, "The problem with neoantigen prediction," Nature Biotechnology, vol. 35, No. 3, (Feb. 2017).
Efremova et al., "Neoantigens Generated by Individual Mutations and Their Role in Cancer Immunity and Immunotherapy," Front. Immunol. 8:1679, (Nov. 28, 2017).
Flechtner, "Antigen-Screening System—Perfecting the Promise of T Cell Therapies for Infectious Disease & Cancer," retrieved from <http://www.drug-dev.com/Main/Back-Issues/Antigenscreeing-System-Perfecting-the-Promise-of-1127.aspx> accessed Dec. 7, 2017.
Fratta, et al., "The biology of cancer testis antigens: Putative function, regulation and therapeutic potential," Molecular Oncology, 5:164-182, (2011).
Garraway, et al., "Lessons from the Cancer Genome," Cell, 153:17-37, (Mar. 28, 2013).
Genocea, "ATLASTM—Don't Predict. Know" retrieved from <https://www.genocea.com/our-science/> accessed Dec. 7, 2017.
Gritstone Mar. 31, 2017, "First Public Data Presented from Gritstone Oncology's Tumor Antigen Identification Platform for Personalized Cancer Immunotherapy," retrieved from <https://gritstoneoncology.com/news-1/2017/5/24/first-public-data-presented-from-gritstone-oncologys-tumor-antigen-identification-platform-for-personalized-cancer-immunotherapy> accessed Dec. 7, 2017.
Gritstone Approach, Scientific Excellence Required in Two Essential Elements, retrieved from <http://gritstoneoncology.com/approach> on Dec. 7, 2017.
Hacohen, et al., "Getting Personal with Neoantigen-Based Therapeutic Cancer Vaccines," Cancer Immunol Res, 1(1): 11-15, (2013).
Harao, et al., "HLA-A2-restricted CTL epitopes of a novel lung cancer-associated cancer testis antigen, cell division cycle associated 1, can induce tumor-reactive CTL," Int J. Cancer, 123: 2616-2625, (2008).
Hoof, et al., "NetMHCpan, a method for MHC class I binding prediction beyond humans," Immunogenetics, 61(1): 1-13, doi:10.1007/s00251-008-341-z, (Jan. 2009).
Huarte, et al., "Enhancing Immunogenicity of a CTL Epitope from Carcinoembryonic Antigen by Selective Amino Acid Replacements," Clinical Cancer Research, vol. 8, 2336-2344, (Jul. 2002).
Ito, et al., "Cancer Neoantigens: A Promising Source of Immunogens for Cancer Immunotherapy," J Clin Cell Immunol, 6:2, (2015).
Ito, et al., "Identification of Bladder Cancer Antigens Recognized by IgG Antibodies of a Patient with Metastatic Bladder Cancer," Int. J. Cancer, 108, 712-724, (2004).
Kawashima, et al., "Identification of HLA-A3-restricted Cytotoxic T Lymphocyte Epitopes from Carcinoembryonic Antigen and HER-2/neu by Primary in vitro Immunization with Peptide-pulsed Dendritic Cells," Cancer Research, 59, 431-435, (Jan. 15, 1999).
Kobayashi, et al., "Identification of a prostate-specific membrane antigen-derived peptide capable of eliciting both cellular and humoral immune responses in HLA-A24+ prostate cancer patients," Cancer Sci, vol. 94, No. 7, (Jul. 2003).
Lu, et al., "Use of Two Predictive Algorithms of the World Wide Web for the Identification of Tumor-reactive T-Cell Epitopes," Cancer Research, 60: 5223-5227, (Sep. 15, 2000).
Nakamura, et al., "Analysis of HLA-A24-restricted peptides of carcinoembryonic antigen using a novel structure-based peptide-HLA docking algorithm," Cancer Sci, vol. 102, No. 4, 690-696, (Apr. 2011).

Neon Therapeutics—Product Pipeline NEO-PV-01 Personalized neoantigen vaccine and NEO-PTC-01 Adoptive T cell therapy, retrieved from <http://neontheapeutics.com/product-pipeline/> on Dec. 7, 2017.
Neon Therapeutics—Product Pipeline NEO-PV-01 Personalized neoantigen vaccine, retrieved from <http://neontheapeutics.com/product-pipeline/> on Dec. 7, 2017.
Niu, et al., "Identification of peptides applicable as vaccines for HLA-A26-positive cancer patients," Cancer Sci, vol. 100, No. 11, 2167-2176, (Nov. 2009).
Quintarelli, et al., "High-avidity cytotoxic T lymphocytes specific for a new PRAME-derived peptide can target leukemic and leukemic-precursor cells," Blood, vol. 117, No. 12, 3353-3362, (Mar. 24, 2011).
Schnupf et al., "Listeriolysin O secreted by Listeria monocytogenes into the host cell cytosol is degraded by the N-end rule pathway," Infect. Immun., 75(11):5135-5147, (2007).
Schumacher et al., "Neoantigens in cancer immunotherapy," Science, 348(6230):69-74, (Apr. 3, 2015).
Scrimieri, et al., "Murine leukemia virus envelope gp70 is a shared biomarker for the high-sensitivity quantification of murine tumor burden," OncoImmunology, 2:11, e26889, (Nov. 2013).
Shahabi, et al., "Live, attenuated strains of Listeria and *Salmonella* as vaccine vectors in cancer treatment," Bioeng. Bugs, 1(4):235-243, (2010).
Shen, et al., "Identification of a novel HLA-A2-restricted mutated Survivin epitope and induction of specfic anti-HCC CTLs that could effectively cross-recognize wild-type Survivin antigen," Cancer Immunol Immunother, 62:393-402, (2013).
Singh et al., "Fusion to listeriolysin O and delivery by Listeria monocytes enhances the immunogenicity of HER-2/neu and reveals subdominant epitopes in the FVB/N mouse," The Journal of Immunology, 175(6):3663-3673, (2005).
Smith, et al., "Vaccines Targeting the Cancer Testis Antigen SSX-2 Elicit HLA-A22 Epitope-Specific Cytolytic T Cells," J Immunother., 34:(8), 569-580, (Oct. 2011).
Suzuki, et al., "Detection of Peptide-Specific Cytotoxic T-Lymphocyte Precursors Used for Specific Immunotherapy of Pancreatic Cancer," Int. J. Cancer, 9, 45-50, (2002).
Tamborero, et al., "Comprehensive identification of mutational cancer driver genes across 12 tumor types," Scientific Reports, 3: 2650, DOI:10.1038/srep02650, (Oct. 2, 2013).
Toes, et al., "Discrete Cleavage Motifs of Constructive and Immunoproteasomes Revealed by Quantitative Analysis of Cleavage Products," J. Exp. Med., vol. 194, No. 1, pp. 1-12, (Jul. 2, 2001).
Uchida, et al., "Ring Finger Protein 43 as a New Target for Cancer Immunotherapy," Clinical Cancer Research, vol. 10, 8577-8586, (Dec. 15, 2004).
Villarreal et al., "Targeting shared hotspot cancer mutations with a Listeria monocytogenes immunotherapy induce potent anti-tumor immunity," American Association for Cancer Research Annual Meeting 2018, (Apr. 16, 2018).
Vogelstein, et al., "Cancer Genome Landscapes," Science, vol. 339, pp. 1546-1558, (Mar. 29, 2013).
Vonderheide, et al., "The Telomerase Catalytic Subunit is a Widely Expressed Tumor-Associated Antigen Recognized by Cytotoxic T Lymphocytes," Immunity, vol. 10, 673-679, (Jun. 1999).
Wood, et al., "Attenuated Listeria monocytogenes: a powerful and versatile vector for the future of tumor immunotherapy," Front. Cell. Infect. Microbiol., 4:51, (2014).
Xiang, et al., "An autologous oral DNA vaccine protects against murine melanoma," Proc. Natl. Acad. Sci. U.S.A., 97(10):5492-5497 and 97(23):12932 (correction), (2000).
Yadav, et al., "Predicting immunogenic tumour mutations by combining mass spectrometry and exome sequencing," Nature, vol. 515, pp. 572-576, and supplemental materials (Nov. 27, 2014).
WO Application PCT/US2017/060415 International Search Report and Written Opinion dated Mar. 27, 2018.
Brockstedt, et al., "Listeria-based cancer vaccines that segregate immunogenicity from toxicity," Proc. Natl. Acad. Sci. U.S.A., 101(38):13832-13837, (2004).

(56) References Cited

OTHER PUBLICATIONS

U.S. Appl. No. 16/759,670, Requirement for Restriction/Election dated Mar. 1, 2023.

* cited by examiner

FIG. 2A

Secretion Signal | Ub | WT1 Peptide 1

FIG. 2B

Secretion Signal | Ub | WT1 Peptide 1 | Shine-Dalgarno | Secretion Signal | Ub | WT1 Peptide 2 | Shine-Dalgarno | Secretion Signal | Ub | WT1 Peptide 3

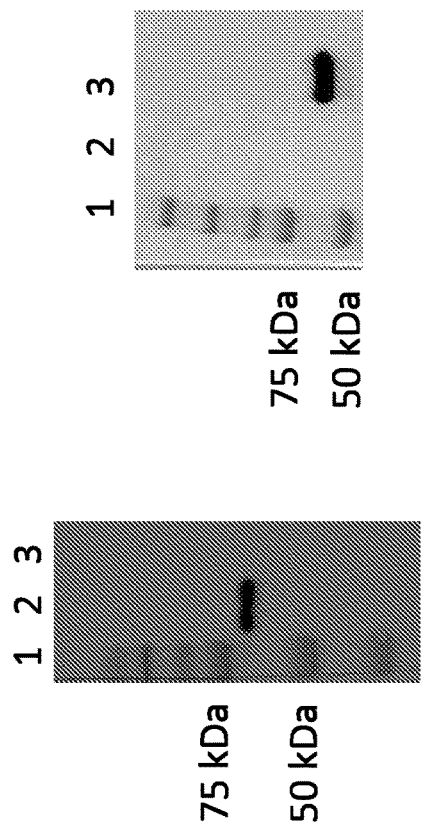
FIG. 3A
FIG. 3B
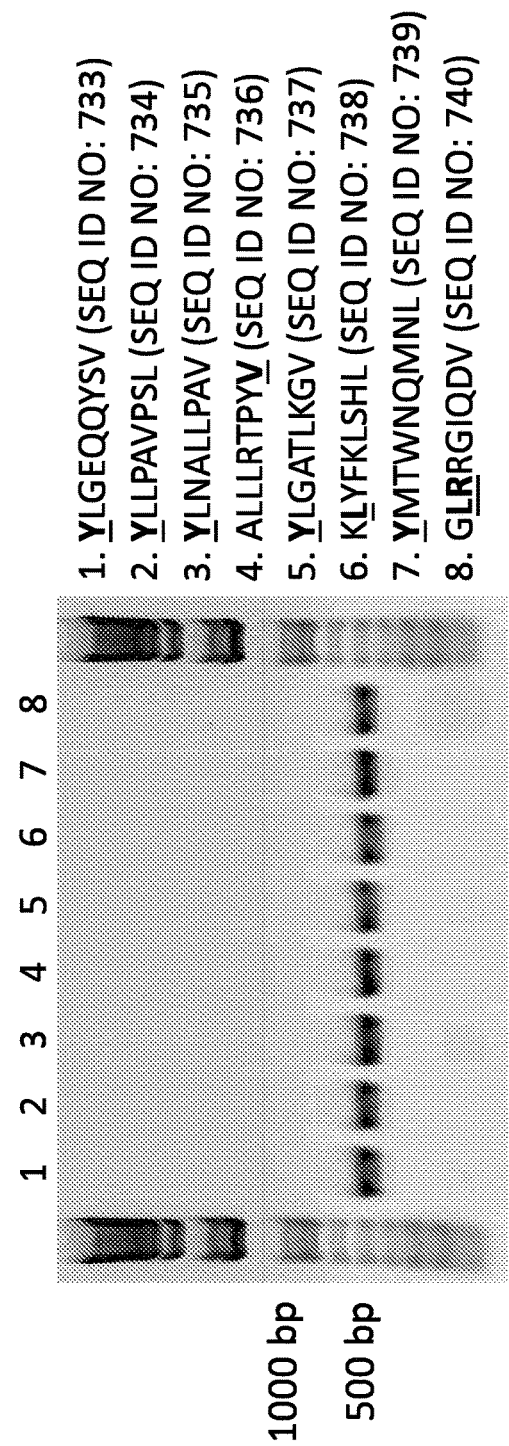
1. YLGEQQYSV (SEQ ID NO: 733)
2. YLLPAVPSL (SEQ ID NO: 734)
3. YLNALLPAV (SEQ ID NO: 735)
4. ALLLRTPYV (SEQ ID NO: 736)
5. YLGATLKGV (SEQ ID NO: 737)
6. KLYFKLSHL (SEQ ID NO: 738)
7. YMTWNQMNL (SEQ ID NO: 739)
8. GLRRGIQDV (SEQ ID NO: 740)
FIG. 4

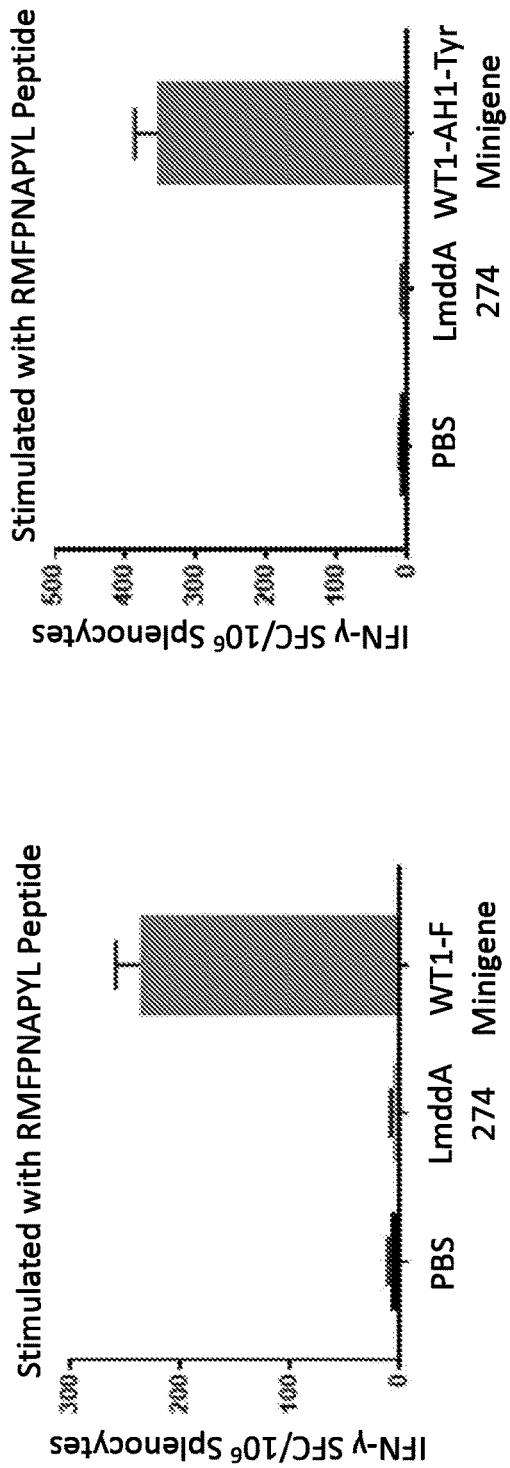
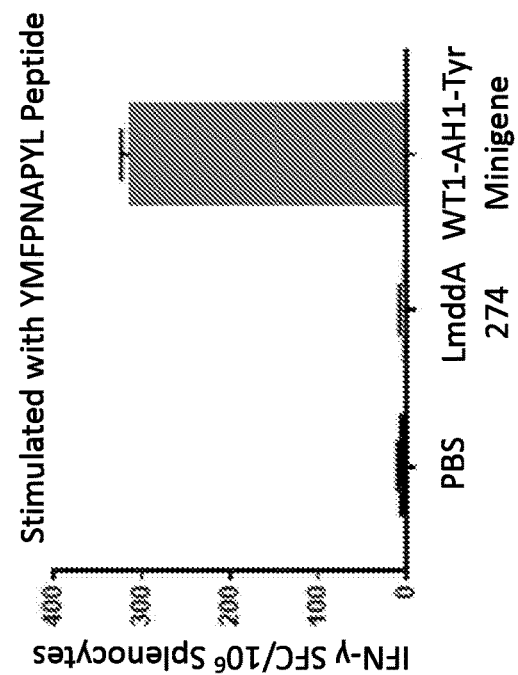
FIG. 7A
FIG. 7B
FIG. 8A
FIG. 8B

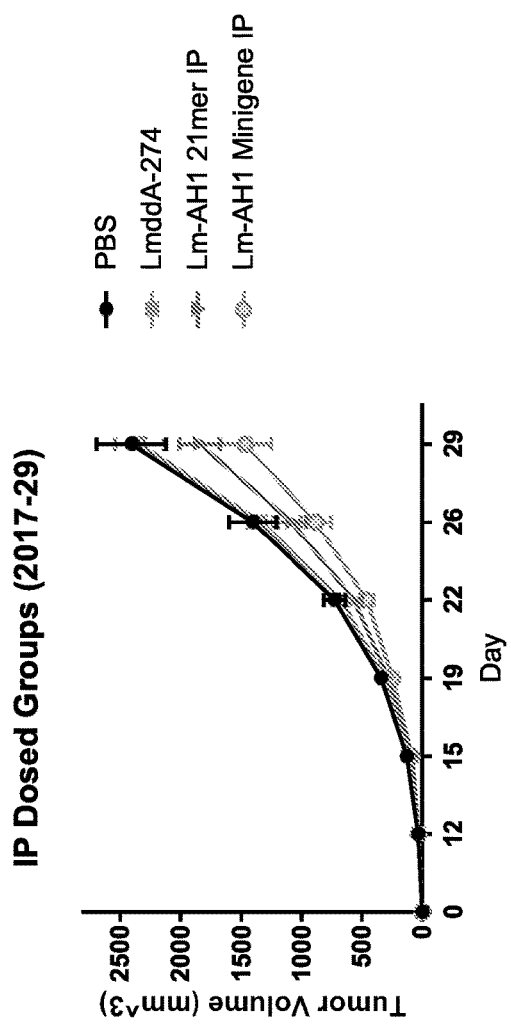
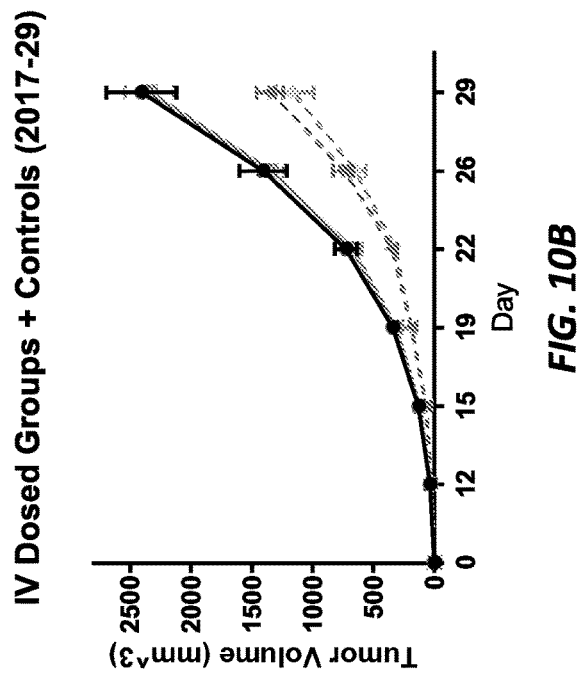
FIG. 10A
FIG. 10B

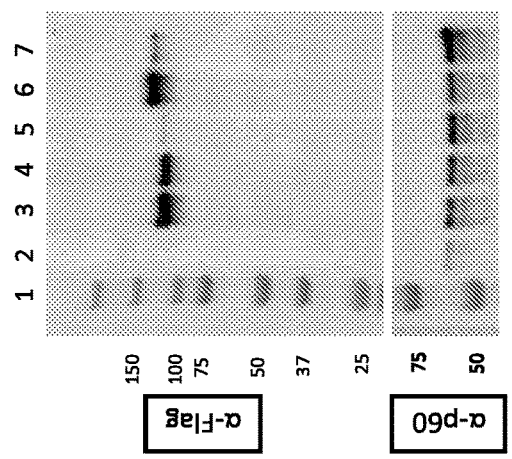
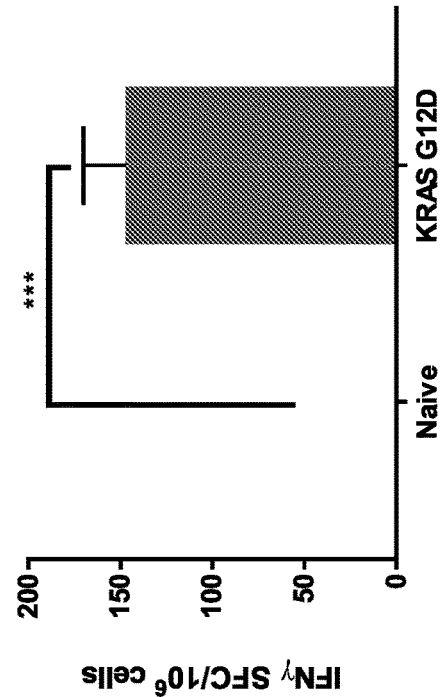
FIG. 23
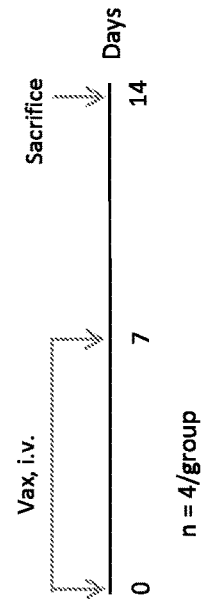
FIG. 24A
FIG. 24B

IMMUNOGENIC COMPOSITIONS TARGETING RECURRENT CANCER MUTATIONS AND METHODS OF USE THEREOF

CROSS-REFERENCE TO RELATED APPLICATIONS

This application is a US National Stage of PCT/US2017/064015 filed Nov. 30, 2017, which claims the benefit of U.S. Application No. 62/428,515, filed Nov. 30, 2016, U.S. Application No. 62/443,483, filed Jan. 6, 2017, and U.S. Application No. 62/583,292, filed Nov. 8, 2017, each of which is herein incorporated by reference in its entirety for all purposes.

REFERENCE TO A SEQUENCE LISTING SUBMITTED AS A TEXT FILE VIA EFS WEB

This application includes an electronic sequence listing in a file named 528306SEQLIST.txt, created on May 6, 2019, and containing 1.89 megabytes, which is herein incorporated by reference in its entirety.

BACKGROUND

Many cancer patients share common mutations in the functional domains of critical tumor driver genes that are the most frequently mutated or that are at least partially responsible for the creating a malignant phenotype. These "hotspot" mutations are commonly shared by cancer patients across multiple tumor types. The acquisition of somatic driver mutations is one of the major mechanisms responsible for the dysregulation of proliferation, invasion, and apoptosis, which are required for oncogenesis. Many of these mutations frequently occur in the functional regions of biologically active proteins (for example, kinase domains or binding domains) or interrupt active sites (for example, phosphorylation sites) resulting in loss-of-function or gain-of-function mutations, or they can occur in such a way that the three-dimensional structure and/or charge balance of the protein is perturbed sufficiently to interfere with normal function.

Pre-clinical evidence and early clinical trial data suggests that the anti-tumor capabilities of the immune system can be harnessed to treat patients with established cancers. The vaccine strategy takes advantage of tumor antigens associated with various types of cancers. Immunizing with live vaccines such as viral or bacterial vectors expressing a tumor-associated antigen is one strategy for eliciting strong CTL responses against tumors.

SUMMARY

Methods and compositions are provided for cancer immunotherapy. In one aspect, provided herein are recombinant *Listeria* strains comprising a nucleic acid comprising a first open reading frame encoding a fusion polypeptide, wherein the fusion polypeptide comprises a PEST-containing peptide fused to two or more antigenic peptides, wherein each antigenic peptide comprises a recurrent cancer mutation, and wherein at least two of the antigenic peptides comprise different recurrent cancer mutations and are fragments of the same cancer-associated protein. Alternatively, each of the antigenic peptides comprises a different recurrent cancer mutation from a different cancer-associated protein. Optionally, each of the antigenic peptides comprises a different recurrent cancer mutation from a single type of cancer. Also provided are such fusion polypeptides and nucleic acids encoding such fusion polypeptides.

In another aspect, provided herein are recombinant *Listeria* strains comprising a nucleic acid comprising a first open reading frame encoding a fusion polypeptide comprising a PEST-containing peptide fused to two or more antigenic peptides, wherein at least one antigenic peptide is from a cancer-associated protein and comprises a recurrent cancer mutation, and at least one antigenic peptide is from a cancer-associated protein and comprises a heteroclitic mutation. Optionally, the PEST-containing peptide comprises a bacterial secretion signal sequence, and the fusion polypeptide further comprises a ubiquitin protein fused to a carboxy-terminal antigenic peptide, wherein the PEST-containing peptide, the two or more antigenic peptides, the ubiquitin, and the carboxy-terminal antigenic peptide are arranged in tandem from the amino-terminal end to the carboxy-terminal end of the fusion polypeptide. Also provided are such fusion polypeptides and nucleic acids encoding such fusion polypeptides.

In another aspect, provided herein are immunogenic compositions, pharmaceutical compositions, or vaccines comprising a recombinant *Listeria* strain comprising a nucleic acid comprising a first open reading frame encoding a fusion polypeptide, wherein the fusion polypeptide comprises a PEST-containing peptide fused to two or more antigenic peptides, wherein each antigenic peptide comprises a recurrent cancer mutation, and wherein at least two of the antigenic peptides comprise different recurrent cancer mutations and are fragments of the same cancer-associated protein. Alternatively, each of the antigenic peptides comprises a different recurrent cancer mutation from a different cancer-associated protein. Optionally, each of the antigenic peptides comprises a different recurrent cancer mutation from a single type of cancer. Also provided are immunogenic compositions, pharmaceutical compositions, or vaccines comprising the fusion polypeptide or a nucleic acid encoding the fusion polypeptide.

In another aspect, provided herein are methods of inducing an immune response against a tumor or cancer in a subject, comprising administering to the subject a recombinant *Listeria* strain comprising a nucleic acid comprising a first open reading frame encoding a fusion polypeptide, wherein the fusion polypeptide comprises a PEST-containing peptide fused to two or more antigenic peptides, wherein each antigenic peptide comprises a recurrent cancer mutation, and wherein at least two of the antigenic peptides comprise different recurrent cancer mutations and are fragments of the same cancer-associated protein. Alternatively, each of the antigenic peptides comprises a different recurrent cancer mutation from a different cancer-associated protein. Optionally, each of the antigenic peptides comprises a different recurrent cancer mutation from a single type of cancer. Also provided are methods of inducing an immune response against a tumor or cancer in a subject, comprising administering to the subject an immunogenic composition, a pharmaceutical composition, or a vaccine comprising such a recombinant *Listeria* strain. Also provided are methods of inducing an immune response against a tumor or cancer in a subject, comprising administering to the subject the fusion polypeptide or a nucleic acid encoding the fusion polypeptide, an immunogenic composition comprising the fusion polypeptide or the nucleic acid encoding the fusion polypeptide, a pharmaceutical composition comprising the fusion polypeptide or the nucleic acid encoding the fusion polypeptide, or a vaccine comprising the fusion polypeptide or the nucleic acid encoding the fusion polypeptide.

In another aspect, provided herein are methods of preventing or treating a tumor or cancer in a subject, comprising administering to the subject a recombinant *Listeria* strain comprising a nucleic acid comprising a first open reading frame encoding a fusion polypeptide, wherein the fusion polypeptide comprises a PEST-containing peptide fused to two or more antigenic peptides, wherein each antigenic peptide comprises a recurrent cancer mutation, and wherein at least two of the antigenic peptides comprise different recurrent cancer mutations and are fragments of the same cancer-associated protein. Alternatively, each of the antigenic peptides comprises a different recurrent cancer mutation from a different cancer-associated protein. Optionally, each of the antigenic peptides comprises a different recurrent cancer mutation from a single type of cancer. Also provided are methods of preventing or treating a tumor or cancer in a subject, comprising administering to the subject an immunogenic composition, a pharmaceutical composition, or a vaccine comprising such a recombinant *Listeria* strain. Also provided are methods of preventing or treating a tumor or cancer in a subject, comprising administering to the subject the fusion polypeptide, a nucleic acid encoding the fusion polypeptide, an immunogenic composition comprising the fusion polypeptide or the nucleic acid encoding the fusion polypeptide, a pharmaceutical composition comprising the fusion polypeptide or the nucleic acid encoding the fusion polypeptide, or a vaccine comprising the fusion polypeptide or the nucleic acid encoding the fusion polypeptide.

In another aspect, provided herein are cell banks comprising one or more recombinant *Listeria* strains comprising a nucleic acid comprising a first open reading frame encoding a fusion polypeptide, wherein the fusion polypeptide comprises a PEST-containing peptide fused to two or more antigenic peptides, wherein each antigenic peptide comprises a recurrent cancer mutation, and wherein at least two of the antigenic peptides comprise different recurrent cancer mutations and are fragments of the same cancer-associated protein. Alternatively, each of the antigenic peptides comprises a different recurrent cancer mutation from a different cancer-associated protein. Optionally, each of the antigenic peptides comprises a different recurrent cancer mutation from a single type of cancer.

In another aspect, provided herein are methods of generating an immunotherapy construct, comprising: (a) selecting a set of recurrent cancer mutations to include in the immunotherapy construct; (b) designing antigenic peptides comprising each of the recurrent cancer mutations; (c) selecting a set of antigenic peptides, comprising testing the hydropathy of the each antigenic peptide, and modifying or deselecting an antigenic peptide if it scores above a selected hydropathy index threshold value; (d) designing a fusion polypeptide comprising each of the selected antigenic peptides; (e) generating a nucleic acid construct encoding the fusion polypeptide. Optionally, each of the recurrent cancer mutations is from the same cancer-associated protein. Optionally, each of the recurrent cancer mutations comprises a different recurrent cancer mutation from a single type of cancer.

In another aspect, provided herein are methods of generating an immunotherapy construct, comprising: (a) selecting a set of recurrent cancer mutations and a set of heteroclitic mutations in cancer-associated proteins to include in the immunotherapy construct; (b) designing antigenic peptides comprising each of the recurrent cancer mutations and each of the heteroclitic mutations; (c) selecting a set of antigenic peptides, comprising testing the hydropathy of the each antigenic peptide, and modifying or deselecting an antigenic peptide if it scores above a selected hydropathy index threshold value; (d) designing a fusion polypeptide comprising each of the selected antigenic peptides; and (e) generating a nucleic acid construct encoding the fusion polypeptide.

BRIEF DESCRIPTION OF THE FIGURES

FIGS. 2A and 2B show schematics of WT1 minigene constructs. FIG. 2A shows a WT1 minigene construct designed to express a single WT1 chimeric polypeptide antigen. FIG. 2B shows a WT1 minigene construct designed to express three separate WT1 chimeric polypeptide antigens.

FIGS. 3A and 3B show Western blots of the Lmdda-WT1-tLLO-FLAG-Ub-heteroclitic phenylalanine minigene construct (FIG. 3A) and the Lmdda-WT1-tLLO-P1-P2-P3-FLAG-Ub-heteroclitic tyrosine minigene construct (FIG. 3B). In FIG. 3A, lane 1 is the ladder, lane 2 is the Lmdda-WT1-tLLO-P1-P2-P3-FLAG-Ub-heteroclitic tyrosine minigene construct (68 kDa), and lane 3 is a negative control. In FIG. 3B, lane 1 is the ladder, lane 2 is the negative control, and lane 3 is the WT1-tLLO-FLAG-Ub-heteroclitic phenylalanine minigene construct (construct #1).

FIG. 4 shows colony PCR results for several Lm-minigene constructs expressing heteroclitic mutant WT1 peptides. Mutated residues are bolded and underlined.

FIGS. 7A and 7B show IFN-γ spot-forming cells (SFC) per million splenocytes stimulated ex vivo with WT1 peptides RMFPNAPYL (SEQ ID NO: 749; FIG. 7A) and FMFPNAPYL (SEQ ID NO: 732; FIG. 7B). The splenocytes are from HLA2 transgenic mice immunized with the WT1-F minigene construct. PBS and LmddA274 were used as negative controls.

FIGS. 8A and 8B show IFN-γ spot-forming cells (SFC) per million splenocytes stimulated ex vivo with WT1 peptides RMFPNAPYL (SEQ ID NO: 749; FIG. 8A) and YMFPNAPYL (SEQ ID NO: 741; FIG. 8B). The splenocytes are from HLA2 transgenic mice immunized with the WT1-AH1-Tyr minigene construct. PBS and LmddA274 were used as negative controls.

FIGS. 10A and 10B show CT26 tumor volume in mice treated with PBS control, LmddA-274 control, Lm AH1_21mer, and Lm AH1_minigene after intraperitoneal (IP) dosing (FIG. 10A) or intravenous (IV) dosing (FIG. 10B).

FIG. 23 shows Western blot data for different breast cancer constructs. The upper left panel shows detection, using an anti-Flag antibody, of breast cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.

FIGS. 24A and 24B show a Lm-HOT (KRAS_G12D) construct induced KRAS-induced specific IFNg immune responses in the periphery of non-tumor-bearing mice. FIG. 24A shows BALB/c mice (n=4/group) were immunized at days 0 and 7 with the Lm-HOT KRAS_G12D construct, and spleens were harvested one week post final immunization (day 14) to assess the cellular immune responses. In FIG. 24B, induction of a TH1 response is shown by the number of KRAS_G12D-specific IFNg spot-forming colonies (SFC) per million splenocytes determined by IFNg ELISpot assay. Splenocytes were stimulated for 18 hours using KRAS_G12D pooled peptides (15-mers overlapping by 9 amino acids; 2.5 μg/mL final concentration) spanning the entire KRAS G12D 21mer antigen target. ***P<0.001. Errors bars indicate SEM; n=4/group.

In FIGS. 25A and 25B, CD45+ leukocyte infiltrate and CD8+ TILs as percentage of total CD45+ cells are shown in treated versus control groups. In FIG. 25C, the induction of a TH1 response is shown by the number of KRAS_G12D-specific IFNg spot-forming colonies (SFC) per million TILs determined by IFNg ELISpot assay. In FIG. 25D, summary plot data show the percentages of FOXP3+CD4+ and FOXP3+CD25+CD4+ Tregs, respectively, of CD45+ TILs and CD4+FOXP3− TILs as percentage of total CD45+ cells. TILs populations were identified by flow cytometry. *P<0.05; P<0.01; *P<0.001; ns not significant. Error bars indicate SEM of n=4/group.

DEFINITIONS

Figure 1:
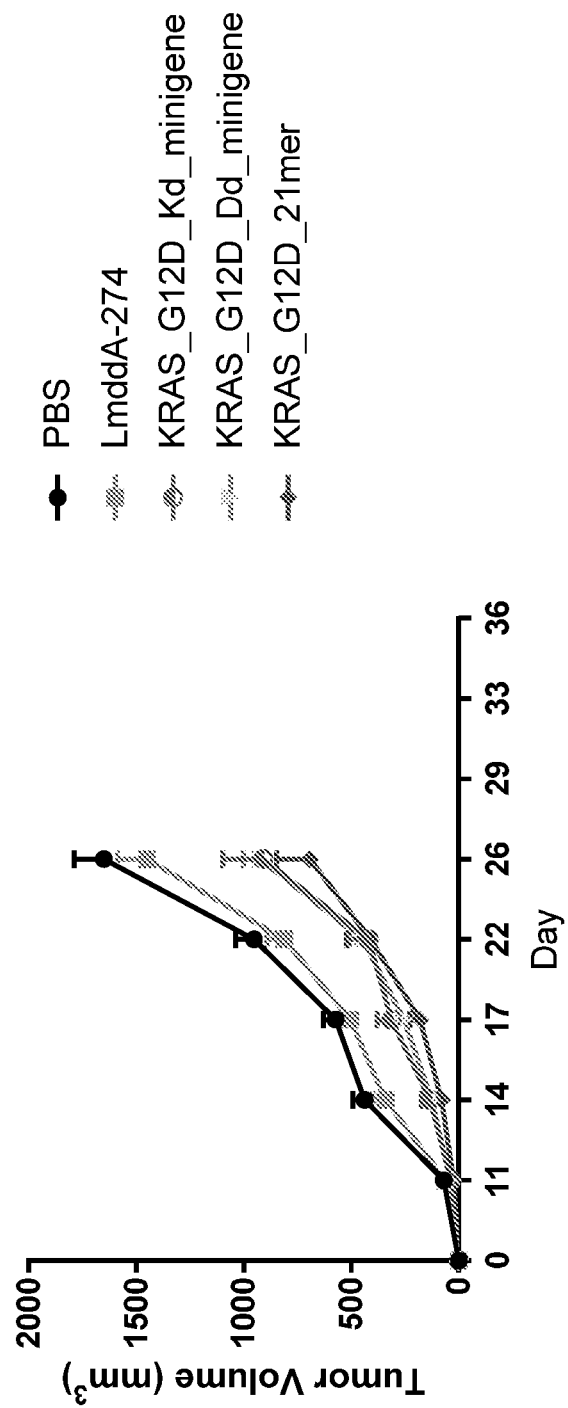
FIG. 1 shows CT26 tumor volume in mice treated with PBS control, LmddA-274 control, Lm KRAS_G12D_Kd_minigene, Lm KRAS_G12D_Dd_minigene, and Lm KRAS-G12D_21mer.

The terms "protein," "polypeptide," and "peptide," used interchangeably herein, refer to polymeric forms of amino acids of any length, including coded and non-coded amino acids and chemically or biochemically modified or derivatized amino acids. The terms include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The term "fusion protein" refers to a protein comprising two or more peptides linked together by peptide bonds or other chemical bonds. The peptides can be linked together directly by a peptide or other chemical bond. For example, a chimeric molecule can be recombinantly expressed as a single-chain fusion protein. Alternatively, the peptides can be linked together by a "linker" such as one or more amino acids or another suitable linker between the two or more peptides.

The terms "nucleic acid" and "polynucleotide," used interchangeably herein, refer to polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

"Codon optimization" refers to a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a fusion polypeptide can be modified to substitute codons having a higher frequency of usage in a given *Listeria* cell or any other host cell as compared to the naturally occurring nucleic acid sequence. Codon usage tables are readily available, for example, at the "Codon Usage Database." The optimal codons utilized by *L. monocytogenes* for each amino acid are shown US 2007/0207170, herein incorporated by reference in its entirety for all purposes. These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "plasmid" or "vector" includes any known delivery vector including a bacterial delivery vector, a viral vector delivery vector, a peptide immunotherapy delivery vector, a DNA immunotherapy delivery vector, an episomal plasmid, an integrative plasmid, or a phage vector. The term "vector" refers to a construct which is capable of delivering, and, optionally, expressing, one or more fusion polypeptides in a host cell.

The term "episomal plasmid" or "extrachromosomal plasmid" refers to a nucleic acid vector that is physically separate from chromosomal DNA (i.e., episomal or extrachromosomal and does not integrated into a host cell's genome) and replicates independently of chromosomal DNA. A plasmid may be linear or circular, and it may be single-stranded or double-stranded. Episomal plasmids may optionally persist in multiple copies in a host cell's cytoplasm (e.g., *Listeria*), resulting in amplification of any genes of interest within the episomal plasmid.

The term "genomically integrated" refers to a nucleic acid that has been introduced into a cell such that the nucleotide sequence integrates into the genome of the cell and is capable of being inherited by progeny thereof. Any protocol may be used for the stable incorporation of a nucleic acid into the genome of a cell.

The term "stably maintained" refers to maintenance of a nucleic acid molecule or plasmid in the absence of selection (e.g., antibiotic selection) for at least 10 generations without detectable loss. For example, the period can be at least 15 generations, 20 generations, at least 25 generations, at least 30 generations, at least 40 generations, at least 50 generations, at least 60 generations, at least 80 generations, at least 100 generations, at least 150 generations, at least 200 generations, at least 300 generations, or at least 500 generations. Stably maintained can refer to a nucleic acid molecule or plasmid being maintained stably in cells in vitro (e.g., in culture), being maintained stably in vivo, or both.

An "open reading frame" or "ORF" is a portion of a DNA which contains a sequence of bases that could potentially encode a protein. As an example, an ORF can be located between the start-code sequence (initiation codon) and the stop-codon sequence (termination codon) of a gene.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety.

"Operable linkage" or being "operably linked" refers to the juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" refers to the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLO- SUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) refers to a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence.

The term "wild type" refers to entities having a structure and/or activity as found in a normal (as contrasted with mutant, diseased, altered, or so forth) state or context. Wild type gene and polypeptides often exist in multiple different forms (e.g., alleles).

The term "isolated" with respect to proteins and nucleic acid refers to proteins and nucleic acids that are relatively purified with respect to other bacterial, viral or cellular components that may normally be present in situ, up to and including a substantially pure preparation of the protein and the polynucleotide. The term "isolated" also includes proteins and nucleic acids that have no naturally occurring counterpart, have been chemically synthesized and are thus substantially uncontaminated by other proteins or nucleic acids, or has been separated or purified from most other cellular components with which they are naturally accompanied (e.g., other cellular proteins, polynucleotides, or cellular components).

"Exogenous" or "heterologous" molecules or sequences are molecules or sequences that are not normally expressed in a cell or are not normally present in a cell in that form. Normal presence includes presence with respect to the particular developmental stage and environmental conditions of the cell. An exogenous or heterologous molecule or sequence, for example, can include a mutated version of a corresponding endogenous sequence within the cell or can include a sequence corresponding to an endogenous sequence within the cell but in a different form (i.e., not within a chromosome). An exogenous or heterologous molecule or sequence in a particular cell can also be a molecule or sequence derived from a different species than a reference species of the cell or from a different organism within the same species. For example, in the case of a *Listeria* strain expressing a heterologous polypeptide, the heterologous polypeptide could be a polypeptide that is not native or endogenous to the *Listeria* strain, that is not normally expressed by the *Listeria* strain, from a source other than the *Listeria* strain, derived from a different organism within the same species.

In contrast, "endogenous" molecules or sequences or "native" molecules or sequences are molecules or sequences that are normally present in that form in a particular cell at a particular developmental stage under particular environmental conditions.

The term "variant" refers to an amino acid or nucleic acid sequence (or an organism or tissue) that is different from the majority of the population but is still sufficiently similar to the common mode to be considered to be one of them (e.g., splice variants).

The term "isoform" refers to a version of a molecule (e.g., a protein) with only slight differences compared to another isoform, or version (e.g., of the same protein). For example, protein isoforms may be produced from different but related genes, they may arise from the same gene by alternative splicing, or they may arise from single nucleotide polymorphisms.

The term "fragment" when referring to a protein means a protein that is shorter or has fewer amino acids than the full length protein. The term "fragment" when referring to a nucleic acid means a nucleic acid that is shorter or has fewer nucleotides than the full length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment. A fragment can also be, for example, a functional fragment or an immunogenic fragment.

The term "analog" when referring to a protein means a protein that differs from a naturally occurring protein by conservative amino acid differences, by modifications which do not affect amino acid sequence, or by both.

The term "functional" refers to the innate ability of a protein or nucleic acid (or a fragment, isoform, or variant thereof) to exhibit a biological activity or function. Such biological activities or functions can include, for example, the ability to elicit an immune response when administered to a subject. Such biological activities or functions can also include, for example, binding to an interaction partner. In the case of functional fragments, isoforms, or variants, these biological functions may in fact be changed (e.g., with respect to their specificity or selectivity), but with retention of the basic biological function.

The terms "immunogenicity" or "immunogenic" refer to the innate ability of a molecule (e.g., a protein, a nucleic acid, an antigen, or an organism) to elicit an immune response in a subject when administered to the subject. Immunogenicity can be measured, for example, by a greater number of antibodies to the molecule, a greater diversity of antibodies to the molecule, a greater number of T-cells specific for the molecule, a greater cytotoxic or helper T-cell response to the molecule, and the like.

The term "antigen" is used herein to refer to a substance that, when placed in contact with a subject or organism (e.g., when present in or when detected by the subject or organism), results in a detectable immune response from the subject or organism. An antigen may be, for example, a lipid, a protein, a carbohydrate, a nucleic acid, or combinations and variations thereof. For example, an "antigenic peptide" refers to a peptide that leads to the mounting of an immune response in a subject or organism when present in or detected by the subject or organism. For example, such an "antigenic peptide" may encompass proteins that are loaded onto and presented on MHC class I and/or class II molecules on a host cell's surface and can be recognized or detected by an immune cell of the host, thereby leading to the mounting of an immune response against the protein. Such an immune response may also extend to other cells within the host, such as diseased cells (e.g., tumor or cancer cells) that express the same protein.

The term "epitope" refers to a site on an antigen that is recognized by the immune system (e.g., to which an antibody binds). An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996), herein incorporated by reference in its entirety for all purposes.

The term "mutation" refers to the any change of the structure of a gene or a protein. For example, a mutation can result from a deletion, an insertion, a substitution, or a rearrangement of chromosome or a protein. An "insertion" changes the number of nucleotides in a gene or the number of amino acids in a protein by adding one or more additional nucleotides or amino acids. A "deletion" changes the number of nucleotides in a gene or the number of amino acids in a protein by reducing one or more additional nucleotides or amino acids.

A "frameshift" mutation in DNA occurs when the addition or loss of nucleotides changes a gene's reading frame. A reading frame consists of groups of 3 bases that each code for one amino acid. A frameshift mutation shifts the grouping of these bases and changes the code for amino acids. The resulting protein is usually nonfunctional. Insertions and deletions can each be frameshift mutations.

A "missense" mutation or substitution refers to a change in one amino acid of a protein or a point mutation in a single nucleotide resulting in a change in an encoded amino acid. A point mutation in a single nucleotide that results in a change in one amino acid is a "nonsynonymous" substitution in the DNA sequence. Nonsynonymous substitutions can also result in a "nonsense" mutation in which a codon is changed to a premature stop codon that results in truncation of the resulting protein. In contrast, a "synonymous" mutation in a DNA is one that does not alter the amino acid sequence of a protein (due to codon degeneracy).

The term "somatic mutation" includes genetic alterations acquired by a cell other than a germ cell (e.g., sperm or egg). Such mutations can be passed on to progeny of the mutated cell in the course of cell division but are not inheritable. In contrast, a germinal mutation occurs in the germ line and can be passed on to the next generation of offspring.

A "recurrent cancer mutation" is a change in the amino acid sequence of a protein that occurs in multiple types of cancer and/or in multiple subjects having a particular types of cancer. Such mutations associated with a cancer can result in tumor-associated antigens that are not normally present in corresponding healthy tissue.

The term "in vitro" refers to artificial environments and to processes or reactions that occur within an artificial environment (e.g., a test tube).

The term "in vivo" refers to natural environments (e.g., a cell or organism or body) and to processes or reactions that occur within a natural environment.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value or variations ±0.5%, 1%, 5%, or 10% from a specified value.

The singular forms of the articles "a," "an," and "the" include plural references unless the context clearly dictates otherwise. For example, the term "an antigen" or "at least one antigen" can include a plurality of antigens, including mixtures thereof.

Statistically significant means $p<0.05$.

DETAILED DESCRIPTION

I. Overview

Provided herein are recombinant fusion polypeptides comprising one or more antigenic peptides (e.g., fused to a PEST-containing peptide) from cancer-associated proteins. The antigenic peptides can comprise one or more or all of an antigenic peptide comprising a recurrent cancer mutation, an antigenic peptide comprising a heteroclitic mutation, or an antigenic peptide fused to a ubiquitin protein. For example, provided herein are recombinant fusion polypeptides comprising two or more antigenic peptides (e.g., fused to a PEST-containing peptide), wherein each antigenic peptide comprises a recurrent cancer mutation, and wherein at least two of the antigenic peptides are fragments of the same cancer-associated protein. Also provided herein are nucleic acids encoding such fusion polypeptides; recombinant bacteria or Listeria strains comprising such fusion polypeptides or such nucleic acids; cell banks comprising such recombinant bacteria or *Listeria* strains; immunogenic compositions, pharmaceutical compositions, and vaccines comprising such fusion polypeptides, such nucleic acids, or such recombinant bacteria or *Listeria* strains; and methods of generating such fusion polypeptides, such nucleic acids, and such recombinant bacteria or *Listeria* strains. Also provided are methods of inducing an anti-tumor-associated-antigen immune response in a subject, methods of inducing an anti-tumor or anti-cancer immune response in a subject, methods of treating a tumor or cancer in a subject, methods of preventing a tumor or cancer in a subject, and methods of protecting a subject against a tumor or cancer using such recombinant fusion polypeptides, nucleic acids, recombinant bacteria or *Listeria* strains, immunogenic compositions, pharmaceutical compositions, or vaccines.

Some therapeutic targets in human cancers are proteins encoded by tumor-driver genes with tumor-specific mutational "hotspots," such as TP53, PIK3CA, PIK3R1, PTEN, KRAS, NRAS, BRAF, and EGFR. Hotspots are areas within the DNA molecule which are most likely to mutate. The acquisition of somatic driver mutations is one of the major mechanisms responsible for the dysregulation of proliferation, invasion, and apoptosis, which are required for oncogenesis. Many of these mutations frequently occur in the functional regions of biologically active proteins (for example, kinase domains or binding domains) or interrupt active sites (for example, phosphorylation sites) resulting in loss-of-function or gain-of-function mutations. Many patients share common mutations in the functional domains of critical tumor driver genes that are the most frequently mutated or that are at least partially responsible for the creating a malignant phenotype. For example, one study evaluated over 11,000 tumors in 41 different tumor types and reported 470 somatic mutational hotspots that affected 275 genes. It was also reported that approximately 55% of all solid tumors have one or more hotspots (Chang et al. (2016) *Nat Biotechnol* 34(2):155-163, herein incorporated by reference in its entirety for all purposes). Evaluating the specific missense amino acid substitutions resulting from these hotspots reveals that many mutations are commonly shared by cancer patients across multiple tumor types. For example, it has been hypothesized that p53 function is compromised in most human tumors while at least half of all tumors exhibit mutation of p53 (Polager and Ginsberg (2009) *Nat Rev. Cancer* 9(10):738-748, herein incorporated by reference in its entirety for all purposes). This mutational "sharing" across patients and tumor types creates an opportunity for the "off the shelf" development of treatment constructs that target these common hotspots. Targeting of acquired tumor-specific or cancer-specific mutations is not prevented by central tolerance and minimizes off-target effects in normal cells. Disclosed herein are such "off the shelf" constructs using *Listeria monocytogenes* (Lm) technology (ADXS-HOT) and their use in therapeutic methods.

The Lm technology has a mechanism of action that incorporates potent innate immune stimulation, delivery of a target peptide directly into the cytosol of dendritic cells and antigen presenting cells, generation of a targeted T cell response, and reduced immune suppression by regulatory T cells and myeloid-derived suppressor cells in the tumor microenvironment. Multiple treatments can be given and/or combined without neutralizing antibodies. The Lm technology can use, for example, live, attenuated, bioengineered Lm bacteria to stimulate the immune system to view tumor cells as potentially bacterial-infected cells and target them for elimination. The technology process can start with a live, attenuated strain of *Listeria* and can add, for example, multiple copies of a plasmid that encodes a fusion protein sequence including a fragment of, for example, the LLO (listeriolysin O) molecule joined to the antigen of interest. This fusion protein is secreted by the *Listeria* inside antigen-presenting cells. This results in a stimulation of both the innate and adaptive arms of the immune system that reduces tumor defense mechanisms and makes it easier for the immune system to attack and destroy the cancer cells.

Immunologically, Lm-based vectors are a far superior platform for the generation of CD8+ dominant T cell responses compared to peptide vaccines. First, there is no need to add adjuvants of filgrastim injections. This is because the live attenuated bacteria vectors inherently trigger numerous innate immune activation triggers which include several TLRs, PAMP, and DAMP receptors and have a potent ability to agonize the STING receptor within the cytosol of the antigen-presenting cells. This is a much broader alteration of the immunologic microenvironment that primes the patients' immune system for an adaptive immune response. Second, the Lm vector is infused intravenously. This allows it to reach significantly more antigen-presenting cells than may reside in a finite area of subcutaneous tissue. It also eliminates the requirement for subcutaneous injections, the use of filgrastim, and the risk of delayed type hypersensitivity. It is also likely to generate high T cell titers faster as optimum CD8+ T cell numbers typically peak after 3 treatments, not greater than 10. Third, Lm promotes a predominant CD8+ T cell response with CD4+ cross-reactivity for T cell help. CD8+ T cells are the most effective at killing cancer cells and because Lm vectors present their antigen in the cytoplasm of the APC, those peptides are rapidly shunted to the proteasome for processing, complexed with MHC Class 1 and transported to the APC surface for presentation to predominantly CD8+ T cells. This should bring the advantage of generating more CD8+ T cells that a subcutaneous Montanide presentation of antigen peptides. Fourth, Lm vectors increase the expression of chemokine and chemokine receptors on tumors and surrounding lymph nodes. This facilitates the attraction of activated T cells to the vicinity of solid tumors. Fifth, Lm vectors decrease the relative number and suppressive function of immunosuppressive cells that may protect a tumor from T cell attack, better enabling T cell killing of cancer cells. This reduction of the immunosuppressive ability of regulatory T cells and myeloid derived suppressor cells will better enable T cells generated against these peptides to have better activity in solid tumors. Sixth, Lm vectors do not generate neutralizing antibodies. Because of this, these vectors can be administered repeatedly for extended periods of time without the loss of efficacy from neutralizing antibodies and the development of delayed-type hypersensitivity or acute hypersensitivity which may include anaphylaxis.

Lm vectors act via multiple immunotherapy mechanisms: potent innate immune stimulation via toll-like receptors (TLRs) and pathogen-associated molecular patterns (PAMPs) including the stimulator of interferon genes (STING) receptor, strong CD8+ and CD4+ T cell responses, epitope spreading, and immune suppression by disabling Tregs and myeloid derived suppressor cells (MDSCs) in the tumor microenvironment. In addition, the unique intracellular life cycle of *Listeria* avoids neutralizing antibodies, allowing for repeat dosing. Lm is also advantageous because it has synergies with checkpoint inhibitors, costimulatory agonists, and others agents. It also has a large capacity and can be adapted to target many different tumor types. As an example, live, attenuated strains of Lm can be bioengineered to secrete an antigen-adjuvant fusion protein comprising, consisting essentially of, or consisting of a truncated fragment of listeriolysin O (tLLO), which has adjuvant properties, and one or more tumor-associated antigens. Upon infusion into a patient, bioengineered Lm can be phagocytosed by antigen-presenting cells, where the fusion protein is secreted by the Lm, processed, and presented onto major histocompatibility complex (MHC) class I and II molecules. Target peptides presented on the surface of the antigen-presenting cells stimulate tumor-associated-antigen-specific $CD4^+$ and $CD8^+$ T cells. Activated $CD8^+$ T cells can then seek out and kill tumor-associated-antigen-expressing cancer cells and modulate the tumor microenvironment to overcome immune suppression.

Lm vectors have some clinical advantages. Any side effects associated with treatment appear in the hours immediately post-infusion while the patient is still in the clinic, are almost exclusively mild-moderate and respond readily to treatment, and resolve the day of dosing without evidence of delayed onset, cumulative toxicity, or lasting sequalae. Practical advantages include the fact that there is no need to administer multiple agents and switch to alternate dosing sites for subsequent administrations.

From a manufacturing standpoint, there are several advantages. First, there is no need to manufacture the individual peptides to high concentrations and high degrees of purity. The Lm bacteria transcribe the DNA simultaneously on multiple copies of DNA plasmids inside the bacteria and secrete these peptides directly into the cytoplasm of the APC, where they are almost immediately transported to the proteasome for processing. Essentially, the peptides are manufactured by the bacteria right at the point of use for antigen processing. Second, Lm vectors are highly scalable. Once the genetic engineering is complete, the bacteria replicate themselves in broth cultures. The cultures can be scaled up to vastly reduce cost of goods. Third, there is no need to formulate in a complex carrier like Montanide or create an emulsion. Fourth, the bacteria are very stable, some more than 5 years, without worry of peptide degradation or breakdown product contamination that can lead to loss of potency of a peptide formulation.

The ADXS-HOT constructs disclosed herein utilize the Lm vector technology to target the specific epitopes (e.g., T cell epitopes) represented by multiple recurrent cancer mutations (e.g., shared tumor driver hotspot mutations) occurring in cancer-associated genes (e.g., key tumor driver genes). As an example, one Lm vector can be prepared that can cover the specific hotspot missense mutations that are found in the majority of patients who share a mutation in a specific tumor driver gene. This approach would allow a single product to represent the potential mutated epitopes that would be found in, for example, 90% or more (e.g., 98% or more) of patients who have an acquired mutation in a particular gene such as TP53, PIK3CA, or NRAS or KRAS. For example, mutated epitopes at 17 positions could cover >90% of the recurrent missense cancer mutations in TP53. Combining the majority of the potential mutations in a tumor driver gene into one product is possible because many of these mutations are shared by a significant proportion of cancer patients. As a result, the total spectrum of potential tumor driver gene missense mutations for solid tumors can be covered within the capacity of one Lm construct. This makes the Lm vector technology a highly efficient and adaptable technology for engineering "off the shelf" hotspot constructs to target common mutations.

As another example, one Lm vector can be prepared that can cover the specific hotspot missense mutations that are found in the majority of patients (or in a certain percentage of patients, such as at least 5%, 10%, 15%, 20%, 25%, 30%, 35%, 40%, 45%, or 50%) who have a specific type of cancer. This approach would allow a single product to represent the potential mutated epitopes that would be found in, for example, 50% or more of patients who have a particular type of cancer. Combining the majority of or a significant percentage of the potential mutations in a particular type of cancer into one product is possible because many of these mutations are shared by a significant proportion of cancer patients. As a result, the total spectrum of potential tumor driver gene missense mutations for solid tumors can be covered within the capacity of one Lm construct. This makes the Lm vector technology a highly efficient and adaptable technology for engineering "off the shelf" hotspot constructs to target common mutations.

ADXS-HOT constructs can be bioengineered to target the most common tumor driver hotspot mutations. These products can be manufactured and available immediately for a patient who is found through biomarker testing to carry a mutation included in the ADXS-HOT product's mutational coverage for a specific tumor driver gene. Likewise, these products can be manufactured and available immediately for a patient who is found through biomarker testing to carry a mutation included in the ADXS-HOT product's mutational coverage for two or more specific tumor driver genes. The presence of this mutation can be determined or confirmed for each patient by rapid PCR testing, Nanostring, DNA sequencing, RNA sequencing, or another diagnostic biomarker procedure, on a biopsy or archived tumor tissue or DNA or RNA sequencing information that may already exist. The ability to use biomarker test results to rapidly confirm eligibility facilitates a rapid delivery of the ADXS-HOT product directly to the patient and eliminates any waiting period needed to develop a customized treatment. Presence of hotspot mutations can be rapidly determined through biomarker testing, and "off the shelf" treatments can be initiated immediately. DNA sequencing is not required, and manufacture of a patient-specific product is not necessary. This "off the shelf" delivery of hotspot-targeted immunotherapies to qualified patients represents a significant therapeutic option in cancer treatment.

Design and use of heteroclitic sequences (i.e., sequence-optimized peptides) derived from tumor-associated antigen genes (e.g., from cancer testis antigens or oncofetal antigens) can increase presentation by MHC Class I alleles. Heteroclitic sequences have been shown to be sufficient to prime a T cell response, to overcome central tolerance, and to elicit a successful cross-reactive immune response to the wild-type peptide. Addition of heteroclitic epitopes to hotspot-targeted immunotherapies can complement the original hotspot mutation peptides in that total patient coverage within a cancer type can approach 100%. We therefore do not need to sequence a patient prior to treatment as we assume that they will express a tumor-associated antigen that we have designed heteroclitic peptides for to cover the most prevalent HLAs (HLA-A0201, HLA-A0301, HLA-A2402, and HLA-B0702).

Use of the minigene construct approach disclosed herein for the expression of specific MHC class I binding antigenic determinants allows for the highly efficient delivery of short peptide sequences to the antigen presentation pathway of professional antigen presenting cells (pAPC). A specific advantage of the minigene technology is that it bypasses the requirement for proteasome mediated degradation of larger proteins in order to liberate short peptide sequences that can be bound and presented on MHC class I molecules. This results in a much higher efficiency of peptide-MHC class I antigen presentation on the surface of the pAPC and, therefore, a much higher level of antigen expression for the priming of antigen specific T cell responses.

In some approaches disclosed herein, up to or more than four distinct attributes can be combined into a single, disease-specific, off-the-shelf product that maximizes target coverage and minimizes off-target toxicities. These attributes can include: attenuated *Listeria monocytogenes* (Lm) vectors, tLLO fusion proteins, hotspot mutations, and optimized peptides derived from cancer testis antigens (CTAs) or oncofetal antigens (OFAs). Lm in the body is actively taken up by antigen-presenting cells and moves into the cytoplasm; therefore, it is an ideal vector for the delivery of antigens to be presented through both the MHC I and II pathways. Lm also produces virulence factors which allow survival in the host cytosol and potently stimulate the immune system. These virulence factors can enhance the immunogenicity of tumor-associated antigens. Multiple plasmids within Lm can encode for expression of tumor-associated antigen fusion proteins (e.g., tLLO fusion proteins) inside antigen-presenting cells, which triggers a powerful CD8+ T cell response along the MHC I pathway. The Lm and tLLO fusion protein can also neutralize the regulatory T cells and MDSCs protecting the tumor, increasing CD8+ T cell efficacy. Having multiple copies of plasmids within the Lm increases antigen presentation and tumor microenvironment effects. The fusion protein can include hotspot peptides and/or sequence-optimized peptides (i.e., peptides with heteroclitic mutations) derived, for example, from CTAs or OFAs. Hotspot mutations are high-value targets against tumor drivers, and targeting them can generate a strong immune response and inhibit tumor proliferation. Incorporating multiple hotspot mutation peptides broadens the patient coverage in the targeted diseases. Hotspots are somatic mutations frequently observed in multiple patients, often in tumor driver genes contributing to oncogenesis. These hotspot mutations represent a source of "shared" or "public" antigens. Hotspots targets in the constructs described herein can be designed to generate epitopes to virtually any of the 12,500+ identified HLA Class I alleles and can be prioritized agnostic to in silico algorithms. OFAs and CTAs are expressed in up to 100% of patients within a cancer indication, but are not expressed in healthy tissue of adults (e.g., normally expressed only in embryonic tissues). Many OFAs/CTAs have primary roles in oncogenesis. Because of OFA/CTAs highly restricted tissue expression in cancer, they are attractive targets for immunotherapy. Adding multiple sequence-optimized, proprietary immunogenic OFA/CTA peptides or tumor-associated antigen peptides (i.e., sequence-optimized to improve immunogenicity) provides additional targets capable of generating strong T cell responses. In combination, these components take advantage of somatic mutations, cancer testis antigens, and oncofetal antigens more capable of generating potent, tumor specific, high strength (avidity) T cells to kill tumor cells than more traditional, over-expressed, native-sequence tumor-associated antigens. Most hotspot mutations and OFA/CTA proteins play critical roles in oncogenesis. Targeting both at once could significantly impair cancer proliferation. Combining hotspot mutations with multiple OFA/CTAs peptides presents multiple high avidity targets in one treatment that are expressed in all patients with the target disease.

Patients with multiple mutations in cancer-associated genes (e.g., tumor driver genes) can be treated with a combination (e.g., a single dosing regimen consisting of two or more immunotherapies) targeting their particular mutated genes identified in biomarker testing, or, alternatively, a combination kit or panel (e.g., a single dosing regimen consisting of two or more immunotherapies) for their type of cancer can be used that covers mutated genes commonly found in patients with that disease (e.g., a lung adenocarcinoma panel, a colorectal cancer panel, and so forth). Patients with a particular type of cancer can then be treated with a fixed combination or panel of ADXS-HOT constructs targeting commonly observed mutated genes in that particular type of cancer. Alternatively, such patients can be treated with a single immunotherapy targeting their particular mutated genes identified in biomarker testing or a single immunotherapy specific for their type of cancer that covers mutated genes found in multiple different cancer-associated proteins found in patients with that disease. All patients with a given tumor type can be treated in the same way. For example, in certain diseases there are relatively few genes that carry mutations in a large percentage of patients. In these instances, for example, it may be more expeditious to give all patients with the same disease type the same combination of ADXS-HOT constructs. For example, 93% of ovarian cancer patients have a mutation in TP53, so there may be no need for a diagnostic test. In colorectal cancer (CRC), four tumor driver genes are mutated most frequently, and most patients will harbor more than one mutation in these four genes. A "standard" combination for CRC could include ADXS-HOT constructs for APC, TP53, PIK3CA, and RAS because tumor driver mutations in CRC include APC in 76% of patients, TP-53 in 52% of patients, RAS (KRAS/NRAS) in 52% of patients, and PIK3CA in 19% of patients. Alternatively, a "standard" for CRC could include a single ADXS-HOT construct including a set of the most common CRC mutations in APC, TP53, PIK3CA, and RAS. There is a great likelihood that most patients would express anywhere from 2-4 of these, so multiple recurrent cancer mutations would be targeted.

The ADXS-HOT immunotherapies disclosed herein have the potential to revolutionize the treatment of cancer by providing highly efficacious, targeted attacks on hotspots with little to no impact on healthy cells. Tumor immunotherapies take advantage of the most effective cancer-fighting agents that nature has devised: the host's own immune cells.

Tumor-specific antigens that arise as a consequence of tumor-specific mutations are important targets for effective cancer immunotherapy. The most effective and longest lasting responses to immunotherapy of cancer can be attributed to amplification of T cell responses against tumor-specific antigens or tumor-specific epitopes associated with mutations in the tumors. Furthermore, mutations in tumor driver genes are most often associated with loss of function or gain of function phenotypes that drive persistence or growth of cancer cells. Targeting these driver mutations specifically may offer the best chance for immunotherapy to inhibit disease progression and eliminate cancer cells without compromising normal cells. Although recurrent cancer mutations may or may not be included in a personalized treatment, the ADXS-HOT approach has inherent advantages over personalized, neoepitope-targeted, patient-specific products for the treatment of cancer. First, it targets what may be the most critical mutations associated with cancer growth. Second, targeting shared, recurrent cancer mutations allows the same product to be used for multiple patients. The capacity of Lm-LLO vectors allows coverage of nearly all of the mutations that may occur in a single gene-targeted product such that the product can treat nearly all patients who have any acquired mutation in a particular cancer-associated gene (e.g., tumor driver gene). ADXS-HOT constructs can be manufactured in bulk, and Lm-LLO products have shown good stability for 5 years or more. In addition, the ability to combine multiple constructs increases coverage. Finally, the ADXS-HOT are ready, on the shelf, and are available for patients to start treatment immediately but still target tumor-specific epitopes. Cost of goods can be kept low by making larger batches as opposed to a one-off per patient product. Product stability for previous LM-LLO constructs, for example, can exceed five years. Patients with advanced cancer may not be able to wait months to begin treatment with a personal neoepitope product, but by leveraging ADXS-HOT panels, treatment against tumor-specific epitopes can start almost immediately.

Multiple Lm-LLO constructs as disclosed herein that will have broad utility across multiple tumor types and multiple patients who share common mutations in tumor driver genes. The products target acquired recurrent cancer mutations that are shared by multiple patients and should have greater immunogenicity than the natural sequence peptide in normal cells, which is protected by tolerance. Mutations in P-53 and PI3 Kinase alone occur in over 50% of all cancer patients, and panels can be formed for major cancers as disclosed herein where hot-spot mutations in tumor driver genes are common.

Multiple ADXS-HOT constructs can be made to provide a "spice rack" approach, driven by biomarker testing determinations. Readily available rapid biomarker testing and/or RNA or DNA sequencing can determine the presence of a target for creation of a personalized medicine "kit" for individual patients. Disease-specific panels can target the majority of patients with a specific disease that share common mutations. Alternatively, a set combination can be given for certain disease types and will include mutations found in a majority of patients with a certain disease without the need for a diagnostic test.

Constructs can be used as a monotherapy, but the potential also exists to use ADXS-HOT constructs as part of a combination treatment regimen either as several individual hotspot products together or in combination with other therapeutic cancer treatments. As an example, where more than one gene is mutated in the same patient, the representative constructs for each gene can be mixed just before infusion. For example, if a patient is found to have missense mutations in hotspots for TP53, RAS, and BRAF, then these three ADXS-HOT products could be given in combination (ADXS-htTP53, ADXS-htRAS, and ADXS-htBRAF) as a treatment regimen. In addition, similar to other Lm constructs, hotspot treatments can be given in combination or sequentially with other cancer treatments like checkpoint inhibitors, costimulatory agonists, or radiation therapy. The reason for this is that animal models and early data from clinical trials have shown that Lm-LLO immunotherapies have the potential for significant synergy with active immunotherapy agents, particularly PD-1 and/or PD-L1 blocking antibodies.

For example, the combination of an Lm-LLO-based vaccine with anti-PD-1 antibody leads to increased antigen-specific immune responses and tumor-infiltrating CD8+ T cells, along with a decrease in immune suppressor cells (Tregs and MDSCs). The combination regimen led to synergistic activity, with significant inhibition of tumor growth and prolonged survival/complete regression of tumors in treated animals. The combination of an Lm-LLO-based vaccine with blocking of PD-1/PD-L1 can lead to overall enhancement of the efficacy of anti-tumor immunotherapy over either agent alone. It was also shown that in vitro infection with Lm results in significant upregulation of surface PD-L1 expression on human monocyte-derived dendritic cells, which suggests the translational capacity of this finding.

Preclinical data also suggests synergy with immune costimulatory agonists like Ox-40 and GITR (Mkrtichyan et al. (2013) *J Immunother Cancer* 1:15, doi: 10.1186/2051-1426-1-15, herein incorporated by reference in its entirety for all purposes). Synergy of Lm-LLO vectors with radiation therapy has been demonstrated in preclinical models (Hannan et al. (2012) *Cancer Immunol Immunother* 61(12):2227-2238, herein incorporated by reference in its entirety for all purposes) and has also been observed in ongoing veterinary trials in non-resected canine osteosarcoma. Lm treatments can also be given sequentially with chemotherapies provided there has been sufficient hematopoietic recovery. In addition, research to date shows there is no development of neutralizing antibodies with Lm vectors, so repeated treatments with a single Lm vector or simultaneous or sequential treatment with multiple vectors is possible.

II. Recombinant Fusion Polypeptides Comprising Recurrent Cancer Mutations

Disclosed herein are recombinant fusion polypeptides comprising a PEST-containing peptide fused to two or more antigenic peptides (i.e., in tandem, such as PEST-peptide1-peptide2), wherein each antigenic peptide comprises a single, recurrent cancer mutation (i.e., a single, recurrent change in the amino acid sequence of a protein, or a sequence encoded by a single, different, nonsynonymous, recurrent cancer mutation in a gene). Also disclosed herein are recombinant fusion polypeptides comprising a PEST-containing peptide fused to two or more antigenic peptides (i.e., in tandem, such as PEST-peptide1-peptide2), wherein each antigenic peptide comprises a single, recurrent cancer mutation (i.e., a single, recurrent change in the amino acid sequence of a protein, or a sequence encoded by a single, different, nonsynonymous, recurrent cancer mutation in a gene), and wherein at least two of the antigenic peptides comprise different recurrent cancer mutations and are fragments of the same cancer-associated protein. Alternatively, each of the antigenic peptides comprises a different recurrent cancer mutation from a different cancer-associated protein. Alternatively, a combination of separate fusion polypeptides can be used in which each antigenic peptide is fused to its own PEST-containing peptide (e.g., PEST1-peptide1; PEST2-peptide2). Optionally, some or all of the fragments are non-contiguous fragments of the same cancer-associated protein. Non-contiguous fragments are fragments that do not occur sequentially in a protein sequence (e.g., the first fragment consists of residues 10-30, and the second fragment consists of residues 100-120; or the first fragment consists of residues 10-30, and the second fragment consists of residues 20-40). Optionally, each of the antigenic peptides comprises a different recurrent cancer mutation from a single type of cancer. For example, the single type of cancer can be non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), or head and neck cancer.

Also disclosed herein are recombinant fusion polypeptides comprising two or more antigenic peptides, wherein each antigenic peptide comprises a single, recurrent cancer mutation (i.e., a single, recurrent change in the amino acid sequence of a protein, or a sequence encoded by a single, different, nonsynonymous, recurrent cancer mutation in a gene), and wherein the fusion polypeptide does not comprise a PEST-containing peptide. Also disclosed herein are recombinant fusion polypeptides comprising two or more antigenic peptides, wherein each antigenic peptide comprises a single, recurrent cancer mutation (i.e., a single, recurrent change in the amino acid sequence of a protein, or a sequence encoded by a single, different, nonsynonymous, recurrent cancer mutation in a gene), wherein at least two of the antigenic peptides comprise different recurrent cancer mutations and are fragments of the same cancer-associated protein, and wherein the fusion polypeptide does not comprise a PEST-containing peptide. Alternatively, each of the antigenic peptides comprises a different recurrent cancer mutation from a different cancer-associated protein. Optionally, some or all of the fragments are non-contiguous fragments of the same cancer-associated protein. Optionally, each of the antigenic peptides comprises a different recurrent cancer mutation from a single type of cancer. For example, the single type of cancer can be non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), or head and neck cancer.

Also provided herein are recombinant fusion polypeptides comprising from N-terminal end to C-terminal end a bacterial secretion sequence, a ubiquitin (Ub) protein, and two or more antigenic peptides (i.e., in tandem, such as Ub-peptide1-peptide2), wherein each antigenic peptide comprises a single, recurrent cancer mutation (i.e., a single, recurrent change in the amino acid sequence of a protein, or a sequence encoded by a single, different, nonsynonymous, recurrent cancer mutation in a gene), and wherein at least two of the antigenic peptides are fragments of the same cancer-associated protein. Alternatively, each of the antigenic peptides comprises a different recurrent cancer mutation from a different cancer-associated protein. Alternatively, a combination of separate fusion polypeptides can be used in which each antigenic peptide is fused to its own secretion sequence and Ub protein (e.g., Ub1-peptide1; Ub2-peptide2). Optionally, some or all of the fragments are non-contiguous fragments of the same cancer-associated protein. Optionally, each of the antigenic peptides comprises a different recurrent cancer mutation from a single type of cancer. For example, the single type of cancer can be non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), or head and neck cancer.

Nucleic acids (termed minigene constructs) encoding such recombinant fusion polypeptides are also disclosed. Such minigene nucleic acid constructs can further comprise two or more open reading frames linked by a Shine-Dalgarno ribosome binding site nucleic acid sequence between each open reading frame. For example, a minigene nucleic acid construct can further comprise two to four open reading frames linked by a Shine-Dalgarno ribosome binding site nucleic acid sequence between each open reading frame. Each open reading frame can encode a different polypeptide. In some nucleic acid constructs, the codon encoding the carboxy terminus of the fusion polypeptide is followed by two stop codons to ensure termination of protein synthesis.

The bacterial signal sequence can be a Listerial signal sequence, such as an Hly or an ActA signal sequence, or any other known signal sequence. In other cases, the signal sequence can be an LLO signal sequence. The signal sequence can be bacterial, can be native to a host bacterium (e.g., *Listeria monocytogenes*, such as a secAl signal peptide), or can be foreign to a host bacterium. Specific examples of signal peptides include an Usp45 signal peptide from *Lactococcus lactis*, a Protective Antigen signal peptide from *Bacillus anthracis*, a secA2 signal peptide such the p60 signal peptide from *Listeria monocytogenes*, and a Tat signal peptide such as a *B. subtilis* Tat signal peptide (e.g., PhoD). In specific examples, the secretion signal sequence is from a *Listeria* protein, such as an $ActA_{300}$ secretion signal or an $ActA_{100}$ secretion signal.

The ubiquitin can be, for example, a full-length protein. The ubiquitin expressed from the nucleic acid construct provided herein can be cleaved at the carboxy terminus from the rest of the recombinant fusion polypeptide expressed from the nucleic acid construct through the action of hydrolases upon entry to the host cell cytosol. This liberates the amino terminus of the fusion polypeptide, producing a peptide in the host cell cytosol.

Selection of, variations of, and arrangement of antigenic peptides within a fusion polypeptide are discussed in detail elsewhere herein, and cancer-associated proteins are discussed in more detail elsewhere herein.

The recombinant fusion polypeptides can comprise one or more tags. For example, the recombinant fusion polypeptides can comprise one or more peptide tags N-terminal and/or C-terminal to the combination of the two or more antigenic peptides. A tag can be fused directly to an antigenic peptide or linked to an antigenic peptide via a linker (examples of which are disclosed elsewhere herein). Examples of tags include the following: FLAG tag, 2×FLAG tag 3×FLAG tag; His tag, 6×His tag; and SIINFEKL (SEQ ID NO: 1007) tag. An exemplary SIINFEKL tag is set forth in SEQ ID NO: 293 (encoded by any one of the nucleic acids set forth in SEQ ID NOS: 278-292). Another exemplary SIINFEKL tag is set forth in SEQ ID NO: 922. An exemplary 3×FLAG tag is set forth in SEQ ID NO: 309 (encoded by any one of the nucleic acids set forth in SEQ ID NOS: 294-308). Another exemplary FLAG tag is set forth in SEQ ID NO: 762. Two or more flags can be used together, such as a 2×FLAG tag and a SIINFEKL (SEQ ID NO: 1007) tag, a 3×FLAG tag and a SIINFEKL (SEQ ID NO: 1007) tag, or a 6×His tag and a SIINFEKL (SEQ ID NO: 1007) tag. If two or more tags are used, they can be located anywhere within the recombinant fusion polypeptide and in any order. For example, the two tags can be at the C-terminus of the recombinant fusion polypeptide, the two tags can be at the N-terminus of the recombinant fusion polypeptide, the two tags can be located internally within the recombinant fusion polypeptide, one tag can be at the C-terminus and one tag at the N-terminus of the recombinant fusion polypeptide, one tag can be at the C-terminus and one internally within the recombinant fusion polypeptide, or one tag can be at the N-terminus and one internally within the recombinant fusion polypeptide. Other tags include chitin binding protein (CBP), maltose binding protein (MBP), glutathione-S-transferase (GST), thioredoxin (TRX), and poly(NANP). Particular recombinant fusion polypeptides comprise a C-terminal SIINFEKL (SEQ ID NO: 1007) tag. Such tags can allow for easy detection of the recombinant fusion protein, confirmation of secretion of the recombinant fusion protein, or for following the immunogenicity of the secreted fusion polypeptide by following immune responses to these "tag" sequence peptides. Such immune response can be monitored using a number of reagents including, for example, monoclonal antibodies and DNA or RNA probes specific for these tags.

The recombinant fusion polypeptides disclosed herein can be expressed by recombinant *Listeria* strains or can be expressed and isolated from other vectors and cell systems used for protein expression and isolation. Recombinant *Listeria* strains comprising expressing such antigenic peptides can be used, for example in immunogenic compositions comprising such recombinant *Listeria* and in vaccines comprising the recombinant *Listeria* strain and an adjuvant. Expression of one or more antigenic peptides as a fusion polypeptides with a nonhemolytic truncated form of LLO, ActA, or a PEST-like sequence in host cell systems in *Listeria* strains and host cell systems other than *Listeria* can result in enhanced immunogenicity of the antigenic peptides.

The recombinant fusion polypeptide can be any molecular weight. For example, the recombinant fusion polypeptide can be less than or no more than about 200, 195, 190, 185, 180, 175, 170, 165, 160, 155, 150, 145, 140, 135, 130, or 125 kilodaltons (kDa). In a specific example, the recombinant fusion polypeptide is less than or no more than about 150 kDa or less than or no more than about 130 kDa. As another example the recombinant fusion polypeptide can be between about 50-200, 50-195, 50-190, 50-185, 50-180, 50-175, 50-170, 50-165, 50-160, 50-155, 50-150, 50-145, 50-140, 50-135, 50-130, 50-125, 100-200, 100-195, 100-190, 100-185, 100-180, 100-175, 100-170, 100-165, 100-160, 100-155, 100-150, 100-145, 100-140, 100-135, 100-130, or 100-125 kDa. In a specific example, the recombinant fusion polypeptide is between about 50-150, 100-150, 50-125, or 100-125 kDa. As another example, the recombinant fusion polypeptide can be at least about 50, 55, 60, 65, 70, 75, 80, 85, 90, 95, 100, 105, 110, 115, 120, or 125 kDa. As a specific example, the recombinant fusion polypeptide can be at least about 100 kDa.

Nucleic acids encoding such recombinant fusion polypeptides are also disclosed. The nucleic acid can be in any form. The nucleic acid can comprise or consist of DNA or RNA, and can be single-stranded or double-stranded. The nucleic acid can be in the form of a plasmid, such as an episomal plasmid, a multicopy episomal plasmid, or an integrative plasmid. Alternatively, the nucleic acid can be in the form of a viral vector, a phage vector, or in a bacterial artificial chromosome. Such nucleic acids can have one open reading frame or can have two or more open reading frames (e.g., an open reading frame encoding the recombinant fusion polypeptide and a second open reading frame encoding a metabolic enzyme). In one example, such nucleic acids can comprise two or more open reading frames linked by a Shine-Dalgarno ribosome binding site nucleic acid sequence between each open reading frame. For example, a nucleic acid can comprise two to four open reading frames linked by a Shine-Dalgarno ribosome binding site nucleic acid sequence between each open reading frame. Each open reading frame can encode a different polypeptide. In some nucleic acids, the codon encoding the carboxy terminus of the fusion polypeptide is followed by two stop codons to ensure termination of protein synthesis.

A. Antigenic Peptides

Each antigenic peptide can be a fragment of a cancer-associated protein (i.e., a contiguous sequence of amino acids from a cancer-associated protein). Each antigenic peptide can be of any length sufficient to induce an immune response, and each antigenic peptide can be the same length or the antigenic peptides can have different lengths. For example, an antigenic peptide disclosed herein can be 5-200, 5-100, 7-200, 7-100, 15-50, or 21-27 amino acids in length, or 15-100, 15-95, 15-90, 15-85, 15-80, 15-75, 15-70, 15-65, 15-60, 15-55, 15-50, 15-45, 15-40, 15-35, 15-30, 20-100, 20-95, 20-90, 20-85, 20-80, 20-75, 20-70, 20-65, 20-60, 20-55, 20-50, 20-45, 20-40, 20-35, 20-30, 11-21, 15-21, 21-31, 31-41, 41-51, 51-61, 61-71, 71-81, 81-91, 91-101, 101-121, 121-141, 141-161, 161-181, 181-201, 8-27, 10-30, 10-40, 15-30, 15-40, 15-25, 1-10, 10-20, 20-30, 30-40, 1-100, 5-75, 5-50, 5-40, 5-30, 5-20, 5-15, 5-10, 1-75, 1-50, 1-40, 1-30, 1-20, 1-15, 1-10, 8-11, or 11-16 amino acids in length. For example, an antigenic peptide can be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids in length. Some specific examples of antigenic peptides are 21 or 27 amino acids in length.

Each antigenic peptide can also be hydrophilic or can score up to or below a certain hydropathy threshold, which can be predictive of secretability in *Listeria monocytogenes* or another bacteria of interest. For example, antigenic peptides can be scored by a Kyte and Doolittle hydropathy index 21 amino acid window, and all scoring above a cutoff (around 1.6) can be excluded as they are unlikely to be secretable by *Listeria monocytogenes*.

Each antigenic peptide can comprise a single recurrent cancer mutation or can comprise two or more recurrent cancer mutations (e.g., two recurrent cancer mutations). For example, an antigenic peptide can comprise more than one recurrent cancer mutation (e.g., 2 or 3 recurrent cancer mutations) because of the close proximity of the mutated residues to each other in the cancer-associated protein. The recurrent cancer mutations can be any type of mutation (e.g., somatic missense mutation or frameshift mutation). The recurrent cancer mutation in each antigenic peptide can be flanked on each side by an equal number of amino acids, or can be flanked on each side by a different number of amino acids (e.g., with 9 amino acids flanking N-terminal and 10 amino acids flanking C-terminal, or with 10 amino acids flanking N-terminal and 13 amino acids flanking C-terminal). The flanking sequence on each side of the recurrent cancer mutation can be the sequence that naturally flanks the mutation in the cancer-associated protein. For example, the recurrent cancer mutation in an antigenic peptide can be flanked on each side by an equal number of amino acids, wherein the flanking sequence is identical to the sequences that naturally flanks the recurrent cancer mutation in the cancer-associated protein. The number of flanking amino acids on each side of the recurrent cancer mutation can be any length, such as 5-30 amino acids flanking each side. As one example, the recurrent cancer mutation can be flanked on each side by at least 5, 6, 7, 8, 9, 10, 11, 12, 13, 14, 15, 16, 17, 18, 19, 20, 21, 22, 23, 24, 25, 30, 35, 40, 45, or 50 amino acids (e.g., by at least 10 amino acids or by at least 13 amino acids). Preferably, at least about 10 flanking amino acids on each side of the detected recurrent cancer mutation are incorporated to accommodate class 1 MHC-1 presentation, in order to provide at least some of the different HLA T-cell receptor (TCR) reading frames, or at least about 13 flanking amino acids on each side of the detected recurrent cancer mutation are incorporated to accommodate class 2 MHC-2 presentation, in order to provide at least some of the different HLA T-cell receptor (TCR) reading frames for CD4+ T cell antigen presentation. However, this does not necessarily need to be the case, and in some cases may not be possible (e.g., if a recurrent cancer mutation occurs in the first 10 amino acids of a protein or the last 10 amino acids of a protein). In some cases, the location of the recurrent cancer mutation in the cancer-associated protein may dictate how many amino acids are flanking on one particular side (e.g., if the mutation is in the first 10 amino acids of the protein or the last 10 amino acids of the protein). In the case of a frameshift mutation, any number of predicted amino acids downstream of the frameshift mutation can be included. For example, all of the predicted amino acids downstream of the frameshift mutation can be included.

The antigenic peptides can be linked together in any manner. For example, the antigenic peptides can be fused directly to each other with no intervening sequence. Alternatively, the antigenic peptides can be linked to each other indirectly via one or more linkers, such as peptide linkers. In some cases, some pairs of adjacent antigenic peptides can be fused directly to each other, and other pairs of antigenic peptides can be linked to each other indirectly via one or more linkers. The same linker can be used between each pair of adjacent antigenic peptides, or any number of different linkers can be used between different pairs of adjacent antigenic peptides. In addition, one linker can be used between a pair of adjacent antigenic peptides, or multiple linkers can be used between a pair of adjacent antigenic peptides.

Any suitable sequence can be used for a peptide linker. As an example, a linker sequence may be, for example, from 1 to about 50 amino acids in length. Some linkers may be hydrophilic. The linkers can serve varying purposes. For example, the linkers can serve to increase bacterial secretion, to facilitate antigen processing, to increase flexibility of the fusion polypeptide, to increase rigidity of the fusion polypeptide, or any other purpose. As a specific example, one or more or all of a flexibility linker, a rigidity linker, and an immunoproteasome processing linker can be used. Examples of such linkers are provided below. In some cases, different amino acid linker sequences are distributed between the antigenic peptides or different nucleic acids encoding the same amino acid linker sequence are distributed between the antigenic peptides (e.g., SEQ ID NOS: 572-582) in order to minimize repeats. This can also serve to reduce secondary structures, thereby allowing efficient transcription, translation, secretion, maintenance, or stabilization of the nucleic acid (e.g., plasmid) encoding the fusion polypeptide within a Lm recombinant vector strain population. Other suitable peptide linker sequences may be chosen, for example, based on one or more of the following factors: (1) their ability to adopt a flexible extended conformation; (2) their inability to adopt a secondary structure that could interact with functional epitopes on the antigenic peptides; and (3) the lack of hydrophobic or charged residues that might react with the functional epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in Maratea et al. (1985) *Gene* 40:39-46; Murphy et al. (1986) *Proc Natl Acad Sci USA* 83:8258-8262; U.S. Pat. Nos. 4,935,233; and 4,751,180, each of which is herein incorporated by reference in its entirety for all purposes. Specific examples of linkers include those in the following table (each of which can be used by itself as a linker, in a linker comprising repeats of the sequence, or in a linker further comprising one or more of the other sequences in the table), although others can also be envisioned (see, e.g., Reddy Chichili et al. (2013) *Protein Science* 22:153-167, herein incorporated by reference in its entirety for all purposes). Unless specified, "n" represents an undetermined number of repeats in the listed linker.

| Peptide Linker | SEQ ID NO: | Purpose |
| --- | --- | --- |
| AAY | N/A | Immunoproteasome Processing |
| GGS | N/A | Flexibility |
| (GAS)$_n$ | N/A | Flexibility |
| (GSA)$_n$ | N/A | Flexibility |
| (G)$_n$; n = 4-8 | N/A | Flexibility |
| (GGGGS)$_n$; n = 1-3 | 313 | Flexibility |
| VGKGGSGG | 314 | Flexibility |
| (PAPAP)$_n$ | 315 | Rigidity |
| (EAAAK)$_n$; n = 1-3 | 316 | Rigidity |
| (AYL)$_n$ | N/A | Antigen Processing |
| (LRA)$_n$ | N/A | Antigen Processing |
| (RLRA)$_n$ | 319 | Antigen Processing |
| ADLVVG | 821 | Immunoproteasome Processing |
| ADLIEATAEEVL | 822 | Immunoproteasome Processing |
| GDGSIVSLAKTA | 823 | Immunoproteasome Processing |
| RDGSVADLAKVA | 824 | Immunoproteasome Processing |
| ADGSVKTLSKVL | 825 | Immunoproteasome Processing |
| GDGSIVDGSKEL | 826 | Immunoproteasome Processing |
| GDGSIKTAVKSL | 827 | Immunoproteasome Processing |
| ADLSVATLAKSL | 828 | Immunoproteasome Processing |
| ADLAVKTLAKVL | 829 | Immunoproteasome Processing |

The VGKGGSGG linker (SEQ ID NO: 314) can be used, for example, as a longer linker after the tLLO and also before the tag sequences to provide additional space between the tLLO and the antigenic portion of the fusion peptide and before the tag sequences. It also can provide flexibility and to charge balance the fusion protein. The EAAAK linker (SEQ ID NO: 316) is a rigid/stiff linker that can be used to facilitate expression and secretion, for example, if the fusion protein would otherwise fold on itself. The GGGGS linker (SEQ ID NO: 313) is a flexible linker that can be used, for example, to add increased flexibility to the fusion protein to help facilitate expression and secretion. The "i20" linkers (e.g., SEQ ID NOS: 821-829) are immunoproteasome linkers that are designed, for example, to help facilitate cleavage of the fusion protein by the immunoproteasome and increase the frequency of obtaining the exact minimal binding fragment that is desired. Combinations of GGGGS and EAAAK linkers (SEQ ID NOS: 313 and 316, respectively) can be used, for example, to alternate flexibility and rigidity to help balance the construct for improved expression and secretion and to help facilitate DNA synthesis by providing more unique codons to choose from.

The fusion polypeptide can comprise any number of antigenic peptides. In some cases, the fusion polypeptide comprises any number of antigenic peptides such that the fusion polypeptide is able to be produced and secreted from a recombinant *Listeria* strain. For example, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 antigenic peptides, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 antigenic polypeptides. In another example, the fusion polypeptide can include a single antigenic peptide. In another example, the fusion polypeptide can include a number of antigenic peptides ranging from about 1-100, 1-5, 5-10, 10-15, 15-20, 10-20, 20-30, 30-40, 40-50, 50-60, 60-70, 70-80, 80-90, 90-100, 5-15, 5-20, 5-25, 15-20, 15-25, 15-30, 15-35, 20-25, 20-35, 20-45, 30-45, 30-55, 40-55, 40-65, 50-65, 50-75, 60-75, 60-85, 70-85, 70-95, 80-95, 80-105, 95-105, 50-100, 1-100, 5-100, 5-75, 5-50, 5-40, 5-30, 5-20, 5-15, 5-10, 1-100, 1-75, 1-50, 1-40, 1-30, 1-20, 1-15, or 1-10 antigenic peptides. In another example, the fusion polypeptide can include up to about 100, 10, 20, 30, 40, or 50 antigenic peptides. In another example, the fusion polypeptide can comprise about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 antigenic peptides. In another example, the fusion polypeptide can comprise at least about 5, 6, 7, 8, 9, 10, 11, 12, 13, 14, 15, 16, 17, 18, 19, 20, 21, 22, 23, 24, or 25 antigenic peptides or between about 5-50, 10-40, or 20-30 antigenic peptides.

In addition, the fusion polypeptide can comprise any number of antigenic peptides from the same cancer-associated protein (i.e., any number of non-contiguous fragments from the same cancer-associated protein). Alternatively, the fusion polypeptide can comprise any number of antigenic peptides from two or more different cancer-associated proteins, such as from 2, 3, 4, 5, 6, 7, 8, 9, or 10 cancer-associated proteins. For example, the two or more cancer-associated proteins can be about 2-30, about 2-25, about 2-20, about 2-15, or about 2-10 cancer-associated proteins. For example, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 antigenic peptides from the same cancer-associated protein, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 antigenic polypeptides from the same cancer-associated protein. Likewise, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 antigenic peptides from the same cancer-associated protein, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 antigenic polypeptides from two or more different cancer-associated proteins. In addition, the fusion polypeptide can comprise any number of non-contiguous antigenic peptides from the same cancer-associated protein (i.e., any number of non-contiguous fragments from the same cancer-associated protein). For example, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 non-contiguous antigenic peptides from the same cancer-associated protein, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 non-contiguous antigenic polypeptides from the same cancer-associated protein. In some cases, at least 50%, 55%, 60%, 65%, 70%, 75%, 80%, 85%, 90%, 95%, 96%, 97%, 98%, 99%, or all of the antigenic peptides are non-contiguous antigenic peptides from the same cancer-associated protein, or at least 50%, 55%, 60%, 65%, 70%, 75%, 80%, 85%, 90%, 95%, 96%, 97%, 98%, 99%, or all of the antigenic peptides that are from a single cancer-associated protein are non-contiguous antigenic peptides from that cancer-associated protein.

Each antigenic peptide can comprise a different (i.e., unique) recurrent cancer mutation. Alternatively, two or more of the antigenic peptides in the fusion polypeptide can comprise the same recurrent cancer mutation. For example, two or more copies of the same antigenic polypeptide can be included in the fusion polypeptide (i.e., the fusion polypeptide comprises two or more copies of the same antigenic peptide). In some fusion polypeptides, at least 50%, 55%, 60%, 65%, 70%, 75%, 80%, 85%, 90%, 95%, 96%, 97%, 98%, or 99% of the antigenic peptides comprise a different (i.e., unique) recurrent cancer mutation that is not present in any of the other antigenic peptides.

In some cases, at least two of the antigenic peptides can comprise overlapping fragments of the same cancer-associated protein. Likewise, the recurrent cancer mutations in at least two of the antigenic peptides can be recurrent cancer mutations that do not occur naturally together in the same subject. For example, two or more of the antigenic peptides can comprise different recurrent cancer mutations at the same amino acid residue of the cancer-associated protein (e.g., R248L, R248Q, and R248W in the protein encoded by TP53).

Some antigenic peptides can comprise at least two different recurrent cancer mutations, at least three different recurrent cancer mutations, or at least four different recurrent cancer mutations.

Any combination of recurrent cancer mutations can be included in the fusion polypeptide. Each of the recurrent cancer mutations can be a somatic missense mutation, or the recurrent cancer mutations can comprise other mutations as well. For example, in some fusion polypeptides, at least 50%, 55%, 60%, 65%, 70%, 75%, 80%, 85%, 90%, 95%, 96%, 97%, 98%, or 99% of the recurrent cancer mutations are somatic missense mutations. As one example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent cancer mutations in the cancer-associated protein. For example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent somatic missense cancer mutations in the cancer-associated protein. As another example, at least 50%, 60%, 70%, 80%, 90%, 95%, 96%, 97%, 98%, or 99% of cancer patients with a mutation in the cancer-associated protein have a recurrent cancer mutation in the cancer-associated protein that is included in the combination of antigenic peptides in the fusion polypeptide. For example, at least 50%, 60%, 70%, 80%, 90%, 95%, 96%, 97%, 98%, or 99% of cancer patients with a somatic missense mutation in the cancer-associated protein have a recurrent cancer mutation in the cancer-associated protein that is included in the combination of antigenic peptides in the fusion polypeptide. As another example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent cancer mutations or most common recurrent somatic missense cancer mutations in a particular type of cancer. As another example, at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of cancer patients with a particular type of cancer have a recurrent cancer mutation that is included in the combination of antigenic peptides in the fusion polypeptide (or in a combination of two or more fusion polypeptides). For example, at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of cancer patients with particular type of cancer have a recurrent cancer mutation that is included in the combination of antigenic peptides in the fusion polypeptide (or in a combination of two or more fusion polypeptides). In a particular example, the antigenic peptides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 different recurrent cancer mutations or different recurrent somatic missense mutations from the same type of cancer, or the antigenic peptides comprise 2-80, 10-60, 10-50, 10-40, or 10-30 different recurrent cancer mutations or different recurrent somatic missense mutations from a single type of cancer. For example, the single type of cancer can be non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), or head and neck cancer.

Each of the antigenic peptides in the fusion polypeptide can comprise a recurrent cancer mutation from the same cancer-associated protein, or the combination of antigenic peptides in the fusion polypeptide can comprise recurrent cancer mutations from two or more cancer-associated proteins. For example, the fusion polypeptide can comprise recurrent cancer mutations from at least 2, 3, 4, 5, 6, 7, 8, 9, 10, 11, 12, 13, 14, 15, 16, 17, 18, 19, or 20 cancer-associated proteins, or 2-5, 5-10, 10-15, or 15-20 cancer-associated proteins. For example, the two or more cancer-associated proteins can be about 2-30, about 2-25, about 2-20, about 2-15, or about 2-10 cancer-associated proteins. In one example, at least 50%, 55%, 60%, 65%, 70%, 75%, 80%, 85%, 90%, 95%, 96%, 97%, 98%, or 99% of the antigenic peptides comprise a recurrent cancer mutation from the same cancer-associated protein. In another example, none of the antigenic peptides comprise a recurrent cancer mutation from the same cancer-associated protein.

Exemplary sequences of antigenic peptides are disclosed elsewhere herein. As an example, an antigenic peptide can comprise, consist essentially of, or consist of a sequence at least 85%, 90%, 91%, 92%, 93%, 94%, 95%, 96%, 97%, 98%, 99%, or 100% identical to any of the antigenic peptide sequences disclosed herein.

B. Cancer-Associated Proteins and Recurrent Cancer Mutations

The fusion polypeptides disclosed herein comprise antigenic peptides comprising recurrent cancer mutations from cancer-associated proteins. Any combination of recurrent cancer mutations disclosed herein can be included in a fusion polypeptide. The term "cancer-associated protein" includes proteins having mutations that occur in multiple types of cancer, that occur in multiple subjects having a particular type of cancer, or that are correlated with the occurrence or progression of one or more types of cancer. For example, a cancer-associated protein can be an oncogenic protein (i.e., a protein with activity that can contribute to cancer progression, such as proteins that regulate cell growth), or it can be a tumor-suppressor protein (i.e., a protein that typically acts to alleviate the potential for cancer formation, such as through negative regulation of the cell cycle or by promoting apoptosis). Preferably, a cancer-associated protein has a "mutational hotspot." A mutational hotspot is an amino acid position in a protein-coding gene that is mutated (preferably by somatic substitutions rather than other somatic abnormalities, such as translocations, amplifications, and deletions) more frequently than would be expected in the absence of selection. Such hotspot mutations can occur across multiple types of cancer and/or can be shared among multiple cancer patients. Mutational hotspots indicate selective pressure across a population of tumor samples. Tumor genomes contain recurrent cancer mutations that "drive" tumorigenesis by affecting genes (i.e., tumor driver genes) that confer selective growth advantages to the tumor cells upon alteration. Such tumor driver genes can be identified, for example, by identifying genes that are mutated more frequently than expected from the background mutation rate (i.e., recurrence); by identifying genes that exhibit other signals of positive selection across tumor samples (e.g., a high rate of non-silent mutations compared to silent mutations, or a bias towards the accumulation of functional mutations); by exploiting the tendency to sustain mutations in certain regions of the protein sequence based on the knowledge that whereas inactivating mutations are distributed along the sequence of the protein, gain-of-function mutations tend to occur specifically in particular residues or domains; or by exploiting the overrepresentation of mutations in specific functional residues, such as phosphorylation sites. Many of these mutations frequently occur in the functional regions of biologically active proteins (for example, kinase domains or binding domains) or interrupt active sites (for example, phosphorylation sites) resulting in loss-of-function or gain-of-function mutations, or they can occur in such a way that the three-dimensional structure and/or charge balance of the protein is perturbed sufficiently to interfere with normal function. Genomic analysis of large numbers of tumors reveals that mutations often occur at a limited number of amino acid positions. Therefore, a majority of the common mutations can be represented by a relatively small number of potential tumor-associated antigens or T cell epitopes.

For example, the cancer-associated protein can be any one of the following:

| Gene | Protein | UniProt |
| --- | --- | --- |
| BRAF (BRAF1, RAFB1) | Serine/threonine-protein kinase B-raf | P15056 |
| EGFR (ERBB, ERBB1, HER1) | Epidermal growth factor receptor | P00533 |
| PIK3CA | Phosphatidylinositol 4,5-bisphosphate 3-kinase catalytic subunit alpha isoform | P42336 |
| PIK3R1 (GRB1) | Phosphatidylinositol 3-kinase regulatory subunit alpha | P27986 |
| PTEN (MMAC1, TEP1) | Phosphatidylinositol 3,4,5-trisphosphate 3-phosphatase and dual-specificity protein phosphatase PTEN | P60484 |
| NRAS | GTPase NRas | P01111 |
| KRAS (KRAS2, RASK2) | GTPase KRas | P01116 |
| HRAS | GTPase HRas | P01112 |
| TP53 (P53) | Cellular tumor antigen p53 | P04637 |

-continued

| Gene | Protein | UniProt |
|---|---|---|
| APC (DP2.5) | Adenomatous polyposis coli protein | P25054 |
| FBXW7 (FBW7, FBX30, SEL10) | F-box/WD repeat-containing protein 7 | Q969H0 |
| KEAP1 (INRF2, KIAA0132, KLHL19) | Kelch-like ECH-associated protein 1 | Q14145 |
| STK11 (LKB1, PJS) | Serine/threonine-protein kinase STK11 | Q15831 |
| NF1 | Neurofibromin | P21359 |
| KMT2D (ALR, MLL2, MLL4) | Histone-lysine N-methyltransferase 2D | O14686 |
| CDKN2A (CDKN2, MTS1) | Cyclin-dependent kinase inhibitor 2A | P42771 |
| NFE2L2 (NRF2) | Nuclear factor erythroid 2-related factor 2 | Q16236 |
| SPOP | Speckle-type POZ protein | O43791 |
| GATA3 | Trans-acting T-cell-specific transcription factor GATA-3 | P23771 |
| AKT1 (PKB, RAC) | RAC-alpha serine/threonine-protein kinase | P31749 |
| MAP3K1 (MAPKKK1, MEKK, MEKK1) | Mitogen-activated protein kinase kinase kinase 1 | Q13233 |
| MAP2K4 (JNKK1, MEK4, MKK4, PRKMK4, SEK1, SERK1, SKK1) | Dual specificity mitogen-activated protein kinase kinase 4 | P45985 |
| CTNNB1 (TNNB, OK/SW-cl.35, PRO2286) | Catenin beta-1 | P35222 |
| ERBB2 (HER2, MLN19, NEU, NGL) | Receptor tyrosine-protein kinase erbB-2 | P04626 |
| SF3B1 (SAP155) | Splicing factor 3B subunit 1 | O75533 |
| SMAD4 (DPC4, MADH4) | Mothers against decapentaplegic homolog 4 | Q13485 |
| PTPN11 (PTP2C, SHPTP2) | Tyrosine-protein phosphatase non-receptor type 11 | Q06124 |
| U2AF1 (U2AF35, U2AFBP, FP793) | Splicing factor U2AF 35 kDa subunit | Q01081 |
| ERBB3 (HER3) | Receptor tyrosine-protein kinase erbB-3 | P21860 |
| FGFR3 (JTK4) | Fibroblast growth factor receptor 3 | P22607 |
| ARID1A (BAF250, BAF250A, C1orf4, OSA1, SMARCF1) | AT-rich interactive domain-containing protein 1A | O14497 |
| MAP2K1 (MEK1, PRKMK1) | Dual specificity mitogen-activated protein kinase kinase 1 | Q02750 |
| FGFR2 (BEK, KGFR, KSAM) | Fibroblast growth factor receptor 2 | P21802 |
| RHOA (ARH12, ARHA, RHO12) | Transforming protein RhoA | P61586 |
| MTOR (FRAP, FRAP1, FRAP2, RAFT1, RAPT1) | Serine/threonine-protein kinase mTOR | P42345 |
| BCL2L12 (BPR) | Bcl-2-like protein 12 | Q9HB09 |
| RAC1 (TC25, MIG5) | Ras-related C3 botulinum toxin substrate 1 | P63000 |
| IDH2 | Isocitrate dehydrogenase [NADP], mitochondrial | P48735 |
| H3F3A (H3.3A, H3F3, PP781) | Histone H3.3 | P84243 |
| PPP2R1A | Serine/threonine-protein phosphatase 2A 65 kDa regulatory subunit A alpha isoform | P30153 |
| POLE (POLE1) | DNA polymerase epsilon catalytic subunit A | Q07864 |
| ATM | Serine-protein kinase ATM | Q13315 |
| EP300 (P300) | Histone acetyltransferase p300 | Q09472 |
| ALK | ALK tyrosine kinase receptor | Q9UM73 |
| RQCD1 (CNOT9, RCD1) | Cell differentiation protein RCD1 homolog | Q92600 |
| GPRIN2 (KIAA0514) | G protein-regulated inducer of neurite outgrowth 2 | O60269 |
| THSD7B (KIAA1679) | Thrombospondin type-1 domain-containing protein 7B | Q9C0I4 |
| CDK4 | Cyclin-dependent kinase 4 | P11802 |
| NUP93 (KIAA0095) | Nuclear pore complex protein Nup93 | Q8N1F7 |

| Gene | Protein | UniProt |
| --- | --- | --- |
| CCND1 (BCL1, PRAD1) | G1/S-specific cyclin-D1 | P24385 |
| FGFR1 (BFGFR, CEK, FGFBR, FLG, FLT2, HBGFR) | Fibroblast growth factor receptor 1 | P11362 |
| MAX (BHLHD4) | Protein max | P61244 |
| VHL | Von Hippel-Lindau disease tumor suppressor | P40337 |
| ACVR1 (ACVRLK2) | Activin receptor type-1 | Q04771 |
| MEF2A (MEF) | Myocyte-specific enhancer factor 2A | Q02078 |
| MYC (BHLHE39) | Myc proto-oncogene protein | P01106 |
| FRMD6 (C14orf31) | FERM domain-containing protein 6 | Q96NE9 |
| SRC (SRC1) | Proto-oncogene tyrosine-protein kinase Src | P12931 |
| KIT (SCFR) | Mast/stem cell growth factor receptor Kit | P10721 |
| KMT2C (HALR, KIAA1506, MLL3) | Histone-lysine N-methyltransferase 2C | Q8NEZ4 |
| FAT1 (CDHF7, FAT) | Protocadherin Fat 1 | Q14517 |
| PBRM1 (BAF180, PB1) | Protein polybromo-1 | Q86U86 |
| SETD2 (HIF1, HYPB, KIAA1732, KMT3A, SET2, HSPC069) | Histone-lysine N-methyltransferase SETD2 | Q9BYW2 |
| CREBBP (CBP) | CREB-binding protein | Q92793 |
| RB1 | Retinoblastoma-associated protein | P06400 |
| SMARCA4 (BAF190A, BRG1, SNF2B, SNF2L4) | Transcription activator BRG1 | P51532 |
| CHD4 | Chromodomain-helicase-DNA-binding protein 4 | Q14839 |
| FLT3 (CD135, FLK2, STK1) | Receptor-type tyrosine-protein kinase FLT3 | P36888 |
| ARID2 (KIAA1557) | AT-rich interactive domain-containing protein 2 | Q68CP9 |
| CDH1 (CDHE, UVO) | Cadherin-1 | P12830 |
| DNMT3A | DNA (cytosine-5)-methyltransferase 3A | Q9Y6K1 |
| ARHGAP35 (GRF1, GRLF1, KIAA1722, P190A, p190ARHOGAP) | Rho GTPase-activating protein 35 | Q9NRY4 |
| BCOR (KIAA1575) | BCL-6 corepressor | Q6W2J9 |
| CTCF | Transcriptional repressor CTCF | P49711 |
| KDM5C (DXS1272E, JARID1C, SMCX, XE169) | Lysine-specific demethylase 5C | P41229 |
| KDM6A (UTX) | Lysine-specific demethylase 6A | O15550 |
| CASP8 (MCH5) | Caspase-8 | Q14790 |
| ASXL1 (KIAA0978) | Putative Polycomb group protein ASXL1 | Q8IXJ9 |
| RASA1 (GAP, RASA) | Ras GTPase-activating protein 1 | P20936 |
| RUNX1 (AML1, CBFA2) | Runt-related transcription factor 1 | Q01196 |
| NPM1 (NPM) | Nucleophosmin | P06748 |
| CDKN1B (KIP1) | Cyclin-dependent kinase inhibitor 1B | P46527 |
| HLA-A (HLAA) | HLA class I histocompatibility antigen, A-2 alpha chain | P01892 |
| B2M (CDABP0092, HDCMA22P) | Beta-2-microglobulin | P61769 |
| RPL5 (MSTP030) | 60S ribosomal protein L5 | P46777 |
| MYD88 | Myeloid differentiation primary response protein MyD88 | Q99836 |
| CBFB | Core-binding factor subunit beta | Q13951 |
| GPS2 | G protein pathway suppressor 2 | Q13227 |

| Gene | Protein | UniProt |
|---|---|---|
| AHNAK2 (C14orf78, KIAA2019) | Protein AHNAK2 | Q8IVF2 |
| ANKRD36C | Ankyrin repeat domain-containing protein 36C | Q5JPF3 |
| CHEK2 (CDS1, CHK2, RAD53) | Serine/threonine-protein kinase Chk2 | O96017 |
| KRTAP4-11 (KAP4.14, KRTAP4-14, KRTAP4.11, KRTAP4.14) | Keratin-associated protein 4-11 | Q9BYQ6 |
| RGPD8 (RANBP2ALPHA, RANBP2L1, RANBP2L3) | RANBP2-like and GRIP domain-containing protein 8 | O14715 |
| FAM47C | Putative protein FAM47C | Q5HY64 |
| ZAN | Zonadhesin | Q9Y493 |
| RXRA (NR2B1) | Retinoic acid receptor RXR-alpha | P19793 |
| IDH1 (PICD) | Isocitrate dehydrogenase [NADP] cytoplasmic | O75874 |
| GNAS (GNAS1, GSP) | Guanine nucleotide-binding protein G(s) subunit alpha isoforms short | P63092 |
| ESR1 (ESR, NR3A1) | Estrogen receptor | P03372 |
| AR (DHTR, NR3C4) | Androgen receptor | P10275 |
| ZNF814 | Putative uncharacterized zinc finger protein 814 | B7Z6K7 |
| ZBTB20 (DPZF, ZNF288) | Zinc finger and BTB domain-containing protein 20 | Q9HC78 |
| XYLT2 (XT2, UNQ3058/PRO9878) | Xylosyltransferase 2 | Q9H1B5 |
| WNT16 | Protein Wnt-16 | Q9UBV4 |
| UBR5 (EDD, EDD1, HYD, KIAA0896) | E3 ubiquitin-protein ligase UBR5 | O95071 |
| TRIM48 (RNF101) | Tripartite motif-containing protein 48 | Q8IWZ4 |
| TGFBR2 | TGF-beta receptor type-2 | P37173 |
| SVIL | Supervillin | O95425 |
| RNF43 | E3 ubiquitin-protein ligase RNF43 | Q68DV7 |
| PLEKHA6 (KIAA0969, PEPP3) | Pleckstrin homology domain-containing family A member 6 | Q9Y2H5 |
| ACVR2A (ACVR2) | Activin receptor type-2A | P27037 |
| ADAM28 (ADAM23, MDCL) | Disintegrin and metalloproteinase domain-containing protein 28 | Q9UKQ2 |
| BMPR2 (PPH1) | Bone morphogenetic protein receptor type-2 | Q13873 |
| C12orf4 | Protein C12orf4 | Q9NQ89 |
| DOCK3 (KIAA0299, MOCA) | Dedicator of cytokinesis protein 3 | Q8IZD9 |
| FHOD3 (FHOS2, KIAA1695) | FH1/FH2 domain-containing protein 3 | Q8IZD9 |
| KIAA2026 | Uncharacterized protein KIAA2026 | Q5HYC2 |
| KRTAP1-5 (KAP1.5, KRTAP1.5) | Keratin-associated protein 1-5 | Q9BYS1 |
| LARP4B (KIAA0217, L4RP5) | La-related protein 4B | Q92615 |
| MBOAT2 (OACT2) | Lysophospholipid acyltransferase 2 | Q6ZWT7 |
| PGM5 (PGMRP) | Phosphoglucomutase-like protein 5 | Q15124 |
| CEACAM5 (CEA) | Carcinoembryonic antigen-related cell adhesion molecule 5 | P06731 |
| GAGE1 | G antigen 1 | Q13065 |
| hTERT (TERT, EST2, TCS1, TRT) | Telomerase reverse transcriptase | O14746 |
| KLHL7 | Kelch-like protein 7 | Q8IXQ5 |
| MAGEA3 (MAGE3) | Melanoma-associated antigen 3 | P43357 |
| MAGEA4 (MAGE4) | Melanoma-associated antigen 4 | P43358 |
| MAGEA6 (MAGE6) | Melanoma-associated antigen 6 | P43360 |
| NUF2 (CDCA1, NUF2R) | Kinetochore protein Nuf2 | Q9BZD4 |
| NYESO1 (NY-ESO-1, CTAG1A, CTAG, CTAG1, ESO1, L4GE2, LAGE2A, CTAG1B, LAGE2B) | Cancer/testis antigen 1 (Autoimmunogenic cancer/testis antigen NY-ESO-1) | P78358 |

-continued

| Gene | Protein | UniProt |
| --- | --- | --- |
| PAGE4 (GAGEC1, JM27) | P antigen family member 4 | O60829 |
| PRAME (MAPE, OIP4) | Melanoma antigen preferentially expressed in tumors | P78395 |
| PSA (KLK3, APS) | Prostate-specific antigen | P07288 |
| PSMA (FOLH1, FOLH, NAALAD1, PSM, GIG27) | Glutamate carboxypeptidase 2 (Prostate-specific membrane antigen) | Q04609 |
| SART3 (KIAA0156, TIP110) | Squamous cell carcinoma antigen recognized by T-cells 3 | Q15020 |
| SSX2 (SSX2A, SSX2B) | Protein SSX2 | Q16385 |
| STEAP1 (PRSS24, STEAP) | Metalloreductase STEAP1 | Q9UHE8 |
| SURVIVIN (BIRC5, API4, IAP4) | Baculoviral IAP repeat-containing protein 5 (Apoptosis inhibitor survivin) | O15392 |

Other tumor-driver genes and cancer-associated proteins having common mutations that occur across multiple cancers or among multiple cancer patients are also known, and sequencing data across multiple tumor samples and multiple tumor types exists. See, e.g., Chang et al. (2016) *Nat Biotechnol* 34(2):155-163; Tamborero et al. (2013) *Sci Rep* 3:2650, each of which is herein incorporated by reference in its entirety.

As a set of specific examples, the cancer-associated protein can be encoded by one of the following genes: BRAF, EGFR, PIK3CA, PIK3R1, PTEN, RAS (e.g., KRAS), TP53, APC, FBXW7, KEAP1, STK11, NF1, KMT2D, CDKN2A, NFE2L2, SPOP, GATA3, AKT1, MAP3K1, and MAP2K4. As a set of specific examples, the cancer-associated protein can be encoded by one of the following genes: BRAF, EGFR, PIK3CA, PIK3R1, PTEN, RAS (e.g., KRAS), TP53, APC, FBXW7, KEAP1, STK11, NF1, KMT2D, CDKN2A, NFE2L2, SPOP, GATA3, AKT1, MAP3K1, MAP2K4, AHNAK2, ANKRD36C, CHEK2, KRTAP4-11, RGPD8, FAM47C, and ZAN. As another set of specific examples, the cancer-associated protein can be encoded by one of the following genes: ACVR2A, ADAM28, AKT1, ANKRD36C, AR, ARID1A, BMPR2, BRAF, CHEK2, C12orf4, CTNNB1, DOCK3, EGFR, ESR1, FBXW7, FGFR3, FHOD3, GNAS, HRAS, IDH1, IDH2, KIAA2026, KRAS, KRTAP1-5, KRTAP4-11, LARP4B, MBOAT2, NFE2L2, PGM5, PIK3CA, PLEKHA6, POLE, PTEN, RGPD8, RNF43, RXRA, SMAD4, SPOP, SVIL, TGFBR2, TP53, TRIM48, UBR5, U2AF1, WNT16, XYLT2, ZBTB20, and ZNF814.

The fusion polypeptides disclosed herein can comprise antigenic peptides comprising any combination of recurrent cancer mutation from any combination of cancer-associated proteins (i.e., one or more cancer-associated proteins) and in any order. The combination of antigenic peptides or the fusion polypeptide can be hydrophilic or can score up to or below a certain hydropathy threshold, which can be predictive of secretability in *Listeria monocytogenes* or another bacteria of interest.

As one example, the cancer-associated protein can be encoded by BRAF, and the antigenic peptides comprise 2 or more, 3 or more, 4 or more, 5 or more, 6 or more, 7 or more, or all of the following recurrent cancer mutations: G466E; G466V; G469A; G469R; G469S; G469V; V600E; and V600K. The wild type BRAF reference sequence is set forth in SEQ ID NO: 361. The mutations can be in any order. For example, the fusion polypeptide can comprise antigenic peptides comprising the following BRAF mutations, from N-terminal to C-terminal: G469V; G469R; V600E; G469S; G466V; V600K; G469A; and G466E. See, e.g., SEQ ID NOS: 1-6. Alternatively, the fusion polypeptide can comprise antigenic peptides comprising the following BRAF mutations, from N-terminal to C-terminal: V600K; G469R; G469V; G466V; G466E; V600E; G469A; and G469S. See, e.g., SEQ ID NOS: 7-12. Alternatively, the fusion polypeptide can comprise antigenic peptides comprising the following BRAF mutations, from N-terminal to C-terminal: G469V; V600K; G469S; G466V; G469A; V600E; G466E; and G469R. See, e.g., SEQ ID NOS: 13-18. Alternatively, the fusion polypeptide can comprise antigenic peptides comprising the following BRAF mutations, from N-terminal to C-terminal: V600E; V600K; G469A; G469S; G469R; G469V; G466V; and G466E. See, e.g., SEQ ID NOS: 19-24. In a specific example, the BRAF antigenic peptides can be 21-mers (e.g., 21-mers fused directly together), each including the naturally occurring 10 amino acids flanking each side of the recurrent cancer mutation.

As another example, the cancer-associated protein can be encoded by EGFR, and the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: R108K; A289V; G598V; E709A; E709K; G719A; G719C; G719S; L747P; L747S; S768I; T790M; L833V/H835L; T833V; L858R; and L861Q. The wild type EGFR reference sequence is set forth in SEQ ID NO: 362. For example, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: R108K; A289V; G598V; E709A; E709K; G719A; G719C; G719S; L747P; L747S; S768I; T790M; L833V/H835L; T833V; L858R; and L861Q. Alternatively, the antigenic peptides comprise 2 or more, 3 or more, 4 or more, 5 or more, 6 or more, 7 or more, 8 or more, 9 or more, 10 or more, or all of the following recurrent cancer mutations: A289V; G598V; E709K; G719A; G719C; G719S; S768I; T790M; L833V/H835L; L858R; and L861Q. The mutations can be in any order. For example, the fusion polypeptide can comprise antigenic peptides comprising the following EGFR mutations, from N-terminal to C-terminal: G719S; L747P; G719C; R108K; S768I; L833V/H835L; T833V; E709A; G598V; T790M; E709K; A289V; L861Q; G719A; L747S; and L858R. See, e.g., SEQ ID NOS: 25-30. Alternatively, the fusion polypeptide can comprise antigenic peptides comprising the following EGFR mutations, from N-terminal to C-terminal: T790M; S768I; G719C; R108K; L747P; G719A; L747S; E709K; T833V; L861Q; E709A; L858R; G598V; A289V; L833V/H835L; and G719S. See, e.g., SEQ ID NOS: 31-36. Alternatively, the fusion polypeptide can comprise antigenic peptides comprising the following EGFR mutations, from N-terminal to C-terminal: R108K; T833V; L747S; T790M; G719C; A289V; L858R; E709A; G719S; E709K; G719A; L747P; G598V; L861Q; S768I; and L833V/H835L. See, e.g., SEQ ID NOS: 37-42. Alternatively, the fusion polypeptide can comprise antigenic peptides comprising the following EGFR mutations, from N-terminal to C-terminal: G719A; L858R; G719C; A289V; T790M; S768I; T833V; G598V; G719S; L747S; L747P; L833V/H835L; E709A; R108K; L861Q; and E709K. See, e.g., SEQ ID NOS: 43-48. Alternatively, the fusion polypeptide can comprise antigenic peptides comprising the following EGFR mutations, from N-terminal to C-terminal: A289V; G598V; E709K; G719A; S768I; G719S; L861Q; T790M; G719C; L833V/H835L; and L858R. See, e.g., SEQ ID NOS: 229-235. In a specific example, the EGFR antigenic peptides can be 21-mers (e.g., 21-mers fused directly together), each including the naturally occurring 10 amino acids flanking each side of the recurrent cancer mutation.

As another example, the cancer-associated protein can be encoded by PIK3CA, and the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, or all of the following recurrent cancer mutations: R38C; R38H; E81K; R88Q; R93Q; R93W; R108H; G118D; L334G; N345K; C420R; E453K; E542K; E545A; E545G; E545K; E545Q; Q546K; Q546R; E726K; M1043I; M1043V; H1047L; H1047R; and G1049R. The wild type PIK3CA reference sequence is set forth in SEQ ID NO: 363. For example, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the following recurrent cancer mutations: R38H; E81K; R88Q; R108H; G118D; N345K; C420R; E542K; E545A; E545G; E545K; Q546K; Q546R; M1043I; H1047L; H1047R; and G1049R. Alternatively, the antigenic peptides comprise 2 or more, 3 or more, 4 or more, 5 or more, 6 or more, 7 or more, or all of the following recurrent cancer mutations: R88Q; E542K; E545A; E545G; E545K; Q546K; H1047L; and H1047. Alternatively, the antigenic peptides comprise 2 or more, 3 or more, 4 or more, 5 or more, 6 or more, 7 or more, 8 or more, or all of the following recurrent cancer mutations: R38H; E81K; R108H; G118D; N345K; C420R; Q546K; M1043I; and G1049R. The mutations can be in any order. For example, the fusion polypeptide can comprise antigenic peptides comprising the following PIK3CA mutations, from N-terminal to C-terminal: M1043V; E545G; E726K; Q546R; L334G; G1049R; M1043I; Q546K; E542K; R93Q; H1047R; R108H; R93W; E81K; R38H; N345K; R88Q; G118D; E545Q; H1047L; E545A; E453K; E545K; R38C; and C420R. See, e.g., SEQ ID NOS: 49-54. Alternatively, the fusion polypeptide can comprise antigenic peptides comprising the following PIK3CA mutations, from N-terminal to C-terminal: E726K; E81K; M1043V; E545A; E545K; R38C; G118D; R93W; E545G; E542K; G1049R; N345K; Q546K; E453K; C420R; H1047L; L334G; E545Q; R88Q; H1047R; M1043I; R93Q; R108H; Q546R; and R38H. See, e.g., SEQ ID NOS: 55-60. Alternatively, the fusion polypeptide can comprise antigenic peptides comprising the following PIK3CA mutations, from N-terminal to C-terminal: R108H; M1043V; R88Q; R93W; R38H; H1047R; E545K; M1043I; Q546R; E542K; N345K; R38C; E545G; E81K; Q546K; R93Q; E453K; G1049R; E545A; C420R; H1047L; L334G; G118D; E726K; and E545Q. See, e.g., SEQ ID NOS: 61-66. Alternatively, the fusion polypeptide can comprise antigenic peptides comprising the following PIK3CA mutations, from N-terminal to C-terminal: N345K; R38H; E545K; G1049R; H1047L; E726K; R88Q; E81K; R93Q; E545Q; L334G; R38C; H1047R; C420R; R93W; Q546K; M1043V; M1043I; E545G; E545A; G118D; E453K; Q546R; R108H; and E542K. See, e.g., SEQ ID NOS: 67-72. Alternatively, the fusion polypeptide can comprise antigenic peptides comprising the following PIK3CA mutations, from N-terminal to C-terminal: E542K; E545K; R88Q; E545A; H1047R; E545G; H1047L; Q546K; R38H; E81K; R108H; N345K; C420R; Q546R; M1043I; G118D; and G1049R. See, e.g., SEQ ID NOS: 236-242. Alternatively, the fusion polypeptide can comprise antigenic peptides comprising the following PIK3CA mutations, from N-terminal to C-terminal: E542K; E545K; R88Q; E545A; H1047R; E545G; H1047L; and Q546K. See, e.g., SEQ ID NOS: 243-249. Alternatively, the fusion polypeptide can comprise antigenic peptides comprising the following PIK3CA mutations, from N-terminal to C-terminal: R38H; E81K; R108H; N345K; C420R; Q546K; M1043I; G118D; and G1049R. See, e.g., SEQ ID NOS: 250-256. In a specific example, the PIK3CA antigenic peptides can be 21-mers (e.g., 21-mers fused directly together), each including the naturally occurring 10 amino acids flanking each side of the recurrent cancer mutation.

As another example, the cancer-associated protein can be encoded by PIK3R1, and the antigenic peptides comprise 2 or more or all of the following recurrent cancer mutations: G376R; N564D; and K567E. The wild type PIK3R1 reference sequence is set forth in SEQ ID NO: 364. The mutations can be in any order. For example, the fusion polypeptide can comprise antigenic peptides comprising the following PIK3R1 mutations, from N-terminal to C-terminal: G376R; N564D; and K567E. See, e.g., SEQ ID NOS: 73-78. Alternatively, the fusion polypeptide can comprise antigenic peptides comprising the following PIK3R1 mutations, from N-terminal to C-terminal: N564D; K567E; and G376R. See, e.g., SEQ ID NOS: 79-84. In a specific example, the PIK3R1 antigenic peptides can be 21-mers (e.g., 21-mers fused directly together), each including the naturally occurring 10 amino acids flanking each side of the recurrent cancer mutation.

As another example, the cancer-associated protein can be encoded by PIK3CA and PIK3R1, and the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, or all of the following recurrent cancer mutations: PIK3CA|R38C; PIK3CA|R38H; PIK3CA|E81K; PIK3CA|R88Q; PIK3CA|R93Q; PIK3CA|R93W; PIK3CA|R108H; PIK3CA|G118D; PIK3CA|L334G; PIK3CA|N345K; PIK3CA|C420R; PIK3CA|E453K; PIK3CA|E542K; PIK3CA|E545A; PIK3CA|E545G; PIK3CA|E545K; PIK3CA|E545Q; PIK3CA|Q546K; PIK3CA|Q546R; PIK3CA|E726K; PIK3CA|M1043I; PIK3CA|M1043V; PIK3CA|H1047L; PIK3CA|H1047R; PIK3CA|G1049R; PIK3R1|G376R;

PIK3R1|N564D; and PIK3R1|K567E. The mutations can be in any order. For example, the fusion polypeptide can comprise antigenic peptides comprising the following PIK3CA and PIK3R1 mutations, from N-terminal to C-terminal: PIK3CA|R38C; PIK3CA|N345K; PIK3CA|E726K; PIK3CA|E453K; PIK3CA|R93Q; PIK3CA|H1047R; PIK3CA|E545A; PIK3CA|M1043V; PIK3R1|N564D; PIK3R1|K567E; PIK3CA|E81K; PIK3CA|R108H; PIK3CA|Q546R; PIK3CA|Q546K; PIK3CA|E545Q; PIK3CA|G1049R; PIK3CA|C420R; PIK3CA|H1047L; PIK3CA|R93W; PIK3CA|R88Q; PIK3CA|M1043I; PIK3CA|E545G; PIK3CA|G118D; PIK3CA|R38H; PIK3R1|G376R; PIK3CA|E542K; PIK3CA|E545K; and PIK3CA|L334G. See, e.g., SEQ ID NOS: 85-90. Alternatively, the fusion polypeptide can comprise antigenic peptides comprising the following PIK3CA and PIK3R1 mutations, from N-terminal to C-terminal: PIK3CA|R38C; PIK3CA|R108H; PIK3CA|C420R; PIK3CA|R93Q; PIK3CA|E453K; PIK3CA|M1043V; PIK3CA|H1047L; PIK3R1|N564D; PIK3CA|E726K; PIK3CA|G118D; PIK3CA|Q546R; PIK3CA|Q546R; PIK3CA|E542K; PIK3CA|E545K; PIK3CA|G1049R; PIK3CA|M1043I; PIK3CA|L334G; PIK3R1|K567E; PIK3CA|R38H; PIK3R1|G376R; PIK3CA|R93W; PIK3CA|H1047R; PIK3CA|E545G; PIK3CA|E81K; PIK3CA|R88Q; PIK3CA|N345K; PIK3CA|E545A; and PIK3CA|E545Q. See, e.g., SEQ ID NOS: 91-96. Alternatively, the fusion polypeptide can comprise antigenic peptides comprising the following PIK3CA and PIK3R1 mutations, from N-terminal to C-terminal: PIK3CA|R108H; PIK3CA|M1043V; PIK3CA|R88Q; PIK3CA|R93W; PIK3CA|R38H; PIK3CA|H1047R; PIK3CA|E545K; PIK3CA|M1043I; PIK3CA|Q546R; PIK3CA|E542K; PIK3CA|N345K; PIK3CA|R38C; PIK3CA|E545G; PIK3CA|E81K; PIK3CA|Q546K; PIK3CA|R93Q; PIK3CA|E453K; PIK3CA|G1049R; PIK3CA|E545A; PIK3CA|C420R; PIK3CA|H1047L; PIK3CA|L334G; PIK3CA|G118D; PIK3CA|E726K; and PIK3CA|E545Q. See, e.g., SEQ ID NOS: 97-102. Alternatively, the fusion polypeptide can comprise antigenic peptides comprising the following PIK3CA and PIK3R1 mutations, from N-terminal to C-terminal: PIK3CA|E545Q; PIK3CA|R93W; PIK3CA|H1047R; PIK3CA|G1049R; PIK3CA|N345K; PIK3CA|Q546R; PIK3CA|E545K; PIK3CA|E453K; PIK3CA|L334G; PIK3CA|H1047L; PIK3R1|G376R; PIK3CA|M1043V; PIK3CA|R88Q; PIK3CA|R38H; PIK3CA|G118D; PIK3R1|K567E; PIK3CA|R38C; PIK3CA|E542K; PIK3CA|Q546K; PIK3CA|E726K; PIK3CA|C420R; PIK3CA|E545A; PIK3CA|R93Q; PIK3R1|N564D; PIK3CA|R108H; PIK3CA|M1043I; PIK3CA|E545G; and PIK3CA|E81K. See, e.g., SEQ ID NOS: 103-108. In a specific example, the PIK3CA and PIK3R1 antigenic peptides can be 21-mers (e.g., 21-mers fused directly together), each including the naturally occurring 10 amino acids flanking each side of the recurrent cancer mutation.

As another example, the cancer-associated protein can be encoded by PTEN, and the antigenic peptides comprise 2 or more, 3 or more, 4 or more, 5 or more, 6 or more, 7 or more, 8 or more, 9 or more, 10 or more, 11 or more, 12 or more, or all of the following recurrent cancer mutations: Y68H; Y88C; D92E; del121-131; R130G; R130L; R130P; R130Q; C136Y; R142W; Y155C; R173H; and P246L. The wild type PTEN reference sequence is set forth in SEQ ID NO: 365. The mutations can be in any order. For example, the fusion polypeptide can comprise antigenic peptides comprising the following PTEN mutations, from N-terminal to C-terminal: del121-131; Y88C; R130G; Y155C; D92E; C136Y; R130Q; Y68H; R142W; R173H; R130L; R130P; and P246L. See, e.g., SEQ ID NOS: 109-114. Alternatively, the fusion polypeptide can comprise antigenic peptides comprising the following PTEN mutations, from N-terminal to C-terminal: R130P; R130G; Y155C; R130L; C136Y; del121-131; P246L; D92E; R173H; Y68H; R130Q; Y88C; and R142W. See, e.g., SEQ ID NOS: 115-120. Alternatively, the fusion polypeptide can comprise antigenic peptides comprising the following PTEN mutations, from N-terminal to C-terminal: R130Q; R130G; del121-131; C136Y; R130L; P246L; Y155C; D92E; R142W; R130P; Y88C; Y68H; and R173H. See, e.g., SEQ ID NOS: 121-126. Alternatively, the fusion polypeptide can comprise antigenic peptides comprising the following PTEN mutations, from N-terminal to C-terminal: del121-131; C136Y; Y68H; R142W; R173H; |R130L; P246L; R130G; R130P; Y88C; D92E; R130Q; and Y155C. See, e.g., SEQ ID NOS: 127-132. In a specific example, the PTEN antigenic peptides can be 21-mers (e.g., 21-mers fused directly together), each including the naturally occurring 10 amino acids flanking each side of the recurrent cancer mutation.

As another example, the cancer-associated protein can be encoded by KRAS, and the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or all of the following recurrent cancer mutations: G12A; G12C; G12D; G12R; G12S; G12V; G13C; G13D; G13R; G13S; G13V; L19F; Q61K; Q61H; Q61L; Q61R; K117N; A146T; A146V; and A164G. The wild type KRAS reference sequence is set forth in SEQ ID NO: 366. The mutations can be in any order. For example, the fusion polypeptide can comprise antigenic peptides comprising the following KRAS mutations, from N-terminal to C-terminal: Q61R; Q61K; Q61L; Q61H; L19F; K117N; G12A; A164G; G12D; G13D; G13S; G12S; A146V; G13R; G13C; G12C; G12R; G13V; G12V; and A146T. See, e.g., SEQ ID NOS: 133-138. Alternatively, the fusion polypeptide can comprise antigenic peptides comprising the following KRAS mutations, from N-terminal to C-terminal: Q61H; K117N; G13C; G13R; G12D; G12S; G12V; G12A; Q61K; G13V; G12C; L19F; Q61R; Q61L; A146V; A164G; G12R; G13S; A146T; and G13D. See, e.g., SEQ ID NOS: 139-144. Alternatively, the fusion polypeptide can comprise antigenic peptides comprising the following KRAS mutations, from N-terminal to C-terminal: G12D; L19F; A146V; Q61H; G12V; A164G; G12C; Q61L; A146T; G13S; G12A; G13V; G13C; G13D; G12R; G12S; Q61R; Q61K; G13R; and K117N. See, e.g., SEQ ID NOS: 145-150. Alternatively, the fusion polypeptide can comprise antigenic peptides comprising the following KRAS mutations, from N-terminal to C-terminal: G13V; G13S; G12V; G12R; A146V; G13D; G12D; K117N; Q61H; G12C; G13C; A146T; G12A; Q61L; Q61K; A164G; G12S; L19F; G13R; and Q61R. See, e.g., SEQ ID NOS: 151-156. In a specific example, the KRAS antigenic peptides can be 21-mers (e.g., 21-mers fused directly together), each including the naturally occurring 10 amino acids flanking each side of the recurrent cancer mutation.

As another example, the cancer-associated protein can be encoded by TP53, and the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, or all of the following recurrent cancer mutations: Y107D; K132N; C141Y; V143A; V157F; Y163C; R175H; C176F; C176Y; H179W; H193R; I195T; V216M; Y220C; Y234C; Y234H; S241F; S242F; G245D; G245S; R248L; R248Q; R248W; R249S; R273C; R273H; R273L; P278L; P278S; R282G; R282W; and R337H. The wild type TP53 reference sequence is set forth in SEQ ID NO: 367. For example, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or all of the following recurrent cancer mutations: Y107D; C141Y; V143A; V157F; Y163C; R175H; C176F; H193R; I195T; V216M; Y220C; Y234C; Y234H; G245D; G245S; R248Q; R248W; R249S; R273C; R273H; R273L; R282G; and R282W. Alternatively, the antigenic peptides comprise 2 or more, 3 or more, 4 or more, 5 or more, 6 or more, 7 or more, 8 or more, 9 or more, 10 or more, or all of the following recurrent cancer mutations: V143A; R175H; H193R; Y220C; G245D; R248Q; R248W; R249S; R273C; R273H; and R282W. Alternatively, the antigenic peptides comprise 2 or more, 3 or more, 4 or more, 5 or more, 6 or more, 7 or more, 8 or more, 9 or more, 10 or more, 11 or more, or all of the following recurrent cancer mutations: Y107D; C141Y; V157F; Y163C; C176F; I195T; V216M; Y234C; Y234H; G245S; R273L; and R282G. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the following recurrent cancer mutations: Y107D; C141Y; V143A; Y163C; C176Y; H179R; H179W; H193R; V216M; Y234H; S241F; G245D; R248Q; R248W; R273C; R273L; and P278S. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the following recurrent cancer mutations: C141Y; R175H; H179R; H193R; V216M; Y234H; G245D; G245S; R248L; R248W; R273C; R273H; P278L; P278S; R282G; R282W; and R337H. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the following recurrent cancer mutations: Y107D; C141Y; V143A; C176F; H179R; V216M; Y220C; S241F; S242F; G245S; R248L; R248W; R273L; P278L; P278S; R282G; and R282W. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the following recurrent cancer mutations: Y107D; K132N; V143A; V157F; Y163C; R175H; C176Y; Y234C; Y234H; S241F; S242F; G245D; G245S; R273C; P278S; R282W; and R337H. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: K132N; V157F; R175H; C176F; I195T; Y220C; Y234C; S242F; G245S; R248L; R249S; R273H; P278L; R282G; R282W; and R337H. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: Y107D; K132N; V143A; V157F; Y163C; C176F; C176Y; H179W; I195T; Y220C; Y234C; S241F; S242F; R248Q; R249S; and R273L. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: K132N; V157F; Y163C; R175H; C176Y; H179W; H193R; I195T; Y234C; Y234H; G245D; R248Q; R249S; R273C; R273H; and R337H. Alternatively, the antigenic peptides comprise 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: C141Y; C176F; H179R; H179W; H193R; I195T; V216M; Y220C; R248L; R248Q; R248W; R249S; R273H; R273L; P278L; and R282G. The mutations can be in any order. For example, the fusion polypeptide can comprise antigenic peptides comprising the following TP53 mutations, from N-terminal to C-terminal: H179W; R273L; R249S; R248Q; Y234H; G245D; Y220C; R248L; H193R; K132N; S242F; Y234C; G245S; C176F; R282W; R273H; R282G; C141Y; R273C; V216M; R337H; R248W; V143A; I195T; P278S; S241F; C176Y; Y107D; R175H; H179R; V157F; P278L; and Y163C. See, e.g., SEQ ID NOS: 157-162. Alternatively, the fusion polypeptide can comprise antigenic peptides comprising the following TP53 mutations, from N-terminal to C-terminal: R248W; R248L; Y220C; Y163C; G245D; Y107D; H179W; V216M; P278S; S241F; R273L; P278L; C176F; C141Y; S242F; R249S; V143A; I195T; R273H; R273C; R282G; H179W; R175H; R248Q; G245S; H193R; R337H; R282W; Y234C; V157F; Y234H; C176Y; and K132N. See, e.g., SEQ ID NOS: 163-166. Alternatively, the fusion polypeptide can comprise antigenic peptides comprising the following TP53 mutations, from N-terminal to C-terminal: R248W; H179R; R273H; Y107D; R337H; R282G; V157F; V143A; Y234H; Y220C; R282W; R248L; S241F; H179W; R273C; C141Y; R249S; P278L; G245S; I195T; R175H; G245D; R273L; K132N; V216M; Y163C; C176F; S242F; Y234C; H193R; R248Q; P278S; and C176Y. See, e.g., SEQ ID NOS: 167-174. Alternatively, the fusion polypeptide can comprise antigenic peptides comprising the following TP53 mutations, from N-terminal to C-terminal: V143A; R282W; V157F; H179W; K132N; Y163C; C176Y; G245D; Y220C; S242F; Y234C; R249S; H179R; R273H; C141Y; R273L; P278S; C176F; R337H; H193R; R273C; R282G; R175H; R248W; P278L; I195T; S241F; R248L; Y234H; V216M; G245S; Y107D; and R248Q. See, e.g., SEQ ID NOS: 175-180. Alternatively, the fusion polypeptide can comprise antigenic peptides comprising the following TP53 mutations, from N-terminal to C-terminal: S241F; G245D; V143A; P278S; R273C; C176Y; Y234H; R248W; V216M; R248Q; C141Y; Y163C; H193R; H179R; H179W; Y107D; and R273L. See, e.g., SEQ ID NOS: 181-186. Alternatively, the fusion polypeptide can comprise antigenic peptides comprising the following TP53 mutations, from N-terminal to C-terminal: K132N; R282W; G245S; Y234C; S242F; R175H; Y220C; V157F; R282G; C176F; R337H; I195T; R249S; P278L; R273H; and R248L. See, e.g., SEQ ID NOS: 187-192. Alternatively, the fusion polypeptide can comprise antigenic peptides comprising the following TP53 mutations, from N-terminal to C-terminal: H193R; P278L; R273C; R248W; H179R; P278S; R248L; V216M; R282G; R337H; R175H; Y234H; G245D; R273H; G245S; R282W; and C141Y. See, e.g., SEQ ID NOS: 193-198. Alternatively, the fusion polypeptide can comprise antigenic peptides comprising the following TP53 mutations, from N-terminal to C-terminal: Y107D; K132N; C176F; C176Y; R273L; Y220C; R248Q; V143A; I195T; R249S; S242F; Y234C; H179W; V157F; Y163C; and S241F. See, e.g., SEQ ID NOS: 199-204. Alternatively, the fusion polypeptide can comprise antigenic peptides comprising the following TP53 mutations, from N-terminal to C-terminal: P278S; C176F; H179R; R282G; S241F; R273L; P278L; C141Y; Y107D; R248W; V216M; R282W; S242F; Y220C; V143A; G245S; and R248L. See, e.g., SEQ ID NOS: 205-210. Alternatively, the fusion polypeptide can comprise antigenic peptides comprising the following TP53 mutations, from N-terminal to C-terminal: R175H; H179W; R249S; Y234H; I195T; R248Q; R273H; C176Y; V157F; H193R; Y234C; K132N; R273C; Y163C; G245D; and R337H. See, e.g., SEQ ID NOS: 211-216. Alternatively, the fusion polypeptide can comprise antigenic peptides comprising the following TP53 mutations, from N-terminal to C-terminal: C176Y; R175H; G245D; R337H; S241F; K132N; V143A; P278S; R282W; Y163C; Y107D; R273C; S242F; G245S; V157F; Y234C; and Y234H. See, e.g., SEQ ID NOS: 217-222. Alternatively, the fusion polypeptide can comprise antigenic peptides comprising the following TP53 mutations, from N-terminal to C-terminal: C176F; R273L; H179R; R282G; Y220C; I195T; C141Y; R248L; R273H; H179W; H193R; R249S; V216M; P278L; R248W; and R248Q. See, e.g., SEQ ID NOS: 223-228. Alternatively, the fusion polypeptide can comprise antigenic peptides comprising the following TP53 mutations, from N-terminal to C-terminal: R248W; R273H; V143A; R249S; R175H; H193R; Y220C; G245D; R248Q; R273C; R282W; Y107D; C141Y; V157F; Y163C; C176F; I195T; V216M; Y234H; G245S; R273L; Y234C; and R282G. See, e.g., SEQ ID NOS: 257-263. Alternatively, the fusion polypeptide can comprise antigenic peptides comprising the following TP53 mutations, from N-terminal to C-terminal: R248W; R273H; V143A; R249S; R175H; H193R; Y220C; G245D; R248Q; R273C; and R282W. See, e.g., SEQ ID NOS: 264-270. Alternatively, the fusion polypeptide can comprise antigenic peptides comprising the following TP53 mutations, fromN-terminal to C-terminal: Y107D; C141Y; V157F; Y163C; C176F; I195T; V216M; Y234H; G245S; R273L; Y234C; and R282G. See, e.g., SEQ ID NOS: 271-277. In a specific example, the TP53 antigenic peptides can be 21-mers (e.g., 21-mers fused directly together), each including the naturally occurring 10 amino acids flanking each side of the recurrent cancer mutation.

In some cases, the recurrent cancer mutations can be from multiple cancer-associated proteins. For example, each of the recurrent cancer mutations in a particular fusion polypeptide (or in a set of fusion polypeptides to be used, for example, in a single dosing regimen) can be a recurrent cancer mutation that occurs in the same type of cancer. As an example, the two or more cancer associated proteins comprise proteins encoded by two or more or all of the following genes: PI3KCA, AKT1, AHNAK2, ERBB2, and TP53. The antigenic peptides can comprise, for example, 2 or more, 3 or more, 4 or more, 5 or more, 6 or more, 7 or more, 8 or more, 9 or more, or 10 or more of the following recurrent cancer mutations: PIK3CA|H1047R; PIK3CA|E545K; PIK3CA|E542K; PIK3CA|H1047L; PIK3CA|Q546K; PIK3CA|E545A; PIK3CA|E545G; AKT1|E17K; AHNAK2|V2016L, ERBB2|L755S, and TP53|R175H. The mutations can be in any order. In a specific example, the antigenic peptides can be 21-mers (e.g., 21-mers fused directly together), each including the naturally occurring 10 amino acids flanking each side of the recurrent cancer mutation. Examples of such 21-mers are set forth in Example 3 and in SEQ ID NOS: 584-594.

As another example, the two or more cancer associated proteins comprise proteins encoded by two or more or all of the following genes: BRAF, KRAS/NRAS, TP53, PIK3CA, and SMAD4. The antigenic peptides can comprise, for example, 2 or more, 3 or more, 4 or more, 5 or more, 6 or more, 7 or more, 8 or more, 9 or more, 10 or more. 11 or more, 12 or more, 13 or more, 14 or more, 15 or more, 16 or more, 17 or more, or 18 or more of the following recurrent cancer mutations: BRAFIV600E; KRAS|G12D; KRAS|G13D; KRAS|G12V; KRAS|G12C; KRAS|Q61K; KRAS|G12A; KRAS|G12S; TP53|R175H; TP53|R248W; TP53|R273C; TP53|R282W; TP53|R273H; TP53|R248Q; TP53|G245S; PIK3CA|E545K; PIK3CA|H1047R; PIK3CA|R88Q; and SMAD4|R361H. The mutations can be in any order. In a specific example, the antigenic peptides can be 21-mers (e.g., 21-mers fused directly together), each including the naturally occurring 10 amino acids flanking each side of the recurrent cancer mutation. Examples of such 21-mers are set forth in Example 3 and in SEQ ID NOS: 595-613.

As another example, the two or more cancer associated proteins comprise proteins encoded by two or more or all of the following genes: KRAS, TP53, EGFR, U2AF1, BRAF, and PIK3CA. The antigenic peptides can comprise, for example, 2 or more, 3 or more, 4 or more, 5 or more, 6 or more, 7 or more, 8 or more, 9 or more, 10 or more. 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, or 28 or more of the following recurrent cancer mutations: KRAS|G12C; KRAS|G12V; KRAS|G12D; KRAS|G12F; KRAS|G12R; KRAS|Q61L; KRAS|G12Y; TP53|R158L; TP53|R273L; TP53|G245V; TP53|R175H; TP53|A159P; TP53|R249M; TP53|R273H; TP53|R280I; TP53|Q144L; TP53|R273C; TP53|R280G; TP53|R280T; EGFR|L858R; EGFR|L861Q; EGFR|G719A; U2AF1|S34F; BRAF1|V600E; BRAF1|G466V; BRAF1|N581S; PIK3CA|E545K; PIK3CA|E726K; and PIK3CA|H1047R. The mutations can be in any order. In a specific example, the antigenic peptides can be 21-mers (e.g., 21-mers fused directly together), each including the naturally occurring 10 amino acids flanking each side of the recurrent cancer mutation. Examples of such 21-mers are set forth in Example 3 and in SEQ ID NOS: 614-643.

In another example, the two or more cancer associated proteins comprise proteins encoded by two or more or all of the following genes: TP53, PIK3CA, NFE2L2, CDKN2A, and PTEN. The antigenic peptides can comprise, for example, 2 or more, 3 or more, 4 or more, 5 or more, 6 or more, 7 or more, 8 or more, 9 or more, 10 or more. 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, 45 or more, 46 or more, 47 or more, 48 or more, 49 or more, 50 or more, 51 or more, 52 or more, 53 or more, 54 or more, 55 or more, 56 or more, 57 or more, 58 or more, or 59 or more of the following recurrent cancer mutations: TP53|Y163C; TP53|R175G; TP53|C242F; TP53|R273L; TP53|H179L; TP53|H193L; TP53|H214R; TP53|Y220C; TP53|Y234C; TP53|G245V; TP53|L111Q; TP53|T125P; TP53|K132R; TP53|C135W; TP53|C141W; TP53|C176F; TP53|C176Y; TP53|H179R; TP53|H179Y; TP53|H193R; TP53|I195S;

TP53|Y205C; TP53|R213G; TP53|V216E; TP53|Y234S; TP53|Y236C; TP53|M237I; TP53|G244C; TP53|G245S; TP53|R248L; TP53|R248P; TP53|R248Q; TP53|R248W; TP53|R249G; TP53|R249S; TP53|R249W; TP53|G266V; TP53|F270I; TP53|R273C; TP53|R273H; TP53|R273P; TP53|R280I; TP53|D281Y; TP53|R282Q; TP53|R282W; PIK3CA|E545K; PIK3CA|E542K; PIK3CA|H1047R; PIK3CA|E726K; PIK3CA|C420R; NFE2L2|E79Q; NFE2L2|R34Q; NFE2L2|L30F; NFE2L2|G81S; NFE2L2|G31A; NFE2L2|D29G; NFE2L2|G81V; CDKN2A|D108Y; CDKN2A|D18N; and PTEN|R130Q. The mutations can be in any order. In a specific example, the antigenic peptides can be 21-mers (e.g., 21-mers fused directly together), each including the naturally occurring 10 amino acids flanking each side of the recurrent cancer mutation. Examples of such 21-mers are set forth in Example 3 and in SEQ ID NOS: 644-703.

As another example, two or more cancer associated proteins comprise proteins encoded by two or more or all of the following genes: ANKRD36C, SPOP, CHEK2, KRTAP4-11, RGPD8, TP53, FAM47C, ZAN, and PIK3CA. The antigenic peptides can comprise, for example, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more of the following recurrent cancer mutations: ANKRD36C|I645T; ANKRD36C|D629Y; ANKRD36C|D629N; SPOP|W131G; SPOP|F133L; SPOP|F133V; SPOP|F133C; SPOP|W131R; SPOP|W131L; CHEK2|K373E; KRTAP4-11|M93V; KRTAP4-11|R51K; KRTAP4-11|L161V; RGPD81P1760A; TP53|R248Q; TP53|G245S; TP53|G245D; FAM47C|N648D; ZAN|L878P; PIK3CA|E542K; and PIK3CA|H1047R. The mutations can be in any order. In a specific example, the antigenic peptides can be 21-mers (e.g., 21-mers fused directly together), each including the naturally occurring 10 amino acids flanking each side of the recurrent cancer mutation. Examples of such 21-mers are set forth in Example 3 and in SEQ ID NOS: 704-724.

As another example, the cancer-associated proteins can comprise proteins encoded by 1 or more, 2 or more, 3 or more, 4 or more, 5 or more or all of the following genes: KRAS, EGFR, U2AF1, BRAF, PIK3CA, and TP53. The antigenic peptides can comprise, for example, 1 or more, 2 or more, 3 or more, 4 or more, 5 or more, 6 or more, 7 or more, 8 or more, 9 or more, 10 or more, or all of the following recurrent cancer mutations: KRAS_G12C, EGFR_L858R, KRAS_G12D, U2AF1_S34F, BRAF_V600E, KRAS_G12V, PIK3CA_E545K, TP53_R158L, KRAS_G12A, EGFR_L861Q, and TP53_R273L. Such mutations are associated with, for example, non-small cell lung cancer (NSCLC). The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, or all of the antigenic peptides in Table 35.

As another example, the cancer-associated proteins can comprise proteins encoded by 1 or more, 2 or more, 3 or more, 4 or more, or all of the following genes: SPOP, CHEK2, RGPD8, ANKRD36C, and AR. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, or all of the following recurrent cancer mutations: SPOP_F133V, CHEK2_K373E, RGPD8_P1760A, ANKRD36C_1634T, ANKRD36C_D629Y, SPOP_W131G, ANKRD36C_D626N, SPOP_F133L, AR_T878A, AR_L702H, AR_W742C, AR_H875Y, and AR_F877L. Such mutations are associated with, for example, prostate cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all of the antigenic peptides in Table 52.

As another example, the cancer-associated proteins can comprise proteins encoded by 1 or more, 2 or more, 3 or more, 4 or more, or all of the following genes: KRAS, U2AF1, TP53, SMAD4, and GNAS. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: KRAS_G12C, KRAS_G12D, U2AF1_S34F, KRAS_G12V, TP53_R248Q, TP53_R248W, TP53_R175H, TP53_R273C, KRAS_G12R, KRAS_Q61H, TP53_R282W, TP53_R273H, TP53_G245S, SMAD4_R361C, GNAS_R201C, and GNAS_R201H. Such mutations are associated with, for example, pancreatic cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the antigenic peptides in Table 68.

As another example, the cancer-associated proteins can comprise proteins encoded by 1 or more, 2 or more, 3 or more, 4 or more, 5 or more, or all of the following genes: PIK3CA, FGFR3, TP53, RXRA, FBXW7, and NFE2L2. The antigenic peptides can comprise, for example, 1 or more, 2 or more, 3 or more, 4 or more, 5 or more, 6 or more, 7 or more, 8 or more, 9 or more, 10 or more, 11 or more, 12 or more, or all of the following recurrent cancer mutations: PIK3CA_E545K, FGFR3_S249C, TP53_R248Q, PIK3CA_E542K, RXRA_S427F, FBXW7_R505G, TP53_R280T, NFE2L2_E79K, FGFR3_R248C, TP53_K132N, TP53 R248W, TP53_R175H, and TP53_R273C. Such mutations are associated with, for example, bladder cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, or all of the antigenic peptides in Table 76.

As another example, the cancer-associated proteins can comprise proteins encoded by 1 or more, 2 or more, or all of the following genes: PIK3CA, AKT1, and ESR1. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, or all of the following recurrent cancer mutations: PIK3CA_E545K, PIK3CA_E542K, PIK3CA_H1047R, AKT1_E17K, PIK3CA_H1047L, PIK3CA_Q546K, PIK3CA_E545A, PIK3CA_E545G, ESRI_K303R, ESRI_D538G, ESRI_Y537S, ESRI_Y537N, ESRI_Y537C, and ESR1_E380Q. Such mutations are associated with, for example, breast cancer (e.g., ER+breast cancer). The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all of the antigenic peptides in Table 87.

As another example, the cancer-associated proteins can comprise proteins encoded by 1 or more, 2 or more, 3 or more, 4 or more, 5 or more, or all of the following genes: PTEN, KRAS, PIK3CA, CTNNB1, FBXW7, and TP53. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: PTEN_R130G, PTEN_R130Q, KRAS_G12D, KRAS_G12V, PIK3CA_H1047R; PIK3CA_R88Q, PIK3CA_E545K, PIK3CA_E542K, CTNNB1_S37F, KRAS_G13D, CTNNB1_S37C, PIK3CA_H1047L, PIK3CA_G118D, KRAS_G12A, FBXW7_R505C, and TP53_R248W. Such mutations are associated with, for example, uterine cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the antigenic peptides in Table 95.

As another example, the cancer-associated protein can comprise the protein encoded by TP53. The antigenic peptides can comprise, for example, 1 or more, 2 or more, 3 or more, 4 or more, 5 or more, 6 or more, 7 or more, 8 or more, 9 or more, 10 or more, 11 or more, or all of the following recurrent cancer mutations: TP53_R248Q, TP53_R248W, TP53_R175H, TP53_R273C, TP53_R282W, TP53_R273H, TP53_Y220C, TP53_I195T, TP53_C176Y, TP53_H179R, TP53_S241F, and TP53_H193R. Such mutations are associated with, for example, ovarian cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, or all of the antigenic peptides in Table 100.

As another example, the cancer-associated proteins can comprise proteins encoded by 1 or more, 2 or more, 3 or more, 4 or more, or all of the following genes: TP53, PIK3CA, IDH1, IDH2, and EGFR. The antigenic peptides can comprise, for example, 1 or more, 2 or more, 3 or more, 4 or more, 5 or more, 6 or more, 7 or more, 8 or more, 9 or more, 10 or more, or all of the following recurrent cancer mutations: TP53_R273L, TP53_R273C, TP53_R273H, PIK3CA_G118D, IDH1_R132C, IDHI_R132G, IDHI_R132H, IDH1_R132S, IDH2_R172K, PIK3CA_E453K, and EGFR_G598V. Such mutations are associated with, for example, low-grade glioma. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, or all of the antigenic peptides in Table 104.

As another example, the cancer-associated proteins can comprise proteins encoded by 1 or more, 2 or more, 3 or more, or all of the following genes: KRAS, BRAF, PIK3CA, and TP53. The antigenic peptides can comprise, for example, 1 or more, 2 or more, 3 or more, 4 or more, 5 or more, 6 or more, 7 or more, 8 or more, 9 or more, 10 or more, 11 or more, or all of the following recurrent cancer mutations: KRAS_G12C, KRAS_G12D, BRAF_V600E, KRAS_G12V, PIK3CA_E545K, TP53_R248W, TP53_R175H, TP53_R273C, PIK3CA_H1047R, TP53_R282W, TP53 R273H, and KRAS_G13D. Such mutations are associated with, for example, colorectal cancer (e.g., MSS colorectal cancer). The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, or all of the antigenic peptides in Table 108.

As another example, the cancer-associated proteins can comprise proteins encoded by 1 or more, 2 or more, 3 or more, 4 or more, 5 or more, 6 or more, 7 or more, 8 or more, or all of the following genes: PIK3CA, CHEK2, RGPD8, ANKRD36C, TP53, ZNF814, KRTAP1-5, KRTAP4-11, andHRAS. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the following recurrent cancer mutations: PIK3CA_E545K, CHEK2_K373E, RGPD8_P1760A, ANKRD36C_I634T, TP53_R248Q, PIK3CA_E542K, TP53_R248W, TP53_R175H, PIK3CA_H1047R, TP53_R282W, TP53_R273H, TP53_G245S, TP53_Y220C, ZNF814_D404E, KRTAP1-5_I88T, KRTAP4-11_L161V, and HRAS_G13V. Such mutations are associated with, for example, head and neck cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the antigenic peptides in Table 112.

As another example, the cancer-associated proteins can comprise proteins encoded by 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, or all of the following genes: KRAS, BRAF, PIK3CA, TRIM48, PTEN, POLE, PGM5, MBOAT2, KIAA2026, FBXW7, C12orf4, ZBTB20, XYLT2, WNT16, UBR5, TGFBR2, SVIL, RNF43, PLEKHA6, LARP4B, FHOD3, DOCK3, BMPR2, ARID1A, ADAM28, and ACVR2A. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, or all of the following recurrent cancer mutations: KRAS_G12D, BRAF_V600E, PIK3CA_H1047R, TRIM48_Y192H, PTEN_R130N, POLE_V411L, POLE_P286R, PIK3CA_R88N, PGM5_I98V, MBOAT2_R43N, KIAA2026_R574C, FBXW7_R465C, C12orf4_R335N, ZBTB20_p.Pro692LeufsTer43, XYLT2_p.Gly529AlafsTer78, WNT16_p.Gly167AlafsTer17, UBR5_p.Glu2121LysfsTer28, TGFBR2_p.Glu150GlyfsTer35, SVIL_p.Met1863TrpfsTer44, RNF43_p.Gly659ValfsTer41, PLEKHA6_p.Val328TyrfsTer172, LARP4B_p.Thr163HisfsTer47, FHOD3_p.Ser336ValfsTer138, DOCK3_p.Pro1852GlnfsTer45, BMPR2_p.Asn583ThrfsTer44, ARID1A_p.Asp1850ThrfsTer33, ADAM28_p.Asn75LysfsTer15, and ACVR2A_p.Lys435GlufsTer19. Such mutations are associated with, for example, DNA mismatch repair deficient cancers or tumors. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, or all of the antigenic peptides in Table 116. An exemplary fusion polypeptide insert sequences (i.e., the peptide sequence downstream of the tLLO) comprises, consists essentially of, or consists of a sequence at least 85%, 90%, 91%, 92%, 93%, 94%, 95%, 96%, 97%, 98%, 99%, or 100% identical to the sequence set forth in SEQ ID NO: 917. A breakdown of the amino acids positions of the individual components in each construct is provided in Table 117.

C. PEST-Containing Peptides

The recombinant fusion proteins disclosed herein comprise a PEST-containing peptide. The PEST-containing peptide may be at the amino terminal (N-terminal) end of the fusion polypeptide . . . (i.e., N-terminal to the antigenic peptides), may be at the carboxy terminal (C-terminal) end of the fusion polypeptide (i.e., C-terminal to the antigenic peptides), or may be embedded within the antigenic peptides. In some recombinant *Listeria* strains and methods, a PEST containing peptide is not part of and is separate from the fusion polypeptide. Fusion of antigenic peptides to a PEST-like sequence, such as an LLO peptide, can enhance the immunogenicity of the antigenic peptides and can increase cell-mediated and antitumor immune responses (i.e., increase cell-mediated and anti-tumor immunity). See, e.g., Singh et al. (2005) *J Immunol* 175(6):3663-3673, herein incorporated by reference in its entirety for all purposes.

A PEST-containing peptide is one that comprises a PEST sequence or a PEST-like sequence. PEST sequences in eukaryotic proteins have long been identified. For example, proteins containing amino acid sequences that are rich in prolines (P), glutamic acids (E), serines (S) and threonines (T) (PEST), generally, but not always, flanked by clusters containing several positively charged amino acids, have rapid intracellular half-lives (Rogers et al. (1986) *Science* 234:364-369, herein incorporated by reference in its entirety for all purposes). Further, it has been reported that these sequences target the protein to the ubiquitin-proteosome pathway for degradation (Rechsteiner and Rogers (1996) *Trends Biochem. Sci.* 21:267-271, herein incorporated by reference in its entirety for all purposes). This pathway is also used by eukaryotic cells to generate immunogenic peptides that bind to MHC class I and it has been hypothesized that PEST sequences are abundant among eukaryotic proteins that give rise to immunogenic peptides (Realini et al. (1994) *FEBS Lett.* 348:109-113, herein incorporated by reference in its entirety for all purposes). Prokaryotic proteins do not normally contain PEST sequences because they do not have this enzymatic pathway. However, a PEST-like sequence rich in the amino acids proline (P), glutamic acid (E), serine (S) and threonine (T) has been reported at the amino terminus of LLO and has been reported to be essential for *L. monocytogenes* pathogenicity (Decatur and Portnoy (2000) *Science* 290:992-995, herein incorporated by reference in its entirety for all purposes). The presence of this PEST-like sequence in LLO targets the protein for destruction by proteolytic machinery of the host cell so that once the LLO has served its function and facilitated the escape of *L. monocytogenes* from the phagosomal or phagolysosomal vacuole, it is destroyed before it can damage the cells.

Identification of PEST and PEST-like sequences is well known in the art and is described, for example, in Rogers et al. (1986) *Science* 234(4774):364-378 and in Rechsteiner and Rogers (1996) *Trends Biochem. Sci.* 21:267-271, each of which is herein incorporated by reference in its entirety for all purposes. A PEST or PEST-like sequence can be identified using the PEST-find program. For example, a PEST-like sequence can be a region rich in proline (P), glutamic acid (E), serine (S), and threonine (T) residues. Optionally, the PEST-like sequence can be flanked by one or more clusters containing several positively charged amino acids. For example, a PEST-like sequence can be defined as a hydrophilic stretch of at least 12 amino acids in length with a high local concentration of proline (P), aspartate (D), glutamate (E), serine (S), and/or threonine (T) residues. In some cases, a PEST-like sequence contains no positively charged amino acids, namely arginine (R), histidine (H), and lysine (K). Some PEST-like sequences can contain one or more internal phosphorylation sites, and phosphorylation at these sites precedes protein degradation.

In one example, the PEST-like sequence fits an algorithm disclosed in Rogers et al. In another example, the PEST-like sequence fits an algorithm disclosed in Rechsteiner and Rogers. PEST-like sequences can also be identified by an initial scan for positively charged amino acids R, H, and K within the specified protein sequence. All amino acids between the positively charged flanks are counted, and only those motifs containing a number of amino acids equal to or higher than the window-size parameter are considered further. Optionally, a PEST-like sequence must contain at least one P, at least one D or E, and at least one S or T.

The quality of a PEST motif can be refined by means of a scoring parameter based on the local enrichment of critical amino acids as well as the motifs hydrophobicity. Enrichment of D, E, P, S, and T is expressed in mass percent (w/w) and corrected for one equivalent of D or E, one1 of P, and one of S or T. Calculation of hydrophobicity can also follow in principle the method of Kyte and Doolittle (1982) *J Mol. Biol.* 157:105, herein incorporated by reference in its entirety for all purposes. For simplified calculations, Kyte-Doolittle hydropathy indices, which originally ranged from −4.5 for arginine to +4.5 for isoleucine, are converted to positive integers, using the following linear transformation, which yielded values from 0 for arginine to 90 for isoleucine: Hydropathy index=10*Kyte-Doolittle hydropathy index+45.

A potential PEST motif's hydrophobicity can also be calculated as the sum over the products of mole percent and hydrophobicity index for each amino acid species. The desired PEST score is obtained as combination of local enrichment term and hydrophobicity term as expressed by the following equation: PEST score=0.55* DEPST−0.5* hydrophobicity index.

Thus, a PEST-containing peptide can refer to a peptide having a score of at least +5 using the above algorithm. Alternatively, it can refer to a peptide having a score of at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 32, at least 35, at least 38, at least 40, or at least 45.

Any other available methods or algorithms known in the art can also be used to identify PEST-like sequences. See, e.g., the CaSPredictor (Garay-Malpartida et al. (2005) Bioinformatics 21 Suppl 1:i169-76, herein incorporated by reference in its entirety for all purposes). Another method that can be used is the following: a PEST index is calculated for each stretch of appropriate length (e.g. a 30-35 amino acid stretch) by assigning a value of one to the amino acids Ser, Thr, Pro, Glu, Asp, Asn, or Gln. The coefficient value (CV) for each of the PEST residues is one and the CV for each of the other AA (non-PEST) is zero.

Examples of PEST-like amino acid sequences are those set forth in SEQ ID NOS: 320-328. One example of a PEST-like sequence is KENSISSMAPPASPPASPKT-PIEKKHADEIDK (SEQ ID NO: 320). Another example of a PEST-like sequence is KENSISSMAPPASPPASPK (SEQ ID NO: 321). However, any PEST or PEST-like amino acid sequence can be used. PEST sequence peptides are known and are described, for example, in U.S. Pat. Nos. 7,635,479; 7,665,238; and US 2014/0186387, each of which is herein incorporated by reference in its entirety for all purposes.

The PEST-like sequence can be from a *Listeria* species, such as from *Listeria monocytogenes*. For example, the *Listeria monocytogenes* ActA protein contains at least four such sequences (SEQ ID NOS: 322-325), any of which are suitable for use in the compositions and methods disclosed herein. Other similar PEST-like sequences include SEQ ID NOS: 329-331. Streptolysin O proteins from *Streptococcus* sp. also contain a PEST sequence. For example, *Streptococcus pyogenes* streptolysin O comprises the PEST sequence KQNTASTETTTTNEQPK (SEQ ID NO: 326) at amino acids 35-51 and *Streptococcus equisimilis* streptolysin O comprises the PEST-like sequence KQNTANTETTTT-NEQPK (SEQ ID NO: 327) at amino acids 38-54. Another example of a PEST-like sequence is from *Listeria seeligeri* cytolysin, encoded by the lso gene: RSEVTISPAETPESP-PATP (e.g., SEQ ID NO: 328).

Alternatively, the PEST-like sequence can be derived from other prokaryotic organisms. Other prokaryotic organisms wherein PEST-like amino acid sequences would be expected include, for example, other *Listeria* species.

(1) Listeriolysin O (LLO)

One example of a PEST-containing peptide that can be utilized in the compositions and methods disclosed herein is a listeriolysin O (LLO) peptide. An example of an LLO protein is the protein assigned GenBank Accession No. P13128 (SEQ ID NO: 332; nucleic acid sequence is set forth in GenBank Accession No. X15127). SEQ ID NO: 332 is a proprotein including a signal sequence. The first 25 amino acids of the proprotein is the signal sequence and is cleaved from LLO when it is secreted by the bacterium, thereby resulting in the full-length active LLO protein of 504 amino acids without the signal sequence. An LLO peptide disclosed herein can comprise the signal sequence or can comprise a peptide that does not include the signal sequence. Exemplary LLO proteins that can be used comprise, consist essentially of, or consist of the sequence set forth in SEQ ID NO: 332 or homologues, variants, isoforms, analogs, fragments, fragments of homologues, fragments of variants, fragments of analogs, and fragments of isoforms of SEQ ID NO: 332. Any sequence that encodes a fragment of an LLO protein or a homologue, variant, isoform, analog, fragment of a homologue, fragment of a variant, or fragment of an analog of an LLO protein can be used. A homologous LLO protein can have a sequence identity with a reference LLO protein, for example, of greater than 70%, 72%, 75%, 78%, 80%, 82%, 83%, 85%, 87%, 88%, 90%, 92%, 93%, 95%, 96%, 97%, 98%, or 99%.

Another example of an LLO protein is set forth in SEQ ID NO: 333. LLO proteins that can be used can comprise, consist essentially of, or consist of the sequence set forth in SEQ ID NO: 333 or homologues, variants, isoforms, analogs, fragments, fragments of homologues, fragments of variants, fragments of analogs, and fragments of isoforms of SEQ ID NO: 333.

Another example of an LLO protein is an LLO protein from the *Listeria monocytogenes* 10403S strain, as set forth in GenBank Accession No.: ZP_01942330 or EBA21833, or as encoded by the nucleic acid sequence as set forth in GenBank Accession No.: NZ_AARZ01000015 or AARZ01000015.1. Another example of an LLO protein is an LLO protein from the *Listeria monocytogenes* 4b F2365 strain (see, e.g., GenBank Accession No.: YP_012823), EGD-e strain (see, e.g., GenBank Accession No.: NP_463733), or any other strain of *Listeria monocytogenes*. Yet another example of an LLO protein is an LLO protein from Flavobacteriales bacterium HTCC2170 (see, e.g., GenBank Accession No.: ZP_01106747 or EAR01433, or encoded by GenBank Accession No.: NZ_AAOC01000003). LLO proteins that can be used can comprise, consist essentially of, or consist of any of the above LLO proteins or homologues, variants, isoforms, analogs, fragments, fragments of homologues, fragments of variants, fragments of analogs, and fragments of isoforms of the above LLO proteins.

Proteins that are homologous to LLO, or homologues, variants, isoforms, analogs, fragments, fragments of homologues, fragments of variants, fragments of analogs, and fragments of isoforms thereof, can also be used. One such example is alveolysin, which can be found, for example, in *Paenibacillus alvei* (see, e.g., GenBank Accession No.: P23564 or AAA22224, or encoded by GenBank Accession No.: M62709). Other such homologous proteins are known.

The LLO peptide can be a full-length LLO protein or a truncated LLO protein or LLO fragment. Likewise, the LLO peptide can be one that retains one or more functionalities of a native LLO protein or lacks one or more functionalities of a native LLO protein. For example, the retained LLO functionality can be allowing a bacteria (e.g., *Listeria*) to escape from a phagosome or phagolysosome, or enhancing the immunogenicity of a peptide to which it is fused. The retained functionality can also be hemolytic function or antigenic function. Alternatively, the LLO peptide can be a non-hemolytic LLO. Other functions of LLO are known, as are methods and assays for evaluating LLO functionality.

An LLO fragment can be a PEST-like sequence or can comprise a PEST-like sequence. LLO fragments can comprise one or more of an internal deletion, a truncation from the C-terminal end, and a truncation from the N-terminal end. In some cases, an LLO fragment can comprise more than one internal deletion. Other LLO peptides can be full-length LLO proteins with one or more mutations.

Some LLO proteins or fragments have reduced hemolytic activity relative to wild type LLO or are non-hemolytic fragments. For example, an LLO protein can be rendered non-hemolytic by deletion or mutation of the activation domain at the carboxy terminus, by deletion or mutation of cysteine 484, or by deletion or mutation at another location. Other LLO proteins are rendered non-hemolytic by a deletion or mutation of the cholesterol binding domain (CBD) as detailed in U.S. Pat. No. 8,771,702, herein incorporated by reference in its entirety for all purposes. The mutations can comprise, for example, a substitution or a deletion. The entire CBD can be mutated, portions of the CBD can be mutated, or specific residues within the CBD can be mutated. For example, the LLO protein can comprise a mutation of one or more of residues C484, W491, and W492 (e.g., C484, W491, W492, C484 and W491, C484 and W492, W491 and W492, or all three residues) of SEQ ID NO: 332 or corresponding residues when optimally aligned with SEQ ID NO: 332 (e.g., a corresponding cysteine or tryptophan residue). As an example, a mutant LLO protein can be created wherein residues C484, W491, and W492 of LLO are substituted with alanine residues, which will substantially reduce hemolytic activity relative to wild type LLO. The mutant LLO protein with C484A, W491A, and W492A mutations is termed "mutLLO."

As another example, a mutant LLO protein can be created with an internal deletion comprising the cholesterol-binding domain. The sequence of the cholesterol-binding domain of SEQ ID NO: 332 set forth in SEQ ID NO: 351. For example, the internal deletion can be a 1-11 amino acid deletion, an 11-50 amino acid deletion, or longer. Likewise, the mutated region can be 1-11 amino acids, 11-50 amino acids, or longer (e.g., 1-50, 1-11, 2-11, 3-11, 4-11, 5-11, 6-11, 7-11, 8-11, 9-11, 10-11, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 12-50, 11-15, 11-20, 11-25, 11-30, 11-35, 11-40, 11-50, 11-60, 11-70, 11-80, 11-90, 11-100, 11-150, 15-20, 15-25, 15-30, 15-35, 15-40, 15-50, 15-60, 15-70, 15-80, 15-90, 15-100, 15-150, 20-25, 20-30, 20-35, 20-40, 20-50, 20-60, 20-70, 20-80, 20-90, 20-100, 20-150, 30-35, 30-40, 30-60, 30-70, 30-80, 30-90, 30-100, or 30-150 amino acids). For example, a mutated region consisting of residues 470-500, 470-510, or 480-500 of SEQ ID NO: 332 will result in a deleted sequence comprising the CBD (residues 483-493 of SEQ ID NO: 332). However, the mutated region can also be a fragment of the CBD or can overlap with a portion of the CBD. For example, the mutated region can consist of residues 470-490, 480-488, 485-490, 486-488, 490-500, or 486-510 of SEQ ID NO: 332. For example, a fragment of the CBD (residues 484-492) can be replaced with a heterologous sequence, which will substantially reduce hemolytic activity relative to wild type LLO. For example, the CBD (ECTGLAWEWWR; SEQ ID NO: 351) can be replaced with a CTL epitope from the antigen NY-ESO-1 (ESLL-MWITQCR; SEQ ID NO: 352), which contains the HLA-A2 restricted epitope 157-165 from NY-ESO-1. The resulting LLO is termed "ctLLO."

In some mutated LLO proteins, the mutated region can be replaced by a heterologous sequence. For example, the mutated region can be replaced by an equal number of heterologous amino acids, a smaller number of heterologous amino acids, or a larger number of amino acids (e.g., 1-50, 1-11, 2-11, 3-11, 4-11, 5-11, 6-11, 7-11, 8-11, 9-11, 10-11, 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 12-50, 11-15, 11-20, 11-25, 11-30, 11-35, 11-40, 11-50, 11-60, 11-70, 11-80, 11-90, 11-100, 11-150, 15-20, 15-25, 15-30, 15-35, 15-40, 15-50, 15-60, 15-70, 15-80, 15-90, 15-100, 15-150, 20-25, 20-30, 20-35, 20-40, 20-50, 20-60, 20-70, 20-80, 20-90, 20-100, 20-150, 30-35, 30-40, 30-60, 30-70, 30-80, 30-90, 30-100, or 30-150 amino acids). Other mutated LLO proteins have one or more point mutations (e.g., a point mutation of 1 residue, 2 residues, 3 residues, or more). The mutated residues can be contiguous or not contiguous.

In one example embodiment, an LLO peptide may have a deletion in the signal sequence and a mutation or substitution in the CBD.

Some LLO peptides are N-terminal LLO fragments (i.e., LLO proteins with a C-terminal deletion). Some LLO peptides are at least 494, 489, 492, 493, 500, 505, 510, 515, 520, or 525 amino acids in length or 492-528 amino acids in length. For example, the LLO fragment can consist of about the first 440 or 441 amino acids of an LLO protein (e.g., the first 441 amino acids of SEQ ID NO: 332 or 333, or a corresponding fragment of another LLO protein when optimally aligned with SEQ ID NO: 332 or 333). Other N-terminal LLO fragments can consist of the first 420 amino acids of an LLO protein (e.g., the first 420 amino acids of SEQ ID NO: 332 or 333, or a corresponding fragment of another LLO protein when optimally aligned with SEQ ID NO: 332 or 333). Other N-terminal fragments can consist of about amino acids 20-442 of an LLO protein (e.g., amino acids 20-442 of SEQ ID NO: 332 or 333, or a corresponding fragment of another LLO protein when optimally aligned with SEQ ID NO: 332 or 333). Other N-terminal LLO fragments comprise any ALLO without the activation domain comprising cysteine 484, and in particular without cysteine 484. For example, the N-terminal LLO fragment can correspond to the first 425, 400, 375, 350, 325, 300, 275, 250, 225, 200, 175, 150, 125, 100, 75, 50, or 25 amino acids of an LLO protein (e.g., the first 425, 400, 375, 350, 325, 300, 275, 250, 225, 200, 175, 150, 125, 100, 75, 50, or 25 amino acids of SEQ ID NO: 332 or 333, or a corresponding fragment of another LLO protein when optimally aligned with SEQ ID NO: 332 or 333). Preferably, the fragment comprises one or more PEST-like sequences. LLO fragments and truncated LLO proteins can contain residues of a homologous LLO protein that correspond to any one of the above specific amino acid ranges. The residue numbers need not correspond exactly with the residue numbers enumerated above (e.g., if the homologous LLO protein has an insertion or deletion relative to a specific LLO protein disclosed herein). Examples of N-terminal LLO fragments include SEQ ID NOS: 334, 335, and 336. LLO proteins that can be used comprise, consist essentially of, or consist of the sequence set forth in SEQ ID NO: 334, 335, or 336 or homologues, variants, isoforms, analogs, fragments, fragments of homologues, fragments of variants, fragments of analogs, and fragments of isoforms of SEQ ID NO: 334, 335, or 336. In some compositions and methods, the N-terminal LLO fragment set forth in SEQ ID NO: 336 is used. An example of a nucleic acid encoding the N-terminal LLO fragment set forth in SEQ ID NO: 336 is SEQ ID NO: 337.

(2) ActA

Another example of a PEST-containing peptide that can be utilized in the compositions and methods disclosed herein is an ActA peptide. ActA is a surface-associated protein and acts as a scaffold in infected host cells to facilitate the polymerization, assembly, and activation of host actin polymers in order to propel a Listeria monocytogenes through the cytoplasm. Shortly after entry into the mammalian cell cytosol, L. monocytogenes induces the polymerization of host actin filaments and uses the force generated by actin polymerization to move, first intracellularly and then from cell to cell. ActA is responsible for mediating actin nucleation and actin-based motility. The ActA protein provides multiple binding sites for host cytoskeletal components, thereby acting as a scaffold to assemble the cellular actin polymerization machinery. The N-terminus of ActA binds to monomeric actin and acts as a constitutively active nucleation promoting factor by stimulating the intrinsic actin nucleation activity. The actA and hly genes are both members of the 10-kb gene cluster regulated by the transcriptional activator PrfA, and actA is upregulated approximately 226-fold in the mammalian cytosol. Any sequence that encodes an ActA protein or a homologue, variant, isoform, analog, fragment of a homologue, fragment of a variant, or fragment of an analog of an ActA protein can be used. A homologous ActA protein can have a sequence identity with a reference ActA protein, for example, of greater than 70%, 72%, 75%, 78%, 80%, 82%, 83%, 85%, 87%, 88%, 90%, 92%, 93%, 95%, 96%, 97%, 98%, or 99%.

One example of an ActA protein comprises, consists essentially of, or consists of the sequence set forth in SEQ ID NO: 338. Another example of an ActA protein comprises, consists essentially of, or consists of the sequence set forth in SEQ ID NO: 339. The first 29 amino acid of the proprotein corresponding to either of these sequences are the signal sequence and are cleaved from ActA protein when it is secreted by the bacterium. An ActA peptide can comprise the signal sequence (e.g., amino acids 1-29 of SEQ ID NO: 338 or 339), or can comprise a peptide that does not include the signal sequence. Other examples of ActA proteins comprise, consist essentially of, or consist of homologues, variants, isoforms, analogs, fragments, fragments of homologues, fragments of isoforms, or fragments of analogs of SEQ ID NO: 338 or 339.

Another example of an ActA protein is an ActA protein from the Listeria monocytogenes 10403S strain (GenBank Accession No.: DQ054585) the NICPBP 54002 strain (GenBank Accession No.: EU394959), the S3 strain (GenBank Accession No.: EU394960), NCTC 5348 strain (GenBank Accession No.: EU394961), NICPBP 54006 strain (GenBank Accession No.: EU394962), M7 strain (GenBank Accession No.: EU394963), S19 strain (GenBank Accession No.: EU394964), or any other strain of Listeria monocytogenes. LLO proteins that can be used can comprise, consist essentially of, or consist of any of the above LLO proteins or homologues, variants, isoforms, analogs, fragments, fragments of homologues, fragments of variants, fragments of analogs, and fragments of isoforms of the above LLO proteins.

ActA peptides can be full-length ActA proteins or truncated ActA proteins or ActA fragments (e.g., N-terminal ActA fragments in which a C-terminal portion is removed). Preferably, truncated ActA proteins comprise at least one PEST sequence (e.g., more than one PEST sequence). In addition, truncated ActA proteins can optionally comprise an ActA signal peptide. Examples of PEST-like sequences contained in truncated ActA proteins include SEQ ID NOS: 322-325. Some such truncated ActA proteins comprise at least two of the PEST-like sequences set forth in SEQ ID NOS: 322-325 or homologs thereof, at least three of the PEST-like sequences set forth in SEQ ID NOS: 322-325 or homologs thereof, or all four of the PEST-like sequences set forth in SEQ ID NOS: 322-325 or homologs thereof. Examples of truncated ActA proteins include those comprising, consisting essentially of, or consisting of about residues 30-122, about residues 30-229, about residues 30-332, about residues 30-200, or about residues 30-399 of a full length ActA protein sequence (e.g., SEQ ID NO: 339). Other examples of truncated ActA proteins include those comprising, consisting essentially of, or consisting of about the first 50, 100, 150, 200, 233, 250, 300, 390, 400, or 418 residues of a full length ActA protein sequence (e.g., SEQ ID NO: 339). Other examples of truncated ActA proteins include those comprising, consisting essentially of, or consisting of about residues 200-300 or residues 300-400 of a full length ActA protein sequence (e.g., SEQ ID NO: 339). For example, the truncated ActA consists of the first 390 amino acids of the wild type ActA protein as described in U.S. Pat. No. 7,655,238, herein incorporated by reference in its entirety for all purposes. As another example, the truncated ActA can be an ActA-N100 or a modified version thereof (referred to as ActA-N100*) in which a PEST motif has been deleted and containing the nonconservative QDNKR (SEQ ID NO: 350) substitution as described in US 2014/0186387, herein incorporated by references in its entirety for all purposes. Alternatively, truncated ActA proteins can contain residues of a homologous ActA protein that corresponds to one of the above amino acid ranges or the amino acid ranges of any of the ActA peptides disclosed herein. The residue numbers need not correspond exactly with the residue numbers enumerated herein (e.g., if the homologous ActA protein has an insertion or deletion, relative to an ActA protein utilized herein, then the residue numbers can be adjusted accordingly).

Examples of truncated ActA proteins include, for example, proteins comprising, consisting essentially of, or consisting of the sequence set forth in SEQ ID NO: 340, 341, 342, or 343 or homologues, variants, isoforms, analogs, fragments of variants, fragments of isoforms, or fragments of analogs of SEQ ID NO: 340, 341, 342, or 343. SEQ ID NO: 340 referred to as ActA/PEST1 and consists of amino acids 30-122 of the full length ActA sequence set forth in SEQ ID NO: 339. SEQ ID NO: 341 is referred to as ActA/PEST2 or LA229 and consists of amino acids 30-229 of the full length ActA sequence set forth in the full-length ActA sequence set forth in SEQ ID NO: 339. SEQ ID NO: 342 is referred to as ActA/PEST3 and consists of amino acids 30-332 of the full-length ActA sequence set forth in SEQ ID NO: 339. SEQ ID NO: 343 is referred to as ActA/PEST4 and consists of amino acids 30-399 of the full-length ActA sequence set forth in SEQ ID NO: 339. As a specific example, the truncated ActA protein consisting of the sequence set forth in SEQ ID NO: 341 can be used.

Examples of truncated ActA proteins include, for example, proteins comprising, consisting essentially of, or consisting of the sequence set forth in SEQ ID NO: 344, 346, 347, or 349 or homologues, variants, isoforms, analogs, fragments of variants, fragments of isoforms, or fragments of analogs of SEQ ID NO: 344, 346, 347, or 349. As a specific example, the truncated ActA protein consisting of the sequence set forth in SEQ ID NO: 344 (encoded by the nucleic acid set forth in SEQ ID NO: 345) can be used. As another specific example, the truncated ActA protein consisting of the sequence set forth in SEQ ID NO: 347 (encoded by the nucleic acid set forth in SEQ ID NO: 348) can be used. SEQ ID NO: 348 is the first 1170 nucleotides encoding ActA in the *Listeria monocytogenes* 10403S strain. In some cases, the ActA fragment can be fused to a heterologous signal peptide. For example, SEQ ID NO: 349 sets forth an ActA fragment fused to an Hly signal peptide.

D. Generating Immunotherapy Constructs Encoding Recombinant Fusion Polypeptides

Also provided herein are methods for generating immunotherapy constructs encoding or compositions comprising the recombinant fusion polypeptides disclosed herein. For example, such methods can comprise selecting a set of recurrent cancer mutations to include in the immunotherapy construct, designing antigenic peptides comprising each of the recurrent cancer mutations (and, for example, testing the hydropathy of the each antigenic peptide, and modifying or deselecting an antigenic peptide if it scores above a selected hydropathy index threshold value), selecting one or more sets of antigenic peptides, designing one or more fusion polypeptides comprising each of the selected antigenic peptides, and generating a nucleic acid construct encoding the fusion polypeptide.

Individual recurrent cancer mutations can be selected based on any criteria. For example, individual selected recurrent cancer mutations can be selected based on frequency of occurrence across multiple types of cancer (e.g., occurrence in at least 1%, 2%, 3%, 4%, 5%, 10%, 15%, 20%, 25%, 30%, 35%, 40%, 45%, 50%, 60%, 70%, 80%, 90%, 95%, or 99% of all cancer patients), frequency of occurrence in a particular type of cancer (e.g., occurrence in at least 1%, 2%, 3%, 4%, 5%, 10%, 15%, 20%, 25%, 30%, 35%, 40%, 45%, 50%, 60%, 70%, 80%, 90%, 95%, or 99% of all patients having a particular type of cancer), location within a functional domain of a cancer-associated protein, status as a known cancer driver mutation, status as a known chemotherapy resistance mutation, or identification as a somatic missense mutation. A particular cancer-associated protein can be selected, for example, if mutations in a particular cancer-associated protein may occur in at least 1%, 2%, 3%, 4%, 5%10%, 15%, 20%, 25%, 30%, 35%, 40%, 4%5% 50%, 60%, 70%, 80%, 90%, 95%, or 99% of all instances of cancer or a particular type of cancer. After selection of one or more cancer-associated proteins, the highest frequency shared somatic mutations can be identified. This can be done, for example, using databases such as COSMIC (Catalogue of Somatic Mutations in Cancer; cancer.Sanger.ac.uk) or Cancer Genome Analysis or other similar cancer-associated gene database. Examples of other such databases include TCGA, IGGC, and cBioportal. The mutations can be ranked, for example, according to one of more of the following: frequency of occurrence in a particular type of cancer or across all cancers; locations within mutational hotspots as disclosed elsewhere herein; and effect of the mutation on function of the protein (e.g., loss of function of a tumor suppressor protein; known cancer "driver" mutations; known chemotherapy resistance mutations). Optionally, one or more of nonsense mutations, deletion mutations, insertion mutations, frameshift mutations, or translocation mutations can be excluded. In some cases, only somatic missense mutations are considered. In some cases, only frameshift (e.g., somatic frameshift mutations) are considered. In some cases, both somatic missense and frameshift mutations are considered.

A set of recurrent cancer mutations can be selected based on one or more additional criteria. For example, the set of recurrent cancer mutations can be selected based on the set including the potential mutated epitopes that would be found in at least 50%, 55%, 60%, 65%, 70%, 75% 80%, 85%, 90%, 95%, 96%, 97%, 98%, or 99% of cancer patients who have a mutation in a single cancer-associated protein, or at least 50%, 55%, 60%, 65%, 70%, 75% 80%, 85%, 90%, 95%, 96%, 97%, 98%, or 99% of cancer patients who have a somatic missense mutation in a single cancer-associated protein. Likewise, the set of recurrent cancer mutations can be selected based on the set including the potential mutated epitopes that would be found in at least 5%, 10%, 15%, 20%, 25%, 30%, 35%, 40%, 45%, 50%, 55%, 60%, 65%, 70%, 75% 80%, 85%, 90%, 95%, 96%, 97%, 98%, or 99% of cancer patients who have a particular type of cancer. The set can also be selected based on the set comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent cancer mutations from a single cancer-associated protein, or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent somatic missense cancer mutations from a single cancer-associated protein. Likewise, the set can also be selected based on the set comprising at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent cancer mutations from a single type of cancer, or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent somatic missense cancer mutations from a single type of cancer. For example, the single type of cancer can be non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), or head and neck cancer. The set can also be selected based on the set comprising no more than 30, 31, 32, 33, 34, 35, 36, 37, 38, 39, 40, 41, 42, 43, 44, 45, 46, 47, 48, 49 or 50 recurrent cancer mutations, or any other threshold based on the capacity for a particular delivery system (e.g., bacterial delivery system). In addition, the set can be selected such that at least 50%, 55%, 60%, 65%, 70%, 75% 80%, 85%, 90%, 95%, 96%, 97%, 98%, 99%, or all of the selected recurrent cancer mutations in step (a) are from a single cancer-associated protein, or that no more than 50%, 45%, 40%, 35%, 30%, 25%, 20%, 15%, 10%, 9%, 8%, 7%, 6%, 5% 4%, 3%, 2%, 1%, or none of the recurrent cancer mutations in step (a) are from the same cancer-associated protein.

In a specific example, mutation data can be sub-stratified by disease indication type. Particular types of mutations can be selected for consideration. For example, recurrent somatic mutations can include missense substitutions and insertions/deletions (INDELs) resulting in in-frame and frameshift mutations. The somatic mutations can be rank-ordered within a specific-indication cohort based on frequency of the total number of mutation events observed across all samples. Mutations occurring with frequencies below a certain frequency (e.g., 1%, 2%, 3%, 4%, 5%, or 10%) can be excluded. Recurrent mutations with disease-indication frequencies equal to and above, e.g., 1%, 2%, 3%, 4%, 5%, or 10% can be selected for panel.

After identification of a set of possible recurrent cancer mutations to include in a fusion polypeptide, sequences for antigenic peptides comprising each recurrent cancer mutation can be selected. Each antigenic peptide can be designed, for example, to comprise a fragment of the cancer-associated protein comprising a recurrent cancer mutation and flanking sequence on each side. Different size antigenic peptides can be used, as disclosed elsewhere herein. Preferably, however, at least about 10 flanking amino acids on each side of the recurrent cancer mutation are incorporated to accommodate class 1 MHC-1 presentation, in order to provide at least some of the different HLA T-cell receptor (TCR) reading frames. For example, an antigenic peptide can be selected to include a recurrent cancer mutation and 10 flanking amino acids from the cancer-associated protein on each side (i.e., a 21-mer). Alternatively, for example, an antigenic peptide can be selected to include a recurrent cancer mutation and 13 flanking amino acids from the cancer-associated protein on each side (i.e., a 27-mer).

The antigenic peptides can then be screened for hydrophobicity or hydrophilicity. Antigenic peptides can be selected, for example, if they are hydrophilic or if they score up to or below a certain hydropathy threshold, which can be predictive of secretability in a particular bacteria of interest (e.g., *Listeria monocytogenes*). For example, antigenic peptides can be scored by Kyte and Doolittle hydropathy index with a 21 amino acid window, all scoring above cutoff (around 1.6) are excluded as they are unlikely to be secretable by *Listeria monocytogenes*. See, e.g., Kyte-Doolittle (1982) *J Mol Biol* 157(1):105-132; herein incorporated by reference in its entirety for all purposes. Alternatively, an antigenic peptide scoring about a selected cutoff can be altered (e.g., changing the length of the antigenic peptide or shifting the region of the cancer-associated protein included in the antigenic peptide (so long as the antigenic peptide still contains the recurrent cancer mutation and sufficient flanking sequence on each side). Other sliding window sizes that can be used include, for example, 9, 11, 13, 15, 17, 19, 21, 23, 25, 27 or more amino acids. For example, the sliding window size can be 9-11 amino acids, 11-13 amino acids, 13-15 amino acids, 15-17 amino acids, 17-19 amino acids, 19-21 amino acids, 21-23 amino acids, 23-25 amino acids, or 25-27 amino acids. Other cutoffs that can be used include, for example, the following ranges 1.2-1.4, 1.4-1.6, 1.6-1.8, 1.8-2.0, 2.0-2.2 2.2-2.5, 2.5-3.0, 3.0-3.5, 3.5-4.0, or 4.0-4.5, or the cutoff can be 1.4, 1.5, 1.7, 1.8, 1.9, 2.0, 2.1, 2.2, 2.3, 2.3, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or 4.5. The cutoff can vary, for example, depending on the genus or species of the bacteria being used to deliver the fusion polypeptide.

Other suitable hydropathy plots or other appropriate scales include, for example, those reported in Rose et al. (1993) *Annu Rev Biomol Struct* 22:381-415; Biswas et al. (2003) *Journal of Chromatography A* 1000:637-655; Eisenberg (1984) *Ann Rev Biochem* 53:595-623; Abraham and Leo (1987) Proteins: Structure, Function and Genetics 2:130-152; Sweet and Eisenberg (1983) *Mol Biol* 171:479-488; Bull and Breese (1974) *Arch Biochem Biophys* 161: 665-670; Guy (1985) *Biophys J* 47:61-70; Miyazawa et al. (1985) *Macromolecules* 18:534-552; Roseman (1988) *J Mol Biol* 200:513-522; Wolfenden et al. (1981) *Biochemistry* 20:849-855; Wilson (1981) *Biochem J* 199:31-41; Cowan and Whittaker (1990) *Peptide Research* 3:75-80; Aboderin (1971) *Int J Biochem* 2:537-544; Eisenberg et al. (1984) *J Mol Biol* 179:125-142; Hopp and Woods (1981) *Proc Natl Acad Sci USA* 78:3824-3828; Manavalan and Ponnuswamy (1978) *Nature* 275:673-674; Black and Mould (1991) *Anal Biochem* 193:72-82; Fauchere and Pliska (1983) *Eur J Med Chem* 18:369-375; Janin (1979) *Nature* 277:491-492; Rao and Argos (1986) *Biochim Biophys Acta* 869:197-214; Tanford (1962) *Am Chem Soc* 84:4240-4274; Welling et al. (1985) *FEBS Lett* 188:215-218; Parker et al. (1986) *Biochemistry* 25:5425-5431; and Cowan and Whittaker (1990) *Peptide Research* 3:75-80, each of which is herein incorporated by reference in its entirety for all purposes.

Optionally, the remaining antigenic peptides can then be scored for their ability to bind to the subject human leukocyte antigen (HLA) type (for example by using the Immune Epitope Database (IED), which includes netMHCpan, ANN, SMMPMBEC. SMM, CombLib_Sidney2008, PickPocket, and netMHCcons) and ranked by best MHC binding score from each antigenic peptide. Other sources include TEpredict or other available MHC binding measurement scales. Cutoffs may be different for different expression vectors such as *Salmonella*.

Optionally, the antigenic peptides can be further screened for immunosuppressive epitopes (e.g., T-reg epitopes, IL-10-inducing T helper epitopes, and so forth) to deselect antigenic peptides or to avoid immunosuppressive influences.

Optionally, a predicative algorithm for immunogenicity of the epitopes can be used to screen the antigenic peptides. However, these algorithms are at best 20% accurate in predicting which peptide will generate a T cell response. Alternatively, no screening/predictive algorithms are used. Alternatively, the antigenic peptides can be screened for immunogenicity. For example, this can comprise contacting one or more T cells with an antigenic peptide, and analyzing for an immunogenic T cell response, wherein an immunogenic T cell response identifies the peptide as an immunogenic peptide. This can also comprise using an immunogenic assay to measure secretion of at least one of CD25, CD44, or CD69 or to measure secretion of a cytokine selected from the group comprising IFN-γ, TNF-α, IL-1, and IL-2 upon contacting the one or more T cells with the peptide, wherein increased secretion identifies the peptide as comprising one or more T cell epitopes.

In a specific example in which target peptides are generated for recurrent mutations, for missense substitutions, the mutant amino acid can be flanked by, e.g., up to 10 wild-type amino acids immediately before and after missense mutation position. For frameshift substitutions, the predicted peptide sequence arising from out-of-frame INDEL substitution can be generated from the annotation transcript and up to, e.g., 10 wild-type amino acids can be added upstream of frameshift mutation position. For in-frame INDEL substitutions, up to, e.g., 10 wild-type amino acid sequences before and after INDEL position can be joined together. Specific identifiers can be generated for each hotspot target peptide that consist of the gene symbol (HGNC format) and mutation substitution information (HGVS format) separated by an underscore. For example, the substitution of glycine for aspartic acid at position 12 in KRAS would create a specific identifier of KRAS_G12D. Target peptides can then subjected to BLAST analysis against the non-redundant protein sequences (nr) database for human. This step can ensure that target peptide sequences generated from frameshift mutations do not represent known, wild-type sequences. For missense substations, this step can ensure that flanking wild-type amino acids match the known human reference proteome.

The selected antigenic peptides can then be arranged into one or more candidate orders for a potential fusion polypeptide. If there are more usable antigenic peptides than can fit into a single plasmid, different antigenic peptides can be assigned priority ranks as needed/desired and/or split up into different fusion polypeptides (e.g., for inclusion in different recombinant *Listeria* strains). Priority rank can be determined by factors such as relative size, priority of transcription, and/or overall hydrophobicity of the translated polypeptide. The antigenic peptides can be arranged so that they are joined directly together without linkers, or any combination of linkers between any number of pairs of antigenic peptides, as disclosed in more detail elsewhere herein. The number of linear antigenic peptides to be included can be determined based on consideration of the number of constructs needed versus the mutational burden, the efficiency of translation and secretion of multiple epitopes from a single plasmid, the MOI needed for each bacteria or Lm comprising a plasmid, the number of recurrent cancer mutations or hotspot mutations in a particular cancer-associated protein, or how many recurrent cancer mutations need to be included to cover at least 50%, 60%, 70%, 80%, 90%, 95%, 96%, 97%, 98%, or 99% of cancer patients with a mutation or somatic mutation in that cancer-associated protein. Likewise, the number of linear antigenic peptides to be included can be determined based in part on consideration of the number of recurrent cancer mutations or hotspot mutations in a particular type of cancer, or how many recurrent cancer mutations need to be included to cover at least 5%, 10%, 15%, 20%, 25%, 30%, 35%, 40%, 45%, 50%, 60%, 70%, 80%, 90%, 95%, 96%, 97%, 98%, or 99% of cancer patients with a particular type of cancer. For example, ranges of linear antigenic peptides can be starting, for example, with about 50, 40, 30, 20, or 10 antigenic peptides per plasmid.

Different possible arrangements of the same antigenic peptides in a fusion polypeptide can be generated through one or more iterations of randomizing the order of the antigenic peptides. Such randomizing can include, for example, randomizing the order of the entire set of antigenic peptides, or can comprise randomizing the order of a subset of the antigenic peptides. For example, if there are 20 antigenic peptides (ordered 1-20), the randomizing can comprise randomizing the order of all 20 peptides or can comprise randomizing the order of only a subset of the peptides (e.g., peptides 1-5 or 6-10). Such randomization of the order can facilitate secretion and presentation of the fusion polypeptide and of each individual antigenic peptide. Alternatively, the order of the antigenic peptides can be generated using selected parameters, such as a predefined ranking of the antigenic peptides.

The combination of antigenic peptides or the entire fusion polypeptide (i.e., comprising the antigenic peptides and the PEST-containing peptide and any tags) can also be scored for hydrophobicity. For example, the entirety of the fused antigenic peptides or the entire fusion polypeptide can be scored for hydropathy by a Kyte and Doolittle hydropathy index with a sliding 21 amino acid window. If any region scores above a cutoff (e.g., around 1.6), the antigenic peptides can be reordered or shuffled within the fusion polypeptide using selected parameters or using randomization until an acceptable order of antigenic peptides is found (i.e., one in which no region scores above the cutoff). Alternatively, any problematic antigenic peptides can be removed or redesigned to be of a different size, or to shift the sequence of the cancer-associated protein included in the antigenic peptide (so long as the antigenic peptide still comprises the recurrent cancer mutation and sufficiently sized flanking sequences). Alternatively or additionally, one or more linkers between antigenic peptides as disclosed elsewhere herein can be added or modified to change the hydrophobicity. As with hydropathy testing for the individual antigenic peptides, other window sizes can be used, or other cutoffs can be used (e.g., depending on the genus or species of the bacteria being used to deliver the fusion polypeptide). In addition, other suitable hydropathy plots or other appropriate scales could be used.

Optionally, the combination of antigenic peptides or the entire fusion polypeptide can be further screened for immunosuppressive epitopes (e.g., T-reg epitopes, IL-10-inducing T helper epitopes, and so forth) to deselect antigenic peptides or to avoid immunosuppressive influences.

A nucleic acid encoding a candidate combination of antigenic peptides or fusion polypeptide can then be designed and optimized. For example, the sequence can be optimized for increased levels of translation, duration of expression, levels of secretion, levels of transcription, and any combination thereof. For example, the increase can be 2-fold to 1000-fold, 2-fold to 500-fold, 2-fold to 100-fold, 2-fold to 50-fold, 2-fold to 20-fold, 2-fold to 10-fold, or 3-fold to 5-fold relative to a control, non-optimized sequence.

For example, the fusion polypeptide or nucleic acid encoding the fusion polypeptide can be optimized for decreased levels of secondary structures possibly formed in the oligonucleotide sequence, or alternatively optimized to prevent attachment of any enzyme that may modify the sequence. Expression in bacterial cells can be hampered, for example, by transcriptional silencing, low mRNA half-life, secondary structure formation, attachment sites of oligonucleotide binding molecules such as repressors and inhibitors, and availability of rare tRNAs pools. The source of many problems in bacterial expressions is found within the original sequence. The optimization of RNAs may include modification of cis acting elements, adaptation of its GC-content, modifying codon bias with respect to non-limiting tRNAs pools of the bacterial cell, and avoiding internal homologous regions. Thus, optimizing a sequence can entail, for example, adjusting regions of very high (>80%) or very low (<30%) GC content. Optimizing a sequence can also entail, for example, avoiding one or more of the following cis-acting sequence motifs: internal TATA-boxes, chi-sites, and ribosomal entry sites; AT-rich or GC-rich sequence stretches; repeat sequences and RNA secondary structures; (cryptic) splice donor and acceptor sites; branch points; or a combination thereof. Optimizing expression can also entail adding sequence elements to flanking regions of a gene and/or elsewhere in the plasmid.

Optimizing a sequence can also entail, for example, adapting the codon usage to the codon bias of host genes (e.g., *Listeria monocytogenes* genes). For example, the codons below can be used for *Listeria monocytogenes*.

| |
|---|
| A = GCA |
| C = TGT |
| D = GAT |
| E = GAA |
| F = TTC |
| G = GGT |
| H = CAT |
| I = ATT |
| K = AAA |
| L = TTA |
| M = ATG |
| N = AAC |
| P = CCA |
| Q = CAA |
| R = CGT |
| S = TCT |
| T = ACA |
| V = GTT |
| W = TGG |
| Y = TAT |
| STOP = TAA |

A nucleic acid encoding a fusion polypeptide can be generated and introduced into a delivery vehicle such as a bacteria strain or *Listeria* strain. Other delivery vehicles may be suitable for DNA immunotherapy or peptide immunotherapy, such as a vaccinia virus or virus-like particle. Once a plasmid encoding a fusion polypeptide is generated and introduced into a bacteria strain or *Listeria* strain, the bacteria or *Listeria* strain can be cultured and characterized to confirm expression and secretion of the fusion polypeptide comprising the antigenic peptides.

III. Recombinant Fusion Polypeptides Comprising Heteroclitic Antigenic Peptides

Disclosed herein are recombinant fusion polypeptides comprising a PEST-containing peptide fused to two or more antigenic peptides (i.e., in tandem, such as PEST-peptide1-peptide2), wherein each antigenic peptide (e.g., from a cancer-associated protein) comprises a heteroclitic mutation. Also disclosed herein are recombinant fusion polypeptides comprising a PEST-containing peptide fused to two or more antigenic peptides (i.e., in tandem, such as PEST-peptide1-peptide2), wherein each antigenic peptide (e.g., from a cancer-associated protein) comprises a heteroclitic mutation, and wherein at least two of the antigenic peptides comprise different heteroclitic mutations and are fragments of the same cancer-associated protein. Alternatively, each of the antigenic peptides comprises a different heteroclitic mutation from a different cancer-associated protein. Alternatively, a combination of separate fusion polypeptides can be used in which each antigenic peptide is fused to its own PEST-containing peptide (e.g., PEST1-peptide1; PEST2-peptide2). Optionally, some or all of the fragments are non-contiguous fragments of the same cancer-associated protein. Non-contiguous fragments are fragments that do not occur sequentially in a protein sequence (e.g., the first fragment consists of residues 10-30, and the second fragment consists of residues 100-120; or the first fragment consists of residues 10-30, and the second fragment consists of residues 20-40).

Also disclosed herein are recombinant fusion polypeptides comprising two or more antigenic peptides, wherein each antigenic peptide (e.g., from a cancer-associated protein) comprises a heteroclitic mutation, wherein at least two of the antigenic peptides comprise different heteroclitic mutations and are fragments of the same cancer-associated protein, and wherein the fusion polypeptide does not comprise a PEST-containing peptide. Also disclosed herein are recombinant fusion polypeptides comprising two or more antigenic peptides, wherein each antigenic peptide (e.g., from a cancer-associated protein) comprises a heteroclitic mutation, wherein at least two of the antigenic peptides comprise different heteroclitic mutations and are fragments of the same cancer-associated protein, and wherein the fusion polypeptide does not comprise a PEST-containing peptide. Alternatively, each of the antigenic peptides comprises a different heteroclitic mutation from a different cancer-associated protein. Optionally, some or all of the fragments are non-contiguous fragments of the same cancer-associated protein.

Also provided herein are recombinant fusion polypeptides comprising from N-terminal end to C-terminal end a bacterial secretion sequence, a ubiquitin (Ub) protein, and two or more antigenic peptides (i.e., in tandem, such as Ub-peptide1-peptide2), wherein each antigenic peptide (e.g., from a cancer-associated protein) comprises a heteroclitic mutation. Alternatively, a combination of separate fusion polypeptides can be used in which each antigenic peptide is fused to its own secretion sequence and Ub protein (e.g., Ub1-peptide1; Ub2-peptide2). Optionally, some or all of the fragments are non-contiguous fragments of the same cancer-associated protein.

Nucleic acids (termed minigene constructs) encoding such recombinant fusion polypeptides are also disclosed. Such minigene nucleic acid constructs can further comprise two or more open reading frames linked by a Shine-Dalgamo ribosome binding site nucleic acid sequence between each open reading frame. For example, a minigene nucleic acid construct can further comprise two to four open reading frames linked by a Shine-Dalgamo ribosome binding site nucleic acid sequence between each open reading frame. Each open reading frame can encode a different polypeptide. In some nucleic acid constructs, the codon encoding the carboxy terminus of the fusion polypeptide is followed by two stop codons to ensure termination of protein synthesis.

The bacterial signal sequence can be a Listerial signal sequence, such as an Hly or an ActA signal sequence, or any other known signal sequence. In other cases, the signal sequence can be an LLO signal sequence. The signal sequence can be bacterial, can be native to a host bacterium (e.g., *Listeria monocytogenes*, such as a secA1 signal peptide), or can be foreign to a host bacterium. Specific examples of signal peptides include an Usp45 signal peptide from *Lactococcus lactis*, a Protective Antigen signal peptide from *Bacillus anthracis*, a secA2 signal peptide such the p60 signal peptide from *Listeria monocytogenes*, and a Tat signal peptide such as a *B. subtilis* Tat signal peptide (e.g., PhoD). In specific examples, the secretion signal sequence is from a *Listeria* protein, such as an $ActA_{300}$ secretion signal or an $ActA_{100}$ secretion signal.

The ubiquitin can be, for example, a full-length protein. The ubiquitin expressed from the nucleic acid construct provided herein can be cleaved at the carboxy terminus from the rest of the recombinant fusion polypeptide expressed from the nucleic acid construct through the action of hydrolases upon entry to the host cell cytosol. This liberates the amino terminus of the fusion polypeptide, producing a peptide in the host cell cytosol.

Selection of, variations of, and arrangement of antigenic peptides within a fusion polypeptide are discussed in detail elsewhere herein, and cancer-associated proteins are discussed in more detail elsewhere herein. The recombinant fusion polypeptides can comprise one or more tags as disclosed in more detail elsewhere herein.

The recombinant fusion polypeptides disclosed herein can be expressed by recombinant *Listeria* strains or can be expressed and isolated from other vectors and cell systems used for protein expression and isolation. Recombinant *Listeria* strains comprising expressing such antigenic peptides can be used, for example in immunogenic compositions comprising such recombinant *Listeria* and in vaccines comprising the recombinant *Listeria* strain and an adjuvant. Expression of one or more antigenic peptides as a fusion polypeptides with a nonhemolytic truncated form of LLO, ActA, or a PEST-like sequence in host cell systems in *Listeria* strains and host cell systems other than *Listeria* can result in enhanced immunogenicity of the antigenic peptides.

The recombinant fusion polypeptide can be any molecular weight. For example, the recombinant fusion polypeptide can be less than or no more than about 200, 195, 190, 185, 180, 175, 170, 165, 160, 155, 150, 145, 140, 135, 130, or 125 kilodaltons (kDa). In a specific example, the recombinant fusion polypeptide is less than or no more than about 150 kDa or less than or no more than about 130 kDa. As another example the recombinant fusion polypeptide can be between about 50-200, 50-195, 50-190, 50-185, 50-180, 50-175, 50-170, 50-165, 50-160, 50-155, 50-150, 50-145, 50-140, 50-135, 50-130, 50-125, 100-200, 100-195, 100-190, 100-185, 100-180, 100-175, 100-170, 100-165, 100-160, 100-155, 100-150, 100-145, 100-140, 100-135, 100-130, or 100-125 kDa. In a specific example, the recombinant fusion polypeptide is between about 50-150, 100-150, 50-125, or 100-125 kDa. As another example, the recombinant fusion polypeptide can be at least about 50, 55, 60, 65, 70, 75, 80, 85, 90, 95, 100, 105, 110, 115, 120, or 125 kDa. As a specific example, the recombinant fusion polypeptide can be at least about 100 kDa.

Nucleic acids encoding such recombinant fusion polypeptides are also disclosed. The nucleic acid can be in any form. The nucleic acid can comprise or consist of DNA or RNA, and can be single-stranded or double-stranded. The nucleic acid can be in the form of a plasmid, such as an episomal plasmid, a multicopy episomal plasmid, or an integrative plasmid. Alternatively, the nucleic acid can be in the form of a viral vector, a phage vector, or in a bacterial artificial chromosome. Such nucleic acids can have one open reading frame or can have two or more open reading frames (e.g., an open reading frame encoding the recombinant fusion polypeptide and a second open reading frame encoding a metabolic enzyme). In one example, such nucleic acids can comprise two or more open reading frames linked by a Shine-Dalgarno ribosome binding site nucleic acid sequence between each open reading frame. For example, a nucleic acid can comprise two to four open reading frames linked by a Shine-Dalgarno ribosome binding site nucleic acid sequence between each open reading frame. Each open reading frame can encode a different polypeptide. In some nucleic acids, the codon encoding the carboxy terminus of the fusion polypeptide is followed by two stop codons to ensure termination of protein synthesis.

A. Heteroclitic Antigenic Peptides

Each heteroclitic antigenic peptide can be a fragment of a cancer-associated protein (i.e., a contiguous sequence of amino acids from a cancer-associated protein) comprising a heteroclitic mutation. Each heteroclitic antigenic peptide can be of any length sufficient to induce an immune response, and each heteroclitic antigenic peptide can be the same length or the heteroclitic antigenic peptides can have different lengths. For example, a heteroclitic antigenic peptide disclosed herein can be 5-100, 15-50, or 21-27 amino acids in length, or 15-100, 15-95, 15-90, 15-85, 15-80, 15-75, 15-70, 15-65, 15-60, 15-55, 15-50, 15-45, 15-40, 15-35, 15-30, 20-100, 20-95, 20-90, 20-85, 20-80, 20-75, 20-70, 20-65, 20-60, 20-55, 20-50, 20-45, 20-40, 20-35, 20-30, 11-21, 15-21, 21-31, 31-41, 41-51, 51-61, 61-71, 71-81, 81-91, 91-101, 101-121, 121-141, 141-161, 161-181, 181-201, 8-27, 10-30, 10-40, 15-30, 15-40, 15-25, 1-10, 10-20, 20-30, 30-40, 1-100, 5-75, 5-50, 5-40, 5-30, 5-20, 5-15, 5-10, 1-75, 1-50, 1-40, 1-30, 1-20, 1-15, 1-10, 8-11, or 11-16 amino acids in length. For example, a heteroclitic antigenic peptide can be 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids in length. For example, a heteroclitic antigenic peptide can be 8-100, 8-50, 8-30, 8-25, 8-22, 8-20, 8-15, 8-14, 8-13, 8-12, 8-11, 7-11, or 8-10 amino acids in length. In one example, a heteroclitic antigenic peptide can be 9 amino acids in length.

Each heteroclitic antigenic peptide can also be hydrophilic or can score up to or below a certain hydropathy threshold, which can be predictive of secretability in *Listeria monocytogenes* or another bacteria of interest. For example, heteroclitic antigenic peptides can be scored by a Kyte and Doolittle hydropathy index 21 amino acid window, and all scoring above a cutoff (around 1.6) can be excluded as they are unlikely to be secretable by *Listeria monocytogenes*.

Each heteroclitic antigenic peptide can comprise a single heteroclitic mutation or can comprise two or more heteroclitic mutations (e.g., two heteroclitic mutations). Exemplary heteroclitic mutant peptides are provided in the following table along with the corresponding wild type (native) peptides. The residues in the wild type peptides that are modified in the corresponding heteroclitic peptides are bolded and underlined.

TABLE 122

Heteroclitic Antigenic Peptides and Corresponding Native Peptides.

| Peptide (GENE_HLA Type) | Heteroclitic Peptide | Native Peptide |
|---|---|---|
| CEACAM5_A0201 | ILIGVLVGV (SEQ ID NO: 798) | IMIGVLVGV (SEQ ID NO: 1009) |
| CEACAM5_A0201 | ILMGVLVGV (SEQ ID NO: 820) | IMIGVLVGV (SEQ ID NO: 1010) |
| CEACAM5_A0301 | HVFGYSWYK (SEQ ID NO: 791) | HLFGYSWYK (SEQ ID NO: 1011) |
| CEACAM5_A2402 | IYPNASLLF (SEQ ID NO: 796) | IYPNASLLI (SEQ ID NO: 1012) |
| CEACAM5_B0702 | IPQVHTQVL (SEQ ID NO: 793) | IPQQHTQVL (SEQ ID NO: 1013) |
| GAGE1_A0301 | SLYYWPRPR (SEQ ID NO: 811) | STYYWPRPR (SEQ ID NO: 1014) |
| GAGE1_B0702 | WPRPRRYVM (SEQ ID NO: 795) | WPRPRRYVQ (SEQ ID NO: 1015) |
| hTERT_A0201_A2402 | IMAKFLHWL (SEQ ID NO: 816) | ILAKFLHWL (SEQ ID NO: 1016) |
| KLHL7_A2402 | VYILGGSQF (SEQ ID NO: 809) | VYILGGSQL (SEQ ID NO: 1017) |
| MAGEA3_A0201_A2402 | KVPEIVHFL (SEQ ID NO: 817) | KVAELVHFL (SEQ ID NO: 1018) |
| MAGEA3_A0301 | YMFPVIFSK (SEQ ID NO: 812) | YFFPVIFSK (SEQ ID NO: 1019) |
| MAGEA3_A2402 | IMPKAGLLF (SEQ ID NO: 810) | IMPKAGLLI (SEQ ID NO: 1020) |
| MAGEA3_B0702 | LPWTMNYPL (SEQ ID NO: 814) | LPTTMNYPL (SEQ ID NO: 1021) |
| MAGEA4_B0702 | MPSLREAAL (SEQ ID NO: 794) | YPSLREAAL (SEQ ID NO: 1022) |
| MAGEA6_A0301 | YLFPVIFSK (SEQ ID NO: 792) | YFFPVIFSK (SEQ ID NO: 1023) |
| NUF2_A0201 | YLMPVNSEV (SEQ ID NO: 807) | YMMPVNSEV (SEQ ID NO: 1024) |
| NUF2_A2402 | VWGIRLEHF (SEQ ID NO: 808) | VYGIRLEHF (SEQ ID NO: 1025) |
| NYESO1_A0201 | RLLEFYLAV (SEQ ID NO: 797) | RLLEFYLAM (SEQ ID NO: 1026) |
| NYESO1_B0702 | APRGPHGGM (SEQ ID NO: 813) | APRGPHGGA (SEQ ID NO: 1027) |
| PAGE4_A0201 | MAPDVVAFV (SEQ ID NO: 804) | EAPDVVAFV (SEQ ID NO: 1028) |
| PRAME_A0201 | NMTHVLYPL (SEQ ID NO: 815) | NLTHVLYPV (SEQ ID NO: 1029) |
| PSA_A0301 | GMAPLILSR (SEQ ID NO: 806) | GAAPLILSR (SEQ ID NO: 1030) |
| PSMA_A2402 | TYSVSFFSW (SEQ ID NO: 805) | TYSVSFDSL (SEQ ID NO: 1031) |
| RNF43_B0702 | NPQPVWLCL (SEQ ID NO: 801) | NSQPVWLCL (SEQ ID NO: 1032) |
| SART3_A0201 | LMQAEAPRL (SEQ ID NO: 803) | LLQAEAPRL (SEQ ID NO: 1033) |
| SSX2_A0201 | RLQGISPKV (SEQ ID NO: 802) | RLQGISPKI (SEQ ID NO: 310) |
| STEAP1_A0201 | LLLGTIHAV (SEQ ID NO: 799) | LLLGTIHAL (SEQ ID NO: 311) |
| STEAP1_A2402 | KYKKFPWWL (SEQ ID NO: 800) | KYKKFPHWL (SEQ ID NO: 312) |
| SURVIVIN_A0201 | KMSSGCAFL (SEQ ID NO: 818) | KHSSGCAFL (SEQ ID NO: 317) |
| SURVIVIN_A2402 | SWFKNWPFF (SEQ ID NO: 819) | STFKNWPFL (SEQ ID NO: 318) |

The heteroclitic antigenic peptides can be linked together in any manner. For example, the heteroclitic antigenic peptides can be fused directly to each other with no intervening sequence. Alternatively, the heteroclitic antigenic peptides can be linked to each other indirectly via one or more linkers, such as peptide linkers. In some cases, some pairs of adjacent heteroclitic antigenic peptides can be fused directly to each other, and other pairs of heteroclitic antigenic peptides can be linked to each other indirectly via one or more linkers. The same linker can be used between each pair of adjacent heteroclitic antigenic peptides, or any number of different linkers can be used between different pairs of adjacent heteroclitic antigenic peptides. In addition, one linker can be used between a pair of adjacent heteroclitic antigenic peptides, or multiple linkers can be used between a pair of adjacent heteroclitic antigenic peptides.

Any suitable sequence can be used for a peptide linker. As an example, a linker sequence may be, for example, from 1 to about 50 amino acids in length. Some linkers may be hydrophilic. The linkers can serve varying purposes. For example, the linkers can serve to increase bacterial secretion, to facilitate antigen processing, to increase flexibility of the fusion polypeptide, to increase rigidity of the fusion polypeptide, or any other purpose. In some cases, different amino acid linker sequences are distributed between the heroclitic antigenic peptides or different nucleic acids encoding the same amino acid linker sequence are distributed between the heteroclitic antigenic peptides (e.g., SEQ ID NOS: 572-582) in order to minimize repeats. This can also serve to reduce secondary structures, thereby allowing efficient transcription, translation, secretion, maintenance, or stabilization of the nucleic acid (e.g., plasmid) encoding the fusion polypeptide within a Lm recombinant vector strain population. Other suitable peptide linker sequences may be chosen, for example, based on one or more of the following factors: (1) their ability to adopt a flexible extended conformation; (2) their inability to adopt a secondary structure that could interact with functional epitopes on the heteroclitic antigenic peptides; and (3) the lack of hydrophobic or charged residues that might react with the functional epitopes. For example, peptide linker sequences may contain Gly, Asn and Ser residues. Other near neutral amino acids, such as Thr and Ala may also be used in the linker sequence. Amino acid sequences which may be usefully employed as linkers include those disclosed in Maratea et al. (1985) *Gene* 40:39-46; Murphy et al. (1986) *Proc Natl Acad Sci USA* 83:8258-8262; U.S. Pat. Nos. 4,935,233; and 4,751,180, each of which is herein incorporated by reference in its entirety for all purposes. Specific examples of linkers are disclosed elsewhere herein.

The fusion polypeptide can comprise any number of heteroclitic antigenic peptides. In some cases, the fusion polypeptide comprises any number of heteroclitic antigenic peptides such that the fusion polypeptide is able to be produced and secreted from a recombinant *Listeria* strain. For example, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 heteroclitic antigenic peptides, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 heteroclitic antigenic polypeptides. In another example, the fusion polypeptide can include a single heteroclitic antigenic peptide. In another example, the fusion polypeptide can include a number of heteroclitic antigenic peptides ranging from about 1-100, 1-5, 5-10, 10-15, 15-20, 10-20, 20-30, 30-40, 40-50, 50-60, 60-70, 70-80, 80-90, 90-100, 5-15, 5-20, 5-25, 15-20, 15-25, 15-30, 15-35, 20-25, 20-35, 20-45, 30-45, 30-55, 40-55, 40-65, 50-65, 50-75, 60-75, 60-85, 70-85, 70-95, 80-95, 80-105, 95-105, 50-100, 1-100, 5-100, 5-75, 5-50, 5-40, 5-30, 5-20, 5-15, 5-10, 1-100, 1-75, 1-50, 1-40, 1-30, 1-20, 1-15, or 1-10 heteroclitic antigenic peptides. In another example, the fusion polypeptide can include up to about 100, 10, 20, 30, 40, or 50 heteroclitic antigenic peptides. In another example, the fusion polypeptide can comprise about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 heteroclitic antigenic peptides.

In addition, the fusion polypeptide can comprise any number of heteroclitic antigenic peptides from the same cancer-associated protein (i.e., any number of non-contiguous fragments from the same cancer-associated protein). Alternatively, the fusion polypeptide can comprise any number of heteroclitic antigenic peptides from two or more different cancer-associated proteins, such as from 2, 3, 4, 5, 6, 7, 8, 9, or 10 cancer-associated proteins. For example, the fusion polypeptide can comprise heteroclitic mutations from at least 2, 3, 4, 5, 6, 7, 8, 9, 10, 11, 12, 13, 14, 15, 16, 17, 18, 19, or 20 cancer-associated proteins, or 2-5, 5-10, 10-15, or 15-20 cancer-associated proteins. For example, the two or more cancer-associated proteins can be about 2-30, about 2-25, about 2-20, about 2-15, or about 2-10 cancer-associated proteins. For example, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 heteroclitic antigenic peptides from the same cancer-associated protein, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 heteroclitic antigenic polypeptides from the same cancer-associated protein. Likewise, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 heteroclitic antigenic peptides from the same cancer-associated protein, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 heteroclitic antigenic polypeptides from two or more different cancer-associated proteins. In addition, the fusion polypeptide can comprise any number of non-contiguous heteroclitic antigenic peptides from the same cancer-associated protein (i.e., any number of non-contiguous fragments from the same cancer-associated protein). For example, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 non-contiguous heteroclitic antigenic peptides from the same cancer-associated protein, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 non-contiguous heteroclitic antigenic polypeptides from the same cancer-associated protein. In some cases, at least 50%, 55%, 60%, 65%, 70%, 75%, 80%, 85%, 90%, 95%, 96%, 97%, 98%, 99%, or all of the heteroclitic antigenic peptides are non-contiguous heteroclitic antigenic peptides from the same cancer-associated protein, or at least 50%, 55%, 60%, 65%, 70%, 75%, 80%, 85%, 90%, 95%, 96%, 97%, 98%, 99%, or all of the heteroclitic antigenic peptides that are from a single cancer-associated protein are non-contiguous heteroclitic antigenic peptides from that cancer-associated protein.

Each heteroclitic antigenic peptide can comprise a different (i.e., unique) heteroclitic mutation. Alternatively, two or more of the heteroclitic antigenic peptides in the fusion polypeptide can comprise the same heteroclitic mutation. For example, two or more copies of the same heteroclitic antigenic polypeptide can be included in the fusion polypeptide (i.e., the fusion polypeptide comprises two or more copies of the same heteroclitic antigenic peptide). In some fusion polypeptides, at least 50%, 55%, 60%, 65%, 70%, 75%, 80%, 85%, 90%, 95%, 96%, 97%, 98%, or 99% of the heteroclitic antigenic peptides comprise a different (i.e., unique) heteroclitic mutation that is not present in any of the other heteroclitic antigenic peptides.

In some cases, at least two of the heteroclitic antigenic peptides can comprise overlapping fragments of the same cancer-associated protein. For example, two or more of the heteroclitic antigenic peptides can comprise different heteroclitic mutations at the same amino acid residue of the cancer-associated protein.

Some heteroclitic antigenic peptides can comprise at least two different heteroclitic mutations, at least three different heteroclitic mutations, or at least four different heteroclitic mutations.

Any combination of heteroclitic mutations can be included in the fusion polypeptide. For example, heteroclitic antigenic peptides can be included that bind to one or more different HLA types. For example, heteroclitic antigenic peptides can be identified that bind to one or more or all of the following HLA types: HLA-A*02:01, HLA-A*03:01, HLA-A*24:02, and HLA-B*07:02.

Each of the heteroclitic antigenic peptides in the fusion polypeptide can comprise a heteroclitic mutation from the same cancer-associated protein, or the combination of heteroclitic antigenic peptides in the fusion polypeptide can comprise heteroclitic mutations from two or more cancer-associated proteins. For example, the fusion polypeptide can comprise heteroclitic mutations from at least 2, 3, 4, 5, 6, 7, 8, 9, 10, 11, 12, 13, 14, 15, 16, 17, 18, 19, or 20 cancer-associated proteins, or 2-5, 5-10, 10-15, or 15-20 cancer-associated proteins. For example, the two or more cancer-associated proteins can be about 2-30, about 2-25, about 2-20, about 2-15, or about 2-10 cancer-associated proteins. In one example, at least 50%, 55%, 60%, 65%, 70%, 75%, 80%, 85%, 90%, 95%, 96%, 97%, 98%, or 99% of the heteroclitic antigenic peptides comprise a heteroclitic mutation from the same cancer-associated protein. In another example, none of the heteroclitic antigenic peptides comprise a heteroclitic mutation from the same cancer-associated protein.

Exemplary sequences of heteroclitic antigenic peptides are disclosed elsewhere herein. As an example, a heteroclitic antigenic peptide can comprise, consist essentially of, or consist of a sequence at least 85%, 90%, 91%, 92%, 93%, 94%, 95%, 96%, 97%, 98%, 99%, or 100% identical to any of the antigenic peptide sequences disclosed herein.

B. Cancer-Associated Proteins and Heteroclitic Mutations

The fusion polypeptides disclosed herein comprise antigenic peptides comprising heteroclitic mutations from cancer-associated proteins. Any combination of heteroclitic mutations disclosed herein can be included in a fusion polypeptide. The term "cancer-associated protein" in the context of heteroclitic peptides refers to proteins whose expression is correlated with the occurrence or progression of one or more types of cancer. Optionally, such proteins includes proteins having mutations that occur in multiple types of cancer, that occur in multiple subjects having a particular type of cancer, or that are correlated with the occurrence or progression of one or more types of cancer. For example, a cancer-associated protein can be an oncogenic protein (i.e., a protein with activity that can contribute to cancer progression, such as proteins that regulate cell growth), or it can be a tumor-suppressor protein (i.e., a protein that typically acts to alleviate the potential for cancer formation, such as through negative regulation of the cell cycle or by promoting apoptosis). Preferably, a cancer-associated protein from which a heteroclitic peptide is derived is a protein that is expressed in a particular type of cancer but is not normally expressed in healthy adult tissue (i.e., a protein with cancer-specific expression, cancer-restricted expression, tumor-specific expression, or tumor-restricted expression). However, a cancer-associated protein does not have to have cancer-specific, cancer-restricted, tumor-specific, or tumor-restricted expression. Examples of proteins that are considered cancer-specific or cancer-restricted are cancer testis antigens or oncofetal antigens. Cancer testis antigens (CTAs) are a large family of tumor-associated antigens expressed in human tumors of different histological origin but not in normal tissue, except for male germ cells. In cancer, these developmental antigens can be re-expressed and can serve as a locus of immune activation. Oncofetal antigens (OFAs) are proteins that are typically present only during fetal development but are found in adults with certain kinds of cancer. The tumor-restricted pattern of expression of CTAs and OFAs make them ideal targets for tumor-specific immunotherapy. Most OFA/CTA proteins play critical roles in oncogenesis.

The term "heteroclitic" refers to a peptide that generates an immune response that recognizes the native peptide from which the heteroclitic peptide was derived (e.g., the peptide not containing the anchor residue mutations). For example, YLMPVNSEV (SEQ ID NO: 726) was generated from YMMPVNSEV (SEQ ID NO: 725) by mutation of residue 2 to methionine. A heteroclitic peptide can generate an immune response that recognizes the native peptide from which the heteroclitic peptide was derived. For example, the immune response against the native peptide generated by vaccination with the heteroclitic peptide can be equal or greater in magnitude than the immune response generated by vaccination with the native peptide. The immune response can be increased, for example, by 2-fold, 3-fold, 5-fold, 7-fold, 10-fold, 15-fold, 20-fold, 30-fold, 50-fold, 100-fold, 150-fold, 200-fold, 300-fold, 500-fold, 1000-fold, or more.

A heteroclitic peptide disclosed herein can bind to one or more human leukocyte antigens (HLA) molecules. HLA molecules, also known as major histocompatibility complex (MHC) molecules, bind peptides and present them to immune cells. The immunogenicity of a peptide can be partially determined by its affinity for HLA molecules. HLA class I molecules interact with CD8 molecules, which are generally present on cytotoxic T lymphocytes (CTL). HLA class II molecules interact with CD4 molecules, which are generally present on helper T lymphocytes. For example, a heteroclitic peptide disclosed herein can bind to an HLA molecule with sufficient affinity to activate a T cell precursor or with sufficient affinity to mediate recognition by a T cell.

A heteroclitic peptide disclosed herein can bind to one or more HLA class II molecules. For example, a heteroclitic peptide can bind to an HLA-DRB molecule, an HLA-DRA molecule, an HLA-DQA1 molecule, an HLA-DQB1 molecule, an HLA-DPA1 molecule, an HLA-DPB 1 molecule, an HLA-DMA molecule, an HLA-DMB molecule, an HLA-DOA molecule, or an HLA-DOB molecule.

A native or heteroclitic peptide disclosed herein can bind to one or more HLA class I molecules. For example, a heteroclitic peptide can bind to an HLA-A molecule, an HLA-B molecule, an HLA-C molecule, an HLA-A0201 molecule, HLA A1, HLA A2, HLA A2.1, HLA A3, HLA A3.2, HLA A11, HLA A24, HLA B7, HLA B27, or HLA B8. Similarly, a heteroclitic peptide can bind to a superfamily of HLA class I molecules, such as the A2 superfamily, the A3 superfamily, the A24 superfamily, the B7 superfamily, the B27 superfamily, the B44 superfamily, the C1 superfamily, or the C4 superfamily.

Heteroclitic peptides can comprise a mutation that enhances binding of the peptide to an HLA class II molecule relative to the corresponding native peptide. Alternatively, or additionally, heteroclitic peptides can comprise a mutation that enhances binding of the peptide to an HLA class I molecule relative to the corresponding native peptide. For example, the mutated residue can be an HLA class II motif anchor residue. "Anchor motifs" or "anchor residues" refers, in another embodiment, to one or a set of preferred residues at particular positions in an HLA-binding sequence (e.g., an HLA class II binding sequence or an HLA class I binding sequence).

Various methods are well-known for generating predicted heteroclitic epitopes with the potential to elicit cross-reactive immunogenic responses to a wild-type epitope. For example, to design heteroclitic epitopes with the potential to elicit cross-reactive immunogenic responses to a wild-type epitope, baseline predicted peptide-MHC binding affinity of the wild-type epitopes can be determined using NetMHCpan 3.0 Server A peptide-MHC binding affinity percent rank of less than or equal to 1.0 is considered a strong binder that is likely to elicit an immune response. Potential heteroclitic epitopes are generated by random substitution of 1 or more amino acids at, but not limited to, positions 1, 2, 3, or the C-terminal position of the wild-type epitope that is predicted to be a strong binder. The peptide-MHC binding affinity of the potential heteroclitic epitopes is then estimated using NetMHCpan 3.0 Server. Heteroclitic epitopes with percentage ranking binding affinities similar to wild-type epitopes and less than or equal to 1.0 percentage rank can be considered potential antigens for future validation.

Other methods for identifying HLA class I and class II residues, and for improving HLA binding by mutating the residues, are well-known. See, e.g., U.S. Pat. Nos. 8,765,687, 7,488,718, 9,233,149, and 7,598,221, each of which is herein incorporated by reference in its entirety for all purposes. For example, methods for predicting MHC class II epitopes are well-known. As one example, the MHC class II epitope can be predicted using TEPITOPE (Meister et al. (1995) *Vaccine* 13:581-591, herein incorporated by reference in its entirety for all purposes). As another example, the MHC class II epitope can be predicted using EpiMatrix (De Groot et al. (1997) *AIDS Res. Hum. Retroviruses* 13:529-531, herein incorporated by reference in its entirety for all purposes). As yet another example, the MHC class II epitope can be predicted using the Predict Method (Yu K et al. (2002) *Mol. Med.* 8:137-148, herein incorporated by reference in its entirety for all purposes). As yet another example, the MHC class II epitope can be predicted using the SYFPEITHI epitope prediction algorithm. SYFPEITHI is a database comprising more than 4500 peptide sequences known to bind class I and class II MHC molecules. SYFPEITHI provides a score based on the presence of certain amino acids in certain positions along the MHC-binding groove. Ideal amino acid anchors are valued at 10 points, unusual anchors are worth 6-8 points, auxiliary anchors are worth 4-6 points, preferred residues are worth 1-4 points; negative amino acid effect on the binding score between −1 and −3. The maximum score for HLA-A*0201 is 36. As yet another example, the MHC class II epitope can be predicted using Rankpep. Rankpep uses position specific scoring matrices (PSSMs) or profiles from sets of aligned peptides known to bind to a given MHC molecule as the predictor of MHC-peptide binding. Rankpep includes information on the score of the peptide and the % optimum or percentile score of the predicted peptide relative to that of a consensus sequence that yields the maximum score, with the selected profile. Rankpep includes a selection of 102 and 80 PSSMs for the prediction of peptide binding to MHC I and MHC II molecules, respectively. Several PSSMs for the prediction of peptide binders of different sizes are usually available for each MHC I molecule. As another example, the MHC class II epitope can be identified using SVMHC (Donnes and Elofsson (2002) *BMC Bioinformatics* 11; 3:25, herein incorporated by reference in its entirety for all purposes).

Methods for identifying MHC class I epitopes are also well-known. As one example, the MHC class I epitope can be predicted using BIMAS software. A BIMAS score is based on the calculation of the theoretical half-life of the MHC-I/$\beta_2$-microglobulin/peptide complex, which is a measure of peptide-binding affinity. The program uses information about HLA-I peptides of 8-10 amino acids in length. The higher the binding affinity of a peptide to the MHC, the higher the likelihood that this peptide represents an epitope. The BIMAS algorithm assumes that each amino acid in the peptide contributes independently to binding to the class I molecule. Dominant anchor residues, which are critical for binding, have coefficients in the tables that are significantly higher than 1. Unfavorable amino acids have positive coefficients that are less than 1. If an amino acid is not known to make either a favorable or unfavorable contribution to binding, then it is assigned the value 1. All the values assigned to the amino acids are multiplied and the resulting running score is multiplied by a constant to yield an estimate of half-time of dissociation. As another example, the MHC class I epitope can be identified using SYFPEITHI. As yet another example, the MHC class I epitope can be identified using SVMHC. As yet another example, the MHC class I epitope can be identified using NetMHC-2.0 (Buus et al. (2003) *Tissue Antigens* 62:378-384, herein incorporated by reference in its entirety for all purposes).

Different residues in HLA binding motifs can be mutated to enhance MHC binding. In one example, a mutation that enhances MHC binding is in the residue at position 1 of the HLA class I binding motif (e.g., a mutation to tyrosine, glycine, threonine, or phenylalanine). As another example, the mutation can be in position 2 of the HLA class I binding motif (e.g., a mutation to leucine, valine, isoleucine, or methionine). As another example, the mutation can be in position 6 of the HLA class I binding motif (e.g., to valine, cysteine, glutamine, or histidine). As another example, the mutation can be in position 9 of the HLA class I binding motif or in the C-terminal position (e.g., to valine, threonine, isoleucine, leucine, alanine, or cysteine). The mutation can be in a primary anchor residue or in a secondary anchor residue. For example, the HLA class I primary anchor residues can be positions 2 and 9, and the secondary anchor residues can be positions 1 and 8 or positions 1, 3, 6, 7, and 8. In another example, a point mutation can be in a position selected from positions 4, 5, and 8.

Similarly, different residues in HLA class II binding sites can be mutated. For example, an HLA class II motif anchor residue can be modified. For example, the P1 position, the P2 position, the P6 position, or the P9 position can be mutated. Alternatively, the P4 position, the P5 position, the P10 position, the P11 position, the P12 position, or the P13 position can be mutated.

The term “cancer-associated protein” includes proteins having mutations that occur in multiple types of cancer, that occur in multiple subjects having a particular type of cancer, or that are correlated with the occurrence or progression of one or more types of cancer. For example, a cancer-associated protein can be an oncogenic protein (i.e., a protein with activity that can contribute to cancer progression, such as proteins that regulate cell growth), or it can be a tumor-suppressor protein (i.e., a protein that typically acts to alleviate the potential for cancer formation, such as through negative regulation of the cell cycle or by promoting apoptosis.

For example, the cancer-associated protein can be any one of the cancer-associated proteins listed elsewhere herein. For example, the cancer-associated protein can be encoded by one of the following genes: CEACAM5, GAGE1, hTERT, KLHL7, MAGEA3, MAGEA4, MAGEA6, NUF2, NYESO1, PAGE4, PRAAME, PSA, PSMA, RNF43, SART3, SSX2, STEAP1, and SURVIVIN.

The fusion polypeptides disclosed herein can comprise heteroclitic antigenic peptides comprising any combination of heteroclitic mutations from any combination of cancer-associated proteins (i.e., one or more cancer-associated proteins) and in any order. The combination of heteroclitic antigenic peptides or the fusion polypeptide can be hydrophilic or can score up to or below a certain hydropathy threshold, which can be predictive of secretability in *Listeria monocytogenes* or another bacteria of interest. In some cases, the heteroclitic antigenic peptides can be from multiple cancer-associated proteins (e.g., two or more cancer-associated proteins).

As one example, the cancer-associated proteins can comprise proteins encoded by 1 or more, 2 or more, 3 or more, 4 or more, 5 or more, 6 or more, or all of the following genes: CEACAM5, MAGEA6, MAGEA4, GAGE1, NYESO1, STEAP1, and RNF43. The heteroclitic antigenic peptides can bind, for example, one or more or all of HLA types A0201, A0301, A2402, and B0702. Such cancer-associated proteins are associated with, for example, non-small cell lung cancer (NSCLC). The heteroclitic antigenic peptides can be in any order. The heteroclitic antigenic peptides can be fused directly together or linked together by linkers, examples of which are disclosed elsewhere herein. In a specific example, one or more or all of the heteroclitic antigenic peptides can be 9-mers (e.g., 9-mers linked together by linkers). Examples of such antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, or all 11 of the heteroclitic antigenic peptides in Table 36.

As another example, the cancer-associated proteins can comprise proteins encoded by 1 or more, 2 or more, 3 or more, 4 or more, 5 or more, 6 or more, 7 or more, 8 or more, or all of the following genes: CEACAM5, MAGEA4, STEAP1, RNF43, SSX2, SART3, PAGE4, PSMA, and PSA. The heteroclitic antigenic peptides can bind, for example, one or more or all of HLA types A0201, A0301, A2402, and B0702. Such cancer-associated proteins are associated with, for example, prostate cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 53.

As another example, the cancer-associated proteins can comprise proteins encoded by 1 or more, 2 or more, 3 or more, 4 or more, 5 or more, or all of the following genes: CEACAM5, STEAP1, MAGEA3, PRAME, hTERT, and SURVIVIN. The heteroclitic antigenic peptides can bind, for example, one or more or all of HLA types A0201, A0301, A2402, and B0702. Such cancer-associated proteins are associated with, for example, pancreatic cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, or all 12 of the heteroclitic antigenic peptides in Table 69.

As another example, the cancer-associated proteins can comprise proteins encoded by 1 or more, 2 or more, 3 or more, 4 or more, 5 or more, 6 or more, 7 or more, or all of the following genes: CEACAM5, GAGE1, NYESO1, RNF43, NUF2, KLHL7, MAGEA3, and PRAME. The heteroclitic antigenic peptides can bind, for example, one or more or all of HLA types A0201, A0301, A2402, and B0702. Such cancer-associated proteins are associated with, for example, bladder cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all 14 of the heteroclitic antigenic peptides in Table 77.

As another example, the cancer-associated proteins can comprise proteins encoded by 1 or more, 2 or more, 3 or more, 4 or more, 5 or more, or all of the following genes: CEACAM5, STEAP1, RNF43, MAGEA3, PRAME, and hTERT. The heteroclitic antigenic peptides can bind, for example, one or more or all of HLA types A0201, A0301, A2402, and B0702. Such cancer-associated proteins are associated with, for example, breast cancer (e.g., ER+breast cancer). The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, or all 11 of the heteroclitic antigenic peptides in Table 88.

As another example, the cancer-associated proteins can comprise proteins encoded by 1 or more, 2 or more, 3 or more, 4 or more, 5 or more, 6 or more, 7 or more, or all of the following genes: CEACAM5, PRAME, hTERT, STEAP1, RNF43, NUF2, KLHL7, and SART3. The heteroclitic antigenic peptides can bind, for example, one or more or all of HLA types A0201, A0301, A2402, and B0702. Such cancer-associated proteins are associated with, for example, uterine cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all 14 of the heteroclitic antigenic peptides in Table 96.

As another example, the cancer-associated proteins can comprise proteins encoded by 1 or more, 2 or more, 3 or more, 4 or more, 5 or more, 6 or more, 7 or more, or all of the following genes: CEACAM5, STEAP1, RNF43, SART3, NUF2, KLHL7, PRAME, and hTERT. The heteroclitic antigenic peptides can bind, for example, one or more or all of HLA types A0201, A0301, A2402, and B0702. Such cancer-associated proteins are associated with, for example, ovarian cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all 14 of the heteroclitic antigenic peptides in Table 101.

As another example, the cancer-associated proteins can comprise proteins encoded by 1 or more, 2 or more, 3 or more, 4 or more, 5 or more, 6 or more, 7 or more, or all of the following genes: CEACAM5, MAGEA6, STEAP1, RNF43, SART3, NUF2, KLHL7, and hTERT. The heteroclitic antigenic peptides can bind, for example, one or more or all of HLA types A0201, A0301, A2402, and B0702. Such cancer-associated proteins are associated with, for example, low-grade glioma. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 105.

As another example, the cancer-associated proteins can comprise proteins encoded by 1 or more, 2 or more, 3 or more, 4 or more, 5 or more, 6 or more, 7 or more, or all of the following genes: CEACAM5, MAGEA6, MAGEA4, GAGE1, NYESO1, STEAP1, RNF43, and MAGEA3. The heteroclitic antigenic peptides can bind, for example, one or more or all of HLA types A0201, A0301, A2402, and B0702. Such cancer-associated proteins are associated with, for example, colorectal cancer (e.g., MSS colorectal cancer). The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 109.

As another example, the cancer-associated proteins can comprise proteins encoded by 1 or more, 2 or more, 3 or more, 4 or more, 5 or more, or all of the following genes: CEACAM5, MAGEA4, STEAP1, NYESO1, PRAME, and hTERT. The heteroclitic antigenic peptides can bind, for example, one or more or all of HLA types A0201, A0301, A2402, and B0702. Such cancer-associated proteins are associated with, for example, head and neck cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 113.

C. PEST-Containing Peptides

The recombinant fusion proteins disclosed herein comprise a PEST-containing peptide. The PEST-containing peptide may at the amino terminal (N-terminal) end of the fusion polypeptide (i.e., N-terminal to the antigenic peptides), may be at the carboxy terminal (C-terminal) end of the fusion polypeptide (i.e., C-terminal to the antigenic peptides), or may be embedded within the antigenic peptides. In some recombinant *Listeria* strains and methods, a PEST containing peptide is not part of and is separate from the fusion polypeptide. Fusion of antigenic peptides to a PEST-like sequence, such as an LLO peptide, can enhance the immunogenicity of the antigenic peptides and can increase cell-mediated and antitumor immune responses (i.e., increase cell-mediated and anti-tumor immunity). See, e.g., Singh et al. (2005) *J Immunol* 175(6):3663-3673, herein incorporated by reference in its entirety for all purposes. PEST-containing peptides are disclosed in more detail elsewhere herein.

D. Generating Immunotherapy Constructs Encoding Recombinant Fusion Polypeptides

Also provided herein are methods for generating immunotherapy constructs encoding or compositions comprising the recombinant fusion polypeptides disclosed herein. For example, such methods can comprise selecting a set of heteroclitic mutations to include in the immunotherapy construct, designing a heteroclitic antigenic peptides comprising each of the heteroclitic mutations (and, for example, testing the hydropathy of the each heteroclitic antigenic peptide, and modifying or deselecting a heteroclitic antigenic peptide if it scores above a selected hydropathy index threshold value), selecting one or more sets of heteroclitic antigenic peptides, designing one or more fusion polypeptides comprising each of the selected heteroclitic antigenic peptides, and generating a nucleic acid construct encoding the fusion polypeptide.

Individual heteroclitic mutations can be selected based on any criteria as discussed in further detail elsewhere herein. For example, individual heteroclitic mutations or heteroclitic peptides can be selected if they are known to generate CD8+ T lymphocyte responses.

After identification of a set of possible heteroclitic mutations to include in a fusion polypeptide, sequences for heteroclitic antigenic peptides comprising each heteroclitic mutation can be selected. Different size antigenic peptides can be used, as disclosed elsewhere herein. For example, heteroclitic mutations or heteroclitic antigenic peptides can be focused, for example, on MHC Class I epitopes consisting of 9 amino acids.

The sequence of the heteroclitic antigenic peptide can then be optimized to enhance binding to MHC Class I molecules. To optimize binding to each HLA, the Peptide MHC Binding Motif and Amino Acid Binding Chart can be assessed from the Immune Epitope Database and Analysis Resource (for example: iedb.org/MHCalleleid/143). The preferred amino acids at the anchor positions can be inserted into the heteroclitic antigenic peptide sequence (e.g., NUF2—wild type: YMMPVNSEV (SEQ ID NO: 725); and NUF2—heteroclitic: YLMPVNSEV (SEQ ID NO: 726)).

The binding affinities of sequence-optimized heteroclitic antigenic peptides can then be assessed, for example, using one of the following algorithms: NetMHC4.0 Server;

NetMHCpan4.0 Server; and mhcflurry v0.2.0. The heteroclitic antigenic peptides can be considered, for example, if predicting binding affinity to a specific HLA is equivalent or stronger than the corresponding native sequence. Selected sequence-optimized heteroclitic antigenic peptides can then be screened for in vitro binding to specific HLAs using ProImmune's REVEAL assay. For example, heteroclitic antigenic peptides with binding affinity >=45% of the REVEAL assay's positive control peptide were considered binders.

The RNA expression level of heteroclitic antigenic peptides can also be measured in a specific-indication in TCGA RNAseqV2 dataset. The percentage of TCGA samples with normalized RNA expression reads greater than 0 can be calculated. Heteroclitic antigenic peptides with TCGA expression in a majority of samples can be prioritized.

Such methods can also comprise, for example, testing the hydropathy of each heteroclitic antigenic peptide, and modifying or deselecting a heteroclitic antigenic peptide if it scores above a selected hydropathy index threshold value), designing one or more fusion polypeptides comprising each of the selected heteroclitic antigenic peptides, and generating a nucleic acid construct encoding the fusion polypeptide. Such methods are disclosed in more detail elsewhere herein.

In a specific example, a literature review can be done to survey the genomic landscape of indication-specific tumor-associated antigens to generate a short-list of potential TAAs. A second literature review can be done to determine if short-list TAAs contain known immunogenic peptides that generate CD8+ T lymphocyte response. This approach can focus, for example, primarily on MHC Class I epitopes consisting of 9 amino acids (9mer) from TAAs. This step can, for example, identify potential target peptides in 9mer format that bind to one of four HLAs types (HLA-A*02:01, HLA-A*03:01, HLA-A*24:02, and HLA-B*07:02).

Target peptides can then be sequence optimized to enhance binding to MHC Class I molecules (aka heteroclitic peptide). To optimize binding to each HLA, the Peptide MHC Binding Motif and Amino Acid Binding Chart can be assessed from the Immune Epitope Database and Analysis Resource (for example: iedb.org/MHCalleleid/143). The preferred amino acids at the anchor positions can be inserted into the target peptide sequence (e.g., NUF2—wild type: YMMPVNSEV (SEQ ID NO: 725); and NUF2—heteroclitic: YLMPVNSEV (SEQ ID NO: 726)). The binding affinities of sequence-optimized target peptides and wild-type target peptides can then be assessed, e.g., using one of the following algorithms: NetMHC4.0 Server; NetMHCpan4.0 Server; and mhcflurry v0.2.0. Sequence-optimized target peptides can be considered, for example, if predicting binding affinity to a specific HLA is equivalent or stronger than the wild-type target peptide sequence. Selected sequence-optimized target peptides can then be screened for in vitro binding to specific HLAs using ProImmune's REVEAL assay. For example, target peptides with binding affinity >=45% of the REVEAL assay's positive control peptide can be considered binders. Finally, the RNA expression level of target peptides can be measured in a specific-indication in TCGA RNAseqV2 dataset. For example, the percentage of TCGA samples with normalized RNA expression reads greater than 0 can be calculated. For example, target peptides with TCGA expression in a majority of samples can be prioritized.

IV. Recombinant Fusion Polypeptides Encoded by Minigene Constructs

Disclosed herein are recombinant fusion polypeptides comprising from N-terminal end to C-terminal end a bacterial secretion signal sequence, a ubiquitin (Ub) protein, and an antigenic peptide (or one or more antigenic peptides) from a cancer-associated protein. If two or more antigenic peptides are included, the antigenic peptides can be in tandem (e.g., Ub-peptide1-peptide2). Alternatively, a combination of separate fusion polypeptides can be used in which each antigenic peptide is fused to its own secretion sequence and Ub protein (e.g., Ub1-peptide1; Ub2-peptide2). Examples of suitable antigenic peptides are disclosed elsewhere herein. The antigenic peptides can comprise recurrent cancer mutations as disclosed elsewhere herein. Alternatively, the antigenic peptides can comprise heteroclitic mutations as disclosed elsewhere herein.

Nucleic acids (termed minigene constructs) encoding such recombinant fusion polypeptides are also disclosed. Such minigene nucleic acid constructs can further comprise two or more open reading frames linked by a Shine-Dalgamo ribosome binding site nucleic acid sequence between each open reading frame. For example, a minigene nucleic acid construct can further comprise two to four open reading frames linked by a Shine-Dalgamo ribosome binding site nucleic acid sequence between each open reading frame. Each open reading frame can encode a different fusion polypeptide comprising from N-terminal end to C-terminal end a bacterial secretion sequence, a ubiquitin (Ub) protein, and one or more antigenic peptides. The codon encoding the carboxy terminus of the fusion polypeptide can be followed by two stop codons to ensure termination of protein synthesis.

In some fusion polypeptides encoded by minigene constructs, there are one or more additional antigenic peptides from cancer-associated proteins (e.g., comprising a recurrent cancer mutation and/or a heteroclitic mutation) between the bacterial secretion sequence and the ubiquitin protein. For example, there can be 1-40, 1-35, 1-30, 1-25, 1-20, 1-15, 1-10, 1-5, 1-4, 1, 2, 3, 4, 5, 6, 7, 8, 9, 10, 11, 12, 13, 14, 15, 16, 17, 18, 19, or 20 additional antigenic peptides between the bacterial secretion sequence and the ubiquitin protein. If there are two or more additional antigenic peptides, they can be fused directly to each other or linked via a peptide linker. Exemplary linkers are disclosed elsewhere herein. The additional antigenic peptides can comprise one or more antigenic peptides comprising recurrent cancer mutations and/or one or more heteroclitic antigenic peptides. Examples of such peptides are disclosed elsewhere herein.

Examples of bacterial secretion signal sequences are disclosed in more detail elsewhere herein. The ubiquitin can be, for example, a full-length protein. An exemplary ubiquitin peptide encoded by a minigene construct comprises, consists essentially of, or consists of the sequence set forth in SEQ ID NO: 747. The ubiquitin expressed from the nucleic acid construct provided herein can be cleaved at the carboxy terminus of the ubiquitin from the rest of the recombinant fusion polypeptide expressed from the nucleic acid construct through the action of hydrolases upon entry to the host cell cytosol. This liberates the rest of the fusion polypeptide, producing a peptide in the host cell cytosol.

Selection of, variations of, and arrangement of antigenic peptides within a fusion polypeptide are discussed in detail elsewhere herein, and methods of generating heteroclitic mutant antigenic peptides are discussed in more detail elsewhere herein. The recombinant fusion polypeptides can comprise one or more tags as disclosed elsewhere herein. For example, the recombinant fusion polypeptides can comprise one or more peptide tags N-terminal and/or C-terminal to the one or more antigenic peptides or to the ubiquitin (e.g., N-terminal to the ubiquitin). A tag can be fused directly to an antigenic peptide or ubiquitin or linked to an antigenic peptide or ubiquitin via a linker (examples of which are disclosed elsewhere herein).

The recombinant fusion polypeptides disclosed herein can be expressed by recombinant *Listeria* strains or can be expressed and isolated from other vectors and cell systems used for protein expression and isolation. Recombinant *Listeria* strains comprising expressing such antigenic peptides can be used, for example in immunogenic compositions comprising such recombinant *Listeria* and in vaccines comprising the recombinant *Listeria* strain and an adjuvant.

Nucleic acids (minigene constructs) encoding such recombinant fusion polypeptides are also disclosed. The nucleic acid can be in any form. The nucleic acid can comprise or consist of DNA or RNA, and can be single-stranded or double-stranded. The nucleic acid can be in the form of a plasmid, such as an episomal plasmid, a multicopy episomal plasmid, or an integrative plasmid. Alternatively, the nucleic acid can be in the form of a viral vector, a phage vector, or in a bacterial artificial chromosome. Such nucleic acids can have one open reading frame or can have two or more open reading frames (e.g., an open reading frame encoding the recombinant fusion polypeptide and a second open reading frame encoding a metabolic enzyme). In one example, such nucleic acids can comprise two or more open reading frames linked by a Shine-Dalgarno ribosome binding site nucleic acid sequence between each open reading frame. For example, a nucleic acid can comprise two to four open reading frames linked by a Shine-Dalgarno ribosome binding site nucleic acid sequence between each open reading frame. Each open reading frame can encode a different polypeptide. The codon encoding the carboxy terminus of the fusion polypeptide can be followed by two stop codons to ensure termination of protein synthesis.

Some exemplary antigenic peptides for inclusion in minigene constructs include those in the table below.

| Peptide (Gene_HLA Type) | Sequence |
| --- | --- |
| STEAP1_A0201 | LLLGTIHAV (SEQ ID NO: 799) |
| CEACAM5_A0201 | ILIGVLVGV (SEQ ID NO: 798) |
| CEACAM5_A2402 | IYPNASLLF (SEQ ID NO: 796) |
| STEAP1_A2402 | KYKKFPWWL (SEQ ID NO: 800) |
| NYESO1_A0201 | RLLEFYLAV (SEQ ID NO: 797) |
| NUF2_A0201 | YLMPVNSEV (SEQ ID NO: 807) |

A. Antigenic Peptides Encoded by Minigene Constructs

Antigenic peptides encoded by the minigene constructs disclosed herein can be recurrent cancer mutation antigenic peptides and/or heteroclitic antigenic peptides (e.g., HLA class I and class II heteroclitic peptides). Examples of such peptides are disclosed elsewhere herein. For example, the antigenic peptide encoded by a minigene construct can be a heteroclitic antigenic peptide that binds to one or more of the following HLA types: HLA-A*02:01, HLA-A*03:01, HLA-A*24:02, and HLA-B*07:02. As a specific example, the antigenic peptide encoded by the minigene construct can be from a protein encoded by one of the following genes: STEAP1, CEACAM5, NYESO1, and NUF2.

The fusion polypeptide encoded by the minigene construct can include a single antigenic peptide or can include two or more antigenic peptides. Each antigenic peptide can be of any length sufficient to induce an immune response, and each antigenic peptide can be the same length or the antigenic peptides can have different lengths. For example, an antigenic peptide encoded by a minigene construct can be 8-100, 8-50, 8-30, 8-25, 8-22, 8-20, 8-15, 8-14, 8-13, 8-12, 8-11, 7-11, or 8-10 amino acids in length. In one example, an antigenic peptide can be 9 amino acids in length.

Each antigenic peptide can also be hydrophilic or can score up to or below a certain hydropathy threshold, which can be predictive of secretability in *Listeria monocytogenes* or another bacteria of interest. For example, antigenic peptides can be scored by a Kyte and Doolittle hydropathy index 21 amino acid window, and all scoring above a cutoff (around 1.6) can be excluded as they are unlikely to be secretable by *Listeria monocytogenes*. Likewise, the combination of antigenic peptides or the fusion polypeptide can be hydrophilic or can score up to or below a certain hydropathy threshold, which can be predictive of secretability in *Listeria monocytogenes* or another bacteria of interest.

If the fusion polypeptide includes more than one antigenic peptide, the antigenic peptides can be linked together in any manner. For example, the antigenic peptides can be fused directly to each other with no intervening sequence. Alternatively, the antigenic peptides can be linked to each other indirectly via one or more linkers, such as peptide linkers. In some cases, some pairs of adjacent antigenic peptides can be fused directly to each other, and other pairs of antigenic peptides can be linked to each other indirectly via one or more linkers. The same linker can be used between each pair of adjacent antigenic peptides, or any number of different linkers can be used between different pairs of adjacent antigenic peptides. In addition, one linker can be used between a pair of adjacent antigenic peptides, or multiple linkers can be used between a pair of adjacent antigenic peptides. Any suitable sequence can be used for a peptide linker. Examples of suitable linkers are disclosed elsewhere herein.

Exemplary sequences of antigenic peptides for use in minigene constructs are disclosed elsewhere herein. As an example, an antigenic peptide can comprise, consist essentially of, or consist of a sequence at least 85%, 90%, 91%, 92%, 93%, 94%, 95%, 96%, 97%, 98%, 99%, or 100% identical to any of the antigenic peptide sequences disclosed herein.

B. Bacterial Secretion Signal Sequences

The bacterial secretion signal sequence can be a Listerial signal sequence, such as an Hly or an ActA signal sequence, or any other known signal sequence. In other cases, the signal sequence can be an LLO signal sequence. An exemplary LLO signal sequence is set forth in SEQ ID NO: 920. For example, a bacterial secretion signal sequence encoded by a minigene construct herein can be an N-terminal fragment of LLO such as that set forth in SEQ ID NO: 336. The signal sequence can be bacterial, can be native to a host bacterium (e.g., *Listeria monocytogenes*, such as a secAl signal peptide), or can be foreign to a host bacterium. Specific examples of signal peptides include an Usp45 signal peptide from *Lactococcus lactis*, a Protective Antigen signal peptide from *Bacillus anthracis*, a secA2 signal peptide such the p60 signal peptide from *Listeria monocytogenes*, and a Tat signal peptide such as a *B. subtilis* Tat signal peptide (e.g., PhoD). In specific examples, the secretion signal sequence is from a *Listeria* protein, such as an $ActA_{300}$ secretion signal or an $ActA_{100}$ secretion signal (comprising the first 100 amino acids of the ActA secretion signal sequence). An exemplary ActA signal sequence is set forth in SEQ ID NO: 921.

C. Generating Immunotherapy Constructs Encoding Recombinant Fusion Polypeptides Encoded by Minigene Constructs Also provided herein are methods for generating immunotherapy constructs encoding or compositions comprising the recombinant fusion polypeptides disclosed herein. For example, such methods can comprise selecting and designing antigenic or immunogenic peptides to include in the immunotherapy construct (and, for example, testing the hydropathy of each antigenic peptide, and modifying or deselecting an antigenic peptide if it scores above a selected hydropathy index threshold value), designing one or more fusion polypeptides comprising each of the selected antigenic peptides, and generating a nucleic acid construct encoding the fusion polypeptide. Such methods are disclosed in more detail elsewhere herein. In addition, methods for generating predicted heteroclitic epitopes with the potential to elicit cross-reactive immunogenic responses to a wild-type epitope are described in more detail elsewhere herein.

V. Recombinant Fusion Polypeptides Comprising Combinations of Recurrent Cancer Mutation Antigenic Peptides, Heteroclitic Antigenic Peptides, and Minigene-Construct-Encoded Peptides The recombinant fusion polypeptides disclosed herein can comprise any combination of antigenic peptides comprising any of the recurrent cancer mutations disclosed herein, antigenic peptides (e.g., from cancer-associated proteins) comprising any of the heteroclitic mutations disclosed herein, and antigenic peptides (e.g., from cancer-associated proteins) expressed from any of the minigene constructs disclosed herein (i.e., antigenic peptides fused to ubiquitin). Any of the antigenic peptides disclosed herein can be included in a recombinant fusion polypeptide. For example, the recombinant fusion polypeptides can comprise recurrent cancer mutation antigenic peptides only, heteroclitic antigenic peptides only, or minigene construct antigenic peptides only. Similarly, the recombinant fusion polypeptides can comprise both recurrent cancer mutation antigenic peptides and heteroclitic antigenic peptides but no minigene construct antigenic peptides. Similarly, the recombinant fusion polypeptides can comprise both recurrent cancer mutation antigenic peptides and minigene construct antigenic peptides but no heteroclitic antigenic peptides. Similarly, the recombinant fusion polypeptides can comprise both heteroclitic antigenic peptides and minigene construct antigenic peptides but no recurrent cancer mutation antigenic peptides.

For example, disclosed herein are recombinant fusion polypeptides comprising a PEST-containing peptide fused to two or more antigenic peptides (i.e., in tandem, such as PEST-peptide1-peptide2), wherein at least one antigenic peptide comprises a recurrent cancer mutation, and at least one antigenic peptide (e.g., from a cancer-associated protein) comprises a heteroclitic mutation. Also herein are recombinant fusion polypeptides comprising a PEST-containing peptide fused to two or more antigenic peptides (i.e., in tandem, such as PEST-peptide1-peptide2), wherein at least one antigenic peptide comprises a recurrent cancer mutation, and at least one antigenic peptide comprises a heteroclitic mutation, and wherein the fusion polypeptide does not comprise a PEST-containing peptide. Examples of recurrent cancer mutations and heteroclitic mutations are disclosed elsewhere herein.

Also disclosed herein are recombinant fusion polypeptides comprising from N-terminal end to C-terminal end a PEST-containing peptide comprising a bacterial secretion signal sequence, one or more antigenic peptides comprising a recurrent cancer mutation, a ubiquitin (Ub) protein, and an antigenic peptide (or one or more antigenic peptides) from a cancer-associated protein. If two or more antigenic peptides are included at the C-terminal end, the antigenic peptides can be in tandem (e.g., Ub-peptide1-peptide2). Alternatively, a combination of separate fusion polypeptides can be used in which each antigenic peptide is fused to its own secretion sequence and Ub protein (e.g., Ub1-peptide1; Ub2-peptide2). Examples of suitable antigenic peptides are disclosed elsewhere herein. Examples of antigenic peptides comprising recurrent cancer mutations are disclosed elsewhere herein.

Also disclosed herein are recombinant fusion polypeptides comprising from N-terminal end to C-terminal end a PEST-containing peptide comprising a bacterial secretion signal sequence, one or more antigenic peptides (e.g., from a cancer-associated protein) comprising a heteroclitic mutation, a ubiquitin (Ub) protein, and an antigenic peptide (or one or more antigenic peptides) from a cancer-associated protein. If two or more antigenic peptides are included at the C-terminal end, the antigenic peptides can be in tandem (e.g., Ub-peptide1-peptide2). Alternatively, a combination of separate fusion polypeptides can be used in which each antigenic peptide is fused to its own secretion sequence and Ub protein (e.g., Ub1-peptide1; Ub2-peptide2). Examples of suitable antigenic peptides are disclosed elsewhere herein. Examples of antigenic peptides comprising heteroclitic mutations are disclosed elsewhere herein.

Also disclosed herein are recombinant fusion polypeptides comprising from N-terminal end to C-terminal end a PEST-containing peptide comprising a bacterial secretion signal sequence, two or more antigenic peptides (wherein at least one antigenic peptide comprises a recurrent cancer mutation, and at least one antigenic peptide (e.g., from a cancer-associated protein) comprises a heteroclitic mutation), a ubiquitin (Ub) protein, and an antigenic peptide (or one or more antigenic peptides) from a cancer-associated protein. If two or more antigenic peptides are included at the C-terminal end, the antigenic peptides can be in tandem (e.g., Ub-peptide1-peptide2). Alternatively, a combination of separate fusion polypeptides can be used in which each antigenic peptide is fused to its own secretion sequence and Ub protein (e.g., Ub1-peptide1; Ub2-peptide2). Examples of suitable antigenic peptides are disclosed elsewhere herein. Examples of antigenic peptides comprising recurrent cancer mutations are disclosed elsewhere herein. Examples of antigenic peptides comprising heteroclitic mutations are disclosed elsewhere herein.

The recombinant fusion polypeptides can comprise one or more tags as disclosed in more detail elsewhere herein. Selection of and examples of recurrent cancer mutation antigenic peptides, heteroclitic antigenic peptides, and minigene construct antigenic peptides are disclosed elsewhere herein. Selection of, variations of, and arrangement of antigenic peptides within a fusion polypeptide are discussed in detail elsewhere herein, and cancer-associated proteins are discussed in more detail elsewhere herein. Examples of PEST-containing peptides and bacterial secretion signal sequences are disclosed elsewhere herein. Generation of immunotherapy constructs encoding such recombinant fusion polypeptides is disclosed elsewhere herein.

The recombinant fusion polypeptides disclosed herein can be expressed by recombinant *Listeria* strains or can be expressed and isolated from other vectors and cell systems used for protein expression and isolation. Recombinant *Listeria* strains comprising expressing such antigenic peptides can be used, for example in immunogenic compositions comprising such recombinant *Listeria* and in vaccines comprising the recombinant *Listeria* strain and an adjuvant. Expression of one or more antigenic peptides as a fusion polypeptides with a nonhemolytic truncated form of LLO, ActA, or a PEST-like sequence in host cell systems in *Listeria* strains and host cell systems other than *Listeria* can result in enhanced immunogenicity of the antigenic peptides.

The fusion polypeptide can comprise any number of antigenic peptides. In some cases, the fusion polypeptide comprises any number of antigenic peptides such that the fusion polypeptide is able to be produced and secreted from a recombinant *Listeria* strain. For example, the fusion polypeptide can comprise at least 3, 4, 5, 6, 7, 8, 9, 10, 11, 12, 13, 14, 15, 16, 17, 18, 19, 20, 21, 22, 23, 24, 25, 26, 27, 28, 29, or 30 antigenic peptides, or 2-50, 2-45, 2-40, 2-35, 2-30, 2-25, 2-20, 2-15, 2-10, 2-5, 5-10, 10-15, 15-20, 20-25, 25-30, 30-35, 35-40, 40-45, or 45-50 antigenic polypeptides. In another example, the fusion polypeptide can include a single antigenic peptide. In another example, the fusion polypeptide can include a number of antigenic peptides ranging from about 1-100, 1-5, 5-10, 10-15, 15-20, 10-20, 20-30, 30-40, 40-50, 50-60, 60-70, 70-80, 80-90, 90-100, 5-15, 5-20, 5-25, 15-20, 15-25, 15-30, 15-35, 20-25, 20-35, 20-45, 30-45, 30-55, 40-55, 40-65, 50-65, 50-75, 60-75, 60-85, 70-85, 70-95, 80-95, 80-105, 95-105, 50-100, 1-100, 5-100, 5-75, 5-50, 5-40, 5-30, 5-20, 5-15, 5-10, 1-100, 1-75, 1-50, 1-40, 1-30, 1-20, 1-15, or 1-10 antigenic peptides. In another example, the fusion polypeptide can include up to about 100, 10, 20, 30, 40, or 50 antigenic peptides. In another example, the fusion polypeptide can comprise about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 antigenic peptides.

In another example, the fusion polypeptide can comprise at least about 5, 6, 7, 8, 9, 10, 11, 12, 13, 14, 15, 16, 17, 18, 19, 20, 21, 22, 23, 24, or 25 antigenic peptides or between about 5-50, 10-40, or 20-30 antigenic peptides. For example, the fusion polypeptide can comprise at least about 2, 3, 4, 5, 6, 7, 8, 9, or 10 antigenic peptides comprising a recurrent cancer mutation or between about 5 to about 30 or about 10 to about 20 antigenic peptides comprising a recurrent cancer mutation and/or can comprise at least about 2, 3, 4, 5, 6, 7, 8, 9, or 10 antigenic peptides comprising a heteroclitic mutation or between about 5 to about 30 or about 10 to about 20 antigenic peptides comprising a heteroclitic mutation.

The antigenic peptides can be from any number of cancer-associated proteins. For example, the fusion polypeptide can comprise antigenic peptides from at least 2, 3, 4, 5, 6, 7, 8, 9, 10, 11, 12, 13, 14, 15, 16, 17, 18, 19, or 20 cancer-associated proteins, or 2-5, 5-10, 10-15, or 15-20 cancer-associated proteins. For example, the cancer-associated proteins can be about 2-30, about 2-25, about 2-20, about 2-15, or about 2-10 cancer-associated proteins.

In fusion polypeptides comprising two or more antigenic peptides comprising a recurrent cancer mutation and/or two or more antigenic peptides comprising a heteroclitic mutation, the antigenic peptides comprising a recurrent cancer mutation can be in tandem, and the antigenic peptides comprising a heteroclitic mutation can be in tandem. Alternatively, the antigenic peptides comprising a recurrent cancer mutation and the antigenic peptides comprising a heteroclitic mutation can be intermixed within the fusion polypeptide.

Components within a fusion polypeptide may be fused directly to each other or linked via linkers (e.g., peptide linkers) as disclosed in more detail elsewhere herein. For example, the peptide linkers used can comprise flexibility linkers and/or rigidity linkers and/or immunoproteasome linkers or can comprise one or more of the linkers set forth in SEQ ID NOS: 310-319 and 821-829 (e.g., to link two or more antigenic peptides). In one examples, the peptide linker upstream of each antigenic peptide comprising a heteroclitic mutation is an immunoproteasome linker or is selected from the linkers set forth in SEQ ID NOS: 821-829.

The VGKGGSGG linker (SEQ ID NO: 314) can be used, for example, as a longer linker after the tLLO and also before the tag sequences to provide additional space between the tLLO and the antigenic portion of the fusion peptide and before the tag sequences. It also can provide flexibility and to charge balance the fusion protein. The EAAAK linker (SEQ ID NO: 316) is a rigid/stiff linker that can be used to facilitate expression and secretion, for example, if the fusion protein would otherwise fold on itself. The GGGGS linker (SEQ ID NO: 313) is a flexible linker that can be used, for example, to add increased flexibility to the fusion protein to help facilitate expression and secretion. The "i20" linkers (e.g., SEQ ID NOS: 821-829) are immunoproteasome linkers that are designed, for example, to help facilitate cleavage of the fusion protein by the immunoproteasome and increase the frequency of obtaining the exact minimal binding fragment that is desired. Combinations of GGGGS and EAAAK linkers (SEQ ID NOS: 313 and 316, respectively) can be used, for example, to alternate flexibility and rigidity to help balance the construct for improved expression and secretion and to help facilitate DNA synthesis by providing more unique codons to choose from.

The recombinant fusion polypeptide can be any molecular weight. For example, the recombinant fusion polypeptide can be less than or no more than about 200, 195, 190, 185, 180, 175, 170, 165, 160, 155, 150, 145, 140, 135, 130, or 125 kilodaltons (kDa). In a specific example, the recombinant fusion polypeptide is less than or no more than about 150 kDa or less than or no more than about 130 kDa. As another example the recombinant fusion polypeptide can be between about 50-200, 50-195, 50-190, 50-185, 50-180, 50-175, 50-170, 50-165, 50-160, 50-155, 50-150, 50-145, 50-140, 50-135, 50-130, 50-125, 100-200, 100-195, 100-190, 100-185, 100-180, 100-175, 100-170, 100-165, 100-160, 100-155, 100-150, 100-145, 100-140, 100-135, 100-130, or 100-125 kDa. In a specific example, the recombinant fusion polypeptide is between about 50-150, 100-150, 50-125, or 100-125 kDa. As another example, the recombinant fusion polypeptide can be at least about 50, 55, 60, 65, 70, 75, 80, 85, 90, 95, 100, 105, 110, 115, 120, or 125 kDa. As a specific example, the recombinant fusion polypeptide can be at least about 100 kDa.

Nucleic acids encoding such recombinant fusion polypeptides are also disclosed. The nucleic acid can be in any form. The nucleic acid can comprise or consist of DNA or RNA, and can be single-stranded or double-stranded. The nucleic acid can be in the form of a plasmid, such as an episomal plasmid, a multicopy episomal plasmid, or an integrative plasmid. Alternatively, the nucleic acid can be in the form of a viral vector, a phage vector, or in a bacterial artificial chromosome. Such nucleic acids can have one open reading frame or can have two or more open reading frames (e.g., an open reading frame encoding the recombinant fusion polypeptide and a second open reading frame encoding a metabolic enzyme). In one example, such nucleic acids can comprise two or more open reading frames linked by a Shine-Dalgarno ribosome binding site nucleic acid sequence between each open reading frame. For example, a nucleic acid can comprise two to four open reading frames linked by a Shine-Dalgarno ribosome binding site nucleic acid sequence between each open reading frame. Each open reading frame can encode a different polypeptide. In some nucleic acids, the codon encoding the carboxy terminus of the fusion polypeptide is followed by two stop codons to ensure termination of protein synthesis.

The fusion polypeptides disclosed herein can comprise antigenic peptides from any combination of cancer-associated proteins (i.e., one or more cancer-associated proteins) and in any order. The combination of antigenic peptides or the fusion polypeptide can be hydrophilic or can score up to or below a certain hydropathy threshold, which can be predictive of secretability in Listeria monocytogenes or another bacteria of interest. In some cases, the antigenic peptides can be from multiple cancer-associated proteins (e.g., two or more cancer-associated proteins).

As one example, the cancer-associated proteins from which recurrent cancer mutation peptides are generated can comprise proteins encoded by 1 or more, 2 or more, 3 or more, 4 or more, 5 or more, or all of the following genes: KRAS, EGFR, U2AF1, BRAF, PIK3CA, and TP53. The antigenic peptides can comprise, for example, 1 or more, 2 or more, 3 or more, 4 or more, 5 or more, 6 or more, 7 or more, 8 or more, 9 or more, 10 or more, or all of the following recurrent cancer mutations: KRAS_G12C, EGFR_L858R, KRAS_G12D, U2AF1_S34F, BRAF_V600E, KRAS_G12V, PIK3CA_E545K, TP53_R158L, KRAS_G12A, EGFR_L861Q, and TP53_R273L. Such mutations are associated with, for example, non-small cell lung cancer (NSCLC). The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, or all of the antigenic peptides in Table 35. The cancer-associated proteins from which heteroclitic antigenic peptides are generated can comprise proteins encoded by 1 or more, 2 or more, 3 or more, 4 or more, 5 or more, 6 or more, or all of the following genes: CEACAM5, MAGEA6, MAGEA4, GAGE1, NYESO1, STEAP1, and RNF43. The heteroclitic antigenic peptides can bind, for example, one or more or all of HLA types A0201, A0301, A2402, and B0702. Such cancer-associated proteins are associated with, for example, non-small cell lung cancer (NSCLC). The heteroclitic antigenic peptides can be in any order. The heteroclitic antigenic peptides can be fused directly together or linked together by linkers, examples of which are disclosed elsewhere herein. In a specific example, one or more or all of the heteroclitic antigenic peptides can be 9-mers (e.g., 9-mers linked together by linkers). Examples of such antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, or all 11 of the heteroclitic antigenic peptides in Table 36. In a specific example, the cancer-associated protein from which the minigene antigenic peptide is generated can comprise protein encoded by CEACAM5. For example, the minigene antigenic peptide can comprise SEQ ID NO: 798 or SEQ ID NO: 796. In one example, the antigenic peptides in the fusion polypeptide can comprise one or more or all of the peptides set forth in Table 35 and Table 36. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 859; SEQ ID NO: 860; SEQ ID NO: 861; SEQ ID NO: 862; SEQ ID NO: 863; SEQ ID NO: 864; SEQ ID NO: 865; SEQ ID NO: 894; SEQ ID NO: 895; SEQ ID NO: 905, SEQ ID NO: 909, SEQ ID NO: 910, SEQ ID NO: 911, or SEQ ID NO: 912. A breakdown of the amino acids positions of the individual components in each construct is provided in Tables 38-51.

As another example, the cancer-associated proteins from which recurrent cancer mutation peptides are generated can comprise proteins encoded by 1 or more, 2 or more, 3 or more, 4 or more, or all of the following genes: SPOP, CHEK2, RGPD8, ANKRD36C, and AR. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, or all of the following recurrent cancer mutations: SPOP_F133V, CHEK2_K373E, RGPD8_P1760A, ANKRD36C_1634T, ANKRD36C_D629Y, SPOP_W131G, ANKRD36C_D626N, SPOP_F133L, AR_T878A, AR_L702H, AR_W742C, AR_H875Y, and AR_F877L. Such mutations are associated with, for example, prostate cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all of the antigenic peptides in Table 52. The cancer-associated proteins from which heteroclitic antigenic peptides are generated can comprise proteins encoded by 1 or more, 2 or more, 3 or more, 4 or more, 5 or more, 6 or more, 7 or more, 8 or more, or all of the following genes: CEACAM5, MAGEA4, STEAP1, RNF43, SSX2, SART3, PAGE4, PSMA, and PSA. The heteroclitic antigenic peptides can bind, for example, one or more or all of HLA types A0201, A0301, A2402, and B0702. Such cancer-associated proteins are associated with, for example, prostate cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 53. In a specific example, the cancer-associated protein from which the minigene antigenic peptide is generated can comprise protein encoded by STEAP1. For example, the minigene antigenic peptide can comprise SEQ ID NO: 799 or SEQ ID NO: 800. In one example, the antigenic peptides in the fusion polypeptide can comprise one or more or all of the peptides set forth in Table 52 and Table 54. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 871; SEQ ID NO: 872; SEQ ID NO: 873; SEQ ID NO: 874; SEQ ID NO: 875; SEQ ID NO: 876; SEQ ID NO: 877; SEQ ID NO: 892; SEQ ID NO: 893; SEQ ID NO: 906, SEQ ID NO: 913, SEQ ID NO: 914, SEQ ID NO: 915, or SEQ ID NO: 916. A breakdown of the amino acids positions of the individual components in each construct is provided in Tables 54-67.

As another example, the cancer-associated proteins from which recurrent cancer mutation peptides are generated can comprise proteins encoded by 1 or more, 2 or more, 3 or more, 4 or more, or all of the following genes: KRAS, U2AF1, TP53, SMAD4, and GNAS. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: KRAS_G12C, KRAS_G12D, U2AF1_S34F, KRAS_G12V, TP53_R248Q, TP53_R248W, TP53_R175H, TP53_R273C, KRAS_G12R, KRAS_Q61H, TP53_R282W, TP53_R273H, TP53_G245S, SMAD4_R361C, GNAS_R201C, and GNAS_R201H. Such mutations are associated with, for example, pancreatic cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the antigenic peptides in Table 68. The cancer-associated proteins from which heteroclitic antigenic peptides are generated can comprise proteins encoded by 1 or more, 2 or more, 3 or more, 4 or more, 5 or more, or all of the following genes: CEACAM5, STEAP1, MAGEA3, PRAME, hTERT, and SURVIVIN. The heteroclitic antigenic peptides can bind, for example, one or more or all of HLA types A0201, A0301, A2402, and B0702. Such cancer-associated proteins are associated with, for example, pancreatic cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, or all 12 of the heteroclitic antigenic peptides in Table 69. In a specific example, the cancer-associated protein from which the minigene antigenic peptide is generated can comprise protein encoded by CEACAM5. For example, the minigene antigenic peptide can comprise SEQ ID NO: 798 or SEQ ID NO: 796. In one example, the antigenic peptides in the fusion polypeptide can comprise one or more or all of the peptides set forth in Table 68 and Table 69. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 866; SEQ ID NO: 867; SEQ ID NO: 868; SEQ ID NO: 869; SEQ ID NO: 870; or SEQ ID NO: 908. A breakdown of the amino acids positions of the individual components in each construct is provided in Tables 70-75.

As another example, the cancer-associated proteins from which recurrent cancer mutation peptides are generated can comprise proteins encoded by 1 or more, 2 or more, 3 or more, 4 or more, 5 or more, or all of the following genes: PIK3CA, FGFR3, TP53, RXRA, FBXW7, and NFE2L2. The antigenic peptides can comprise, for example, 1 or more, 2 or more, 3 or more, 4 or more, 5 or more, 6 or more, 7 or more, 8 or more, 9 or more, 10 or more, 11 or more, 12 or more, or all of the following recurrent cancer mutations: PIK3CA_E545K, FGFR3_S249C, TP53_R248Q, PIK3CA_E542K, RXRA_S427F, FBXW7_R505G, TP53_R280T, NFE2L2_E79K, FGFR3_R248C, TP53_K132N, TP53_R248W, TP53_R175H, and TP53_R273C. Such mutations are associated with, for example, bladder cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, or all of the antigenic peptides in Table 76. The cancer-associated proteins from which heteroclitic antigenic peptides are generated can comprise proteins encoded by 1 or more, 2 or more, 3 or more, 4 or more, 5 or more, 6 or more, 7 or more, or all of the following genes: CEACAM5, GAGE1, NYESO1, RNF43, NUF2, KLHL7, MAGEA3, and PRAME. The heteroclitic antigenic peptides can bind, for example, one or more or all of HLA types A0201, A0301, A2402, and B0702. Such cancer-associated proteins are associated with, for example, bladder cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all 14 of the heteroclitic antigenic peptides in Table 77. In a specific example, the cancer-associated protein from which the minigene antigenic peptide is generated can comprise protein encoded by NYESO1 or NUF2. For example, the minigene antigenic peptide can comprise SEQ ID NO: 797 or SEQ ID NO: 800. In one example, the antigenic peptides in the fusion polypeptide can comprise one or more or all of the peptides set forth in Table 76 and Table 77. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 878; SEQ ID NO: 879; SEQ ID NO: 880; SEQ ID NO: 881; SEQ ID NO: 882; SEQ ID NO: 888; SEQ ID NO: 889; SEQ ID NO: 890; or SEQ ID NO: 891. A breakdown of the amino acids positions of the individual components in each construct is provided in Tables 78-86.

As another example, the cancer-associated proteins from which recurrent cancer mutation peptides are generated can comprise proteins encoded by 1 or more, 2 or more, or all of the following genes: PIK3CA, AKT1, and ESR1. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, or all of the following recurrent cancer mutations: PIK3CA_E545K, PIK3CA_E542K, PIK3CA_H1047R, AKT1_E17K, PIK3CA_H1047L, PIK3CA_Q546K, PIK3CA_E545A, PIK3CA_E545G, ESRI_K303R, ESRI_D538G, ESRI_Y537S, ESR1_Y537N, ESRI_Y537C, and ESR1_E380Q. Such mutations are associated with, for example, breast cancer (e.g., ER+breast cancer). The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all of the antigenic peptides in Table 87. The cancer-associated proteins from which heteroclitic antigenic peptides are generated can comprise proteins encoded by 1 or more, 2 or more, 3 or more, 4 or more, 5 or more, or all of the following genes: CEACAM5, STEAP1, RNF43, MAGEA3, PRAME, and hTERT. The heteroclitic antigenic peptides can bind, for example, one or more or all of HLA types A0201, A0301, A2402, and B0702. Such cancer-associated proteins are associated with, for example, breast cancer (e.g., ER+breast cancer). The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, or all 11 of the heteroclitic antigenic peptides in Table 88. In a specific example, the cancer-associated protein from which the minigene antigenic peptide is generated can comprise protein encoded by STEAP1. For example, the minigene antigenic peptide can comprise SEQ ID NO: 799 or SEQ ID NO: 800. In one example, the antigenic peptides in the fusion polypeptide can comprise one or more or all of the peptides set forth in Table 87 and Table 88. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 883; SEQ ID NO: 884; SEQ ID NO: 885; SEQ ID NO: 886; SEQ ID NO: 887; or SEQ ID NO: 907. A breakdown of the amino acids positions of the individual components in each construct is provided in Tables 89-94.

As another example, the cancer-associated proteins from which recurrent cancer mutation peptides are generated can comprise proteins encoded by 1 or more, 2 or more, 3 or more, 4 or more, 5 or more, or all of the following genes: PTEN, KRAS, PIK3CA, CTNNB1, FBXW7, and TP53. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the following recurrent cancer mutations: PTEN_R130G, PTEN_R130Q, KRAS_G12D, KRAS_G12V, PIK3CA_H1047R; PIK3CA_R88Q, PIK3CA_E545K, PIK3CA_E542K, CTNNB1_S37F, KRAS_G13D, CTNNB1_S37C, PIK3CA_H1047L, PIK3CA_G118D, KRAS_G12A, FBXW7_R505C, and TP53_R248W. Such mutations are associated with, for example, uterine cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, or all of the antigenic peptides in Table 95. The cancer-associated proteins from which heteroclitic antigenic peptides are generated can comprise proteins encoded by 1 or more, 2 or more, 3 or more, 4 or more, 5 or more, 6 or more, 7 or more, or all of the following genes: CEACAM5, PRAME, hTERT, STEAP1, RNF43, NUF2, KLHL7, and SART3. The heteroclitic antigenic peptides can bind, for example, one or more or all of HLA types A0201, A0301, A2402, and B0702. Such cancer-associated proteins are associated with, for example, uterine cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all 14 of the heteroclitic antigenic peptides in Table 96. In a specific example, the cancer-associated protein from which the minigene antigenic peptide is generated can comprise protein encoded by STEAP1. For example, the minigene antigenic peptide can comprise SEQ ID NO: 799 or SEQ ID NO: 800. In one example, the antigenic peptides in the fusion polypeptide can comprise one or more or all of the peptides set forth in Table 95 and Table 96. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 896; SEQ ID NO: 897;

or SEQ ID NO: 904. A breakdown of the amino acids positions of the individual components in each construct is provided in Tables 97-99.

As another example, the cancer-associated proteins from which recurrent cancer mutation peptides are generated can comprise TP53. The antigenic peptides can comprise, for example, 1 or more, 2 or more, 3 or more, 4 or more, 5 or more, 6 or more, 7 or more, 8 or more, 9 or more, 10 or more, 11 or more, or all of the following recurrent cancer mutations: TP53_R248Q, TP53_R248W, TP53_R175H, TP53_R273C, TP53_R282W, TP53_R273H, TP53_Y220C, TP53_I195T, TP53_C176Y, TP53_H179R, TP53_S241F, and TP53_H193R. Such mutations are associated with, for example, ovarian cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, or all of the antigenic peptides in Table 100. The cancer-associated proteins from which heteroclitic antigenic peptides are generated can comprise proteins encoded by 1 or more, 2 or more, 3 or more, 4 or more, 5 or more, 6 or more, 7 or more, or all of the following genes: CEACAM5, STEAP1, RNF43, SART3, NUF2, KLHL7, PRAME, and hTERT. The heteroclitic antigenic peptides can bind, for example, one or more or all of HLA types A0201, A0301, A2402, and B0702. Such cancer-associated proteins are associated with, for example, ovarian cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, or all 14 of the heteroclitic antigenic peptides in Table 101. In a specific example, the cancer-associated protein from which the minigene antigenic peptide is generated can comprise protein encoded by STEAP1. For example, the minigene antigenic peptide can comprise SEQ ID NO: 799. In one example, the antigenic peptides in the fusion polypeptide can comprise one or more or all of the peptides set forth in Table 100 and Table 101. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 898 or 899. A breakdown of the amino acids positions of the individual components in each construct is provided in Tables 102-103.

As another example, the cancer-associated proteins from which recurrent cancer mutation peptides are generated can comprise proteins encoded by 1 or more, 2 or more, 3 or more, 4 or more, or all of the following genes: TP53, PIK3CA, IDH1, IDH2, and EGFR. The antigenic peptides can comprise, for example, 1 or more, 2 or more, 3 or more, 4 or more, 5 or more, 6 or more, 7 or more, 8 or more, 9 or more, 10 or more, or all of the following recurrent cancer mutations: TP53_R273L, TP53_R273C, TP53_R273H, PIK3CA_G118D, IDH1_R132C, IDH1_R132G, IDH1_R132H, IDH1_R132S, IDH2_R172K, PIK3CA_E453K, and EGFR_G598V. Such mutations are associated with, for example, low-grade glioma. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, or all of the antigenic peptides in Table 104. The cancer-associated proteins from which heteroclitic antigenic peptides are generated can comprise proteins encoded by 1 or more, 2 or more, 3 or more, 4 or more, 5 or more, 6 or more, 7 or more, or all of the following genes: CEACAM5, MAGEA6, STEAP1, RNF43, SART3, NUF2, KLHL7, and hTERT. The heteroclitic antigenic peptides can bind, for example, one or more or all of HLA types A0201, A0301, A2402, and B0702. Such cancer-associated proteins are associated with, for example, low-grade glioma. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 105. In a specific example, the cancer-associated protein from which the minigene antigenic peptide is generated can comprise protein encoded by NUF2. For example, the minigene antigenic peptide can comprise SEQ ID NO: 807. In one example, the antigenic peptides in the fusion polypeptide can comprise one or more or all of the peptides set forth in Table 104 and Table 105. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 900 or SEQ ID NO: 901. A breakdown of the amino acids positions of the individual components in each construct is provided in Tables 106-107.

As another example, the cancer-associated proteins from which recurrent cancer mutation peptides are generated can comprise proteins encoded by 1 or more, 2 or more, 3 or more, or all of the following genes: KRAS, BRAF, PIK3CA, and TP53. The antigenic peptides can comprise, for example, 1 or more, 2 or more, 3 or more, 4 or more, 5 or more, 6 or more, 7 or more, 8 or more, 9 or more, 10 or more, 11 or more, or all of the following recurrent cancer mutations: KRAS_G12C, KRAS_G12D, BRAF_V600E, KRAS_G12V, PIK3CA_E545K, TP53 R248W, TP53_R175H, TP53_R273C, PIK3CA_H1047R, TP53_R282W, TP53_R273H, and KRAS_G13D. Such mutations are associated with, for example, colorectal cancer (e.g., MSS colorectal cancer). The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, or all of the antigenic peptides in Table 108. The cancer-associated proteins from which heteroclitic antigenic peptides are generated can comprise proteins encoded by 1 or more, 2 or more, 3 or more, 4 or more, 5 or more, 6 or more, 7 or more, or all of the following genes: CEACAM5, MAGEA6, MAGEA4, GAGE1, NYESO1, STEAP1, RNF43, and MAGEA3. The heteroclitic antigenic peptides can bind, for example, one or more or all of HLA types A0201, A0301, A2402, and B0702. Such cancer-associated proteins are associated with, for example, colorectal cancer (e.g., MSS colorectal cancer). The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 109. In a specific example, the cancer-associated protein from which the minigene antigenic peptide is generated can comprise protein encoded by STEAP1. For example, the minigene antigenic peptide can comprise SEQ ID NO: 799. In one example, the antigenic peptides in the fusion polypeptide can comprise one or more or all of the peptides set forth in Table 108 and Table 109. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 902 or SEQ ID NO: 903. A breakdown of the amino acids positions of the individual components in each construct is provided in Tables 110-111.

As another example, the cancer-associated proteins from which recurrent cancer mutation peptides are generated can comprise proteins encoded by 1 or more, 2 or more, 3 or more, 4 or more, 5 or more, 6 or more, 7 or more, 8 or more, or all of the following genes: PIK3CA, CHEK2, RGPD8, ANKRD36C, TP53, ZNF814, KRTAP1-5, KRTAP4-11, and HRAS. The antigenic peptides can comprise, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the following recurrent cancer mutations: PIK3CA_E545K, CHEK2_K373E, RGPD8_P1760A, ANKRD36C_I634T, TP53_R248Q, PIK3CA_E542K, TP53_R248W, TP53_R175H, PIK3CA_H1047R, TP53_R282W, TP53_R273H, TP53_G245S, TP53_Y220C, ZNF814_D404E, KRTAP1-5_188T, KRTAP4-11_L161V, and HRAS_G13V. Such mutations are associated with, for example, head and neck cancer. The mutations can be in any order. The antigenic peptides can be fused directly together or linked together by linkers, examples of which are disclosed elsewhere herein. In a specific example, one or more or all of the antigenic peptides can be 21-mers (e.g., 21-mers linked together by linkers), each including the naturally occurring 10 amino acids flanking each side of the recurrent cancer mutation. Examples of such antigenic peptides are provided in Example 11. The antigenic peptides can include, for example, 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, or all of the antigenic peptides in Table 112. The cancer-associated proteins from which heteroclitic antigenic peptides are generated can comprise proteins encoded by 1 or more, 2 or more, 3 or more, 4 or more, 5 or more, or all of the following genes: CEACAM5, MAGEA4, STEAP1, NYESO1, PRAME, and hTERT. The heteroclitic antigenic peptides can bind, for example, one or more or all of HLA types A0201, A0301, A2402, and B0702. Such cancer-associated proteins are associated with, for example, head and neck cancer. The heteroclitic antigenic peptides can be in any order. The heteroclitic antigenic peptides can be fused directly together or linked together by linkers, examples of which are disclosed elsewhere herein. In a specific example, one or more or all of the antigenic peptides can be 9-mers (e.g., 9-mers linked together by linkers). Examples of such heteroclitic antigenic peptides are provided in Example 11. The heteroclitic antigenic peptides can include, for example, 1 or more, 2 or more, 3 or more, 4 or more, 5 or more, 6 or more, 7 or more, 8 or more, 9 or more, or all 10 of the heteroclitic antigenic peptides in Table 113. In a specific example, the cancer-associated protein from which the minigene antigenic peptide is generated can comprise protein encoded by STEAP1. For example, the minigene antigenic peptide can comprise SEQ ID NO: 799. In one example, the antigenic peptides in the fusion polypeptide can comprise one or more or all of the peptides set forth in Table 112 and Table 113. Exemplary fusion polypeptide insert sequences (i.e., the peptide sequence downstream of the tLLO) comprise, consist essentially of, or consist of sequences at least 85%, 90%, 91%, 92%, 93%, 94%, 95%, 96%, 97%, 98%, 99%, or 100% identical to one of the sequence set forth in SEQ ID NO: 918 or SEQ ID NO: 919. A breakdown of the amino acids positions of the individual components in each construct is provided in Tables 114-115.

Also provided herein are methods for generating immunotherapy constructs encoding or compositions comprising the recombinant fusion polypeptides disclosed herein. For example, such methods can comprise selecting and designing antigenic or immunogenic peptides to include in the immunotherapy construct (and, for example, testing the hydropathy of each antigenic peptide, and modifying or deselecting an antigenic peptide if it scores above a selected hydropathy index threshold value), designing one or more fusion polypeptides comprising each of the selected antigenic peptides, and generating a nucleic acid construct encoding the fusion polypeptide. Such methods are disclosed in more detail elsewhere herein. As a specific example, such a method can comprise: (a) selecting a set of recurrent cancer mutations and a set of heteroclitic mutations in cancer-associated proteins to include in the immunotherapy construct; (b) designing antigenic peptides comprising each of the recurrent cancer mutations and each of the heteroclitic mutations; (c) selecting a set of antigenic peptides, comprising testing the hydropathy of the each antigenic peptide, and modifying or deselecting an antigenic peptide if it scores above a selected hydropathy index threshold value; (d) designing a fusion polypeptide comprising each of the selected antigenic peptides; and (e) generating a nucleic acid construct encoding the fusion polypeptide.

The individual selected recurrent cancer mutations can be selected in step (a), for example, based on one or more of the following criteria: (i) frequency of occurrence across multiple types of cancers or a particular type of cancer; (ii) location within a functional domain of a cancer-associated protein; (iii) status as a known cancer driver mutation or chemotherapy resistance mutation; and (iv) identification as a somatic missense mutation or a somatic frameshift mutation. Likewise, the set of recurrent cancer mutations selected in step (a) can be selected based on one or more of the following criteria: (i) the set includes no more than about 30, 31, 32, 33, 34, 35, 36, 37, 38, 39, 40, 41, 42, 43, 44, 45, 46, 47, 48, 49 or 50 recurrent cancer mutations and/or no more than about 30, 31, 32, 33, 34, 35, 36, 37, 38, 39, 40, 41, 42, 43, 44, 45, 46, 47, 48, 49 or 50 heteroclitic mutations; (ii) the set includes recurrent cancer mutations that would be found in at least 5%, 10%, 15%, 20%, 25%, 30%, 35%, 40%, 45%, 50%, 55%, 60%, 65%, 70%, 75% 80%, 85%, 90%, 95%, 96%, 97%, 98%, or 99% of cancer patients who have a single type of cancer; and (iii) the set comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent cancer mutations or recurrent somatic missense mutations from a single type of cancer.

The individual selected heteroclitic mutations can be selected in step (a), for example, based on one or more of the following criteria: (i) ability to bind to one or more of the following HLA types: HLA-A*02:01, HLA-A*03:01, HLA-A*24:02, and HLA-B*07:02; (ii) ability to generate a CD8+ T lymphocyte response; and (iii) binding affinity to a specific HLA that is equivalent or stronger than the corresponding wild type sequence. Likewise, the set of heteroclitic mutations selected in step (a) can be selected based on collective ability to bind to one or more or all of the following HLA types: HLA-A*02:01, HLA-A*03:01, HLA-A*24:02, and HLA-B*07:02.

One or more or all of the antigenic peptides designed in step (b) to comprise a recurrent cancer mutation can be designed, for example, to comprise a fragment of the cancer-associated protein comprising the recurrent cancer mutation and flanking sequence on each side. For example, one or more or all of the antigenic peptides comprising a recurrent cancer mutation can include at least about 10 flanking amino acids on each side of the recurrent cancer mutation.

One or more or all of the antigenic peptides designed in step (b) to comprise a heteroclitic mutation can be designed, for example, to have a preferred amino acid at an anchor position.

The antigenic peptides can be selected in step (c), for example, if they are below a hydropathy threshold predictive of secretability in *Listeria monocytogenes*. For example, the antigenic peptides can be scored by a Kyte and Doolittle hydropathy index 21 amino acid window, and any peptides scoring above a cutoff of about 1.6 can be excluded or are modified to score below the cutoff. Likewise, the hydropathy of the fusion polypeptide can be tested, followed by either reordering the antigenic peptides or removing problematic antigenic peptides if any region of the fusion polypeptide scores above a selected hydropathy index threshold value (e.g., a Kyte and Doolittle hydropathy index with a sliding 21 amino acid window, wherein the threshold value is about 1.6). In addition, the fusion polypeptide can be designed to have a molecular weight of, for example, no more than about 150 kDa, or no more than about 120 kDa. For example, the recombinant fusion polypeptide can be less than or no more than about 200, 195, 190, 185, 180, 175, 170, 165, 160, 155, 150, 145, 140, 135, 130, or 125 kilodaltons (kDa). In a specific example, the recombinant fusion polypeptide is less than or no more than about 150 kDa or less than or no more than about 130 kDa. As another example the recombinant fusion polypeptide can be between about 50-200, 50-195, 50-190, 50-185, 50-180, 50-175, 50-170, 50-165, 50-160, 50-155, 50-150, 50-145, 50-140, 50-135, 50-130, 50-125, 100-200, 100-195, 100-190, 100-185, 100-180, 100-175, 100-170, 100-165, 100-160, 100-155, 100-150, 100-145, 100-140, 100-135, 100-130, or 100-125 kDa. In a specific example, the recombinant fusion polypeptide is between about 50-150, 100-150, 50-125, or 100-125 kDa. As another example, the recombinant fusion polypeptide can be at least about 50, 55, 60, 65, 70, 75, 80, 85, 90, 95, 100, 105, 110, 115, 120, or 125 kDa. As a specific example, the recombinant fusion polypeptide can be at least about 100 kDa. Other parameters for design and selection of antigenic peptides and fusion polypeptides are disclosed in more detail elsewhere herein and can also be used.

VI. Recombinant Bacteria or *Listeria* Strains

Also provided herein are recombinant bacterial strains, such as a *Listeria* strain, comprising a recombinant fusion polypeptide disclosed herein or a nucleic acid encoding the recombinant fusion polypeptide as disclosed elsewhere herein. Preferably, the bacterial strain is a *Listeria* strain, such as a *Listeria monocytogenes* (Lm) strain. Lm has a number of inherent advantages as a vaccine vector. The bacterium grows very efficiently in vitro without special requirements, and it lacks LPS, which is a major toxicity factor in gram-negative bacteria, such as *Salmonella*. Genetically attenuated Lm vectors also offer additional safety as they can be readily eliminated with antibiotics, in case of serious adverse effects, and unlike some viral vectors, no integration of genetic material into the host genome occurs.

The recombinant *Listeria* strain can be any *Listeria* strain. Examples of suitable *Listeria* strains include *Listeria seeligeri*, *Listeria grayi*, *Listeria ivanovii*, *Listeria murrayi*, *Listeria welshimeri*, *Listeria monocytogenes* (Lm), or any other *Listeria* species known in the art. Preferably, the recombinant *listeria* strain is a strain of the species *Listeria monocytogenes*. Examples of *Listeria monocytogenes* strains include the following: *L. monocytogenes* 10403S wild type (see, e.g., Bishop and Hinrichs (1987) *J Immunol* 139:2005-2009; Lauer et al. (2002) *J Bact* 184:4177-4186); *L. monocytogenes* DP-L4056, which is phage cured (see, e.g., Lauer et al. (2002) *J Bact* 184:4177-4186); *L. monocytogenes* DP-L4027, which is phage cured and has an hly gene deletion (see, e.g., Lauer et al. (2002) *J 127 Bact* 184:4177-4186; Jones and Portnoy (1994) *Infect Immunity* 65:5608-5613); *L. monocytogenes* DP-L4029, which is phage cured and has an actA gene deletion (see, e.g., Lauer et al. (2002) *J Bact* 184:4177-4186; Skoble et al. (2000) *J Cell Biol* 150:527-538); *L. monocytogenes* DP-L4042 (delta PEST) (see, e.g., Brockstedt et al. (2004) *Proc Natl Acad Sci. USA* 101:13832-13837 and supporting information); *L. monocytogenes* DP-L4097 (LLO-S44A) (see, e.g., Brockstedt et al. (2004) *Proc Natl Acad Sci USA* 101:13832-13837 and supporting information); *L. monocytogenes* DP-L4364 (delta lplA; lipoate protein ligase) (see, e.g., Brockstedt et al. (2004) *Proc Natl Acad Sci USA* 101:13832-13837 and supporting information); *L. monocytogenes* DP-L4405 (delta in/A) (see, e.g., Brockstedt et al. (2004) *Proc Natl Acad Sci USA* 101:13832-13837 and supporting information); *L. monocytogenes* DP-L4406 (delta inlB) (see, e.g., Brockstedt et al. (2004) *Proc Natl Acad Sci USA* 101:13832-13837 and supporting information); *L. monocytogenes* CS- L0001 (delta actA; delta inlB) (see, e.g., Brockstedt et al. (2004) *Proc Natl Acad Sci USA* 101:13832-13837 and supporting information); *L. monocytogenes* CS-L0002 (delta actA; delta lplA) (see, e.g., Brockstedt et al. (2004) *Proc Natl Acad Sci USA* 101:13832-13837 and supporting information); *L. monocytogenes* CS-L0003 (LLO L461T; delta lplA) (see, e.g., Brockstedt et al. (2004) *Proc Natl Acad Sci USA* 101:13832-13837 and supporting information); *L. monocytogenes* DP-L4038 (delta actA; LLO L461T) (see, e.g., Brockstedt et al. (2004) *Proc Natl Acad Sci USA* 101:13832-13837 and supporting information); *L. monocytogenes* DP-L4384 (LLO S44A; LLO L461T) (see, e.g., Brockstedt et al. (2004) *Proc Natl Acad Sci USA* 101:13832-13837 and supporting information); a *L. monocytogenes* strain with an lplA1 deletion (encoding lipoate protein ligase LplA1) (see, e.g., O'Riordan et al. (2003) *Science* 302:462-464); *L. monocytogenes* DP-L4017 (10403S with LLO L461T) (see, e.g., U.S. Pat. No. 7,691,393); *L. monocytogenes* EGD (see, e.g., GenBank Accession No. AL591824). In another embodiment, the *Listeria* strain is *L. monocytogenes* EGD-e (see GenBank Accession No. NC_003210; ATCC Accession No. BAA-679); *L. monocytogenes* DP-L4029 (actA deletion, optionally in combination with uvrAB deletion (DP-L4029uvrAB) (see, e.g., U.S. Pat. No. 7,691,393); *L. monocytogenes* actA-linlB—double mutant (see, e.g., ATCC Accession No. PTA-5562); *L. monocytogenes* lplA mutant or hly mutant (see, e.g., US 2004/0013690); *L. monocytogenes* dal/dat double mutant (see, e.g., US 2005/0048081). Other *L. monocytogenes* strains includes those that are modified (e.g., by a plasmid and/or by genomic integration) to contain a nucleic acid encoding one of, or any combination of, the following genes: hly (LLO; listeriolysin); iap (p60); inlA; inlB; inlC; dal (alanine racemase); dat (D-amino acid aminotransferase); plcA; plcB; actA; or any nucleic acid that mediates growth, spread, breakdown of a single walled vesicle, breakdown of a double walled vesicle, binding to a host cell, or uptake by a host cell. Each of the above references is herein incorporated by reference in its entirety for all purposes.

The recombinant bacteria or *Listeria* can have wild-type virulence, can have attenuated virulence, or can be avirulent. For example, a recombinant *Listeria* of can be sufficiently virulent to escape the phagosome or phagolysosome and enter the cytosol. Such *Listeria* strains can also be live-attenuated *Listeria* strains, which comprise at least one attenuating mutation, deletion, or inactivation as disclosed elsewhere herein. Preferably, the recombinant *Listeria* is an attenuated auxotrophic strain. An auxotrophic strain is one that is unable to synthesize a particular organic compound required for its growth. Examples of such strains are described in U.S. Pat. No. 8,114,414, herein incorporated by reference in its entirety for all purposes.

Preferably, the recombinant *Listeria* strain lacks antibiotic resistance genes. For example, such recombinant *Listeria* strains can comprise a plasmid that does not encode an antibiotic resistance gene. However, some recombinant *Listeria* strains provided herein comprise a plasmid comprising a nucleic acid encoding an antibiotic resistance gene. Antibiotic resistance genes may be used in the conventional selection and cloning processes commonly employed in molecular biology and vaccine preparation. Exemplary antibiotic resistance genes include gene products that confer resistance to ampicillin, penicillin, methicillin, streptomycin, erythromycin, kanamycin, tetracycline, chloramphenicol (CAT), neomycin, hygromycin, and gentamicin.

A. Bacteria or *Listeria* Strains Comprising Recombinant Fusion Polypeptides or Nucleic Acids Encoding Recombinant Fusion Polypeptides The recombinant bacterial strains (e.g., *Listeria* strains) disclosed herein comprise a recombinant fusion polypeptide disclosed herein or a nucleic acid encoding the recombinant fusion polypeptide as disclosed elsewhere herein.

In bacteria or *Listeria* strains comprising a nucleic acid encoding a recombinant fusion protein, the nucleic acid can be codon optimized. The optimal codons utilized by *L. monocytogenes* for each amino acid are shown US 2007/0207170, herein incorporated by reference in its entirety for all purposes. A nucleic acid is codon-optimized if at least one codon in the nucleic acid is replaced with a codon that is more frequently used by *L. monocytogenes* for that amino acid than the codon in the original sequence.

The nucleic acid can be present in an episomal plasmid within the bacteria or *Listeria* strain and/or the nucleic acid can be genomically integrated in the bacteria or *Listeria* strain. Some recombinant bacteria or *Listeria* strains comprise two separate nucleic acids encoding two recombinant fusion polypeptides as disclosed herein: one nucleic acid in an episomal plasmid, and one genomically integrated in the bacteria or *Listeria* strain.

The episomal plasmid can be one that is stably maintained in vitro (in cell culture), in vivo (in a host), or both in vitro and in vivo. If in an episomal plasmid, the open reading frame encoding the recombinant fusion polypeptide can be operably linked to a promoter/regulatory sequence in the plasmid. If genomically integrated in the bacteria or *Listeria* strain, the open reading frame encoding the recombinant fusion polypeptide can be operably linked to an exogenous promoter/regulatory sequence or to an endogenous promoter/regulatory sequence. Examples of promoters/regulatory sequences useful for driving constitutive expression of a gene are well known and include, for example, an hly, hlyA, actA, prfA, and p60 promoters of *Listeria*, the *Streptococcus* bac promoter, the *Streptomyces griseus* sgiA promoter, and the *B. thuringiensis* phaZ promoter. In some cases, an inserted gene of interest is not interrupted or subjected to regulatory constraints which often occur from integration into genomic DNA, and in some cases, the presence of the inserted heterologous gene does not lead to rearrangement or interruption of the cell's own important regions.

Such recombinant bacteria or *Listeria* strains can be made by transforming a bacteria or *Listeria* strain or an attenuated bacteria or *Listeria* strain described elsewhere herein with a plasmid or vector comprising a nucleic acid encoding the recombinant fusion polypeptide. The plasmid can be an episomal plasmid that does not integrate into a host chromosome. Alternatively, the plasmid can be an integrative plasmid that integrates into a chromosome of the bacteria or *Listeria* strain. The plasmids used herein can also be multicopy plasmids. Methods for transforming bacteria are well known, and include calcium-chloride competent cell-based methods, electroporation methods, bacteriophage-mediated transduction, chemical transformation techniques, and physical transformation techniques. See, e.g., de Boer et al. (1989) *Cell* 56:641-649; Miller et al. (1995) *FASEB J* 9:190-199; Sambrook et al. (1989) *Molecular Cloning: A Laboratory Manual*, Cold Spring Harbor Laboratory, New York; Ausubel et al. (1997) *Current Protocols in Molecular Biology*, John Wiley & Sons, New York; Gerhardt et al., eds., 1994, Methods for General and Molecular Bacteriology, American Society for Microbiology, *Washington, D.C.*; and Miller, 1992, *A Short Course in Bacterial Genetics*, Cold Spring Harbor Laboratory Press, Cold Spring Harbor, N.Y., each of which is herein incorporated by reference in its entirety for all purposes.

Bacteria or *Listeria* strains with genomically integrated heterologous nucleic acids can be made, for example, by using a site-specific integration vector, whereby the bacteria or *Listeria* comprising the integrated gene is created using homologous recombination. The integration vector can be any site-specific integration vector that is capable of infecting a bacteria or *Listeria* strain. Such an integration vector can comprise, for example, a PSA attPP' site, a gene encoding a PSA integrase, a U153 attPP' site, a gene encoding a U153 integrase, an A118 attPP' site, a gene encoding an A118 integrase, or any other known attPP' site or any other phage integrase.

Such bacteria or *Listeria* strains comprising an integrated gene can also be created using any other known method for integrating a heterologous nucleic acid into a bacteria or *Listeria* chromosome. Techniques for homologous recombination are well known, and are described, for example, in Baloglu et al. (2005) *Vet Microbiol* 109(1-2):11-17); Jiang et al. 2005) *Acta Biochim Biophys Sin* (Shanghai) 37(1):19-24), and U.S. Pat. No. 6,855,320, each of which is herein incorporated by reference in its entirety for all purposes.

Integration into a bacteria or Listerial chromosome can also be achieved using transposon insertion. Techniques for transposon insertion are well known, and are described, for example, for the construction of DP-L967 by Sun et al. (1990) *Infection and Immunity* 58: 3770-3778, herein incorporated by reference in its entirety for all purposes. Transposon mutagenesis can achieve stable genomic insertion, but the position in the genome where the heterologous nucleic acids has been inserted is unknown.

Integration into a bacterial or Listerial chromosome can also be achieved using phage integration sites (see, e.g., Lauer et al. (2002) *J Bacteriol* 184(15):4177-4186, herein incorporated by reference in its entirety for all purposes). For example, an integrase gene and attachment site of a bacteriophage (e.g., U153 or PSA listeriophage) can be used to insert a heterologous gene into the corresponding attachment site, which may be any appropriate site in the genome (e.g. comK or the 3' end of the arg tRNA gene). Endogenous prophages can be cured from the utilized attachment site prior to integration of the heterologous nucleic acid. Such methods can result, for example, in single-copy integrants. In order to avoid a "phage curing step," a phage integration system based on PSA phage can be used (see, e.g., Lauer et al. (2002) *J Bacteriol* 184:4177-4186, herein incorporated by reference in its entirety for all purposes). Maintaining the integrated gene can require, for example, continuous selection by antibiotics. Alternatively, a phage-based chromosomal integration system can be established that does not require selection with antibiotics. Instead, an auxotrophic host strain can be complemented. For example, a phage-based chromosomal integration system for clinical applications can be used, where a host strain that is auxotrophic for essential enzymes, including, for example, D-alanine racemase is used (e.g., Lm dal(−)dat(−)).

Conjugation can also be used to introduce genetic material and/or plasmids into bacteria. Methods for conjugation are well known, and are described, for example, in Nikodinovic et al. (2006) *Plasmid* 56(3):223-227 and Auchtung et al. (2005) *Proc Natl Acad Sci USA* 102(35):12554-12559, each of which is herein incorporated by reference in its entirety for all purposes.

In a specific example, a recombinant bacteria or *Listeria* strain can comprise a nucleic acid encoding a recombinant fusion polypeptide genomically integrated into the bacteria or *Listeria* genome as an open reading frame with an endogenous actA sequence (encoding an ActA protein) or an endogenous hly sequence (encoding an LLO protein). For example, the expression and secretion of the fusion polypeptide can be under the control of the endogenous actA promoter and ActA signal sequence or can be under the control of the endogenous hly promoter and LLO signal sequence. As another example, the nucleic acid encoding a recombinant fusion polypeptide can replace an actA sequence encoding an ActA protein or an hly sequence encoding an LLO protein.

Selection of recombinant bacteria or *Listeria* strains can be achieved by any means. For example, antibiotic selection can be used. Antibiotic resistance genes may be used in the conventional selection and cloning processes commonly employed in molecular biology and vaccine preparation. Exemplary antibiotic resistance genes include gene products that confer resistance to ampicillin, penicillin, methicillin, streptomycin, erythromycin, kanamycin, tetracycline, chloramphenicol (CAT), neomycin, hygromycin, and gentamicin. Alternatively, auxotrophic strains can be used, and an exogenous metabolic gene can be used for selection instead of or in addition to an antibiotic resistance gene. As an example, in order to select for auxotrophic bacteria comprising a plasmid encoding a metabolic enzyme or a complementing gene provided herein, transformed auxotrophic bacteria can be grown in a medium that will select for expression of the gene encoding the metabolic enzyme (e.g., amino acid metabolism gene) or the complementing gene. Alternatively, a temperature-sensitive plasmid can be used to select recombinants or any other known means for selecting recombinants.

B. Attenuation of Bacteria or *Listeria* Strains

The recombinant bacteria strains (e.g., recombinant *Listeria* strains) disclosed herein can be attenuated. The term "attenuation" encompasses a diminution in the ability of the bacterium to cause disease in a host animal. For example, the pathogenic characteristics of an attenuated *Listeria* strain may be lessened compared with wild-type *Listeria*, although the attenuated *Listeria* is capable of growth and maintenance in culture. Using as an example the intravenous inoculation of BALB/c mice with an attenuated *Listeria*, the lethal dose at which 50% of inoculated animals survive ($LD_{50}$) is preferably increased above the LDso of wild-type *Listeria* by at least about 10-fold, more preferably by at least about 100-fold, more preferably at least about 1,000 fold, even more preferably at least about 10,000 fold, and most preferably at least about 100,000-fold. An attenuated strain of *Listeria* is thus one that does not kill an animal to which it is administered, or is one that kills the animal only when the number of bacteria administered is vastly greater than the number of wild-type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. Attenuated strains are environmentally safe in that they are incapable of uncontrolled replication (1) Methods of Attenuating Bacteria and *Listeria* Strains Attenuation can be accomplished by any known means. For example, such attenuated strains can be deficient in one or more endogenous virulence genes or one or more endogenous metabolic genes. Examples of such genes are disclosed herein, and attenuation can be achieved by inactivation of any one of or any combination of the genes disclosed herein. Inactivation can be achieved, for example, through deletion or through mutation (e.g., an inactivating mutation). The term "mutation" includes any type of mutation or modification to the sequence (nucleic acid or amino acid sequence) and may encompass a deletion, a truncation, an insertion, a substitution, a disruption, or a translocation. For example, a mutation can include a frameshift mutation, a mutation which causes premature termination of a protein, or a mutation of regulatory sequences which affect gene expression. Mutagenesis can be accomplished using recombinant DNA techniques or using traditional mutagenesis technology using mutagenic chemicals or radiation and subsequent selection of mutants. Deletion mutants may be preferred because of the accompanying low probability of reversion. The term "metabolic gene" refers to a gene encoding an enzyme involved in or required for synthesis of a nutrient utilized or required by a host bacteria. For example, the enzyme can be involved in or required for the synthesis of a nutrient required for sustained growth of the host bacteria. The term "virulence" gene includes a gene whose presence or activity in an organism's genome that contributes to the pathogenicity of the organism (e.g., enabling the organism to achieve colonization of a niche in the host (including attachment to cells), immunoevasion (evasion of host's immune response), immunosuppression (inhibition of host's immune response), entry into and exit out of cells, or obtaining nutrition from the host).

A specific example of such an attenuated strain is *Listeria monocytogenes* (Lm) dal(−)dat(−) (Lmdd). Another example of such an attenuated strain is Lm dal(−)dat(−)ΔactA (LmddA). See, e.g., US 2011/0142791, herein incorporated by references in its entirety for all purposes. LmddA is based on a *Listeria* strain which is attenuated due to the deletion of the endogenous virulence gene actA. Such strains can retain a plasmid for antigen expression in vivo and in vitro by complementation of the dal gene. Alternatively, the LmddA can be a dal dat actA *Listeria* having mutations in the endogenous dal, dat, and actA genes. Such mutations can be, for example, a deletion or other inactivating mutation.

Another specific example of an attenuated strain is Lm prfA(−) or a strain having a partial deletion or inactivating mutation in the prfA gene. The PrfA protein controls the expression of a regulon comprising essential virulence genes required by Lm to colonize its vertebrate hosts; hence the prfA mutation strongly impairs PrfA ability to activate expression of PrfA-dependent virulence genes.

Yet another specific example of an attenuated strain is Lm inlB(−)actA(−) in which two genes critical to the bacterium's natural virulence-internalin B and actA—are deleted.

Other examples of attenuated bacteria or *Listeria* strains include bacteria or *Listeria* strains deficient in one or more endogenous virulence genes. Examples of such genes include actA, prfA, plcB, plcA, inlA, inlB, inlC, inlJ, and bsh in *Listeria*. Attenuated *Listeria* strains can also be the double mutant or triple mutant of any of the above-mentioned strains. Attenuated *Listeria* strains can comprise a mutation or deletion of each one of the genes, or comprise a mutation or deletion of, for example, up to ten of any of the genes provided herein (e.g., including the actA, prfA, and dal dat genes). For example, an attenuated *Listeria* strain can comprise a mutation or deletion of an endogenous internalin C (inlC) gene and/or a mutation or deletion of an endogenous actA gene. Alternatively, an attenuated *Listeria* strain can comprise a mutation or deletion of an endogenous internalin B (inlB) gene and/or a mutation or deletion of an endogenous actA gene. Alternatively, an attenuated *Listeria* strain can comprise a mutation or deletion of endogenous inlB, in/C, and actA genes. Translocation of *Listeria* to adjacent cells is inhibited by the deletion of the endogenous actA gene and/or the endogenous inlC gene or endogenous inlB gene, which are involved in the process, thereby resulting in high levels of attenuation with increased immunogenicity and utility as a strain backbone. An attenuated *Listeria* strain can also be a double mutant comprising mutations or deletions of both plcA and plcB. In some cases, the strain can be constructed from the EGD *Listeria* backbone.

A bacteria or *Listeria* strain can also be an auxotrophic strain having a mutation in a metabolic gene. As one example, the strain can be deficient in one or more endogenous amino acid metabolism genes. For example, the generation of auxotrophic strains of *Listeria* deficient in D-alanine, for example, may be accomplished in a number of ways that are well known, including deletion mutations, insertion mutations, frameshift mutations, mutations which cause premature termination of a protein, or mutation of regulatory sequences which affect gene expression. Deletion mutants may be preferred because of the accompanying low probability of reversion of the auxotrophic phenotype. As an example, mutants of D-alanine which are generated according to the protocols presented herein may be tested for the ability to grow in the absence of D-alanine in a simple laboratory culture assay. Those mutants which are unable to grow in the absence of this compound can be selected.

Examples of endogenous amino acid metabolism genes include a vitamin synthesis gene, a gene encoding pantothenic acid synthase, a D-glutamic acid synthase gene, a D-alanine amino transferase (dat) gene, a D-alanine racemase (dal) gene, dga, a gene involved in the synthesis of diaminopimelic acid (DAP), a gene involved in the synthesis of Cysteine synthase A (cysK), a vitamin-B12 independent methionine synthase, trpA, trpB, trpE, asnB, gltD, gltB, leuA, argG, and thrC. The *Listeria* strain can be deficient in two or more such genes (e.g., dat and dal). D-glutamic acid synthesis is controlled in part by the dal gene, which is involved in the conversion of D-glu+pyr to alpha-ketoglutarate+D-ala, and the reverse reaction.

As another example, an attenuated *Listeria* strain can be deficient in an endogenous synthase gene, such as an amino acid synthesis gene. Examples of such genes include folP, a gene encoding a dihydrouridine synthase family protein, ispD, ispF, a gene encoding a phosphoenolpyruvate synthase, hisF, hisH, fliI, a gene encoding a ribosomal large subunit pseudouridine synthase, ispD, a gene encoding a bifunctional GMP synthase/glutamine amidotransferase protein, cobS, cobB, cbiD, a gene encoding a uroporphyrin-III C-methyltransferase/uroporphyrinogen-III synthase, cobQ, uppS, truB, dxs, mvaS, dapA, ispG,folC, a gene encoding a citrate synthase, argJ, a gene encoding a 3-deoxy-7-phosphoheptulonate synthase, a gene encoding an indole-3-glycerol-phosphate synthase, a gene encoding an anthranilate synthase/glutamine amidotransferase component, menB, a gene encoding a menaquinone-specific isochorismate synthase, a gene encoding a phosphoribosylformylglycinamidine synthase I or II, a gene encoding a phosphoribosylaminoimidazole-succinocarboxamide synthase, carB, carA, thyA, mgsA, aroB, hepB, rluB, ilvB, ilvN, alsS, fabF,fabH, a gene encoding a pseudouridine synthase, pyrG, truA, pabB, and an atp synthase gene (e.g., atpC, atpD-2, aptG, atpA-2, and so forth).

Attenuated *Listeria* strains can be deficient in endogenous phoP, aroA, aroC, aroD, or plcB. As yet another example, an attenuated *Listeria* strain can be deficient in an endogenous peptide transporter. Examples include genes encoding an ABC transporter/ATP-binding/permease protein, an oligopeptide ABC transporter/oligopeptide-binding protein, an oligopeptide ABC transporter/permease protein, a zinc ABC transporter/zinc-binding protein, a sugar ABC transporter, a phosphate transporter, a ZIP zinc transporter, a drug resistance transporter of the EmrB/QacA family, a sulfate transporter, a proton-dependent oligopeptide transporter, a magnesium transporter, a formate/nitrite transporter, a spermidine/putrescine ABC transporter, a Na/Pi-cotransporter, a sugar phosphate transporter, a glutamine ABC transporter, a major facilitator family transporter, a glycine betaine/L-proline ABC transporter, a molybdenum ABC transporter, a techoic acid ABC transporter, a cobalt ABC transporter, an ammonium transporter, an amino acid ABC transporter, a cell division ABC transporter, a manganese ABC transporter, an iron compound ABC transporter, a maltose/maltodextrin ABC transporter, a drug resistance transporter of the Bcr/CflA family, and a subunit of one of the above proteins.

Other attenuated bacteria and *Listeria* strains can be deficient in an endogenous metabolic enzyme that metabolizes an amino acid that is used for a bacterial growth process, a replication process, cell wall synthesis, protein synthesis, metabolism of a fatty acid, or for any other growth or replication process. Likewise, an attenuated strain can be deficient in an endogenous metabolic enzyme that can catalyze the formation of an amino acid used in cell wall synthesis, can catalyze the synthesis of an amino acid used in cell wall synthesis, or can be involved in synthesis of an amino acid used in cell wall synthesis. Alternatively, the amino acid can be used in cell wall biogenesis. Alternatively, the metabolic enzyme is a synthetic enzyme for D-glutamic acid, a cell wall component.

Other attenuated *Listeria* strains can be deficient in metabolic enzymes encoded by a D-glutamic acid synthesis gene, dga, an alr (alanine racemase) gene, or any other enzymes that are involved in alanine synthesis. Yet other examples of metabolic enzymes for which the *Listeria* strain can be deficient include enzymes encoded by serC (a phosphoserine aminotransferase), asd (aspartate betasemialdehyde dehydrogenase; involved in synthesis of the cell wall constituent diaminopimelic acid), the gene encoding gsaB-glutamate-1-semialdehyde aminotransferase (catalyzes the formation of 5-aminolevulinate from (S)-4-amino-5-oxopentanoate), hemL (catalyzes the formation of 5-aminolevulinate from (S)-4-amino-5-oxopentanoate), aspB (an aspartate aminotransferase that catalyzes the formation of oxalozcetate and L-glutamate from L-aspartate and 2-oxoglutarate), argF-1 (involved in arginine biosynthesis), aroE (involved in amino acid biosynthesis), aroB (involved in 3-dehydroquinate biosynthesis), aroD (involved in amino acid biosynthesis), aroC (involved in amino acid biosynthesis), hisB (involved in histidine biosynthesis), hisD (involved in histidine biosynthesis), hisG (involved in histidine biosynthesis), metX (involved in methionine biosynthesis), proB (involved in proline biosynthesis), argR (involved in arginine biosynthesis), argJ(involved in arginine biosynthesis), thiI (involved in thiamine biosynthesis), LMOf2365_1652 (involved in tryptophan biosynthesis), aroA (involved in tryptophan biosynthesis), ilvD (involved in valine and isoleucine biosynthesis), ilvC (involved in valine and isoleucine biosynthesis), leuA (involved in leucine biosynthesis), dapF (involved in lysine biosynthesis), and thrB (involved in threonine biosynthesis) (all GenBank Accession No. NC_002973).

An attenuated *Listeria* strain can be generated by mutation of other metabolic enzymes, such as a tRNA synthetase. For example, the metabolic enzyme can be encoded by the trpS gene, encoding tryptophanyltRNA synthetase. For example, the host strain bacteria can be Δ(trpS aroA), and both markers can be contained in an integration vector.

Other examples of metabolic enzymes that can be mutated to generate an attenuated *Listeria* strain include an enzyme encoded by murE (involved in synthesis of diaminopimelic acid; GenBank Accession No: NC_003485), LMOf2365_2494 (involved in teichoic acid biosynthesis), WecE (Lipopolysaccharide biosynthesis protein rffA; GenBank Accession No: AE014075.1), or amiA (an N-acetylmuramoyl-L-alanine amidase). Yet other examples of metabolic enzymes include aspartate aminotransferase, histidinol-phosphate aminotransferase (GenBank Accession No. NP_466347), or the cell wall teichoic acid glycosylation protein GtcA.

Other examples of metabolic enzymes that can be mutated to generate an attenuated *Listeria* strain include a synthetic enzyme for a peptidoglycan component or precursor. The component can be, for example, UDP-N-acetylmuramylpentapeptide, UDP-N-acetylglucosamine, MurNAc-(pentapeptide)-pyrophosphoryl-undecaprenol, GlcNAc-p-(1,4)-MurNAc-(pentapeptide)-pyrophosphorylundecaprenol, or any other peptidoglycan component or precursor.

Yet other examples of metabolic enzymes that can be mutated to generate an attenuated *Listeria* strain include metabolic enzymes encoded by murG, murD, murA-1, or murA-2 (all set forth in GenBank Accession No. NC_002973). Alternatively, the metabolic enzyme can be any other synthetic enzyme for a peptidoglycan component or precursor. The metabolic enzyme can also be a transglycosylase, a trans-peptidase, a carboxy-peptidase, any other class of metabolic enzyme, or any other metabolic enzyme. For example, the metabolic enzyme can be any other *Listeria* metabolic enzyme or any other *Listeria monocytogenes* metabolic enzyme.

Other bacterial strains can be attenuated as described above for *Listeria* by mutating the corresponding orthologous genes in the other bacterial strains.

(2) Methods of Complementing Attenuated Bacteria and *Listeria* Strains

The attenuated bacteria or *Listeria* strains disclosed herein can further comprise a nucleic acid comprising a complementing gene or encoding a metabolic enzyme that complements an attenuating mutation (e.g., complements the auxotrophy of the auxotrophic *Listeria* strain). For example, a nucleic acid having a first open reading frame encoding a fusion polypeptide as disclosed herein can further comprise a second open reading frame comprising the complementing gene or encoding the complementing metabolic enzyme. Alternatively, a first nucleic acid can encode the fusion polypeptide and a separate second nucleic acid can comprise the complementing gene or encode the complementing metabolic enzyme.

The complementing gene can be extrachromosomal or can be integrated into the bacteria or *Listeria* genome. For example, the auxotrophic *Listeria* strain can comprise an episomal plasmid comprising a nucleic acid encoding a metabolic enzyme. Such plasmids will be contained in the *Listeria* in an episomal or extrachromosomal fashion. Alternatively, the auxotrophic *Listeria* strain can comprise an integrative plasmid (i.e., integration vector) comprising a nucleic acid encoding a metabolic enzyme. Such integrative plasmids can be used for integration into a *Listeria* chromosome. Preferably, the episomal plasmid or the integrative plasmid lacks an antibiotic resistance marker.

The metabolic gene can be used for selection instead of or in addition to an antibiotic resistance gene. As an example, in order to select for auxotrophic bacteria comprising a plasmid encoding a metabolic enzyme or a complementing gene provided herein, transformed auxotrophic bacteria can be grown in a medium that will select for expression of the gene encoding the metabolic enzyme (e.g., amino acid metabolism gene) or the complementing gene. For example, a bacteria auxotrophic for D-glutamic acid synthesis can be transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. Similarly, a bacterium auxotrophic for D-alanine synthesis will grow in the absence of D-alanine when transformed and expressing a plasmid comprising a nucleic acid encoding an amino acid metabolism enzyme for D-alanine synthesis. Such methods for making appropriate media comprising or lacking necessary growth factors, supplements, amino acids, vitamins, antibiotics, and the like are well-known and are available commercially.

Once the auxotrophic bacteria comprising the plasmid encoding a metabolic enzyme or a complementing gene provided herein have been selected in appropriate medium, the bacteria can be propagated in the presence of a selective pressure. Such propagation can comprise growing the bacteria in media without the auxotrophic factor. The presence of the plasmid expressing the metabolic enzyme or the complementing gene in the auxotrophic bacteria ensures that the plasmid will replicate along with the bacteria, thus continually selecting for bacteria harboring the plasmid. Production of the bacteria or *Listeria* strain can be readily scaled up by adjusting the volume of the medium in which the auxotrophic bacteria comprising the plasmid are growing.

In one specific example, the attenuated strain is a strain having a deletion of or an inactivating mutation in dal and dat (e.g., *Listeria monocytogenes* (Lm) dal(−)dat(−) (Lmdd) or Lm dal(−)dat(−)ΔactA (LmddA)), and the complementing gene encodes an alanine racemase enzyme (e.g., encoded by dal gene) or a D-amino acid aminotransferase enzyme (e.g., encoded by dat gene). An exemplary alanine racemase protein can have the sequence set forth in SEQ ID NO: 353 (encoded by SEQ ID NO: 355; GenBank Accession No: AF038438) or can be a homologue, variant, isoform, analog, fragment, fragment of a homologue, fragment of a variant, fragment of an analog, or fragment of an isoform of SEQ ID NO: 353. The alanine racemase protein can also be any other *Listeria* alanine racemase protein. Alternatively, the alanine racemase protein can be any other gram-positive alanine racemase protein or any other alanine racemase protein. An exemplary D-amino acid aminotransferase protein can have the sequence set forth in SEQ ID NO: 354 (encoded by SEQ ID NO: 356; GenBank Accession No: AF038439) or can be a homologue, variant, isoform, analog, fragment, fragment of a homologue, fragment of a variant, fragment of an analog, or fragment of an isoform of SEQ ID NO: 354. The D-amino acid aminotransferase protein can also be any other *Listeria* D-amino acid aminotransferase protein. Alternatively, the D-amino acid aminotransferase protein can be any other gram-positive D-amino acid aminotransferase protein or any other D-amino acid aminotransferase protein.

In another specific example, the attenuated strain is a strain having a deletion of or an inactivating mutation in prfA (e.g., Lm prfA(−)), and the complementing gene encodes a PrfA protein. For example, the complementing gene can encode a mutant PrfA (D133V) protein that restores partial PrfA function. An example of a wild type PrfA protein is set forth in SEQ ID NO: 357 (encoded by nucleic acid set forth in SEQ ID NO: 358), and an example of a D133V mutant PrfA protein is set forth in SEQ ID NO: 359 (encoded by nucleic acid set forth in SEQ ID NO: 360). The complementing PrfA protein can be a homologue, variant, isoform, analog, fragment, fragment of a homologue, fragment of a variant, fragment of an analog, or fragment of an isoform of SEQ ID NO: 357 or 359. The PrfA protein can also be any other *Listeria* PrfA protein. Alternatively, the PrfA protein can be any other gram-positive PrfA protein or any other PrfA protein.

In another example, the bacteria strain or *Listeria* strain can comprise a deletion of or an inactivating mutation in an actA gene, and the complementing gene can comprise an actA gene to complement the mutation and restore function to the *Listeria* strain.

Other auxotroph strains and complementation systems can also be adopted for the use with the methods and compositions provided herein.

C. Preparation and Storage of Bacteria or *Listeria* Strains

The recombinant bacteria strain (e.g., *Listeria* strain) optionally has been passaged through an animal host. Such passaging can maximize efficacy of the *Listeria* strain as a vaccine vector, can stabilize the immunogenicity of the *Listeria* strain, can stabilize the virulence of the *Listeria* strain, can increase the immunogenicity of the *Listeria* strain, can increase the virulence of the *Listeria* strain, can remove unstable sub-strains of the *Listeria* strain, or can reduce the prevalence of unstable sub-strains of the *Listeria* strain. Methods for passaging a recombinant *Listeria* strain through an animal host are well known in the art and are described, for example, in US 2006/0233835, herein incorporated by reference in its entirety for all purposes.

The recombinant bacteria strain (e.g., *Listeria* strain) can be stored in a frozen cell bank or stored in a lyophilized cell bank. Such a cell bank can be, for example, a master cell bank, a working cell bank, or a Good Manufacturing Practice (GMP) cell bank. Examples of "Good Manufacturing Practices" include those defined by 21 CFR 210-211 of the United States Code of Federal Regulations. However, "Good Manufacturing Practices" can also be defined by other standards for production of clinical-grade material or for human consumption, such as standards of a country other than the United States. Such cell banks can be intended for production of clinical-grade material or can conform to regulatory practices for human use.

Such a cell bank can comprise, for example, 1-5, 5-10, 10-15, 15-20, 20-25, 25-30, 30-35, 35-40, 40-45, or 45-50 or more recombinant *Listeria* strains disclosed herein. Such recombinant *Listeria* strains can comprise recurrent cancer mutations in, for example, 1-5, 5-10, 10-15, 15-20, 20-25, 25-30, 30-35, 35-40, 40-45, or 45-50 cancer-associated proteins. For example, the recombinant *Listeria* strains can comprise the 2, 3, 4, 5, 6, 7, 8, 9, 10, 11, 12, 13, 14, 15, 16, 17, 18, 19, 20, 21, 22, 23, 24, 25, 26, 27, 28, 29, or 30 most common recurrent cancer mutations in each cancer-associated protein. Likewise, for each cancer-associated protein, at least 50%, 60%, 70%, 80%, 90%, 95%, 96%, 97%, 98%, or 99% of cancer patients with a mutation in the cancer-associated protein have a recurrent cancer mutation in the cancer-associated protein that is included in the combination of antigenic peptides in the recombinant *Listeria* strains in the cell bank.

Recombinant bacteria strains (e.g., *Listeria* strains) can also be from a batch of vaccine doses, from a frozen stock, or from a lyophilized stock.

Such cell banks, frozen stocks, or batches of vaccine doses can, for example, exhibit viability upon thawing of greater than 90%. The thawing, for example, can follow storage for cryopreservation or frozen storage for 24 hours. Alternatively, the storage can last, for example, for 2 days, 3 days, 4 days, 1 week, 2 weeks, 3 weeks, 1 month, 2 months, 3 months, 5 months, 6 months, 9 months, or 1 year.

The cell bank, frozen stock, or batch of vaccine doses can be cryopreserved, for example, by a method that comprises growing a culture of the bacteria strain (e.g., *Listeria* strain) in a nutrient media, freezing the culture in a solution comprising glycerol, and storing the *Listeria* strain at below −20° C. The temperature can be, for example, about −70° C. or between about −70 to about −80° C. Alternatively, the cell bank, frozen stock, or batch of vaccine doses can be cryopreserved by a method that comprises growing a culture of the *Listeria* strain in a defined medium, freezing the culture in a solution comprising glycerol, and storing the *Listeria* strain at below −20° C. The temperature can be, for example, about −70° C. or between about −70 to about −80° C. Any defined microbiological medium may be used in this method.

The culture (e.g., the culture of a Listeria vaccine strain that is used to produce a batch of Listeria vaccine doses) can be inoculated, for example, from a cell bank, from a frozen stock, from a starter culture, or from a colony. The culture can be inoculated, for example, at mid-log growth phase, at approximately mid-log growth phase, or at another growth phase.

The solution used for freezing optionally contain another colligative additive or additive with anti-freeze properties in place of glycerol or in addition to glycerol. Examples of such additives include, for example, mannitol, DMSO, sucrose, or any other colligative additive or additive with anti-freeze properties.

The nutrient medium utilized for growing a culture of a bacteria strain (e.g., a *Listeria* strain) can be any suitable nutrient medium. Examples of suitable media include, for example, LB; TB; a modified, animal-product-free Terrific Broth; or a defined medium.

The step of growing can be performed by any known means of growing bacteria. For example, the step of growing can be performed with a shake flask (such as a baffled shake flask), a batch fermenter, a stirred tank or flask, an airlift fermenter, a fed batch, a continuous cell reactor, an immobilized cell reactor, or any other means of growing bacteria.

Optionally, a constant pH is maintained during growth of the culture (e.g. in a batch fermenter). For example, the pH can be maintained at about 6.0, at about 6.5, at about 7.0, at about 7.5, or about 8.0. Likewise, the pH can be, for example, from about 6.5 to about 7.5, from about 6.0 to about 8.0, from about 6.0 to about 7.0, from about 6.0 to about 7.0, or from about 6.5 to about 7.5.

Optionally, a constant temperature can be maintained during growth of the culture. For example, the temperature can be maintained at about 37° C. or at 37° C. Alternatively, the temperature can be maintained at 25° C., 27° C., 28° C., 30° C., 32° C., 34° C., 35° C., 36° C., 38° C., or 39° C.

Optionally, a constant dissolved oxygen concentration can be maintained during growth of the culture. For example, the dissolved oxygen concentration can be maintained at 20% of saturation, 15% of saturation, 16% of saturation, 18% of saturation, 22% of saturation, 25% of saturation, 30% of saturation, 35% of saturation, 40% of saturation, 45% of saturation, 50% of saturation, 55% of saturation, 60% of saturation, 65% of saturation, 70% of saturation, 75% of saturation, 80% of saturation, 85% of saturation, 90% of saturation, 95% of saturation, 100% of saturation, or near 100% of saturation.

Methods for lyophilization and cryopreservation of recombinant bacteria strains (e.g., *Listeria* strains are known. For example, a *Listeria* culture can be flash-frozen in liquid nitrogen, followed by storage at the final freezing temperature. Alternatively, the culture can be frozen in a more gradual manner (e.g., by placing in a vial of the culture in the final storage temperature). The culture can also be frozen by any other known method for freezing a bacterial culture.

The storage temperature of the culture can be, for example, between −20 and −80° C. For example, the temperature can be significantly below −20° C. or not warmer than −70° C. Alternatively, the temperature can be about −70° C., −20° C., −30° C., −40° C., −50° C., −60° C., −80° C., −30 to −70° C., −40 to −70° C., −50 to −70° C., −60 to −70° C., −30 to −80° C., −40 to −80° C., −50 to −80° C., −60 to −80° C., or −70 to −80° C. Alternatively, the temperature can be colder than 70° C. or colder than −80° C.

VII. Immunogenic Compositions, Pharmaceutical Compositions, and Vaccines

Also provided are immunogenic compositions, pharmaceutical compositions, or vaccines comprising a recombinant fusion polypeptide as disclosed herein, a nucleic acid encoding a recombinant fusion polypeptide as disclosed herein, or a recombinant bacteria or *Listeria* strain as disclosed herein. An immunogenic composition comprising a *Listeria* strain can be inherently immunogenic by virtue of its comprising a *Listeria* strain and/or the composition can also further comprise an adjuvant. Other immunogenic compositions comprise DNA immunotherapy or peptide immunotherapy compositions.

The term "immunogenic composition" refers to any composition containing an antigen that elicits an immune response against the antigen in a subject upon exposure to the composition. The immune response elicited by an immunogenic composition can be to a particular antigen or to a particular epitope on the antigen.

An immunogenic composition can comprise a single recombinant fusion polypeptide as disclosed herein, a nucleic acid encoding a recombinant fusion polypeptide as disclosed herein, or a recombinant bacteria or *Listeria* strain as disclosed herein, or it can comprise multiple different recombinant fusion polypeptides as disclosed herein, nucleic acids encoding recombinant fusion polypeptides as disclosed herein, or recombinant bacteria or *Listeria* strains as disclosed herein. A first recombinant fusion polypeptide is different from a second recombinant fusion polypeptide, for example, if it includes one antigenic peptide that the second recombinant fusion polypeptide does not. The two recombinant fusion polypeptides can include many of the same antigenic peptides and still be considered different. As one example, an immunogenic composition can comprise 2, 3, 4, 5, 6, 7, 8, 9, 10, 11, 12, 13, 14, 15, 16, 17, 18, 19, or 20 recombinant fusion polypeptides, nucleic acids encoding recombinant fusion polypeptides, or recombinant bacteria or *Listeria* strains. Alternatively, an immunogenic composition can comprise a mixture of 1-2, 1-5, 1-10, 1-20 or 1-40, or a mixture of 1-5, 5-10, 10-15, 15-20, 10-20, 20-30, 30-40, or 40-50 recombinant fusion polypeptides, nucleic acids encoding recombinant fusion polypeptides, or recombinant bacteria or *Listeria* strains. Such different recombinant fusion polypeptides, nucleic acids encoding recombinant fusion polypeptides, or recombinant bacteria or *Listeria* strains can be administered concomitantly to a subject or sequentially to a subject. Sequential administration can be particularly useful when a drug substance comprising a recombinant *Listeria* strain (or recombinant fusion polypeptide or nucleic acid) disclosed herein is in different dosage forms (e.g., one agent is a tablet or capsule and another agent is a sterile liquid) and/or is administered on different dosing schedules (e.g., one composition from the mixture is administered at least daily and another is administered less frequently, such as once weekly, once every two weeks, or once every three weeks). The multiple recombinant fusion polypeptides, nucleic acids encoding recombinant fusion polypeptides, or recombinant bacteria or *Listeria* strains can each comprise a different set of antigenic peptides. Alternatively, two or more of the recombinant fusion polypeptides, nucleic acids encoding recombinant fusion polypeptides, or recombinant bacteria or *Listeria* strains can comprise the same set of antigenic peptides (e.g., the same set of antigenic peptides in a different order). The recombinant fusion polypeptides, nucleic acids encoding recombinant fusion polypeptides, or recombinant bacteria or *Listeria* strains can comprise antigenic peptides from a single cancer-associated protein or from multiple cancer-associated proteins (e.g., 2, 3, 4, 5, 6, 7, 8, 9, 10, 11, 12, 13, 14, 15, 16, 17, 18, 19, or 20 cancer-associated proteins). In addition, the combination of recombinant fusion polypeptides, nucleic acids encoding recombinant fusion polypeptides, or recombinant bacteria or *Listeria* strains can comprise any number of different antigenic peptides, such as about 1-5, 5-10, 10-15, 15-20, 20-25, 25-30, 30-35, 35-40, 40-45, 45-50, 50-60, 60-70, 70-80, 80-90, 90-100, 100-120, 120-140, 140-160, 160-180, 180-200, 200-220, 220-240, 240-260, 260-280, 280-300, 300-320, 320-340, 340-360, 360-380, or 380-400 different antigenic peptides. The number of different antigenic peptides can be up to about 100, above about 100, up to about 10, up to about 20, up to about 50 antigenic peptides. Alternatively, it can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 antigenic peptides or about 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 antigenic peptides or about 5-15, 5-20, 5-25, 15-20, 15-25, 15-30, 15-35, 20-25, 20-35, 20-45, 30-45, 30-55, 40-55, 40-65, 50-65, 50-75, 60-75, 60-85, 70-85, 70-95, 80-95, 80-105 or 95-105 antigenic peptides or about 1-5, 1-10, 1-20, 1-30, 1-50, 1-60, 1-70, 1-80, 1-90, 1-100, 1-110, 1-150, 1-200, 1-250, 1-300, or 1-500 antigenic peptides.

Any combination of recurrent cancer mutations can be included in the immunogenic composition. Each of the recurrent cancer mutations can be a somatic missense mutation, or the recurrent cancer mutations can comprise other mutations as well. For example, in some immunogenic compositions, at least 50%, 55%, 60%, 65%, 70%, 75%, 80%, 85%, 90%, 95%, 96%, 97%, 98%, or 99% of the recurrent cancer mutations are somatic missense mutations. As one example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent cancer mutations in the cancer-associated protein. For example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent somatic missense cancer mutations in the cancer-associated protein. As another example, at least 50%, 60%, 70%, 80%, 90%, 95%, 96%, 97%, 98%, or 99% of cancer patients with a mutation in the cancer-associated protein have a recurrent cancer mutation in the cancer-associated protein that is included in the combination of antigenic peptides in the immunogenic composition. For example, at least 50%, 60%, 70%, 80%, 90%, 95%, 96%, 97%, 98%, or 99% of cancer patients with a somatic missense mutation in the cancer-associated protein have a recurrent cancer mutation in the cancer-associated protein that is included in the combination of antigenic peptides in the immunogenic composition. As another example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent cancer mutations or most common recurrent somatic missense cancer mutations in a particular type of cancer. As another example, at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of cancer patients with a particular type of cancer have a recurrent cancer mutation that is included in the combination of antigenic peptides in the immunogenic composition. For example, at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of cancer patients with particular type of cancer have a recurrent cancer mutation that is included in the combination of antigenic peptides in the immunogenic composition. In a particular example, the antigenic peptides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 different recurrent cancer mutations or different recurrent somatic missense mutations from the same type of cancer, or the antigenic peptides comprise 2-80, 10-60, 10-50, 10-40, or 10-30 different recurrent cancer mutations or different recurrent somatic missense mutations from a single type of cancer. For example, the single type of cancer can be non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), or head and neck cancer.

An immunogenic composition can additionally comprise an adjuvant (e.g., two or more adjuvants), a cytokine, a chemokine, or combination thereof. Optionally, an immunogenic composition can additionally comprises antigen presenting cells (APCs), which can be autologous or can be allogeneic to the subject.

The term adjuvant includes compounds or mixtures that enhance the immune response to an antigen. For example, an adjuvant can be a non-specific stimulator of an immune response or substances that allow generation of a depot in a subject which when combined with an immunogenic composition disclosed herein provides for an even more enhanced and/or prolonged immune response. An adjuvant can favor, for example, a predominantly Th1-mediated immune response, a Th1-type immune response, or a Th1-mediated immune response. Likewise, an adjuvant can favor a cell-mediated immune response over an antibody-mediated response. Alternatively, an adjuvant can favor an antibody-mediated response. Some adjuvants can enhance the immune response by slowly releasing the antigen, while other adjuvants can mediate their effects by any of the following mechanisms: increasing cellular infiltration, inflammation, and trafficking to the injection site, particularly for antigen-presenting cells (APC); promoting the activation state of APCs by upregulating costimulatory signals or major histocompatibility complex (MHC) expression; enhancing antigen presentation; or inducing cytokine release for indirect effect.

Examples of adjuvants include saponin QS21, CpG oligonucleotides, unmethylated CpG-containing oligonucleotides, MPL, TLR agonists, TLR4 agonists, TLR9 agonists, RESIQUIMOD®, imiquimod, cytokines or nucleic acids encoding the same, chemokines or nucleic acids encoding same, IL-12 or a nucleic acid encoding the same, IL-6 or a nucleic acid encoding the same, and lipopolysaccharides. Another example of a suitable adjuvant is Montanide ISA 51. Montanide ISA 51 contains a natural metabolizable oil and a refined emulsifier. Other examples of a suitable adjuvant include granulocyte/macrophage colony-stimulating factor (GM-CSF) or a nucleic acid encoding the same and keyhole limpet hemocyanin (KLH) proteins or nucleic acids encoding the same. The GM-CSF can be, for example, a human protein grown in a yeast (*S. cerevisiae*) vector. GM-CSF promotes clonal expansion and differentiation of hematopoietic progenitor cells, antigen presenting cells (APCs), dendritic cells, and T cells. Yet another example of a suitable adjuvant is detoxified listeriolysin O (dtLLO) protein. One example of a dtLLO suitable for use as an adjuvant is encoded by SEQ ID NO: 583. A dtLLO encoded by a sequence at least 90%, 95%, 96%, 97%, 98%, or 99% identical to SEQ ID NO: 583 is also suitable for use as an adjuvant. Other examples of adjuvants include growth factors or nucleic acids encoding the same, cell populations, Freund's incomplete adjuvant, aluminum phosphate, aluminum hydroxide, BCG (bacille Calmette-Guerin), alum, interleukins or nucleic acids encoding the same, quill glycosides, monophosphoryl lipid A, liposomes, bacterial mitogens, bacterial toxins, or any other type of known adjuvant (see, e.g., Fundamental Immunology, 5th ed. (August 2003): William E. Paul (Editor); Lippincott Williams & Wilkins Publishers; Chapter 43: Vaccines, GJV Nossal, which is herein incorporated by reference in its entirety for all purposes.

An immunogenic composition can further comprise one or more immunomodulatory molecules. Examples include interferon gamma, a cytokine, a chemokine, and a T cell stimulant.

An immunogenic composition can be in the form of a vaccine or pharmaceutical composition. The terms "vaccine" and "pharmaceutical composition" are interchangeable and refer to an immunogenic composition in a pharmaceutically acceptable carrier for in vivo administration to a subject. A vaccine may be, for example, a peptide vaccine (e.g., comprising a recombinant fusion polypeptide as disclosed herein), a DNA vaccine (e.g., comprising a nucleic acid encoding a recombinant fusion polypeptide as disclosed herein), or a vaccine contained within and delivered by a cell (e.g., a recombinant *Listeria* as disclosed herein). A vaccine may prevent a subject from contracting or developing a disease or condition and/or a vaccine may be therapeutic to a subject having a disease or condition. Methods for preparing peptide vaccines are well known and are described, for example, in EP 1408048, US 2007/0154953, and Ogasawara et al. (1992) *Proc. Natl Acad Sci USA* 89:8995-8999, each of which is herein incorporated by reference in its entirety for all purposes. Optionally, peptide evolution techniques can be used to create an antigen with higher immunogenicity. Techniques for peptide evolution are well known and are described, for example, in U.S. Pat. No. 6,773,900, herein incorporated by reference in its entirety for all purposes.

A "pharmaceutically acceptable carrier" refers to a vehicle for containing an immunogenic composition that can be introduced into a subject without significant adverse effects and without having deleterious effects on the immunogenic composition. That is, "pharmaceutically acceptable" refers to any formulation which is safe, and provides the appropriate delivery for the desired route of administration of an effective amount of at least one immunogenic composition for use in the methods disclosed herein. Pharmaceutically acceptable carriers or vehicles or excipients are well known. Descriptions of suitable pharmaceutically acceptable carriers, and factors involved in their selection, are found in a variety of readily available sources such as, for example, *Remington's Pharmaceutical Sciences*, 18th ed., 1990, herein incorporated by reference in its entirety for all purposes. Such carriers can be suitable for any route of administration (e.g., parenteral, enteral (e.g., oral), or topical application). Such pharmaceutical compositions can be buffered, for example, wherein the pH is maintained at a particular desired value, ranging from pH 4.0 to pH 9.0, in accordance with the stability of the immunogenic compositions and route of administration.

Suitable pharmaceutically acceptable carriers include, for example, sterile water, salt solutions such as saline, glucose, buffered solutions such as phosphate buffered solutions or bicarbonate buffered solutions, alcohols, gum arabic, vegetable oils, benzyl alcohols, polyethylene glycols, gelatine, carbohydrates (e.g., lactose, amylose or starch), magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, and the like. Pharmaceutical compositions or vaccines may also include auxiliary agents including, for example, diluents, stabilizers (e.g., sugars and amino acids), preservatives, wetting agents, emulsifiers, pH buffering agents, viscosity enhancing additives, lubricants, salts for influencing osmotic pressure, buffers, vitamins, coloring, flavoring, aromatic substances, and the like which do not deleteriously react with the immunogenic composition.

For liquid formulations, for example, pharmaceutically acceptable carriers may be aqueous or non-aqueous solutions, suspensions, emulsions, or oils. Non-aqueous solvents include, for example, propylene glycol, polyethylene glycol, and injectable organic esters such as ethyl oleate. Aqueous carriers include, for example, water, alcoholic/aqueous solutions, emulsions or suspensions, including saline and buffered media. Examples of oils include those of petroleum, animal, vegetable, or synthetic origin, such as peanut oil, soybean oil, mineral oil, olive oil, sunflower oil, and fish-liver oil. Solid carriers/diluents include, for example, a gum, a starch (e.g., corn starch, pregeletanized starch), a sugar (e.g., lactose, mannitol, sucrose, or dextrose), a cellulosic material (e.g., microcrystalline cellulose), an acrylate (e.g., polymethylacrylate), calcium carbonate, magnesium oxide, talc, or mixtures thereof.

Optionally, sustained or directed release pharmaceutical compositions or vaccines can be formulated. This can be accomplished, for example, through use of liposomes or compositions wherein the active compound is protected with differentially degradable coatings (e.g., by microencapsulation, multiple coatings, and so forth). Such compositions may be formulated for immediate or slow release. It is also possible to freeze-dry the compositions and use the lyophilisates obtained (e.g., for the preparation of products for injection).

An immunogenic composition, pharmaceutical composition, or vaccine disclosed herein may also comprise one or more additional compounds effective in preventing or treating cancer. For example, the additional compound may comprise a compound useful in chemotherapy, such as amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil (5-FU), gemcitabine, gliadelimplants, hydroxycarbamide, idarubicin, ifosfamide, irinotecan, leucovorin, liposomaldoxorubicin, liposomaldaunorubicin, lomustine, melphalan, mercaptopurine, mesna, methotrexate, mitomycin, mitoxantrone, oxaliplatin, paclitaxel (Taxol), pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. The additional compound can also comprise other biologics, including HERCEPTIN® (trastuzumab) against the HER2 antigen, AVASTIN® (bevacizumab) against VEGF, or antibodies to the EGF receptor, such as ERBITUX® (cetuximab), and VECTIBIX® (panitumumab). The additional compound can also comprise, for example, an additional immunotherapy.

An additional compound can also comprise an immune checkpoint inhibitor antagonist, such as a PD-1 signaling pathway inhibitor, a CD-80/86 and CTLA-4 signaling pathway inhibitor, a T cell membrane protein 3 (TIM3) signaling pathway inhibitor, an adenosine A2a receptor (A2aR) signaling pathway inhibitor, a lymphocyte activation gene 3 (LAG3) signaling pathway inhibitor, a killer immunoglobulin receptor (KIR) signaling pathway inhibitor, a CD40 signaling pathway inhibitor, or any other antigen-presenting cell/T cell signaling pathway inhibitor. Examples of immune checkpoint inhibitor antagonists include an anti-PD-L1/PD-L2 antibody or fragment thereof, an anti-PD-1 antibody or fragment thereof, an anti-CTLA-4 antibody or fragment thereof, or an anti-B7-H4 antibody or fragment thereof. An additional compound can also comprise a T cell stimulator, such as an antibody or functional fragment thereof binding to a T-cell receptor co-stimulatory molecule, an antigen presenting cell receptor binding co-stimulatory molecule, or a member of the TNF receptor superfamily. The T-cell receptor co-stimulatory molecule can comprise, for example, CD28 or ICOS. The antigen presenting cell receptor binding co-stimulatory molecule can comprise, for example, a CD80 receptor, a CD86 receptor, or a CD46 receptor. The TNF receptor superfamily member can comprise, for example, glucocorticoid-induced TNF receptor (GITR), OX40 (CD134 receptor), 4-1BB (CD137 receptor), or TNFR25. See, e.g., WO2016100929, WO2016011362, and WO2016011357, each of which is incorporated by reference in its entirety for all purposes.

VIII. Therapeutic Methods

The recombinant fusion polypeptides, nucleic acids encoding recombinant fusion polypeptides, recombinant bacteria or *Listeria* strains, immunogenic compositions, pharmaceutical compositions, and vaccines disclosed herein can be used in various methods. For example, they can be used in methods of inducing an anti-tumor-associated-antigen immune response in a subject, in methods of inducing an anti-tumor or anti-cancer immune response in a subject, in methods of treating a tumor or cancer in a subject, in methods of preventing a tumor or cancer in a subject, or in methods of protecting a subject against a tumor or cancer. They can also be used in methods of increasing the ratio of T effector cells to regulatory T cells (Tregs) in the spleen and tumor of a subject, wherein the T effector cells are targeted to a tumor-associated antigen. They can also be used in methods for increasing tumor-associated-antigen T cells in a subject, increasing survival time of a subject having a tumor or cancer, delaying the onset of cancer in a subject, or reducing tumor or metastasis size in a subject.

A method of inducing an anti-tumor-associated-antigen immune response in a subject can comprise, for example, administering to the subject a recombinant fusion polypeptide, a nucleic acid encoding a recombinant fusion polypeptide, a recombinant bacteria or *Listeria* strain, an immunogenic composition, a pharmaceutical composition, or a vaccine disclosed herein (e.g., that comprises a recombinant fusion polypeptide comprising the tumor-associated antigen or a nucleic acid encoding the recombinant fusion polypeptide). An anti-tumor-associated-antigen immune response can thereby be induced in the subject. For example, in the case of a recombinant *Listeria* strain, the *Listeria* strain can express the fusion polypeptide, thereby eliciting an immune response in the subject. The immune response can comprise, for example, a T-cell response, such as a CD4+FoxP3− T cell response, a CD8+ T cell response, or a CD4+FoxP3− and CD8+ T cell response. Such methods can also increase the ratio of T effector cells to regulatory T cells (Tregs) in the spleen and tumor microenvironments of the subject, allowing for a more profound anti-tumor response in the subject.

A method of inducing an anti-tumor or anti-cancer immune response in a subject can comprise, for example, administering to the subject a recombinant fusion polypeptide, a nucleic acid encoding a recombinant fusion polypeptide, a recombinant bacteria or *Listeria* strain, an immunogenic composition, a pharmaceutical composition, or a vaccine disclosed herein. An anti-tumor or anti-cancer immune response can thereby be induced in the subject. For example, in the case of a recombinant *Listeria* strain, the *Listeria* strain can express the fusion polypeptide, thereby eliciting an anti-tumor or anti-cancer response in the subject.

A method of treating a tumor or cancer in a subject (e.g., wherein the tumor or cancer expresses one or more tumor-associated antigens or has one or more recurrent cancer mutations), can comprise, for example, administering to the subject a recombinant fusion polypeptide, a nucleic acid encoding a recombinant fusion polypeptide, a recombinant bacteria or *Listeria* strain, an immunogenic composition, a pharmaceutical composition, or a vaccine disclosed herein. The subject can then mount an immune response against the tumor or cancer expressing the one or more tumor-associated antigens or the one or more recurrent cancer mutations, thereby treating the tumor or cancer in the subject.

A method of preventing a tumor or cancer in a subject or protecting a subject against developing a tumor or cancer (e.g., wherein the tumor or cancer is associated with expression of one or more tumor-associated antigens or one or more recurrent cancer mutations), can comprise, for example, administering to the subject a recombinant fusion polypeptide, a nucleic acid encoding a recombinant fusion polypeptide, a recombinant bacteria or *Listeria* strain, an immunogenic composition, a pharmaceutical composition, or a vaccine disclosed herein. The subject can then mount an immune response against the one or more tumor-associated antigens or the one or more recurrent cancer mutations, thereby preventing a tumor or cancer or protecting the subject against developing a tumor or cancer.

In some of the above methods, two or more (e.g., 2, 3, 4, 5, 6, 7, 8, 9, 10, 11, 12, 13, 14, 15, 16, 17, 18, 19, 20 or more) recombinant fusion polypeptides, nucleic acids encoding recombinant fusion polypeptides, recombinant bacteria or *Listeria* strains, immunogenic compositions, pharmaceutical compositions, or vaccines are administered. For example, a first *Listeria* strain comprising antigenic peptides comprising recurrent cancer mutations from a first cancer-associated protein can be administered, and a second *Listeria* strain comprising antigenic peptides comprising recurrent cancer mutations from a second cancer-associated protein can be administered. The multiple recombinant fusion polypeptides, nucleic acids encoding recombinant fusion polypeptides, recombinant bacteria or *Listeria* strains, immunogenic compositions, pharmaceutical compositions, or vaccines can be administered sequentially in any order or combination, or can be administered simultaneously in any combination. As an example, if four different *Listeria* strains are being administered, they can be administered sequentially, they can be administered simultaneously, or they can be administered in any combination (e.g., administering the first and second strains simultaneously and subsequently administering the third and fourth strains simultaneously). Optionally, in the case of sequential administration, the compositions can be administered during the same immune response, preferably within 0-10 or 3-7 days of each other. The multiple recombinant fusion polypeptides, nucleic acids encoding recombinant fusion polypeptides, recombinant bacteria or *Listeria* strains, immunogenic compositions, pharmaceutical compositions, or vaccines can each comprise a different set of antigenic peptides. Alternatively, two or more can comprise the same set of antigenic peptides (e.g., the same set of antigenic peptides in a different order). The multiple recombinant fusion polypeptides, nucleic acids encoding recombinant fusion polypeptides, recombinant bacteria or *Listeria* strains, immunogenic compositions, pharmaceutical compositions, or vaccines can comprise antigenic peptides from two or more cancer-associated proteins (e.g., 2, 3, 4, 5, 6, 7, 8, 9, 10, 11, 12, 13, 14, 15, 16, 17, 18, 19, or 20 cancer-associated proteins). In addition, the combination of multiple recombinant fusion polypeptides, nucleic acids encoding recombinant fusion polypeptides, recombinant bacteria or *Listeria* strains, immunogenic compositions, pharmaceutical compositions, or vaccines can comprise about 5-10, 10-15, 15-20, 20-25, 25-30, 30-35, 35-40, 40-45, 45-50, 50-60, 60-70, 70-80, 80-90, 90-100, 100-120, 120-140, 140-160, 160-180, 180-200, 200-220, 220-240, 240-260, 260-280, 280-300, 300-320, 320-340, 340-360, 360-380, or 380-400 different antigenic peptides.

In any of the above methods, any combination of recurrent cancer mutations can be included in the administered recombinant fusion polypeptides, nucleic acids encoding recombinant fusion polypeptides, recombinant bacteria or *Listeria* strains, immunogenic compositions, pharmaceutical compositions, or vaccines. Each of the recurrent cancer mutations can be a somatic missense mutation, or the recurrent cancer mutations can comprise other mutations as well. For example, in some methods, at least 50%, 55%, 60%, 65%, 70%, 75%, 80%, 85%, 90%, 95%, 96%, 97%, 98%, or 99% of the recurrent cancer mutations are somatic missense mutations. As one example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent cancer mutations in the cancer-associated protein. For example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent somatic missense cancer mutations in the cancer-associated protein. As another example, at least 50%, 60%, 70%, 80%, 90%, 95%, 96%, 97%, 98%, or 99% of cancer patients with a mutation in the cancer-associated protein have a recurrent cancer mutation in the cancer-associated protein that is included in the combination of antigenic peptides administered. For example, at least 50%, 60%, 70%, 80%, 90%, 95%, 96%, 97%, 98%, or 99% of cancer patients with a somatic missense mutation in the cancer-associated protein have a recurrent cancer mutation in the cancer-associated protein that is included in the combination of antigenic peptides administered. As another example, the antigenic peptides can comprise at least 50%, 55%, 60%, 65%, 70%, 75%, 80%, 85%, 90%, 95%, 96%, 97%, 98%, 99%, or 100% of the 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 most common recurrent cancer mutations or most common recurrent somatic missense cancer mutations in a particular type of cancer. As another example, at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of cancer patients with a particular type of cancer have a recurrent cancer mutation that is included in the combination of antigenic peptides administered. For example, at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of cancer patients with particular type of cancer have a recurrent cancer mutation that is included in the combination of antigenic peptides administered. In a particular example, the antigenic peptides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 different recurrent cancer mutations or different recurrent somatic missense mutations from the same type of cancer, or the antigenic peptides comprise 2-80, 10-60, 10-50, 10-40, or 10-30 different recurrent cancer mutations or different recurrent somatic missense mutations from a single type of cancer. For example, the single type of cancer can be non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), or head and neck cancer.

Any of the above methods can further comprise screening the subject for and identifying one or more recurrent cancer mutations prior to the administering step, and then administering to the subject a recombinant fusion polypeptide, a nucleic acid encoding a recombinant fusion polypeptide, a recombinant bacteria or *Listeria* strain, an immunogenic composition, a pharmaceutical composition, or a vaccine comprising antigenic peptides comprising the one or more recurrent cancer mutations identified in the subject. Alternatively, in cases in which the subject has a cancer associated with recurrent cancer mutations in one or more cancer-associated proteins, the method can comprise administering to the subject a recombinant fusion polypeptide, a nucleic acid encoding a recombinant fusion polypeptide, a recombinant bacteria or *Listeria* strain, an immunogenic composition, a pharmaceutical composition, or a vaccine comprising the recurrent cancer mutations associated with the cancer. For example mutations in a particular cancer-associated protein may occur in at least 1%, 2%, 3%, 4%, 5%, 10%, 15%, 20%, 25%, 30%, 35%, 40%, 45%, 50%, 60%, 70%, 80%, 90%, 95%, or 99% of all instances of a particular type of cancer, or mutations at a particular residue (i.e., hotspot) or set of residues (i.e., hotspots) in a cancer-associated protein may occur in at least 1%, 2%, 3%, 4%, 5%, 10%, 15%, 20%, 25%, 30%, 35%, 40%, 45%, 50%, 60%, 70%, 80%, 90%, 95%, or 99% of all instances of a particular type of cancer. Likewise, a particular recurrent cancer mutation may occur in at least 1%, 2%, 3%, 4%, 5%, 10%, 15%, 20%, 25%, 30%, 35%, 40%, 45%, 50%, 60%, 70%, 80%, 90%, 95%, or 99% of all instances of a particular type of cancer (e.g., all subjects having a particular type of cancer). Similarly, a particular set of recurrent cancer mutations may occur in at least 1%, 2%, 3%, 4%, 5%, 10%, 15%, 20%, 25%, 30%, 35%, 40%, 45%, 50%, 60%, 70%, 80%, 90%, 95%, or 99% of all instances of a particular type of cancer (e.g., all subjects having a particular type of cancer).

Cancer is a physiological condition in mammals that is typically characterized by unregulated cell growth and proliferation. Cancers can be hematopoietic malignancies or solid tumors (i.e., masses of cells that result from excessive cell growth or proliferation, including pre-cancerous legions). Metastatic cancer refers to a cancer that has spread from the place where it first started to another place in the body. Tumors formed by metastatic cancer cells are called a metastatic tumor or a metastasis, which is a term also used to refer to the process by which cancer cells spread to other parts of the body. In general, metastatic cancer has the same name and same type of cancer cells as the original, or primary, cancer. Examples of solid tumors include melanoma, carcinoma, blastoma, and sarcoma. Hematologic malignancies include, for example, leukemia or lymphoid malignancies, such as lymphoma. Exemplary categories of cancers include brain, breast, gastrointestinal, genitourinary, gynecologic, head and neck, heme, skin and thoracic. Brain malignancies include, for example, glioblastoma, high-grade pontine glioma, low-grade glioma, medulloblastoma, neuroblastoma, and pilocytic astrocytoma. Gastrointestinal cancers include, for example, colorectal, gallbladder, hepatocellular, pancreas, PNET, gastric, and esophageal. Genitourinary cancers include, for example, adrenocortical, bladder, kidney chromophobe, renal (clear cell), renal (papillary), rhabdoid cancers, and prostate. Gynecologic cancers include, for example, uterine carcinosarcoma, uterine endometrial, serous ovarian, and cervical. Head and neck cancers include, for example, thyroid, nasopharyngeal, head and neck, and adenoid cystic. Heme cancers include, for example, multiple myeloma, myelodysplasia, mantle-cell lymphoma, acute lymphoblastic leukemia (ALL), non-lymphoma, chronic lymphocytic leukemia (CLL), and acute myeloid leukemia (AML). Skin cancers includes, for example, cutaneous melanoma and squamous cell carcinoma. Thoracic cancers include, for example, squamous lung, small-cell lung, and lung adenocarcinoma.

More particular examples of such cancers include squamous cell cancer or carcinoma (e.g., oral squamous cell carcinoma), myeloma, oral cancer, juvenile nasopharyngeal angiofibroma, neuroendocrine tumors, lung cancer, cancer of the peritoneum, hepatocellular cancer, gastric or stomach cancer including gastrointestinal cancer, pancreatic cancer, glioma, glioblastoma, glial tumors, cervical cancer, ovarian cancer, liver cancer, bladder cancer, hepatoma, hepatocellular carcinoma, breast cancer, triple-negative breast cancer, colon cancer, rectal cancer, colorectal cancer, endometrial cancer or uterine cancer or carcinoma, salivary gland carcinoma, kidney or renal cancer (e.g., renal cell carcinoma), prostate cancer, vulval cancer, thyroid cancer, hepatic carcinoma, anal carcinoma, penile carcinoma, fibrosarcoma, gallbladder cancer, osteosarcoma, mesothelioma, as well as head and neck cancer. A cancer can also be a brain cancer or another type of CNS or intracranial tumor. For example, a subject can have an astrocytic tumor (e.g., astrocytoma, anaplastic astrocytoma, glioblastoma, pilocytic astrocytoma, subependymal giant cell astrocytoma, pleomorphic xanthoastrocytoma), oligodendroglial tumor (e.g., oligodendroglioma, anaplastic oligodendroglioma), ependymal cell tumor (e.g., ependymoma, anaplastic ependymoma, myxopapillary ependymoma, subependymoma), mixed glioma (e.g., mixed oligoastrocytoma, anaplastic oligoastrocytoma), neuroepithelial tumor of uncertain origin (e.g., polar spongioblastoma, astroblastoma, gliomatosis cerebri), tumor of the choroid plexus (e.g., choroid plexus papilloma, choroid plexus carcinoma), neuronal or mixed neuronal-glial tumor (e.g., gangliocytoma, dyplastic gangliocytoma of cerebellum, ganglioglioma, anaplastic ganglioglioma, desmoplastic infantile ganglioma, central neurocytoma, dysembryoplastic neuroepthelial tumor, olfactory neuroblastoma), pineal parenchyma tumor (e.g., pineocytoma, pineoblastoma, mixed pineocytoma/pineoblastoma), or tumor with mixed neuroblastic or glioblastic elements (e.g., medulloepithelioma, medulloblastoma, neuroblastoma, retinoblastoma, ependymoblastoma). Other examples of cancer include low-grade glioma, non-small cell lung cancer (NSCLC), estrogen-receptor-positive (ER+) breast cancer, and DNA mismatch repair deficient cancers or tumors. A cancer is called estrogen-receptor-positive if it has receptors for estrogen. Another example of a cancer is a microsatellite stable (MSS) colorectal cancer.

The term "treat" or "treating" refers to both therapeutic treatment and prophylactic or preventative measures, wherein the object is to prevent or lessen the targeted tumor or cancer. Treating may include one or more of directly affecting or curing, suppressing, inhibiting, preventing, reducing the severity of, delaying the onset of, slowing the progression of, stabilizing the progression of, inducing remission of, preventing or delaying the metastasis of, reducing/ameliorating symptoms associated with the tumor or cancer, or a combination thereof. For example, treating may include increasing expected survival time or decreasing tumor or metastasis size. The effect (e.g., suppressing, inhibiting, preventing, reducing the severity of, delaying the onset of, slowing the progression of, stabilizing the progression of, inducing remission of, preventing or delaying the metastasis of, reducing/ameliorating symptoms of, and so forth, can be relative to a control subject not receiving a treatment or receiving a placebo treatment. The term "treat" or "treating" can also refer to increasing percent chance of survival or increasing expected time of survival for a subject with the tumor or cancer (e.g., relative to a control subject not receiving a treatment or receiving a placebo treatment). In one example, "treating" refers to delaying progression, expediting remission, inducing remission, augmenting remission, speeding recovery, increasing efficacy of alternative therapeutics, decreasing resistance to alternative therapeutics, or a combination thereof (e.g., relative to a control subject not receiving a treatment or receiving a placebo treatment). The terms "preventing" or "impeding" can refer, for example to delaying the onset of symptoms, preventing relapse of a tumor or cancer, decreasing the number or frequency of relapse episodes, increasing latency between symptomatic episodes, preventing metastasis of a tumor or cancer, or a combination thereof. The terms "suppressing" or "inhibiting" can refer, for example, to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

The term "subject" refers to a mammal (e.g., a human) in need of therapy for, or susceptible to developing, a tumor or a cancer. The term subject also refers to a mammal (e.g., a human) that receives either prophylactic or therapeutic treatment. The subject may include dogs, cats, pigs, cows, sheep, goats, horses, rats, mice, non-human mammals, and humans. The term "subject" does not necessarily exclude an individual that is healthy in all respects and does not have or show signs of cancer or a tumor.

An individual is at increased risk of developing a tumor or a cancer if the subject has at least one known risk-factor (e.g., genetic, biochemical, family history, and situational exposure) placing individuals with that risk factor at a statistically significant greater risk of developing the tumor or cancer than individuals without the risk factor.

A "symptom" or "sign" refers to objective evidence of a disease as observed by a physician or subjective evidence of a disease, such as altered gait, as perceived by the subject. A symptom or sign may be any manifestation of a disease. Symptoms can be primary or secondary. The term "primary" refers to a symptom that is a direct result of a particular disease or disorder (e.g., a tumor or cancer), while the term "secondary" refers to a symptom that is derived from or consequent to a primary cause. The recombinant fusion polypeptides, nucleic acids encoding the recombinant fusion polypeptides, the immunogenic compositions, the pharmaceutical compositions, and the vaccines disclosed herein can treat primary or secondary symptoms or secondary complications.

The recombinant fusion polypeptides, nucleic acids encoding recombinant fusion polypeptides, recombinant bacteria or *Listeria* strains, immunogenic compositions, pharmaceutical compositions, or vaccines are administered in an effective regime, meaning a dosage, route of administration, and frequency of administration that delays the onset, reduces the severity, inhibits further deterioration, and/or ameliorates at least one sign or symptom of the tumor or cancer. Alternatively, the recombinant fusion polypeptides, nucleic acids encoding recombinant fusion polypeptides, recombinant bacteria or *Listeria* strains, immunogenic compositions, pharmaceutical compositions, or vaccines are administered in an effective regime, meaning a dosage, route of administration, and frequency of administration that induces an immune response to a heterologous antigen in the recombinant fusion polypeptide (or encoded by the nucleic acid), the recombinant bacteria or *Listeria* strain, the immunogenic composition, the pharmaceutical composition, or the vaccine, or in the case of recombinant bacteria or *Listeria* strains, that induces an immune response to the bacteria or *Listeria* strain itself. If a subject is already suffering from the tumor or cancer, the regime can be referred to as a therapeutically effective regime. If the subject is at elevated risk of developing the tumor or cancer relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients. For example, a regime can be considered therapeutically or prophylactically effective if an individual treated patient achieves an outcome more favorable than the mean outcome in a control population of comparable patients not treated by methods described herein, or if a more favorable outcome is demonstrated in treated patients versus control patients in a controlled clinical trial (e.g., a phase II, phase II/III or phase III trial) at the $p<0.05$ or 0.01 or even 0.001 level.

Exemplary dosages for a recombinant *Listeria* strain are, for example, $1\times10^6$-$1\times10^7$ CFU, $1\times10^7$-$1\times10^8$ CFU, $1\times10^8$-$3.31\times10^{10}$ CFU, $1\times10^9$-$3.31\times10^{10}$ CFU, $5$-$500\times10^8$ CFU, $7$-$500\times10^8$ CFU, $10$-$500\times10^8$ CFU, $20$-$500\times10^8$ CFU, $30$-$500\times10^8$ CFU, $50$-$500\times10^8$ CFU, $70$-$500\times10^8$ CFU, $100$-$500\times10^8$ CFU, $150$-$500\times10^8$ CFU, $5$-$300\times10^8$ CFU, $5$-$200\times10^8$ CFU, $5$-$15\times10^8$ CFU, $5$-$100\times10^8$ CFU, $5$-$70\times10^8$ CFU, $5$-$50\times10^8$ CFU, $5$-$30\times10^8$ CFU, $5$-$20\times10^8$ CFU, $1$-$30\times10^9$ CFU, $1$-$20\times10^9$ CFU, $2$-$30\times10^9$ CFU, $1$-$10\times10^9$ CFU, $2$-$10\times10^9$ CFU, $3$-$10\times10^9$ CFU, $2$-$7\times10^9$ CFU, $2$-$5\times10^9$ CFU, and $3$-$5\times10^9$ CFU. Other exemplary dosages for a recombinant *Listeria* strain are, for example, $1\times10^7$ organisms, $1.5\times10^7$ organisms, $2\times10^8$ organisms, $3\times10^7$ organisms, $4\times10^7$ organisms, $5\times10^7$ organisms, $6\times10^7$ organisms, $7\times10^7$ organisms, $8\times10^7$ organisms, $10\times10^7$ organisms, $1.5\times10^8$ organisms, $2\times10^8$ organisms, $2.5\times10^8$ organisms, $3\times10^8$ organisms, $3.3\times10^8$ organisms, $4\times10^8$ organisms, $5\times10^8$ organisms, $1\times10^9$ organisms, $1.5\times10^9$ organisms, $2\times10^9$ organisms, $3\times10^9$ organisms, $4\times10^9$ organisms, $5\times10^9$ organisms, $6\times10^9$ organisms, $7\times10^9$ organisms, $8\times10^9$ organisms, $10\times10^9$ organisms, $1.5\times10^{10}$ organisms, $2\times10^{10}$ organisms, $2.5\times10^{10}$ organisms, $3\times10^{10}$ organisms, $3.3\times10^{10}$ organisms, $4\times10^{10}$ organisms, and $5\times10^{10}$ organisms. The dosage can depend on the condition of the patient and response to prior treatment, if any, whether the treatment is prophylactic or therapeutic, and other factors.

Administration can be by any suitable means. For example, administration can be parenteral, intravenous, oral, subcutaneous, intra-arterial, intracranial, intrathecal, intracerebroventricular, intraperitoneal, topical, intranasal, intramuscular, intra-ocular, intrarectal, conjunctival, transdermal, intradermal, vaginal, rectal, intratumoral, parcanceral, transmucosal, intravascular, intraventricular, inhalation (aerosol), nasal aspiration (spray), sublingual, aerosol, suppository, or a combination thereof. For intranasal administration or application by inhalation, solutions or suspensions of the recombinant fusion polypeptides, nucleic acids encoding recombinant fusion polypeptides, recombinant bacteria or *Listeria* strains, immunogenic compositions, pharmaceutical compositions, or vaccines mixed and aerosolized or nebulized in the presence of the appropriate carrier are suitable. Such an aerosol may comprise any recombinant fusion polypeptide, nucleic acids encoding a recombinant fusion polypeptide, recombinant bacteria or *Listeria* strain, immunogenic composition, pharmaceutical composition, or vaccine described herein. Administration may also be in the form of a suppository (e.g., rectal suppository or urethral suppository), in the form of a pellet for subcutaneous implantation (e.g., providing for controlled release over a period of time), or in the form of a capsule. Administration may also be via injection into a tumor site or into a tumor. Regimens of administration can be readily determined based on factors such as exact nature and type of the tumor or cancer being treated, the severity of the tumor or cancer, the age and general physical condition of the subject, body weight of the subject, response of the individual subject, and the like.

The frequency of administration can depend on the half-life of the recombinant fusion polypeptides, nucleic acids encoding recombinant fusion polypeptides, recombinant bacteria or *Listeria* strains, immunogenic compositions, pharmaceutical compositions, or vaccines in the subject, the condition of the subject, and the route of administration, among other factors. The frequency can be, for example, daily, weekly, monthly, quarterly, or at irregular intervals in response to changes in the subject's condition or progression of the tumor or cancer being treated. The course of treatment can depend on the condition of the subject and other factors. For example, the course of treatment can be several weeks, several months, or several years (e.g., up to 2 years). For example, repeat administrations (doses) may be undertaken immediately following the first course of treatment or after an interval of days, weeks or months to achieve tumor regression or suppression of tumor growth. Assessment may be determined by any known technique, including diagnostic methods such as imaging techniques, analysis of serum tumor markers, biopsy, or the presence, absence, or amelioration of tumor-associated symptoms. As a specific example, the recombinant fusion polypeptides, nucleic acids encoding recombinant fusion polypeptides, recombinant bacteria or *Listeria* strains, immunogenic compositions, pharmaceutical compositions, or vaccines can be administered every 3 weeks for up to 2 years. In one example, a recombinant fusion polypeptide, a nucleic acid encoding a recombinant fusion polypeptide, a recombinant bacteria or *Listeria* strain, an immunogenic composition, a pharmaceutical composition, or a vaccine disclosed herein is administered in increasing doses in order to increase the T-effector cell to regulatory T cell ratio and generate a more potent anti-tumor immune response. Anti-tumor immune responses can be further strengthened by providing the subject with cytokines including, for example, IFN-γ, TNF-α, and other cytokines known to enhance cellular immune response. See, e.g., U.S. Pat. No. 6,991,785, herein incorporated by reference in its entirety for all purposes.

Some methods may further comprise "boosting" the subject with additional recombinant fusion polypeptides, nucleic acids encoding recombinant fusion polypeptides, recombinant bacteria or *Listeria* strains, immunogenic compositions, pharmaceutical compositions, or vaccines or administering the recombinant fusion polypeptides, nucleic acids encoding recombinant fusion polypeptides, recombinant bacteria or *Listeria* strains, immunogenic compositions, pharmaceutical compositions, or vaccines multiple times. "Boosting" refers to administering an additional dose to a subject. For example, in some methods, 2 boosts (or a total of 3 inoculations) are administered, 3 boosts are administered, 4 boosts are administered, 5 boosts are administered, or 6 or more boosts are administered. The number of dosages administered can depend on, for example, the response of the tumor or cancer to the treatment.

Optionally, the recombinant fusion polypeptide, nucleic acids encoding a recombinant fusion polypeptide, recombinant bacteria or *Listeria* strain, immunogenic composition, pharmaceutical composition, or vaccine used in the booster inoculation is the same as the recombinant fusion polypeptide, recombinant bacteria or *Listeria* strain, immunogenic composition, pharmaceutical composition, or vaccine used in the initial "priming" inoculation. Alternatively, the booster recombinant fusion polypeptide, recombinant bacteria or *Listeria* strain, immunogenic composition, pharmaceutical composition, or vaccine is different from the priming recombinant fusion polypeptide, recombinant bacteria or *Listeria* strain, immunogenic composition, pharmaceutical composition, or vaccine. Optionally, the same dosages are used in the priming and boosting inoculations. Alternatively, a larger dosage is used in the booster, or a smaller dosage is used in the booster. The period between priming and boosting inoculations can be experimentally determined. For example, the period between priming and boosting inoculations can be 1 week, 2 weeks, 3 weeks, 4 weeks, 5 weeks, 6-8 weeks, or 8-10 weeks.

Heterologous prime boost strategies have been effective for enhancing immune responses and protection against numerous pathogens. See, e.g., Schneider et al. (1999) *Immunol. Rev.* 170:29-38; Robinson (2002) *Nat. Rev. Immunol.* 2:239-250; Gonzalo et al. (2002) *Vaccine* 20:1226-1231; and Tanghe (2001) *Infect. Immun.* 69:3041-3047, each of which is herein incorporated by reference in its entirety for all purposes. Providing antigen in different forms in the prime and the boost injections can maximize the immune response to the antigen. DNA vaccine priming followed by boosting with protein in adjuvant or by viral vector delivery of DNA encoding antigen is one effective way of improving antigen-specific antibody and $CD4^+$ T-cell responses or $CD8^+$ T-cell responses. See, e.g., Shiver et al. (2002) *Nature* 415: 331-335; Gilbert et al. (2002) *Vaccine* 20:1039-1045; Billaut-Mulot et al. (2000) *Vaccine* 19:95-102; and Sin et al. (1999) *DNA Cell Biol.* 18:771-779, each of which is herein incorporated by reference in its entirety for all purposes. As one example, adding CRL1005 poloxamer (12 kDa, 5% POE) to DNA encoding an antigen can enhance T-cell responses when subjects are vaccinated with a DNA prime followed by a boost with an adenoviral vector expressing the antigen. See, e.g., Shiver et al. (2002) *Nature* 415:331-335, herein incorporated by reference in its entirety for all purposes. As another example, a vector construct encoding an immunogenic portion of an antigen and a protein comprising the immunogenic portion of the antigen can be administered. See, e.g., US 2002/0165172, herein incorporated by reference in its entirety for all purposes. Similarly, an immune response of nucleic acid vaccination can be enhanced by simultaneous administration of (e.g., during the same immune response, preferably within 0-10 or 3-7 days of each other) a polynucleotide and polypeptide of interest. See, e.g., U.S. Pat. No. 6,500,432, herein incorporated by reference in its entirety for all purposes.

The therapeutic methods disclosed herein can also comprise administering one or more additional compounds effective in preventing or treating cancer. For example, an additional compound may comprise a compound useful in chemotherapy, such as amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil (5-FU), gemcitabine, gliadelimplants, hydroxycarbamide, idarubicin, ifosfamide, irinotecan, leucovorin, liposomaldoxorubicin, liposomaldaunorubicin, lomustine, melphalan, mercaptopurine, mesna, methotrexate, mitomycin, mitoxantrone, oxaliplatin, paclitaxel (Taxol), pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Alternatively, an additional compound can also comprise other biologics, including HERCEPTIN® (trastuzumab) against the HER2 antigen, AVASTIN® (bevacizumab) against VEGF, or antibodies to the EGF receptor, such as ERBITUX® (cetuximab), and VECTIBIX® (panitumumab). Alternatively, an additional compound can comprise other immunotherapies. Alternatively, the additional compound can be an indoleamine 2,3-dioxygenase (IDO) pathway inhibitor, such as 1-methyltryptophan (1MT), 1-methyltryptophan (1MT), Necrostatin-1, Pyridoxal Isonicotinoyl Hydrazone, Ebselen, 5-Methylindole-3-carboxaldehyde, CAY10581, an anti-IDO antibody, or a small molecule IDO inhibitor. IDO inhibition can enhance the efficacy of chemotherapeutic agents. The therapeutic methods disclosed herein can also be combined with radiation, stem cell treatment, surgery, or any other treatment.

Such additional compounds or treatments can precede the administration of a recombinant fusion polypeptide, a nucleic acid encoding a recombinant fusion polypeptide, a recombinant bacteria or *Listeria* strain, an immunogenic composition, a pharmaceutical composition, or a vaccine disclosed herein, follow the administration of a recombinant fusion polypeptide, a nucleic acid encoding a recombinant fusion polypeptide, a recombinant bacteria or *Listeria* strain, an immunogenic composition, a pharmaceutical composition, or a vaccine disclosed herein, or be simultaneous to the administration of a recombinant fusion polypeptide, a nucleic acid encoding a recombinant fusion polypeptide, a recombinant bacteria or *Listeria* strain, an immunogenic composition, a pharmaceutical composition, or a vaccine disclosed herein.

Targeted immunomodulatory therapy is focused primarily on the activation of costimulatory receptors, for example by using agonist antibodies that target members of the tumor necrosis factor receptor superfamily, including 4-1BB, OX40, and GITR (glucocorticoid-induced TNF receptor-related). The modulation of GITR has demonstrated potential in both antitumor and vaccine settings. Another target for agonist antibodies are co-stimulatory signal molecules for T cell activation. Targeting costimulatory signal molecules may lead to enhanced activation of T cells and facilitation of a more potent immune response. Co-stimulation may also help prevent inhibitory influences from checkpoint inhibition and increase antigen-specific T cell proliferation.

*Listeria*-based immunotherapy acts by inducing the de novo generation of tumor antigen-specific T cells that infiltrate and destroy the tumor and by reducing the numbers and activities of immunosuppressive regulatory T cells (Tregs) and myeloid-derived suppressor cells (MDSCs) in the tumor microenvironment. Antibodies (or functional fragments thereof) for T cell co-inhibitory or co-stimulatory receptors (e.g., checkpoint inhibitors CTLA-4, PD-1, TIM-3, LAG3 and co-stimulators CD137, OX40, GITR, and CD40) can have synergy with *Listeria*-based immunotherapy.

Thus, some methods can comprise further administering a composition comprising an immune checkpoint inhibitor antagonist, such as a PD-1 signaling pathway inhibitor, a CD-80/86 and CTLA-4 signaling pathway inhibitor, a T cell membrane protein 3 (TIM3) signaling pathway inhibitor, an adenosine A2a receptor (A2aR) signaling pathway inhibitor, a lymphocyte activation gene 3 (LAG3) signaling pathway inhibitor, a killer immunoglobulin receptor (KIR) signaling pathway inhibitor, a CD40 signaling pathway inhibitor, or any other antigen-presenting cell/T cell signaling pathway inhibitor. Examples of immune checkpoint inhibitor antagonists include an anti-PD-L1/PD-L2 antibody or fragment thereof, an anti-PD-1 antibody or fragment thereof, an anti-CTLA-4 antibody or fragment thereof, or an anti-B7-H4 antibody or fragment thereof. For example, an anti PD-1 antibody can be administered to a subject at 5-10 mg/kg every 2 weeks, 5-10 mg/kg every 3 weeks, 1-2 mg/kg every 3 weeks, 1-10 mg/kg every week, 1-10 mg/kg every 2 weeks, 1-10 mg/kg every 3 weeks, or 1-10 mg/kg every 4 weeks.

Likewise, some methods can further comprise administering a T cell stimulator, such as an antibody or functional fragment thereof binding to a T-cell receptor co-stimulatory molecule, an antigen presenting cell receptor binding co-stimulatory molecule, or a member of the TNF receptor superfamily. The T-cell receptor co-stimulatory molecule can comprise, for example, CD28 or ICOS. The antigen presenting cell receptor binding co-stimulatory molecule can comprise, for example, a CD80 receptor, a CD86 receptor, or a CD46 receptor. The TNF receptor superfamily member can comprise, for example, glucocorticoid-induced TNF receptor (GITR), OX40 (CD134 receptor), 4-1BB (CD137 receptor), or TNFR25.

For example, some methods can further comprise administering an effective amount of a composition comprising an antibody or functional fragment thereof binding to a T-cell receptor co-stimulatory molecule or an antibody or functional fragment thereof binding to an antigen presenting cell receptor binding a co-stimulatory molecule. The antibody can be, for example, an anti-TNF receptor antibody or antigen-binding fragment thereof (e.g., TNF receptor superfamily member glucocorticoid-induced TNF receptor (GITR), OX40 (CD134 receptor), 4-1BB (CD137 receptor), or TNFR25), an anti-OX40 antibody or antigen-binding fragment thereof, or an anti-GITR antibody or antigen binding fragment thereof. Alternatively, other agonistic molecules can be administered (e.g., GITRL, an active fragment of GITRL, a fusion protein containing GITRL, a fusion protein containing an active fragment of GITRL, an antigen presenting cell (APC)/T cell agonist, CD134 or a ligand or fragment thereof, CD137 or a ligand or fragment thereof, or an inducible T cell costimulatory (ICOS) or a ligand or fragment thereof, or an agonistic small molecule).

In a specific example, some methods can further comprise administering an anti-CTLA-4 antibody or a functional fragment thereof and/or an anti-CD137 antibody or functional fragment thereof. For example, the anti-CTLA-4 antibody or a functional fragment thereof or the anti-CD137 antibody or functional fragment thereof can be administered about 72 hours after the first dose of recombinant fusion polypeptide, nucleic acids encoding a recombinant fusion polypeptide, recombinant bacteria or *Listeria* strain, immunogenic composition, pharmaceutical composition, or vaccine, or about 48 hours after the first dose of recombinant fusion polypeptide, nucleic acids encoding a recombinant fusion polypeptide, recombinant bacteria or *Listeria* strain, immunogenic composition, pharmaceutical composition, or vaccine. The anti-CTLA-4 antibody or a functional fragment thereof or anti-CD137 antibody or functional fragment thereof can be administered at a dose, for example, of about 0.05 mg/kg and about 5 mg/kg. A recombinant *Listeria* strain or immunogenic composition comprising a recombinant *Listeria* strain can be administered at a dose, for example, of about $1 \times 10^9$ CFU. Some such methods can further comprise administering an effective amount of an anti-PD-1 antibody or functional fragment thereof.

Methods for assessing efficacy of cancer immunotherapies are well known and are described, for example, in Dzojic et al. (2006) *Prostate* 66(8):831-838; Naruishi et al. (2006) *Cancer Gene Ther.* 13(7):658-663, Sehgal et al. (2006) *Cancer Cell Int.* 6:21), and Heinrich et al. (2007) *Cancer Immunol Immunother* 56(5):725-730, each of which is herein incorporated by reference in its entirety for all purposes. As one example, for prostate cancer, a prostate cancer model can be to test methods and compositions disclosed herein, such as a TRAMP-C2 mouse model, a 178-2 BMA cell model, a PAIII adenocarcinoma cells model, a PC-3M model, or any other prostate cancer model.

Alternatively or additionally, the immunotherapy can be tested in human subjects, and efficacy can be monitored using known. Such methods can include, for example, directly measuring CD4+ and CD8+ T cell responses, or measuring disease progression (e.g., by determining the number or size of tumor metastases, or monitoring disease symptoms such as cough, chest pain, weight loss, and so forth). Methods for assessing the efficacy of a cancer immunotherapy in human subjects are well known and are described, for example, in Uenaka et al. (2007) *Cancer Immun.* 7:9 and Thomas-Kaskel et al. (2006) *Int J Cancer* 119(10):2428-2434, each of which is herein incorporated by reference in its entirety for all purposes.

IX. Kits

Also provided are kits comprising a reagent utilized in performing a method disclosed herein or kits comprising a composition, tool, or instrument disclosed herein.

For example, such kits can comprise a recombinant fusion polypeptide disclosed herein, a nucleic acid encoding a recombinant fusion polypeptide disclosed herein, a recombinant bacteria or *Listeria* strain disclosed herein, an immunogenic composition disclosed herein, a pharmaceutical composition disclosed herein, or a vaccine disclosed herein. Such kits can additionally comprise an instructional material which describes use of the recombinant fusion polypeptide, the nucleic acid encoding the recombinant fusion polypeptide, the recombinant *Listeria* strain, the immunogenic composition, the pharmaceutical composition, or the vaccine to perform the methods disclosed herein. Such kits can optionally further comprise an applicator. Although model kits are described below, the contents of other useful kits will be apparent in light of the present disclosure.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

LISTING OF EMBODIMENTS

The subject matter disclosed herein includes, but is not limited to, the following embodiments.

1. A recombinant *Listeria* strain comprising a nucleic acid comprising a first open reading frame encoding a fusion polypeptide, wherein the fusion polypeptide comprises a PEST-containing peptide fused to two or more antigenic peptides, wherein each antigenic peptide comprises a recurrent cancer mutation, and wherein at least two of the antigenic peptides comprise different recurrent cancer mutations and are fragments of the same cancer-associated protein.

2. The recombinant *Listeria* strain of embodiment 1, wherein each antigenic peptide is a fragment of a cancer-associated protein and is about 5-100, 15-50, or 21-27 amino acids in length.

3. The recombinant *Listeria* strain of any preceding embodiment, wherein each antigenic peptide comprises a recurrent cancer mutation flanked on each side by an equal number of amino acids.

4. The recombinant *Listeria* strain of any preceding embodiment, wherein each antigenic peptide comprises a recurrent cancer mutation flanked on each side by at least 10 or at least 13 amino acids.

5. The recombinant *Listeria* strain of any preceding embodiment, wherein the two or more antigenic peptides are fused directly to each other without intervening sequence.

6. The recombinant *Listeria* strain of any one of embodiments 1-4, wherein the two or more antigenic peptides are linked to each other via peptide linkers.

7. The recombinant *Listeria* strain of embodiment 6, wherein one or more of the linkers set forth in SEQ ID NOS: 310-319 are used to link the two or more antigenic peptides.

8. The recombinant *Listeria* strain of any preceding embodiment, wherein no region of the fusion polypeptide scores above a cutoff of around 1.6 when scored for hydropathy by a Kyte and Doolittle hydropathy index with a sliding 21 amino acid window.

9. The recombinant *Listeria* strain of any preceding embodiment, wherein the fusion polypeptide comprises at least 3, 4, 5, 6, 7, 8, 9, 10, 11, 12, 13, 14, 15, 16, 17, 18, 19, 20, 21, 22, 23, 24, 25, 26, 27, 28, 29, or 30 antigenic peptides from the same cancer-associated protein or 3-40 antigenic peptides from the same cancer-associated protein, or wherein the fusion polypeptide comprises at least 2, 3, 4, 5, 6, 7, 8, 9, 10, 11, 12, 13, 14, 15, 16, 17, 18, 19, 20, 21, 22, 23, 24, 25, 26, 27, 28, 29, or 30 non-contiguous antigenic peptides from the same cancer-associated protein or 2-40 non-contiguous antigenic peptides from the same cancer-associated protein.

10. The recombinant *Listeria* strain of embodiment 9, wherein the antigenic peptides comprise the 2, 3, 4, 5, 6, 7, 8, 9, 10, 11, 12, 13, 14, 15, 16, 17, 18, 19, 20, 21, 22, 23, 24, 25, 26, 27, 28, 29, or 30 most common recurrent cancer mutations in the cancer-associated protein.

11. The recombinant *Listeria* strain of embodiment 10, wherein the antigenic peptides comprise the 2, 3, 4, 5, 6, 7, 8, 9, 10, 11, 12, 13, 14, 15, 16, 17, 18, 19, 20, 21, 22, 23, 24, 25, 26, 27, 28, 29, or 30 most common recurrent somatic missense cancer mutations in the cancer-associated protein.

12. The recombinant *Listeria* strain of any preceding embodiment, wherein at least 50%, 60%, 70%, 80%, 90%, 95%, 96%, 97%, 98%, or 99% of cancer patients with a mutation in the cancer-associated protein have a recurrent cancer mutation in the cancer-associated protein that is included in the combination of antigenic peptides in the recombinant *Listeria* strain.

13. The recombinant *Listeria* strain of any preceding embodiment, wherein at least 50%, 60%, 70%, 80%, 90%, 95%, 96%, 97%, 98%, or 99% of cancer patients with a somatic missense mutation in the cancer-associated protein have a recurrent cancer mutation in the cancer-associated protein that is included in the combination of antigenic peptides in the recombinant *Listeria* strain.

14. The recombinant *Listeria* strain of any preceding embodiment, wherein the recurrent cancer mutations in at least two of the antigenic peptides are from the same cancer-associated protein and do not occur naturally together.

15. The recombinant *Listeria* strain of any preceding embodiment, wherein at least two of the antigenic peptides are overlapping fragments of the same cancer-associated protein.

16. The recombinant *Listeria* strain of embodiment 15, wherein the recurrent cancer mutations in at least two of the antigenic peptides are from the same cancer-associated protein and occur at the same amino acid residue of the cancer-associated protein.

17. The recombinant *Listeria* strain of embodiment 16, wherein the fusion polypeptide comprises two or more copies of a single antigenic peptide, or wherein two of the antigenic peptides comprise the same recurrent cancer mutation.

18. The recombinant *Listeria* of any one of embodiments 1-16, wherein each antigenic peptide comprises a different recurrent cancer mutation.

19. The recombinant *Listeria* strain of any preceding embodiment, wherein each recurrent cancer mutation in the fusion polypeptide is a somatic missense mutation.

20. The recombinant *Listeria* strain of any preceding embodiment, wherein the antigenic peptides are from the cancer associated protein and one or more additional proteins.

21. The recombinant *Listeria* strain of any preceding embodiment, wherein the cancer-associated protein is an oncogenic protein or a tumor suppressor protein.

22. The recombinant *Listeria* strain of any one of embodiments 1-19, wherein the cancer-associated protein is encoded by one of the following human genes: TP53, PIK3CA, APC, CTNNB1, CDKN2A, NFE2L2, BRAF, KRAS, EGFR, ERBB2, SF3B1, FBXW7, PIK3R1, SMAD4, SPOP, PTPN11, NRAS, PTEN, HRAS, U2AF1, ERBB3, FGFR3, ARID1A, MAP2K1, FGFR2, RHOA, MTOR, BCL2L12, RAC1, IDH2, H3F3A, PPP2R1A, POLE, ATM, EP300, ALK, RQCD1, GPRIN2, THSD7B, CDK4, NUP93, CCND1, FGFR1, MAX, VHL, ACVR1, MEF2A, MYC, FRMD6, SRC, KIT, KEAP1, STKl1, NF1, KMT2D, GATA3, AKT1, MAP3K1, MAP2K4, KMT2C, FAT1, PBRM1, SETD2, CREBBP, RB1, SMARCA4, CHD4, FLT3, ARID2, CDH1, DNMT3A, ARHGAP35, BCOR, CTCF, KDM5C, KDM6A, CASP8, ASXL1, RASA1, RUNX1, NPM1, CDKN1B, HLA-A, B2M, RPL5, MYD88, CBFB, and GPS2, or wherein the cancer-associated protein is encoded by one of the following human genes: TP53, PIK3CA, APC, CTNNB1, CDKN2A, NFE2L2, BRAF, KRAS, EGFR, ERBB2, SF3B1, FBXW7, PIK3R1, SMAD4, SPOP, PTPN11, NRAS, PTEN, HRAS, U2AF1, ERBB3, FGFR3, ARID1A, MAP2K1, FGFR2, RHOA, MTOR, BCL2L12, RAC1, IDH2, H3F3A, PPP2R1A, POLE, ATM, EP300, ALK, RQCD1, GPRIN2, THSD7B, CDK4, NUP93, CCND1, FGFR1, MAX, VHL, ACVR1, MEF2A, MYC, FRMD6, SRC, KIT, KEAP1, STK11, NF1, KMT2D, GATA3, AKT1, MAP3K1, MAP2K4, KMT2C, FAT1, PBRM1, SETD2, CREBBP, RB1, SMARCA4, CHD4, FLT3, ARID2, CDH1, DNMT3A, ARHGAP35, BCOR, CTCF, KDM5C, KDM6A, CASP8, ASXL1, RASA1, RUNX1, NPM1, CDKN1B, HLA-A, B2M, RPL5, MYD88, CBFB, GPS2, AHNAK2, ANKRD36C, CHEK2, KRTAP4-11, RGPD8, FAM47C, and ZAN.

23. The recombinant *Listeria* strain of embodiment 22, wherein the cancer-associated protein is encoded by one of the following genes: BRAF, EGFR, PIK3CA, PIK3R1, PTEN, KRAS, TP53, APC, FBXW7, KEAP1, STK11, NF1, KMT2D, CDKN2A, NFE2L2, SPOP, GATA3, AKT1, MAP3K1, and MAP2K4, or wherein the cancer-associated protein is encoded by one of the following genes: BRAF, EGFR, PIK3CA, PIK3R1, PTEN, KRAS, TP53, APC, FBXW7, KEAP1, STKl1, NF1, KMT2D, CDKN2A, NFE2L2, SPOP, GATA3, AKT1, MAP3K1, MAP2K4, AHNAK2, ANKRD36C, CHEK2, KRTAP4-11, RGPD8, FAM47C, and ZAN.

24. The recombinant *Listeria* strain of embodiment 23, wherein the cancer-associated protein is encoded by BRAF, and the antigenic peptides comprise two or more or all of the following recurrent cancer mutations: G466E; G466V; G469A; G469R; G469S; G469V; V600E; and V600K.

25. The recombinant *Listeria* strain of embodiment 24, wherein the fusion polypeptide comprises antigenic peptides comprising the following recurrent cancer mutations in one of the following N-terminal to C-terminal orders: (a) G469V; G469R; V600E; G469S; G466V; V600K; G469A; and G466E; (b) V600K; G469R; G469V; G466V; G466E; V600E; G469A; and G469S; (c) G469V; V600K; G469S; G466V; G469A; V600E; G466E; and G469R; and (d) V600E; V600K; G469A; G469S; G469R; G469V; G466V; and G466E.

26. The recombinant *Listeria* strain of embodiment 25, wherein the combination of the antigenic peptides in the fusion polypeptide comprises a sequence at least 90%, 95%, 96%, 97%, 98%, 99%, or 100% identical to one of SEQ ID NOS: 2, 8, 14, and 20.

27. The recombinant *Listeria* strain of embodiment 26, wherein the portion of the open reading frame encoding the combination of the antigenic peptides comprises a sequence at least 90%, 95%, 96%, 97%, 98%, 99%, or 100% identical to one of SEQ ID NOS: 1, 7, 13, and 19.

28. The recombinant *Listeria* strain of embodiment 23, wherein the cancer-associated protein is encoded by EGFR, and the antigenic peptides comprise two or more of the following recurrent cancer mutations: R108K; A289V; G598V; E709A; E709K; G719A; G719C; G719S; L747P; L747S; S768I; T790M; L833V/H835L; T833V; L858R; and L861Q.

29. The recombinant *Listeria* strain of embodiment 28, wherein the fusion polypeptide comprises antigenic peptides comprising the following recurrent cancer mutations in one of the following N-terminal to C-terminal orders: (a) G719S; L747P; G719C; R108K; S768I; L833V/H835L; T833V; E709A; G598V; T790M; E709K; A289V; L861Q; G719A; L747S; and L858R; (b) T790M; S768I; G719C; R108K; L747P; G719A; L747S; E709K; T833V; L861Q; E709A; L858R; G598V; A289V; L833V/H835L; and G719S; (c) R108K; T833V; L747S; T790M; G719C; A289V; L858R; E709A; G719S; E709K; G719A; L747P; G598V; L861Q; S768I; and L833V/H835L; (d) G719A; L858R; G719C; A289V; T790M; S768I; T833V; G598V; G719S; L747S; L747P; L833V/H835L; E709A; R108K; L861Q; and E709K; and (e) A289V; G598V; E709K; G719A; S768I; G719S; L861Q; T790M; G719C; L833V/H835L; and L858R.

30. The recombinant *Listeria* strain of embodiment 29, wherein the combination of the antigenic peptides in the fusion polypeptide comprises a sequence at least 90%, 95%, 96%, 97%, 98%, 99%, or 100% identical to one of SEQ ID NOS: 26, 32, 38, 44, and 231.

31. The recombinant *Listeria* strain of embodiment 30, wherein the portion of the open reading frame encoding the combination of the antigenic peptides comprises a sequence at least 90%, 95%, 96%, 97%, 98%, 99%, or 100% identical to one of SEQ ID NOS: 25, 31, 37, 43, 229, and 230.

32. The recombinant *Listeria* strain of embodiment 23, wherein the cancer-associated protein is encoded by PIK3CA, and the antigenic peptides comprise two or more or all of the following recurrent cancer mutations: R38C; R38H; E81K; R88Q; R93Q; R93W; R108H; G118D; L334G; N345K; C420R; E453K; E542K; E545A; E545G; E545K; E545Q; Q546K; Q546R; E726K; M1043I; M1043V; H1047L; H1047R; and G1049R.

33. The recombinant *Listeria* strain of embodiment 32, wherein the antigenic peptides comprise two or more or all of the following recurrent cancer mutations: R88Q; E542K; E545A; E545G; E545K; Q546K; H1047L; and H1047R.

34. The recombinant *Listeria* strain of embodiment 32, wherein the antigenic peptides comprise two or more or all of the following recurrent cancer mutations: R38H; E81K; R108H; G118D; N345K; C420R; Q546R; M1043I; and G1049R.

35. The recombinant *Listeria* strain of embodiment 32, wherein the fusion polypeptide comprises antigenic peptides comprising the following recurrent cancer mutations in one of the following N-terminal to C-terminal orders: (a) M1043V; E545G; E726K; Q546R; L334G; G1049R; M1043I; Q546K; E542K; R93Q; H1047R; R108H; R93W; E81K; R38H; N345K; R88Q; G118D; E545Q; H1047L; E545A; E453K; E545K; R38C; and C420R; (b) E726K; E81K; M1043V; E545A; E545K; R38C; G118D; R93W; E545G; E542K; G1049R; N345K; Q546K; E453K; C420R; H1047L; L334G; E545Q; R88Q; H1047R; M1043I; R93Q; R108H; Q546R; and R38H; (c) R108H; M1043V; R88Q; R93W; R38H; H1047R; E545K; M1043I; Q546R; E542K; N345K; R38C; E545G; E81K; Q546K; R93Q; E453K; G1049R; E545A; C420R; H1047L; L334G; Gi 18D; E726K; and E545Q; (d) N345K; R38H; E545K; G1049R; H1047L; E726K; R88Q; E81K; R93Q; E545Q; L334G; R38C; H1047R; C420R; R93W; Q546K; M1043V; M1043I; E545G; E545A; G118D; E453K; Q546R; R108H; and E542K; (e) E542K; E545K; R88Q; E545A; H1047R; E545G; H1047L; Q546K; R38H; E81K; R108H; N345K; C420R; Q546R; M1043I; G118D; and G1049R; (f) E542K; E545K; R88Q; E545A; H1047R; E545G; H1047L; and Q546K; and (g) R38H; E81K; R108H; N345K; C420R; Q546R; M1043I; G118D; and G1049R.

36. The recombinant *Listeria* strain of embodiment 35, wherein the combination of the antigenic peptides in the fusion polypeptide comprises a sequence at least 90%, 95%, 96%, 97%, 98%, 99%, or 100% identical to one of SEQ ID NOS: 50, 56, 62, 68, 238, 245, and 252.

37. The recombinant *Listeria* strain of embodiment 36, wherein the portion of the open reading frame encoding the combination of the antigenic peptides comprises a sequence at least 90%, 95%, 96%, 97%, 98%, 99%, or 100% identical to one of SEQ ID NOS: 49, 55, 61, 67, 236, 237, 243, 244, 250, and 251.

38. The recombinant *Listeria* strain of embodiment 23, wherein the cancer-associated protein is encoded by PIK3R1, and the antigenic peptides comprise two or more or all of the following recurrent cancer mutations: G376R; N564D; and K567E.

39. The recombinant *Listeria* strain of embodiment 38, wherein the fusion polypeptide comprises antigenic peptides comprising the following recurrent cancer mutations in one of the following N-terminal to C-terminal orders: (a) G376R; N564D; and K567E; and (b) N564D; K567E; and G376R.

40. The recombinant *Listeria* strain of embodiment 39, wherein the combination of the antigenic peptides in the fusion polypeptide comprises a sequence at least 90%, 95%, 96%, 97%, 98%, 99%, or 100% identical to one of SEQ ID NOS: 74 and 80.

41. The recombinant *Listeria* strain of embodiment 40, wherein the portion of the open reading frame encoding the combination of the antigenic peptides comprises a sequence at least 90%, 95%, 96%, 97%, 98%, 99%, or 100% identical to one of SEQ ID NOS: 73 and 79.

42. The recombinant *Listeria* strain of embodiment 23, wherein the cancer-associated protein is encoded by PIK3CA, and the antigenic peptides from PIK3CA comprise two or more or all of the following recurrent PIK3CA mutations: R38C; R38H; E81K; R88Q; R93Q; R93W; R108H; G118D; L334G; N345K; C420R; E453K; E542K; E545A; E545G; E545K; E545Q; Q546K; Q546R; E726K; M1043I; M1043V; H1047L; H1047R; and G1049R; and wherein the antigenic peptides further comprise antigenic peptides from the protein encoded by PIK3R1, and the antigenic peptides from PIK3R1 comprise two or more or all of the following recurrent PIK3R1 mutations: G376R; N564D; and K567E.

43. The recombinant *Listeria* strain of embodiment 42, wherein the fusion polypeptide comprises antigenic peptides comprising the following recurrent cancer mutations in one of the following N-terminal to C-terminal orders: (a) PIK3CA|R38C; PIK3CA|N345K; PIK3CA|E726K; PIK3CA|E453K; PIK3CA|R93Q; PIK3CA|H1047R; PIK3CA|E545A; PIK3CA|M1043V; PIK3R1|N564D; PIK3R1|K567E; PIK3CA|E81K; PIK3CA|R108H; PIK3CA|Q546R; PIK3CA|Q546K; PIK3CA|E545Q; PIK3CA|G1049R; PIK3CA|C420R; PIK3CA|H1047L; PIK3CA|R93W; PIK3CA|R88Q; PIK3CA|M1043I; PIK3CA|E545G; PIK3CA|G118D; PIK3CA|R38H; PIK3R1|G376R; PIK3CA|E542K; PIK3CA|E545K; and PIK3CA|L334G; (b) PIK3CA|R38C; PIK3CA|R108H; PIK3CA|C420R; PIK3CA|R93Q; PIK3CA|E453K; PIK3CA|M1043V; PIK3CA|H1047L; PIK3R1|N564D; PIK3CA|E726K; PIK3CA|G118D; PIK3CA|Q546K; PIK3CA|Q546R; PIK3CA|E542K; PIK3CA|E545K; PIK3CA|G1049R; PIK3CA|M1043I; PIK3CA|L334G; PIK3R1|K567E; PIK3CA|R38H; PIK3R1|G376R; PIK3CA|R93W; PIK3CA|H1047R; PIK3CA|E545G; PIK3CA|E81K; PIK3CA|R88Q; PIK3CA|N345K; PIK3CA|E545A; and PIK3CA|E545Q; (c) PIK3CA|R108H; PIK3CA|M1043V; PIK3CA|R88Q; PIK3CA|R93W; PIK3CA|R38H; PIK3CA|H1047R; PIK3CA|E545K; PIK3CA|M1043I; PIK3CA|Q546R; PIK3CA|E542K; PIK3CA|N345K; PIK3CA|R38C; PIK3CA|E545G; PIK3CA|E81K; PIK3CA|Q546K; PIK3CA|R93Q; PIK3CA|E453K; PIK3CA|G1049R; PIK3CA|E545A; PIK3CA|C420R; PIK3CA|H1047L; PIK3CA|L334G; PIK3CA|G118D; PIK3CA|E726K; and PIK3CA|E545Q; and (d) PIK3CA|E545Q; PIK3CA|R93W; PIK3CA|H1047R; PIK3CA|G1049R; PIK3CA|N345K; PIK3CA|Q546R; PIK3CA|E545K; PIK3CA|E453K; PIK3CA|L334G; PIK3CA|H1047L; PIK3R1|G376R; PIK3CA|M1043V; PIK3CA|R88Q; PIK3CA|R38H; PIK3CA|G118D; PIK3R1|K567E; PIK3CA|R38C; PIK3CA|E542K; PIK3CA|Q546K; PIK3CA|E726K; PIK3CA|C420R; PIK3CA|E545A; PIK3CA|R93Q;

PIK3R1|N564D; PIK3CA|R108H; PIK3CA|M1043I; PIK3CA|E545G; and PIK3CA|E81K.

44. The recombinant *Listeria* strain of embodiment 43, wherein the combination of the antigenic peptides in the fusion polypeptide comprises a sequence at least 90%, 95%, 96%, 97%, 98%, 99%, or 100% identical to one of SEQ ID NOS: 86, 92, 98, and 104.

45. The recombinant *Listeria* strain of embodiment 44, wherein the portion of the open reading frame encoding the combination of the antigenic peptides comprises a sequence at least 90%, 95%, 96%, 97%, 98%, 99%, or 100% identical to one of SEQ ID NOS: 85, 91, 97, and 103.

46. The recombinant *Listeria* strain of embodiment 23, wherein the cancer-associated protein is encoded by PTEN, and the antigenic peptides comprise two or more or all of the following recurrent cancer mutations: Y68H; Y88C; D92E; del121-131; R130G; R130L; R130P; R130Q; C136Y; R142W; Y155C; R173H; and P246L.

47. The recombinant *Listeria* strain of embodiment 46, wherein the fusion polypeptide comprises antigenic peptides comprising the following recurrent cancer mutations in one of the following N-terminal to C-terminal orders: (a) del121-131; Y88C; R130G; Y155C; D92E; C136Y; R130Q; Y68H; R142W; R173H; R130L; R130P; and P246L; (b) R130P; R130G; Y155C; R130L; C136Y; del121-131; P246L; D92E; R173H; Y68H; R130Q; Y88C; and R142W; (c) R130Q; R130G; del121-131; C136Y; R130L; P246L; Y155C; D92E; R142W; R130P; Y88C; Y68H; and R173H; and (d) del121-131; C136Y; Y68H; R142W; R173H; |R130L; P246L; R130G; R130P; Y88C; D92E; R130Q; and Y155C.

48. The recombinant *Listeria* strain of embodiment 47, wherein the combination of the antigenic peptides in the fusion polypeptide comprises a sequence at least 90%, 95%, 96%, 97%, 98%, 99%, or 100% identical to one of SEQ ID NOS: 110, 116, 122, and 128.

49. The recombinant *Listeria* strain of embodiment 48, wherein the portion of the open reading frame encoding the combination of the antigenic peptides comprises a sequence at least 90%, 95%, 96%, 97%, 98%, 99%, or 100% identical to one of SEQ ID NOS: 109, 115, 121, and 127.

50. The recombinant *Listeria* strain of embodiment 23, wherein the cancer-associated protein is encoded by KRAS, and the antigenic peptides comprise two or more or all of the following recurrent cancer mutations: G12A; G12C; G12D; G12R; G12S; G12V; G13C; G13D; G13R; G13S; G13V; L19F; Q61K; Q61H; Q61L; Q61R; K117N; A146T; A146V; and A164G.

51. The recombinant *Listeria* strain of embodiment 50, wherein the fusion polypeptide comprises antigenic peptides comprising the following recurrent cancer mutations in one of the following N-terminal to C-terminal orders: (a) Q61R; Q61K; Q61L; Q61H; L19F; K117N; G12A; A164G; G12D; G13D; G13S; G12S; A146V; G13R; G13C; G12C; G12R; G13V; G12V; and A146T; (b) Q61H; K117N; G13C; G13R; G12D; G12S; G12V; G12A; Q61K; G13V; G12C; L19F; Q61R; Q61L; A146V; A164G; G12R; G13S; A146T; and G13D; (c) G12D; L19F; A146V; Q61H; G12V; A164G; G12C; Q61L; A146T; G13S; G12A; G13V; G13C; G13D; G12R; G12S; Q61R; Q61K; G13R; and K117N; and (d) G13V; G13S; G12V; G12R; A146V; G13D; G12D; K117N; Q61H; G12C; G13C; A146T; G12A; Q61L; Q61K; A164G; G12S; L19F; G13R; and Q61R.

52. The recombinant *Listeria* strain of embodiment 51, wherein the combination of the antigenic peptides in the fusion polypeptide comprises a sequence at least 90%, 95%, 96%, 97%, 98%, 99%, or 100% identical to one of SEQ ID NOS: 134, 140, 146, and 152.

53. The recombinant *Listeria* strain of embodiment 52, wherein the portion of the open reading frame encoding the combination of the antigenic peptides comprises a sequence at least 90%, 95%, 96%, 97%, 98%, 99%, or 100% identical to one of SEQ ID NOS: 133, 139, 145, and 151.

54. The recombinant *Listeria* strain of embodiment 23, wherein the cancer-associated protein is encoded by TP53, and the antigenic peptides comprise two or more or all of the following recurrent cancer mutations: Y107D; K132N; C141Y; V143A; V157F; Y163C; R175H; C176F; C176Y; H179R; H179W; H193R; I195T; V216M; Y220C; Y234C; Y234H; S241F; S242F; G245D; G245S; R248L; R248Q; R248W; R249S; R273C; R273H; R273L; P278L; P278S; R282G; R282W; and R337H.

55. The recombinant *Listeria* strain of embodiment 54, wherein the antigenic peptides comprise two or more or all of the following recurrent cancer mutations: Y107D; C141Y; V143A; V157F; Y163C; R175H; C176F; H193R; I195T; V216M; Y220C; Y234C; Y234H; G245D; G245S; R248Q; R248W; R249S; R273C; R273H; R273L; R282G; and R282W.

56. The recombinant *Listeria* strain of embodiment 54, wherein the antigenic peptides comprise two or more or all of the following recurrent cancer mutations: V143A; R175H; H193R; Y220C; G245D; R248Q; R248W; R249S; R273C; R273H; and R282W.

57. The recombinant *Listeria* strain of embodiment 54, wherein the antigenic peptides comprise two or more or all of the following recurrent cancer mutations: Y107D; C141Y; V157F; Y163C; C176F; I195T; V216M; Y234C; Y234H; G245S; R273L; and R282G.

58. The recombinant *Listeria* strain of embodiment 54, wherein the antigenic peptides comprise: (a) two or more or all of the following recurrent cancer mutations: Y107D; C141Y; V143A; Y163C; C176Y; H179R; H179W; H193R; V216M; Y234H; S241F; G245D; R248Q; R248W; R273C; R273L; and P278S; (b) two or more or all of the following recurrent cancer mutations: C141Y; R175H; H179R; H193R; V216M; Y234H; G245D; G245S; R248L; R248W; R273C; R273H; P278L; P278S; R282G; R282W; and R337H; (c) two or more or all of the following recurrent cancer mutations: Y107D; C141Y; V143A; C176F; H179R; V216M; Y220C; S241F; S242F; G245S; R248L; R248W; R273L; P278L; P278S; R282G; and R282W; or (d) two or more or all of the following recurrent cancer mutations: Y107D; K132N; V143A; V157F; Y163C; R175H; C176Y; Y234C; Y234H; S241F; S242F; G245D; G245S; R273C; P278S; R282W; and R337H.

59. The recombinant *Listeria* strain of embodiment 54, wherein the antigenic peptides comprise: (a) two or more or all of the following recurrent cancer mutations: K132N; V157F; R175H; C176F; I195T; Y220C; Y234C; S242F; G245S; R248L; R249S; R273H; P278L; R282G; R282W; and R337H; (b) two or more or all of the following recurrent cancer mutations: Y107D; K132N; V143A; V157F; Y163C; C176F; C176Y; H179W; I195T; Y220C; Y234C; S241F; S242F; R248Q; R249S; and R273L; (c) two or more or all of the following recurrent cancer mutations: K132N; V157F; Y163C; R175H; C176Y; H179W; H193R; I195T; Y234C; Y234H; G245D; R248Q; R249S; R273C; R273H; and R337H; or (d) two or more or all of the following recurrent cancer mutations: C141Y; C176F; H179R; H179W; H193R; I195T; V216M; Y220C; R248L; R248Q; R248W; R249S; R273H; R273L; P278L; and R282G.

60. The recombinant *Listeria* strain of embodiment 54, wherein the fusion polypeptide comprises antigenic peptides comprising the following recurrent cancer mutations in one of the following N-terminal to C-terminal orders: (a) H179W; R273L; R249S; R248Q; Y234H; G245D; Y220C; R248L; H193R; K132N; S242F; Y234C; G245S; C176F; R282W; R273H; R282G; C141Y; R273C; V216M; R337H; R248W; V143A; I195T; P278S; S241F; C176Y; Y107D; R175H; H179R; V157F; P278L; and Y163C; (b) R248W; R248L; Y220C; Y163C; G245D; Y107D; H179R; V216M; P278S; S241F; R273L; P278L; C176F; C141Y; S242F; R249S; V143A; I195T; R273H; R273C; R282G; H179W; R175H; R248Q; G245S; H193R; R337H; R282W; Y234C; V157F; Y234H; C176Y; and K132N; (c) R248W; H179R; R273H; Y107D; R337H; R282G; V157F; V143A; Y234H; Y220C; R282W; R248L; S241F; H179W; R273C; C141Y; R249S; P278L; G245S; I195T; R175H; G245D; R273L; K132N; V216M; Y163C; C176F; S242F; Y234C; H193R; R248Q; P278S; and C176Y; (d) V143A; R282W; V157F; H179W; K132N; Y163C; C176Y; G245D; Y220C; S242F; Y234C; R249S; H179R; R273H; C141Y; R273L; P278S; C176F; R337H; H193R; R273C; R282G; R175H; R248W; P278L; I195T; S241F; R248L; Y234H; V216M; G245S; Y107D; and R248Q; (e) S241F; G245D; V143A; P278S; R273C; C176Y; Y234H; R248W; V216M; R248Q; C141Y; Y163C; H193R; H179R; H179W; Y107D; and R273L; (f) K132N; R282W; G245S; Y234C; S242F; R175H; Y220C; V157F; R282G; C176F; R337H; I195T; R249S; P278L; R273H; and R248L; (g) H193R; P278L; R273C; R248W; H179R; P278S; R248L; V216M; R282G; R337H; R175H; Y234H; G245D; R273H; G245S; R282W; and C141Y; (h) Y107D; K132N; C176F; C176Y; R273L; Y220C; R248Q; V143A; I195T; R249S; S242F; Y234C; H179W; V157F; Y163C; and S241F; (i) P278S; C176F; H179R; R282G; S241F; R273L; P278L; C141Y; Y107D; R248W; V216M; R282W; S242F; Y220C; V143A; G245S; and R248L; (j) R175H; H179W; R249S; Y234H; I195T; R248Q; R273H; C176Y; V157F; H193R; Y234C; K132N; R273C; Y163C; G245D; and R337H; (k) C176Y; R175H; G245D; R337H; S241F; K132N; V143A; P278S; R282W; Y163C; Y107D; R273C; S242F; G245S; V157F; Y234C; and Y234H; (l) C176F; R273L; H179R; R282G; Y220C; I195T; C141Y; R248L; R273H; H179W; H193R; R249S; V216M; P278L; R248W; and R248Q; (m) R248W; R273H; V143A; R249S; R175H; H193R; Y220C; G245D; R248Q; R273C; R282W; Y107D; C141Y; V157F; Y163C; C176F; I195T; V216M; Y234H; G245S; R273L; Y234C; and R282G; (n) R248W; R273H; V143A; R249S; R175H; H193R; Y220C; G245D; R248Q; R273C; and R282W; and (o) Y107D; C141Y; V157F; Y163C; C176F; I195T; V216M; Y234H; G245S; R273L; Y234C; and R282G.

61. The recombinant *Listeria* strain of embodiment 60, wherein the combination of the antigenic peptides in the fusion polypeptide comprises a sequence at least 90%, 95%, 96%, 97%, 98%, 99%, or 100% identical to one of SEQ ID NOS: 158, 164, 170, 176, 182, 188, 194, 200, 206, 212, 218, 224, 259, 266, and 273.

62. The recombinant *Listeria* strain of embodiment 61, wherein the portion of the open reading frame encoding the combination of the antigenic peptides comprises a sequence at least 90%, 95%, 96%, 97%, 98%, 99%, or 100% identical to one of SEQ ID NOS: 157, 163, 169, 175, 181, 187, 193, 199, 205, 211, 217, 223, 257, 258, 264, 265, 271, and 272.

62b. The recombinant *Listeria* strain of any one of embodiments 20-23, wherein the antigenic peptides are from two or more cancer associated proteins.

62c. The recombinant *Listeria* strain of embodiment 62b, wherein the two or more cancer associated proteins are 2, 3, 4, 5, 6, 7, 8, 9, or 10 cancer-associated proteins.

62d. The recombinant *Listeria* strain of embodiment 62b or 62c, wherein the antigenic peptides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 different recurrent cancer mutations from the same type of cancer, or wherein the antigenic peptides comprise 2-80, 10-60, 10-50, 10-40, or 10-30 different recurrent cancer mutations from a single type of cancer, or wherein the antigenic peptides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 different recurrent somatic missense cancer mutations from a single type of cancer, or wherein the antigenic peptides comprise 2-80, 10-60, 10-50, 10-40, or 10-30 different recurrent somatic missense cancer mutations from a single type of cancer.

62e. The recombinant *Listeria* strain of any one of embodiment 62b-62d, wherein: (a) the two or more cancer associated proteins comprise proteins encoded by two or more or all of the following genes: PI3KCA, AKT1, AHNAK2, ERBB2, and TP53; (b) the two or more cancer associated proteins comprise proteins encoded by two or more or all of the following genes: BRAF, KRAS/NRAS, TP53, PIK3CA, and SMAD4; (c) the two or more cancer associated proteins comprise proteins encoded by two or more or all of the following genes: KRAS, TP53, EGFR, U2AF1, BRAF, and PIK3CA; (d) the two or more cancer associated proteins comprise proteins encoded by two or more or all of the following genes: TP53, PIK3CA, NFE2L2, CDKN2A, and PTEN; or (e) the two or more cancer associated proteins comprise proteins encoded by two or more or all of the following genes: ANKRD36C, SPOP, CHEK2, KRTAP4-11, RGPD8, TP53, FAM47C, ZAN, and PIK3CA.

62f. The recombinant *Listeria* strain of embodiment 62e, wherein the antigenic peptides comprise two or more or all of the following recurrent cancer mutations: PIK3CA|H1047R; PIK3CA|E545K; PIK3CA|E542K; PIK3CA|H1047L; PIK3CA|Q546K; PIK3CA|E545A; PIK3CA|E545G; AKT1|E17K; AHNAK2|V2016L, ERBB2|L755S, and TP53|R175H.

62g. The recombinant *Listeria* strain of embodiment 62e, wherein the antigenic peptides comprise two or more or all of the following recurrent cancer mutations: BRAF|V600E; KRAS|G12D; KRAS|G13D; KRAS|G12V; KRAS|G12C; KRAS|Q61K; KRAS|G12A; KRAS|G12S; TP53|R175H; TP53|R248W; TP53|R273C; TP53|R282W; TP53|R273H; TP53|R248Q; TP53|G245S; PIK3CA|E545K; PIK3CA|H1047R; PIK3CA|R88Q; and SMAD4|R361H.

62h. The recombinant *Listeria* strain of embodiment 62e, wherein the antigenic peptides comprise two or more or all of the following recurrent cancer mutations: KRAS|G12C; KRAS|G12V; KRAS|G12D; KRAS|G12F; KRAS|G12R; KRAS|Q61L; KRAS|G12Y; TP53|R158L; TP53|R273L; TP53|G245V; TP53|R175H; TP53|A159P; TP53|R249M; TP53|R273H; TP53|R280I; TP53|Q144L; TP53|R273C; TP53|R280G; TP53|R280T; EGFR|L858R; EGFR|L861Q; EGFR|G719A; U2AF1|S34F; BRAF1|V600E; BRAF1|G466V; BRAF1|N581S; PIK3CA|E545K; PIK3CA|E726K; and PIK3CA|H1047R.

62i. The recombinant *Listeria* strain of embodiment 62e, wherein the antigenic peptides comprise two or more or all of the following recurrent cancer mutations: TP53|Y163C; TP53|R175G; TP53|C242F; TP53|R273L; TP53|H179L; TP53|H193L; TP53|H214R; TP53|Y220C; TP53|Y234C; TP53|G245V; TP53|L111Q; TP53|T125P; TP53|K132R; TP53|C135W; TP53|C141W; TP53|C176F; TP53|C176Y; TP53|H179R; TP53|H179Y; TP53|H193R; TP53|I195S; TP53|Y205C; TP53|R213G; TP53|V216E; TP53|Y234S; TP53|Y236C; TP53|M237I; TP53|G244C; TP53|G245S; TP53|R248L; TP53|R248P; TP53|R248Q; TP53|R248W; TP53|R249G; TP53|R249S; TP53|R249W; TP53|G266V; TP53|F270I; TP53|R273C; TP53|R273H; TP53|R273P; TP53|R280I; TP53|D281Y; TP53|R282Q; TP53|R282W; PIK3CA|E545K; PIK3CA|E542K; PIK3CA|H1047R; PIK3CA|E726K; PIK3CA|C420R; NFE2L2|E79Q; NFE2L2|R34Q; NFE2L2|L30F; NFE2L2|G81S; NFE2L2|G31A; NFE2L2|D29G; NFE2L2|G81V; CDKN2A|D108Y; CDKN2A|D18N; and PTEN|R130Q.

62j. The recombinant *Listeria* strain of embodiment 62e, wherein the antigenic peptides comprise two or more or all of the following recurrent cancer mutations: ANKRD36C|I645T; ANKRD36C|D629Y; ANKRD36C|D629N; SPOP|W131G; SPOP|F133L; SPOP|F133V; SPOP|F133C; SPOP|W131R; SPOP|W131L; CHEK2|K373E; KRTAP4-11|M93V; KRTAP4-11|R51K; KRTAP4-11|L161V; RGPD8|P1760A; TP53|R248Q; TP53|G245S; TP53|G245D; FAM47C|N648D; ZAN|L878P; PIK3CA|E542K; and PIK3CA|H1047R.

63. The recombinant *Listeria* strain of any preceding embodiment, wherein the fusion polypeptide further comprises one or more peptide tags N-terminal and/or C-terminal to the combination of the two or more antigenic peptides.

64. The recombinant *Listeria* strain of embodiment 63, wherein the one or more peptide tags comprise one or more of the following: 3×FLAG tag; 6×His tag; and SIINFEKL (SEQ ID NO: 1007) tag.

65. The recombinant *Listeria* strain of any preceding embodiment, wherein the PEST-containing peptide is on the N-terminal end of the fusion polypeptide.

66. The recombinant *Listeria* strain of any preceding embodiment, wherein the PEST-containing peptide is a listeriolysin O (LLO) protein or a fragment thereof or an ActA protein or a fragment thereof.

67. The recombinant *Listeria* strain of embodiment 66, wherein the PEST-containing peptide is an N-terminal fragment of LLO.

68. The recombinant *Listeria* strain of embodiment 67, wherein the N-terminal fragment of LLO has the sequence set forth in SEQ ID NO: 336.

69. The recombinant *Listeria* strain of embodiment 66, wherein the PEST-containing peptide is the LLO protein or the fragment thereof and comprises a mutation in a cholesterol-binding domain.

70. The recombinant *Listeria* strain of embodiment 69, wherein the LLO mutation comprises one of the following: (1) a substitution of residues C484, W491, or W492 of SEQ ID NO: 332 or corresponding substitutions when the LLO protein is optimally aligned with SEQ ID NO: 332; or (2) a deletion of 1-11 amino acids within the residues 483-493 of SEQ ID NO: 332 or a corresponding deletion when the LLO protein is optimally aligned with SEQ ID NO: 332.

71. The recombinant *Listeria* strain of any preceding embodiment, wherein the nucleic acid is operably integrated into the *Listeria* genome.

72. The recombinant *Listeria* strain of any one of embodiments 1-70, wherein the nucleic acid is in an episomal plasmid.

73. The recombinant *Listeria* strain of any preceding embodiment, wherein the nucleic acid does not confer antibiotic resistance upon the recombinant *Listeria* strain.

74. The recombinant *Listeria* strain of any preceding embodiment, wherein the recombinant *Listeria* strain is attenuated.

75. The recombinant *Listeria* strain of any preceding embodiment, wherein the recombinant *Listeria* strain is an auxotrophic *Listeria* strain.

76. The recombinant *Listeria* strain of embodiment 74 or 75, wherein the attenuated *Listeria* strain comprises a mutation in one or more endogenous genes that inactivates the one or more endogenous genes.

77. The recombinant *Listeria* strain of embodiment 76, wherein the one or more endogenous genes comprise prfA.

78. The recombinant *Listeria* strain of embodiment 76, wherein the one or more endogenous genes comprise actA.

79. The recombinant *Listeria* strain of embodiment 76, wherein the one or more endogenous genes comprise actA and inlB.

80. The recombinant *Listeria* strain of embodiment 76, wherein the one or more endogenous genes comprise actA, dal, and dat.

81. The recombinant *Listeria* strain of any preceding embodiment, wherein the nucleic acid comprises a second open reading frame encoding a metabolic enzyme.

82. The recombinant *Listeria* strain of embodiment 81, wherein the metabolic enzyme is an alanine racemase enzyme or a D-amino acid aminotransferase enzyme.

83. The recombinant *Listeria* strain of any preceding embodiment, wherein the fusion polypeptide is expressed from an hly promoter, a prfA promoter, an actA promoter, or a p60 promoter.

84. The recombinant *Listeria* strain of embodiment 83, wherein the fusion polypeptide is expressed from an hly promoter.

85. The recombinant *Listeria* strain of any preceding embodiment, wherein the recombinant *Listeria* strain is a recombinant *Listeria monocytogenes* strain.

86. The recombinant *Listeria* strain of any one of embodiments 1-65, wherein the recombinant *Listeria* strain is an attenuated *Listeria monocytogenes* strain comprising a deletion of or inactivating mutation in prfA, wherein the nucleic acid is in an episomal plasmid and comprises a second open reading frame encoding a D133V PrfA mutant protein.

87. The recombinant *Listeria* strain of any one of embodiments 1-65, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

88. The recombinant *Listeria* strain of any one of embodiments 1-65, wherein recombinant *Listeria* strain is an attenuated *Listeria monocytogenes* strain comprising a deletion of or inactivating mutation in actA and inlB, wherein the nucleic acid is genomically integrated, and wherein the PEST-containing peptide is an ActA protein or a fragment thereof.

89. The recombinant *Listeria* strain of any preceding embodiment, wherein the recombinant *Listeria* strain has been passaged through an animal host.

90. The recombinant *Listeria* strain of any preceding embodiment, wherein the recombinant *Listeria* strain is capable of escaping a phagolysosome.

91. An immunogenic composition comprising the recombinant *Listeria* strain of any preceding embodiment.

92. The immunogenic composition of embodiment 91, wherein the immunogenic comprises a combination of two or more recombinant *Listeria* strain, wherein each recombinant *Listeria* strain comprises a different set of antigenic peptides or the same set of antigenic peptides in a different order.

93. The immunogenic composition of embodiment 92, wherein each recombinant *Listeria* strain comprises a different set of antigenic peptides.

94. The immunogenic composition of embodiment 92 or 93, wherein the two or more recombinant *Listeria* strains comprise 2, 3, 4, 5, 6, 7, 8, 9, 10, 11, 12, 13, 14, 15, 16, 17, 18, 19, or 20 recombinant *Listeria* strains.

95. The immunogenic composition of any one of embodiments 92-94, wherein the two or more recombinant *Listeria* strains comprise antigenic peptides from two or more cancer-associated proteins.

96. The immunogenic composition of embodiment 95, wherein the two or more cancer-associated proteins are 2, 3, 4, 5, 6, 7, 8, 9, or 10 cancer-associated proteins.

97. The immunogenic composition of embodiment 95 or 96, wherein the two or more cancer-associated proteins are encoded by two or more of the following human genes: TP53, PIK3CA, APC, CTNNB1, CDKN2A, NFE2L2, BRAF, KRAS, EGFR, ERBB2, SF3B1, FBXW7, PIK3R1, SMAD4, SPOP, PTPN11, NRAS, PTEN, HRAS, U2AF1, ERBB3, FGFR3, ARID1A, MAP2K1, FGFR2, RHOA, MTOR, BCL2L12, RAC1, IDH2, H3F3A, PPP2R1A, POLE, ATM, EP300, ALK, RQCD1, GPRIN2, THSD7B, CDK4, NUP93, CCND1, FGFR1, MAX, VHL, ACVR1, MEF2A, MYC, FRMD6, SRC, KIT, KEAP1, STKJ1, NF1, KMT2D, GATA3, AKT1, MAP3K1, MAP2K4, KMT2C, FAT1, PBRM1, SETD2, CREBBP, RB1, SMARCA4, CHD4, FLT3, ARID2, CDH1, DNMT3A, ARHGAP35, BCOR, CTCF, KDM5C, KDM6A, CASP8, ASXL1, RASA1, RUNX1, NPM1, CDKN1B, HLA-A, B2M, RPL5, MYD88, CBFB, and GPS2, or wherein the two or more cancer-associated proteins are encoded by two or more of the following human genes: TP53, PIK3CA, APC, CTNNB1, CDKN2A, NFE2L2, BRAF, KRAS, EGFR, ERBB2, SF3B1, FBXW7, PIK3R1, SMAD4, SPOP, PTPN11, NRAS, PTEN, HRAS, U2AF1, ERBB3, FGFR3, ARID1A, MAP2K1, FGFR2, RHOA, MTOR, BCL2L12, RAC1, IDH2, H3F3A, PPP2R1A, POLE, ATM, EP300, ALK, RQCD1, GPRIN2, THSD7B, CDK4, NUP93, CCND1, FGFR1, MAX, VHL, ACVR1, MEF2A, MYC, FRMD6, SRC, KIT, KEAP1, STKI1, NF1, KMT2D, GATA3, AKT1, MAP3K1, MAP2K4, KMT2C, FAT1, PBRM1, SETD2, CREBBP, RB1, SMARCA4, CHD4, FLT3, ARID2, CDH1, DNMT3A, ARHGAP35, BCOR, CTCF, KDM5C, KDM6A, CASP8, ASXL1, RASA1, RUNX1, NPM1, CDKN1B, HLA-A, B2M, RPL5, MYD88, CBFB, GPS2, AHNAK2, ANKRD36C, CHEK2, KRTAP4-11, RGPD8, FAM47C, and ZAN.

98. The immunogenic composition of embodiment 97, wherein the two or more cancer-associated proteins are encoded by two or more of the following human genes: BRAF, EGFR, PIK3CA, PIK3R1, PTEN, KRAS, TP53, APC, FBXW7, KEAP1, STK11, NF1, KMT2D, CDKN2A, NFE2L2, SPOP, GATA3, AKT1, MAP3K1, and MAP2K4, or wherein the two or more cancer-associated proteins are encoded by two or more of the following human genes: BRAF, EGFR, PIK3CA, PIK3R1, PTEN, KRAS, TP53, APC, FBXW7, KEAP1, STK11, NF1, KMT2D, CDKN2A, NFE2L2, SPOP, GATA3, AKT1, MAP3K1, MAP2K4, AHNAK2, ANKRD36C, CHEK2, KRTAP4-11, RGPD8, FAM47C, and ZAN.

99. The immunogenic composition of any one of embodiments 92-98, wherein the combination of recombinant *Listeria* strains comprises about 5-10, 10-15, 15-20, 20-25, 25-30, 30-35, 35-40, 40-45, 45-50, 50-60, 60-70, 70-80, 80-90, 90-100, 100-120, 120-140, 140-160, 160-180, 180-200, 200-220, 220-240, 240-260, 260-280, or 280-300 different antigenic peptides.

100. The immunogenic composition of any one of embodiments 91-99, wherein the immunogenic composition further comprises an adjuvant.

101. The immunogenic composition of embodiment 100, wherein the adjuvant comprises a granulocyte/macrophage colony-stimulating factor (GM-CSF) protein, a nucleotide molecule encoding a GM-CSF protein, saponin QS21, monophosphoryl lipid A, or an unmethylated CpG-containing oligonucleotide.

102. A method of inducing an immune response against a tumor or cancer in a subject, comprising administering to the subject the recombinant *Listeria* strain of any one of embodiments 1-90 or the immunogenic composition of any one of embodiments 91-101.

103. A method of preventing or treating a tumor or cancer in a subject, comprising administering to the subject the recombinant *Listeria* strain of any one of embodiments 1-90 or the immunogenic composition of any one of embodiments 91-101.

104. The method of embodiment 102 or 103, wherein multiple different recombinant *Listeria* strains or multiple immunogenic compositions are administered to the subject.

105. The method of embodiment 104, wherein the multiple different recombinant *Listeria* strains or multiple immunogenic compositions are administered to the subject simultaneously.

106. The method of embodiment 104, wherein the multiple different recombinant *Listeria* strains or multiple immunogenic compositions are administered to the subject sequentially.

107. The method of any one of embodiments 104-106, wherein the multiple different recombinant *Listeria* strains or multiple immunogenic compositions each comprises a different set of antigenic peptides or the same set of antigenic peptides in a different order.

108. The method of embodiment 107, wherein each recombinant *Listeria* strain or immunogenic composition comprises a different set of antigenic peptides.

109. The method of any one of embodiments 104-108, wherein the multiple recombinant *Listeria* strains or multiple immunogenic compositions comprise 2, 3, 4, 5, 6, 7, 8, 9, 10, 11, 12, 13, 14, 15, 16, 17, 18, 19, or 20 recombinant *Listeria* strains or immunogenic compositions.

110. The method of any one of embodiments 104-109, wherein the multiple recombinant *Listeria* strains or multiple immunogenic compositions comprise antigenic peptides from two or more cancer-associated proteins.

111. The method of embodiment 110, wherein the two or more cancer-associated proteins are 2, 3, 4, 5, 6, 7, 8, 9, or 10 cancer-associated proteins.

112. The method of any one of embodiments 104-111, wherein the combination of recombinant *Listeria* strains or immunogenic compositions comprises about 5-10, 10-15, 15-20, 20-25, 25-30, 30-35, 35-40, 40-45, 45-50, 50-60, 60-70, 70-80, 80-90, 90-100, 100-120, 120-140, 140-160, 160-180, 180-200, 200-220, 220-240, 240-260, 260-280, or 280-300 different antigenic peptides.

113. The method of any one of embodiments 102-112, wherein the method further comprises administering an immune checkpoint inhibitor antagonist.

114. The method of embodiment 113, wherein the immune checkpoint inhibitor comprises an anti-PD-1 antibody or an antigen-binding fragment thereof and/or an anti-CTLA-4 antibody or an antigen-binding fragment thereof.

115. The method of any one of embodiments 102-114, wherein the method further comprises administering a T cell stimulator.

116. The method of embodiment 115, wherein the T cell stimulator comprises an anti-OX40 antibody or an antigen-binding fragment thereof or an anti-GITR antibody or an antigen-binding fragment thereof.

117. The method of any one of embodiments 102-116, wherein the subject has a cancer associated with recurrent cancer mutations in one or more cancer-associated proteins, and the recombinant *Listeria* strain administered or the immunogenic composition administered comprises antigenic peptides comprising the recurrent cancer mutations associated with the cancer.

118. The method of any one of embodiments 102-117, wherein the method comprises screening the subject for and identifying one or more recurrent cancer mutations prior to the administering step, wherein the recombinant *Listeria* strain or the immunogenic composition administered to the subject comprises antigenic peptides comprising the one or more recurrent cancer mutations identified in the subject.

119. A cell bank comprising one or more recombinant *Listeria* strains as in any one of embodiments 1-90.

120. The cell bank of embodiment 119, wherein the cell bank is a frozen cell bank or a lyophilized cell bank.

121. The cell bank of embodiment 119 or 120, wherein the cell bank comprises 2-5, 5-10, 10-15, 15-20, 20-25, 25-30, 30-35, 35-40, 40-45, or 45-50 or more recombinant *Listeria* strains.

122. The cell bank of any one of embodiments 119-121, wherein the one or more recombinant *Listeria* strains comprise antigenic peptides comprising recurrent cancer mutations from 2-5, 5-10, 10-15, 15-20, 20-25, 25-30, 30-35, 35-40, 40-45, or 45-50 cancer-associated proteins.

123. The cell bank of embodiment 122, wherein the one or more recombinant *Listeria* strains comprise antigenic peptides comprising the 2, 3, 4, 5, 6, 7, 8, 9, 10, 11, 12, 13, 14, 15, 16, 17, 18, 19, 20, 21, 22, 23, 24, 25, 26, 27, 28, 29, or 30 most common recurrent cancer mutations in each cancer-associated protein.

124. The cell bank of embodiment 122 or 123, wherein for each cancer-associated protein, at least 50%, 60%, 70%, 80%, 90%, 95%, 96%, 97%, 98%, or 99% of cancer patients with a mutation in the cancer-associated protein have a recurrent cancer mutation in the cancer-associated protein that is included in the combination of antigenic peptides in the recombinant *Listeria* strains in the cell bank.

125. A method of generating an immunotherapy construct, comprising: (a) selecting a set of recurrent cancer mutations to include in the immunotherapy construct; (b) designing antigenic peptides comprising each of the recurrent cancer mutations; (c) selecting a set of antigenic peptides, comprising testing the hydropathy of the each antigenic peptide, and modifying or deselecting an antigenic peptide if it scores above a selected hydropathy index threshold value; (d) designing a fusion polypeptide comprising each of the selected antigenic peptides; and (e) generating a nucleic acid construct encoding the fusion polypeptide.

126. The method of embodiment 125, wherein the individual selected recurrent cancer mutations are selected in step (a) based on one or more of the following criteria: (a) frequency of occurrence across multiple types of cancers or a particular type of cancer; (b) location within a functional domain of a cancer-associated protein; (c) status as a known cancer driver mutation or chemotherapy resistance mutation; and (c) identification as a somatic missense mutation.

127. The method of embodiment 125 or 126, wherein the set of recurrent cancer mutations selected in step (a) is selected based on one or more of the following criteria: (a) the set includes the potential mutated epitopes that would be found in at least 50%, 55%, 60%, 65%, 70%, 75% 80%, 85%, 90%, 95%, 96%, 97%, 98%, or 99% of cancer patients who have a mutation in a single cancer-associated protein; (b) the set includes the potential mutated epitopes that would be found in at least 50%, 55%, 60%, 65%, 70%, 75% 80%, 85%, 90%, 95%, 96%, 97%, 98%, or 99% of cancer patients who have a somatic missense mutation in a single cancer-associated protein; (c) the set comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent cancer mutations from a single cancer-associated protein; (d) the set comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent somatic missense cancer mutations from a single cancer-associated protein; and (e) the set includes no more than 30, 31, 32, 33, 34, 35, 36, 37, 38, 39, 40, 41, 42, 43, 44, 45, 46, 47, 48, 49 or 50 recurrent cancer mutations; (f) at least 50%, 55%, 60%, 65%, 70%, 75% 80%, 85%, 90%, 95%, 96%, 97%, 98%, 99%, or all of the selected recurrent cancer mutations in step (a) are from a single cancer-associated protein; (g) the set includes the potential mutated epitopes that would be found in at least 5%, 10%, 15%, 20%, 25%, 30%, 35%, 40%, 45%, 50%, 55%, 60%, 65%, 70%, 75% 80%, 85%, 90%, 95%, 96%, 97%, 98%, or 99% of cancer patients who have a particular type of cancer; (h) the set comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent cancer mutations from a single type of cancer; and (i) the set comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent somatic missense cancer mutations from a single type of cancer.

128. The method of any one of embodiments 125-127, wherein each antigenic peptide is designed in step (b) to comprise a fragment of the cancer-associated protein comprising a recurrent cancer mutation and flanking sequence on each side.

129. The method of embodiment 128, wherein each antigenic peptide includes at least about 10 flanking amino acids on each side.

130. The method of any one of embodiments 125-129, wherein antigenic peptides are selected in step (c) if they are below a hydropathy threshold predictive of secretability in *Listeria monocytogenes*.

131. The method of embodiment 130, wherein the antigenic peptides are scored by a Kyte and Doolittle hydropathy index 21 amino acid window, and any peptides scoring above a cutoff of about 1.6 are excluded or are modified to score below the cutoff.

132. The method of any one of embodiments 125-131, wherein step (c) further comprises scoring and selecting antigenic peptides based on the ability of the antigenic peptides to bind subject HLA.

133. The method of any one of embodiments 125-132, wherein step (c) further comprises screening the antigenic peptides for immunosuppressive epitopes, wherein antigenic peptides having immunosuppressive epitopes are deselected or modified such that they do not have an immunosuppressive epitope.

134. The method any one of embodiments 125-133, wherein step (c) further comprises screening the antigenic peptides for immunogenicity.

135. The method of any one of embodiments 125-134, wherein the order of antigenic peptides in the fusion polypeptide in step (d) is selected using randomization.

136. The method of any one of embodiments 125-135, wherein step (d) further comprises testing the hydropathy of the fusion polypeptide, and either reordering the antigenic peptides or removing problematic antigenic peptides if any region of the fusion polypeptide scores above a selected hydropathy index threshold value.

137. The method of embodiment 136, wherein the fusion polypeptide is scored by a Kyte and Doolittle hydropathy index with a sliding 21 amino acid window, and wherein the threshold value is about 1.6.

138. The method of any one of embodiments 125-137, wherein step (e) further comprises optimizing the nucleic acid sequence.

139. The method of embodiment 138, wherein the optimization comprises codon optimization.

140. The method of embodiment 138 or 139, wherein the optimization comprises adjusting regions of very high (>80%) or very low (<30%) GC content or avoiding one or more of the following cis-acting sequence motifs: internal TATA-boxes, chi-sites, and ribosomal entry sites; AT-rich or GC-rich sequence stretches; repeat sequences and predicted RNA secondary structures; (cryptic) splice donor and acceptor sites; and branch points.

141. The method of any one of embodiments 125-140, further comprising introducing the nucleic acid into a *Listeria monocytogenes* strain and confirming expression and secretion of the encoded fusion polypeptide.

The subject matter disclosed herein also includes, but is not limited to, the following embodiments.

1. A recombinant *Listeria* strain comprising a nucleic acid comprising a first open reading frame encoding a fusion polypeptide comprising a PEST-containing peptide fused to two or more antigenic peptides, wherein at least one antigenic peptide is from a cancer-associated protein and comprises a recurrent cancer mutation, and at least one antigenic peptide is from a cancer-associated protein and comprises a heteroclitic mutation.

2. The recombinant *Listeria* strain of embodiment 1, wherein the PEST-containing peptide comprises a bacterial secretion signal sequence, and the fusion polypeptide further comprises a ubiquitin protein fused to a carboxy-terminal antigenic peptide, wherein the PEST-containing peptide, the two or more antigenic peptides, the ubiquitin, and the carboxy-terminal antigenic peptide are arranged in tandem from the amino-terminal end to the carboxy-terminal end of the fusion polypeptide.

3. The recombinant *Listeria* strain of embodiment 2, wherein the carboxy-terminal antigenic peptide is from a cancer-associated protein and comprises a heteroclitic mutation.

4. The recombinant *Listeria* strain of embodiment 2 or 3, wherein the carboxy-terminal antigenic peptide is about 7-11, 8-10, or 9 amino acids in length.

5. The recombinant *Listeria* strain of any one of embodiments 2-4, wherein the carboxy-terminal antigenic peptide binds to one or more of the following HLA types: HLA-A*02:01, HLA-A*03:01, HLA-A*24:02, and HLA-B*07:02.

6. The recombinant *Listeria* strain of any one of embodiments 2-5, wherein the carboxy-terminal antigenic peptide is from a protein encoded by one of the following genes: STEAP1, CEACAM5, NYESO1, and NUF2.

7. The recombinant *Listeria* strain of embodiment 6, wherein the carboxy-terminal antigenic peptide is selected from the peptides set forth in SEQ ID NOS: 796, 797, 798, 799, 800, and 807.

8. The recombinant *Listeria* strain of any preceding embodiment, wherein each antigenic peptide is a fragment of a cancer-associated protein and is about 7-200 amino acids in length.

9. The recombinant *Listeria* strain of any preceding embodiment, wherein the fusion polypeptide comprises at least about 5, 6, 7, 8, 9, 10, 11, 12, 13, 14, 15, 16, 17, 18, 19, 20, 21, 22, 23, 24, or 25 antigenic peptides or comprises between about 5-50, 10-40, or 20-30 antigenic peptides.

10. The recombinant *Listeria* strain of any preceding embodiment, wherein the fusion polypeptide comprises at least about 2, 3, 4, 5, 6, 7, 8, 9, or 10 antigenic peptides comprising a recurrent cancer mutation or between about 5-30 or 10-20 antigenic peptides comprising a recurrent cancer mutation, and/or wherein the fusion polypeptide comprises at least about 2, 3, 4, 5, 6, 7, 8, 9, or 10 antigenic peptides comprising a heteroclitic mutation or between about 5-30 or 10-20 antigenic peptides comprising a heteroclitic mutation.

11. The recombinant *Listeria* strain of embodiment 10, wherein the antigenic peptides comprising a recurrent cancer mutation are in tandem, and the antigenic peptides comprising a heteroclitic mutation are in tandem.

12. The recombinant *Listeria* strain of embodiment 10, wherein the antigenic peptides comprising a recurrent cancer mutation and the antigenic peptides comprising a heteroclitic mutation are intermixed within the fusion polypeptide.

13. The recombinant *Listeria* strain of any preceding embodiment, wherein the two or more antigenic peptides are linked to each other via peptide linkers.

14. The recombinant *Listeria* strain of embodiment 13, wherein the peptide linkers comprise flexibility linkers and/or rigidity linkers and/or immunoproteasome processing linkers, or wherein one or more of the linkers set forth in SEQ ID NOS: 313-316, 319, and 821-829 are used to link the two or more antigenic peptides.

15. The recombinant *Listeria* strain of embodiment 14, wherein the peptide linker upstream of one or more of the antigenic peptides comprising a heteroclitic mutation is an immunoproteasome processing linker or is selected from the linkers set forth in SEQ ID NOS: 821-829.

16. The recombinant *Listeria* strain of any preceding embodiment, wherein no region of the fusion polypeptide scores above a cutoff of around 1.6 when scored for hydropathy by a Kyte and Doolittle hydropathy index with a sliding 21 amino acid window.

17. The recombinant *Listeria* strain of any preceding embodiment, wherein at least two of the antigenic peptides comprise different recurrent cancer mutations and are fragments of the same cancer-associated protein.

18. The recombinant *Listeria* strain of any preceding embodiment, wherein the recurrent cancer mutations in at least two of the antigenic peptides are from the same cancer-associated protein and do not occur naturally together.

19. The recombinant *Listeria* strain of any preceding embodiment, wherein at least two of the antigenic peptides are overlapping fragments of the same cancer-associated protein.

20. The recombinant *Listeria* strain of embodiment 19, wherein the recurrent cancer mutations in at least two of the antigenic peptides are from the same cancer-associated protein and occur at the same amino acid residue of the cancer-associated protein.

21. The recombinant *Listeria* strain of embodiment 20, wherein two of the antigenic peptides comprise the same recurrent cancer mutation.

22. The recombinant *Listeria* strain of any one of embodiments 1-20, wherein each antigenic peptide comprising a recurrent cancer mutation comprises a different recurrent cancer mutation.

23. The recombinant *Listeria* strain of any preceding embodiment, wherein each recurrent cancer mutation in the fusion polypeptide is a somatic frameshift mutation or a somatic missense mutation.

24. The recombinant *Listeria* strain of embodiment 23, wherein each recurrent cancer mutation in the fusion polypeptide is a somatic missense mutation.

25. The recombinant *Listeria* strain of any preceding embodiment, wherein one or more or all of the antigenic peptides comprising a recurrent cancer mutation have an equal number of amino acids flanking each side of the recurrent cancer mutation.

26. The recombinant *Listeria* strain of embodiment 25, wherein the number of flanking amino acids on each side of the recurrent cancer mutation is at least 10 amino acids.

27. The recombinant *Listeria* strain of any preceding embodiment, wherein the antigenic peptides comprise the 2, 3, 4, 5, 6, 7, 8, 9, or 10 most common recurrent cancer mutations or recurrent somatic missense cancer mutations from a particular type of cancer.

28. The recombinant *Listeria* strain of any preceding embodiment, wherein at least about 5%, 10%, 15%, 20%, 25%, 30%, 35%, 40%, 35%, 50%, 60%, 70%, 80%, or 90% of patients with a particular type of cancer have a recurrent cancer mutation that is included in the combination of antigenic peptides in the fusion polypeptide.

29. The recombinant *Listeria* strain of any preceding embodiment, wherein the antigenic peptides comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, or 30 different recurrent cancer mutations or recurrent somatic missense cancer mutations from a particular type of cancer, or wherein the antigenic peptides comprise about 2-80, 10-60, 10-50, 10-40, or 10-30 different recurrent cancer mutations or recurrent somatic missense cancer mutations from a particular type of cancer.

30. The recombinant *Listeria* strain of any one of embodiments 27-29, wherein the particular type of cancer is non-small cell lung cancer, prostate cancer, pancreatic cancer, bladder cancer, breast cancer, uterine cancer, ovarian cancer, low-grade glioma, colorectal cancer, or head and neck cancer.

31. The recombinant *Listeria* strain of any preceding embodiment, wherein the antigenic peptides are from two or more cancer-associated proteins.

32. The recombinant *Listeria* strain of embodiment 31, wherein the two or more cancer-associated proteins are at least about 2, 3, 4, 5, 6, 7, 8, 9, or 10 cancer-associated proteins, or wherein the two or more cancer-associated proteins are about 2-30, 2-25, 2-20, 2-15, or 2-10 cancer-associated proteins.

33. The recombinant *Listeria* strain of any preceding embodiment, wherein the antigenic peptides comprise recurrent cancer mutations from proteins encoded by one or more of the following genes: ACVR2A, ADAM28, AKT1, ANKRD36C, AR, ARID1A, BMPR2, BRAF, CHEK2, C12orf4, CTNNB1, DOCK3, EGFR, ESR1, FBXW7, FGFR3, FHOD3, GNAS, HRAS, IDH1, IDH2, KIAA2026, KRAS\, KRTAP1-5, KRTAP4-11, LARP4B, MBOAT2, NFE2L2, PGM5, PIK3CA, PLEKHA6, POLE, PTEN, RGPD8, RNF43, RXRA, SMAD4, SPOP, SVIL, TGFBR2, TP53, TRIM48, UBR5, U2AF1, WNT16, XYLT2, ZBTB20, and ZNF814.

34. The recombinant *Listeria* strain of embodiment 33, wherein: (a) the antigenic peptides comprise recurrent cancer mutations from proteins encoded by one or more or all of the following genes: KRAS\, EGFR, U2AF1, BRAF, PIK3CA, and TP53; (b) the antigenic peptides comprise recurrent cancer mutations from proteins encoded by one or more or all of the following genes: SPOP, CHEK2, RGPD8, ANKRD36C, and AR; (c) the antigenic peptides comprise recurrent cancer mutations from proteins encoded by one or more or all of the following genes: KRAS\, U2AF1, TP53, SMAD4, and GNAS; (d) the antigenic peptides comprise recurrent cancer mutations from proteins encoded by one or more or all of the following genes: PIK3CA, FGFR3, TP53, RXRA, FBXW7, and NFE2L2; (e) the antigenic peptides comprise recurrent cancer mutations from proteins encoded by one or more or all of the following genes: PIK3CA, AKT1, and ESR1; (f) the antigenic peptides comprise recurrent cancer mutations from proteins encoded by one or more or all of the following genes: PTEN, KRAS\, PIK3CA, CTNNB1, FBXW7, and TP53; (g) the antigenic peptides comprise recurrent cancer mutations from proteins encoded by one or more or all of the following genes: TP53; (h) the antigenic peptides comprise recurrent cancer mutations from proteins encoded by one or more or all of the following genes: TP53, PIK3CA, IDH1, IDH2, and EGFR; (i) the antigenic peptides comprise recurrent cancer mutations from proteins encoded by one or more or all of the following genes: KRAS\, BRAF, PIK3CA, and TP53; or (j) the antigenic peptides comprise recurrent cancer mutations from proteins encoded by one or more or all of the following genes: PIK3CA, CHEK2, RGPD8, ANKRD36C, TP53, ZNF814, KRTAP1-5, KRTAP4-11, and HRAS.

35. The recombinant *Listeria* strain of embodiment 34, wherein: (a) the antigenic peptides comprise one or more or all of the following recurrent cancer mutations: KRAS\_G12C, EGFR_L858R, KRAS\_G12D, U2AF1_S34F, BRAF_V600E, KRAS\_G12V, PIK3CA_E545K, TP53_R158L, KRAS\_G12A, EGFR_L861Q, and TP53_R273L; (b) the antigenic peptides comprise one or more or all of the following recurrent cancer mutations: SPOP_F133V, CHEK2_K373E, RGPD8_P1760A, ANKRD36C_I634T, ANKRD36C_D629Y, SPOP_W131G, ANKRD36C_D626N, SPOP_F133L, AR_T878A, AR_L702H, AR_W742C, AR_H875Y, and AR_F877L; (c) the antigenic peptides comprise one or more or all of the following recurrent cancer mutations: KRAS\_G12C, KRAS\_G12D, U2AF1_S34F, KRAS\_G12V, TP53_R248Q, TP53_R248W, TP53_R175H, TP53_R273C, KRAS\_G12R, KRAS\_Q61H, TP53_R282W, TP53_R273H, TP53_G245S, SMAD4_R361C, GNAS_R201C, and GNAS_R201H; (d) the antigenic peptides comprise one or more or all of the following recurrent cancer mutations: PIK3CA_E545K, FGFR3_S249C, TP53_R248Q, PIK3CA_E542K, RXRA_S427F, FBXW7_R505G, TP53_R280T, NFE2L2_E79K, FGFR3_R248C, TP53_K132N, TP53_R248W, TP53_R175H, and TP53_R273C; (e) the antigenic peptides comprise one or more or all of the following recurrent cancer mutations: PIK3CA_E545K, PIK3CA_E542K, PIK3CA_H1047R, AKT1_E17K, PIK3CA_H1047L, PIK3CA_Q546K, PIK3CA_E545A, PIK3CA_E545G, ESR1_K303R, ESR1_D538G, ESR1_Y537S, ESR1_Y537N, ESR1_Y537C, and ESR1_E380Q; (f) the antigenic peptides comprise one or more or all of the following recurrent cancer mutations: PTEN_R130G, PTEN_R130Q, KRAS\_G12D, KRAS\_G12V, PIK3CA_H1047R; PIK3CA_R88Q, PIK3CA_E545K, PIK3CA_E542K, CTNNB1_S37F, KRAS\_G13D, CTNNB1_S37C, PIK3CA_H1047L, PIK3CA_G118D, KRAS\_G12A, FBXW7_R505C, and TP53_R248W; (g) the antigenic peptides comprise one or more or all of the following recurrent cancer mutations: TP53_R248Q, TP53_R248W, TP53_R175H, TP53_R273C, TP53_R282W, TP53_R273H, TP53_Y220C, TP53_I195T, TP53_C176Y, TP53_H179R, TP53_S241F, and TP53_H193R; (h) the antigenic peptides comprise one or more or all of the following recurrent cancer mutations: TP53_R273L, TP53_R273C, TP53_R273H, PIK3CA_G118D, IDH1_R132C, IDH1_R132G, IDH1_R132H, IDH1_R132S, IDH2_R172K, PIK3CA_E453K, and EGFR_G598V; (i) the antigenic peptides comprise one or more or all of the following recurrent cancer mutations: KRAS\_G12C, KRAS\_G12D, BRAF_V600E, KRAS\_G12V, PIK3CA_E545K, TP53_R248W, TP53_R175H, TP53_R273C, PIK3CA_H1047R, TP53_R282W, TP53_R273H, and KRAS\_G13D; or (j) the antigenic peptides comprise one or more or all of the following recurrent cancer mutations: PIK3CA_E545K, CHEK2_K373E, RGPD8_P1760A, ANKRD36C_I634T, TP53_R248Q, PIK3CA_E542K, TP53 R248W, TP53_R175H, PIK3CA_H1047R, TP53_R282W, TP53_R273H, TP53_G245S, TP53_Y220C, ZNF814_D404E, KRTAP1-5_188T, KRTAP4-11_L161V, and HRAS_G13V.

36. The recombinant *Listeria* strain of embodiment 35, wherein: (a) the antigenic peptides comprise one or more or all of the peptides set forth in Table 35; (b) the antigenic peptides comprise one or more or all of the peptides set forth in Table 52; (c) the antigenic peptides comprise one or more or all of the peptides set forth in Table 68; (d) the antigenic peptides comprise one or more or all of the peptides set forth in Table 76; (e) the antigenic peptides comprise one or more or all of the peptides set forth in Table 87; (f) the antigenic peptides comprise one or more or all of the peptides set forth in Table 95; (g) the antigenic peptides comprise one or more or all of the peptides set forth in Table 100; (h) the antigenic peptides comprise one or more or all of the peptides set forth in Table 104; (i) the antigenic peptides comprise one or more or all of the peptides set forth in Table 108; or (j) the antigenic peptides comprise one or more or all of the peptides set forth in Table 112.

37. The recombinant *Listeria* strain of any preceding embodiment, wherein each antigenic peptide comprising a heteroclitic mutation is about 7-11, 8-10, or 9 amino acids in length.

38. The recombinant *Listeria* strain of any preceding embodiment, wherein the antigenic peptides comprising a heteroclitic mutation bind to one or more or all of the following HLA types: HLA-A*02:01, HLA-A*03:01, HLA-A*24:02, and HLA-B*07:02.

39. The recombinant *Listeria* strain of any preceding embodiment, wherein the antigenic peptides comprise heteroclitic mutations in proteins encoded by one or more of the following genes: CEACAM5, GAGE1, hTERT, KLHL7, MAGEA3, MAGEA4, MAGEA6, NUF2, NYESO1, PAGE4, PRAME, PSA, PSMA, RNF43, SART3, SSX2, STEAP1, and SURVIVIN.

40. The recombinant *Listeria* strain of embodiment 39, wherein: (a) the antigenic peptides comprise heteroclitic mutations in proteins encoded by one or more or all of the following genes: CEACAM5, MAGEA6, MAGEA4, GAGE1, NYESO1, STEAP1, and RNF43; (b) the antigenic peptides comprise heteroclitic mutations in proteins encoded by one or more or all of the following genes: CEACAM5, MAGEA4, STEAP1, RNF43, SSX2, SART3, PAGE4, PSMA, and PSA; (c) the antigenic peptides comprise heteroclitic mutations in proteins encoded by one or more or all of the following genes: CEACAM5, STEAP1, MAGEA3, PRAME, hTERT, and SURVIVIN; (d) the antigenic peptides comprise heteroclitic mutations in proteins encoded by one or more or all of the following genes: CEACAM5, GAGE1, NYESO1, RNF43, NUF2, KLHL7, MAGEA3, and PRAME; (e) the antigenic peptides comprise heteroclitic mutations in proteins encoded by one or more or all of the following genes: CEACAM5, STEAP1, RNF43, MAGEA3, PRAME, and hTERT, (f) the antigenic peptides comprise heteroclitic mutations in proteins encoded by one or more or all of the following genes: CEACAM5, PRAME, hTERT, STEAP1, RNF43, NUF2, KLHL7, and SART3; (g) the antigenic peptides comprise heteroclitic mutations in proteins encoded by one or more or all of the following genes: CEACAM5, STEAP1, RNF43, SART3, NUF2, KLHL7, PRAME, and hTERT; (h) the antigenic peptides comprise heteroclitic mutations in proteins encoded by one or more or all of the following genes: CEACAM5, MAGEA6, STEAP1, RNF43, SART3, NUF2, KLHL7, and hTERT; (i) the antigenic peptides comprise heteroclitic mutations in proteins encoded by one or more or all of the following genes: CEACAM5, MAGEA6, MAGEA4, GAGE1, NYESO1, STEAP1, RNF43, and MAGEA3; or (j) the antigenic peptides comprise heteroclitic mutations in proteins encoded by one or more or all of the following genes: CEACAM5, MAGEA4, STEAP1, NYESO1, PRAME, and hTERT.

41. The recombinant *Listeria* strain of embodiment 40, wherein: (a) the antigenic peptides comprise one or more or all of the peptides set forth in Table 36; (b) the antigenic peptides comprise one or more or all of the peptides set forth in Table 53; (c) the antigenic peptides comprise one or more or all of the peptides set forth in Table 69; (d) the antigenic peptides comprise one or more or all of the peptides set forth in Table 77; (e) the antigenic peptides comprise one or more or all of the peptides set forth in Table 88; (f) the antigenic peptides comprise one or more or all of the peptides set forth in Table 96; (g) the antigenic peptides comprise one or more or all of the peptides set forth in Table 101; (h) the antigenic peptides comprise one or more or all of the peptides set forth in Table 105; (i) the antigenic peptides comprise one or more or all of the peptides set forth in Table 109; or (j) the antigenic peptides comprise one or more or all of the peptides set forth in Table 113.

42. The recombinant *Listeria* strain of any preceding embodiment, wherein: (a) the antigenic peptides comprise one or more or all of the peptides set forth in Tables 35 and 36; (b) the antigenic peptides comprise one or more or all of the peptides set forth in Tables 52 and 53; (c) the antigenic peptides comprise one or more or all of the peptides set forth in Tables 68 and 69; (d) the antigenic peptides comprise one or more or all of the peptides set forth in Tables 76 and 77; (e) the antigenic peptides comprise one or more or all of the peptides set forth in Tables 87 and 88; (f) the antigenic peptides comprise one or more or all of the peptides set forth in Tables 95 and 96; (g) the antigenic peptides comprise one or more or all of the peptides set forth in Tables 100 and 101; (h) the antigenic peptides comprise one or more or all of the peptides set forth in Tables 104 and 105; (i) the antigenic peptides comprise one or more or all of the peptides set forth in Tables 108 and 109; or (j) the antigenic peptides comprise one or more or all of the peptides set forth in Tables 112 and 113.

43. The recombinant *Listeria* strain of embodiment 42, wherein: (a) the fusion polypeptide comprises the sequence set forth in any one of SEQ ID NOS: 859, 860, 861, 862, 863, 864, 865, 894, 895, and 905; (b) the fusion polypeptide comprises the sequence set forth in any one of SEQ ID NOS: 871, 872, 873, 874, 875, 876, 877, 892, 893, and 906; (c) the fusion polypeptide comprises the sequence set forth in any one of SEQ ID NOS: 866, 867, 868, 869, 870, and 908; (d) the fusion polypeptide comprises the sequence set forth in any one of SEQ ID NOS: 878, 879, 880, 881, 882, 888, 889, 890, and 891; (e) the fusion polypeptide comprises the sequence set forth in any one of SEQ ID NOS: 883, 884, 885, 886, 887, and 907; (f) the fusion polypeptide comprises the sequence set forth in any one of SEQ ID NOS: 896, 897, and 904; (g) the fusion polypeptide comprises the sequence set forth in any one of SEQ ID NOS: 898 and 899; (h) the fusion polypeptide comprises the sequence set forth in any one of SEQ ID NOS: 900 and 901; (i) the fusion polypeptide comprises the sequence set forth in any one of SEQ ID NOS: 902 and 903; or (j) the fusion polypeptide comprises the sequence set forth in any one of SEQ ID NOS: 918 and 919.

44. The recombinant *Listeria* strain of any preceding embodiment, wherein the fusion polypeptide has a molecular weight of no more than about 150 kDa or no more than about 125 kDa.

45. The recombinant *Listeria* strain of embodiment 1 or 2, wherein the antigenic peptides comprise recurrent cancer mutations from proteins encoded by all of the following genes: KRAS\, EGFR, U2AF1, BRAF, PIK3CA, and TP53, or the recombinant *Listeria* strain of any preceding embodiment, wherein the antigenic peptides comprise recurrent cancer mutations from proteins encoded by all of the following genes: KRAS\, EGFR, U2AF1, BRAF, PIK3CA, and TP53.

46. The recombinant *Listeria* strain of embodiment 45, wherein the antigenic peptides comprise all of the following recurrent cancer mutations: KRAS\_G12C, EGFR_L858R, KRAS\_G12D, U2AF1_S34F, BRAF_V600E, KRAS\_G12V, PIK3CA_E545K, TP53_R158L, KRAS\_G12A, EGFR\L861Q, and TP53_R273L.

47. The recombinant *Listeria* strain of embodiment 46, wherein the antigenic peptides comprise all of the peptides set forth in Table 35.

48. The recombinant *Listeria* strain of embodiment 1 or 2, wherein the antigenic peptides comprise heteroclitic mutations in proteins encoded by all of the following genes: CEACAM5, MAGEA6, MAGEA4, GAGE1, NYESO1, STEAP1, and RNF43, or the recombinant *Listeria* strain of any preceding embodiment, wherein the antigenic peptides comprise heteroclitic mutations in proteins encoded by all of the following genes: CEACAM5, MAGEA6, MAGEA4, GAGE1, NYESO1, STEAP1, and RNF43.

49. The recombinant *Listeria* strain of embodiment 48, wherein the antigenic peptides comprise all of the peptides set forth in Table 36.

50. The recombinant *Listeria* strain of embodiment 47 or 49, wherein the antigenic peptides comprise all of the peptides set forth in Tables 35 and 36.

51. The recombinant *Listeria* strain of embodiment 50, wherein one or more of the antigenic peptides comprising a recurrent cancer mutation are preceded by the linker set forth in SEQ ID NO: 316, and wherein one or more of the antigenic peptides comprising a heteroclitic mutation are preceded by the linker set forth in any one of SEQ ID NOS: 821-829.

52. The recombinant *Listeria* strain of embodiment 51, wherein the fusion polypeptide comprises the sequence set forth in SEQ ID NO: 895.

53. The recombinant *Listeria* strain of embodiment 1 or 2, wherein the antigenic peptides comprise recurrent cancer mutations from proteins encoded by all of the following genes: SPOP, CHEK2, RGPD8, ANKRD36C, and AR, or the recombinant *Listeria* strain of any preceding embodiment, wherein the antigenic peptides comprise recurrent cancer mutations from proteins encoded by all of the following genes: SPOP, CHEK2, RGPD8, ANKRD36C, and AR.

54. The recombinant *Listeria* strain of embodiment 53, wherein the antigenic peptides comprise all of the following recurrent cancer mutations: SPOP_F133V, CHEK2_K373E, RGPD8_P1760A, ANKRD36C_1634T, ANKRD36C_D629Y, SPOP_W131G, ANKRD36C_D626N, SPOP_F133L, AR_T878A, AR_L702H, AR_W742C, AR_H875Y, and AR_F877L.

55. The recombinant *Listeria* strain of embodiment 54, wherein the antigenic peptides comprise all of the peptides set forth in Table 52.

56. The recombinant *Listeria* strain of embodiment 1 or 2, wherein the antigenic peptides comprise heteroclitic mutations in proteins encoded by all of the following genes: CEACAM5, MAGEA4, STEAP1, RNF43, SSX2, SART3, PAGE4, PSMA, and PSA, or the recombinant *Listeria* strain of any preceding embodiment, wherein the antigenic peptides comprise heteroclitic mutations in proteins encoded by all of the following genes: CEACAM5, MAGEA4, STEAP1, RNF43, SSX2, SART3, PAGE4, PSMA, and PSA.

57. The recombinant *Listeria* strain of embodiment 56, wherein the antigenic peptides comprise all of the peptides set forth in Table 53.

58. The recombinant *Listeria* strain of embodiment 55 or 57, wherein the antigenic peptides comprise all of the peptides set forth in Tables 52 and 53.

59. The recombinant *Listeria* strain of embodiment 58, wherein one or more of the antigenic peptides comprising a recurrent cancer mutation are preceded by the linker set forth in SEQ ID NO: 316, and wherein one or more of the antigenic peptides comprising a heteroclitic mutation are preceded by the linker set forth in any one of SEQ ID NOS: 821-829.

60. The recombinant *Listeria* strain of embodiment 59, wherein the fusion polypeptide comprises the sequence set forth in SEQ ID NO: 893.

61. A recombinant *Listeria* strain comprising a nucleic acid comprising a first open reading frame encoding a fusion polypeptide, wherein the fusion polypeptide comprises a PEST-containing peptide fused to two or more antigenic peptides, wherein each antigenic peptide comprises a recurrent cancer mutation, and wherein at least two of the antigenic peptides comprise different recurrent cancer mutations and are fragments of the same cancer-associated protein; or a recombinant *Listeria* strain comprising a nucleic acid comprising a first open reading frame encoding a fusion polypeptide, wherein the fusion polypeptide comprises a PEST-containing peptide fused to two or more antigenic peptides, wherein at least two of the antigenic peptides comprise different recurrent cancer mutations and are fragments of the same cancer-associated protein.

62. The recombinant *Listeria* strain of embodiment 61, wherein the recurrent cancer mutations in at least two of the antigenic peptides are from the same cancer-associated protein and do not occur naturally together.

63. The recombinant *Listeria* strain of embodiment 61 or 62, wherein at least two of the antigenic peptides are overlapping fragments of the same cancer-associated protein.

64. The recombinant *Listeria* strain of embodiment 63, wherein the recurrent cancer mutations in at least two of the antigenic peptides are from the same cancer-associated protein and occur at the same amino acid residue of the cancer-associated protein.

65. The recombinant *Listeria* strain of any one of embodiments 61-64, wherein one or more of the recurrent cancer mutations in the fusion polypeptide is a somatic missense mutation.

66. The recombinant *Listeria* strain of any one of embodiments 61-65, wherein one or more of the recurrent cancer mutations in the fusion polypeptide is a somatic frameshift mutation.

67. The recombinant *Listeria* strain of any one of embodiments 61-66, wherein the antigenic peptides comprise recurrent cancer mutations from proteins encoded by one or more or all of the following genes: KRAS\, BRAF, PIK3CA, TRIM48, PTEN, POLE, PGM5, MBOAT2, KIAA2026, FBXW7, C12orf4, ZBTB20, XYLT2, WNT16, UBR5, TGFBR2, SVIL, RNF43, PLEKHA6, LARP4B, FHOD3, DOCK3, BMPR2, ARID1A, ADAM28, and ACVR2A.

68. The recombinant *Listeria* strain of embodiment 67, wherein the antigenic peptides comprise one or more or all of the following recurrent cancer mutations: TRIM48_Y192H, PTEN_R130N, POLE_V411L, POLE_P286R, PIK3CA_H1047R, PIK3CA_R88N, PGM5_I98V, MBOAT2_R43N, KRAS\_G12D, KIAA2026_R574C, FBXW7_R465C, C12orf4_R335N, BRAF_V600E, ZBTB20_p.Pro692LeufsTer43, XYLT2_p.Gly529AlafsTer78, WNT16_p.Gly167AlafsTer17, UBR5_p.Glu2121LysfsTer28, TGFBR2_p.Glu150GlyfsTer35, SVIL_p.Met1863TrpfsTer44, RNF43_p.Gly659ValfsTer41, PLEKHA6_p.Val328TyrfsTer172, LARP4B_p.Thr163HisfsTer47, FHOD3_p.Ser336ValfsTer138, DOCK3_p.Pro1852GlnfsTer45, BMPR2_p.Asn583ThrfsTer44, ARID1A_p.Asp1850ThrfsTer33, ADAM28_p.Asn75LysfsTer15, and ACVR2A_p.Lys435GlufsTer19.

69. The recombinant *Listeria* strain of embodiment 68, wherein the antigenic peptides comprise one or more or all of the peptides set forth in Table 116.

70. The recombinant *Listeria* strain of embodiment 69, wherein the fusion polypeptide comprises the sequence set forth in any one of SEQ ID NO: 917.

71. The recombinant *Listeria* strain of any preceding embodiment, wherein the fusion polypeptide further comprises one or more peptide tags N-terminal and/or C-terminal to the combination of the two or more antigenic peptides, wherein the one or more peptide tags comprise one or both of the following: FLAG tag and SIINFEKL (SEQ ID NO: 1007) tag.

72. The recombinant *Listeria* strain of any preceding embodiment, wherein the PEST-containing peptide is on the N-terminal end of the fusion polypeptide.

73. The recombinant *Listeria* strain of embodiment 72, wherein the PEST-containing peptide is an N-terminal fragment of LLO.

74. The recombinant *Listeria* strain of embodiment 73, wherein the N-terminal fragment of LLO has the sequence set forth in SEQ ID NO: 336.

75. The recombinant *Listeria* strain of any preceding embodiment, wherein the nucleic acid is in an episomal plasmid.

76. The recombinant *Listeria* strain of any preceding embodiment, wherein the nucleic acid does not confer antibiotic resistance upon the recombinant *Listeria* strain.

77. The recombinant *Listeria* strain of any preceding embodiment, wherein the recombinant *Listeria* strain is an attenuated, auxotrophic *Listeria* strain.

78. The recombinant *Listeria* strain of embodiment 77, wherein the attenuated, auxotrophic *Listeria* strain comprises a mutation in one or more endogenous genes that inactivates the one or more endogenous genes.

79. The recombinant *Listeria* strain of embodiment 78, wherein the one or more endogenous genes comprise actA, dal, and dat.

80. The recombinant *Listeria* strain of any preceding embodiment, wherein the nucleic acid comprises a second open reading frame encoding a metabolic enzyme.

81. The recombinant *Listeria* strain of embodiment 80, wherein the metabolic enzyme is an alanine racemase enzyme or a D-amino acid aminotransferase enzyme.

82. The recombinant *Listeria* strain of any preceding embodiment, wherein the fusion polypeptide is expressed from an hly promoter.

83. The recombinant *Listeria* strain of any preceding embodiment, wherein the recombinant *Listeria* strain is a recombinant *Listeria monocytogenes* strain.

84. The recombinant *Listeria* strain of any preceding embodiment, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

85. An immunogenic composition comprising the recombinant *Listeria* strain of any preceding embodiment.

86. The immunogenic composition of embodiment 85, wherein the immunogenic composition comprises a combination of two or more recombinant *Listeria* strains, wherein each recombinant *Listeria* strain comprises a different set of antigenic peptides or the same set of antigenic peptides in a different order.

87. The immunogenic composition of embodiment 86, wherein each recombinant *Listeria* strain comprises a different set of antigenic peptides.

88. The immunogenic composition of embodiment 87, wherein the combination of recombinant *Listeria* strains comprises about 5-10, 10-15, 15-20, 20-25, 25-30, 30-35, 35-40, 40-45, 45-50, 50-60, 60-70, 70-80, 80-90, 90-100, 100-120, 120-140, 140-160, 160-180, 180-200, 200-220, 220-240, 240-260, 260-280, or 280-300 different antigenic peptides.

89. The immunogenic composition of any one of embodiments 85-88, wherein the immunogenic composition further comprises an adjuvant.

90. The immunogenic composition of embodiment 89, wherein the adjuvant comprises a granulocyte/macrophage colony-stimulating factor (GM-CSF) protein, a nucleotide molecule encoding a GM-CSF protein, saponin QS21, monophosphoryl lipid A, an unmethylated CpG-containing oligonucleotide, or a detoxified listeriolysin O protein.

91. A method of inducing an immune response against a tumor or cancer in a subject, comprising administering to the subject the recombinant *Listeria* strain of any one of embodiments 1-84 or the immunogenic composition of any one of embodiments 85-90.

92. A method of preventing or treating a tumor or cancer in a subject, comprising administering to the subject the recombinant *Listeria* strain of any one of embodiments 1-84 or the immunogenic composition of any one of embodiments 85-90.

93. The method of embodiment 91 or 92, wherein multiple different recombinant *Listeria* strains or multiple different immunogenic compositions are administered to the subject.

94. The method of embodiment 93, wherein the multiple different recombinant *Listeria* strains or multiple different immunogenic compositions are administered to the subject simultaneously.

95. The method of embodiment 93, wherein the multiple different recombinant *Listeria* strains or multiple different immunogenic compositions are administered to the subject sequentially.

96. The method of any one of embodiments 93-95, wherein the multiple recombinant *Listeria* strains or multiple different immunogenic compositions comprise about 2, 3, 4, 5, 6, 7, 8, 9, 10, 11, 12, 13, 14, 15, 16, 17, 18, 19, or 20 recombinant *Listeria* strains or immunogenic compositions.

97. The method of any one of embodiments 93-96, wherein the subject has a cancer associated with one or more recurrent cancer mutations in one or more cancer-associated proteins, and the recombinant *Listeria* strain or the immunogenic composition administered to the subject comprises antigenic peptides comprising one or more recurrent cancer mutations associated with the cancer.

98. The method of embodiment 97, wherein the method comprises screening the subject for and identifying at least one of the one or more recurrent cancer mutations prior to the administering step, wherein the recombinant *Listeria* strain or the immunogenic composition administered to the subject comprises antigenic peptides comprising the at least one of the one or more recurrent cancer mutations identified in the subject.

99. The method of any embodiment 97, wherein the method does not comprise screening the subject for and identifying recurrent cancer mutations prior to the administering step.

100. A cell bank comprising one or more recombinant *Listeria* strains as in any one of embodiments 1-84.

101. The cell bank of embodiment 100, wherein the cell bank is a frozen cell bank or a lyophilized cell bank.

102. A method of generating an immunotherapy construct, comprising: (a) selecting a set of recurrent cancer mutations and a set of heteroclitic mutations in cancer-associated proteins to include in the immunotherapy construct; (b) designing antigenic peptides comprising each of the recurrent cancer mutations and each of the heteroclitic mutations; (c) selecting a set of antigenic peptides, comprising testing the hydropathy of the each antigenic peptide, and modifying or deselecting an antigenic peptide if it scores above a selected hydropathy index threshold value; (d) designing a fusion polypeptide comprising each of the selected antigenic peptides; and (e) generating a nucleic acid construct encoding the fusion polypeptide.

103. The method of embodiment 102, wherein the recurrent cancer mutations are selected in step (a) based on one or more of the following criteria: (i) frequency of occurrence across multiple types of cancers or a particular type of cancer; (ii) location within a functional domain of a cancer-associated protein; (iii) status as a known cancer driver mutation or chemotherapy resistance mutation; and (iv) identification as a somatic missense mutation or a somatic frameshift mutation.

104. The method of embodiment 102 or 103, wherein the heteroclitic mutations are selected in step (a) based on one or more of the following criteria: (i) ability to bind to one or more of the following HLA types: HLA-A*02:01, HLA-A*03:01, HLA-A*24:02, and HLA-B*07:02; (ii) ability to generate a CD8+ T lymphocyte response; and (iii) binding affinity to a specific HLA type that is equivalent or stronger than the corresponding wild type sequence.

105. The method of any one of embodiments 102-104, wherein the set of recurrent cancer mutations selected in step (a) is selected based on one or more of the following criteria: (i) the set includes no more than about 30, 31, 32, 33, 34, 35, 36, 37, 38, 39, 40, 41, 42, 43, 44, 45, 46, 47, 48, 49 or 50 recurrent cancer mutations and/or no more than about 30, 31, 32, 33, 34, 35, 36, 37, 38, 39, 40, 41, 42, 43, 44, 45, 46, 47, 48, 49 or 50 heteroclitic mutations; (ii) the set includes recurrent cancer mutations that would be found in at least about 5%, 10%, 15%, 20%, 25%, 30%, 35%, 40%, 45%, 50%, 55%, 60%, 65%, 70%, 75% 80%, 85%, 90%, 95%, 96%, 97%, 98%, or 99% of cancer patients who have a particular type of cancer; and (iii) the set comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 different recurrent cancer mutations or recurrent somatic missense mutations from a particular type of cancer.

106. The method of any one of embodiments 102-105, wherein each antigenic peptide designed in step (b) to comprise a recurrent cancer mutation is designed to comprise a fragment of the cancer-associated protein comprising the recurrent cancer mutation and flanking sequence on each side.

107. The method of embodiment 106, wherein one or more or all of the antigenic peptides comprising a recurrent cancer mutation include at least about 10 flanking amino acids on each side of the recurrent cancer mutation.

108. The method of any one of embodiments 102-107, wherein one or more or all of the antigenic peptides comprising a heteroclitic mutation are designed to have a preferred amino acid at an anchor position.

109. The method of any one of embodiments 102-108, wherein antigenic peptides are selected in step (c) if they are below a hydropathy threshold predictive of secretability in *Listeria monocytogenes*.

110. The method of embodiment 109, wherein the antigenic peptides are scored by a Kyte and Doolittle hydropathy index 21 amino acid window, and any peptides scoring above a cutoff of about 1.6 are excluded or are modified to score below the cutoff.

111. The method of any one of embodiments 102-110, wherein step (c) further comprises scoring and selecting antigenic peptides based on the ability of the antigenic peptides to bind subject HLA.

112. The method of any one of embodiments 102-111, wherein the order of antigenic peptides in the fusion polypeptide in step (d) is selected using randomization.

113. The method of any one of embodiments 102-112, wherein the fusion polypeptide is designed to have a molecular weight of no more than about 150 kDa or no more than about 125 kDa.

114. The method of any one of embodiments 102-113, wherein step (d) further comprises testing the hydropathy of the fusion polypeptide, and either reordering the antigenic peptides or removing problematic antigenic peptides if any region of the fusion polypeptide scores above a selected hydropathy index threshold value.

115. The method of embodiment 114, wherein the fusion polypeptide is scored by a Kyte and Doolittle hydropathy index with a sliding 21 amino acid window, and wherein the threshold value is about 1.6.

116. The method of any one of embodiments 102-115, wherein step (e) further comprises optimizing the nucleic acid sequence.

117. The method of embodiment 116, wherein the optimization comprises codon optimization.

118. The method of any one of embodiments 102-117, further comprising introducing the nucleic acid into a *Listeria monocytogenes* strain and confirming expression and secretion of the encoded fusion polypeptide.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

| SEQ ID NO | Type | Description |
| --- | --- | --- |
| 1 | DNA | BRAF1 Insert (no Tags) |
| 2 | Protein | BRAF1 Insert (no Tags) |
| 3 | DNA | (1) 3xFLAG-BRAF1-SIINFEKL |
| 4 | Protein | (1) 3xFLAG-BRAF1-SIINFEKL |
| 5 | DNA | (2) BRAF1-3xFLAG-SIINFEKL |
| 6 | Protein | (2) BRAF1-3xFLAG-SIINFEKL |
| 7 | DNA | BRAF2 Insert (no Tags) |
| 8 | Protein | BRAF2 Insert (no Tags) |
| 9 | DNA | (3) 3xFLAG-BRAF2-SIINFEKL |
| 10 | Protein | (3) 3xFLAG-BRAF2-SIINFEKL |
| 11 | DNA | (4) BRAF2-3xFLAG-SIINFEKL |
| 12 | Protein | (4) BRAF2-3xFLAG-SIINFEKL |
| 13 | DNA | BRAF3 Insert (no Tags) |
| 14 | Protein | BRAF3 Insert (no Tags) |
| 15 | DNA | (5) 3xFLAG-BRAF3-SIINFEKL |
| 16 | Protein | (5) 3xFLAG-BRAF3-SIINFEKL |
| 17 | DNA | (6) BRAF3-3xFLAG-SIINFEKL |
| 18 | Protein | (6) BRAF3-3xFLAG-SIINFEKL |
| 19 | DNA | BRAF4 Insert (no Tags) |
| 20 | Protein | BRAF4 Insert (no Tags) |
| 21 | DNA | (7) 3xFLAG-BRAF4-SIINFEKL |
| 22 | Protein | (7) 3xFLAG-BRAF4-SIINFEKL |
| 23 | DNA | (8) BRAF4-3xFLAG-SIINFEKL |
| 24 | Protein | (8) BRAF4-3xFLAG-SIINFEKL |
| 25 | DNA | EGFR1 Insert (no Tags) |
| 26 | Protein | EGFR1 Insert (no Tags) |
| 27 | DNA | (9) 3xFLAG-EGFR1-SIINFEKL |
| 28 | Protein | (9) 3xFLAG-EGFR1-SIINFEKL |
| 29 | DNA | (10) EGFR1-3xFLAG-SIINFEKL |
| 30 | Protein | (10) EGFR1-3xFLAG-SIINFEKL |
| 31 | DNA | EGFR2 Insert (no Tags) |
| 32 | Protein | EGFR2 Insert (no Tags) |
| 33 | DNA | (11) 3xFLAG-EGFR2-SIINFEKL |
| 34 | Protein | (11) 3xFLAG-EGFR2-SIINFEKL |
| 35 | DNA | (12) EGFR2-3xFLAG-SIINFEKL |
| 36 | Protein | (12) EGFR2-3xFLAG-SIINFEKL |
| 37 | DNA | EGFR3 Insert (no Tags) |
| 38 | Protein | EGFR3 Insert (no Tags) |
| 39 | DNA | (13) 3xFLAG-EGFR3-SIINFEKL |
| 40 | Protein | (13) 3xFLAG-EGFR3-SIINFEKL |
| 41 | DNA | (14) EGFR3-3xFLAG-SIINFEKL |
| 42 | Protein | (14) EGFR3-3xFLAG-SIINFEKL |
| 43 | DNA | EGFR4 Insert (no Tags) |
| 44 | Protein | EGFR4 Insert (no Tags) |
| 45 | DNA | (15) 3xFLAG-EGFR4-SIINFEKL |

-continued

| SEQ ID NO | Type | Description |
|---|---|---|
| 46 | Protein | (15) 3xFLAG-EGFR4-SIINFEKL |
| 47 | DNA | (16) EGFR4-3xFLAG-SIINFEKL |
| 48 | Protein | (16) EGFR4-3xFLAG-SIINFEKL |
| 49 | DNA | PIK3CA1 Insert (no Tags) |
| 50 | Protein | PIK3CA1 Insert (no Tags) |
| 51 | DNA | (17) 3xFLAG-PIK3CA1-SIINFEKL |
| 52 | Protein | (17) 3xFLAG-PIK3CA1-SIINFEKL |
| 53 | DNA | (18) PIK3CA1-3xFLAG-SIINFEKL |
| 54 | Protein | (18) PIK3CA1-3xFLAG-SIINFEKL |
| 55 | DNA | PIK3CA2 Insert (no Tags) |
| 56 | Protein | PIK3CA2 Insert (no Tags) |
| 57 | DNA | (19) 3xFLAG-PIK3CA2-SIINFEKL |
| 58 | Protein | (19) 3xFLAG-PIK3CA2-SIINFEKL |
| 59 | DNA | (20) PIK3CA2-3xFLAG-SIINFEKL |
| 60 | Protein | (20) PIK3CA2-3xFLAG-SIINFEKL |
| 61 | DNA | PIK3CA3 Insert (no Tags) |
| 62 | Protein | PIK3CA3 Insert (no Tags) |
| 63 | DNA | (21) 3xFLAG-PIK3CA3-SIINFEKL |
| 64 | Protein | (21) 3xFLAG-PIK3CA3-SIINFEKL |
| 65 | DNA | (22) PIK3CA3-3xFLAG-SIINFEKL |
| 66 | Protein | (22) PIK3CA3-3xFLAG-SIINFEKL |
| 67 | DNA | PIK3CA4 Insert (no Tags) |
| 68 | Protein | PIK3CA4 Insert (no Tags) |
| 69 | DNA | (23) 3xFLAG-PIK3CA4-SIINFEKL |
| 70 | Protein | (23) 3xFLAG-PIK3CA4-SIINFEKL |
| 71 | DNA | (24) PIK3CA4-3xFLAG-SIINFEKL |
| 72 | Protein | (24) PIK3CA4-3xFLAG-SIINFEKL |
| 73 | DNA | PIK3R1-1 Insert (no Tags) |
| 74 | Protein | PIK3R1-1 Insert (no Tags) |
| 75 | DNA | (25) 3xFLAG-PIK3R1-1-SIINFEKL |
| 76 | Protein | (25) 3xFLAG-PIK3R1-1-SIINFEKL |
| 77 | DNA | (26) PIK3R1-1-3xFLAG-SIINFEKL |
| 78 | Protein | (26) PIK3R1-1-3xFLAG-SIINFEKL |
| 79 | DNA | PIK3R1-2 Insert (no Tags) |
| 80 | Protein | PIK3R1-2 Insert (no Tags) |
| 81 | DNA | (27) 3xFLAG-PIK3R1-2-SIINFEKL |
| 82 | Protein | (27) 3xFLAG-PIK3R1-2-SIINFEKL |
| 83 | DNA | (28) PIK3R1-2-3xFLAG-SIINFEKL |
| 84 | Protein | (28) PIK3R1-2-3xFLAG-SIINFEKL |
| 85 | DNA | PIK3combo1 Insert (no Tags) |
| 86 | Protein | PIK3combo1 Insert (no Tags) |
| 87 | DNA | (29) 3xFLAG-PIK3combo1-SIINFEKL |
| 88 | Protein | (29) 3xFLAG-PIK3combo1-SIINFEKL |
| 89 | DNA | (30) PIK3combo1-3xFLAG-SIINFEKL |
| 90 | Protein | (30) PIK3combo1-3xFLAG-SIINFEKL |
| 91 | DNA | PIK3combo2 Insert (no Tags) |
| 92 | Protein | PIK3combo2 Insert (no Tags) |
| 93 | DNA | (31) 3xFLAG-PIK3combo2-SIINFEKL |
| 94 | Protein | (31) 3xFLAG-PIK3combo2-SIINFEKL |
| 95 | DNA | (32) PIK3combo2-3xFLAG-SIINFEKL |
| 96 | Protein | (32) PIK3combo2-3xFLAG-SIINFEKL |
| 97 | DNA | PIK3combo3 Insert (no Tags) |
| 98 | Protein | PIK3combo3 Insert (no Tags) |
| 99 | DNA | (33) 3xFLAG-PIK3combo3-SIINFEKL |
| 100 | Protein | (33) 3xFLAG-PIK3combo3-SIINFEKL |
| 101 | DNA | (34) PIK3combo3-3xFLAG-SIINFEKL |
| 102 | Protein | (34) PIK3combo3-3xFLAG-SIINFEKL |
| 103 | DNA | PIK3combo4 Insert (no Tags) |
| 104 | Protein | PIK3combo4 Insert (no Tags) |
| 105 | DNA | (35) 3xFLAG-PIK3combo4-SIINFEKL |
| 106 | Protein | (35) 3xFLAG-PIK3combo4-SIINFEKL |
| 107 | DNA | (36) PIK3combo4-3xFLAG-SIINFEKL |
| 108 | Protein | (36) PIK3combo4-3xFLAG-SIINFEKL |
| 109 | DNA | PTEN1 Insert (no Tags) |
| 110 | Protein | PTEN1 Insert (no Tags) |
| 111 | DNA | (37) 3xFLAG-PTEN1-SIINFEKL |
| 112 | Protein | (37) 3xFLAG-PTEN1-SIINFEKL |
| 113 | DNA | (38) PTEN1-3xFLAG-SIINFEKL |
| 114 | Protein | (38) PTEN1-3xFLAG-SIINFEKL |
| 115 | DNA | PTEN2 Insert (no Tags) |
| 116 | Protein | PTEN2 Insert (no Tags) |
| 117 | DNA | (39) 3xFLAG-PTEN2-SIINFEKL |
| 118 | Protein | (39) 3xFLAG-PTEN2-SIINFEKL |
| 119 | DNA | (40) PTEN2-3xFLAG-SIINFEKL |
| 120 | Protein | (40) PTEN2-3xFLAG-SIINFEKL |
| 121 | DNA | PTEN3 Insert (no Tags) |
| 122 | Protein | PTEN3 Insert (no Tags) |

-continued

| SEQ ID NO | Type | Description |
|---|---|---|
| 123 | DNA | (41) 3xFLAG-PTEN3-SIINFEKL |
| 124 | Protein | (41) 3xFLAG-PTEN3-SIINFEKL |
| 125 | DNA | (42) PTEN3-3xFLAG-SIINFEKL |
| 126 | Protein | (42) PTEN3-3xFLAG-SIINFEKL |
| 127 | DNA | PTEN4 Insert (no Tags) |
| 128 | Protein | PTEN4 Insert (no Tags) |
| 129 | DNA | (43) 3xFLAG-PTEN4-SIINFEKL |
| 130 | Protein | (43) 3xFLAG-PTEN4-SIINFEKL |
| 131 | DNA | (44) PTEN4-3xFLAG-SIINFEKL |
| 132 | Protein | (44) PTEN4-3xFLAG-SIINFEKL |
| 133 | DNA | KRAS1 Insert (no Tags) |
| 134 | Protein | KRAS1 Insert (no Tags) |
| 135 | DNA | (45) 3xFLAG-KRAS1-SIINFEKL |
| 136 | Protein | (45) 3xFLAG-KRAS1-SIINFEKL |
| 137 | DNA | (46) KRAS1-3xFLAG-SIINFEKL |
| 138 | Protein | (46) KRAS1-3xFLAG-SIINFEKL |
| 139 | DNA | KRAS2 Insert (no Tags) |
| 140 | Protein | KRAS2 Insert (no Tags) |
| 141 | DNA | (47) 3xFLAG-KRAS2-SIINFEKL |
| 142 | Protein | (47) 3xFLAG-KRAS2-SIINFEKL |
| 143 | DNA | (48) KRAS2-3xFLAG-SIINFEKL |
| 144 | Protein | (48) KRAS2-3xFLAG-SIINFEKL |
| 145 | DNA | KRAS3 Insert (no Tags) |
| 146 | Protein | KRAS3 Insert (no Tags) |
| 147 | DNA | (49) 3xFLAG-KRAS3-SIINFEKL |
| 148 | Protein | (49) 3xFLAG-KRAS3-SIINFEKL |
| 149 | DNA | (50) KRAS3-3xFLAG-SIINFEKL |
| 150 | Protein | (50) KRAS3-3xFLAG-SIINFEKL |
| 151 | DNA | KRAS4 Insert (no Tags) |
| 152 | Protein | KRAS4 Insert (no Tags) |
| 153 | DNA | (51) 3xFLAG-KRAS4-SIINFEKL |
| 154 | Protein | (51) 3xFLAG-KRAS4-SIINFEKL |
| 155 | DNA | (52) KRAS4-3xFLAG-SIINFEKL |
| 156 | Protein | (52) KRAS4-3xFLAG-SIINFEKL |
| 157 | DNA | TP53 33mer1 Insert (no Tags) |
| 158 | Protein | TP53 33mer1 Insert (no Tags) |
| 159 | DNA | (53) 3xFLAG-TP53 33mer1-SIINFEKL |
| 160 | Protein | (53) 3xFLAG-TP53 33mer 1-SIINFEKL |
| 161 | DNA | (54) TP53 33mer1-3xFLAG-SIINFEKL |
| 162 | Protein | (54) TP53 33mer1-3xFLAG-SIINFEKL |
| 163 | DNA | TP53 33mer2 Insert (no Tags) |
| 164 | Protein | TP53 33mer2 Insert (no Tags) |
| 165 | DNA | (55) 3xFLAG-TP53 33mer2-SIINFEKL |
| 166 | Protein | (55) 3xFLAG-TP53 33mer2-SIINFEKL |
| 167 | DNA | (56) TP53 33mer2-3xFLAG-SIINFEKL |
| 168 | Protein | (56) TP53 33mer2-3xFLAG-SIINFEKL |
| 169 | DNA | TP53 33mer3 Insert (no Tags) |
| 170 | Protein | TP53 33mer3 Insert (no Tags) |
| 171 | DNA | (57) 3xFLAG-TP53 33mer3-SIINFEKL |
| 172 | Protein | (57) 3xFLAG-TP53 33mer3-SIINFEKL |
| 173 | DNA | (58) TP53 33mer3-3xFLAG-SIINFEKL |
| 174 | Protein | (58) TP53 33mer3-3xFLAG-SIINFEKL |
| 175 | DNA | TP53 33mer4 Insert (no Tags) |
| 176 | Protein | TP53 33mer4 Insert (no Tags) |
| 177 | DNA | (59) 3xFLAG-TP53 33mer4-SIINFEKL |
| 178 | Protein | (59) 3xFLAG-TP53 33mer4-SIINFEKL |
| 179 | DNA | (60) TP53 33mer4-3xFLAG-SIINFEKL |
| 180 | Protein | (60) TP53 33mer4-3xFLAG-SIINFEKL |
| 181 | DNA | TP53 17merA Insert (no Tags) |
| 182 | Protein | TP53 17merA Insert (no Tags) |
| 183 | DNA | (61) 3xFLAG-TP53 17merA-SIINFEKL |
| 184 | Protein | (61) 3xFLAG-TP53 17merA-SIINFEKL |
| 185 | DNA | (62) TP53 17merA-3xFLAG-SIINFEKL |
| 186 | Protein | (62) TP53 17merA-3xFLAG-SIINFEKL |
| 187 | DNA | TP53 16merA Insert (no Tags) |
| 188 | Protein | TP53 16merA Insert (no Tags) |
| 189 | DNA | (63) 3xFLAG-TP53 16merA-SIINFEKL |
| 190 | Protein | (63) 3xFLAG-TP53 16merA-SIINFEKL |
| 191 | DNA | (64) TP53 16merA-3xFLAG-SIINFEKL |
| 192 | Protein | (64) TP53 16merA-3xFLAG-SIINFEKL |
| 193 | DNA | TP53 17merB Insert (no Tags) |
| 194 | Protein | TP53 17merB Insert (no Tags) |
| 195 | DNA | (65) 3xFLAG-TP53 17merB-SIINFEKL |
| 196 | Protein | (65) 3xFLAG-TP53 17merB-SIINFEKL |
| 197 | DNA | (66) TP53 17merB-3xFLAG-SIINFEKL |
| 198 | Protein | (66) TP53 17merB-3xFLAG-SIINFEKL |
| 199 | DNA | TP53 16merB Insert (no Tags) |

| SEQ ID NO | Type | Description |
| --- | --- | --- |
| 200 | Protein | TP53 16merB Insert (no Tags) |
| 201 | DNA | (67) 3xFLAG-TP53 16merB-SIINFEKL |
| 202 | Protein | (67) 3xFLAG-TP53 16merB-SIINFEKL |
| 203 | DNA | (68) TP53 16merB-3xFLAG-SIINFEKL |
| 204 | Protein | (68) TP53 16merB-3xFLAG-SIINFEKL |
| 205 | DNA | TP53 17merC Insert (no Tags) |
| 206 | Protein | TP53 17merC Insert (no Tags) |
| 207 | DNA | (69) 3xFLAG-TP53 17merC-SIINFEKL |
| 208 | Protein | (69) 3xFLAG-TP53 17merC-SIINFEKL |
| 209 | DNA | (70) TP53 17merC-3xFLAG-SIINFEKL |
| 210 | Protein | (70) TP53 17merC-3xFLAG-SIINFEKL |
| 211 | DNA | TP53 16merC Insert (no Tags) |
| 212 | Protein | TP53 16merC Insert (no Tags) |
| 213 | DNA | (71) 3xFLAG-TP53 16merC-SIINFEKL |
| 214 | Protein | (71) 3xFLAG-TP53 16merC-SIINFEKL |
| 215 | DNA | (72) TP53 16merC-3xFLAG-SIINFEKL |
| 216 | Protein | (72) TP53 16merC-3xFLAG-SIINFEKL |
| 217 | DNA | TP53 17merD Insert (no Tags) |
| 218 | Protein | TP53 17merD Insert (no Tags) |
| 219 | DNA | (73) 3xFLAG-TP53 17merD-SIINFEKL |
| 220 | Protein | (73) 3xFLAG-TP53 17merD-SIINFEKL |
| 221 | DNA | (74) TP53 17merD-3xFLAG-SIINFEKL |
| 222 | Protein | (74) TP53 17merD-3xFLAG-SIINFEKL |
| 223 | DNA | TP53 16merD Insert (no Tags) |
| 224 | Protein | TP53 16merD Insert (no Tags) |
| 225 | DNA | (75) 3xFLAG-TP53 16merD-SIINFEKL |
| 226 | Protein | (75) 3xFLAG-TP53 16merD-SIINFEKL |
| 227 | DNA | (76) TP53 16merD-3xFLAG-SIINFEKL |
| 228 | Protein | (76) TP53 16merD-3xFLAG-SIINFEKL |
| 229 | DNA | EGFR Insert MP v1 (no Tags) |
| 230 | DNA | EGFR Insert MP v2 (no Tags) |
| 231 | Protein | EGFR Insert MP (no Tags) |
| 232 | DNA | (77) 3xFLAG-EGFR-SIINFEKL MP |
| 233 | Protein | (77) 3xFLAG-EGFR-SIINFEKL MP |
| 234 | DNA | (78) EGFR-3xFLAG-SIINFEKL MP |
| 235 | Protein | (78) EGFR-3xFLAG-SIINFEKL MP |
| 236 | DNA | PIK3CAall Insert MP v1 (no Tags) |
| 237 | DNA | PIK3CAall Insert MP v2 (no Tags) |
| 238 | Protein | PIK3CAall Insert MP (no Tags) |
| 239 | DNA | (79) 3xFLAG-PIK3CAall-SIINFEKL MP |
| 240 | Protein | (79) 3xFLAG-PIK3CAall-SIINFEKL MP |
| 241 | DNA | (80) PIK3CAall-3xFLAG-SIINFEKL MP |
| 242 | Protein | (80) PIK3CAall-3xFLAG-SIINFEKL MP |
| 243 | DNA | PIK3CAmajor Insert MP v1 (no Tags) |
| 244 | DNA | PIK3CAmajor Insert MP v2 (no Tags) |
| 245 | Protein | PIK3CAmajor Insert MP (no Tags) |
| 246 | DNA | (81) 3xFLAG-PIK3CAmajor-SIINFEKL MP |
| 247 | Protein | (81) 3xFLAG-PIK3CAmajor-SIINFEKL MP |
| 248 | DNA | (82) PIK3CAmajor-3xFLAG-SIINFEKL MP |
| 249 | Protein | (82) PIK3CAmajor-3xFLAG-SIINFEKL MP |
| 250 | DNA | PIK3CAminor Insert MP v1 (no Tags) |
| 251 | DNA | PIK3CAminor Insert MP v2 (no Tags) |
| 252 | Protein | PIK3CAminor Insert MP (no Tags) |
| 253 | DNA | (83) 3xFLAG-PIK3CAminor-SIINFEKL MP |
| 254 | Protein | (83) 3xFLAG-PIK3CAminor-SIINFEKL MP |
| 255 | DNA | (84) PIK3CAminor-3xFLAG-SIINFEKL MP |
| 256 | Protein | (84) PIK3CAminor-3xFLAG-SIINFEKL MP |
| 257 | DNA | TP53all Insert MP v1 (no Tags) |
| 258 | DNA | TP53all Insert MP v2 (no Tags) |
| 259 | Protein | TP53all Insert MP (no Tags) |
| 260 | DNA | (85) 3xFLAG-TP53all-SIINFEKL MP |
| 261 | Protein | (85) 3xFLAG-TP53all-SIINFEKL MP |
| 262 | DNA | (86) TP53all-3xFLAG-SIINFEKL MP |
| 263 | Protein | (86) TP53all-3xFLAG-SIINFEKL MP |
| 264 | DNA | TP53major Insert MP v1 (no Tags) |
| 265 | DNA | TP53major Insert MP v2 (no Tags) |
| 266 | Protein | TP53major Insert MP (no Tags) |
| 267 | DNA | (87) 3xFLAG-TP53major-SIINFEKL MP |
| 268 | Protein | (87) 3xFLAG-TP53major-SIINFEKL MP |
| 269 | DNA | (88) TP53major-3xFLAG-SIINFEKL MP |
| 270 | Protein | (88) TP53major-3xFLAG-SIINFEKL MP |
| 271 | DNA | TP53minor Insert MP v1 (no Tags) |
| 272 | DNA | TP53minor Insert MP v2 (no Tags) |
| 273 | Protein | TP53minor Insert MP (no Tags) |
| 274 | DNA | (89) 3xFLAG-TP53minor-SIINFEKL MP |
| 275 | Protein | (89) 3xFLAG-TP53minor-SIINFEKL MP |
| 276 | DNA | (90) TP53minor-3xFLAG-SIINFEKL MP |

-continued

| SEQ ID NO | Type | Description |
|---|---|---|
| 277 | Protein | (90) TP53minor-3xFLAG-SIINFEKL MP |
| 278 | DNA | SIINFEKL Tag v1 |
| 279 | DNA | SIINFEKL Tag v2 |
| 280 | DNA | SIINFEKL Tag v3 |
| 281 | DNA | SIINFEKL Tag v4 |
| 282 | DNA | SIINFEKL Tag v5 |
| 283 | DNA | SIINFEKL Tag v6 |
| 284 | DNA | SIINFEKL Tag v7 |
| 285 | DNA | SIINFEKL Tag v8 |
| 286 | DNA | SIINFEKL Tag v9 |
| 287 | DNA | SIINFEKL Tag v10 |
| 288 | DNA | SIINFEKL Tag v11 |
| 289 | DNA | SIINFEKL Tag v12 |
| 290 | DNA | SIINFEKL Tag v13 |
| 291 | DNA | SIINFEKL Tag v14 |
| 292 | DNA | SIINFEKL Tag v15 |
| 293 | Protein | SIINFEKL Tag |
| 294 | DNA | 3xFLAG Tag v1 |
| 295 | DNA | 3xFLAG Tag v2 |
| 296 | DNA | 3xFLAG Tag v3 |
| 297 | DNA | 3xFLAG Tag v4 |
| 298 | DNA | 3xFLAG Tag v5 |
| 299 | DNA | 3xFLAG Tag v6 |
| 300 | DNA | 3xFLAG Tag v7 |
| 301 | DNA | 3xFLAG Tag v8 |
| 302 | DNA | 3xFLAG Tag v9 |
| 303 | DNA | 3xFLAG Tag v10 |
| 304 | DNA | 3xFLAG Tag v11 |
| 305 | DNA | 3xFLAG Tag v12 |
| 306 | DNA | 3xFLAG Tag v13 |
| 307 | DNA | 3xFLAG Tag v14 |
| 308 | DNA | 3xFLAG Tag v15 |
| 309 | Protein | 3xFLAG Tag |
| 310 | Protein | SSX2__A0201 Native Peptide |
| 311 | Protein | STEAP1__A0201 Native Peptide |
| 312 | Protein | STEAP1__A2402 Native Peptide |
| 313 | Protein | Peptide Linker v4 |
| 314 | Protein | Peptide Linker v5 |
| 315 | Protein | Peptide Linker v6 |
| 316 | Protein | Peptide Linker v7 |
| 317 | Protein | SURVIVIN__A0201 Native Peptide |
| 318 | Protein | SURVIVIN__A2402 Native Peptide |
| 319 | Protein | Peptide Linker v10 |
| 320 | Protein | PEST-Like Sequence v1 |
| 321 | Protein | PEST-Like Sequence v2 |
| 322 | Protein | PEST-Like Sequence v3 |
| 323 | Protein | PEST-Like Sequence v4 |
| 324 | Protein | PEST-Like Sequence v5 |
| 325 | Protein | PEST-Like Sequence v6 |
| 326 | Protein | PEST-Like Sequence v7 |
| 327 | Protein | PEST-Like Sequence v8 |
| 328 | Protein | PEST-Like Sequence v9 |
| 329 | Protein | PEST-Like Sequence v10 |
| 330 | Protein | PEST-Like Sequence v11 |
| 331 | Protein | PEST-Like Sequence v12 |
| 332 | Protein | LLO Protein v1 |
| 333 | Protein | LLO Protein v2 |
| 334 | Protein | N-Terminal Truncated LLO v1 |
| 335 | Protein | N-Terminal Truncated LLO v2 |
| 336 | Protein | N-Terminal Truncated LLO v3 |
| 337 | DNA | Nucleic Acid Encoding N-Terminal Truncated LLO v3 |
| 338 | Protein | ActA Protein v1 |
| 339 | Protein | ActA Protein v2 |
| 340 | Protein | ActA Fragment v1 |
| 341 | Protein | ActA Fragment v2 |
| 342 | Protein | ActA Fragment v3 |
| 343 | Protein | ActA Fragment v4 |
| 344 | Protein | ActA Fragment v5 |
| 345 | DNA | Nucleic Acid Encoding ActA Fragment v5 |
| 346 | Protein | ActA Fragment v6 |
| 347 | Protein | ActA Fragment v7 |
| 348 | DNA | Nucleic Acid Encoding ActA Fragment v7 |
| 349 | Protein | ActA Fragment Fused to Hly Signal Peptide |
| 350 | Protein | ActA Substitution |
| 351 | Protein | Cholesterol-Binding Domain of LLO |
| 352 | Protein | HLA-A2 restricted Epitope from NY-ESO-1 |
| 353 | Protein | Lm Alanine Racemase |

-continued

| SEQ ID NO | Type | Description |
|---|---|---|
| 354 | Protein | Lm D-Amino Acid Aminotransferase |
| 355 | DNA | Nucleic Acid Encoding Lm Alanine Racemase |
| 356 | DNA | Nucleic Acid Encoding Lm D-Amino Acid Aminotransferase |
| 357 | Protein | Wild Type PrfA |
| 358 | DNA | Nucleic Acid Encoding Wild Type PrfA |
| 359 | Protein | D133V PrfA |
| 360 | DNA | Nucleic Acid Encoding D133V PrfA |
| 361 | Protein | WT BRAF |
| 362 | Protein | WT EGFR |
| 363 | Protein | WT PIK3CA |
| 364 | Protein | WT PIK3R1 |
| 365 | Protein | WT PTEN |
| 366 | Protein | WT KRAS |
| 367 | Protein | WT TP53 |
| 368-571 | Protein | See Example 1 |
| 572 | DNA | 4X Glycine Linker G1 |
| 573 | DNA | 4X Glycine Linker G2 |
| 574 | DNA | 4X Glycine Linker G3 |
| 575 | DNA | 4X Glycine Linker G4 |
| 576 | DNA | 4X Glycine Linker G5 |
| 577 | DNA | 4X Glycine Linker G6 |
| 578 | DNA | 4X Glycine Linker G7 |
| 579 | DNA | 4X Glycine Linker G8 |
| 580 | DNA | 4X Glycine Linker G9 |
| 581 | DNA | 4X Glycine Linker G10 |
| 582 | DNA | 4X Glycine Linker G11 |
| 583 | Protein | dtLLO |
| 584-594 | Protein | See Example 3 |
| 595-613 | Protein | See Example 3 |
| 614-643 | Protein | See Example 3 |
| 644-703 | Protein | See Example 3 |
| 704-724 | Protein | See Example 3 |
| 725 | Protein | NUF2 Wild Type |
| 726 | Protein | NUF2 Heteroclitic |
| 727 | DNA | Adv16 f |
| 728 | DNA | Adv295 r |
| 729 | Protein | KRAS_G12D_21-Mer Insert |
| 730 | Protein | KRAS_G12D_Kd Minigene Insert |
| 731 | Protein | KRAS_G12D_Dd Minigene Insert |
| 732 | Protein | Heteroclitic WT1 Peptide v1A (WT1-F) |
| 733 | Protein | Heteroclitic WT1 Peptide v2 |
| 734 | Protein | Heteroclitic WT1 Peptide v3 |
| 735 | Protein | Heteroclitic WT1 Peptide v5 |
| 736 | Protein | Heteroclitic WT1 Peptide v8 |
| 737 | Protein | Heteroclitic WT1 Peptide v4 |
| 738 | Protein | Heteroclitic WT1 Peptide v7 |
| 739 | Protein | Heteroclitic WT1 Peptide v9 |
| 740 | Protein | Heteroclitic WT1 Peptide v6 |
| 741 | Protein | Heteroclitic WT1 Peptide v1B (WT1-A1) |
| 742 | Protein | WT1-FLAG-Ub-heteroclitic phenylalanine minigene construct |
| 743 | Protein | Wild-Type WT1 Peptide v14-WT1-427 long |
| 744 | Protein | Wild-Type WT1 Peptide v15-WT1-331 long |
| 745 | Protein | Heteroclitic WT1 Peptide v1D (WT1-122A1-long) |
| 746 | Protein | Native WT1 Peptide v1B |
| 747 | Protein | Ubiquitin |
| 748 | Protein | WT1-P1-P2-P3-FLAG-Ub-heteroclitic tyrosine minigene construct |
| 749 | Protein | Wild-Type WT1 Peptide v1 (A1) |
| 750 | Protein | Wild-Type WT1 Peptide v2 |
| 751 | Protein | Wild-Type WT1 Peptide v3 |
| 752 | Protein | Wild-Type WT1 Peptide v5 |
| 753 | Protein | Wild-Type WT1 Peptide v8 |
| 754 | Protein | Wild-Type WT1 Peptide v4 |
| 755 | Protein | Wild-Type WT1 Peptide v7 |
| 756 | Protein | Wild-Type WT1 Peptide v9 |
| 757 | Protein | Wild-Type WT1 Peptide v6 |
| 758 | Protein | Adpgk + Dpagt1 Insert |
| 759 | Protein | Adpgk Minigene Insert |
| 760 | Protein | Dpagt1 Minigene Insert |
| 761 | Protein | AH1 Heteroclitic Peptide |
| 762 | Protein | FLAG Tag |
| 763 | Protein | AR_T878A 21mer |
| 764 | Protein | AR_L702H 21mer |
| 765 | Protein | AR_W742C 21mer |
| 766 | Protein | AR_H875Y 21mer |
| 767 | Protein | AR_F877L 21mer |
| 768 | Protein | AR_H875Y_T878A 24mer |
| 769 | Protein | FGFR3_S249C 21mer |

-continued

| SEQ ID NO | Type | Description |
|---|---|---|
| 770 | Protein | RXRA__S427F 21mer |
| 771 | Protein | FBXW7__R505G 21mer |
| 772 | Protein | NFE2L2__E79K 21mer |
| 773 | Protein | FGFR3__R248C 21mer |
| 774 | Protein | ESR1__K303R 21mer |
| 775 | Protein | ESR1__D538G 21mer |
| 776 | Protein | ESR1__Y537S 21mer |
| 777 | Protein | ESR1__Y537N 21mer |
| 778 | Protein | ESR1__Y537C 21mer |
| 779 | Protein | ESR1__E380Q 21mer |
| 780 | Protein | SMAD4__R361C 21mer |
| 781 | Protein | GNAS__R201C 21mer |
| 782 | Protein | GNAS__R201H 21mer |
| 783 | Protein | CTNNB1__S37F 21mer |
| 784 | Protein | CTNNB1__S37C 21mer |
| 785 | Protein | FBXW7__R505C 21mer |
| 786 | Protein | IDH1__R132C 21mer |
| 787 | Protein | IDH1__R132G 21mer |
| 788 | Protein | IDH1__R132H 21mer |
| 789 | Protein | IDH1__R132S 21mer |
| 790 | Protein | IDH2__R172K 21mer |
| 791 | Protein | CEACAM5__A0301 9mer |
| 792 | Protein | MAGEA6__A0301 9mer |
| 793 | Protein | CEACAM5__B0702 9mer |
| 794 | Protein | MAGEA4__B0702 9mer |
| 795 | Protein | GAGE1__B0702 9mer |
| 796 | Protein | CEACAM5__A2402 9mer |
| 797 | Protein | NYESO1__A0201 9mer |
| 798 | Protein | CEACAM5__A0201 9mer |
| 799 | Protein | STEAP1__A0201 9mer |
| 800 | Protein | STEAP1__A2402 9mer |
| 801 | Protein | RNF43__B0702 9mer |
| 802 | Protein | SSX2__A0201 9mer |
| 803 | Protein | SART3__A0201 9mer |
| 804 | Protein | PAGE4__A0201 9mer |
| 805 | Protein | PSMA__A2402 9mer |
| 806 | Protein | PSA__A0301 9mer |
| 807 | Protein | NUF2__A0201 9mer |
| 808 | Protein | NUF2__A2402 9mer |
| 809 | Protein | KLHL7__A2402 9mer |
| 810 | Protein | MAGEA3__A2402 9mer |
| 811 | Protein | GAGE1__A0301 9mer |
| 812 | Protein | MAGEA3__A0301 9mer |
| 813 | Protein | NYESO1__B0702 9mer |
| 814 | Protein | MAGEA3__B0702 9mer |
| 815 | Protein | PRAME__A0201 9mer |
| 816 | Protein | hTERT__A0201__A2402 9mer |
| 817 | Protein | MAGEA3__A0201__A2402 9mer |
| 818 | Protein | SURVIVIN__A0201 9mer |
| 819 | Protein | SURVIVIN__A2402 9mer |
| 820 | Protein | CEACAM5__A0201 9mer |
| 821 | Protein | Linker |
| 822 | Protein | Linker |
| 823 | Protein | Linker |
| 824 | Protein | Linker |
| 825 | Protein | Linker |
| 826 | Protein | Linker |
| 827 | Protein | Linker |
| 828 | Protein | Linker |
| 829 | Protein | Linker |
| 830 | Protein | ZNF814__D404E |
| 831 | Protein | KRTAP1-5__I88T |
| 832 | Protein | KRTAP4-11__L161V |
| 833 | Protein | HRAS__G13V |
| 834 | Protein | TRIM48__Y192H |
| 835 | Protein | PTEN__R130N |
| 836 | Protein | POLE__V411L |
| 837 | Protein | POLE__P286R |
| 838 | Protein | PIK3CA__R88N |
| 839 | Protein | PGM5__I98V |
| 840 | Protein | MBOAT2__R43N |
| 841 | Protein | KIAA2026__R574C |
| 842 | Protein | FBXW7__R465C |
| 843 | Protein | C12orf4__R335N |
| 844 | Protein | ZBTB20__p.Pro692LeufsTer43 |
| 845 | Protein | XYLT2__p.Gly529AlafsTer78 |
| 846 | Protein | WNT16__p.Gly167AlafsTer17 |

| SEQ ID NO | Type | Description |
|---|---|---|
| 847 | Protein | UBR5_p.Glu2121LysfsTer28 |
| 848 | Protein | TGFBR2_p.Glu150GlyfsTer35 |
| 849 | Protein | SVIL_p.Met1863TrpfsTer44 |
| 850 | Protein | RNF43_p.Gly659ValfsTer41 |
| 851 | Protein | PLEKHA6_p.Val328TyrfsTer172 |
| 852 | Protein | LARP4B_p.Thr163HisfsTer47 |
| 853 | Protein | FHOD3_p.Ser336ValfsTer138 |
| 854 | Protein | DOCK3_p.Pro1852GlnfsTer45 |
| 855 | Protein | BMPR2_p.Asn583ThrfsTer44 |
| 856 | Protein | ARID1A_p.Asp1850ThrfsTer33 |
| 857 | Protein | ADAM28_p.Asn75LysfsTer15 |
| 858 | Protein | ACVR2A_p.Lys435GlufsTer19 |
| 859 | Protein | NSCLC HOT EVO2 EAAAK.G4S (A) |
| 860 | Protein | NSCLC HOT G4S (A) |
| 861 | Protein | NSCLC HOT EVO2 EAAAK-G4S mix (A) |
| 862 | Protein | NSCLC HOT EVO2 EAAAK.i20 (A) |
| 863 | Protein | NSCLC HOT EVO2 G4S.i20 (A) |
| 864 | Protein | NSCLC HOT EVO 2 G4S LS#1 (A) |
| 865 | Protein | NSCLC HOT EVO 2 G4S LS#2 (A) |
| 866 | Protein | PANC HOT EVO2 EAAAK.G4S (A) |
| 867 | Protein | PANC HOT G4S (A) |
| 868 | Protein | PANC HOT EVO2 EAAAK-G4S mix (A) |
| 869 | Protein | PANC HOT EVO2 EAAAK.i20 (A) |
| 870 | Protein | PANC HOT EVO2 G4S.i20 (A) |
| 871 | Protein | ProStar EVO2 EAAAK.G4S (A) |
| 872 | Protein | ProStar EVO2 G4S (A) |
| 873 | Protein | ProStar EVO2 EAAAK-G4S mix (A) |
| 874 | Protein | ProStar EVO2 EAAAK.i20 (A) |
| 875 | Protein | ProStar EVO2 G4S.i20 (A) |
| 876 | Protein | ProStar EVO 2 G4S LS#1 (A) |
| 877 | Protein | ProStar EVO 2 G4S LS#2 (A) |
| 878 | Protein | Bladder HOT EVO2 EAAAK.G4S (A) |
| 879 | Protein | Bladder HOT G4S (A) |
| 880 | Protein | Bladder HOT EVO2 EAAAK-G4S mix (A) |
| 881 | Protein | Bladder HOT EVO2 EAAAK.i20 (A) |
| 882 | Protein | Bladder HOT EVO2 G4S.i20 (A) |
| 883 | Protein | Breast HOT EVO2 EAAAK.G4S (A) |
| 884 | Protein | Breast HOT G4S (A) |
| 885 | Protein | Breast HOT EVO2 EAAAK-G4S mix (A) |
| 886 | Protein | Breast HOT EVO2 EAAAK.i20 (A) |
| 887 | Protein | Breast HOT EVO2 G4S.i20 (A) |
| 888 | Protein | Bladder HOT EVO2 EAAAK.G4S (B) |
| 889 | Protein | Bladder HOT EVO2 EAAAK.i20 (B) |
| 890 | Protein | Bladder HOT EVO2 EAAAK.G4S NUF minigene (B) |
| 891 | Protein | Bladder HOT EVO2 EAAAK.i20_NUF minigene (B) |
| 892 | Protein | ProStar EVO2 EAAAK.G4S (B) |
| 893 | Protein | ProStar EVO2 EAAAK.i20 (B) |
| 894 | Protein | NSCLC HOT EVO2 EAAAK.G4S (B) |
| 895 | Protein | NSCLC HOT EVO2 EAAAK.i20 (B) |
| 896 | Protein | Uterine HOT EVO2 EAAAK.G4S |
| 897 | Protein | Uterine HOT EVO2 EAAAK.i20 |
| 898 | Protein | Ovarian HOT EVO2 EAAAK.G4S (C) |
| 899 | Protein | Ovarian HOT EVO2 EAAAK.i20 (C) |
| 900 | Protein | LGG HOT EVO2 EAAAK.G4S NUF minigene (C) |
| 901 | Protein | LGG HOT EVO2 EAAAK.i20_NUF minigene (C) |
| 902 | Protein | CRC MSS EVO2 EAAAK.G4S (C) |
| 903 | Protein | CRC MSS EVO2 EAAAK.i20 (C) |
| 904 | Protein | Uterine A24 HOT |
| 905 | Protein | NSCLC A24 HOT |
| 906 | Protein | Prostar A24 HOT |
| 907 | Protein | Breast A24 HOT |
| 908 | Protein | Pancreas A24 HOT |
| 909 | Protein | NSCLC HS + HC |
| 910 | Protein | NSCLC HS + MG |
| 911 | Protein | NSCLC HC + MG |
| 912 | Protein | NSCLC HC only |
| 913 | Protein | Prostar HS + HC |
| 914 | Protein | Prostar HS + MG |
| 915 | Protein | Prostar HC + MG |
| 916 | Protein | Prostar HC only |
| 917 | Protein | DNA Mismatch Repair HOT EVO2 EAAAK.G4S |
| 918 | Protein | Head & Neck HOT EVO2 EAAAK.G4S |
| 919 | Protein | Head & Neck HOT EVO2 EAAAK.i20 |
| 920 | Protein | LLO Signal Sequence |
| 921 | Protein | ActA Signal Sequence |
| 922 | Protein | SIINFEKL Tag |
| 923 | DNA | NSCLC HOT EVO2 EAAAK.G4S |

-continued

| SEQ ID NO | Type | Description |
|---|---|---|
| 924 | DNA | NSCLC HOT G4S |
| 925 | DNA | NSCLC HOT EVO2 EAAAK-G4S mix |
| 926 | DNA | NSCLC HOT EVO2 EAAAK.i20 |
| 927 | DNA | NSCLC HOT EVO2 G4S.i20 |
| 928 | DNA | NSCLC HOT EVO 2 G4S LS#1 |
| 929 | DNA | NSCLC HOT EVO 2 G4S LS#2 |
| 930 | DNA | NSCLC HOT EVO2 EAAAK G4S |
| 931 | DNA | NSCLC HOT G4S |
| 932 | DNA | NSCLC HOT EVO2 EAAAK-G4S mix |
| 933 | DNA | NSCLC HOT EVO2 EAAAK i20 |
| 934 | DNA | NSCLC HOT EVO2 G4S i20 |
| 935 | DNA | NSCLC HOT EVO 2 G4S LS#1 |
| 936 | DNA | NSCLC HOT EVO 2 G4S LS#2 |
| 937 | DNA | NSCLC HOT EVO2 EAAAK.G4S |
| 938 | DNA | NSCLC HOT EVO2 EAAAK.i20 |
| 939 | DNA | NSCLC HOT EVO2 EAAAK G4S v2 |
| 940 | DNA | NSCLC HOT EVO2 EAAAK i20 v2 |
| 941 | DNA | In house NSCLC HOT EVO2 EAAAKi20 |
| 942 | DNA | ProStar EVO2 EAAAK.G4S |
| 943 | DNA | ProStar EVO2 G4S |
| 944 | DNA | ProStar EVO2 EAAAK-G4S mix |
| 945 | DNA | ProStar EVO2 EAAAK.i20 |
| 946 | DNA | ProStar EVO2 G4S.i20 |
| 947 | DNA | ProStar EVO 2 G4S LS#1 |
| 948 | DNA | ProStar EVO 2 G4S LS#2 |
| 949 | DNA | ProStar EVO2 EAAAK.G4S |
| 950 | DNA | ProStar EVO2 G4S |
| 951 | DNA | ProStar EVO2 EAAAK-G4S mix |
| 952 | DNA | ProStar EVO2 EAAAK.i20 |
| 953 | DNA | ProStar EVO2 G4S.i20 |
| 954 | DNA | ProStar EVO 2 G4S LS#1 |
| 955 | DNA | ProStar EVO 2 G4S LS#2 |
| 956 | DNA | ProStar EVO2 EAAAK.G4S |
| 957 | DNA | ProStar EVO2 EAAAK.i20 |
| 958 | DNA | ProStar EVO2 EAAAK G4S v4 |
| 959 | DNA | ProStar EVO2 EAAAK i20 v4 |
| 960 | DNA | In house NSCLC HOT EVO2 EAAAKi20 |
| 961 | DNA | Bladder HOT Evo2 G4S |
| 962 | DNA | Bladder HOT Evo2 G4S |
| 963 | DNA | Bladder HOT EVO2 EAAAK.G4S |
| 964 | DNA | Bladder HOT G4S |
| 965 | DNA | Bladder HOT EVO2 EAAAK-G4S mix |
| 966 | DNA | Bladder HOT EVO2 EAAAK.i20 |
| 967 | DNA | Bladder HOT EVO2 G4S.i20 |
| 968 | DNA | Bladder HOT EVO2 EAAAK.G4S |
| 969 | DNA | Bladder HOT G4S |
| 970 | DNA | Bladder HOT EVO2 EAAAK-G4S mix |
| 971 | DNA | Bladder HOT EVO2 EAAAK.i20 |
| 972 | DNA | Bladder HOT EVO2 G4S.i20 |
| 973 | DNA | Bladder HOT EVO2 EAAAK G4S v2 |
| 974 | DNA | Bladder HOT EVO2 EAAAK i20 v2 |
| 975 | DNA | Bladder HOT EVO2 EAAAK G4S NUF minigene v3 |
| 976 | DNA | Bladder HOT EVO2 EAAAK i20 NUF minigene v3 |
| 977 | DNA | Bladder HOT EVO2 EAAAK G4S NUF minigene v3 |
| 978 | DNA | Bladder HOT EVO2 EAAAK i20 NUF minigene v3 |
| 979 | DNA | Breast HOT EVO2 EAAAK.G4S |
| 980 | DNA | Breast HOT G4S |
| 981 | DNA | Breast HOT EVO2 EAAAK-G4S mix |
| 982 | DNA | Breast HOT EVO2 EAAAK.i20 |
| 983 | DNA | Breast HOT EVO2 G4S.i20 |
| 984 | DNA | Breast HOT EVO2 EAAAK.G4S |
| 985 | DNA | Breast HOT G4S |
| 986 | DNA | Breast HOT EVO2 EAAAK-G4S mix |
| 987 | DNA | Breast HOT EVO2 EAAAK.i20 |
| 988 | DNA | Breast HOT EVO2 G4S.i20 |
| 989 | DNA | PANC HOT EVO2 EAAAK G4S |
| 990 | DNA | PANC HOT G4S |
| 991 | DNA | PANC HOT EVO2 EAAAK-G4S mix |
| 992 | DNA | PANC HOT EVO2 EAAAK i20 |
| 993 | DNA | PANC HOT EVO2 G4S i20 |
| 994 | DNA | PANC HOT EVO2 EAAAK G4S |
| 995 | DNA | PANC HOT G4S |
| 996 | DNA | PANC HOT EVO2 EAAAK-G4S mix |
| 997 | DNA | PANC HOT EVO2 EAAAK i20 |
| 998 | DNA | PANC HOT EVO2 G4S i20 |
| 999 | DNA | CRC MSS EVO2 EAAAK G4S |
| 1000 | DNA | CRC MSS EVO2 EAAAK i20 |

-continued

| SEQ ID NO | Type | Description |
|---|---|---|
| 1001 | DNA | CRC MSS EVO2 EAAAK G4S |
| 1002 | DNA | CRC MSS EVO2 EAAAK i20 |
| 1003 | Protein | Lm-AH1 21mer Insert |
| 1004 | Protein | Lm-AH1 Minigene Insert |
| 1005 | Protein | Lm-AH1 HC Insert |
| 1006 | Protein | AH1 Wild Type |
| 1007 | Protein | SIINFEKL Peptide |
| 1008 | Protein | Linker |
| 1009 | Protein | CEACAM5_A0201 Native Peptide |
| 1010 | Protein | CEACAM5_A0201 Native Peptide |
| 1011 | Protein | CEACAM5_A0301 Native Peptide |
| 1012 | Protein | CEACAM5_A2402 Native Peptide |
| 1013 | Protein | CEACAM5_B0702 Native Peptide |
| 1014 | Protein | GAGE1_A0301 Native Peptide |
| 1015 | Protein | GAGE1_B0702 Native Peptide |
| 1016 | Protein | hTERT_A0201_A2402 Native Peptide |
| 1017 | Protein | KLHL7_A2402 Native Peptide |
| 1018 | Protein | MAGEA3_A0201_A2402 Native Peptide |
| 1019 | Protein | MAGEA3_A0301 Native Peptide |
| 1020 | Protein | MAGEA3_A2402 Native Peptide |
| 1021 | Protein | MAGEA3_B0702 Native Peptide |
| 1022 | Protein | MAGEA4_B0702 Native Peptide |
| 1023 | Protein | MAGEA6_A0301 Native Peptide |
| 1024 | Protein | NUF2_A0201 Native Peptide |
| 1025 | Protein | NUF2_A2402 Native Peptide |
| 1026 | Protein | NYESO1_A0201 Native Peptide |
| 1027 | Protein | NYESO1_B0702 Native Peptide |
| 1028 | Protein | PAGE4_A0201 Native Peptide |
| 1029 | Protein | PRAME_A0201 Native Peptide |
| 1030 | Protein | PSA_A0301 Native Peptide |
| 1031 | Protein | PSMA_A2402 Native Peptide |
| 1032 | Protein | RNF43_B0702 Native Peptide |
| 1033 | Protein | SART3_A0201 Native Peptide |
| 1034-1052 | DNA | NSCLC KRAS G12C Sequences |
| 1053-1071 | DNA | NSCLC EGFR L858R Sequences |
| 1072-1090 | DNA | NSCLC KRAS G12D Sequences |
| 1091-1109 | DNA | NSCLC U2AF S34F Sequences |
| 1110-1128 | DNA | NSCLC BRAF V600E Sequences |
| 1129-1147 | DNA | NSCLC KRAS G12V Sequences |
| 1148-1166 | DNA | NSCLC PIK3CA E545K Sequences |
| 1167-1185 | DNA | NSCLC TP53 R158L Sequences |
| 1186-1204 | DNA | NSCLC KRAS G12A Sequences |
| 1205-1223 | DNA | NSCLC EGFR L861Q Sequences |
| 1224-1242 | DNA | NSCLC TP53 R273L Sequences |
| 1243-1260 | DNA | Prostate SPOP F133V Sequences |
| 1261-1278 | DNA | Prostate CHEK2 K373E Sequences |
| 1279-1296 | DNA | Prostate RGPD8 P1760A Sequences |
| 1297-1314 | DNA | Prostate ANKRD36C I634T Sequences |
| 1315-1332 | DNA | Prostate ANKRD36C D629Y Sequences |
| 1333-1350 | DNA | Prostate SPOP W131G Sequences |
| 1351-1368 | DNA | Prostate ANKRD36C D626N Sequences |
| 1369-1386 | DNA | Prostate SPOP F133L Sequences |
| 1387-1404 | DNA | Prostate AR T878A Sequences |
| 1405-1422 | DNA | Prostate AR L702H Sequences |
| 1423-1440 | DNA | Prostate AR H875Y Sequences |
| 1441-1458 | DNA | Prostate AR F877L Sequences |
| 1459-1476 | DNA | Prostate AR H875Y_T878A Sequences |
| 1477-1494 | DNA | Bladder PIK3CA E545K Sequences |
| 1495-1512 | DNA | Bladder FGFR3 S249C Sequences |
| 1513-1530 | DNA | Bladder TP53 R248Q Sequences |
| 1531-1548 | DNA | Bladder PIK3CA E542K Sequences |
| 1549-1566 | DNA | Bladder RXRA S427F Sequences |
| 1567-1584 | DNA | Bladder FBXW7 R505G Sequences |
| 1585-1602 | DNA | Bladder TP53 R280T Sequences |
| 1603-1620 | DNA | Bladder NFE2L2 E79K Sequences |
| 1621-1638 | DNA | Bladder FGFR3 R248C Sequences |
| 1639-1656 | DNA | Bladder TP53 K132N Sequences |
| 1657-1674 | DNA | Bladder TP53 R248W Sequences |
| 1675-1692 | DNA | Bladder TP53 R175H Sequences |
| 1693-1710 | DNA | Bladder TP53 R273C Sequences |
| 1711-1720 | DNA | Breast PIK3CA E545K Sequences |
| 1721-1730 | DNA | Breast PIK3CA E542K Sequences |
| 1731-1740 | DNA | Breast PIK3CA H1047R Sequences |
| 1741-1750 | DNA | Breast AKT1 E17K Sequences |
| 1751-1760 | DNA | Breast PIK3CA H1047L Sequences |
| 1761-1770 | DNA | Breast PIK3CA Q546K Sequences |
| 1771-1780 | DNA | Breast PIK3CA E545A Sequences |

-continued

| SEQ ID NO | Type | Description |
|---|---|---|
| 1781-1790 | DNA | Breast PIK3CA E545G Sequences |
| 1791-1800 | DNA | Breast ESR1 K303R Sequences |
| 1801-1810 | DNA | Breast ESR1 D538G Sequences |
| 1811-1820 | DNA | Breast ESR1 Y537S Sequences |
| 1821-1830 | DNA | Breast ESR1 Y537N Sequences |
| 1831-1840 | DNA | Breast ESR1 Y537C Sequences |
| 1841-1850 | DNA | Breast ESR1 E380Q Sequences |
| 1851-1860 | DNA | Pancreas KRAS G12C Sequences |
| 1861-1870 | DNA | Pancreas KRAS G12D Sequences |
| 1871-1880 | DNA | Pancreas U2AF1 S34F Sequences |
| 1881-1890 | DNA | Pancreas KRAS G12V Sequences |
| 1891-1900 | DNA | Pancreas TP53 R248Q Sequences |
| 1901-1910 | DNA | Pancreas TP53 R248W Sequences |
| 1911-1920 | DNA | Pancreas TP53 R175H Sequences |
| 1921-1930 | DNA | Pancreas TP53 R273C Sequences |
| 1931-1940 | DNA | Pancreas KRAS G12R Sequences |
| 1941-1950 | DNA | Pancreas KRAS Q61H Sequences |
| 1951-1960 | DNA | Pancreas TP53 R282W Sequences |
| 1961-1970 | DNA | Pancreas TP53 R273H Sequences |
| 1971-1980 | DNA | Pancreas TP53 G245S Sequences |
| 1981-1990 | DNA | Pancreas SMAD4 R361C Sequences |
| 1991-2000 | DNA | Pancreas GNAS R201C Sequences |
| 2001-2010 | DNA | Pancreas GNAS R201H Sequences |
| 2011-2014 | DNA | Colorectal KRAS G12C Sequences |
| 2015-2018 | DNA | Colorectal KRAS G12D Sequences |
| 2019-2022 | DNA | Colorectal BRAF V600E Sequences |
| 2023-2026 | DNA | Colorectal KRAS G12V Sequences |
| 2027-2030 | DNA | Colorectal PIK3CA E545K Sequences |
| 2031-2034 | DNA | Colorectal TP53 R248W Sequences |
| 2035-2038 | DNA | Colorectal TP53 R175H Sequences |
| 2039-2042 | DNA | Colorectal TP53 R273C Sequences |
| 2043-2046 | DNA | Colorectal PIK3CA H1047R Sequences |
| 2047-2050 | DNA | Colorectal TP53 R282W Sequences |
| 2051-2054 | DNA | Colorectal TP53 R273H Sequences |
| 2055-2058 | DNA | Colorectal KRAS G13D Sequences |
| 2059-2077 | DNA | NSCLC CEACAM5 A0301 Sequences |
| 2078-2096 | DNA | NSCLC MAGEA6 A0301 Sequences |
| 2097-2115 | DNA | NSCLC CEACAM5 B0702 Sequences |
| 2116-2134 | DNA | NSCLC MAGEA4 B0702 Sequences |
| 2135-2153 | DNA | NSCLC GAGE1 B0702 Sequences |
| 2154-2172 | DNA | NSCLC CEACAM5 A2402 Sequences |
| 2173-2191 | DNA | NSCLC NYESO1 A0201 Sequences |
| 2192-2210 | DNA | NSCLC CEACAM5 A0201 Sequences |
| 2211-2228 | DNA | Prostate MAGEA4 B0702 Sequences |
| 2229-2246 | DNA | Prostate STEAP1 A0201 Sequences |
| 2247-2264 | DNA | Prostate STEAP1 A2402 Sequences |
| 2265-2282 | DNA | Prostate SSX2 A0201 Sequences |
| 2283-2300 | DNA | Prostate SART3 A0201 Sequences |
| 2301-2318 | DNA | Prostate PAGE4 A0201 Sequences |
| 2319-2336 | DNA | Prostate PSMA A2402 Sequences |
| 2337-2354 | DNA | Prostate PSA A0301 Sequences |
| 2355-2372 | DNA | Bladder GAGE1 B0702 Sequences |
| 2373-2390 | DNA | Bladder NYESO1 A0201 Sequences |
| 2391-2408 | DNA | Bladder NUF2 A0201 Sequences |
| 2409-2426 | DNA | Bladder NUF2 A2402 Sequences |
| 2427-2444 | DNA | Bladder KLHL7 A2402 Sequences |
| 2445-2462 | DNA | Bladder MAGEA3 A2402 Sequences |
| 2463-2480 | DNA | Bladder GAGE1 A0301 Sequences |
| 2481-2498 | DNA | Bladder MAGEA3 A0301 Sequences |
| 2499-2516 | DNA | Bladder NYESO1 B0702 Sequences |
| 2517-2534 | DNA | Bladder MAGEA3 B0702 Sequences |
| 2535-2544 | DNA | Breast CEACAM5 A0301 Sequences |
| 2545-2554 | DNA | Breast CEACAM5 B0702 Sequences |
| 2555-2564 | DNA | Breast CEACAM5 A2402 Sequences |
| 2565-2574 | DNA | Breast CEACAM5 A0201 Sequences |
| 2575-2584 | DNA | Breast STEAP1 A0201 Sequences |
| 2585-2594 | DNA | Breast STEAP1 A2402 Sequences |
| 2595-2604 | DNA | Breast RNFF43 B0702 Sequences |
| 2605-2614 | DNA | Breast MAGEA3 A2402 Sequences |
| 2615-2624 | DNA | Breast MAGEA3 A0301 Sequences |
| 2625-2634 | DNA | Breast PRAME A0201 Sequences |
| 2635-2644 | DNA | Breast hTERT A0201_A2402 Sequences |
| 2645-2654 | DNA | Pancreas CEACAM5 A0301 Sequences |
| 2655-2664 | DNA | Pancreas CEACAM5 B0702 Sequences |
| 2665-2674 | DNA | Pancreas CEACAM5 A2402 Sequences |
| 2675-2684 | DNA | Pancreas CEACAM5 A0201 Sequences |
| 2685-2694 | DNA | Pancreas STEAP1 A0201 Sequences |

-continued

| SEQ ID NO | Type | Description |
|---|---|---|
| 2695-2704 | DNA | Pancreas STEAP1 A2402 Sequences |
| 2705-2714 | DNA | Pancreas MAGEA3 A0301 Sequences |
| 2715-2724 | DNA | Pancreas PRAME A0201 Sequences |
| 2725-2734 | DNA | Pancreas hTERT A0201_A2402 Sequences |
| 2735-2744 | DNA | Pancreas MAGEA3 A0201_A2402 Sequences |
| 2745-2754 | DNA | Pancreas SURVIVIN A0201 Sequences |
| 2755-2764 | DNA | Pancreas SURVIVIN A2402 Sequences |
| 2765-2768 | DNA | Colorectal CEACAM5 A0301 Sequences |
| 2769-2772 | DNA | Colorectal MAGEA6 A0301 Sequences |
| 2773-2776 | DNA | Colorectal CEACAM5 B0702 Sequences |
| 2777-2780 | DNA | Colorectal MAGEA4 B0702 Sequences |
| 2781-2784 | DNA | Colorectal GAGE1 B0702 Sequences |
| 2785-2788 | DNA | Colorectal CEACAM5 A2402 Sequences |
| 2789-2792 | DNA | Colorectal NYESO1 A0201 Sequences |
| 2793-2796 | DNA | Colorectal STEAP1 A0201 Sequences |
| 2797-2800 | DNA | Colorectal RNF43 B0702 Sequences |
| 2801-2804 | DNA | Colorectal MAGEA3 A0201_A2402 Sequences |
| 2805-2822 | DNA | Prostate AR-W742C Sequences |
| 2823 | DNA | NSCLC STEAP1 A0201 Sequence |
| 2824 | DNA | NSCLC STEAP1 S2402 Sequence |
| 2825 | DNA | NSCLC RNF43 B0702 Sequence |
| 2826 | DNA | Prostate CEACAM5 B0702 Sequence |
| 2827 | DNA | Prostate RNF43 B0702 Sequence |
| 2828 | DNA | Bladder CEACAM5 A0301 Sequence |
| 2829 | DNA | Bladder CEACAM5 A0201 Sequence |
| 2830 | DNA | Bladder RNF43 B0702 Sequence |
| 2831 | DNA | Bladder PRAME A0201 Sequence |
| 2832 | DNA | NSCLC HS + HC |
| 2833 | DNA | NSCLC HS + MG |
| 2834 | DNA | NSCLC HS + MG |
| 2835 | DNA | NSCLC HC + MG |
| 2836 | DNA | NSCLC HC only |
| 2837 | DNA | NSCLC HC only |
| 2838 | DNA | Prostar HS + HC |
| 2839 | DNA | Prostar HS + MG |
| 2840 | DNA | Prostar HC + MG |
| 2841 | DNA | Prostar HC + MG |
| 2842 | DNA | Prostar HC only |
| 2843 | DNA | NSCLC HOT EVO2 EAAAK.G45 |
| 2844 | DNA | NSCLC HOT EVO2 EAAAK.i20 |
| 2845 | DNA | NSCLC HOT EVO2 EAAAK G45 v2 |
| 2846 | DNA | NSCLC HOT EVO2 EAAAK i20 v2 |
| 2847 | DNA | Prostar HC + MG |
| 2848 | DNA | NSCLC HS + MG |

EXAMPLES

Example 1. Design of ADXS-HOT Constructs for Tumor-Associated Proteins

We selected seven initial tumor-associated proteins with recurrent cancer mutations on which to focus preclinical development efforts for ADXS-HOT constructs (see Table 1). These seven tumor-associated proteins were selected because they have recurrent cancer mutations commonly presented in a large number of patients across multiple cancer types. Other ADXS-HOT constructs in production target commonly observed tumor drivers across multiple cancers, as well as additional mutated gene targets commonly observed in major cancer types like non-small cell lung cancer, colorectal cancer, breast cancer, ovarian cancer, head and neck cancer, and others.

TABLE 1

Biomarker Expression Initial Selected Tumor Targets

| ADXS- | % Patients with Mutation (All Cancers - Combined Cohort)* | % Patients with Mutation (Specific Cancers)* |
|---|---|---|
| TP53m (mutated) | 36% | Ovarian (93%), lung squamous cell carcinoma (83%), head and neck (67%), esophageal adenocarcinoma (65%), colorectal (52%), bladder (52%), lung adenocarcinoma (51%), breast (31%), glioblastoma multiforme (28%), endometrial (28%), diffuse large B-cell lymphoma (22%), melanoma (17%), chronic lymphocytic leukemia (10%), acute myeloid leukemia (8%), multiple myeloma (7%), kidney clear cell (3%) |
| PIK3CAm | 14% | Endometrial (53%), breast (32%), colorectal (19%), head and neck (18%), bladder (18%), lung squamous cell carcinoma (15%), glioblastoma multiforme (10%), lung adenocarcinoma (4%) |

TABLE 1-continued

Biomarker Expression Initial Selected Tumor Targets

| ADXS- | % Patients with Mutation (All Cancers - Combined Cohort)* | % Patients with Mutation (Specific Cancers)* |
|---|---|---|
| PIK3R1m | 3% | Endometrial (33%), glioblastoma multiforme (11%), breast (2%) |
| PTENm | 7% | Endometrial (65%), glioblastoma multiforme (30%), breast (3%), head and neck (2%) |
| RASm (KRAS, NRAS, HRAS) | 7% | KRAS: colorectal (43%), lung adenocarcinoma (26%), endometrial (21%), multiple myeloma (21%), acute myeloid leukemia (4%), bladder (1%) NRAS: melanoma (23%), multiple myeloma (17%), colorectal (9%), acute myeloid leukemia (7%) HRAS: bladder (5%), head and neck (3%) |
| BRAFm | 3% | Melanoma (73%), colorectal cancer (9%), lung adenocarcinoma (6%), multiple myeloma (6%), diffuse large B-cell lymphoma (5%) |
| EGFRm | 4% | Glioblastoma multiforme (26%), lung adenocarcinoma (10%), lung squamous cell carcinoma (3%) |

*% Expression as represented in the BROAD Institute's Tumor Portal dataset

For each recurrent cancer mutation included in the constructs, a peptide of 21 amino acids in length was designed. In some cases, however, a peptide of a different length was used, such as 20 amino acids or 24 amino acids (e.g., with 9 amino acids flanking N-terminal and 10 amino acids flanking C-terminal, or with 10 amino acids flanking N-terminal and 13 amino acids flanking C-terminal). And in some cases, peptides comprising 2 or 3 recurrent cancer mutations were designed because of the close proximity of the mutated residues to each other in the protein. Examples of such peptides that are 23, 37, 39, or 53 amino acids in length are disclosed below.

The 21-mer peptides were designed to be fragments of the cancer-associated protein in which the recurrent cancer mutations occurs, including the recurrent cancer mutation and 10 amino acids of flanking sequence on each side. Antigenic peptides were scored by a Kyte and Doolittle hydropathy index with a 21 amino acid window, and peptides scoring above a cutoff of around 1.6 were excluded as they are unlikely to be secretable by Listeria monocytogenes. Constructs were designed with the peptides in multiple different orders generated by randomization. For each ordering of the peptides, constructs were designed with a 3×FLAG tag at the N-terminus and a SIINFEKL (SEQ ID NO: 1007) tag at the C-terminus, or with a 3×FLAG tag and a SIINFEKL (SEQ ID NO: 1007) tag at the C-terminus. Each ordering of the peptides was scored by a Kyte and Doolittle hydropathy index with a sliding 21 amino acid window, and if any region for a particular ordering of peptides scored above a cutoff of around 1.6, the order of the peptides was reshuffled until the ordering of peptides resulted in a polypeptide with no regions scoring above the cutoff.

For the BRAF constructs, 8 recurrent cancer mutations were included in the constructs: G466E; G466V; G469A; G469R; G469S; G469V; V600E; and V600K. The reference wild type BRAF sequence is set forth in SEQ ID NO: 361. Constructs were designed with the peptides comprising the 8 recurrent cancer mutations in 4 different orders from N-terminal to C-terminal. Sequences for the constructs are found in SEQ ID NOS: 1-24. The order of the hotspot mutation 21-mers in SEQ ID NOS: 1-6 is as follows: BRAF\G469V; BRAF\G469R; BRAF\V600E; BRAF\G469S; BRAF\G466V; BRAF\V600K; BRAF\G469A; and BRAF\G466E. The order of the hotspot mutation 21-mers in SEQ ID NOS: 7-12 is as follows: BRAF\V600K; BRAF\G469R; BRAF\G469V, BRAF\G466V, BRAF\G466E; BRAF\V600E; BRAF\G469A; and BRAF\G469S. The order of the hotspot mutation 21-mers in SEQ ID NOS: 13-18 is as follows: BRAF\G469V; BRAF\V600K; BRAF\G469S; BRAF\G466V; BRAF\G469A; BRAF\V600E; BRAF\G466E; and BRAF\G469R. The order of the hotspot mutation 21-mers in SEQ ID NOS: 19-24 is as follows: BRAF\V600E; BRAF\V600K; BRAF\G469A; BRAF\G469S; BRAF\G469R; BRAF\G469V; BRAF\G466V; and BRAF\G466E. Examples of antigenic peptides includes in the constructs are provided in Table 2.

TABLE 2

BRAF Antigenic Peptides.

| BRAF Wild Type | Mutated |
|---|---|
| 466WT:<br>QITVGQRIGSGSFGTVYKGKW (SEQ ID NO: 368) | G466V: QITVGQRIGSVSFGTVYKGKW (SEQ ID NO: 371)<br>G466E: QITVGQRIGSESFGTVYKGKW (SEQ ID NO: 372) |
| 469WT:<br>VGQRIGSGSFGTVYKGKWHGD (SEQ ID NO: 369) | G469R: VGQRIGSGSFRTVYKGKWHGD (SEQ ID NO: 373)<br>G469V: VGQRIGSGSFVTVYKGKWHGD (SEQ ID NO: 374)<br>G469S: VGQRIGSGSFSTVYKGKWHGD (SEQ ID NO: 375)<br>G469A: VGQRIGSGSFATVYKGKWHGD (SEQ ID NO: 376) |
| 600WT:<br>VKIGDFGLATVKSRWSGSHQF (SEQ ID NO: 370) | V600E: VKIGDFGLATEKSRWSGSHQF (SEQ ID NO: 377)<br>V600K: VKIGDFGLATKKSRWSGSHQF (SEQ ID NO: 378) |

For the EGFR constructs, 16 recurrent cancer mutations were included in the constructs: R108K; A289V; G598V; E709A; E709K; G719A; G719C; G719S; L747P; L747S; S768I; T790M; L833V/H835L; T833V; L858R; and L861Q. The reference wild type EGFR sequence is set forth in SEQ ID NO: 362. As indicated by the L833V/H835L and T833V mutations, position 833 can be "H" or "T" in different non-mutated versions of EGFR. In some constructs, the following 16 recurrent cancer mutations were included: R108K; A289V; G598V; E709A; E709K; G719A; G719C; G719S; L747P; L747S; S768I; T790M; L833V/H835L; T833V; L858R; and L861Q. Constructs were designed with the peptides comprising the 8 recurrent cancer mutations in 4 different orders from N-terminal to C-terminal. Sequences for these constructs are set forth in SEQ ID NOS: 25-48. The order of the hotspot mutation 21-mers in SEQ ID NOS: 25-30 is as follows: EGFR\G719S; EGFR\L747P; EGFR\G719C; EGFR\R108K; EGFR\S768I; {EGFR\L833V/H835L 23-mer}; EGFR\T833V; EGFR\E709A; EGFR\G598V; EGFR\T790M; EGFR\E709K; EGFR\A289V; EGFR\L861Q; EGFR\G719A; EGFR\L747S; and EGFR\L858R. The order of the hotspot mutation 21-mers in SEQ ID NOS: 31-36 is as follows: EGFR\T790M; EGFR\S768I; EGFR\G719C; EGFR\R108K; EGFR\L747P; EGFR\G719A; EGFR\L747S; EGFR\E709K; EGFR\T833V; EGFR\L861Q; EGFR\E709A; EGFR\L858R; EGFR\G598V; EGFR\A289V; {EGFR|L833V/H835L-23-mer}; and EGFR\G719S. The order of the hotspot mutation 21-mers in SEQ ID NOS: 37-42 is as follows: EGFR\R108K; EGFR\T833V; EGFR\L747S; EGFR\T790M; EGFR\G719C; EGFR\A289V; EGFR\L858R; EGFR\E709A; EGFR\G719S; EGFR\E709K; EGFR\G719A; EGFR\L747P; EGFR\G598V; EGFR\L861Q; EGFR\S768I; and {EGFR\L833V/H835L-23-mer}. The order of the hotspot mutation 21-mers in SEQ ID NOS: 43-48 is as follows: EGFR\G719A; EGFR|L858R; EGFR\G719C; EGFR\A289V; EGFR\T790M; EGFR\S768I; EGFR\T833V; EGFR\G598V; EGFR\G719S; EGFR\L747S; EGFR\L747P; {EGFR\L833V/H835L 23-mer}; EGFR\E709A; EGFR|R108K; EGFR|L861Q; and EGFR|E709K. In other EGFR constructs, the following 11 recurrent cancer mutations were included: A289V; G598V; E709K; G719A; G719C; G719S; S768I; T790M; L833V/H835L; L858R; and L861Q. Sequences for these constructs are set forth in SEQ ID NOS: 229-235. The order of the hotspot mutation 21-mers in SEQ ID NOS: 229-235 is as follows: EGFR|A289V; EGFR|G598V; EGFR|E709K; EGFR|G719A; EGFR|S768I; EGFR|G719S; EGFR|L861Q; EGFR|T790M; EGFR|G719C; {EGFR|L833V/H835L-23-mer}; and EGFR|L858R. Examples of antigenic peptides includes in the constructs are provided in Table 3.

TABLE 3

EGFR Antigenic Peptides.

| EGFR Wild Type | Mutated |
|---|---|
| 108WT: RIPLENLQIIRGNMYYENSYA (SEQ ID NO: 379) | R108K: RIPLENLQIIKGNMYYENSYA (SEQ ID NO: 391) |
| 289WT: VNPEGKYSFGATCVKKCPRNY (SEQ ID NO: 380) | A289V: VNPEGKYSFGVTCVKKCPRNY (SEQ ID NO: 392) |
| 598WT: GPHCVKTCPAGVMGENNTLVW (SEQ ID NO: 381) | G598V: GPHCVKTCPAVVMGENNTLVW (SEQ ID NO: 393) |
| 709WT: PNQALLRILKETEFKKIKVLG (SEQ ID NO: 382) | E709K: PNQALLRILKKTEFKKIKVLG (SEQ ID NO: 394) E709A: PNQALLRILKATEFKKIKVLG (SEQ ID NO: 395) |
| 719WT: ETEFKKIKVLGSGAFGTVYKG (SEQ ID NO: 383) | G719A: ETEFKKIKVLASGAFGTVYKG (SEQ ID NO: 396) G719S: ETEFKKIKVLSSGAFGTVYKG (SEQ ID NO: 397) G719C: ETEFKKIKVLCSGAFGTVYKG (SEQ ID NO: 398) |
| 747WT: KVKIPVAIKELREATSPKANK (SEQ ID NO: 384) | L747S: KVKIPVAIKESREATSPKANK (SEQ ID NO: 399) L747P: KVKIPVAIKEPREATSPKANK (SEQ ID NO: 400) |
| 768WT: EILDEAYVMASVDNPHVCRLL (SEQ ID NO: 385) | S768I: EILDEAYVMAIVDNPHVCRLL (SEQ ID NO: 401) |
| 790WT: ICLTSTVQLITQLMPFGCLLD (SEQ ID NO: 386) | T790M: ICLTSTVQLIMQLMPFGCLLD (SEQ ID NO: 402) |
| 833WTv1: KGMNYLEDRRLVHRDLAARNVLV (SEQ ID NO: 387) | L833V/H835L (23-mer): KGMNYLEDRRVVLRDLAARNVLV (SEQ ID NO: 403) |
| 833WTv2: KGMNYLEDRRTVHRDLAARNV (SEQ ID NO: 388) | T833V: KGMNYLEDRRVVHRDLAARNV (SEQ ID NO: 404) |
| 858WT: PQHVKITDFGLAKLLGAEEKE (SEQ ID NO: 389) | L858R: PQHVKITDFGRAKLLGAEEKE (SEQ ID NO: 405) |

TABLE 3-continued

EGFR Antigenic Peptides.

| EGFR Wild Type | Mutated |
|---|---|
| 861WT: VKITDFGLAKLLGAEEKEYHA (SEQ ID NO: 390) | L861Q: VKITDFGLAKQLGAEEKEYHA (SEQ ID NO: 406) |

For some of the PIK3CA\constructs, 25 recurrent cancer mutations were included in the constructs: R38C; R38H; E81K; R88Q; R93Q; R93W; R108H; G118D; L334G; N345K; C420R; E453K; E542K; E545A; E545G; E545K; E545Q; Q546K; Q546R; E726K; M1043I; M1043V; H1047L; H1047R; and G1049R. The wild type PIK3CA\reference sequence is set forth in SEQ ID NO: 363. Constructs were designed with the peptides comprising the 25 recurrent cancer mutations in 4 different orders from N-terminal to C-terminal. Sequences for the constructs are found in SEQ ID NOS: 49-72. The order of the hotspot mutation 21-mers in SEQ ID NOS: 49-54 is as follows: PIK3CA\M1043V; PIK3CA\E545G; PIK3CA\E726K; PIK3CA\Q546R; PIK3CA\L334G; PIK3CA\G1049R; PIK3CA\M1043I; PIK3CA\Q546K; PIK3CA\E542K; PIK3CA\R93Q; PIK3CA\H1047R; PIK3CA\R108H; PIK3CA\R93W; PIK3CA\E81K; PIK3CA\R38H; PIK3CA\N345K; PIK3CA\R88Q; PIK3CA\G18D; PIK3CA\E545Q; PIK3CA\H1047L; PIK3CA\E545A; PIK3CA\E453K; PIK3CA\E545K; PIK3CA\R38C; and PIK3CA\C420R. The order of the hotspot mutation 21-mers in SEQ ID NOS: 55-60 is as follows: PIK3CA\E726K; PIK3CA\E81K; PIK3CA\M1043V; PIK3CA\E545A; PIK3CA\E545K; PIK3CA\R38C; PIK3CA\G18D; PIK3CA\R93W; PIK3CA\E545G; PIK3CA\E542K; PIK3CA\G1049R; PIK3CA\N345K; PIK3CA\Q546K; PIK3CA\E453K; PIK3CA\C420R; PIK3CA\H1047L; PIK3CA\L334G; PIK3CA\E545Q; PIK3CA\R88Q; PIK3CA\H1047R; PIK3CA\M1043I; PIK3CA\R93Q; PIK3CA\R08H; PIK3CA\Q546R; and PIK3CA\R38H. The order of the hotspot mutation 21-mers in SEQ ID NOS: 61-66 is as follows: PIK3CA\R108H; PIK3CA\M1043V; PIK3CA\R88Q; PIK3CA\R93W; PIK3CA\R38H; PIK3CA\H1047R; PIK3CA\E545K; PIK3CA\M1043I; PIK3CA\Q546R; PIK3CA\E542K; PIK3CA\N345K PIK3CA\R38C; PIK3CA\E545G; PIK3CA\E81K; PIK3CA\Q546K; PIK3CA\R93Q; PIK3CA\E453K; PIK3CA\G1049R; PIK3CA\E545A; PIK3CA\C420R; PIK3CA\H1047L; PIK3CA\L334G; PIK3CA\G118D; PIK3CA\E726K; and PIK3CA\E545Q. The order of the hotspot mutation 21-mers in SEQ ID NOS: 67-72 is as follows: PIK3CA\N345K; PIK3CA\R38H; PIK3CA\E545K; PIK3CA\G1049R; PIK3CA\H1047L; PIK3CA\E726K; PIK3CA\R88Q; PIK3CA\E8K; PIK3CA\R93Q; PIK3CA\E545Q; PIK3CA\L334G; PIK3CA\R38C; PIK3CA\H1047R; PIK3CA\C420R; PIK3CA\R93W; PIK3CA\Q546K; PIK3CA\M1043V; PIK3CA\M1043I; PIK3CA\E545G; PIK3CA\E545A; PIK3CA\G18D; PIK3CA\E453K; PIK3CA\Q546R; PIK3CA\R108H; and PIK3CA\E542K. In other PIK3CA constructs, 17 recurrent cancer mutations were included in the constructs: R38H; E81K; R88Q; R108H; G118D; N345K; C420R; E542K; E545A; E545G; E545K; Q546K; Q546R; M1043I; H1047L; H1047R; and G1049R. Sequences for the constructs are found in SEQ ID NOS: 236-242. The order of the hotspot mutation 21-mers in SEQ ID NOS: 236-242 is as follows: PIK3CA\E542K; PIK3CA\E545K; PIK3CA\R88Q; PIK3CA\E545A; PIK3CA\H1047R; PIK3CA\E545G; PIK3CA\H1047L; {PIK3CA\Q546K 20-mer}; PIK3CA\R38H; PIK3CA\E8K; PIK3CA\R108H; PIK3CA\N345K; PIK3CA\C420R; PIK3CA\Q546R; PIK3CA\M043I; PIK3CA\G18D; and PIK3CA\G049R. In other PIK3CA\constructs, 8 recurrent cancer mutations were included in the constructs: R88Q; E542K; E545A; E545G; E545K; Q546K; H1047L; and H1047. Sequences for the constructs are found in SEQ ID NOS: 243-249. The order of the hotspot mutation 21-mers in SEQ ID NOS: 243-249 is as follows: PIK3CA\E542K; PIK3CA\E545K; PIK3CA\R88Q; PIK3CA\E545A; PIK3CA\H047R; PIK3CA\E545G; PIK3CA\H047L; and {PIK3CA\Q546K-20-mer}. In other PIK3CA\constructs, 9 recurrent cancer mutations were included in the constructs: R38H; E81K; R108H; G118D; N345K; C420R; Q546R; M1043I; and G1049R. Sequences for the constructs are found in SEQ ID NOS: 250-256. The order of the hotspot mutation 21-mers in SEQ ID NOS: 250-256 is as follows: PIK3CA\R38H; PIK3CA\E8K; PIK3CA\R108H; PIK3CA\N345K; PIK3CA\C420R; PIK3CA\Q546R; PIK3CA\M1043I; PIK3CA\G18D; and PIK3CA\G1049R. Examples of antigenic peptides includes in the constructs are provided in Table 4.

TABLE 4

PIK3CA Antigenic Peptides.

| PIK3CA Wild Type | Mutated |
|---|---|
| 38WT: NGMIVTLECLREATLITIKHE (SEQ ID NO: 407) | R38H: NGMIVTLECLHEATLITIKHE (SEQ ID NO: 424)<br>R38C: NGMIVTLECLCEATLITIKHE (SEQ ID NO: 425) |
| 81WT: VSVTQEAEREEFFDETRRLCD (SEQ ID NO: 408) | E81K: VSVTQEAEREKFFDETRRLCD (SEQ ID NO: 426) |
| 88WT: EREEFFDETRRLCDLRLFQPF (SEQ ID NO: 409) | R88Q: EREEFFDETRQLCDLRLFQPF (SEQ ID NO: 427) |
| 93WT: FDETRRLCDLRLFQPFLKVIE (SEQ ID NO: 410) | R93W: FDETRRLCDLWLFQPFLKVIE (SEQ ID NO: 428)<br>R93Q: FDETRRLCDLQLFQPFLKVIE (SEQ ID NO: 429) |

TABLE 4-continued

PIK3CA Antigenic Peptides.

| PIK3CA Wild Type | Mutated |
|---|---|
| 108WT: FLKVIEPVGNREEKILNREIG (SEQ ID NO: 411) | R108H: FLKVIEPVGNHEEKILNREIG (SEQ ID NO: 430) |
| 118WT: REEKILNREIGFAIGMPVCEF (SEQ ID NO: 412) | G118D: REEKILNREIDFAIGMPVCEF (SEQ ID NO: 431) |
| 334WT: TKSLWVINSALRIKILCATYV (SEQ ID NO: 413) | L334G: TKSLWVINSAGRIKILCATYV (SEQ ID NO: 432) |
| 345WT: RIKILCATYVNVNIRDIDKIY (SEQ ID NO: 414) | N345K: RIKILCATYVKVNIRDIDKIY (SEQ ID NO: 433) |
| 420WT: KGRKGAKEEHCPLAWGNINLF (SEQ ID NO: 415) | C420R: KGRKGAKEEHRPLAWGNINLF (SEQ ID NO: 434) |
| 453WT: LNLWPVPHGLEDLLNPIGVTG (SEQ ID NO: 416) | E453K: LNLWPVPHGLKDLLNPIGVTG (SEQ ID NO: 435) |
| 542WT: KAISTRDPLSEITEQEKDFLW (SEQ ID NO: 417) | E542K: KAISTRDPLSKITEQEKDFLW (SEQ ID NO: 436) |
| 545WT: STRDPLSEITEQEKDFLWSHR (SEQ ID NO: 418) | E545K: STRDPLSEITKQEKDFLWSHR (SEQ ID NO: 437)<br>E545A: STRDPLSEITAQEKDFLWSHR (SEQ ID NO: 438)<br>E545G: STRDPLSEITGQEKDFLWSHR (SEQ ID NO: 439)<br>E545Q: STRDPLSEITQQEKDFLWSHR (SEQ ID NO: 440) |
| 546WT: TRDPLSEITEQEKDFLWSHRH (SEQ ID NO: 419) | Q546K (20-mer): RDPLSEITEKEKDFLWSHRH (SEQ ID NO: 441)<br>Q546K (21-mer): TRDPLSEITEKEKDFLWSHRH (SEQ ID NO: 442)<br>Q546R: TRDPLSEITEREKDFLWSHRH (SEQ ID NO: 443) |
| 726WT: TDILKQEKKDETQKVQMKFLV (SEQ ID NO: 420) | E726K: TDILKQEKKDKTQKVQMKFLV (SEQ ID NO: 444) |
| 1043WT: QEALEYFMKQMNDAHHGGWTT (SEQ ID NO: 421) | M1043I: QEALEYFMKQINDAHHGGWTT (SEQ ID NO: 445)<br>M1043V: QEALEYFMKQVNDAHHGGWTT (SEQ ID NO: 446) |
| 1047WT: EYFMKQMNDAHHGGWTTKMDW (SEQ ID NO: 422) | H1047R: EYFMKQMNDARHGGWTTKMDW (SEQ ID NO: 447)<br>H1047L: EYFMKQMNDALHGGWTTKMDW (SEQ ID NO: 448) |
| 1049WT: FMKQMNDAHHGGWTTKMDWIF (SEQ ID NO: 423) | G1049R: FMKQMNDAHHRGWTTKMDWIF (SEQ ID NO: 449) |

For the PIK3R1 constructs, 3 recurrent cancer mutations were included in the constructs: G376R; N564D; and K567E. The wild type PIK3R1 reference sequence is set forth in SEQ ID NO: 364. Constructs were designed with the peptides comprising the 3 recurrent cancer mutations in 2 different orders from N-terminal to C-terminal. Sequences for these constructs are set forth in SEQ ID NOS: 73-84. The order of the hotspot mutation 21-mers in SEQ ID NOS: 73-78 is as follows: PIK3R1\G376R; PIK3R1\N564D; and PIK3R1\K567E. The order of the hotspot mutation 21-mers in SEQ ID NOS: 79-84 is as follows: PIK3R1\N564D; PIK3R1\K567E; and PIK3R1\G376R. Examples of antigenic peptides includes in the constructs are provided in Table 5.

TABLE 5

PIK3R Antigenic Peptides.

| PIK3R Wild Type | Mutated |
|---|---|
| 376WT: GDYTLTLRKGGNNKLIKIFHR (SEQ ID NO: 450) | G376R: GDYTLTLRKGRNNKLIKIFHR (SEQ ID NO: 453) |
| 564WT: AEYREIDKRMNSIKPDLIQLR (SEQ ID NO: 451) | N564D: AEYREIDKRMDSIKPDLIQLR (SEQ ID NO: 454) |

TABLE 5-continued

PIK3R Antigenic Peptides.

| PIK3R Wild Type | Mutated |
| --- | --- |
| 567WT: REIDKRMNSIKPDLIQLRKTR (SEQ ID NO: 452) | K567E: REIDKRMNSIEPDLIQLRKTR (SEQ ID NO: 455) |

For PIK3CA/PIK3R1 combination constructs, 28 recurrent cancer mutations were included in the constructs: PIK3CA\R38C; PIK3CA\R38H; PIK3CA\E81K; PIK3CA\R88Q; PIK3CA\R93Q; PIK3CA\R93W; PIK3CA\R108H; PIK3CA\G118D; PIK3CA\L334G; PIK3CA\N345K; PIK3CA\C420R; PIK3CA\E453K; PIK3CA\E542K; PIK3CA\E545A; PIK3CA\E545G; PIK3CA\E545K; PIK3CA\E545Q; PIK3CA\Q546K; PIK3CA\Q546R; PIK3CA\E726K; PIK3CA\M1043I; PIK3CA\M1043V; PIK3CA\H1047L; PIK3CA\H1047R; PIK3CA\G1049R; PIK3R1\G376R; PIK3R1\N564D; and PIK3R1\K567E. Constructs were designed with the peptides comprising the 28 recurrent cancer mutations in 4 different orders from N-terminal to C-terminal. Sequences for these constructs are set forth in SEQ ID NOS: 85-108. The order of the hotspot mutation 21-mers in SEQ ID NOS: 85-90 is as follows: PIK3CA\R38C; PIK3CA\N345K; PIK3CA\E726K; PIK3CA\E453K; PIK3CA\R93Q; PIK3CA\H1047R; PIK3CA\E545A; PIK3CA\M1043V; PIK3R1\N564D; PIK3R1\K567E; PIK3CA\E81K; PIK3CA\R108H; PIK3CA\Q546R; PIK3CA\Q546K; PIK3CA\E545Q; PIK3CA\G1049R; PIK3CA\C420R; PIK3CA\H1047L; PIK3CA\R93W; PIK3CA\R88Q; PIK3CA\M1043I; PIK3CA\E545G; PIK3CA\G18D; PIK3CA\R38H; PIK3R1\G376R; PIK3CA\E542K; PIK3CA\E545K; and PIK3CA\L334G. The order of the hotspot mutation 21-mers in SEQ ID NOS: 91-96 is as follows: PIK3CA\R38C; PIK3CA\R108H; PIK3CA\C420R; PIK3CA\R93Q; PIK3CA\E453K; PIK3CA\M1043V; PIK3CA\H1047L; PIK3R1\N564D; PIK3CA\E726K; PIK3CA\G18D; PIK3CA\Q546K; PIK3CA\Q546R; PIK3CA\E542K; PIK3CA\E545K; PIK3CA\G1049R; PIK3CA\M1043I; PIK3CA\L334G; PIK3R1\K567E; PIK3CA\R38H; PIK3R1\G376R; PIK3CA\R93W; PIK3CA\H1047R; PIK3CA\E545G; PIK3CA\E81K; PIK3CA\R88Q; PIK3CA\N345K; PIK3CA\E545A; and PIK3CA\E545Q. The order of the hotspot mutation 21-mers in SEQ ID NOS: 97-102 is as follows: PIK3CA\R108H; PIK3CA\M1043V; PIK3CA\R88Q; PIK3CA\R93W; PIK3CA\R38H; PIK3CA\H1047R; PIK3CA\E545K; PIK3CA\M1043I; PIK3CA\Q546R; PIK3CA\E542K; PIK3CA\N345K; PIK3CA\R38C; PIK3CA\E545G; PIK3CA\E81K; PIK3CA\Q546K; PIK3CA\R93Q; PIK3CA\E453K; PIK3CA\G1049R; PIK3CA\E545A; PIK3CA\C420R; PIK3CA\H1047L; PIK3CA\L334G; PIK3CA\G18D; PIK3CA\E726K; and PIK3CA\E545Q. The order of the hotspot mutation 21-mers in SEQ ID NOS: 103-108 is as follows: PIK3CA\E545Q; PIK3CA\R93W; PIK3CA\H1047R; PIK3CA\G1049R; PIK3CA\N345K; PIK3CA\Q546R; PIK3CA\E545K; PIK3CA\E453K; PIK3CA\L334G; PIK3CA\H1047L; PIK3R1\G376R; PIK3CA\M1043V; PIK3CA\R88Q; PIK3CA\R38H; PIK3CA\G118D; PIK3R1\K567E; PIK3CA\R38C; PIK3CA\E542K; PIK3CA\Q546K; PIK3CA\E726K; PIK3CA\C420R; PIK3CA\E545A; PIK3CA\R93Q; PIK3R1\N564D; PIK3CA\R108H; PIK3CA\M1043I; PIK3CA\E545G; and PIK3CA\E81K.

For the PTEN constructs, 13 recurrent cancer mutations were included in the constructs: Y68H; Y88C; D92E; del121-131; R130G; R130L; R130P; R130Q; C136Y; R142W; Y155C; R173H; and P246L. The wild type PTEN reference sequence is set forth in SEQ ID NO: 365. Constructs were designed with the peptides comprising the 13 recurrent cancer mutations in 4 different orders from N-terminal to C-terminal. Sequences for these constructs are set forth in SEQ ID NOS: 109-132. The order of the hotspot mutation 21-mers in SEQ ID NOS: 109-114 is as follows: PTEN\delta121-131; PTEN\Y88C; PTEN\R130G; PTEN\Y155C; PTEN\D92E; PTEN\C136Y; PTEN\R130Q; PTEN\Y68H; PTEN\R142W; PTEN\R173H; PTEN\R130L; PTEN\R130P; and PTEN\P246L. The order of the hotspot mutation 21-mers in SEQ ID NOS: 115-120 is as follows: PTEN\R130P; PTEN\R130G; PTEN\Y55C; PTEN\R130L; PTEN\C36Y; PTEN\delta121-131; PTEN\P246L; PTEN\D92E; PTEN\R173H; PTEN Y68H; PTEN\R130Q; PTEN Y88C; and PTEN\R142W. The order of the hotspot mutation 21-mers in SEQ ID NOS: 121-126 is as follows: PTEN\R130Q; PTEN\R130G; PTEN\delta121-131; PTEN\C36Y; PTEN\R130L; PTEN\P246L; PTEN\Y55C; PTEN\D92E; PTEN\R142W; PTEN\R130P; PTEN Y88C; PTEN\Y68H; and PTEN\R173H. The order of the hotspot mutation 21-mers in SEQ ID NOS: 127-132 is as follows: PTEN\delta121-131; PTEN\C136Y; PTEN\Y68H; PTEN\R142W; PTEN\R173H; PTEN\R130L; PTEN\P246L; PTEN\R130G; PTEN\R130P; PTEN Y88C; PTEN\D92E; PTEN\R130Q; and PTEN\Y55C. Examples of antigenic peptides includes in the constructs are provided in Table 6.

TABLE 6

PTEN Antigenic Peptides.

| PTEN Wild Type | Mutated |
| --- | --- |
| 68WT: DSKHKNHYKIYNLCAERHYDT (SEQ ID NO: 456) | Y68H: DSKHKNHYKIHNLCAERHYDT (SEQ ID NO: 466) |
| 88WT: TAKFNCRVAQYPFEDHNPPQL (SEQ ID NO: 457) | Y88C: TAKFNCRVAQCPFEDHNPPQL (SEQ ID NO: 467) |
| 92WT: NCRVAQYPFEDHNPPQLELIK (SEQ ID NO: 458) | D92E: NCRVAQYPFEEHNPPQLELIK (SEQ ID NO: 468) |

TABLE 6-continued

PTEN Antigenic Peptides.

| PTEN Wild Type | Mutated |
| --- | --- |
| 121-131WT: WLSEDDNHVAAIHCKAGKGRTGVMICAYLLH (SEQ ID NO: 459) | 4121-131 (20-mer): WLSEDDNHVAGVMICAYLLH (SEQ ID NO: 469) |
| 130WT: AAIHCKAGKGRTGVMICAYLL (SEQ ID NO: 460) | R130Q: AAIHCKAGKGQTGVMICAYLL (SEQ ID NO: 470)<br>R130G: AAIHCKAGKGGTGVMICAYLL (SEQ ID NO: 471)<br>R130L: AAIHCKAGKGLTGVMICAYLL (SEQ ID NO: 472)<br>R130P: AAIHCKAGKGPTGVMICAYLL (SEQ ID NO: 473) |
| 136WT: AGKGRTGVMICAYLLHRGKFL (SEQ ID NO: 461) | C136Y: AGKGRTGVMIYAYLLHRGKFL (SEQ ID NO: 474) |
| 142WT: GVMICAYLLHRGKFLKAQEAL (SEQ ID NO: 462) | R142W: GVMICAYLLHWGKFLKAQEAL (SEQ ID NO: 475) |
| 155WT: FLKAQEALDFYGEVRTRDKKG (SEQ ID NO: 463) | Y155C: FLKAQEALDFCGEVRTRDKKG (SEQ ID NO: 476) |
| 173WT: KKGVTIPSQRRYVYYYSYLLK (SEQ ID NO: 464) | R173H: KKGVTIPSQRHYVYYYSYLLK (SEQ ID NO: 477) |
| 246WT: DKFMYFEFPQPLPVCGDIKVE (SEQ ID NO: 465) | P246L: DKFMYFEFPQLLPVCGDIKVE (SEQ ID NO: 478) |

For the KRAS\constructs, 20 recurrent cancer mutations were included in the constructs: G12A; G12C; G12D; G12R; G12S; G12V; G13C; G13D; G13R; G13S; G13V; L19F; Q61K; Q61H; Q61L; Q61R; K117N; A146T; A146V, and A164G. The wild type KRAS\reference sequence is set forth in SEQ ID NO: 366. Constructs were designed with the peptides comprising the 20 recurrent cancer mutations in 4 different orders from N-terminal to C-terminal. Sequences for these constructs are set forth in SEQ ID NOS: 133-156. The order of the hotspot mutation 21-mers in SEQ ID NOS: 133-138 is as follows: KRAS\Q61R; KRAS\Q61K; KRAS\Q61L; KRAS\Q61H; KRAS\L19F; KRAS\K117N; KRAS\G12A; KRAS\A164G; RAS\G12D; KRAS\G13D; KRAS\G13S; KRAS\G12S; KRAS\A146V; KRAS\G13R; KRAS\G13C; KRAS\G12C; KRAS\G12R; KRAS\G13V; KRAS\G12V; and KRAS\A146T. The order of the hotspot mutation 21-mers in SEQ ID NOS: 139-144 is as follows: KRAS\Q61H; KRAS\K117N; KRAS\G13C; KRAS\G13R; KRAS\G12D; KRAS\G12S; KRAS\G12V; KRAS\G12A; KRAS\Q61K; KRAS\G13V; KRAS\G12C; KRAS\L19F; KRAS\Q61R; KRAS\Q61L; KRAS\A146V; KRAS\A164G; KRAS\G12R; KRAS\G3S; KRAS\A146T; and KRAS\G3D. The order of the hotspot mutation 21-mersin SEQ ID NOS: 145-150 is as follows: KRAS\G12D; KRAS\L19F; KRAS\A146V; KRAS\Q61H; KRAS\G12V; KRAS\A164G; KRAS\G12C; KRAS\Q61L; KRAS\A146T; KRAS\G13S; KRAS\G12A; KRAS\G13V; KRAS\G13C; KRAS\G13D; KRAS\G12R; KRAS\G12S; KRAS\Q61R; KRAS\Q61K; KRAS\G13R; and KRAS\K17N. The order of the hotspot mutation 21-mers in SEQ ID NOS: 151-156 is as follows: KRAS\G13V; KRAS\G13S; KRAS\G12V; KRAS\G12R; KRAS\A146V; KRAS\G13D; KRAS\G12D; KRAS\K17N; KRAS\Q61H; KRAS\G12C; KRAS\G13C; KRAS\A146T; KRAS\G12A; KRAS\Q61L; KRAS\Q61K; KRAS\A164G; KRAS\G12S; KRAS\L19F; KRAS\G13R; and KRAS\Q61R. Examples of antigenic peptides includes in the constructs are provided in Table 7.

TABLE 7

KRAS Antigenic Peptides.

| KRAS Wild Type | Mutated |
| --- | --- |
| 12WT: TEYKLVVVGAGGVGKSALTIQ (SEQ ID NO: 479) | G12C: TEYKLVVVGACGVGKSALTIQ (SEQ ID NO: 486)<br>G12A: TEYKLVVVGAAGVGKSALTIQ (SEQ ID NO: 487)<br>G12S: TEYKLVVVGASGVGKSALTIQ (SEQ ID NO: 488)<br>G12D: TEYKLVVVGADGVGKSALTIQ (SEQ ID NO: 489)<br>G12R: TEYKLVVVGARGVGKSALTIQ (SEQ ID NO: 490)<br>G12V: TEYKLVVVGAVGVGKSALTIQ (SEQ ID NO: 491) |
| 13WT: EYKLVVVGAGGVGKSALTIQL (SEQ ID NO: 480) | G13D: EYKLVVVGAGDVGKSALTIQL (SEQ ID NO: 492)<br>G13C: EYKLVVVGAGCVGKSALTIQL (SEQ ID NO: 493)<br>G13S: EYKLVVVGAGSVGKSALTIQL (SEQ ID NO: 494)<br>G13V: EYKLVVVGAGVVGKSALTIQL (SEQ ID NO: 495)<br>G13R: EYKLVVVGAGRVGKSALTIQL (SEQ ID NO: 496) |

TABLE 7-continued

KRAS Antigenic Peptides.

| KRAS Wild Type | Mutated |
|---|---|
| 19WT: VGAGGVGKSALTIQLIQNHFV (SEQ ID NO: 481) | L19F: VGAGGVGKSAFTIQLIQNHFV (SEQ ID NO: 497) |
| 61WT: CLLDILDTAGQEEYSAMRDQY (SEQ ID NO: 482) | Q61H: CLLDILDTAGHEEYSAMRDQY (SEQ ID NO: 498)<br>Q61R: CLLDILDTAGREEYSAMRDQY (SEQ ID NO: 499)<br>Q61L: CLLDILDTAGLEEYSAMRDQY (SEQ ID NO: 500)<br>Q61K: CLLDILDTAGKEEYSAMRDQY (SEQ ID NO: 501) |
| 117WT: EDVPMVLVGNKCDLPSRTVDT (SEQ ID NO: 483) | K117N: EDVPMVLVGNNCDLPSRTVDT (SEQ ID NO: 502) |
| 146WT: SYGIPFIETSAKTRQGVDDAF (SEQ ID NO: 484) | A146T: SYGIPFIETSTKTRQGVDDAF (SEQ ID NO: 503)<br>A146V: SYGIPFIETSVKTRQGVDDAF (SEQ ID NO: 504) |
| 164WT: DAFYTLVREIAKHKEKMSKDG (SEQ ID NO: 485) | A164G: DAFYTLVREIGKHKEKMSKDG (SEQ ID NO: 505) |

For some of the TP53 constructs, 33 recurrent cancer mutations were included in the constructs: Y107D; K132N; C141Y; V143A; V157F; Y163C; R175H; C176F; C176Y; H179R; H179W; H193R; I195T; V216M; Y220C; Y234C; Y234H; S241F; S242F; G245D; G245S; R248L; R248Q; R248W; R249S; R273C; R273H; R273L; P278L; P278S; R282G; R282W; and R337H. The wild type TP53 reference sequence is set forth in SEQ ID NO: 367. Constructs were designed with the peptides comprising the 33 recurrent cancer mutations in 4 different orders from N-terminal to C-terminal. Sequences for these constructs are set forth in SEQ ID NOS: 157-180. The order of the hotspot mutation 21-mers in SEQ ID NOS: 157-162 is as follows: TP53\H179W; TP53\R273L; TP53\R249S; TP53\R248Q; TP53\Y234H; TP53\G245D; TP53\Y220C; TP53\R248L; TP53\H193R; TP53\K132N; TP53\S242F; TP53\Y234C; TP53\G245S; TP53\C176F; TP53\R282W; TP53\R273H; TP53\R282G; TP53\C41Y; TP53\R273C; TP53\V216M; TP53\R337H; TP53\R248W; TP53\V143A; TP53\I195T; TP53\P278S; TP53\S241F; TP53\C176Y; TP53\Y07D; TP53\R175H; TP53\H179R; TP53\V157F; TP53\P278L; and TP53\Y63C. The order of the hotspot mutation 21-mers in SEQ ID NOS: 163-168 is as follows: TP53\R248W; TP53\R248L; TP53\Y220C; TP53\Y63C; TP53\G245D; TP53\Y07D; TP53\H179R; TP53\V216M; TP53\P278S; TP53\S241F; TP53\R273L; TP53\P278L; TP53\C176F; TP53\C41Y; TP53\S242F; TP53\R249S; TP53\V143A; TP53\I195T; TP53\R273H; TP53\R273C; TP53\R282G; TP53\H179W; TP53\R175H; TP53\R248Q; TP53\G245S; TP53\H193R; TP53\R337H; TP53\R282W; TP53\Y234C; TP53\V157F; TP53\Y234H; TP53\C176Y; and TP53\K132N. The order of the hotspot mutation 21-mers in SEQ ID NOS: 169-174 is as follows: TP53\R248W; TP53\H179R; TP53\R273H; TP53\Y07D; TP53\R337H; TP53\R282G; TP53\V157F; TP53\V143A; TP53\Y234H; TP53\Y220C; TP53\R282W; TP53\R248L; TP53\S241F; TP53\H179W; TP53\R273C; TP53\C41Y; TP53\R249S; TP53\P278L; TP53\G245S; TP53\I195T; TP53\R175H; TP53\G245D; TP53\R273L; TP53\K132N; TP53\V216M; TP53\Y63C; TP53\C176F; TP53\S242F; TP53\Y234C; TP53\H193R; TP53\R248Q; TP53\P278S; and TP53\C176Y. The order of the hotspot mutation 21-mers in SEQ ID NOS: 175-180 is as follows: TP53\V143A; TP53\R282W; TP53\V157F; TP53\H179W; TP53\K132N; TP53\Y63C; TP53\C176Y; TP53\G245D; TP53\Y220C; TP53\S242F; TP53\Y234C; TP53\R249S; TP53\H179R; TP53\R273H; TP53\C41Y; TP53\R273L; TP53\P278S; TP53\C176F; TP53\R337H; TP53\H193R; TP53\R273C; TP53\R282G; TP53\R175H; TP53\R248W; TP53\P278L; TP53\I195T; TP53\S241F; TP53\R248L; TP53\Y234H; TP53\V216M; TP53\G245S; TP53\Y107D; and TP53\R248Q. For other TP53\constructs, 23 recurrent cancer mutations were included in the constructs: Y107D; C141Y; V143A; V157F; Y163C; R175H; C176F; H193R; I195T; V216M; Y220C; Y234C; Y234H; G245D; G245S; R248Q; R248W; R249S; R273C; R273H; R273L; R282G; and R282W. Sequences for these constructs are set forth in SEQ ID NOS: 257-263. The order of the hotspot mutation 21-mers in SEQ ID NOS: 257-263 is as follows: TP53\R248W; {TP53\R273H-24-mer}; TP53\V143A; TP53\R249S; {TP53\R175H-TP53\H193R-39-mer combined}; TP53\Y220C; {TP53\G245D-20-mer}; TP53\R248Q; TP53\R273C; TP53\R282W; {TP53\Y107D-20-mer}; {TP53\C41Y-TP53\V157F-37-mer combined}; {TP53\Y63C-TP53\C176F-TP53\I195T-53-mer combined}; {TP53\V216M-TP53\Y234H-39-mer combined}; TP53\G245S; TP53\R273L; TP53\Y234C; and TP53\R282G. For other TP53\constructs, 11 recurrent cancer mutations were included in the constructs: V143A; R175H; H193R; Y220C; G245D; R248Q; R248W; R249S; R273C; R273H; and R282W. Sequences for these constructs are set forth in SEQ ID NOS: 264-270. The order of the hotspot mutation 21-mers in SEQ ID NOS: 264-270 is as follows: TP53\R248W; TP53\R273H; TP53\V143A; TP53\R249S; {TP53\R175H-TP53\H193R-39-mer combined}; TP53\Y220C; {TP53\G245D-20-mer}; TP53\R248Q; TP53\R273C; and TP53\R282W. For other TP53\constructs, 12 recurrent cancer mutations were included in the constructs: Y107D; C141Y; V157F; Y163C; C176F; I195T; V216M; Y234C; Y234H; G245S; R273L; and R282G. Sequences for these constructs are set forth in SEQ ID NOS: 271-277. The order of the hotspot mutation 21-mers in SEQ ID NOS: 271-277 is as follows: TP53\Y07D; {TP53\C141Y-TP53\V157F-37-mer combined}; {TP53\Y63C-TP53\C176F-TP53\I195T-53-mer combined}; {TP53\V216M-TP53\Y234H-39-mer combined}; TP53\G245S; TP53\R273L; TP53\Y234C; and TP53\R282G. Other TP53 constructs were designed to comprise different combination of 17 recurrent cancer mutations. For other TP53\constructs, 17 recurrent cancer mutations were included in the constructs: Y107D; C141Y; V143A; Y163C; C176Y; H179R; H179W; H193R; V216M; Y234H; S241F; G245D; R248Q; R248W; R273C; R273L; and P278S. Sequences for these constructs are set forth in SEQ ID NOS: 181-186. The order of the hotspot mutation 21-mers in SEQ ID NOS: 181-186 is as follows: TP53\S241F; TP53\G245D; TP53\V143A; TP53\P278S; TP53\R273C; TP53\C176Y; TP53\Y234H; TP53\R248W; TP53\V216M; TP53\R248Q; TP53\C41Y; TP53\Y63C; TP53\H193R; TP53\H179R; TP53\H179W; TP53\Y07D; and TP53\R273L. For other TP53\constructs, 17 recurrent cancer mutations were included in the constructs: C141Y; R175H; H179R; H193R; V216M; Y234H; G245D; G245S; R248L; R248W; R273C; R273H; P278L; P278S; R282G; R282W; and R337H. Sequences for these constructs are set forth in SEQ ID NOS: 193-198. The order of the hotspot mutation 21-mers in SEQ ID NOS: 193-198 is as follows: TP53\H193R; TP53\P278L; TP53\R273C; TP53\R248W; TP53\H179R; TP53\P278S; TP53\R248L; TP53\V216M; TP53\R282G; TP53\R337H; TP53\R175H, TP53\Y234H; TP53\G245D; TP53\R273H; TP53\G245S; TP53\R282W; and TP53\C41Y. For other TP53\constructs, 17 recurrent cancer mutations were included in the constructs: Y107D; C141Y; V143A; C176F; H179R; V216M; Y220C; S241F; S242F; G245S; R248L; R248W; R273L; P278L; P278S; R282G; and R282W. Sequences for these constructs are set forth in SEQ ID NOS: 205-210. The order of the hotspot mutation 21-mers in SEQ ID NOS: 205-210 is as follows: TP53\P278S; TP53\C176F; TP53\H179R; TP53\R282G; TP53\S241F; TP53\R273L; TP53\P278L; TP53\C41Y; TP53\Y07D; TP53\R248W; TP53\V216M; TP53\R282W; TP53\S242F; TP53\Y220C; TP53\V143A; TP53\G245S; and TP53\R248L. For other TP53 constructs, 17 recurrent cancer mutations were included in the constructs: Y107D; K132N; V143A; V157F; Y163C; R175H; C176Y; Y234C; Y234H; S241F; S242F; G245D; G245S; R273C; P278S; R282W; and R337H. Sequences for these constructs are set forth in SEQ ID NOS: 217-222. The order of the hotspot mutation 21-mers in SEQ ID NOS: 217-222 is as follows: TP53\C176Y; TP53\R175H; TP53\G245D; TP53\R337H; TP53\S241F; TP53\K132N; TP53\V143A; TP53\P278S; TP53\R282W; TP53\Y63C; TP53\Y07D; TP53\R273C; TP53\S242F; TP53\G245S; TP53\V157F; TP53\Y234C; and TP53\Y234H. Other TP53\constructs were designed to comprise different combination of 16 recurrent cancer mutations. For other TP53\constructs, 16 recurrent cancer mutations were included in the constructs: K132N; V157F; R175T; C176F; I195T; Y220C; Y234C; S242F; G245S; R248L; R249S; R273H; P278L; R282G; R282W; and R337H. Sequences for these constructs are set forth in SEQ ID NOS: 187-192. The order of the hotspot mutation 21-mers in SEQ ID NOS: 187-192 is as follows: TP53\K132N; TP53\R282W; TP53\G245S; TP53\Y234C; TP53\S242F; TP53\R175H; TP53\Y220C; TP53\V157F; TP53\R282G; TP53\C176F; TP53\R337H; TP53\II95T; TP53\R249S; TP53\P278L; TP53\R273H; and TP53\R248L. For other TP53\constructs, 16 recurrent cancer mutations were included in the constructs: Y107D; K132N; V143A; V157F; Y163C; C176F; C176Y; H179W; 1195T; Y220C; Y234C; S241F; S242F; R248Q; R249S; and R273L. Sequences for these constructs are set forth in SEQ ID NOS: 199-204. The order of the hotspot mutation 21-mers in SEQ ID NOS: 199-204 is as follows: TP53\Y07D; TP53\K132N; TP53\C176F; TP53\C176Y; TP53\R273L; TP53\Y220C; TP53\R248Q; TP53\V143A; TP53\II95T; TP53\R249S; TP53\S242F; TP53\Y234C; TP53\H179W; TP53\V157F; TP53\Y63C; and TP53\S241F. For other TP53\constructs, 16 recurrent cancer mutations were included in the constructs: K132N; V157F; Y163C; R175H; C176Y; H179W; H193R; 1195T; Y234C; Y234H; G245D; R248Q; R249S; R273C; R273H; and R337H. Sequences for these constructs are set forth in SEQ ID NOS: 211-216. The order of the hotspot mutation 21-mers in SEQ ID NOS: 211-216 is as follows: TP53\R175H; TP53\H179W; TP53\R249S; TP53\Y234H; TP53\I95T; TP53\R248Q; TP53\R273H; TP53\C176Y; TP53\V157F; TP53\H193R; TP53\Y234C; TP53\K132N; TP53\R273C; TP53\Y63C; TP53\G245D; and TP53\R337H. For other TP53 constructs, 16 recurrent cancer mutations were included in the constructs: C141Y; C176F; H179R; H179W; H193R; 1195T; V216M; Y220C; R248L; R248Q; R248W; R249S; R273H; R273L; P278L; and R282G. Sequences for these constructs are set forth in SEQ ID NOS: 223-228. The order of the hotspot mutation 21-mers in SEQ ID NOS: 223-228 is as follows: TP53\C176F; TP53\R273L; TP53\H179R; TP53\R282G; TP53\Y220C; TP53\II95T; TP53\C41Y; TP53\R248L; TP53\R273H; TP53\H179W; TP53\H193R; TP53\R249S; TP53\V216M; TP53\P278L; TP53\R248W; and TP53\R248Q. Examples of antigenic peptides includes in the constructs are provided in Table 8.

TABLE 8

| TP53 Antigenic Peptides. | |
|---|---|
| TP53 Wild Type | Mutated |
| 107WT: SSSVPSQKTYQGSYGFRLGFLHSGTAK (SEQ ID NO: 506) | Y107D (20-mer): PSQKTYQGSDGFRLGFLHSG (SEQ ID NO: 533)<br>Y107D (21-mer): VPSQKTYQGSDGFRLGFLHSG (SEQ ID NO: 534) |
| 132WT: VTCTYSPALNKMFCQLAKTCP (SEQ ID NO: 507) | K132N: VTCTYSPALNNMFCQLAKTCP (SEQ ID NO: 535) |
| 141WT: PALNKMFCQLAKTCPVQLWVDSTP (SEQ ID NO: 508) | C141Y: NKMFCQLAKTYPVQLWVDSTP (SEQ ID NO: 536) |
| 141/157WT: PALNKMFCQLAKTCPVQLWVDSTPPPGTRVR AMAIYKQSQ (SEQ ID NO: 509) | C141Y/V157F (37-mer): NKMFCQLAKTYPVQLWVDSTPPPGTRFRAMAI YKQSQ (SEQ ID NO: 537) |
| 143WT: MFCQLAKTCPVQLWVDSTPPP (SEQ ID NO: 510) | V143A: MFCQLAKTCPAQLWVDSTPPP (SEQ ID NO: 538) |

TABLE 8-continued

TP53 Antigenic Peptides.

| TP53 Wild Type | Mutated |
| --- | --- |
| 157WT: VDSTPPPGTRVRAMAIYKQSQ (SEQ ID NO: 511) | V157F: VDSTPPPGTRFRAMAIYKQSQ (SEQ ID NO: 539) |
| 163WT: PGTRVRAMAIYKQSQHMTEVV (SEQ ID NO: 512) | Y163C: PGTRVRAMAICKQSQHMTEVV (SEQ ID NO: 540) |
| 163/176/195WT: PGTRVRAMAIYKQSQHMTEVVRRCPHHERCSDSDGLAPPQHLIRVEGNLRVEY (SEQ ID NO: 513) | Y163C/C176F/I195T (53-mer): PGTRVRAMAICKQSQHMTEVVRRFPHHERCSDSDGLAPPQHLTRVEGNLRVEY (SEQ ID NO: 541) |
| 175WT: QSQHMTEVVRRCPHHERCSDS (SEQ ID NO: 514) | R175H: QSQHMTEVVRHCPHHERCSDS (SEQ ID NO: 542) |
| 175/193WT: QSQHMTEVVRRCPHHERCSDSDGLAPPQHLIRVEGNLRV (SEQ ID NO: 515) | R175H/H193R (39-mer): QSQHMTEVVRHCPHHERCSDSDGLAPPQRLIRVEGNLRV (SEQ ID NO: 543) |
| 176WT: SQHMTEVVRRCPHHERCSDSD (SEQ ID NO: 516) | C176F: SQHMTEVVRRFPHHERCSDSD (SEQ ID NO: 544)<br>C176Y: SQHMTEVVRRYPHHERCSDSD (SEQ ID NO: 545) |
| 179WT: MTEVVRRCPHHERCSDSDGLA (SEQ ID NO: 517) | H179R: MTEVVRRCPHRERCSDSDGLA (SEQ ID NO: 546)<br>H179W: MTEVVRRCPHWERCSDSDGLA (SEQ ID NO: 547) |
| 193WT: SDSDGLAPPQHLIRVEGNLRV (SEQ ID NO: 518) | H193R: SDSDGLAPPQRLIRVEGNLRV (SEQ ID NO: 548) |
| 195WT: SDGLAPPQHLIRVEGNLRVEY (SEQ ID NO: 519) | I195T: SDGLAPPQHLTRVEGNLRVEY (SEQ ID NO: 549) |
| 216WT: LDDRNTFRHSVVVPYEPPEVG (SEQ ID NO: 520) | V216M: LDDRNTFRHSMVVPYEPPEVG (SEQ ID NO: 550) |
| 216/234WT: LDDRNTFRHSVVVPYEPPEVGSDCTTIHYNMCNSSCMG (SEQ ID NO: 521) | V216M/Y234H (39-mer): LDDRNTFRHSMVVPYEPPEVGSDCTTIHENYMCNSSCMG (SEQ ID NO: 551) |
| 220WT: NTFRHSVVVPYEPPEVGSDCT (SEQ ID NO: 522) | Y220C: NTFRHSVVVPCEPPEVGSDCT (SEQ ID NO: 552) |
| 234WT: EVGSDCTTIHYNYMCNSSCMG (SEQ ID NO: 523) | Y234H: EVGSDCTTIHENYMCNSSCMG (SEQ ID NO: 553)<br>Y234C: EVGSDCTTIHCNYMCNSSCMG (SEQ ID NO: 554) |
| 241WT: TIHYNYMCNSSCMGGMNRRPI (SEQ ID NO: 524) | S241F: TIHYNYMCNSFCMGGMNRRPI (SEQ ID NO: 555) |
| 242WT: IHYNYMCNSSSMGGMNRRPIL (SEQ ID NO: 525) | S242F: IHYNYMCNSSFMGGMNRRPIL (SEQ ID NO: 556) |
| 245WT: NYMCNSSCMGGMNRRPILTII (SEQ ID NO: 526) | G245D (20-mer): YMCNSSCMGDMNRRPILTII (SEQ ID NO: 557)<br>G245D (21-mer): NYMCNSSCMGDMNRRPILTII (SEQ ID NO: 723)<br>G245S: NYMCNSSCMGSMNRRPILTII (SEQ ID NO: 558) |
| 248WT: CNSSCMGGMNRRPILTIITLE (SEQ ID NO: 527) | R248W: CNSSCMGGMNWRPILTIITLE (SEQ ID NO: 559)<br>R248Q: CNSSCMGGMNQRPILTIITLE (SEQ ID NO: 560)<br>R248L: CNSSCMGGMNLRPILTIITLE (SEQ ID NO: 561) |

TABLE 8-continued

TP53 Antigenic Peptides.

| TP53 Wild Type | Mutated |
|---|---|
| 249WT: NSSCMGGMNRRPILTIITLED (SEQ ID NO: 528) | R249S: NSSCMGGMNRSPILTIITLED (SEQ ID NO: 562) |
| 273WT: NLLGRNSFEVRVCACPGRDRR (SEQ ID NO: 529) | R273H (21-mer): NLLGRNSFEVHVCACPGRDRR (SEQ ID NO: 563)<br>R273H (24-mer): NLLGRNSFEVHVCACPGRDRRTEE (SEQ ID NO: 564)<br>R273C: NLLGRNSFEVCVCACPGRDRR (SEQ ID NO: 565)<br>R273L: NLLGRNSFEVLVCACPGRDRR (SEQ ID NO: 566) |
| 278WT: NSFEVRVCACPGRDRRTEEEN (SEQ ID NO: 530) | P278L: NSFEVRVCACLGRDRRTEEEN (SEQ ID NO: 567)<br>P278S: NSFEVRVCACSGRDRRTEEEN (SEQ ID NO: 568) |
| 282WT: VRVCACPGRDRRTEEENLRKK (SEQ ID NO: 531) | R282W: VRVCACPGRDWRTEEENLRKK (SEQ ID NO: 569)<br>R282G: VRVCACPGRDGRTEEENLRKK (SEQ ID NO: 570) |
| 337WT: YFTLQIRGRERFEMFRELNEA (SEQ ID NO: 532) | R337H: YFTLQIRGREHFEMFRELNEA (SEQ ID NO: 571) |

Also in development are an additional set of constructs for cancer-associated proteins that are frequently mutated in certain high impact cancers in additional to those common across all cancers. These diseases include squamous and adenocarcinoma of the lung, colorectal cancer, breast cancer, ovarian cancer, and others.

TABLE 9

Biomarker Expression Additional Selected Tumor Targets.

| ADXS- | % Patients with Mutation (All Cancers - Combined Cohort)* | % Patients with Mutation (Specific Cancers)* |
|---|---|---|
| APC | 6% | Colorectal (76%) |
| KEAP1 | 2% | Lung adenocarcinoma (14%), lung squamous cell carcinoma (12%) |
| STK11 | 2% | Lung adenocarcinoma (10%), combined cohort (2%) |
| NF1 | 4% | Glioblastoma multiforme (10%), lung adenocarcinoma (10%), combined cohort (2%) |
| KMT2D (MLL2) | 5% | Bladder (26%), diffuse large B-cell lymphoma (20%), lung squamous cell carcinoma (20%), head and neck (15%) |
| CDKN2A | 3% | Head and neck (20%), lung squamous cell carcinoma (15%), melanoma (15%), esophageal adenocarcinoma (6%), lung adenocarcinoma (5%) |
| NFE2L2 | 2% | Lung squamous cell carcinoma (15%), bladder (9%), head and neck (5%) |
| SPOP | 1% | Prostate (10%), endometrial (8%) |
| FBXW7 | 3% | Colorectal (16%), endometrial (16%), bladder (10%), lung squamous cell carcinoma (5%) |

*% Expression as represented in the BROAD Institute's Tumor Portal dataset

Out of these constructs several panels can be devised that cover shared mutated epitopes that are characteristic of most major types of cancers. Disease-specific panels being developed from ADXS-HOT constructs could include those in Table 10.

TABLE 10

Exemplary Panels.

| Panel | % Patients with Mutation (Specific Cancers)* |
|---|---|
| Colorectal Cancer Panel | APC (76%), TP53 (52%), KRAS (43%), PIK3CA (19%), FBXW7 (16%), NRAS (9%), BRAF (9%) |
| Adenocarcinoma of the Lung Panel | TP53 (51%), KRAS (26%), KEAP1 (14%), EGFR (10%), NF1 (10%), BRAF (6%), CDKN2A (5%), PIK3 (PIK3CA or PIK3R1) (4%) |
| Squamous Cell Lung Cancer Panel | TP53 (83%), MLL2 (20%), CDKN2A (15%), PIK3CA (15%), NFE2L2 (15%), KEAP1 (12%) |
| Ovarian Cancer Panel | TP53 (94%), BRCA1 (3%), NF1 (4%), RB1 (2%) |
| Breast Cancer Panel (subtype-specific versions also possible) | PIK3 (PIK3CA or PIK3R1) (34%), TP53 (31%), GATA3 (9%), MAP3K1/2K4 (9%), PTEN (3%), KRAS (1%), AKT1 (1%), RB1 (1%) |

*% Expression as represented in the BROAD Institute's Tumor Portal dataset

Moreover, recurrent hotspot mutations are identified in more than eleven thousand human tumors, spanning more than 40 cancer types with 470 somatic substitution hotspots in 275 genes identified. See, e.g., Chang et al. (2016) *Nat Biotechnol* 34(2):155-163, herein incorporated by reference in its entirety for all purposes (providing a distribution of tumor types, the breakdown of known and classified hotspots, and the number of hotspots in each of 49 genes with two or more hotspots detected within a cohort). This landscape provides a great opportunity for the development of additional ADXS-HOT constructs to expand the number of "off the shelf" treatments to broader cancer patient populations.

Example 2. Colorectal Cancer Immunotherapy Strategy: HOTSPOT Constructs

Oncogenesis of colorectal cancer (CRC) is driven by the acquisition and accumulation of somatic mutations. APC mutation is involved early in adenoma formation, followed by oncogenic mutation of KRAS that promotes the transition from intermediate adenomas to carcinomas with TP53 inactivation as a late event. Additional mutations can be acquired in PIK3CA, FBXW7, NRAS, and BRAF that contribute as tumor drivers and may confer (or be selected by) resistance to treatments like EGFR inhibition.

Recently, the advent of large-scale PCR-based sequencing has been used to depict the genomic landscape of CRC and a number of high-frequency mutated genes have been identified as "gene mountains" because of the commonality of shared mutations in these genes. They are comprised by somatic mutations occurring in critical tumor driver genes including APC, KRAS\, TP53, FBXW7, PIK3CA, NRAS, and BRAF. Additional lower frequency shared mutation gene clusters have also been identified. However, the vast majority CRC tumors can be characterized by the incorporation one or more of representative mutations in these commonly observed shared tumor drive "gene mountains." Somatic mutations in these key tumor driver genes frequently occur in critical amino acid positions of the peptide that interfere with the function of the molecule in what can be described as mutational "hotspots." These types of shared mutations provide the opportunity to generate an immunotherapy that focuses on the majority of the commonly observed shared mutation epitopes in these tumor driver genes as opposed to neoantigens that are specific to an individual patient. As an example, the BRAF gene can exhibit a very well-characterized tumor-specific antigen associated with the somatic substitution at position 600 of V to E.

BRAF mutation is also known to be associated with shortened survival in patients with late-stage CRC. As a simple example, the vast majority of mutations that occur in BRAF are at amino acid position 600, represented as V600E, with the only other shared mutation that occurs with a significant frequency being BRAF\G469V (or G469A). Thus, covering these three specific shared epitopes with an immunization could generate T cell responses against any somatic mutation that is likely to occur in BRAF in more than 99% of the cases. Patients identified with this high risk mutation could be treated with an immunotherapy that targets this biomarker in an attempt to eliminate the cells associated with this prognosis.

A series Lm-LLO constructs are under development that will target the vast majority of tumor-specific epitopes that arise as a consequence of tumor-specific mutations in common tumor driver genes. These products will be based on our Lm-LLO platform, and each one is intended to cover ≥99% of the potential mutations that are observed in a particular gene. The presence of key recurrent cancer mutations in tumor driver genes can be diagnosed through specific PCR-based kits or otherwise divulged through DNA or RNA sequencing. These constructs can be given in combinations if the patient has more than one recurrent cancer mutation simply by mixing the individual hot-spot constructs prior to administration. The application of these agents to colorectal cancer could be particularly useful since the commonly mutated genes have been clearly identified and most patients share a mutation in several of these tumor driver genes. These include, for example, mutations in APC, TP53, PIK3CA, KRAS\, and BRAF.

Microsatellite instability (MSI) resulting from defects in DNA mismatch repair, causes a high mutational burden in 10-25% of sporadic (non-Lynch syndrome) CRC, but is also associated with better prognosis and has been response to checkpoint inhibition. Recent data suggest that these patients are more effectively treated with checkpoint inhibitor monotherapy. Therefore, the greatest medical need in CRC is for the 85-90% of patients with microsatellite stable (MSS) CRC.

Recent data suggest that MSS CRC can become sensitive to checkpoint inhibition treatment if the tumor becomes immunologically "hot" or infiltrated with lymphocytes associated with the expression of a TH-1 supportive microenvironment (ASCO 2016, oral presentation, abstract, met inhibition of MSS CRC followed by PD-1). Our Lm-LLO vectors have been found to contribute significant innate immune stimulation supporting TH-1 type T-cell immunity culminating in increased infiltration of T cells into solid tumor microenvironments along with reduction in the suppressive ability of Tregs and MDSCs (Wallecha et al. (2013) *J Immunother* 36:468-476; Chen et al. (2014) *Cancer Immunol Res* 2(9):911-922; and Mkrtichyan et al. (2013) *J Immunother Cancer* 1:15. doi: 10.1186/2051-1426-1-15, each of which is herein incorporated by reference in its entirety for all purposes).

These effects could contribute collectively in altering the MSS CRC microenvironment to make it "hot" if a tumor-specific target is presented. In addition, these constructs have been shown to induce epitope spreading. These treatments could be effective as monotherapy when targeting tumor-specific antigens that arise as a consequence of tumor-specific mutations in tumor driver genes, and could also greatly enhance their susceptibility to checkpoint inhibition treatment. In vitro studies of Lm-LLO constructs have demonstrated synergy in vitro and ongoing combination trials have demonstrated that they can be safely combined with checkpoint inhibitors.

Based on the known expression of recurrent cancer mutations in tumor driver genes for CRC, the development of a CRC specific ADXS-HOT treatment of MSS CRC would be directed against the following targets. The intention is to develop a panel of gene-specific constructs that could either be selected for combination treatment based on a diagnostic screen, or combined in a set combination strategy intended to be given to all MSS CRC patients. The CRC panel would include at a minimum the following tumor driver hotspot targeted constructs ("m" for mutated): mAPC (found in 76% of CRC patients), mTP53 (52% of patients), mRAS {KRAS\/NRAS} (52% of patients {43%/9% of patients, respectively}), mPIK3CA\(19% of patients), mBRAF (9% of patients).

There could be two treatment options developed from these constructs for CRC. One would be personalized for the patient based on expression of biomarkers from a Nanostring or PCR-based diagnostic, or DNA or RNA sequencing.

TABLE 11

Expression of Driver Targets in Different Patients.

| Driver Target | Patient A | Patient B | Patient C |
|---|---|---|---|
| mAPC | X | X | |
| mTP53 | X | | X |
| mPIK3CA/mPIK3R1 | | X | X |
| mKRAS | X | | |
| mBRAF | X | | X |

The other option is to give all patients with a common disease type the same combination mixture. For the personalized medicine approach, a combination of constructs from the panel would be assembled into a kit for a patient based on their biomarker testing results, and mixed together on site just prior to treatment. Additional targets can be added to the panel going forward. Several other tumor driver mutation target constructs will also be prepared to target genes that are frequently mutated in other diseases including squamous and adenocarcinoma of the lung, breast cancer and ovarian cancer. Some of these other constructs may also be useful in the CRC panel as they become available.

For the generalized common disease-specific mixture, all patients with the qualifying disease type would be given the same combination of constructs. For MSS CRC, this combination would include APC, TP53, PIK3CA, and RAS, and (potentially) BRAF. Since the somatic tumor driver mutations are found in CRC include mAPC in 76% of patients, mTP53 in 52% of patients, mRAS {KRAS\/NRAS} in 52% of patients, and mPIK3CA in 19% of patients, there is a great likelihood that most patients would express anywhere from 2-4 or 2-5 of these representative mutated tumor driver genes, so multiple driver gene mutations would be targeted.

The potential also exists to use ADXS-HOT constructs as part of a combination treatment regimen either as several individual hotspot products together or in combination with other therapeutic cancer treatments. Similar to other of our Lm constructs, hotspot treatments can be given in combination or sequentially with other cancer treatments like checkpoint inhibitors, costimulatory agonists, or radiation therapy. The reason for this is that animal models and early data from clinical trials have shown that Lm-LLO immunotherapies have the potential for significant synergy with active immunotherapy agents, such as PD-1 and/or PD-L1 blocking antibodies.

The combination of an Lm-LLO-based vaccine with anti-PD-1 antibody leads to increased antigen-specific immune responses and tumor-infiltrating CD8+ T cells, along with a decrease in immune suppressor cells (Tregs and MDSCs). The combination regimen led to synergistic activity, with significant inhibition of tumor growth and prolonged survival/complete regression of tumors in treated animals. The combination of an Lm-LLO-based vaccine with blocking of PD-1/PD-L1 can lead to overall enhancement of the efficacy of anti-tumor immunotherapy over either agent alone. It was also shown that in vitro infection with Lm results in significant upregulation of surface PD-L1 expression on human monocyte-derived dendritic cells, which suggests the translational capacity of this finding.

Data presented at the American Association for Cancer Research Annual Meeting in 2016 (Sikora abstract, Advaxis reception data presentation) provided evidence supporting the upregulation of PD-1 and activation of T cells by an Lm-LLO agent in human head and neck tumors. Data from the study showed increased immune activation within the tumor microenvironment, including upregulation of PD-1 and PD-L1 expression, reduction of Tregs and MDSCs, and infiltration of CD8+ and CD4+ T cells. These observations suggest potentially strong synergy with an anti-PD-1 antibody (Wolf et al. (2013) *J Immunol* 190(6):2501-2509, herein incorporated by reference in its entirety for all purposes).

Preclinical data also suggest synergy with immune costimulatory agonists like Ox-40 and GITR (Mkrtichyan et al. (2013) *J Immunother Cancer* 1:15. doi: 10.1186/2051-1426-1-15, herein incorporated by reference in its entirety for all purposes). Synergy of Lm-LLO vectors with radiation therapy has been demonstrated in preclinical models (Hannan et. al. (2012) *Cancer Immunol Immunother* 61(12): 2227-2238, herein incorporated by reference in its entirety for all purposes) and has also been observed in ongoing veterinary trials in non-resected canine osteosarcoma. Lm-LLO treatments can also be given sequentially with chemotherapies provided there has been sufficient hematopoietic recovery. In addition, research to date shows there is no development of neutralizing antibodies with Lm vectors, so repeated treatments with a single Lm vector or simultaneous or sequential treatment with multiple vectors is possible.

ADXS-HOT immunotherapies as disclosed herein have the potential to revolutionize the treatment of cancer by providing highly efficacious, targeted attacks on hotspots with little to no impact on healthy cells. Tumor immunotherapies take advantage of the most effective cancer-fighting agents that nature has devised: the host's own immune cells. Successful application of these the ADXS-HOT CRC program in an effective regimen for MSS CRC has the potential to be developed into an effective immunotherapy option for this devastating disease where one currently does not exist.

Example 3. Design of Cancer-Type-Specific HOTSPOT Constructs

We selected five initial cancer types with recurrent cancer mutations on which to focus preclinical development efforts for ADXS-HOT constructs. These include luminal A breast cancer, colorectal adenocarcinoma, NSCLC adenocarcinoma, squamous cell cancer, and prostate cancer.

Luminal A Breast Cancer

A total of 11 hotspot mutations across 5 genes were selected for the luminal A breast cancer ADXS-HOT constructs. This panel of hotspot mutations covers 50.6% of all luminal A breast cancer patients.

TABLE 12

Exemplary Luminal A Breast Cancer Panel.
Luminal A Breast Cancer Panel

| Gene- | Hotspots | # of 21-mers | % patients covered |
|---|---|---|---|
| PI3KCA | H1047R, E545K, E542K, H1047L, Q546K, E545A, E545G | 7 | 42.6% |
| AKT1 | E17K | 1 | 4.6% |
| AHNAK2 | V2016L | 1 | 2.1% |
| ERBB2 | L755S | 1 | <1% |
| TP53 | R175H | 1 | <1% |

For each recurrent cancer mutation included in the constructs, a peptide of 21 amino acids in length was designed.

TABLE 13

Exemplary Luminal A Breast Cancer Panel 21-Mers.
Luminal A Breast Cancer Panel 21-Mers

| Gene | Hotspot Mutation | Sequence | SEQ ID NO |
|---|---|---|---|
| AHNAK2 | V2061L | QVDVKLPEGHLPEGAGLKGHL | 584 |
| AKT1 | E17K | VKEGWLHKRGKYIKTWRPRYF | 585 |
| ERBB2 | L755S | AGVGSPYVSRSLGICLTSTVQ | 586 |
| PIK3CA | H1047R | EYFMKQMNDARHGGWTTKMDW | 587 |
| PIK3CA | E545K | STRDPLSEITKQEKDFLWSHR | 588 |
| PIK3CA | E542K | KAISTRDPLSKITEQEKDFLW | 589 |
| PIK3CA | H1047L | EYFMKQMNDALHGGWTTKMDW | 590 |
| PIK3CA | Q546K | TRDPLSEITEKEKDFLWSHRH | 591 |
| PIK3CA | E545A | STRDPLSEITAQEKDFLWSHR | 592 |
| PIK3CA | E545G | STRDPLSEITGQEKDFLWSHR | 593 |
| TP53 | R175H | QSQHMTEVVRHCPHHERCSDS | 594 |

The 21-mer peptides were designed to be fragments of the cancer-associated protein in which the recurrent cancer mutations occurs, including the recurrent cancer mutation and 10 amino acids of flanking sequence on each side. Antigenic peptides were scored by a Kyte and Doolittle hydropathy index with a 21 amino acid window, and peptides scoring above a cutoff of around 1.6 were excluded as they are unlikely to be secretable by *Listeria monocytogenes*. Constructs will be designed with the peptides in multiple different orders generated by randomization. Each ordering of the peptides will be scored by a Kyte and Doolittle hydropathy index with a sliding 21 amino acid window, and if any region for a particular ordering of peptides scores above a cutoff of around 1.6, the order of the peptides will be reshuffled until the ordering of peptides resulted in a polypeptide with no regions scoring above the cutoff.

Colorectal Adenocarcinoma

A total of 17 hotspot mutations across 6 genes were selected for the colorectal adenocarcinoma ADXS-HOT constructs. This panel of hotspot mutations covers 42.8% of all colorectal cancer patients and 58% of microsatellite-stable patients.

TABLE 14

Exemplary Colorectal Adenocarcinoma Panel.
Colorectal Adenocarcinoma Panel

| Gene- | Hotspots | # of 21-mers | % patients covered |
|---|---|---|---|
| BRAF | V600E | 1 | 30.8% |
| KRAS/NRAS | G12D, G13D, G12V, G12C, Q61K, G12A, G12S | 7 | 5.3% |
| TP53 | R175H, R248W, R273C, R282W, R273H, R248Q, G245S | 1 | 3.0% |
| PIK3CA | E545K, H1047R, R88Q | 3 | 2.7% |
| SMAD4 | R361H | 1 | 1.0% |

For each recurrent cancer mutation included in the constructs, a peptide of 21 amino acids in length was designed.

TABLE 15

Exemplary Colorectal Adenocarcinoma Panel 21-Mers.
Colorectal Adenocarcinoma Panel 21-Mers

| Gene | Hotspot Mutation | Sequence | SEQ ID NO |
|---|---|---|---|
| BRAF | V600E | VKIGDFGLATEKSRWSGSHQF | 595 |
| KRAS | G12D | TEYKLVVVGADGVGKSALTIQ | 596 |
| KRAS | G12V | TEYKLVVVGAVGVGKSALTIQ | 597 |
| KRAS | G13D | EYKLVVVGAGDVGKSALTIQL | 598 |
| KRAS | G12C | TEYKLVVVGACGVGKSALTIQ | 599 |
| KRAS | G12A | TEYKLVVVGAAGVGKSALTIQ | 600 |
| KRAS | G12S | TEYKLVVVGASGVGKSALTIQ | 601 |
| NRAS | Q61K | CLLDILDTAGKEEYSAMRDQY | 602 |
| PIK3CA | E545K | STRDPLSEITKQEKDFLWSHR | 603 |
| PIK3CA | H1047R | EYFMKQMNDARHGGWTTKMDW | 604 |
| PIK3CA | R88Q | EREEFFDETRQLCDLRLFQPF | 605 |
| SMAD4 | R361H | DGYVDPSGGDHFCLGQLSNVH | 606 |
| TP53 | R175H | QSQHMTEVVRHCPHHERCSDS | 607 |
| TP53 | R248W | CNSSCMGGMNWRPILTIITLE | 608 |
| TP53 | R273C | NLLGRNSFEVCVCACPGRDRR | 609 |

TABLE 15-continued

Exemplary Colorectal Adenocarcinoma Panel 21-Mers.
Colorectal Adenocarcinoma Panel 21-Mers

| Gene | Hotspot Mutation | Sequence | SEQ ID NO |
|---|---|---|---|
| TP53 | R282W | VRVCACPGRDWRTEEENLRKK | 610 |
| TP53 | R273H | NLLGRNSFEVHVCACPGRDRR | 611 |
| TP53 | R248Q | CNSSCMGGMNQRPILTIITLE | 612 |
| TP53 | G245S | NYMCNSSCMGSMNRRPILTII | 613 |

The 21-mer peptides were designed to be fragments of the cancer-associated protein in which the recurrent cancer mutations occurs, including the recurrent cancer mutation and 10 amino acids of flanking sequence on each side. Antigenic peptides were scored by a Kyte and Doolittle hydropathy index with a 21 amino acid window, and peptides scoring above a cutoff of around 1.6 were excluded as they are unlikely to be secretable by *Listeria monocytogenes*. Constructs will be designed with the peptides in multiple different orders generated by randomization. Each ordering of the peptides will be scored by a Kyte and Doolittle hydropathy index with a sliding 21 amino acid window, and if any region for a particular ordering of peptides scores above a cutoff of around 1.6, the order of the peptides will be reshuffled until the ordering of peptides resulted in a polypeptide with no regions scoring above the cutoff.

Lung Adenocarcinoma

A total of 30 hotspot mutations across 6 genes were selected for the lung adenocarcinoma (NSCLC) ADXS-HOT constructs. This panel of hotspot mutations covers 53.5% of all lung adenocarcinoma patients.

TABLE 16

Exemplary Lung Adenocarcinoma Panel.
Lung Adenocarcinoma Panel

| Gene | Hotspots | # of 21-mers | % patients covered |
|---|---|---|---|
| KRAS | G12C, G12V, G12D, G12F, G12R, Q61L, G12Y | 7 | 32.5% |
| TP53 | R158L, R273L, G245V, R175H, A159P, R249M, R273H, R280I, Q144L, R273C, R280G, R280T | 12 | 7.6% |
| EGFR | L858R, L861Q, G719A | 3 | 6.2% |
| U2AF1 | S34F | 1 | 2.6% |
| BRAF | V600E, G466V, N581S | 3 | 2.6% |
| PIK3CA | E545K, E726K, H1047R | 3 | 2.0% |

For each recurrent cancer mutation included in the constructs, a peptide of 21 amino acids in length was designed.

TABLE 17

Exemplary Lung Adenocarcinoma Panel 21-Mers.
Lung Adenocarcinoma Panel 21-Mers

| Gene | Hotspot Mutation | Sequence | SEQ ID NO |
|---|---|---|---|
| BRAF | V600E | VKIGDFGLATEKSRWSGSHQF | 614 |
| BRAF | G466V | QITVGQRIGSVSFGTVYKGKW | 615 |
| BRAF | N581S | SIIHRDLKSNSIFLHEDLTVK | 616 |
| EGFR | L858R | PQHVKITDFGRAKLLGAEEKE | 617 |
| EGFR | L861Q | VKITDFGLAKQLGAEEKEYHA | 618 |
| EGFR | G719A | ETEFKKIKVLASGAFGTVYKG | 619 |
| KRAS | G12C | TEYKLVVVGACGVGKSALTIQ | 620 |
| KRAS | G12V | TEYKLVVVGAVGVGKSALTIQ | 621 |
| KRAS | G12A | TEYKLVVVGAAGVGKSALTIQ | 622 |
| KRAS | G12D | TEYKLVVVGADGVGKSALTIQ | 623 |
| KRAS | G12F | TEYKLVVVGAFGVGKSALTIQ | 624 |
| KRAS | G12R | TEYKLVVVGARGVGKSALTIQ | 625 |
| KRAS | Q61L | CLLDILDTAGLEEYSAMRDQY | 626 |
| KRAS | G12Y | TEYKLVVVGAYGVGKSALTIQ | 627 |
| PIK3CA | E545K | STRDPLSEITKQEKDFLWSHR | 628 |
| PIK3CA | E726K | TDILKQEKKDKTQKVQMKFLV | 629 |
| PIK3CA | H1047R | EYFMKQMNDARHGGWTTKMDW | 630 |
| TP53 | R158L | DSTPPPGTRVLAMAIYKQSQH | 631 |
| TP53 | R273L | NLLGRNSFEVLVCACPGRDRR | 632 |
| TP53 | G245V | NYMCNSSCMGVMNRRPILTII | 633 |
| TP53 | R175H | QSQHMTEVVRHCPHHERCSDS | 634 |
| TP53 | A159P | STPPPGTRVRPMAIYKQSQHM | 635 |
| TP53 | R249M | NSSCMGGMNRMPILTIITLED | 636 |
| TP53 | R273H | NLLGRNSFEVHVCACPGRDRR | 637 |
| TP53 | R280I | FEVRVCACPGIDRRTEEENLR | 638 |
| TP53 | Q144L | FCQLAKTCPVLLWVDSTPPPG | 639 |
| TP53 | R273C | NLLGRNSFEVCVCACPGRDRR | 640 |
| TP53 | R280G | FEVRVCACPGGDRRTEEENLR | 641 |
| TP53 | R280T | FEVRVCACPGTDRRTEEENLR | 642 |
| U2AF1 | S34F | IGACRHGDRCFRLHNKPTFSQ | 643 |

The 21-mer peptides were designed to be fragments of the cancer-associated protein in which the recurrent cancer mutations occurs, including the recurrent cancer mutation and 10 amino acids of flanking sequence on each side. Antigenic peptides were scored by a Kyte and Doolittle hydropathy index with a 21 amino acid window, and peptides scoring above a cutoff of around 1.6 were excluded as they are unlikely to be secretable by *Listeria monocytogenes*. Constructs will be designed with the peptides in multiple different orders generated by randomization. Each ordering of the peptides will be scored by a Kyte and Doolittle hydropathy index with a sliding 21 amino acid window, and if any region for a particular ordering of peptides scores above a cutoff of around 1.6, the order of the peptides will be reshuffled until the ordering of peptides resulted in a polypeptide with no regions scoring above the cutoff.

NSCLC Squamous Cell Cancer

A total of 60 hotspot mutations across 5 genes were selected for the NSCLC squamous cell cancer ADXS-HOT constructs. This panel of hotspot mutations covers 52.3% of all NSCLC squamous cancer patients.

TABLE 18

Exemplary NSCLC Squamous Cell Cancer Panel.
NSCLC Squamous Cell Cancer Panel

| Gene | Hotspot Mutation | Sequence | SEQ ID NO |
|---|---|---|---|
| TP53 | R273H, R175G, R273L, H179K, Y163C + 40 others | 45 | 33% |
| PIK3CA | E545K, E542K, H1047R, | 5 | 8.0% |
| NFE2L2 | E726K, C420R E79Q, R34Q, L30F, G81S, G31A, D29G, G81V | 7 | 8.0% |
| CDKN2A | D108Y, D18N | 2 | 2.3% |
| PTEN | R130Q | 1 | 1.0% |

For each recurrent cancer mutation included in the constructs, a peptide of 21 amino acids in length was designed.

TABLE 19

Exemplary NSCLC Squamous Cell Cancer Panel 21-Mers.
NSCLC Squamous Cell Cancer Panel 21-Mers

| Gene | Hotspot Mutation | Sequence | SEQ ID NO |
|---|---|---|---|
| CDKN2A | D108Y | HRAGARLDVRYAWGRLPVDLA | 644 |
| CDKN2A | D108N | HRAGARLDVRNAWGRLPVDLA | 645 |
| NFE2L2 | E79Q | AFFAQLQLDEQTGEFLPIQPA | 646 |
| NFE2L2 | R34Q | WRQDIDLGVSQEVFDFSQRRK | 647 |
| NFE2L2 | L30F | IDILWRQDIDFGVSREVFDFS | 648 |
| NFE2L2 | G81S | FAQLQLDEETSEFLPIQPAQH | 649 |
| NFE2L2 | G31A | DILWRQDIDLAVSREVFDFSQ | 650 |
| NFE2L2 | D29G | LIDILWRQDIGLGVSREVFDF | 651 |
| NFE2L2 | G81V | FAQLQLDEETVEFLPIQPAQH | 652 |
| PIK3CA | E545K | STRDPLSEITKQEKDFLWSHR | 653 |
| PIK3CA | E542K | KAISTRDPLSKITEQEKDFLW | 654 |
| PIK3CA | H1047R | EYFMKQMNDARHGGWTTKMDW | 655 |
| PIK3CA | E726K | TDILKQEKKDTQKVQMKFLV | 656 |
| PIK3CA | C420R | KGRKGAKEEHRPLAWGNINLF | 657 |
| PTEN | R130Q | AAIHCKAGKGQTGVMICAYLL | 658 |
| TP53 | Y163C | PGTRVRAMAICKQSQHMTEVV | 659 |
| TP53 | R175G | QSQHMTEVVRGCPHHERCSDS | 660 |
| TP53 | C242F | IHYNYMCNSSFMGGMNRRPIL | 661 |
| TP53 | R273L | NLLGRNSFEVLVCACPGRDRR | 662 |
| TP53 | H179L | MTEVVRRCPHLERCSDSDGLA | 663 |
| TP53 | H193L | SDSDGLAPPQLLIRVEGNLRV | 664 |
| TP53 | H214R | EYLDDRNTFRRSVVVPYEPPE | 665 |
| TP53 | Y220C | NTFRHSVVVPCEPPEVGSDCT | 666 |
| TP53 | Y234C | EVGSDCTTIHCNYMCNSSCMG | 667 |
| TP53 | G245V | NYMCNSSCMGVMNRRPILTII | 668 |
| TP53 | L111Q | KTYQGSYGFRQGFLHSGTAKS | 669 |
| TP53 | T125P | HSGTAKSVTCPYSPALNKMFC | 670 |
| TP53 | K132R | VTCTYSPALNRMFCQLAKTCP | 671 |
| TP53 | C135W | TYSPALNKMFWQLAKTCPVQL | 672 |
| TP53 | C141W | NKMFCQLAKTWPVQLWVDSTP | 673 |
| TP53 | C176F | SQHMTEVVRRFPHHERCSDSD | 674 |
| TP53 | C176Y | SQHMTEVVRRYPHHERCSDSD | 675 |
| TP53 | H179R | MTEVVRRCPHRERCSDSDGLA | 676 |
| TP53 | H179Y | MTEVVRRCPHYERCSDSDGLA | 677 |
| TP53 | H193R | SDSDGLAPPQRLIRVEGNLRV | 678 |
| TP53 | I195S | SDGLAPPQHLSRVEGNLRVEY | 679 |
| TP53 | Y205C | IRVEGNLRVECLDDRNTFRHS | 680 |
| TP53 | R213G | VEYLDDRNTFGHSVVVPYEPP | 681 |
| TP53 | V216E | LDDRNTFRHSEVVPYEPPEVG | 682 |
| TP53 | Y234S | EVGSDCTTIHSNYMCNSSCMG | 683 |
| TP53 | Y236C | GSDCTTIHYNCMCNSSCMGGM | 684 |
| TP53 | M237I | SDCTTIHYNYICNSSCMGGMN | 685 |
| TP53 | G244C | YNYMCNSSCMCGMNRRPILTI | 686 |
| TP53 | G245S | NYMCNSSCMGSMNRRPILTII | 687 |
| TP53 | R248L | CNSSCMGGMNLRPILTIITLE | 688 |
| TP53 | R248P | CNSSCMGGMNPRPILTIITLE | 689 |
| TP53 | R248Q | CNSSCMGGMNQRPILTIITLE | 690 |
| TP53 | R248W | CNSSCMGGMNWRPILTIITLE | 691 |
| TP53 | R249G | NSSCMGGMNRGPILTIITLED | 692 |
| TP53 | R249S | NSSCMGGMNRSPILTIITLED | 693 |
| TP53 | R249W | NSSCMGGMNRWPILTIITLED | 694 |
| TP53 | G266V | TLEDSSGNLLVRNSFEVRVCA | 695 |
| TP53 | F270I | SSGNLLGRNSIEVRVCACPGR | 696 |
| TP53 | R273C | NLLGRNSFEVCVCACPGRDRR | 697 |
| TP53 | R273H | NLLGRNSFEVHVCACPGRDRR | 698 |
| TP53 | R273P | NLLGRNSFEVPVCACPGRDRR | 699 |
| TP53 | R280I | FEVRVCACPGIDRRTEEENLR | 700 |
| TP53 | D281Y | EVRVCACPGRYRRTEEENLRK | 701 |

TABLE 19-continued

Exemplary NSCLC Squamous Cell Cancer Panel 21-Mers.
NSCLC Squamous Cell Cancer Panel 21-Mers

| Gene | Hotspot Mutation | Sequence | SEQ ID NO |
|---|---|---|---|
| TP53 | R282Q | VRVCACPGRDQRTEEENLRKK | 702 |
| TP53 | R282W | VRVCACPGRDWRTEEENLRKK | 703 |

The 21-mer peptides were designed to be fragments of the cancer-associated protein in which the recurrent cancer mutations occurs, including the recurrent cancer mutation and 10 amino acids of flanking sequence on each side. Antigenic peptides were scored by a Kyte and Doolittle hydropathy index with a 21 amino acid window, and peptides scoring above a cutoff of around 1.6 were excluded as they are unlikely to be secretable by *Listeria monocytogenes*. Constructs will be designed with the peptides in multiple different orders generated by randomization. Each ordering of the peptides will be scored by a Kyte and Doolittle hydropathy index with a sliding 21 amino acid window, and if any region for a particular ordering of peptides scores above a cutoff of around 1.6, the order of the peptides will be reshuffled until the ordering of peptides resulted in a polypeptide with no regions scoring above the cutoff.

Prostate Cancer

A total of 21 hotspot mutations across 9 genes were selected for the prostate cancer panel. This panel of hotspot mutations covers 27.6% of all prostate cancer patients.

TABLE 20

Exemplary Prostate Cancer Panel.
Prostate Cancer Panel

| Gene- | Hotspots | # of 21-mers | % patients covered |
|---|---|---|---|
| ANKRD36C | I645T, D629Y, D629N | 3 | 5.8% |
| SPOP | W131G, F133L, F133V, F133C, W131R, W131L | 6 | 5.8% |
| CHEK2 | K373E | 1 | 4.0% |
| KRTAP4-11 | M93V, R51K, L161V | 3 | 3.4% |
| RGPD8 | P1760A | 1 | 3.0% |
| TP53 | R248Q, G245S, G245D | 3 | 2.2% |
| FAM47C | N648D | 1 | 1.2% |
| ZAN | L878P | 1 | 1.2% |
| PIK3CA | E542K, H1047R | 2 | 1.0% |

For each recurrent cancer mutation included in the constructs, a peptide of 21 amino acids in length was designed.

TABLE 21

Exemplary Prostate Cancer Panel 21-Mers.
Prostate Cancer Panel 21-Mers

| Gene | Hotspot Mutation | Sequence | SEQ ID NO |
|---|---|---|---|
| ANKRD36C | I634T | TSDEKDSVSNTATEIKEGQQS | 704 |
| ANKRD36C | D629Y | PAEKATSDEKYSVSNIATEIK | 705 |
| ANKRD36C | D626N | QKQPAEKATSNEKDSVSNIAT | 706 |
| CHEK2 | K373E | LIKITDFGHSEILGETSLMRT | 707 |
| FAM47C | N648D | RMYSLRPEPPDTGVSHLCPEP | 708 |
| KRTAP4-11 | M93V | SCCKPQCCQSVCCQPTCCRPR | 709 |
| KRTAP4-11 | R51K | RPSCCVSSCCKPQCCQSVCCQ | 710 |
| KRTAP4-11 | L161V | ESSCCRPCCCVRPVCGGVSCH | 711 |
| PIK3CA | E542K | KAISTRDPLSKITEQEKDFLW | 712 |
| PIK3CA | H1047R | EYFMKQMNDARHGGWTTKMDW | 713 |
| RGPD8 | P1760A | AAVAQDEEENASRSSG* | 714 |
| SPOP | W131G | RAYRFVQGKDGGFKKFIRRDF | 715 |
| SPOP | F133L | YRFVQGKDWGLKKFIRRDFLL | 716 |
| SPOP | F133V | YRFVQGKDWGVKKFIRRDFLL | 717 |
| SPOP | F133C | YRFVQGKDWGCKKFIRRDFLL | 718 |
| SPOP | W131R | RAYRFVQGKDRGFKKFIRRDF | 719 |
| SPOP | W131L | RAYRFVQGKDLGFKKFIRRDF | 720 |
| TP53 | R248Q | CNSSCMGGMNQRPILTIITLE | 721 |
| TP53 | G245S | NYMCNSSCMGSMNRRPILTII | 722 |
| TP53 | G245D | NYMCNSSCMGDMNRRPILTII | 723 |
| ZAN | L878P | PEKLTIPTEKPTIPTEKPTIP | 724 |

The 21-mer peptides were designed to be fragments of the cancer-associated protein in which the recurrent cancer mutations occurs, including the recurrent cancer mutation and 10 amino acids of flanking sequence on each side. Antigenic peptides were scored by a Kyte and Doolittle hydropathy index with a 21 amino acid window, and peptides scoring above a cutoff of around 1.6 were excluded as they are unlikely to be secretable by *Listeria monocytogenes*. Constructs will be designed with the peptides in multiple different orders generated by randomization. Each ordering of the peptides will be scored by a Kyte and Doolittle hydropathy index with a sliding 21 amino acid window, and if any region for a particular ordering of peptides scores above a cutoff of around 1.6, the order of the peptides will be reshuffled until the ordering of peptides resulted in a polypeptide with no regions scoring above the cutoff.

Example 4. In Silico Methodology for ADXS_HOT Construct Design

Constructs were designed with peptides having hotspot mutations, heteroclitic peptides from tumor-associated antigen genes, and minigene constructs expressing a heteroclitic peptide. Additional constructs were designed to include these three elements alone or in any combination.

Hotspot mutations are somatic alterations that are recurrently altered across a large number of cancer patients. Many patients share common mutations in the functional domains of critical tumor driver genes that are the most frequently mutated or that are at least partially responsible for the creating a malignant phenotype. As described elsewhere herein, this mutational "sharing" across patients and tumor types creates an opportunity for the "off the shelf" development of treatment constructs that target these common hotspots. Hotspots targets we included range in overall frequency from 16%-80% in an indication. As there are 12,500+ MHC class I HLA types, including target peptides to cover every possible Class I binder would allow us to be able to treat any potential patient that harbors the right HLA/mutation combination. For example, by providing a 21mer hotspot target peptide having a hotspot mutation and 10 flanking amino acids from the cancer-associated protein on each side, the 21-mer target peptide will cover every 8mer, 9mer, 10mer, or 11mer peptide containing the hotspot missense mutation. By including every potential Class I epitope (8mer to 11mer), a hotspot panel could in principal cover any potential overlap with any of the known 12,500+ MHC class I molecules. Hotspots targets in ADXS_HOT constructs are designed to generate epitopes to virtually any of the 12,500+ identified HLA Class I alleles and are prioritized agnostic to in silico algorithms.

In addition to the hotspot peptides, heteroclitic sequences (i.e., sequence-optimized peptides) were designed to increase presentation by MHC Class I alleles. Heteroclitic peptides were derived by altering peptides expressed by tumor-associated antigen genes, as these represent genes that are expressed in tumor tissue, but have minimal expression in normal, healthy tissue. In particular, the heteroclitic peptides were designed from cancer-associated proteins such as cancer testis antigens or oncofetal antigens (i.e., were designed from tumor-associated antigens). Cancer testis antigens (CTAs) are a large family of tumor-associated antigens expressed in human tumors of different histological origin but not in normal tissue, except for male germ cells. In cancer, these developmental antigens can be re-expressed and can serve as a locus of immune activation. Oncofetal antigens (OFAs) are proteins that are typically present only during fetal development but are found in adults with certain kinds of cancer. The tumor-restricted pattern of expression of CTAs and OFAs make them ideal targets for tumor-specific immunotherapy. The combination of multiple hotspot peptides and OFA/CTAs maximizes patient coverage. Most hotspot mutations and OFA/CTA proteins play critical roles in oncogenesis. Targeting both at once can significantly impair cancer proliferation. Combining hotspot mutations with multiple OFA/CTAs peptides presents multiple high avidity targets in one treatment that are expressed in potentially all patients with the target disease. For example, constructs can be designed so that each patient expresses at least one target mutation. Hotspot peptides that the patient does not express do not elicit any immune response. Adding proprietary sequence-optimized peptides (i.e., heteroclitic peptides) can increase coverage up to 100% of patient population for an indication.

Heteroclitics were designed to the four most prevalent HLAs in North America from genes with up to 100% expression in a cancer type. The HLA types chosen included A0201, A0301, A2402, and B0702, which have frequencies of 47.8%, 20.6%, 20.6%, and 28.7%, respectively in Caucasian in North America, and frequencies of 16.8%, 23.8%, 8.9%, and 16.0% in African Americans in North America. This increases the odds of at least 1 peptide-MHC combination per patient. Heteroclitic sequences have been shown to be sufficient to prime a T cell response, to overcome central tolerance, and to elicit a successful cross-reactive immune response to the wild-type peptide. Addition of heteroclitic epitopes complements the hotspot mutation peptides in that total patient coverage within a cancer type approaches 100%. We therefore do not need to sequence a patient prior to treatment as we assume that they will express a tumor-associated antigen that we have designed heteroclitic peptides for to cover the most prevalent HLAs (HLA-A0201, HLA-A0301, HLA-A2402, and HLA-B0702).

Heteroclitic peptides to HLA-A0201 that had immunogenicity information from the literature were selected to be minigene epitopes in several constructs. Heteroclitic peptides to HLA-A2402 were also used in several constructs. Use of the minigene construct approach for the expression of specific MHC class I binding antigenic determinants in addition to the hotspot peptide approach and/or heteroclitic peptide approach disclosed herein allows for the highly efficient delivery of short peptide sequences to the antigen presentation pathway of professional antigen presenting cells (pAPC). A specific advantage of the minigene technology is that it bypasses the requirement for proteasome mediated degradation of larger proteins in order to liberate short peptide sequences that can be bound and presented on MHC class I molecules. This results in a much higher efficiency of peptide-MHC class I antigen presentation on the surface of the pAPC and, therefore, a much higher level of antigen expression for the priming of antigen specific T cell responses. Hotspots To identify recurrent somatic mutations "hotspots," publically available mutation databases were utilized. Databases included TCGA, ICGC, COSMIC, cBioportal, and so forth.

Mutation data were sub-stratified by disease indication type. In other words, all indication-specific samples were selected for mutation frequency calculations.

Recurrent somatic mutations included missense substitutions and INDELs resulting in in-frame and frameshift mutations.

Somatic mutations were rank-ordered within a specific-indication cohort based on frequency of the total number of mutation events observed across all samples.

Mutations occurring with frequencies below 1% were excluded.

Recurrent mutations with disease-indication frequencies equal to and above 1% were selected for panel.

Target peptides were generated for recurrent mutations. For missense substitutions, the mutant amino acid was flanked by up to 10 wild-type amino acids immediately before and after missense mutation position. For frameshift substitutions, the predicted peptide sequence arising from out-of-frame INDEL substitution was generated from annotation transcript and up to 10 wild-type amino acids are added upstream of frameshift mutation position. For in-frame INDEL substitutions, up to 10 wild-type amino acid sequences before and after INDEL position were joined together.

Specific identifiers were generated for each hotspot target peptide that consist of the gene symbol (HGNC format) and mutation substitution information (HGVS format) separated by an underscore. For example, the substitution of glycine for aspartic acid at position 12 in KRAS\would create a specific identifier of KRAS\_G12D.

Target peptides were then subjected to BLAST analysis against the non-redundant protein sequences (nr) database for human. This step ensured that target peptide sequences generate from frameshift mutations did not represent known, wild-type sequences. For missense substations, this step ensured that flanking wild-type amino acids matched the known human reference proteome.

Tumor-Associated Antigen Peptides (TAAPs)—Heteroclitic Mutations

A literature review was done to survey the genomic landscape of indication-specific tumor-associated antigens to generate a short-list of potential TAAs.

A second literature review was done to determine if short-list TAAs contained known immunogenic peptides that generate CD8+ T lymphocyte response. This approach focused primarily on MHC Class I epitopes consisting of 9 amino acids (9mer) from TAAs. This step identified potential TAAPs in 9mer format that bind to one of four HLAs types (HLA-A*02:01, HLA-A*03:01, HLA-A*24:02, and HLA-B*07:02).

TAAPs were sequence optimized to enhance binding to MHC Class I molecules (aka heteroclitic peptide). To optimize binding to each HLA, the Peptide MHC Binding Motif and Amino Acid Binding Chart were assessed from the Immune Epitope Database and Analysis Resource (for example: iedb.org/MHCalleleid/143). The preferred amino acids at the anchor positions were inserted into the TAAP sequence (e.g., NUF2—wild type: YMMPVNSEV (SEQ ID NO: 725); and NUF2—heteroclitic: YLMPVNSEV (SEQ ID NO: 726)).

The binding affinities of sequence-optimized TAAPs and wild-type TAAP sequences were then assessed using one of the following algorithms: NetMHC4.0 Server; NetMHC-pan4.0 Server; and mhcflurry v0.2.0.

Sequence-optimized TAAPs were considered if predicting binding affinity to a specific HLA was equivalent or stronger than the wild-type TAAP sequence.

Selected sequence-optimized TAAPs were then screened for in vitro binding to specific HLAs using ProImmune's REVEAL assay. TAAPs with binding affinity >=45% of the REVEAL assay's positive control peptide were considered binders.

Finally, the RNA expression level of TAAPs were measured in a specific-indication in TCGA RNAseqV2 dataset. The percentage of TCGA samples with normalized RNA expression reads greater than 0 were calculated. TAAPs with TCGA expression in a majority of samples were prioritized.

Example 5. Exemplary Protocol for Ligation of Insert into Vector, Transfection into Lm, Sequencing, PCR Confirmation, and Western Blot Confirmation of Lm Expression Synthesized DNA was received from an appropriate vendor (GENEWIZ, GenScript, or others). The desired insert contained the restriction sites XhoI and XmaI on the flanking ends to allow for molecular manipulations. The vendor ligated the insert into a shuttle vector of their choice (typically a pUC vector). The insert must be cut out of the pUC vector and ligated into the pAdv134 vector. Once this was completed, expression studies were performed in the LmddA strain.

Restriction Enzyme Digest of pAdv134 Vector and Insert

Goal: To cut out the proper bands of both the pAdv134 vector and the insert (in pUC or like shuttle vector) to ensure they had the correct sticky ends so that they could later be ligated together.

(1) Set up a restriction enzyme digest of 1.2 µg of DNA with the following reaction: DNA (~1.2 µg); XhoI; XmaI; 10× CutSmart buffer (final concentration of 1×); and water (if needed). To the vector DNA only, added 1 µL of CIP so that self-ligation was prevented.

(2) Quick mixed and spun of digests and left at 37° C. for 2-3 hours.

(3) Added 6×loading dye to each digest to a final 1×concentration.

(4) Loaded the entire digest on a 1% agarose gel.

(5) Loaded 10 µL of an appropriate DNA ladder so that size may be monitored on the agarose gel.

(6) Ran the agarose gel at 120V for ~45 minutes.

(7) Visualized and extracted the appropriate sized bands for each DNA sample from the agarose gel.

(8) Using a gel extraction kit (Zymo Clean Gel DNA Recovery Kit Cat. No. D4002/Zymo Research), purified the extracted bands.

(9) Measured the concentration of the purified DNA using a Nanodrop (or like, small-volume spectrophotometer.

(10) Loaded 1 µL of the final purified DNA (+1×loading dye) on a 1% agarose gel alongside an appropriate DNA ladder.

(11) Ran the agarose gel at 120V for ~45 minutes to ensure single, appropriately sized bands.

Ligation

Goal: To piece together the insert DNA with the pAdv134 vector to obtain a fully circular piece of DNA including both insert and pAdv134.

(1) Set up the ligation reaction: linearized (XhoI/XmaI cut) and purified pAdv134 vector (50 ng); cut (XhoI/XmaI) and purified insert (100 ng); 2 µL of 10× T4 ligase buffer (final concentration of 1×); 1 µL of T4 ligase; and water to a total volume of 20 µL.

(2) Quick mixed and spun of ligation reactions.

(3) Incubated ligation reaction in a thermocycler with the following parameters: (Step 1) 22° C. for 2 hrs; (Step 2) 16° C. for 4 hrs; and (Step 3) 4° C. overnight.

(4) Using a PCR purification kit (DNA Clean and Concentrator-5: Cat. No. D4003/Zymo Research), purified the ligation reaction through a column to rid excess salts and enzymes. Followed the protocol provided in the kit but eluted with a final volume of 10 µL of water.

Transformation

Goal: To allow the ligated plasmid product to gain entry into the E. coli MB2159 strain. Additionally, to allow ≥ doubling of E. coli cells containing the plasmid.

(1) On ice, gently thawed 1 vial (75 µL aliquot) of E. coli MB2159 electrocompetent cells.

(2) Added 5 µL of purified ligation reaction to the thawed E. coli MB2159 electrocompetent cells.

(3) Transferred the cell suspension to a 1 mm electroporation cuvette and gently tapped to the bottom.

(4) Pulsed the cuvette 1× with the following settings on an electroporator: V=1800 V; R=200 Q; and C=25 µF.

(5) Immediately added 900 µL SOC medium directly to the cuvette (gently pipette up and down a few times to resuspend cells).

(6) Transferred SOC medium with the electroporated cells to a 14 mL Falcon tube and grew shaking at 200 rpm for 1 hour at 37° C.

(7) Plated out 200 µL of the cell suspension onto an LB plate.

(8) Incubated the plate at 37° C. overnight.

(9) The following morning, picked colonies.

Clone Confirmation

Goal: To identify colonies that contain the pDNA.

(1) Prepared a PCR master mix to assess the number of colonies being examined for pDNA: 10 µL TERRA™ PCR Direct Red Dye Premix; 0.5 µL Forward Primer (5' catcgat-cactctgga (SEQ ID NO: 727)); 0.5 µL Reverse Primer (5' ctaactccaatgttacttg (SEQ ID NO: 728)); 9 µL water; colony (added in step 2) for a total volume of 20 µL.

(2) For each colony that needed to be assessed, performed the following steps: (a) picked up the colony with a pipette tip and re-streaked it on a fresh LB plate, trying to drag the colony around to obtain isolated colonies the following day; and (b) with some colony still on the tip, tapped/swirled it into the appropriate PCR reaction tube.

(3) Once finished with the colony restreaking, placed the new plate(s) at 37° C. overnight.

(4) Ran the PCR reaction in a thermocycler with the following program settings: 98° C. for 3 minutes; 98° C. for 30 seconds; 58° C. for 30 seconds (repeat for 34 cycles (35 cycles total)); 68° C. for 2 minutes; 72° C. for 5 minutes; and 4° C. until ready to run.

(5) Loaded 10 μL of PCR onto a 1% agarose gel, making sure to include 10 μL of 1 kB+ DNA ladder in a separate lane.

(6) Ran the agarose gel at 120V for ~45 minutes.

(7) Visualized the gel, looking for amplicons of the appropriate size. Those that were correct could be considered viable options for final pDNA constructs.

(8) The following day, removed the re-streaked plate(s) from the incubator in the morning and stored at 4° C. until later that afternoon.

(9) In the late afternoon, picked 1 colony and inoculated it into 200 μL of LB for each correct construct desired.

(10) The following morning, followed the midi prep directions for the NUCLEOBOND® Xtra Midi EF kit by Macherey-Nagel.

(11) Once the pDNA has been concentrated, measured the concentration using a Nanodrop spectrophotometer (or equivalent for small volumes). Ensured that the concentration was ~300 ng/μL and the A260/280 ratio was ~1.8.

(12) Sent the pDNA for Sanger sequencing to confirm 100% sequence match to reference.

Transformation into Listeria monocytogenes

Goal: To transform the plasmid DNA into the LmddA strain.

(1) On ice, gently thawed 1 vial (50 μL aliquot) of LmddA electrocompetent cells.

(2) Added 500 μg of plasmid DNA to the thawed LmddA electrocompetent cells.

(3) Incubated on ice for 5 minutes.

(4) Transferred the cell suspension to a 1 mm electroporation cuvette and gently tapped to the bottom.

(5) Pulsed the cuvette 1× with the following settings on an electroporator: V=1000 V; R=400 Ω; and C=25 μF.

(6) Immediately added 900 μL BHI+0.5M sucrose directly to the cuvette (gently pipetted up and down a few times to resuspend cells).

(7) Transferred cell suspension to a 14 mL Falcon tube and grew shaking at 200 rpm for 1 hour at 30° C.

(8) Plated out 100 μL of the cell suspension onto a BHI+100 μg/mL streptomycin plate.

(9) Incubated the plate at 37° C. for ~24 hours.

(10) Picked two colonies to restreak onto anew BHI+100 μg/mL streptomycin plate to obtain single colony isolates.

(11) Incubated the plate at 37° C. for ~24 hours.

(12) The following evening, picked one isolated colony from the restruck plate (step 11 plate) and grew it up in 3 mL BHI+100 μg/mL streptomycin at 30° C., stationary, overnight.

(13) The following morning, made a glycerol stock from the overnight culture by taking 500 μL of culture, adding it to a cryovial, then adding 500 μL of 50% glycerol. Mix well.

(14) Stored the glycerol stocks at −80° C.

Quality Control on Glycerol Stocks

Goal: Ensure the pDNA that was transformed into the LmddA strain aligns to the correct sequence ID.

(1) Prepared a PCR master mix to assess the number of glycerol stocks being examined for pDNA insertion size: 10 μL TERRA™ PCR Direct Red Dye Premix; 0.5 μL Forward Primer (5' catcgatcactctgga (SEQ ID NO: 727)); 5 μL Reverse Primer (5' ctaactccaatgttacttg (SEQ ID NO: 728)); 9 μL water; and glycerol stock material to a total volume of 20 μL.

(2) For each glycerol stock that needed to be assessed, performed the following steps: (a) with the glycerol stock on dry ice, took a pipette tip and scooped up a bit of material from the stock; and (b) tapped/swirled it into the appropriate PCR reaction tube.

(3) Ran the PCR reaction in a thermocycler with the following program settings: 98° C. for 3 minutes; 98° C. for 30 seconds; 58° C. for 30 seconds (repeat for 34 cycles (35 cycles total)); 68° C. for 2 minutes; 72° C. for 5 minutes; and 4° C. until ready to run.

(4) Loaded 10 μL of PCR onto a 1% agarose gel, making sure to include 10 μL of 1 kB+ DNA ladder in a separate lane.

(5) Ran the agarose gel at 120V for ~45 minutes.

(6) Visualized the gel, looking for amplicons of the appropriate size. This was the first step towards verification.

(7) Using a gel extraction kit (Zymo Clean Gel DNA Recovery Kit Cat. No. D4002/Zymo Research), purified the extracted bands, making sure to elute in water for the final step (otherwise, followed the kit's protocol).

(8) Sent the extracted DNA for Sanger sequencing to confirm sequence identify. This was the final step towards verification.

Lm Expression Studies

Goal: To visualize the amount of protein expression by our target antigen(s). This was assessed through the use of a FLAG tag at the 3' end of the construct. Loading was controlled by using an anti-p60 antibody.

(1) Streaked out the glycerol stock of interest onto a BHI+100 μg/mL streptomycin plate. Streaked so that single colonies would be able to be isolated the following day.

(2) Incubated the plate at 37° C. for ~24 hours.

(3) The following evening, inoculated one colony into 3 mL of TSB+100 μg/mL streptomycin.

(4) Incubated the culture(s) at 37° C., shaking at 200 rpm, overnight.

(5) The following morning, added 1 mL of culture to a 1.5 mL tube.

(6) Centrifuged for 5 minutes at 6000 g at 4° C.

(7) While spinning, prepared SDS-PAGE loading buffer: 10% 2-mercaptoethanol in 4×Laemmli buffer (example, 50 μL BME into 450 μL 4×Laemmli). Also, prechilled transfer tubes to 4° C.

(8) Transferred the 1 mL supernatant to a new, prechilled 1.5 mL tube. Avoided pellet.

(9) Prepared SDS-PAGE sample tubes at room temperature: (a) added 90 μL of supernatant to a new 1.5 mL tube; (b) added 30 μL of prepared Laemmli loading buffer; (c) added a LidLock to cap the tubes (prevents popping open during heating); (d) "boiled" the samples for 10 minutes (98° C. worked fine); (e) while boiling, placed the remainder of the supernatant sample at −20° C. for long term storage;

and (f) let the heated samples sit for a few minutes prior to removing the LidLock (relieves pressure).

(10) Prepared the SDS-PAGE gels (one gel for anti-Flag and one for anti-p60): (a) removed the comb and tape across the bottom; (b) assembled the gels in the Mini-PROTEAN Tetra Cell (can hold up to 4 gels); (c) prepared running buffer (made 1× running buffer by creating a 10% 10×Tris-Gly/SDS buffer in water (need about 1.2 L to run 4 gels simultaneously); and (d) filled the inner and outer chamber with running buffer to the designated level.

(11) Loaded 7 µl of standard (ladder) to appropriate well(s).

(12) Loaded 14 µl of sample per well.

(13) Ran the system for ~90 minutes: (a) ran at 90V until the dye front was into the gel (~10 minutes); and (b) increased to 120V until achieved appropriate separation (~1.5 hours).

(14) Once completed, cracked open the cassettes with the cassette opening lever by aligning with arrows on the cassette.

(15) Proceeded with transfer.

(16) Opened the appropriate number of Trans-Blot Turbo Midi Transfer Packs (PVDF)—one pack will transfer 2 of the above used gels ("mini gels").

(17) Placed the membrane and bottom stack into the transfer base of the Trans-Blot Turbo transfer system—used a roller to remove bubbles.

(18) Gently removed any excess acrylamide (very bottom of gel and top lanes) with a sharp instrument.

(19) Removed the trimmed gel(s) from the cassette and placed directly on top of the PVDF membrane that was sitting in the transfer base—used the roller to remove bubbles.

(20) Placed the top stack of prewet papers from the Trans-Blot Turbo Midi Transfer Pack on top of the gel(s)—used the roller to remove bubbles.

(21) Gently but firmly placed the top of the Trans-Blot Turbo transfer unit on top of the stack; then, while pushing down, locked the cassette lid into place.

(22) Placed the cassette into the Trans-Blot Turbo Transfer unit.

(23) Began the transfer.

(24) While the transfer was running, prepared 75 mL of working iBind Solution for the next section (a 72 mL volume covers 4 mini gels—each iBind Flex machine can process 2 mini gels, so processing 4 gels needs 2 machines): added 59.25 mL water; added 750 µL 100× Additive; added 15 mL 5×Buffer; and kept at 4° C. until use.

(25) While the transfer was running, prepared antibody solutions (volumes shown per blot): (a) primary: added 2 mL of prepared iBind Flex solution to a 15 mL conical+1:1000 primary (2 µL)*; and (b) secondary: added 2 mL of prepared iBind Flex solution to a 15 mL conical+1:1000 secondary (2 µL)* (*dilutions may change based on antibody used—shown here are for u-Flag and u-p60 blots (all at 1:1000)).

(26) Once completed, opened the transfer cassette(s) and removed the membrane(s)—placed into water, gently rocking until ready for blotting.

(27) Set up the correct reagent trays in the iBind Flex machine(s).

(28) Added an iBind Flex card to the machine(s).

(29) Pre-wet the card with 10 mL of prepared iBind Flex solution.

(30) Added an additional 1 mL of prepared iBind Flex solution to the area where each mini blot will lay immediately prior to placing membrane on the card.

(31) Using guide grids, placed blot(s) protein-side down in the appropriate area with low molecular weight closest to the stack.

(32) Rolled the blots to remove any air bubbles.

(33) Closed and pushed down the latch on the lid.

(34) Added the reagents to the reagent tray (volumes here are for mini gels): (a) Lane 1: 2 mL per blot of primary antibody (previously prepared in iBind Flex solution); (b) Lane 2: 2 mL per blot of prepared iBind Flex solution; (c) Lane 3: 2 mL per blot of secondary antibody (previously prepared in iBind Flex solution); and (d) Lane 4: 6 mL per blot of prepared iBind Flex solution.

(35) Closed the reagent cover and recorded the start time for the incubation.

(36) Let incubation proceed for at least 3 hours but up to O/N.

(37) Once time had passed, opened the lid to the reagent reservoir to ensure all liquid was gone.

(38) Removed the membranes and rinsed/stored in water.

(39) Discarded the iBind Flex card.

(40) Mixed equal parts of Super Signal West Dura Stable Peroxide Solution and Luminol/Enhancer Solution in a tube.

(41) Turned on the GE AI600. While it was warming up, added the developing reagent to the first blot: (a) decanted all water from the membrane; (b) added the membrane to the internal compartment of a plastic sheet protector; (c) added 1 mL of prepared developing solution directly to the membrane and placed the top of the sheet protector down on top of the solution/blot; eliminated any bubbles; and (d) let the membrane incubate for ~1-5 minutes.

(42) Imaged the blot.

(43) Rinsed and saved blots at 4° C. in water or discarded if not further needed.

Example 6. Proof of Concept: Therapeutic Efficacy of Lm-KRAS\_G12D Hotspot Constructs in a CT26 Challenge Studies This study determined the therapeutic efficacy of the Lm-KRAS\G12D hotspot constructs in suppressing CT26 tumor growth. The KRAS\_G12D mutation targeted here in the CT26 mouse model is identical to the human KRAS\_G12D hotspot identified in many human tumor indications. Additionally, this study assessed the efficacy of the KRAS\_G12D construct delivered as a non-minigene or delivered as a minigene construct. The KRAS\_G12D $K^d$ and $D^d$ constructs were designed using the hotspot heteroclitic design strategy used for predicting immunogenic 9mers that bind specific MHC alleles (MHC-I $K^d$ and MHC-I $D^d$). However, these constructs were not given a heteroclitic mutation as the target naturally has a HOT spot mutation.

Treatment Schedule

Lm-KRAS\_G12D hotspot vaccinations began as described in Table 1 and 2, followed with two boosts at one-week intervals. The details of the implantation and dosing schedules are given in Table 22.

TABLE 22

Treatments Schedule.

| Group (N = 10) | CT26 Implantation $3 \times 10^5$ cells | Titer CFU/mL | Weekly Dose: Lm $1 \times 10^8$ (IP/200 µL/mouse) | Weekly Dose: Lm $1 \times 10^8$ (IP/200 µL/mouse) | Weekly Dose: Lm $1 \times 10^8$ (IP/200 µL/mouse) |
|---|---|---|---|---|---|
| Naïve (PBS) | 14JUL17 | N/A | 18JUL17 | 25JUL17 | 1AUG17 |
| LmddA-274 | 14JUN17 | $1.4 \times 10^9$ | 18JUL17 | 25JUL17 | 1AUG17 |
| KRAS_G12D_Kd_mini | 14JUN17 | $1.2 \times 10^9$ | 18JUL17 | 25JUL17 | 1AUG17 |
| KRAS_G12D_Dd_mini | 14JUN17 | $1.6 \times 10^9$ CFU | 18JUL17 | 25JUL17 | 1AUG17 |
| KRAS_G12D_21mer | 14JUN17 | $1.8 \times 10^9$ | 18JUL17 | 25JUL17 | 1AUG17 |
| Lm-AH1 minigene (IV Dosing) | 14JUN17 | $7.6 \times 10^8$ | 18JUL17 | 25JUL17 | 1AUG17 |

Experimental Details

Tumor Cell Line Expansion. CT26 cell line (mouse colon carcinoma cell line) was cultured in RPMI with 10% FBS.

Tumor Inoculation. On Day 0, (14 Jun. 2017) CT26 cells will be trypsinized with 0.25% trypsin (1×) and washed twice with media at the appropriate concentration in PBS ($5 \times 10^5$ cells/mouse). CT26 cells were implanted subcutaneously in the right flank of each mouse.

Treatment. Vaccine preparation was as follows: (a) thawed 1 vial form −80° C. in 37° C. water bath; (b) spun at 14,000 rpm for 2 min and discarded supernatant; (c) washed 2 times with 1 mL PBS and discarded PBS; and (d) re-suspended to a final concentration of $5 \times 10^8$ CFU/mL. Dosing started 4 days after tumor implantation.

TABLE 23

Construct Sequences.

| Construct | Sequence |
|---|---|
| KRAS_G12D_21mer | VGKGGSGGGGGGSTEYKLVVVGADGVGKSALTIQGG GGSVGKGGSGGDYKDHDGDYKDHDIDYKDDDKADGS VKTLSKVLSIINFEKL (SEQ ID NO: 729) G12D 21mer: 14-34 FLAG tag: 48-68 SIINFEKL tag: 69-88 |
| KRAS_G12D_Kd minigene | DYKDHDGDYKDHDIDYKDDDKQIFVKTLTGKTITLE VEPSDTIENVKAKIQDKEGIPPDQQRLIFAGKQLED GRTLSDYNIQKESTLHLVLRLRGGADGVGKSAL (SEQ ID NO: 730) FLAG tag: 1-21 Ubiquitin: 22-96 G12D K$^d$ 9mer: 97-105 |
| KRAS_G12D_Dd minigene | DYKDHDGDYKDHDIDYKDDDKQIFVKTLTGKTITLE VEPSDTIENVKAKIQDKEGIPPDQQRLIFAGKQLED GRTLSDYNIQKESTLHLVLRLRGGDGVGKSALTI (SEQ ID NO: 731) FLAG tag: 1-21 Ubiquitin: 22-96 G12D D$^d$ 10mer: 97-106 |

Results and Conclusion

The KRAS\_G12D hotspot mutation was able to significantly control tumor growth in the murine CT26 colorectal cancer model. See FIG. 1. These data provided a strong proof of concept for targeting shared hotspot mutations. Additionally, the KRAS\_G12D hotspot used here was identical to the KRAS\_G12D hotspot mutation identified in various human cancer indications.

Furthermore, the KRAS\_G12D hotspot construct was able to effectively control tumor growth whether it was delivered as a 21mer or as a minigene. See FIG. 1. The efficacy of the minigene constructs strongly supported the design strategy for predicting and selecting minigene constructs based on in silico predictive MHC binding algorithms.

CT26 Challenge Study with Lm NSCLC HOT EVO2 EAAAK.i20 (B) (EAAAK=SEQ ID NO: 316)

Figure 34:
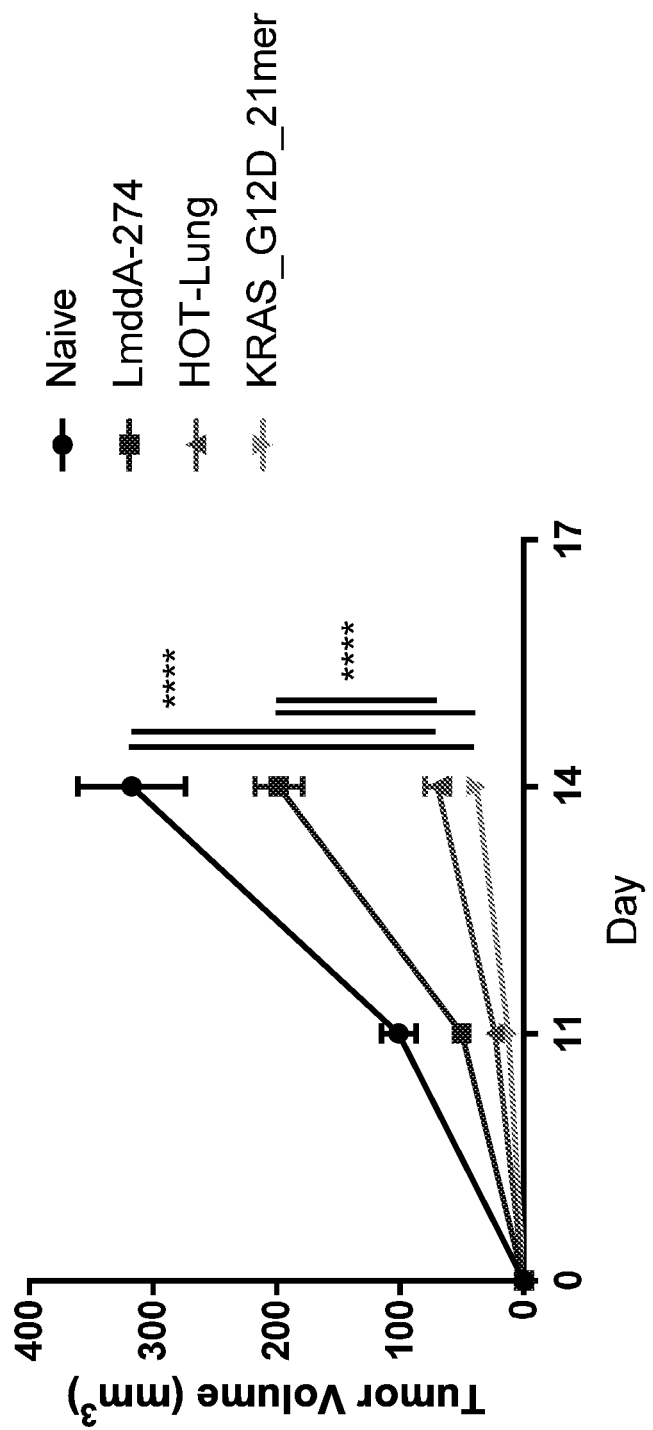
FIG. 34 shows CT26 tumor volume in naïve mice and mice treated with LmddA-274 control, Lm KRAS-G12D_21mer, and Lm NSCLC HOT EVO2 EAAAK.i20 (B) (HOT-Lung) (EAAAK=SEQ ID NO: 316). **** indicates P<0.001; error bars indicate SEM of n=10/group.

A similar experiment was performed to determine the therapeutic efficacy of the Lm NSCLC HOT EVO2 EAAAK.i20 (B) (EAAAK=SEQ ID NO: 316) hotspot construct (fusion polypeptide insert sequence set forth in SEQ ID NO: 895) in suppressing CT26 tumor growth. It is known that KRAS\mutations are frequent drivers of the linear and uniform evolution of spontaneous human cancers. The same KRAS\gene is mutated in the CT26 colorectal mouse model (KRAS\_G12D). Therefore, given that the Lm NSCLC HOT EVO2 EAAAK.i20 (B) (EAAAK=SEQ ID NO: 316) hotspot construct contains the same KRAS\_G12D mutational target as our KRAS\_G12D_21mer, we hypothesized that the Lm NSCLC HOT EVO2 EAAAK.i20 (B) (EAAAK=SEQ ID NO: 316) hotspot construct would suppress tumor growth in a similar fashion. Naïve BALB/c mice were implanted with 300,000 CT26 colorectal tumor cells in the flank. Four days after tumor implantation, mice were immunized with all Lm-constructs (LmddA-274 (Control), Lm NSCLC HOT EVO2 EAAAK.i20 (B) (EAAAK=SEQ ID NO: 316) hotspot construct (indicated as HOT-Lung in FIG. 34), and HOT-Lm KRAS\_G12D construct), followed with a boost one week after initial immunization. The data shown in FIG. 34 show the group tumor measurements. The data shown in FIG. 34 clearly demonstrate that the Lm NSCLC HOT EVO2 EAAAK.i20 (B) (EAAAK=SEQ ID NO: 316) hotspot construct can significantly suppress tumor progression compared to the control groups (Naïve and LmddA-274). There was not significant difference between the Lm NSCLC HOT EVO2 EAAAK.i20 (B) (EAAAK=SEQ ID NO: 316) hotspot construct and the KRAS\_G12D_21mer construct. The results demonstrate that the Lm NSCLC HOT EVO2 EAAAK.i20 (B) (EAAAK=SEQ ID NO: 316) hotspot construct can significantly control tumor growth equivalent to the KRAS\_G12D_21mer construct, highlighting its antitumor properties.

T Cell Data

BALB/c mice (n=4/group) were immunized at days 0 and 7 with the Lm-HOT KRAS\_G12D-21mer construct, and spleens were harvested one week post final immunization (day 14) to assess the cellular immune responses. FIGS. 24A and 24B demonstrate that the Lm-HOT KRAS\_G12D therapy can induce antigen-specific T cell responses in non-tumor bearing mice. Lm-HOT therapy augmented effector T cell function over controls, as evidenced by increased levels of splenic KRAS\-specific IFNg ELISpot responses. The induction of a TH1 responses is shown by the number of KRAS\_G12D-specific IFNg spot-forming colonies (SFC) per million splenocytes determined by IFNg ELISpot assay. Splenocytes were stimulated for 18 hours using KRAS\_G12D pooled peptides (15-mers overlapping by 9 amino acids; 2.5 μg/mL final concentration) spanning the entire KRAS\G12D 21mer antigen target.

Figure 25A:
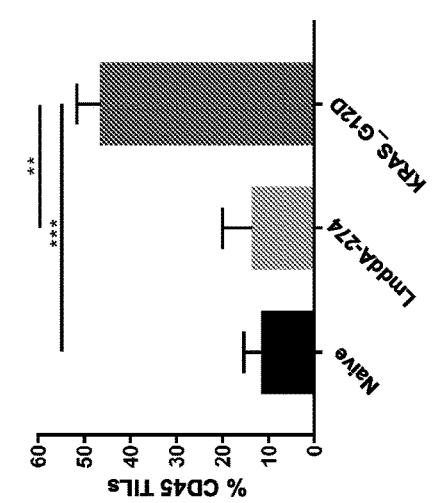
FIGS. 25A-25D show Lm-HOT construct therapy altered the cellular composition of the tumor immune microenvironment in the CT26 colorectal tumor model and induced KRAS tumor-specific T cells. Naïve BALB/c mice were implanted with 300,000 CT26 colorectal tumor cells in the flank. Four days after tumor implantation, mice were immunized with the HOT-Lm KRAS_G12D construct, followed with a boost one week after initial immunization. TILs from tumors of treated CT26 mice were harvested 14 days after tumor implantation.
Figure 25B:
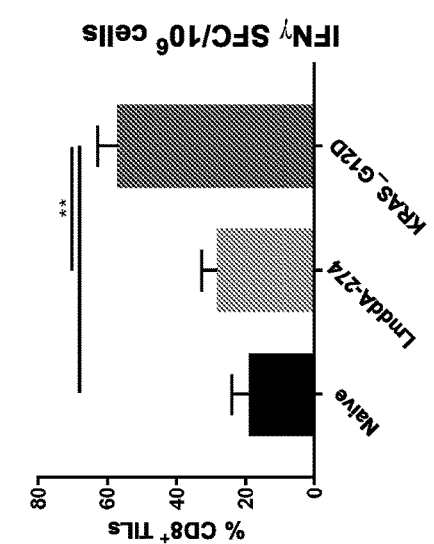
Figure 25C:
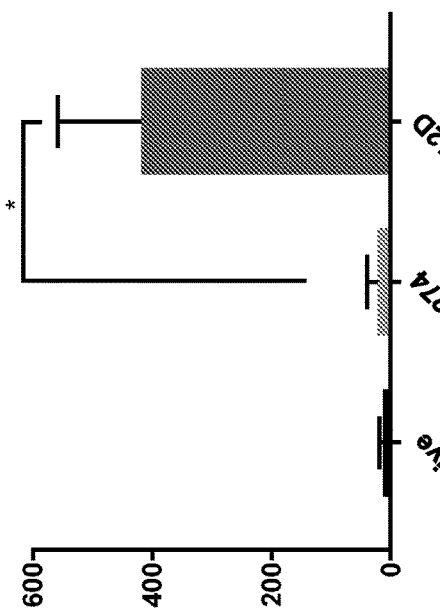
Figure 25D:
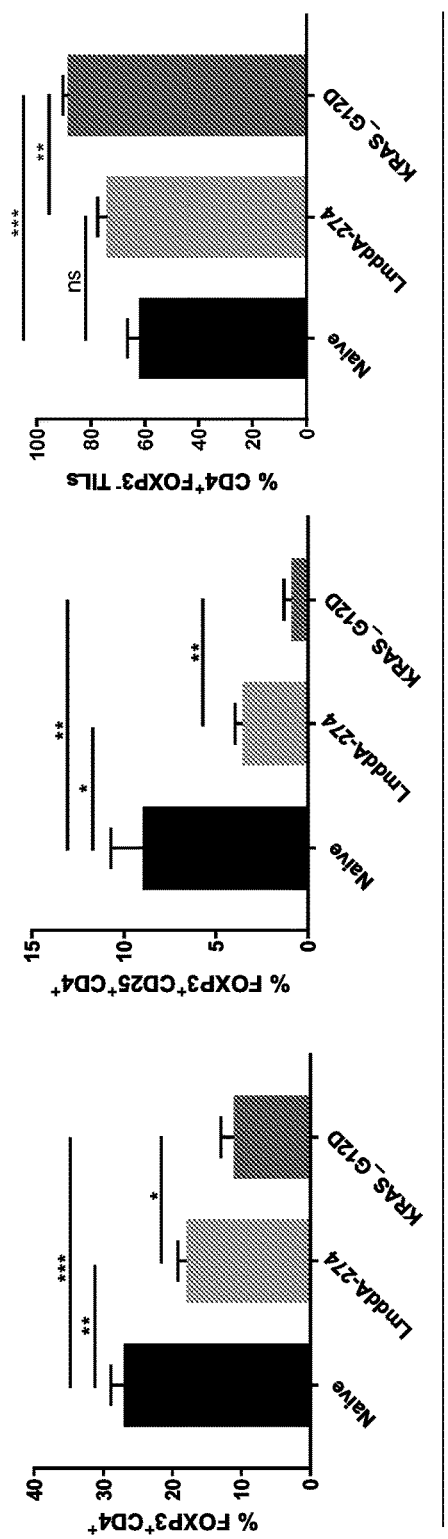

FIGS. 25A-25D show that Lm-HOT KRAS\-G12D therapy can alter the tumor immune microenvironment. Naïve BALB/c mice were implanted with 300,000 CT26 colorectal tumor cells in the flank. Four days after tumor implantation, mice were immunized with the HOT-Lm KRAS\_G12D construct, followed with a boost one week after initial immunization. TILs from tumors of treated CT26 mice were harvested 14 days after tumor implantation. Vaccine therapy altered the tumor-infiltrating lymphocyte (TIL) composition in the CT26 colorectal tumor model. Vaccine therapy showed significantly increased infiltration of total CD45 population, the percentage of tumor-infiltrating CD8 T cells, and significantly reduced the percentage of tumor-infiltrating CD4 Tregs. Furthermore, FIG. 25C shows that Lm-HOT constructs can drive KRAS\-specific tumor-infiltrating T cell responses. Consequently, Lm-HOT therapy significantly suppressed tumor growth in the CT26 colorectal tumor model.

Example 7. Proof of Concept: Efficacy of Lm Heteroclitic WT1 Minigene Fusion Protein Constructs The peptide minigene expression system was used to assess unique heteroclitic minigenes targeting the Wilms tumor protein. This expression system was designed to facilitate cloning of panels of recombinant proteins containing distinct peptide moieties at the carboxy-terminus. This is accomplished by a simple PCR reaction utilizing a sequence encoding one of the Signal Sequence (SS)-Ubiquitin (Ub)-Antigenic Peptide constructs as a template. By using a primer that extends into the carboxy-terminal region of the Ub sequence and introducing codons for the desired peptide sequence at the 3' end of the primer, a new SS-Ub-Peptide sequence can be generated in a single PCR reaction. The 5' primer encoding the bacterial promoter and first few nucleotides of the signal sequence (e.g., LLO or ActA$_{1-100}$ secretion signal) can be the same for all constructs. The constructs generated using this strategy are represented schematically in FIGS. 2A and 2B.

One of the advantages of the minigene system is that it will be possible to load cells with multiple peptides using a single *Listeria* vector construct. Multiple peptides can be introduce into recombinant attenuated *Listeria* (e.g., Lmdda) using a modification of the single peptide expression system described above. A chimeric protein encoding multiple distinct peptides from sequential SS-Ub-Peptide sequences can be encoded in one insert. See, e.g., FIG. 2B. Shine-Dalgamo ribosome binding sites can be introduced before each SS-Ub-Peptide coding sequence to enable separate translation of each of the peptide constructs. FIG. 2B demonstrates a schematic representation of a construct designed to express three separate peptide antigens from one strain of recombinant *Listeria*.

To assess the expression of tLLO-WT1-heteroclitic fusion proteins by ADXS Lmdda *Listeria* constructs, unique heteroclitic minigenes targeting the Wilms Tumor 1 protein were generated in the pAdv134 plasmid and transformed into Lmdda. The pAdv134 tLLO plasmid encodes the N-terminal LLO fragment set forth in SEQ ID NO: 336. The tLLO-WT1 heteroclitic fusion proteins comprise from N-terminal end to C-terminal end: the N-terminal LLO fragment set forth in SEQ ID NO: 336, followed by the FLAG tag set forth in SEQ ID NO: 762, followed by the ubiquitin sequence set forth in SEQ ID NO: 747, followed by a heteroclitic WT19-mer listed in Table 24, below.

TABLE 24

Heteroclitic WT1 Peptides.

| Construct # | WT1 9-Mer (Heteroclitic AA Bolded and Underlined) | SEQ ID NO |
|---|---|---|
| 1 | FMFPNAPYL | 732 |
| 2 | YLGEQQYSV | 733 |
| 3 | YLLPAVPSL | 734 |
| 4 | YLNALLPAV | 735 |
| 5 | ALLLRTPYV | 736 |
| 6 | YLGATLKGV | 737 |
| 7 | KLYFKLSHL | 738 |
| 8 | YMTWNQMNL | 739 |
| 9 | GLRRGIQDV | 740 |
| 10 | YMFPNAPYL | 741 |

The combined WT1-tLLO-FLAG-Ub-heteroclitic phenylalanine construct (construct #1) is set forth in SEQ ID NO: 742 (tLLO=1-441; FLAG=442-462; ubiquitin=463-537; heteroclitic phenylalanine peptide=538-546). One additional construct (Lmdda-WT1-tLLO-P1-P2-P3-FLAG-UB-heteroclitic tyrosine minigene construct) was generated that targets 3 WT1 peptides (P1-P2-P3; SEQ ID NOS: 743 (RSDELVRHHNMHQRNMTKL), 744 (PGCNK-RYFKLSHLQMHSRKHTG), and 745 (SGQAYMFPNAPYLPSCLES), respectively). Each 'P' peptide is comprised of 19-22 amino acids, sufficient in length to provide additional CD4 T helper epitopes. The three peptides are separated by linkers. The P3 peptide contains a heteroclitic mutation converting SGQARMFPNAPYLPSCLES (SEQ ID NO: 746) to SGQAYMFPNAPYLPSCLES (SEQ ID NO: 745). In addition to the heteroclitic P3 peptide, the Lmdda-WT1-tLLO-P1-P2-P3-FLAG-UB-heteroclitic tyrosine minigene construct contains a ubiquitin-YMFPNAPYL (SEQ ID NO: 741) moiety at the C-terminus. The combined WT1-tLLO-P1-P2-P3-FLAG-UB-heteroclitic tyrosine minigene construct is set forth in SEQ ID NO: 748 (tLLO=1-441; wild-type WT1 peptide v14-WT1-427 long=442-460; wild type WT1 peptide v15-WT1-331 long=466-487; heteroclitic WT1 peptide v1B-WT1-122A1-long=493-511; FLAG=512-532; ubiquitin=533-607; heteroclitic tyrosine peptide=608-616). Each individual Lmdda construct was assayed by Western blot for tLLO-fusion protein expression of the unique heteroclitic WT1 minigene product.

Construct #1 (Lmdda-WT1-tLLO-FLAG-Ub-heteroclitic phenylalanine minigene construct) and the Lmdda-WT1-tLLO-P1-P2-P3-FLAG-UB-heteroclitic tyrosine minigene construct were assayed by Western blot for tLLO-fusion protein expression of the unique heteroclitic WT1 minigene product. Single colonies from plates containing Lm WT1 minigene constructs were used to inoculate an overnight culture in 6 mL of Brain Heart Infusion (BHI) broth in a dry shaking incubator at 37° C. The following day, 1:10 dilution of the original overnight culture were re-suspended in 9 mL of fresh BHI and grown in the dry shaking incubator at 37° C. until reaching an $OD_{600}$=0.6. Cells were pelleted by 2-minute centrifugation at 13000 RPM. Sample supernatant were collected and run on SDS-PAGE. Samples were prepared by diluting 75 µL of sample with 25 µL of 4×LDS Sample Buffer (Cat #161-0747), boiled at 98° C. for 10 minutes, placed on ice, and then centrifuged at max speed for 10 minutes at 4° C. 13 µL of the sample was run on 4-15% precast protein gel (BioRad Cat #4561086). Protein gels were transferred using the Trans-Blot Turbo transfer apparatus (Cat #170-4155) and PVDF Midi transfer packs (Bio-Rad #170-4157). Blots were incubated with anti-FLAG monoclonal Antibody (Sigma F1804) or anti-LLO (Abcam ab200538) as primary and goat anti-mouse IgG-HRP conjugated (sc2005) as a secondary antibody. The blots were then incubated on iBind Flex (Invitrogen cat #1772866), washed, and then developed by Super Signal West Dura Extended Duration Substrate (ThermoFisher #34076); the images were developed on the Amersham Imager 600 (GE).

Expression and secretion of the unique tLLO-WT1-heteroclitic minigene fusion proteins was confirmed. Anti-Flag tag antibody Western blots of culture supernatant from construct #1 and the Lmdda-WT1-P1-P2-P3-YMFPNAPYL (SEQ ID NO: 741) Heteroclitic tyrosine+minigene construct are shown in FIGS. 3A and 3B, respectively. We were able to detect a protein band corresponding to the correct size and identity for each individual tLLO-WT1-heteroclitic minigene fusion protein. These data demonstrate the ability for heteroclitic peptides targeting multiple peptide fragments within the WT1 protein to be generated using the pAdv134 plasmid and Lmdda Listeria strain.

For constructs #2-9 in Table 24, each individual Lmdda construct was assayed by colony PCR in order to detect plasmid DNA from each unique tLLO-fusion protein containing heteroclitic WT1 minigenes.

TABLE 25

Materials.

| Material | Vendor | Catalog #/Sequence |
|---|---|---|
| DreamTaq DNA Polymerase | ThermoFisher | EP0702 |
| Forward Primer (Adv16 f)* | ThermoFisher | 5'-catcgatcactctgga-3' (SEQ ID NO: 727) |
| Reverse Primer (Adv295 r)* | ThermoFisher | 5'-ctaactccaatgttacttg-3' (SEQ ID NO: 728) |
| 10 mM dNTPs | NEB | N0447S |
| TrackIt 1 kB Plus DNA Ladder | ThermoFisher | 10488085 |

Procedure

The general colony PCR procedure that was used is as follows. Obtained plate with large colonies (generally, plates grown at 37° C. for 24 hours work well for this procedure). Created master mix for PCR as follows.

| Reagent | Volume (µL) |
|---|---|
| PCR water | 16 |
| DreamTaq 10x Buffer | 2 |
| Forward primer | 0.5 |

-continued

| Reagent | Volume (µL) |
|---|---|
| Reverse primer | 0.5 |
| 10 mM dNTPs | 0.5 |
| Dream Taq Polymerase | 0.5 |
| | =20 |

Aliquoted 20 µL of master mix into each PCR tube. Using a pipette tip (10-20 µL volume works best), scooped up a generous volume from one colony. Tapped the pipette tip into the PCR tube several times and swirled around to dislodge the bacteria. Ran the PCR reaction(s) in a thermocycler using the following PCR program.

| Step | Temp (° C.) | Time |
|---|---|---|
| 1 | 94 | 2 minutes |
| 2 | 94 | 30 seconds |
| 3 | 55* | 30 seconds |
| 4 | 72 | 1 minute |
| | repeat steps 2-4 an additional 29x | |
| 5 | 72 | 5 minutes |
| 6 | 4 | ∞ |

Removed PCR tubes from the thermocycler, added 4 µL of 6x loading dye. Ran 10 µL of each PCR reaction on a 1% agarose gel, alongside 10 µL of the 1 kb+ DNA ladder. The primers added an additional 163 base pairs to the product. The forward primer bound 70 base pairs upstream of the 3' end of tLLO (includes the XhoI site). The reverse primer bound 93 base pairs downstream of the stop sites (includes the XmaI site).

Representative colony PCR results showing Lmdda strains containing pAdv134 WT1-heteroclitic plasmids #2-9 from Table 24 are shown in FIG. 4. We were able to detect a DNA band corresponding to the correct size and identity for each individual tLLO-WT1-heteroclitic minigene plasmid. These data demonstrate the ability for heteroclitic peptides targeting multiple peptide fragments within the WT1 protein to be generated using the pAdv134 plasmid and Lmdda Listeria strain, which indicates that such constructs can be used as therapeutic compositions to target WT1 to create or enhance immune responses against WT1 and WT1-expressing cancers and tumors.

To assess the generation of WT1-specific T cell responses in AAD mice using two different WT1 constructs, ELISpots was performed to determine the desired vaccine-induced Ag-specific responses. The AAD mice (B6.Cg-Tg(HLA-A/H2-D)2Enge/J; The Jackson Laboratory—Stock No.: 004191) are transgenic mice that express an interspecies hybrid class I MHC gene, AAD, which contains the alpha-1 and alpha-2 domains of the human HLA-A2.1 gene and the alpha-3 transmembrane and cytoplasmic domains of the mouse H-2 Da gene, under the direction of the human HLA-A2.1 promoter. This transgenic strain enables the modeling of human T cell immune responses to HLA-A2 presented antigens, and may be useful in testing of vaccines for infectious diseases or cancer therapy. The immunization schedule is provided in Table 26. The mice that were used were female C57BL/6 mice aged 8-10 weeks.

TABLE 26

Immunization Schedule.

| Vaccine/ Group | Titer- CFU/mL | Mice/ Group | Dose 1 (IP/200 µL/ mouse) | Dose 2 (IP/200 µL/ mouse) | Harvest |
|---|---|---|---|---|---|
| 1- PBS | N/A | 5 | Day 0 | Day 12 | Day 18 |
| 2- LmddA 274 | ~1 × 10$^9$ | 5 | Day 0 | Day 12 | Day 18 |
| 3- WT1Fm-FLAG-Ub-9 (WT1-F minigene) | ~1 × 10$^9$ | 5 | Day 0 | Day 12 | Day 18 |
| 4- LmddA + pAdv134-WT1m:Ub-9 (WT1-AH1-Tyr minigene) | ~1 × 10$^9$ | 5 | Day 0 | Day 12 | Day 18 |

Vaccine Preparations. Briefly, each glycerol stock was streaked over required nutrient plate and grown overnight. A single colony was used for growth in an overnight culture of Brain Heart Infusion (BHI) broth under antibiotic selection. Overnight cultures were used at a 1:10 (vol/vol) dilution to inoculate fresh BHI broth. Bacteria were incubated in an orbital shaker for 1-3 hours at 37° C. to mid-log phase, an OD of ~0.6-0.7. Mice were infected with 1×10$^9$ CFU Lm by i.p. inoculation in PBS.

ELISPOT. On day 18, mice were sacrificed by CO2 asphyxiation in accordance with IACUC protocols, spleens were harvested, and splenocyte single-cell suspensions were plated on 96-well plates and stimulated with either the wild-type or heteroclitic peptide (Table 27). Similar experiments are done with other wild-type and heteroclitic peptide pairs (Table 28). An ELISPOT assay was used to enumerate antigen specific CD8 T Cells responding to either the wild-type or heteroclitic peptides. The full ELISPOT protocol was as per CTL immunospot.

TABLE 27

Wild-Type and Heteroclitic WT1 Peptides.

| Wild-Type Peptide | Negative Control | Heteroclitic Peptides |
|---|---|---|
| RMFPNAPYL (SEQ ID NO: 749) | RPMI Empty Media | FMFPNAPYL (SEQ ID NO: 732) YMFPNAPYL (SEQ ID NO: 741) |

TABLE 28

Wild-Type and Heteroclitic WT1 Peptides.

| Wild-Type | Heteroclitic |
|---|---|
| SLGEQQYSV (SEQ ID NO: 750) | YLGEQQYSV (SEQ ID NO: 733) |
| ALLPAVPSL (SEQ ID NO: 751) | YLLPAVPSL (SEQ ID NO: 734) |
| DLNALLPAV (SEQ ID NO: 752) | YLNALLPAV (SEQ ID NO: 735) |
| ALLLRTPYS (SEQ ID NO: 753) | ALLLRTPYV (SEQ ID NO: 736) |
| NLGATLKGV (SEQ ID NO: 754) | YLGATLKGV (SEQ ID NO: 737) |
| KRYFKLSHL (SEQ ID NO: 755) | KLYFKLSHL (SEQ ID NO: 738) |

TABLE 28-continued

Wild-Type and Heteroclitic WT1 Peptides.

| Wild-Type | Heteroclitic |
|---|---|
| CMTWNQMNL (SEQ ID NO: 756) | YMTWNQMNL (SEQ ID NO: 739) |
| GVFRGIQDV (SEQ ID NO: 757) | GLRRGIQDV (SEQ ID NO: 740) |

A generic ELISPOT protocol is provided below.

DAY 0 (Sterile Conditions). Prepared Capture Solution by diluting the Capture Antibody according to specific protocol. Many cytokines benefit from pre-wetting the PVDF membrane with 70% ethanol for 30 sec and washing with 150 µL of PBS three times before adding 80 µL of the Capture Solution into each well. Incubated plate overnight at 4° C. in a humidified chamber.

DAY 1 (Sterile Conditions). Prepared CTL-TEST™ Medium by adding 1% fresh L-glutamine. Prepared antigen/mitogen solutions at 2× final concentration in CTL-TEST™ Medium. Decanted plate with coating antibody from Day 0 and washed one time with 150 µL PBS. Plated antigen/mitogen solutions, 100 µL/well. After thawing PBMC or isolating white blood cells with density gradient, adjusted PBMC to desired concentration in CTL-TEST™ Medium, e.g., 3 million/mL corresponding to 300,000 cells/well (however, cell numbers can be adjusted according to expected spot counts since 100,000-800,000 cells/well will provide linear results). While processing PBMC and until plating, kept cells at 37° C. in humidified incubator, 5-9% CO$_2$. Plated PBMC, 100 µL/well using large orifice tips. Once completed, gently tapped the sides of the plate and immediately placed into a 37° C. humidified incubator, 5-9% CO$_2$. Incubated for 24-72 hours depending on your cytokine. Did not stack plates. Avoided shaking plates by carefully opening and shutting incubator door. Did not touch plates during incubation.

DAY2. Prepared Wash Solutions for the day: PBS, distilled water and Tween-PBS. Prepared Detection Solution by diluting Detection Antibody according to specific protocol. Washed plate two times with PBS and then two times with 0.05% Tween-PBS, 200 µL/well each time. Added 80 µL/well Detection Solution. Incubated at RT, 2h. Prepared Tertiary Solution by diluting the Tertiary Antibody according to specific protocol. Washed plate three times with 0.05% Tween-PBS, 200 µL/well. Added 80 µL/well of Strep-AP Solution. Incubated at RT, 30 min. Prepared Developer Solution according to your specific protocol. Washed plate two times with 0.05% Tween-PBS, and then two times with distilled water, 200 µL/well each time. Add Developer Solution, 80 µL/well. Incubated at RT, 10-20 min. Stopped reaction by gently rinsing membrane with tap water, decanted, and repeated three times. Removed protective underdrain of the plate and rinsed back of plate with tap water. Air dried plate for 2 hours face-down in running hood or on paper towels for 24 hours on bench top. Scanned and counted plate.

Figure 5:
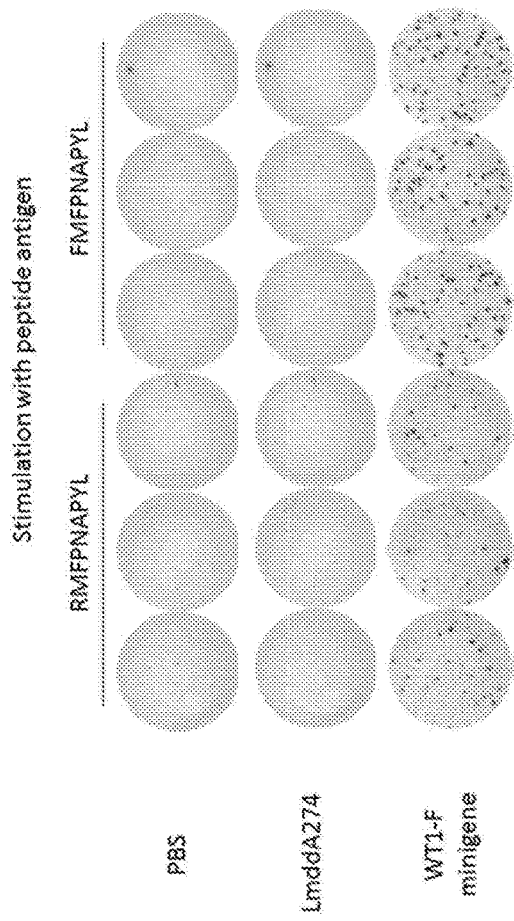
FIG. 5 shows an ELISPOT assay in splenocytes stimulated ex vivo with WT1 peptides RMFPNAPYL (SEQ ID NO: 749) and FMFPNAPYL (SEQ ID NO: 732). The splenocytes are from HLA2 transgenic mice immunized with the WT1-F minigene construct. PBS and LmddA274 were used as negative controls.

HLA-A2 transgenic B6 mice were vaccinated as described, and splenocytes were stimulated ex vivo with specific WT1 peptides (RMFPNAPYL (SEQ ID NO: 749), FMFPNAPYL (SEQ ID NO 732)) and analyzed by IFNg ELISpot assay. Heteroclitic vaccination (WT1-F minigene: FMFPNAPYL; SEQ ID NO: 732) induced Ag-specific T cell responses in immunized HLA2 transgenic mice. See FIG. 5 and FIG. 7B. In addition, heteroclitic vaccination elicited T cell responses that cross-reacted with the native WT1 tumor antigen (RMFPNAPYL; SEQ ID NO: 749). See FIG. 5 and FIG. 7A. The data demonstrated that vaccination with the WT1-F heteroclitic minigene vaccine can elicit T cells that are cross-reactive with the WT1-native tumor antigen (RMFPNAPYL; SEQ ID NO: 749). Overall, the data demonstrated that the heteroclitic minigene vaccine can elicit T cells that cross-react with the native tumor antigen.

Figure 6:
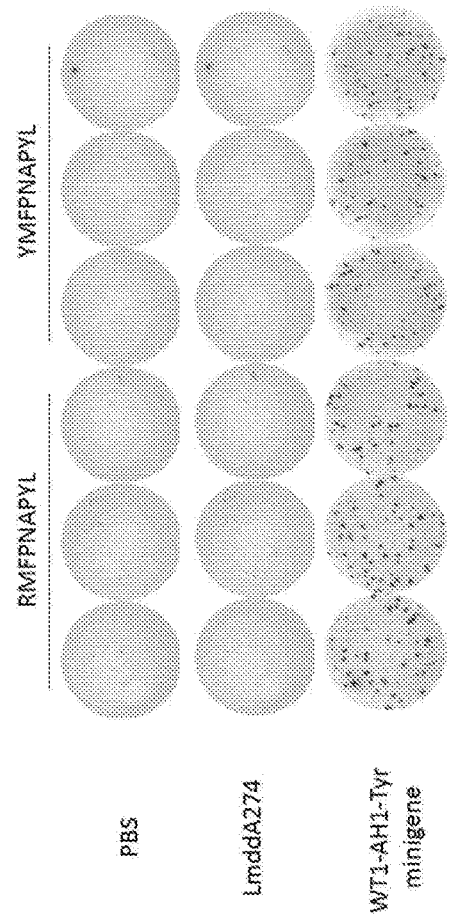
FIG. 6 shows an ELISPOT assay in splenocytes stimulated ex vivo with WT1 peptides RMFPNAPYL (SEQ ID NO: 749) and YMFPNAPYL (SEQ ID NO: 741). The splenocytes are from HLA2 transgenic mice immunized with the WT1-AH1-Tyr minigene construct. PBS and LmddA274 were used as negative controls.

HLA-A2 transgenic B6 mice were vaccinated as described and splenocytes were harvested. The ability of T cells to produce IFNg in response to vaccine-specific YMFPNAPYL peptide (SEQ ID NO: 741) or native WT1 peptide (RMFPNAPYL; SEQ ID NO: 749) was determined by IFNg ELISpot assay. Heteroclitic vaccination (WT1-AH1-Tyr minigene: YMFPNAPYL; SEQ ID NO: 741) induced Ag-specific T cell responses in immunized HLA2 transgenic mice. See FIG. 6 and FIG. 8B. In addition, heteroclitic vaccination elicited T cell responses that cross-react with the native WT1 tumor antigen (RMFPAPYL; SEQ ID NO: 749). See FIG. 6 and FIG. 8A.

Example 8. Proof of Concept: Therapeutic Efficacy of Lm MC38 Constructs in the MC38-Based Transplantable Colorectal Tumor Model Using C57BL/6 Female Mice This study investigated therapeutic efficacy of various MC38 constructs (non-minigenes and minigenes) in controlling established MC38 tumors. MC38 tumors are a tumor model using the MC38 cell line, which was derived from a mouse colon adenocarcinoma. Tumor volume and survival were observed. Two mutations present in all MC38 tumor models were tested in 21mer non-minigene form and in minigene form. One mutation was in the mouse Adpgk gene (ADP-dependent glucokinase; UniProt Accession No. Q8VDL4), and one mutation was in the mouse Dpagt1 gene (UDP-N-acetylglucosamine--dolichyl-phosphate N-acetyl-glucosaminephosphotransferase; UniProt Accession No. P42867). These mutations were identified from Yadav et al. (2014) *Nature* 515(7528):572-576, herein incorporated by reference in its entirety for all purposes.

Treatment Schedule

Once tumors were palpable (Day 8-15 Jun. 2017) mice were dosed once per week with various (Lm) MC38 constructs intraperitoneally (IP), for 3 consecutive weeks (indefinitely).

TABLE 29

Treatments Schedule

| Group (N = 10) | MC38 Implant $3 \times 10^5$ cells | Titer CFU/mL | Weekly Dose: Lm $1 \times 10^8$ (IP/200 µL/mouse) | Weekly Dose: Lm $1 \times 10^8$ (IP/200 µL/mouse) |
|---|---|---|---|---|
| PBS | 07JUN17 | NA | 15JUN17 | 22JUN17 |
| LmddA-274 (empty vector control) | 07JUN17 | $1.4 \times 10^9$ | 15JUN17 | 22JUN17 |
| Lin-Adpgk + Dpagt1 (5145-29897) | 07JUN17 | $6.9 \times 10^8$ | 15JUN17 | 22JUN17 |
| Adpgk minigene | 07JUN17 | $5.1 \times 10^8$ | 15JUN17 | 22JUN17 |
| Dpagt1 minigene | 07JUN17 | $5.3 \times 10^8$ | 15JUN17 | 22JUN17 |

Experimental Details

Tumor Cell Line Expansion. MC38 cells were split at 1:5 dilution and grown in a medium (IMDM Complete medium (c-RPMI); FBS at 10% (50 mL); Glutamax at 5 mL). On Day 0 (7 Jun. 2017), MC38 cells were cultured in IMDM and reached mid- to late-log phase of growth (~50% confluency). The cells were trypsinized with 0.25% trypsin (1×) for 2 minutes at RT. Trypsin was inhibited with 3 times volume complete media, and centrifuged at 1200 rpm for 5 minutes. The pellet was re-suspended in media (without antibiotics) and counted with MoxiFlow by BC.

Tumor Inoculation. Cells were counted and re-suspended at a concentration of $2 \times 10^5$ cells/200 uL/mouse. Tumor cells were injected subcutaneously in the right flank of each mouse.

Treatment. Vaccine preparation was as follows: (a) thawed 1 vial form −80° C. in 37° C. water bath; (b) spun at 14,000 rpm for 2 min and discarded supernatant; (c) washed 2 times with 1 mL PBS and discarded PBS; and (d) re-suspended to a final concentration of $5 \times 10^8$ CFU/mL.

TABLE 30

Construct Sequences.

| Construct | Insert Sequence |
|---|---|
| Adpgk + Dpagt1 | ASMTNMELMGGGGSSIIVFNLL (SEQ ID NO: 758) Adpgk Antigenic Sequence: 1-9 Dpagt1 Antigenic Sequence: 15-22 |
| Adpgk Minigene | QIFVKTLTGKTITLEVEPSDTIENVKAKIQDKEGI PPDQQRLIFAGKQLEDGRTLSDYNIQKESTLHLVL RLRGGASMTNMELM (SEQ ID NO: 759) Ubiquitin: 1-75 Adpgk Antigenic Sequence: 76-84 |
| Dpagt1 Minigene | QIFVKTLTGKTITLEVEPSDTIENVKAKIQDKEGI PPDQQRLIFAGKQLEDGRTLSDYNIQKESTLHLVL RLRGGSIIVFNLL (SEQ ID NO: 760) Ubiquitin: 1-75 Dpagt1 Antigenic Sequence: 76-83 |

Results and Conclusions

Figure 9:
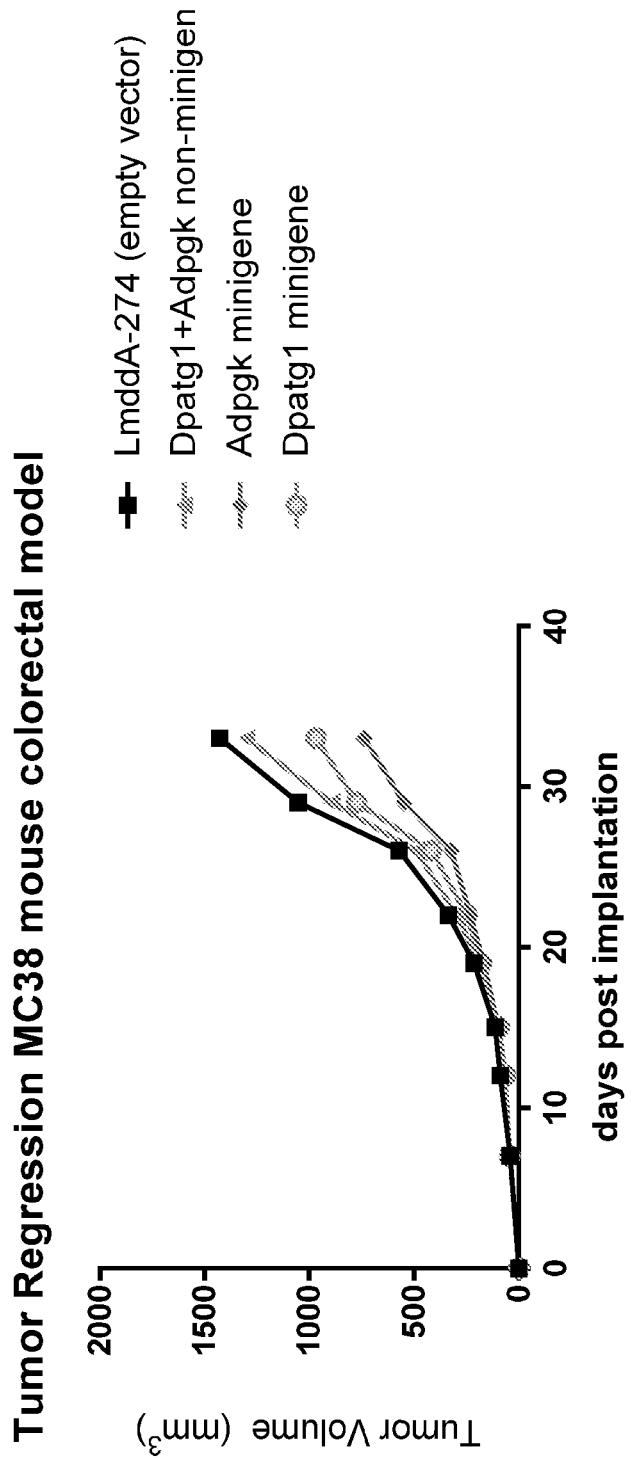
FIG. 9 shows MC38 tumor volume in mice treated with LmddA-274 control, Lm Dpagt1+Adpgk non-minigene, Lm Adpgk minigene, and Lm Dpagt1 minigene.

When mice were immunized with either Adpgk or Dpagt1 as minigenes, MC38 tumor volume was significantly reduced compared to LmddA-274 empty vector control and compared to the combined Adpgk and Dpagt1 mutations targeted in a non-minigene form. See FIG. 9.

Example 9. Proof of Concept: Therapeutic Efficacy of Non-Minigene and Minigene Lm-AH1 Constructs in a CT26 Challenge Study This study examined the therapeutic efficacy of Lm-AH1 constructs, including minigene and non-minigene constructs, in suppressing CT26 tumor growth. The constructs express fusion polypeptides comprising wild type peptides from gp70. AH1 refers to a bioactive nanomeric peptide derived from envelope glycoprotein 70 (gp70) of endogenous murine leukemia virus (MuLV), and is expressed by BALB/c-derived CT26 colorectal carcinomas. See, e.g., Scrimieri et al. (2013) *Oncoimmunology* 2(11):e26889, herein incorporated by reference in its entirety for all purposes.

Treatment Schedule

Lm-AH1 vaccination began 7-9 days after tumor implantation, followed with two boosts at one-week intervals. The details of the implantation and dosing schedules are given in Table 31.

TABLE 32

Construct Sequences.

| Construct | Sequence |
| --- | --- |
| Lm-AH1 21mer | VGKGGSGGGGGSPRVTYHSPSYVYHQFERRAKYG GGGSVGKGGSGGDYKDHDGDYKDHDIDYKDDDKAD GSVKTLSKVLSIINFEKLPRVTYHSPSYVYHQFER RAKY (SEQ ID NO: 1003) Antigenic 21-mer: 89-109 |
| Lm-AH1 Minigene | DYKDHDGDYKDHDIDYKDDDKQIFVKTLTGKTITL EVEPSDTIENVKAKIQDKEGIPPDQQRLIFAGKQL EDGRTLSDYNIQKESTLHLVLRLRGGSPSYVYHQF (SEQ ID NO: 1004) Ubiquitin: 22-96 Antigenic 9-mer: 97-105 |

Results and Conclusions

Here we demonstrated that the most effective route of administration for AH1 vaccines in the CT26 model is via IV

TABLE 31

Treatments Schedule.

| Group (N = 10) | CT26 Implantation 5 × 10⁵ cells | Titer CFU/mL | Weekly Dose: Lm 1 × 10⁸ (IP/200 µL/mouse) | Weekly Dose: Lm 1 × 10⁸ (IP/200 µL/mouse) | Weekly Dose: Lm 1 × 10⁸ (IP/200 µL/mouse) |
| --- | --- | --- | --- | --- | --- |
| Naïve (PBS) | 14JUN17 | N/A | 26JUN17 | 03JUL17 | 10JUL17 |
| LmddA-274 | 14JUN17 | 1.4 × 10⁹ | 26JUN17 | 03JUL17 | 10JUL17 |
| 3Lm-AH1 21mer (IV Dosing) | 14JUN17 | 5.6 × 10⁸ | 26JUN17 | 03JUL17 | 10JUL17 |
| Lm-AH1 21mer (IP Dosing) | 14JUN17 | 5.6 × 10⁸ | 26JUN17 | 03JUL17 | 10JUL17 |
| Lm-AH1 minigene (IV Dosing) | 14JUN17 | 7.6 × 10⁸ | 26JUN17 | 03JUL17 | 10JUL17 |
| Lm-AH1 minigene (IP dosing) | 14JUN17 | 7.6 × 10⁸ | 26JUN17 | 03JUL17 | 10JUL17 |

Experimental Details

Tumor Cell Line Expansion. CT26 cell line were cultured in RPMI with 10% FBS.

Tumor Inoculation. On Day 0, (14 Jun. 2017) CT26 cells will be trypsinized with 0.25% trypsin (1×) and washed twice with media at the appropriate concentration in PBS ($5 \times 10^5$ cells/mouse). CT26 cells were implanted subcutaneously in the right flank of each mouse.

Treatment. Vaccine preparation was as follows: (a) thawed 1 vial form −80° C. in 37° C. water bath; (b) spun at 14,000 rpm for 2 min and discarded supernatant; (c) washed 2 times with 1 mL PBS and discarded PBS; and (d) re-suspended to a final concentration of $5 \times 10^8$ CFU/mL.

dosing. Additionally, minigene constructs perform slightly better than the non-minigene counterparts, although this result is not statistically different. See FIGS. 10A and 10B. These data support efficacy of Lm constructs in both minigene and non-minigene form.

Example 10. Proof of Concept: Therapeutic Efficacy of Heteroclitic Lm-AH1 Constructs in a CT26 Challenge Study This study examined if Lm AH1-HC heteroclitic minigene vaccine could control or suppress CT26 tumor growth.

Treatment Schedule

Heteroclitic AH1-HC vaccination began as described in Table 33, followed with two boosts at one-week intervals with the recommended vaccine.

TABLE 33

Treatments Schedule.

| Group (N = 10) | CT26 Implantation 3 × 10⁵ cells | Titer CFU/mL | Weekly Dose: Lm 1 × 10⁸ (IV/200 uL/ mouse) | Weekly Dose: Lm 1 × 10⁸ (IV/200 uL/ mouse) | Weekly Dose: Lm 1 × 10⁸ (IV/200 uL/ mouse) |
|---|---|---|---|---|---|
| Naïve | Aug. 7, 2017 | N/A | Aug. 10, 2017 | Aug. 17, 2017 | Aug. 24, 2017 |
| AH1-HC | Aug. 7, 2017 | 6 × 10⁸ | Aug. 10, 2017 | Aug. 17, 2017 | Aug. 24, 2017 |

Experimental Details

Vaccine Dosing Details. AH1-HC refers to mice primed and boosted with heteroclitic AH1-HC vaccine.

Tumor Cell Line Expansion. CT26 cell line were cultured in RPMI with 10% FBS.

Tumor Inoculation. On Day 0, (14 Jun. 2017) CT26 cells will be trypsinized with 0.25% trypsin (1×) and washed twice with media at the appropriate concentration in PBS (3×10⁵ cells/mouse). CT26 cells were implanted subcutaneously in the right flank of each mouse.

Treatment. Vaccine preparation was as follows: (a) thawed 1 vial form −80° C. in 37° C. water bath; (b) spun at 14,000 rpm for 2 min and discarded supernatant; (c) washed 2 times with 1 mL PBS and discarded PBS; and (d) re-suspended to a final concentration of 5×10⁸ CFU/mL. Vaccine dosing began 3-4 days after tumor implantation.

TABLE 34

Construct Sequences.

| Construct | Sequence |
|---|---|
| Lm-AH1 HC | DYKDHDGDYKDHDIDYKDDDKQIFVKTLTGK TITLEVEPSDTIENVKAKIQDKEGIPPDQQR LIFAGKQLEDGRTLSDYNIQKESTLHLVLRL RGGMPKYAYHML (SEQ ID NO: 1005) Ubiquitin: 22-96 Heteroclitic AH1 9mer: 97-105 |
| AH1 Wild Type | SPSYVYHQF (SEQ ID NO: 1006) |

TABLE 34-continued

Construct Sequences.

| Construct | Sequence |
|---|---|
| AH1 Heteroclitic | MPKYAYHML (SEQ ID NO: 761) |

Results and Conclusions

Figure 11:
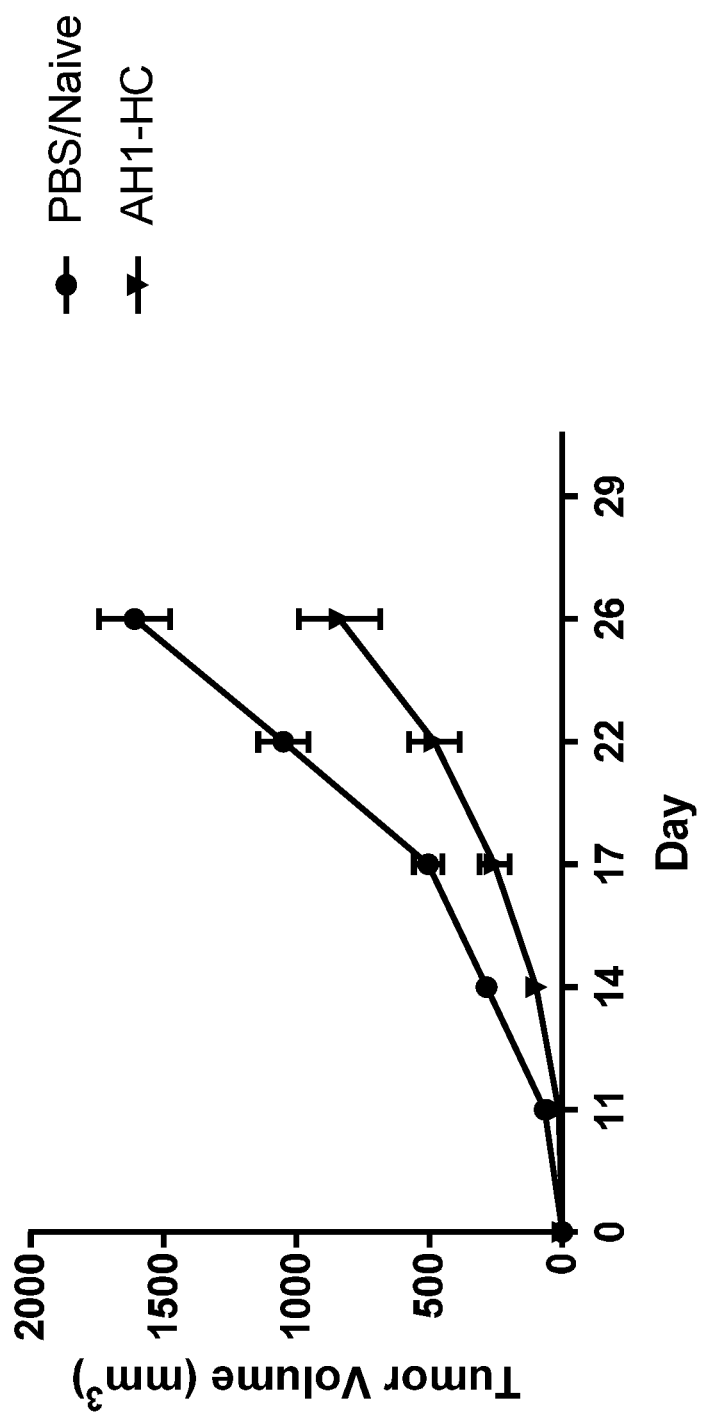
FIG. 11 shows CT26 tumor volume in mice treated with PBS control or Lm AH1_HC.

The Lm-AH1 HC construct was able to significantly control tumor growth in the murine CT26 colorectal cancer model. See FIG. 11.

Example 11. Design and Expression of Cancer-Type-Specific HOTSPOT Constructs with Heteroclitic Peptides and Minigenes We selected cancer types with recurrent cancer mutations on which to focus preclinical development efforts for ADXS-HOT constructs. These included non-small cell lung cancer, prostate cancer, pancreatic cancer, bladder cancer, breast cancer (e.g., ER+breast cancer), uterine cancer, ovarian cancer, low-grade glioma, colorectal cancer (e.g., MSS colorectal cancer), head and neck cancer, and DNA mismatch repair deficient cancers. Exemplary amino acid sequences for the constructs are provided throughout the Example. Exemplary nucleic acid sequences encoding such constructs are provided, for example, in SEQ ID NOS: 923-1002 and 2832-2848. Table 123 provides a summary of the constructs. The last column indicates the number of tumor-associated antigen (e.g., CTA/OFA) genes in the previous column that were expressed in at least 90% of The Cancer Genome Atlas (TCGA) patients for that indication. For example 3 TAA genes were expressed in over 90% of NSCLC patients. The rest of the TAA genes were expressed in <90% of the population of TCGA NSCLC patients.

TABLE 123

Summary of ADXS-HOT Constructs.

| Disease Panel | # Genes | # Hotspots | % Patients with ≥1 Hotspots | Sequence-Optimized Tumor-Associated Antigen (TAA) Peptides (e.g., CTA/OFA Genes) | # TAA Genes Expressed in >90% of Patients |
|---|---|---|---|---|---|
| NSCLC | 6 | 11 | 43 | CEACAM5, MAGE-A6, NY-ESO1, MAGE-A3, MAGE-A4, GAGE1 | 3 |
| Prostate | 5 | 14 | 16 | PSA, PSMA, STEAP1, SART3, TARP, PAGE-4, SSX2, MAGE-A4 | 7 |
| Breast (ER+) | 3 | 14 | 47 | STEAP1, RNF53, CEACAM5, PRAME, TERT, MAGE-A3 | 4 |
| CRC (MSS) | 4 | 12 | 58 | CEACAM5, MAGE-A6, MAGE-A3, MAGE-A4, NY-ESO1, GAGE1 | 2 |
| Head and Neck | 9 | 17 | 34 | CEACAM5, STEAP1, TERT, PRAME, MAGE-A4, NY-ESO1 | 4 |
| Pancreatic | 5 | 16 | 87 | STEAP1, SURVIVN, CEACAM5, PRAME, TERT, MAGE-A3 | 3 |
| Bladder | 6 | 14 | 43 | NUF2, KLHL7, MAGE-A3, NY-ESO1, GAGE1 | 4 |
| Ovarian | 1 | 12 | 25 | STEAP1, RNF43, SART3, KLHL7, NUF2, PRAME, TERT, CEACAM5, MAGE-A6 | 6 |

TABLE 123-continued

Summary of ADXS-HOT Constructs.

| Disease Panel | # Genes | # Hotspots | % Patients with ≥1 Hotspots | Sequence-Optimized Tumor-Associated Antigen (TAA) Peptides (e.g., CTA/OFA Genes) | # TAA Genes Expressed in >90% of Patients |
|---|---|---|---|---|---|
| Glioma | 5 | 11 | 80 | KLHL7, NUF2, RNF43, SART3, STEAP1, TERT, MAGE-A6, CEACAM5 | 4 |
| Uterine | 6 | 16 | 64 | STEAP1, RNF43, SART3, KLHL7, NUF2, PRAME, TERT, CEACAM5, MAGE-A6 | 4 |
| DNA Mismatch Repair Deficient | 26 | 29 | 54 | N/A | N/A |

Non-Small Cell Lung Cancer (NSCLC) Hotspot/Heteroclitic/Minigene Constructs

A total of 11 hotspot mutations across 6 genes were selected as described in Example 4 and elsewhere herein for the NSCLC ADXS-HOT constructs. This panel of hotspot mutations covers 43% o of all non-small cell lung cancer patients (i.e., 43% o of non-small cell lung cancer patients will have at least one of the hotspot mutations from the panel). For each recurrent cancer mutation included in the constructs, a peptide of 21 amino acids in length was designed as described in Example 4 and elsewhere herein. The peptides are shown in Table 35. The hotspot mutation in each is bolded and underlined.

TABLE 35

Exemplary NSCLC Panel Hotspot 21-Mers.
NSCLC Panel Hotspot 21-Mers

| Gene | Hotspot Mutation | % Prevalence in NSCLC Patients | Sequence | SEQ ID NO | Representative Nucleic Acid SEQ ID NOS |
|---|---|---|---|---|---|
| KRAS | G12C | 15.0 | TEYKLVVVGACGVGKSALTIQ | 486 | 1034-1052 |
| EGFR | L858R | 4.1 | PQHVKITDFGRAKLLGAEEKE | 405 | 1053-1071 |
| KRAS | G12D | 2.6 | TEYKLVVVGADGVGKSALTIQ | 489 | 1072-1090 |
| U2AF1 | S34F | 2.5 | IGACRHGDRCFRLHNKPTFSQ | 643 | 1091-1109 |
| BRAF | V600E | 1.4 | VKIGDFGLATEKSRWSGSHQF | 377 | 1110-1128 |
| KRAS | G12V | 6.4 | TEYKLVVVGAVGVGKSALTIQ | 491 | 1129-1147 |
| PIK3CA | E545K | 1.4 | STRDPLSEITKQEKDFLWSHR | 437 | 1148-1166 |
| TP53 | R158L | 1.4 | DSTPPPGTRVLAMAIYKQSQH | 631 | 1167-1185 |
| KRAS | G12A | 5.2 | TEYKLVVVGAAGVGKSALTIQ | 487 | 1186-1204 |
| EGFR | L861Q | 1.0 | VKITDFGLAKQLGAEEKEYHA | 406 | 1205-1223 |

TABLE 35-continued

Exemplary NSCLC Panel Hotspot 21-Mers.
NSCLC Panel Hotspot 21-Mers

| Gene | Hotspot Mutation | % Prevalence in NSCLC Patients | Sequence | SEQ ID NO | Representative Nucleic Acid SEQ ID NOS |
|---|---|---|---|---|---|
| TP53 | R273L | 1.0 | NLLGRNSFEVLVCACPGRDRR | 566 | 1224-1242 |

A total of 11 peptides with heteroclitic mutations across 7 genes were selected for the NSCLC ADXS-HOT constructs. For each heteroclitic mutation, a peptide of 9 amino acids in length was designed as described in Example 4 and elsewhere herein. The peptides are shown in Table 36. The heteroclitic mutation in each is as described in Table 122.

TABLE 36

Exemplary NSCLC Panel Heteroclitic 9-Mers.
NSCLC Panel Heteroclitic 9-Mers

| Gene | HLA Type | Sequence | SEQ ID NO | Representative Nucleic Acid SEQ ID NOS |
|---|---|---|---|---|
| CEACAM5 | A0301 | HVFGYSWYK | 791 | 2059-2077 |
| MAGEA6 | A0301 | YLFPVIFSK | 792 | 2078-2096 |
| CEACAM5 | B0702 | IPQVHTQVL | 793 | 2097-2115 |
| MAGEA4 | B0702 | MPSLREAAL | 794 | 2116-2134 |
| GAGE1 | B0702 | WPRPRRYVM | 795 | 2135-2153 |
| CEACAM5 | A2402 | IYPNASLLF | 796 | 2154-2172 |
| NYESO1 | A0201 | RLLEFYLAV | 797 | 2173-2191 |
| CEACAM5 | A0201 | ILIGVLVGV | 798 | 2192-2210 |
| STEAP1 | A0201 | LLLGTIHAV | 799 | 2823 |
| STEAP1 | A2402 | KYKKFPWWL | 800 | 2824 |
| RNF43 | B0702 | NPQPVWLCL | 801 | 2825 |

The in silico predicted binding affinity and in vitro binding affinity of the heteroclitic 9-mer peptides are provided in Table 36B. The in silico predicted binding affinity is based on the NetMHC4.0 algorithm, which predicts peptide binding to MHC class I molecules in terms of 50% o inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 36B are the percent expression of each gene in patients with NSCLC (The Cancer Genome Atlas (TCGA) database), the HLA allele being tested, and whether the wild-type peptide corresponding to each heteroclitic peptide is known to be immunogenic. For a construct including each of the heteroclitic peptides in Table 36B, 100% of NSCLC patients with HLA type A*02:01 express at least one of the TAA genes, 100% of NSCLC patients with HLA type A*03:01 express at least one of the TAA genes, 100% of NSCLC patients with HLA type A*24:02 express at least one of the TAA genes, and 100% of NSCLC patients with HLA type B*07:02 express at least one of the TAA genes.

the heteroclitic peptides are C-terminal to the hotspot peptides. In some constructs, the heteroclitic peptides are interspersed among the hotspot peptides. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37. The VGKGGSGG linker (SEQ ID NO: 314) can be used, for example, as a longer linker after the tLLO and also before the tag sequences to provide additional space between the tLLO and the antigenic portion of the fusion peptide and before the tag sequences. It also can provide flexibility and to charge balance the fusion protein. The EAAAK linker (SEQ ID NO: 316) is a rigid/stiff linker that can be used to facilitate expression and secretion, for example, if the fusion protein would otherwise fold on itself. The GGGGS linker (SEQ ID NO: 313) is a flexible linker that can be used, for example, to add increased flexibility to the fusion protein to help facilitate expression and secretion. The "i20" linkers (e.g., SEQ ID NOS: 821-829) are immunoproteasome linkers that are designed, for example, to help facilitate cleavage of the fusion protein by the immunoproteasome and increase the frequency of obtaining the exact minimal binding fragment that is desired. These can be used, for example, around the heteroclitic peptide sequences because the exact minimal 8mer-to-11mer desired to be generated is known. Combinations of GGGGS and EAAAK linkers (SEQ ID NOS: 313 and 316, respectively) can be used, for example, to alternate flexibility and rigidity to help balance the construct for improved expression and secretion and to help facilitate DNA synthesis by providing more unique codons to choose from. Combinations of EAAAK linkers (SEQ ID NO: 316) and "i20" linkers can be used, for example, by providing the rigid EAAAK (SEQ ID NO: 316) linker around the 21mer

TABLE 36B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| CEACAM5 | 100 | A*02:01 | 6.92 | 170.7 | Yes |
| CEACAM5 | 100 | A*24:02 | 6.22 | 77.2 | Yes |
| CEACAM5 | 100 | A*03:01 | 9.69 | 85.4 | Yes |
| CEACAM5 | 100 | B*07:02 | 8.36 | 88.3 | Yes |
| STEAP1 | 100 | A*02:01 | 5.77 | 188.4 | Yes |
| STEAP1 | 100 | A*24:02 | 47.48 | 104.7 | unknown |
| RNF43 | 100 | B*07:02 | 161.95 | 65.4 | Yes |
| MAGE-A6 | 53 | A*03:01 | 12.83 | 103.7 | unknown |
| NY-ES01 | 50 | A*02:01 | 4.61 | 212.9 | unknown |
| MAGE-A4 | 35 | B*07:02 | 7.67 | 49.5 | unknown |
| GAGE1 | 10 | B*07:02 | 2.58 | 58.5 | unknown |
| Additional Heteroclitic 9-Mers | | | | | |
| MAGE-A3[&] | 50 | A*02:01 | 50.31 | 168.7 | Yes |
| MAGE-A3[&] | 50 | A*24:02 | 2966 | 102.4 | unknown |

[#]NetMHC4.0
[^]% relative to positive control peptide binding
[&]SEQ ID NO: 817

Constructs were designed to encode a fusion polypeptide comprising tLLO fused to the hotspot peptides and one or more or all of the heteroclitic peptides, with the C-terminal heteroclitic peptide following a ubiquitin peptide. In some constructs, the ubiquitin was fused to the CEACAM5_A0201 heteroclitic peptide. In some of the constructs, the ubiquitin was fused to the CEACAM5_A2402 heteroclitic peptide. In some constructs, hotspot peptides and "i20" linkers around the heteroclitic sequences for which we know the exact 9mer desired to be generated. Combinations of GGGGS linkers (SEQ ID NO: 313) and "i20" linkers can be used, for example, by providing the flexible GGGGS (SEQ ID NO: 313) linker around the 21mer hotspot peptides and "i20" linkers around the heteroclitic sequences for which we know the exact 9mer desired to be generated.

TABLE 37

Linkers.

| Linker Sequence | SEQ ID NO. | Function |
|---|---|---|
| VGKGGSGG | 314 | Flexible |
| EAAAK | 316 | Rigid |
| GGGGS | 313 | Flexible |
| ADLVVG | 821 | Immunoproteasome Processing |
| ADLIEATAEEVL | 822 | Immunoproteasome Processing |
| GDGSIVSLAKTA | 823 | Immunoproteasome Processing |
| RDGSVADLAKVA | 824 | Immunoproteasome Processing |
| ADGSVKTLSKVL | 825 | Immunoproteasome Processing |
| GDGSIVDGSKEL | 826 | Immunoproteasome Processing |
| GDGSIKTAVKSL | 827 | Immunoproteasome Processing |
| ADLSVATLAKSL | 828 | Immunoproteasome Processing |
| ADLAVKTLAKVL | 829 | Immunoproteasome Processing |

Exemplary fusion polypeptide insert sequences (i.e., the peptide sequence downstream of the tLLO) include the following: (1) NSCLC HOT EVO2 EAAAK.G4S (A) (SEQ ID NO: 859; EAAAK=SEQ ID NO: 316; G4S=SEQ ID NO: 313); (2) NSCLC HOT G4S (A) (SEQ ID NO: 860; G4S=SEQ ID NO: 313); (3) NSCLC HOT EVO2 EAAAK-G4S mix (A) (SEQ ID NO: 861; EAAAK=SEQ ID NO: 316; G4S=SEQ ID NO: 313); (4) NSCLC HOT EVO2 EAAAK.i20 (A) (SEQ ID NO: 862; EAAAK=SEQ ID NO: 316); (5) NSCLC HOT EVO2 G4S.i20 (A) (SEQ ID NO: 863; G4S=SEQ ID NO: 313); (6) NSCLC HOT EVO 2 G4S LS #1 (A) (SEQ ID NO: 864; G4S=SEQ ID NO: 313); (7) NSCLC HOT EVO 2 G4S LS #2 (A) (SEQ ID NO: 865; G4S=SEQ ID NO: 313); (8) NSCLC HOT EVO2 EAAAK.G4S (B) (SEQ ID NO: 894; EAAAK=SEQ ID NO: 316; G4S=SEQ ID NO: 313); (9) NSCLC HOT EVO2 EAAAK.i20 (B) (SEQ ID NO: 895; EAAAK=SEQ ID NO: 316); and (10) NSCLC A24 HOT (SEQ ID NO: 905). A breakdown of the amino acids positions of the individual components in each construct is provided in Tables 38-47. For the (B) constructs, additional heteroclitic epitopes were added to complement the original hotspot mutation peptides so that total patient coverage within a cancer type approaches 100%. Any patient will therefore likely express a tumor-associated antigen that we have designed heteroclitic peptides for to cover the most prevalent HLAs (HLA-A0201, HLA-A0301, HLA-A2402, and HLA-B0702). For the A24 constructs, the 9-mer in the minigene was replaced by an A24 9mer. A24 (HLA-A2402) is the HLA type commonly found in Asia. For the LS constructs, the antigenic peptides in the fusion polypeptide were reordered based on hydrophobicity and charge. G4S (SEQ ID NO: 313), EAAAK (SEQ ID NO: 316), and i20 refer to inclusion of flexible linkers, rigid linkers, and immunoproteasome processing linkers, respectively.

TABLE 38

Positions of Components of NSCLC HOT EVO2 EAAAK.G4S (A) Insert.

14-34: KRAS_G12C
40-60: EGFR_L858R
66-86: KRAS_G12D
92-112: U2AF1_S34F
118-138: BRAF_V600E
144-164: KRAS_G12V
170-190: PIK3CA_E545K
196-216: TP53_R158L
222-242: KRAS_G12A
248-268: EGFR_L861Q
274-294: TP53_R273L
300-308: CEACAM5_A0301
314-322: MAGEA6_A0301
328-336: CEACAM5_B0702
342-350: MAGEA4_B0702
356-364: GAGE1_B0702
370-378: CEACAM5_A2402
384-392: NYESO1_A0201
406-426: FLAG
427-446: Linker-SIINFEKL
452-526: Ubiquitin
527-535: CEACAM5_A0201_MINI

TABLE 39

Positions of Components of NSCLC HOT G4S (A) Insert.

14-34: KRAS_G12C
40-60: EGFR_L858R
66-86: KRAS_G12D
92-112: U2AF1_S34F
118-138: BRAF_V600E
144-164: KRAS_G12V
170-190: PIK3CA_E545K
196-216: TP53_R158L
222-242: KRAS_G12A
248-268: EGFR_L861Q
274-294: TP53_R273L
300-308: CEACAM5_A0301
314-322: MAGEA6_A0301
328-336: CEACAM5_B0702
342-350: MAGEA4_B0702
356-364: GAGE1_B0702
370-378: CEACAM5_A2402
384-392: NYESO1_A0201
406-426: FLAG
427-446: Linker-SIINFEKL
452-526: Ubiquitin
527-535: CEACAM5_A0201_MINI

TABLE 40

Positions of Components of NSCLC HOT EVO2 EAAAK-G4S mix (A) Insert.

14-34: KRAS_G12C
40-60: EGFR_L858R
66-86: KRAS_G12D
92-112: U2AF1_S34F
118-138: BRAF_V600E
144-164: KRAS_G12V
170-190: PIK3CA_E545K
196-216: TP53_R158L
222-242: KRAS_G12A
248-268: EGFR_L861Q
274-294: TP53_R273L
300-308: CEACAM5_A0301
314-322: MAGEA6_A0301
328-336: CEACAM5_B0702
342-350: MAGEA4_B0702
356-364: GAGE1_B0702
370-378: CEACAM5_A2402

TABLE 40-continued

Positions of Components of NSCLC HOT EVO2 EAAAK-G4S mix (A) Insert.

384-392: NYESO1__A0201
406-426: FLAG
427-446: Linker-SIINFEKL
452-526: Ubiquitin
527-535: CEACAM5__A0201__MINI

TABLE 41

Positions of Components of NSCLC HOT EVO2 EAAAK.i20 (A) Insert.

14-34: KRAS__G12C
40-60: EGFR__L858R
66-86: KRAS__G12D
92-112: U2AF1__S34F
118-138: BRAF__V600E
144-164: KRAS__G12V
170-190: PIK3CA__E545K
196-216: TP53__R158L
222-242: KRAS__G12A
248-268: EGFR__L861Q
274-294: TP53__R273L
307-315: CEACAM5__A0301
328-336: MAGEA6__A0301
349-357: CEACAM5__B0702
370-378: MAGEA4__B0702
391-399: GAGE1__B0702
412-420: CEACAM5__A2402
433-441: NYESO1__A0201
462-482: FLAG
483-502: Linker-SIINFEKL
509-583: Ubiquitin
584-592: CEACAM5__A0201__MINI

TABLE 42

Positions of Components of NSCLC HOT EVO2 G4S.i20 (A) Insert.

14-34: KRAS__G12C
40-60: EGFR__L858R
66-86: KRAS__G12D
92-112: U2AF1__S34F
118-138: BRAF__V600E
144-164: KRAS__G12V
170-190: PIK3CA__E545K
196-216: TP53__R158L
222-242: KRAS__G12A
248-268: EGFR__L861Q
274-294: TP53__R273L
307-315: CEACAM5__A0301
328-336: MAGEA6__A0301
349-357: CEACAM5__B0702
370-378: MAGEA4__B0702
391-399: GAGE1__B0702
412-420: CEACAM5__A2402
433-441: NYESO1__A0201
462-482: FLAG
483-502: Linker-SIINFEKL
509-583: Ubiquitin
584-592: CEACAM5__A0201__MINI

TABLE 43

Positions of Components of NSCLC HOT EVO 2 G4S LS#1 (A) Insert.

14-22: GAGE1__B0702
28-36: NYESO1__A0201
42-62: U2AF1__S34F

TABLE 43-continued

Positions of Components of NSCLC HOT EVO 2 G4S LS#1 (A) Insert.

68-76: MAGEA4__B0702
82-102: PIK3CA__E545K
108-116: CEACAM5__A2402
122-142: TP53__R158L
148-168: KRAS__G12A
174-194: BRAF__V600E
200-208: MAGEA6__A0301
214-234: EGFR__L858R
240-260: KRAS__G12D
266-274: CEACAM5__A0301
280-300: KRAS__G12C
306-326: TP53__R273L
332-340: CEACAM5__B0702
346-366: EGFR__L861Q
372-392: KRAS__G12V
406-426: FLAG
427-446: Linker-SIINFEKL
451-526: Ubiquitin
527-535: CEACAM5__A0201__MINI

TABLE 44

Positions of Components of NSCLC HOT EVO 2 G4S LS#2 (A) Insert.

9-17: GAGE1__B0702
23-31: NYESO1__A0201
37-57: U2AF1__S34F
63-71: CEACAM5__A2402
77-97: PIK3CA__E545K
103-111: MAGEA6__A0301
117-137: TP53__R158L
143-163: KRAS__G12C
169-189: BRAF__V600E
195-215: KRAS__G12V
221-241: EGFR__L858R
247-255: CEACAM5__B0702
261-269: CEACAM5__A0301
275-295: KRAS__G12D
301-321: TP53__R273L
327-347: KRAS__G12A
353-373: EGFR__L861Q
379-387: MAGEA4__B0702
406-426: FLAG
427-446: Linker-SIINFEKL
451-526: Ubiquitin
527-535: CEACAM5__A0201__MINI

TABLE 45

Positions of Components of NSCLC HOT EVO2 EAAAK.G4S (B) Insert.

14-34: KRAS__G12C
40-60: EGFR__L858R
66-86: KRAS__G12D
92-112: U2AF1__S34F
118-138: BRAF__V600E
144-164: KRAS__G12V
170-190: PIK3CA__E545K
196-216: TP53__R158L
222-242: KRAS__G12A
248-268: EGFR__L861Q
274-294: TP53__R273L
300-308: CEACAM5__A0301
314-322: MAGEA6__A0301
328-336: CEACAM5__B0702
342-350: MAGEA4__B0702
356-364: GAGE1__B0702
370-378: CEACAM5__A2402
384-392: NYESO1__A0201
398-406: STEAP1__A0201

TABLE 45-continued

Positions of Components of NSCLC
HOT EVO2 EAAAK.G4S (B) Insert.

412-420: STEAP1_A2402
426-434: RNF43_B0702
448-468: FLAG
469-488: Linker-SIINFEKL
494-568: Ubiquitin
569-577: CEACAM5_A0201_MINI

TABLE 46

Positions of Components of NSCLC
HOT EVO2 EAAAK.i20 (B) Insert.

14-34: KRAS_G12C
40-60: EGFR_L858R
66-86: KRAS_G12D
92-112: U2AF1_S34F
118-138: BRAF_V600E
144-164: KRAS_G12V
170-190: PIK3CA_E545K
196-216: TP53_R158L
222-242: KRAS_G12A
248-268: EGFR_L861Q
274-294: TP53_R273L
307-315: CEACAM5_A0301
328-336: MAGEA6_A0301
349-357: CEACAM5_B0702
370-378: MAGEA4_B0702
391-399: GAGE1_B0702
412-420: CEACAM5_A2402
433-441: NYESO1_A0201
454-462: STEAP1_A0201
475-483: STEAP1_A2402
496-504: RNF43_B0702
525-545: FLAG
546-565: Linker-SIINFEKL
572-646: Ubiquitin
647-655: CEACAM5_A0201_MINI

TABLE 47

Positions of Components of NSCLC A24 HOT Insert.

14-34: KRAS_G12C
40-60: EGFR_L858R
66-86: KRAS_G12D
92-112: U2AF1_S34F
118-138: BRAF_V600E
144-164: KRAS_G12V
170-190: PIK3CA_E545K
196-216: TP53_R158L
222-242: KRAS_G12A
248-268: EGFR_L861Q
274-294: TP53_R273L
307-315: CEACAM5_A0301
328-336: MAGEA6_A0301
349-357: CEACAM5_B0702
370-378: MAGEA4_B0702
391-399: GAGE1_B0702
412-420: CEACAM5_A0201
433-441: NYESO1_A0201
454-462: STEAP1_A0201
475-483: STEAP1_A2402
496-504: RNF43_B0702
525-545: FLAG
546-565: Linker-SIINFEKL
572-646: Ubiquitin
647-655: CEACAM5_A2402 MINI Constructs were also designed to encode a fusion polypeptide comprising tLLO fused to the hotspot peptides and one or more or all of the heteroclitic peptides without a ubiquitin peptide (i.e., hotspot peptides plus heteroclitic peptides with no "minigene"). The tLLO, hotspot peptide and heteroclitic peptide components of the fusion polypeptides were joined by various linkers selected from those in Table 37. An exemplary fusion polypeptide insert sequence (i.e., the peptide sequence downstream of the tLLO) is NSCLC HS+HC (SEQ ID NO: 909).

Constructs were also designed to encode a fusion polypeptide comprising tLLO fused to the hotspot peptides with no heteroclitic peptides other than a ubiquitin peptide fused to a heteroclitic peptide at the C-terminal end (i.e., hotspot peptides plus "minigene" with no additional heteroclitic peptides). The tLLO, hotspot peptide, and ubiquitin/heteroclitic peptide components of the fusion polypeptides were joined by various linkers selected from those in Table 37. An exemplary fusion polypeptide insert sequence (i.e., the peptide sequence downstream of the tLLO) is NSCLC HS+MG (SEQ ID NO: 910).

Constructs were also designed to encode a fusion polypeptide comprising tLLO fused to one or more heteroclitic peptides, with the C-terminal heteroclitic peptide following a ubiquitin peptide (i.e., heteroclitic peptides and "minigene" with no hotspot peptides). The tLLO, heteroclitic peptide, and ubiquitin/heteroclitic peptide components of the fusion polypeptides were joined by various linkers selected from those in Table 37. An exemplary fusion polypeptide insert sequence (i.e., the peptide sequence downstream of the tLLO) is NSCLC HC+MG (SEQ ID NO: 911).

Constructs were also designed to encode a fusion polypeptide comprising tLLO fused to one or more heteroclitic peptides without any ubiquitin peptide and without any hotspot peptides (i.e., heteroclitic peptides with no "minigene" and with no hotspot peptides). The tLLO and heteroclitic peptide components of the fusion polypeptides were joined by various linkers selected from those in Table 37. An exemplary fusion polypeptide insert sequence (i.e., the peptide sequence downstream of the tLLO) is NSCLC HC only (SEQ ID NO: 912).

A breakdown of the amino acids positions of the individual components in each construct is provided in Tables 48-51.

TABLE 48

Positions of Components of NSCLC HS + HC Insert.

14-34: KRAS_G12C
40-60: EGFR_L858R
66-86: KRAS_G12D
92-112: U2AF1_S34F
118-138: BRAF_V600E
144-164: KRAS_G12V
170-190: PIK3CA_E545K
196-216: TP53_R158L
222-242: KRAS_G12A
248-268: EGFR_L861Q
274-294: TP53_R273L
307-315: CEACAM5_A0301
328-336: MAGEA6_A0301
349-357: CEACAM5_B0702
370-378: MAGEA4_B0702
391-399: GAGE1_B0702
412-420: CEACAM5_A2402
433-441: NYESO1_A0201
454-462: STEAP1_A0201
475-483: STEAP1_A2402
496-504: RNF43_B0702
525-545: FLAG
546-565: Linker-SIINFEKL
572-580: CEACAM5_A0201_MINI

TABLE 49

Positions of Components of NSCLC HS + MG Insert.

14-34: KRAS_G12C
40-60: EGFR_L858R
66-86: KRAS_G12D
92-112: U2AF1_S34F
118-138: BRAF_V600E
144-164: KRAS_G12V
170-190: PIK3CA_E545K
196-216: TP53_R158L
222-242: KRAS_G12A
248-268: EGFR_L861Q
274-294: TP53_R273L
303-323: FLAG
324-343: Linker-SIINFEKL
350-424: Ubiquitin
425-433: CEACAM5_A0201_MINI

TABLE 50

Positions of Components of NSCLC HC + MG Insert.

21-29: CEACAM5_A0301
42-50: MAGEA6_A0301
63-71: CEACAM5_B0702
84-92: MAGEA4_B0702
105-113: GAGE1_B0702
126-134: CEACAM5_A2402
147-155: NYESO1_A0201
168-176: STEAP1_A0201
189-197: STEAP1_A2402
210-218: RNF43_B0702
239-259: FLAG
260-279: Linker-SIINFEKL
286-360: Ubiquitin
361-369: CEACAM5_A0201_MINI

TABLE 51

Positions of Components of NSCLC HC Only Insert.

Figure 12:
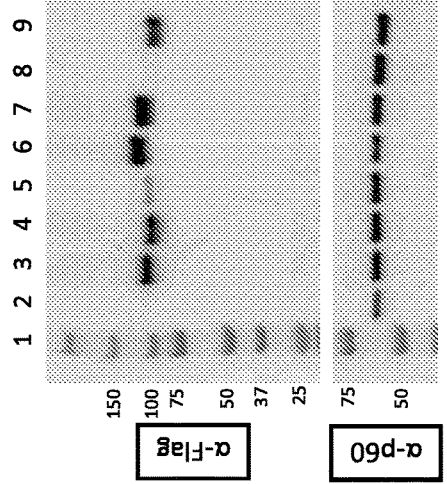
FIG. 12 shows Western blot data for different NSCLC constructs. The upper left panel shows detection, using an anti-Flag antibody, of NSCLC constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 18:
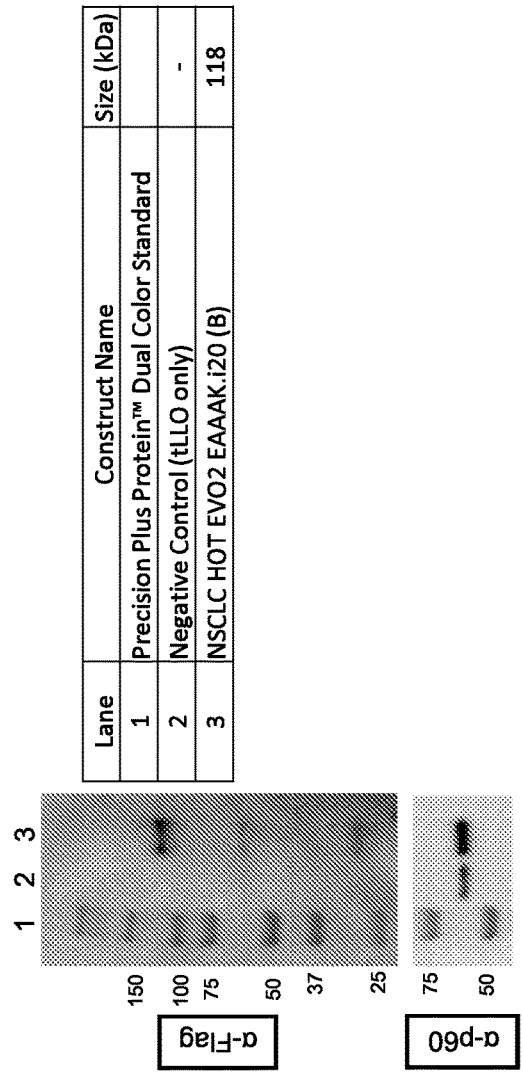
FIG. 18 shows Western blot data for different NSCLC constructs. The upper left panel shows detection, using an anti-Flag antibody, of NSCLC constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 27:
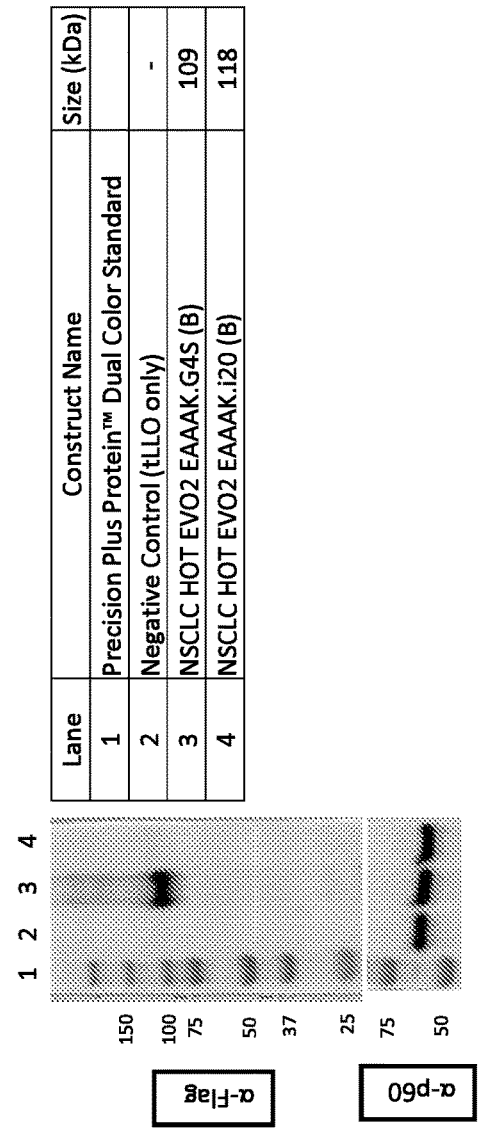
FIG. 27 shows Western blot data for different non-small cell lung cancer (NSCLC) constructs. The upper left panel shows detection, using an anti-Flag antibody, of NSCLC constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 32:
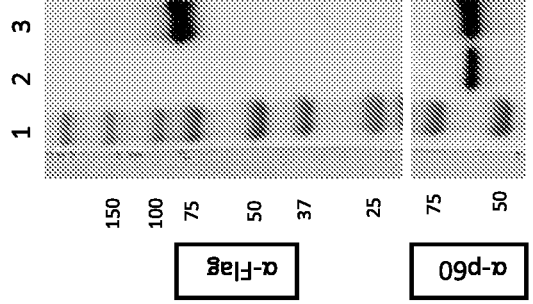
FIG. 32 shows Western blot data for a non-small cell lung cancer (NSCLC) construct. The upper left panel shows detection, using an anti-Flag antibody, of NSCLC constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.

21-29: CEACAM5_A0301
42-50: MAGEA6_A0301
63-71: CEACAM5_B0702
84-92: MAGEA4_B0702
105-113: GAGE1_B0702
126-134: CEACAM5_A2402
147-155: NYESO1_A0201
168-176: STEAP1_A0201
189-197: STEAP1_A2402
210-218: RNF43_B0702
239-259: FLAG
260-279: Linker-SIINFEKL
286-294: CEACAM5_A0201_MINI To assess the expression of tLLO-antigenic-peptide fusion proteins by Lmdda *Listeria* constructs, the DNA constructs were generated as described elsewhere herein and transformed into Lmdda. Each individual Lmdda construct was assayed by Western blot for tLLO fusion polypeptide expression using an anti-FLAG antibody. FIGS. 12 and 18 show expression and secretion of the tLLO fusion polypeptide into supernatant by Lmdda for various NSCLS constructs. The constructs visualized on these Western blots all fall between 103-125 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing. FIG. 27 shows expression and secretion of the tLLO fusion polypeptide into supernatant by Lmdda for the NSCLC HOT EVO2 EAAAK.G4S (B) (EAAAK=SEQ ID NO: 316; G4S=SEQ ID NO: 313) and NSCLC HOT EVO2 EAAAK.i20 (B) (EAAAK=SEQ ID NO: 316) constructs. The constructs visualized on these Western blots fall between 103-125 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing. FIG. 32 shows expression and secretion of the tLLO fusion polypeptide into supernatant by Lmdda for the NSCLC HS+MG construct. The expression data shown demonstrate the ability of the LmddA strain to express and secrete the HOT constructs at levels that should be more than sufficient for antigen processing.

Prostate Cancer Hotspot/Heteroclitic/Minigene Constructs

A total of 14 hotspot mutations across 5 genes were selected as described in Example 4 and elsewhere herein for the prostate cancer ADXS-HOT constructs. This panel of hotspot mutations covers 16% of all prostate cancer patients (i.e., 16% of prostate cancer patients will have at least one of the hotspot mutations from the panel). For each recurrent cancer mutation included in the constructs, a peptide of 21 amino acids in length was designed as described in Example 4 and elsewhere herein. However, the RGPD_P1760A hotspot peptide was only 16 amino acids because the mutation is near the C-terminus of RGPD. In addition, the AR_H875Y_T878A double hotspot peptide, which includes two adjacent hotspot mutations, is 24 amino acids in length. The peptides are shown in Table 52. The hotspot mutation(s) in each is bolded and underlined.

TABLE 52

Exemplary Prostate Cancer Panel Hotspot Peptides.
Prostate Cancer Panel Hotspot 21-Mers

| Gene | Hotspot Mutation | % Prevalence in Prostate Cancer Patients | Sequence | SEQ ID NO | Representative Nucleic Acid SEQ ID NOS |
|---|---|---|---|---|---|
| SPOP | F133V | 1.2 | YRFVQKDWGVKKFIRRDFLL | 717 | 1243-1260 |
| CHEK2 | K373E | 4.0 | LIKITDFGHSEILGETSLMRT | 707 | 1261-1278 |
| RGPD8 | P1760A | 3.0 | AAVAQDEEENASRSSG | 714 | 1279-1296 |
| ANKRD36C | I634T | 2.6 | TSDEKDSVSNTATEIKEGQQS | 704 | 1297-1314 |

TABLE 52-continued

Exemplary Prostate Cancer Panel Hotspot Peptides.
Prostate Cancer Panel Hotspot 21-Mers

| Gene | Hotspot Mutation | % Prevalence in Prostate Cancer Patients | Sequence | SEQ ID NO | Representative Nucleic Acid SEQ ID NOS |
|---|---|---|---|---|---|
| ANKRD36C | D629Y | 1.8 | PAEKATSDEKYSVSNIATEIK | 705 | 1315-1332 |
| SPOP | W131G | 1.6 | RAYRFVQGKDGGFKKFIRRDF | 715 | 1333-1350 |
| ANKRD36C | D626N | 1.4 | QKQPAEKATSNEKDSVSNIAT | 706 | 1351-1368 |
| SPOP | F133L | 1.4 | YRFVQGKDWGLKKFIRRDFLL | 716 | 1369-1386 |
| AR | T878A | *associated with drug resistance | QPIARELHQFAFDLLIKSHMV | 763 | 1387-1404 |
| AR | L702H | *associated with drug resistance | NNQPDSFAALHSSLNELGERQ | 764 | 1405-1422 |
| AR | W742C | *associated with drug resistance W | DDQMAVIQYSCMGLMVFAMG | 765 | 2805-2822 |
| AR | H875Y | *associated with drug resistance | DSVQPIARELYQFTFDLLIKS | 766 | 1423-1440 |
| AR | F877L | *associated with drug resistance | VQPIARELHQLTFDLLIKSHM | 767 | 1441-1458 |
| AR | H875Y_T878A | *associated with drug resistance V | DSVQPIARELYQFAFDLLIKSHM | 768 | 1459-1476 |

A total of 10 peptides with heteroclitic mutations across 9 genes were selected for the prostate cancer ADXS-HOT constructs. For each heteroclitic mutation, a peptide of 9 amino acids in length was designed as described in Example 4 and elsewhere herein. The peptides are shown in Table 53. The heteroclitic mutation in each is as described in Table 122.

TABLE 53

Exemplary Prostate Cancer Panel
Heteroclitic 9-Mers.
Prostate Cancer Panel Heteroclitic 9-Mers

| Gene | HLA Type | Sequence | SEQ ID NO | Representative Nucleic Acid SEQ ID NOS |
|---|---|---|---|---|
| CEACAM5 | B0702 | IPQVHTQVL | 793 | 2826 |
| MAGEA4 | B0702 | MPSLREAAL | 794 | 2211-2228 |
| STEAP1 | A0201 | LLLGTIHAV | 799 | 2229-2246 |
| STEAP1 | A2402 | KYKKFPWWL | 800 | 2247-2264 |
| RNF43 | B0702 | NPQPVWLCL | 801 | 2827 |
| SSX2 | A0201 | RLQGISPKV | 802 | 2265-2282 |
| SART3 | A0201 | LMQAEAPRL | 803 | 2283-2300 |
| PAGE4 | A0201 | MAPDVVAFV | 804 | 2301-2318 |
| PSMA | A2402 | TYSVSFFSW | 805 | 2319-2336 |
| PSA | A0301 | GMAPLILSR | 806 | 2337-2354 |

The in silico predicted binding affinity and in vitro binding affinity of the heteroclitic 9-mer peptides are provided in Table 53B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 53B are the percent expression of each gene in patients with prostate cancer (The Cancer Genome Atlas database), the HLA allele being tested, and whether the wild-type peptide corresponding to each heteroclitic peptide is known to be immunogenic. For a construct including each of the heteroclitic peptides in Table 53B, 100% of prostate cancer patients with HLA type A*02:01 express at least one of the TAA genes, 100% of prostate cancer patients with HLA type A*03:01 express at least one of the TAA genes, 100% of prostate cancer patients with HLA type A*24:02 express at least one of the TAA genes, and 100% of prostate cancer patients with HLA type B*07:02 express at least one of the TAA genes.

genic peptides in the fusion polypeptide were reordered based on hydrophobicity and charge. G4S (SEQ ID NO: 313), EAAAK (SEQ ID NO: 316), and i20 refer to inclusion

TABLE 53B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| PSA | 100 | A*03:01 | 179.39 | 103.5 | Yes |
| PSMA | 100 | A*24:02 | 20.45 | 96.2 | Yes |
| STEAP1 | 100 | A*02:01 | 5.77 | 188.4 | Yes |
| STEAP1 | 100 | A*24:02 | 47.48 | 104.7 | unknown |
| SART3 | 100 | A*02:01 | 235.57 | 160.0 | Yes |
| RNF43 | 100 | B*07:02 | 161.95 | 65.4 | Yes |
| PAGE4 | 99 | A*02:01 | 39.32 | 126.6 | unknown |
| CEACAM5 | 95 | B*07:02 | 8.36 | 88.3 | Yes |
| SSX2 | 13 | A*02:01 | 31.02 | 179.5 | Yes |
| MAGE-A4 | 6 | B*07:02 | 7.67 | 49.5 | unknown |

[#]NetMHC4.0
[^]% relative to positive control peptide binding

Constructs were designed to encode a fusion polypeptide comprising tLLO fused to the hotspot peptides and one or more or all of the heteroclitic peptides, with the C-terminal heteroclitic peptide following a ubiquitin peptide. In some constructs, the ubiquitin was fused to the STEAP1_A0201 heteroclitic peptide. In some of the constructs, the ubiquitin was fused to the STEAP1_A2402 heteroclitic peptide. In some constructs, the heteroclitic peptides are C-terminal to the hotspot peptides. In some constructs, the heteroclitic peptides are interspersed among the hotspot peptides. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) ProStar EVO2 EAAAK.G4S (A) (SEQ ID NO: 871; EAAAK=SEQ ID NO: 316; G4S=SEQ ID NO: 313); (2) ProStar EVO2 G4S (A) (SEQ ID NO: 872; G4S=SEQ ID NO: 313); (3) ProStar EVO2 EAAAK-G4S mix (A) (SEQ ID NO: 873; EAAAK=SEQ ID NO: 316; G4S=SEQ ID NO: 313); (4) ProStar EVO2 EAAAK.i20 (A) (SEQ ID NO: 874; EAAAK=SEQ ID NO: 316); (5) ProStar EVO2 G4S.i20 (A) (SEQ ID NO: 875; G4S=SEQ ID NO: 313); (6) ProStar EVO 2 G4S LS #1 (A) (SEQ ID NO: 876; G4S=SEQ ID NO: 313); (7) ProStar EVO 2 G4S LS #2 (A) (SEQ ID NO: 877; G4S=SEQ ID NO: 313); (8) ProStar EVO2 EAAAK.G4S (B) (SEQ ID NO: 892; EAAAK=SEQ ID NO: 316; G4S=SEQ ID NO: 313); (9) ProStar EVO2 EAAAK.i20 (B) (SEQ ID NO: 893; EAAAK=SEQ ID NO: 316); and (10) Prostar A24 HOT (SEQ ID NO: 906). A breakdown of the amino acids positions of the individual components in each construct is provided in Tables 54-63. For the (B) constructs, additional heteroclitic epitopes were added to complement the original hotspot mutation peptides so that total patient coverage within a cancer type approaches 100%. Any patient will therefore likely express a tumor-associated antigen that we have designed heteroclitic peptides for to cover the most prevalent HLAs (HLA-A0201, HLA-A0301, HLA-A2402, and HLA-B0702). For the A24 construct, the 9-mer in the minigene was replaced by an A24 9mer. A24 (HLA-A2402) is the HLA type commonly found in Asia. For the LS constructs, the antiof flexible linkers, rigid linkers, and immunoproteasome processing linkers, respectively.

TABLE 54

Positions of Components of ProStar EVO2 EAAAK.G4S (A) Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L
347-355: SSX2_A0201
361-369: SART3_A0201
375-383: PAGE4_A0201
389-397: STEAP1_A2402
403-411: PSMA_A2402
417-425: PSA_A0301
431-439: MAGEA4_B0702
445-468: AR_H875Y_T878A
482-502: FLAG
503-522: Linker-SIINFEKL
528-602: Ubiquitin
603-611: STEAP1_A0201_MINI

TABLE 55

Positions of Components of ProStar EVO2 G4S (A) Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L

TABLE 55-continued

Positions of Components of ProStar EVO2 G4S (A) Insert.

347-355: SSX2_A0201
361-369: SART3_A0201
375-383: PAGE4_A0201
389-397: STEAP1_A2402
403-411: PSMA_A2402
417-425: PSA_A0301
431-439: MAGEA4_B0702
445-468: AR_H875Y_T878A
482-502: FLAG
503-522: Linker-SIINFEKL
528-602: Ubiquitin
603-611: STEAP1_A0201_MINI

TABLE 56

Positions of Components of ProStar EVO2 EAAAK-G4S mix (A) Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L
347-355: SSX2_A0201
361-369: SART3_A0201
375-383: PAGE4_A0201
389-397: STEAP1_A2402
403-411: PSMA_A2402
417-425: PSA_A0301
431-439: MAGEA4_B0702
445-468: AR_H875Y_T878A
482-502: FLAG
503-522: Linker-SIINFEKL
528-602: Ubiquitin
603-611: STEAP1_A0201_MINI

TABLE 57

Positions of Components of ProStar EVO2 EAAAK.i20 (A) Insert.

14-34: SPOP_F133V
40-60: CHEK2_K373E
46-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L
354-362: SSX2_A0201
375-383: SART3_A0201
396-404: PAGE4_A0201
417-425: STEAP1_A2402
438-446: PSMA_A2402
459-467: PSA_A0301
480-488: MAGEA4_B0702

TABLE 57-continued

Positions of Components of ProStar EVO2 EAAAK.i20 (A) Insert.

501-524: AR_H875Y_T878A
545-565: FLAG
566-585: Linker-SIINFEKL
591-665: Ubiquitin
666-674: STEAP1_A0201_MINI

TABLE 58

Positions of Components of ProStar EVO2 G4S.i20 (A) Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L
354-362: SSX2_A0201
375-383: SART3_A0201
396-404: PAGE4_A0201
417-425: STEAP1_A2402
438-446: PSMA_A2402
459-467: PSA_A0301
480-488: MAGEA4_B0702
501-524: AR_H875Y_T878A
545-565: FLAG
566-585: Linker-SIINFEKL
591-665: Ubiquitin
666-674: STEAP1_A0201_MINI

TABLE 59

Positions of Components of ProStar EVO 2 G4S LS#1 (A) Insert.

14-22: STEAP1_A2402
28-36: PAGE4_A0201
42-62: ANKRD36C_D626N
68-88: AR_F877L
94-114: SPOP_W131G
120-140: AR_W742C
146-166: ANKRD36C_I634T
172-192: CHEK2_K373E
198-218: SPOP_F133L
224-232: PSMA_A2402
238-258: AR_L702H
264-284: AR_T878A
290-310: SPOP_F133V
316-324: PSA_A0301
330-338: SSX2_A0201
344-364: AR_H875Y
370-385: RGPD8_P1760A
391-399: MAGEA4_B0702
405-425: ANKRD36C_D629Y
431-454: AR_H875Y_T878A
460-468: SART3_A0201
482-502: FLAG
503-522: Linker-SIINFEKL
528-602: Ubiquitin
603-611: STEAP1_A0201_MINI

TABLE 60

Positions of Components of ProStar EVO 2 G4S LS#2 (A) Insert.

14-22: STEAP1_A2402
28-36: PAGE4_A0201
42-62: ANKRD36C_D626N
68-88: AR_W742C
94-114: SPOP_W131G
120-128: PSMA_A2402
134-154: ANKRD36C_I634T
160-168: PSA_A0301
174-194: SPOP_F133L
200-208: MAGEA4_B0702
214-234: AR_L702H
240-263: AR_H875Y_T878A
269-289: SPOP_F133V
295-315: AR_H875Y
321-329: SSX2_A0201
335-355: AR_T878A
361-376: RGPD8_P1760A
382-402: CHEK2_K373E
408-428: ANKRD36C_D629Y
434-454: AR_F877L
460-468: SART3_A0201
482-502: FLAG
503-522: Linker-SIINFEKL
528-602: Ubiquitin
603-611: STEAP1_A0201_MINI

TABLE 61

Positions of Components of ProStar EVO2 EAAAK.G4S (B) Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L
347-355: SSX2_A0201
361-369: SART3_A0201
375-383: PAGE4_A0201
389-397: STEAP1_A2402
403-411: PSMA_A2402
417-425: PSA_A0301
431-439: MAGEA4_B0702
445-453: CEACAM5_B0702
459-467: RNF43_B0702
473-496: AR_H875Y_T878A
510-530: FLAG
531-550: Linker-SIINFEKL
556-630: Ubiquitin
631-639: STEAP1_A0201_MINI

TABLE 62

Positions of Components of ProStar EVO2 EAAAK.i20 (B) Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H

TABLE 62-continued

Positions of Components of ProStar EVO2 EAAAK.i20 (B) Insert.

269-289: AR_W742C
295-315: AR_H875Y
321-341: AR_F877L
354-362: SSX2_A0201
375-383: SART3_A0201
396-404: PAGE4_A0201
417-425: STEAP1_A2402
438-446: PSMA_A2402
459-467: PSA_A0301
480-488: MAGEA4_B0702
501-509: CEACAM5_B0702
522-530: RNF43_B0702
543-566: AR_H875Y_T878A
580-600: FLAG
601-620: Linker-SIINFEKL
626-700: Ubiquitin
701-709: STEAP1_A0201_MINI

TABLE 63

Positions of Components of Prostar A24 HOT Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L
354-362: SSX2_A0201
375-383: SART3_A0201
396-404: PAGE4_A0201
417-425: STEAP1_A0201
438-446: PSMA_A2402
459-467: PSA_A0301
480-488: MAGEA4_B0702
501-509: CEACAM5_B0702
522-530: RNF43_B0702
543-566: AR_H875Y_T878A
580-600: FLAG
601-620: Linker-SIINFEKL
626-700: Ubiquitin
701-709: STEAP1_A2402 MINI Constructs were also designed to encode a fusion polypeptide comprising tLLO fused to the hotspot peptides and one or more or all of the heteroclitic peptides without a ubiquitin peptide (i.e., hotspot peptides plus heteroclitic peptides with no "minigene"). The tLLO, hotspot peptide and heteroclitic peptide components of the fusion polypeptides were joined by various linkers selected from those in Table 37. An exemplary fusion polypeptide insert sequence (i.e., the peptide sequence downstream of the tLLO) is Prostar HS+HC (SEQ ID NO: 913).

Constructs were also designed to encode a fusion polypeptide comprising tLLO fused to the hotspot peptides other than the AR-H875Y-T878A with no heteroclitic peptides other than a ubiquitin peptide fused to a heteroclitic peptide at the C-terminal end (i.e., hotspot peptides plus "minigene" with no additional heteroclitic peptides). The tLLO, hotspot peptide, and ubiquitin/heteroclitic peptide components of the fusion polypeptides were joined by various linkers selected from those in Table 37. An exemplary fusion polypeptide insert sequence (i.e., the peptide sequence downstream of the tLLO) is Prostar HS+MG (SEQ ID NO: 914).

Constructs were also designed to encode a fusion polypeptide comprising tLLO fused to one or more heteroclitic peptides and the AR-H875Y-T878A peptide, with the C-terminal heteroclitic peptide following a ubiquitin peptide (i.e., heteroclitic peptides and "minigene" with only the double hotspot peptide). The tLLO, heteroclitic peptide, and ubiquitin/heteroclitic peptide components of the fusion polypeptides were joined by various linkers selected from those in Table 37. An exemplary fusion polypeptide insert sequence (i.e., the peptide sequence downstream of the tLLO) is Prostar HC+MG (SEQ ID NO: 915).

Constructs were also designed to encode a fusion polypeptide comprising tLLO fused to one or more heteroclitic peptides and the AR-H875Y-T878A peptide without any ubiquitin peptide and without any hotspot peptides other than the double hotspot AR-H875Y-T878A peptide (i.e., heteroclitic peptides with no "minigene" and with only the double hotspot peptide). The tLLO and heteroclitic peptide components of the fusion polypeptides were joined by various linkers selected from those in Table 37. An exemplary fusion polypeptide insert sequence (i.e., the peptide sequence downstream of the tLLO) is Prostar HC only (SEQ ID NO: 916).

A breakdown of the amino acids positions of the individual components in each construct is provided in Tables 64-67.

TABLE 64

Positions of Components of Prostar HS + HC Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C
295-315: AR_H875Y
321-341: AR_F877L
354-362: SSX2_A0201
375-383: SART3_A0201
396-404: PAGE4_A0201
417-425: STEAP1_A2402
438-446: PSMA_A2402
459-467: PSA_A0301
480-488: MAGEA4_B0702
501-509: CEACAM5_B0702
522-530: RNF43_B0702
543-566: AR_H875Y_T878A
580-600: FLAG
601-620: Linker-SIINFEKL
626-634: STEAP1_A0201_MINI

TABLE 65

Positions of Components of Prostar HS + MG Insert.

14-34: SPOP_F133V
40-60: CHEK2_K373E
66-81: RGPD8_P1760A
87-107: ANKRD36C_I634T
113-133: ANKRD36C_D629Y
139-159: SPOP_W131G
165-185: ANKRD36C_D626N
191-211: SPOP_F133L
217-237: AR_T878A
243-263: AR_L702H
269-289: AR_W742C

TABLE 65-continued

Positions of Components of Prostar HS + MG Insert.

295-315: AR_H875Y
321-341: AR_F877L
350-370: FLAG
371-390: Linker-SIINFEKL
396-470: Ubiquitin
471-479: STEAP1_A0201_MINI

TABLE 66

Positions of Components of Prostar HC + MG Insert.

21-29: SSX2_A0201
42-50: SART3_A0201
63-71: PAGE4_A0201
84-92: STEAP1_A2402
105-113: PSMA_A2402
126-134: PSA_A0301
147-155: MAGEA4_B0702
168-176: CEACAM5_B0702
189-197: RNF43_B0702
210-233: AR_H875Y_T878A
247-267: FLAG
268-287: Linker-SIINFEKL
293-367: Ubiquitin
368-376: STEAP1_A0201_MINI

TABLE 67

Positions of Components of Prostar HC Only Insert.

Figure 13:
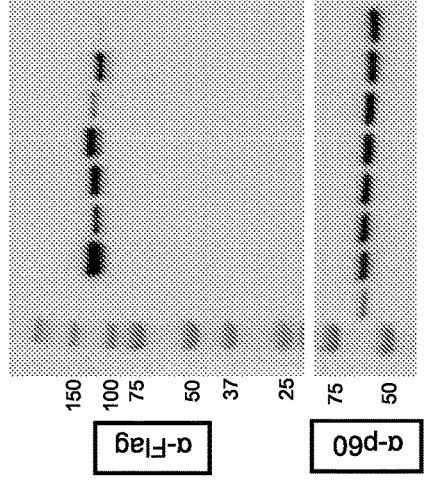
FIG. 13 shows Western blot data for different prostate cancer constructs. The upper left panel shows detection, using an anti-Flag antibody, of prostate cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 19:
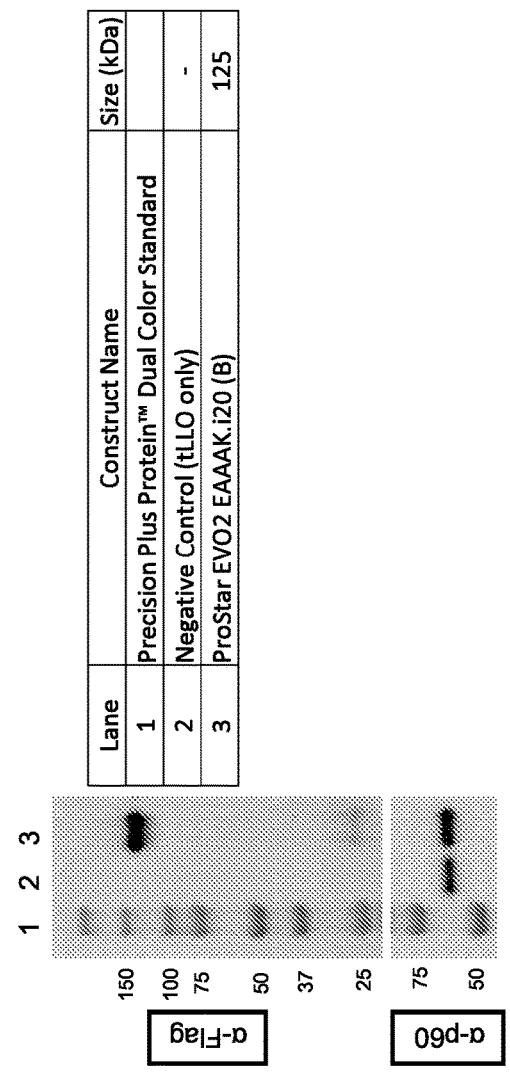
FIG. 19 shows Western blot data for different prostate cancer constructs. The upper left panel shows detection, using an anti-Flag antibody, of prostate cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 28:
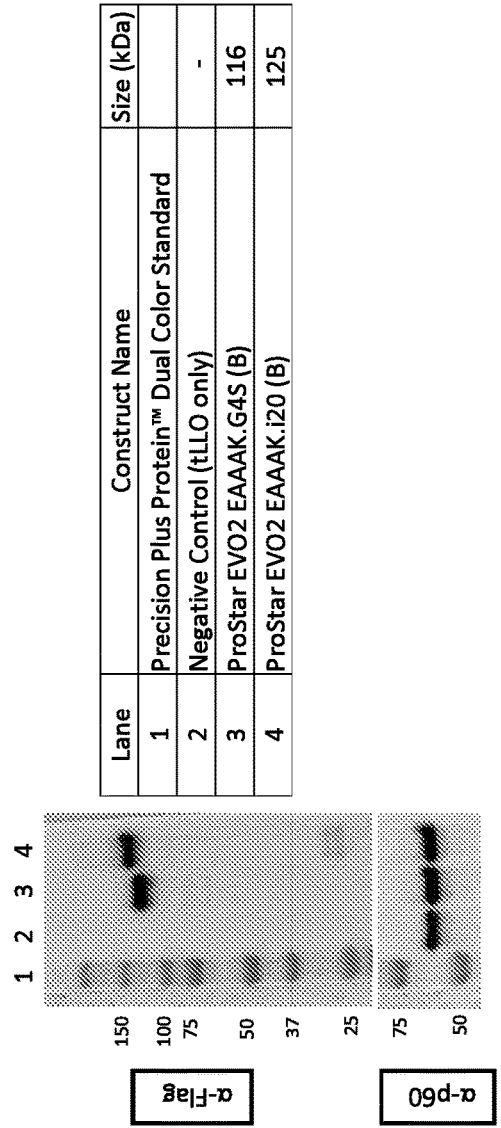
FIG. 28 shows Western blot data for different prostate cancer constructs. The upper left panel shows detection, using an anti-Flag antibody, of prostate cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 33:
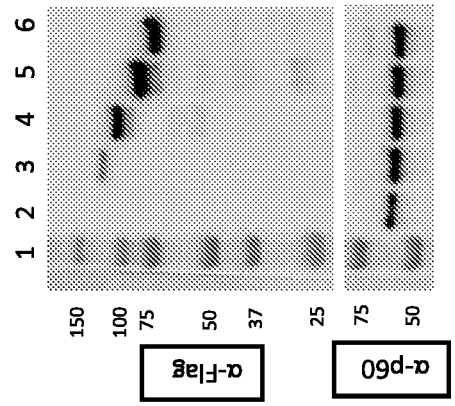
FIG. 33 shows Western blot data for different prostate cancer constructs. The upper left panel shows detection, using an anti-Flag antibody, of prostate cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.

21-29: SSX2_A0201
42-50: SART3_A0201
63-71: PAGE4_A0201
84-92: STEAP1_A2402
105-113: PSMA_A2402
126-134: PSA_A0301
147-155: MAGEA4_B0702
168-176: CEACAM5_B0702
189-197: RNF43_B0702
210-233: AR_H875Y_T878A
247-267: FLAG
268-287: Linker-SIINFEKL
292-300: STEAP1_A0201_MINI To assess the expression of tLLO-antigenic-peptide fusion proteins by Lmdda *Listeria* constructs, the DNA constructs were generated as described elsewhere herein and transformed into Lmdda. Each individual Lmdda construct was assayed by Western blot for tLLO fusion polypeptide expression using an anti-FLAG antibody. FIGS. 13 and 19 show expression and secretion of the tLLO fusion polypeptide into supernatant by Lmdda for various prostate cancer constructs. The constructs visualized on these Western blots all fall between 103-125 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing. FIG. 28 shows expression and secretion of the tLLO fusion polypeptide into supernatant by Lmdda for the ProStar EVO2 EAAAK.G4S (B) (EAAAK=SEQ ID NO: 316; G4S=SEQ ID NO: 313) and ProStar EVO2 EAAAK.i20 (B) (EAAAK=SEQ ID NO: 316) constructs. The constructs visualized on these Western blots fall between 103-125 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing. FIG. 33 shows expression and secretion of the tLLO fusion polypeptide into supernatant by Lmdda for the ProStar HS+HC, ProStar HS+MG, ProStar HC+MG, and ProStar HC only constructs. The expression data shown demonstrate the ability of the LmddA strain to express and secrete the HOT constructs at levels that should be more than sufficient for antigen processing. Pancreatic Cancer Hotspot/Heteroclitic/Minigene Constructs A total of 16 hotspot mutations across 5 genes were selected as described in Example 4 and elsewhere herein for the pancreatic cancer ADXS-HOT constructs. This panel of hotspot mutations covers 87 of all pancreatic cancer patients (i.e., 87i of pancreatic cancer patients will have at least one of the hotspot mutations from the panel). For each recurrent cancer mutation included in the constructs, a peptide of 21 amino acids in length was designed as described in Example 4 and elsewhere herein. The peptides are shown in Table 68. The hotspot mutation in each is bolded and underlined.

TABLE 68

Exemplary Pancreatic Cancer Panel Hotspot Peptides.
Pancreatic Cancer Panel Hotspot 21-Mers

| Gene | Hotspot Mutation | % Prevalence in Pancreatic Cancer Patients | Sequence | Representative SEQ ID NO | Nucleic Acid SEQ ID NOS |
|---|---|---|---|---|---|
| KRAS | G12C | 1.7 | TEYKLVVVGACGVGKSALTIQ | 486 | 1851-1860 |
| KRAS | G12D | 36.3 | TEYKLVVVGADGVGKSALTIQ | 489 | 1861-1870 |
| U2AF1 | S34F | 1.2 | IGACRHGDRCFRLHNKPTFSQ | 643 | 1871-1880 |
| KRAS | G12V | 29.4 | TEYKLVVVGAVGVGKSALTIQ | 491 | 1881-1890 |
| TP53 | R248Q | 1.5 | CNSSCMGGMNQRPILTIITLE | 560 | 1891-1900 |
| TP53 | R248W | 1.4 | CNSSCMGGMNWRPILTIITLE | 559 | 1901-1910 |
| TP53 | R175H | 4.0 | QSQHMTEVVRHCPHHERCSDS | 542 | 1911-1920 |
| TP53 | R273C | 1.5 | NLLGRNSFEVCVCACPGRDRR | 565 | 1921-1930 |
| KRAS | G12R | 15.7 | TEYKLVVVGARGVGKSALTIQ | 490 | 1931-1940 |
| KRAS | Q61H | 4.6 | CLLDILDTAGHEEYSAMRDQY | 498 | 1941-1950 |
| TP53 | R282W | 2.5 | VRVCACPGRDWRTEEENLRKK | 569 | 1951-1960 |
| TP53 | R273H | 2.0 | NLLGRNSFEVHVCACPGRDRR | 563 | 1961-1970 |
| TP53 | G245S | 1.2 | NYMCNSSCMGSMNRRPILTII | 558 | 1971-1980 |
| SMAD4 | R361C | 1.0 | DGYVDPSGGDCFCLGQLSNVH | 780 | 1981-1990 |
| GNAS | R201C | 1.0 | VPSDQDLLRCCVLTSGIFETK | 781 | 1991-2000 |
| GNAS | R201H | 1.0 | VPSDQDLLRCHVLTSGIFETK | 782 | 2001-2010 |

A total of 12 peptides with heteroclitic mutations across 6 genes were selected for the pancreatic cancer ADXS-HOT constructs. For each heteroclitic mutation, a peptide of 9 amino acids in length was designed as described in Example 4 and elsewhere herein. The peptides are shown in Table 69. The heteroclitic mutation in each is as described in Table 122.

TABLE 69

Exemplary Pancreatic Cancer Panel Heteroclitic 9-Mers.
Pancreatic Cancer Panel Heteroclitic 9-Mers

| Gene | HLA Type | Sequence | SEQ ID NO | Representative Nucleic Acid SEQ ID NOS |
|---|---|---|---|---|
| CEACAM5 | A0301 | HVFGYSWYK | 791 | 2645-2654 |
| CEACAM5 | B0702 | IPQVHTQVL | 793 | 2655-2664 |
| CEACAM5 | A2402 | IYPNASLLF | 796 | 2665-2674 |
| CEACAM5 | A0201 | ILIGVLVGV | 798 | 2675-2684 |
| STEAP1 | A0201 | LLLGTIHAV | 799 | 2685-2694 |
| STEAP1 | A2402 | KYKKFPWWL | 800 | 2695-2704 |
| MAGEA3 | A0301 | YMFPVIFSK | 812 | 2705-2714 |
| PRAME | A0201 | NMTHVLYPL | 815 | 2715-2724 |
| hTERT | A0201_A2402 | IMAKFLHWL | 816 | 2725-2734 |
| MAGEA3 | A0201_A2402 | KVPEIVHFL | 817 | 2735-2744 |
| SURVIVIN | A0201 | KMSSGCAFL | 818 | 2745-2754 |
| SURVIVIN | A2402 | SWFKNWPFF | 819 | 2755-2764 |

The in silico predicted binding affinity and in vitro binding affinity of the heteroclitic 9-mer peptides are provided in Table 69B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 69B are the percent expression of each gene in patients with pancreatic cancer (The Cancer Genome Atlas database), the HLA allele being tested, and whether the wild-type peptide corresponding to each heteroclitic peptide is known to be immunogenic. For a construct including each of the heteroclitic peptides in Table 69B, 100% of pancreatic cancer patients with HLA type A*02:01 express at least one of the TAA genes, 98% of pancreatic cancer patients with HLA type A*03:01 express at least one of the TAA genes, 100% of pancreatic cancer patients with HLA type A*24:02 express at least one of the TAA genes, and 98% of pancreatic cancer patients with HLA type B*07:02 express at least one of the TAA genes.

TABLE 69B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| STEAP1 | 100 | A*02:01 | 5.77 | 188.4 | Yes |
| STEAP1 | 100 | A*24:02 | 47.48 | 104.7 | unknown |
| SURVIVIN | 100 | A*02:01 | 11.66 | 149.0 | Yes |
| SURVIVIN | 100 | A*24:02 | 12.86 | 144.0 | Yes |
| CEACAM5 | 98 | A*02:01 | 6.92 | 170.7 | Yes |
| CEACAM5 | 98 | A*03:01 | 9.69 | 85.4 | Yes |
| CEACAM5 | 98 | B*07:02 | 8.36 | 88.3 | Yes |
| CEACAM5 | 98 | A*24:02 | 6.22 | 77.2 | Yes |
| PRAME | 87 | A*02:01 | 11.72 | 139.4 | Yes |
| TERT | 80 | A*02:01 | 7.04 | 123.3 | Yes |
| TERT | 80 | A*24:02 | 2197.84 | 142.3 | unknown |
| MAGE-A3 | 11 | A*02:01 | 50.31 | 168.7 | Yes |
| MAGE-A3 | 11 | A*24:02 | 2966 | 102.4 | unknown |
| MAGE-A3 | 11 | A*03:01 | 9.40 | 85.4 | unknown |

[#]NetMHC4.0
[^]% relative to positive control peptide binding

Constructs were designed to encode a fusion polypeptide comprising tLLO fused to the hotspot peptides and one or more or all of the heteroclitic peptides, with the C-terminal heteroclitic peptide following a ubiquitin peptide. In some constructs, the ubiquitin was fused to the CEACAM5_A0201 heteroclitic peptide. In some of the constructs, the ubiquitin was fused to the CEACAM5_A2402 heteroclitic peptide. The heteroclitic peptides were C-terminal to the hotspot peptides. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) PANC HOT EVO2 EAAAK.G4S (A) (SEQ ID NO: 866; EAAAK=SEQ ID NO: 316; G4S=SEQ ID NO: 313); (2) PANC HOT G4S (A) (SEQ ID NO: 867; G4S=SEQ ID NO: 313); (3) PANC HOT EVO2 EAAAK-G4S mix (A) (SEQ ID NO: 868; EAAAK=SEQ ID NO: 316; G4S=SEQ ID NO: 313); (4) PANC HOT EVO2 EAAAK.i20 (A) (SEQ ID NO: 869; EAAAK=SEQ ID NO: 316); (5) PANC HOT EVO2 G4S.i20 (A) (SEQ ID NO: 870; G4S=SEQ ID NO: 313); and (6) Pancreas A24 HOT (SEQ ID NO: 908). A breakdown of the amino acids positions of the individual components in each construct is provided in Tables 70-75. For the A24 construct, the 9-mer in the minigene was replaced by an A24 9mer. A24 (HLA-A2402) is the HLA type commonly found in Asia. G4S (SEQ ID NO: 313), EAAAK (SEQ ID NO: 316), and 20 refer to inclusion of flexible linkers, rigid linkers, and immunoproteasome processing linkers, respectively.

TABLE 70

Positions of Components of PANC HOT EVO2 EAAAK.G4S (A) Insert.

14-34: KRAS_G12D
40-60: KRAS_G12V
66-86: KRAS_G12R
92-112: KRAS_Q61H
118-138: TP53_R175H
144-164: TP53_R282W

TABLE 70-continued

Positions of Components of PANC HOT EVO2 EAAAK.G4S (A) Insert.

170-190: TP53_R273H
196-216: KRAS_G12C
222-242: TP53_R248Q
248-268: TP53_R273C
274-294: TP53_R248W
300-320: TP53_G245S
326-346: U2AF1_S34F
352-372: SMAD4_R361C
378-398: GNAS_R201C
404-424: GNAS_R201H
430-438: STEAP1_A0201
444-452: PRAME_A0201
458-466: hTERT_A0201_A2402
472-480: CEACAM5_A0301
486-494: MAGEA3_A0301
500-508: STEAP1_A2402
514-522: CEACAM5_A2402
528-536: CEACAM5_B0702

TABLE 70-continued

Positions of Components of PANC HOT EVO2 EAAAK.G4S (A) Insert.

542-550: MAGEA3_A0201_A2402
556-564: SURVIVIN_A0201
570-578: SURVIVIN_A2402
592-612: FLAG
613-632: Linker-SIINFEKL
639-713: Ubiquitin
714-722: CEACAM5_A0201_MINI

TABLE 71

Positions of Components of PANC HOT G4S (A) Insert.

14-24: KRAS_G12D
40-60: KRAS_G12V
66-86: KRAS_G12R
92-112: KRAS_Q61H
118-138: TP53_R175H
144-164: TP53_R282W
170-190: TP53_R273H
196-216: KRAS_G12C
222-242: TP53_R248Q
248-268: TP53_R273C
274-294: TP53_R248W
300-320: TP53_G245S
326-346: U2AF1_S34F
352-372: SMAD4_R361C
378-398: GNAS_R201C
404-424: GNAS_R201H
430-438: STEAP1_A0201
444-452: PRAME_A0201
458-466: hTERT_A0201_A2402
472-480: CEACAM5_A0301
486-494: MAGEA3_A0301
500-508: STEAP1_A2402
514-522: CEACAM5_A2402
528-536: CEACAM5_B0702
542-550: MAGEA3_A0201_A2402
556-564: SURVIVIN_A0201
570-578: SURVIVIN_A2402
592-612: FLAG
613-632: Linker-SIINFEKL
639-713: Ubiquitin
714-722: CEACAM5_A0201_MINI

TABLE 72

Positions of Components of PANC HOT EVO2 EAAAK-G4S mix (A) Insert.

14-34: KRAS_G12D
40-60: KRAS_G12V
66-86: KRAS_G12R
92-112: KRAS_Q61H
118-138: TP53_R175H
144-164: TP53_R282W
170-190: TP53_R273H
196-216: KRAS_G12C
222-242: TP53_R248Q
248-268: TP53_R273C
274-294: TP53_R248W
300-320: TP53_G245S
326-346: U2AF1_S34F
352-372: SMAD4_R361C
378-398: GNAS_R201C
404-424: GNAS_R201H
430-438: STEAP1_A0201
444-452: PRAME_A0201
458-466: hTERT_A0201_A2402
472-480: CEACAM5_A0301
486-494: MAGEA3_A0301
500-508: STEAP1_A2402
514-522: CEACAM5_A2402

TABLE 72-continued

Positions of Components of PANC HOT EVO2 EAAAK-G4S mix (A) Insert.

528-536: CEACAM5_B0702
542-550: MAGEA3_A0201_A2402
556-564: SURVIVIN_A0201
570-578: SURVIVIN_A2402
592-612: FLAG
613-632: Linker-SIINFEKL
639-713: Ubiquitin
714-722: CEACAM5_A0201_MINI

TABLE 73

Positions of Components of PANC HOT EVO2 EAAAK.i20 (A) Insert.

14-24: KRAS_G12D
40-60: KRAS_G12V
66-86: KRAS_G12R
92-112: KRAS_Q61H
118-138: TP53_R175H
144-164: TP53_R282W
170-190: TP53_R273H
196-216: KRAS_G12C
222-242: TP53_R248Q
248-268: TP53_R273C
274-294: TP53_R248W
300-320: TP53_G245S
326-346: U2AF1_S34F
352-372: SMAD4_R361C
378-398: GNAS_R201C
404-424: GNAS_R201H
437-445: STEAP1_A0201
458-466: PRAME_A0201
479-487: hTERT_A0201_A2402
500-508: CEACAM5_A0301
521-529: MAGEA3_A0301
542-550: STEAP1_A2402
563-571: CEACAM5_A2402
584-592: CEACAM5_B0702
605-613: MAGEA3_A0201_A2402
626-634: SURVIVIN_A0201
647-655: SURVIVIN_A2402
676-696: FLAG
697-716: Linker-SIINFEKL
723-797: Ubiquitin
798-806: CEACAM5_A0201_MINI

TABLE 74

Positions of Components of PANC HOT EVO2 G4S.i20 (A) Insert.

14-24: KRAS_G12D
40-60: KRAS_G12V
66-86: KRAS_G12R
92-112: KRAS_Q61H
118-138: TP53_R175H
144-164: TP53_R282W
170-190: TP53_R273H
196-216: KRAS_G12C
222-242: TP53_R248Q
248-268: TP53_R273C
274-294: TP53_R248W
300-320: TP53_G245S
326-346: U2AF1_S34F
352-372: SMAD4_R361C
378-398: GNAS_R201C
404-424: GNAS_R201H
437-445: STEAP1_A0201
458-466: PRAME_A0201
479-487: hTERT_A0201_A2402
500-508: CEACAM5_A0301
521-529: MAGEA3_A0301

TABLE 74-continued

Positions of Components of PANC HOT EVO2 G4S.i20 (A) Insert.

542-550: STEAP1__A2402
563-571: CEACAM5__A2402
584-592: CEACAM5__B0702
605-613: MAGEA3__A0201__A2402
626-634: SURVIVIN__A0201
647-655: SURVIVIN__A2402
676-696: FLAG
697-716: Linker-SIINFEKL
723-797: Ubiquitin
798-806: CEACAM5__A0201__MINI

TABLE 75

Positions of Components of Pancreas A24 HOT Insert.

Figure 17:
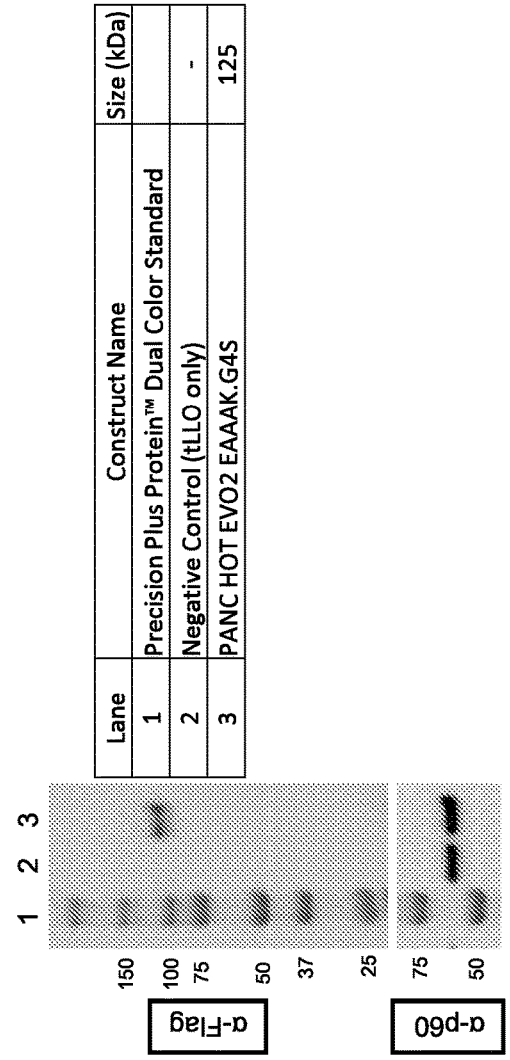
FIG. 17 shows Western blot data for different pancreatic cancer constructs. The upper left panel shows detection, using an anti-Flag antibody, of pancreatic cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 30:
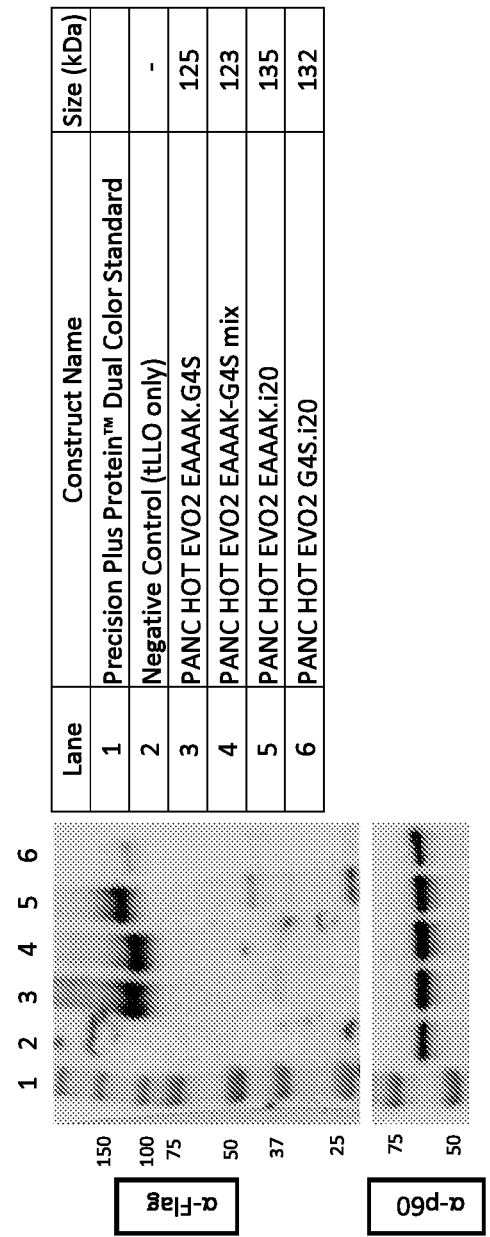
FIG. 30 shows Western blot data for different pancreatic cancer constructs. The upper left panel shows detection, using an anti-Flag antibody, of pancreatic cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.

14-24: KRAS_G12D
40-60: KRAS_G12V
66-86: KRAS_G12R
92-112: KRAS_Q61H
118-138: TP53__R175H
144-164: TP53__R282W
170-190: TP53__R273H
196-216: KRAS_G12C
222-242: TP53__R248Q
248-268: TP53__R273C
274-294: TP53__R248W
300-320: TP53__G245S
326-346: U2AF1__S34F
352-372: SMAD4__R361C
378-398: GNAS__R201C
404-424: GNAS__R201H
437-445: STEAP1__A0201
458-466: PRAME__A0201
479-487: hTERT__A0201__A2402
500-508: CEACAM5__A0301
521-529: MAGEA3__A0301
542-550: STEAP1__A2402
563-571: CEACAM5__A0201
584-592: CEACAM5__B0702
605-613: MAGEA3__A0201__A2402
626-634: SURVIVIN__A0201
647-655: SURVIVIN__A2402
676-696: FLAG
697-716: Linker-SIINFEKL
723-797: Ubiquitin
798-806: CEACAM5__A2402 MINI To assess the expression of tLLO-antigenic-peptide fusion proteins by Lmdda *Listeria* constructs, the DNA constructs were generated as described elsewhere herein and transformed into Lmdda. Each individual Lmdda construct was assayed by Western blot for tLLO fusion polypeptide expression using an anti-FLAG antibody. FIG. 17 shows expression and secretion of the tLLO fusion polypeptide into supernatant by Lmdda for the PANC HOT EVO2 EAAK G4S (EAAAK=SEQ ID NO: 316; G4S=SEQ ID NO: 313) construct. The construct visualized on these Western blots falls between 103-125 kDa and is similarly sized to the majority of constructs found within this filing. While these sizes indicate fairly large proteins, the expression data shown demonstrate the ability of the LmddA strain to express and secrete the HOT constructs at levels that should be more than sufficient for antigen processing. FIG. 30 shows expression and secretion of the tLLO fusion polypeptide into supernatant by Lmdda for the PANC HOT EVO2 EAAAK.G4S (EAAAK=SEQ ID NO: 316; G4S=SEQ ID NO: 313), PANC HOT EVO2 EAAAK-G4S mix (EAAAK=SEQ ID NO: 316; G4S=SEQ ID NO: 313), PANC HOT EVO2 EAAAK.i20 (EAAAK=SEQ ID NO: 316), and PANC HOT EVO2 G4S.i20 (G4S=SEQ ID NO: 313) constructs. The constructs visualized on these Western blots fall between 103-135 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing.

Bladder Cancer Hotspot/Heteroclitic/Minigene Constructs

A total of 13 hotspot mutations across 6 genes were selected as described in Example 4 and elsewhere herein for the bladder cancer ADXS-HOT constructs. This panel of hotspot mutations covers 43% of all bladder cancer patients (i.e., 43% of bladder cancer patients will have at least one of the hotspot mutations from the panel). For each recurrent cancer mutation included in the constructs, a peptide of 21 amino acids in length was designed as described in Example 4 and elsewhere herein. The peptides are shown in Table 76. The hotspot mutation in each is bolded and underlined.

TABLE 76

Exemplary Bladder Cancer Panel Hotspot Peptides.
Bladder Cancer Panel Hotspot 21-Mers

| Gene | Hotspot Mutation | % Prevalence in Bladder Cancer Patients | Sequence | SEQ ID NO | Representative Nucleic Acid SEQ ID NOS |
|---|---|---|---|---|---|
| PIK3CA | E545K | 7.6 | STRDPLSEITKQEKDFLWSHR | 437 | 1477-1494 |
| FGFR3 | S249C | 6.9 | QTYTLDVLERCPHRPILQAGL | 769 | 1495-1512 |
| TP53 | R248Q | 5.3 | CNSSCMGGMNQRPILTIITLE | 560 | 1513-1530 |
| PIK3CA | E542K | 4.6 | KAISTRDPLSKITEQEKDFLW | 436 | 1531-1548 |
| RXRA | S427F | 3.8 | KLLLRLPALRFIGLKCLEHLF | 770 | 1549-1566 |
| FBXW7 | R505G | 3.0 | HVLMGHVAAVGCVQYDGRRVV | 771 | 1567-1584 |
| TP53 | R280T | 2.3 | FEVRVCACPGTDRRTEEENLR | 642 | 1585-1602 |

TABLE 76-continued

Exemplary Bladder Cancer Panel Hotspot Peptides.
Bladder Cancer Panel Hotspot 21-Mers

| Gene | Hotspot Mutation | % Prevalence in Bladder Cancer Patients | Sequence | SEQ ID NO | Representative Nucleic Acid SEQ ID NOS |
|---|---|---|---|---|---|
| NFE2L2 | E79K | 1.5 | AFFAQLQLDEKTGEFLPIQPA | 772 | 1603-1620 |
| FGFR3 | R248C | 1.5 | RQTYTLDVLECSPHRPILQAG | 773 | 1621-1638 |
| TP53 | K132N | 1.5 | VTCTYSPALNNMFCQLAKTCP | 535 | 1639-1656 |
| TP53 | R248W | 1.5 | CNSSCMGGMNWRPILTIITLE | 559 | 1657-1674 |
| TP53 | R175H | 1.5 | QSQHMTEVVRHCPHHERCSDS | 542 | 1675-1692 |
| TP53 | R273C | 1.5 | NLLGRNSFEVCVCACPGRDRR | 565 | 1693-1710 |

A total of 14 peptides with heteroclitic mutations across 8 genes were selected for the bladder cancer ADXS-HOT constructs. For each heteroclitic mutation, a peptide of 9 amino acids in length was designed as described in Example 4 and elsewhere herein. The peptides are shown in Table 77. The heteroclitic mutation in each is as described in Table 122.

TABLE 77

Exemplary Bladder Cancer Panel Heteroclitic 9-Mers.
Bladder Cancer Panel Heteroclitic 9-Mers

| Gene | HLA Type | Sequence | SEQ ID NO | Representative Nucleic Acid SEQ ID NOS |
|---|---|---|---|---|
| CEACAM5 | A0301 | HVFGYSWYK | 791 | 2828 |
| GAGE1 | B0702 | WPRPRRYVM | 795 | 2355-2372 |
| NYESO1 | A0201 | RLLEFYLAV | 797 | 2373-2390 |
| CEACAM5 | A0201 | ILIGVLVGV | 798 | 2829 |
| RNF43 | B0702 | NPQPVWLCL | 801 | 2830 |
| NUF2 | A0201 | YLMPVNSEV | 807 | 2391-2408 |
| NUF2 | A2402 | VWGIRLEHF | 808 | 2409-2426 |
| KLHL7 | A2402 | VYILGGSQF | 809 | 2427-2444 |
| MAGEA3 | A2402 | IMPKAGLLF | 810 | 2445-2462 |
| GAGE1 | A0301 | SLYWPRPR | 811 | 2463-2480 |
| MAGEA3 | A0301 | YMFPVIFSK | 812 | 2481-2498 |
| NYESO1 | B0702 | APRGPHGGM | 813 | 2499-2516 |

TABLE 77-continued

Exemplary Bladder Cancer Panel Heteroclitic 9-Mers.
Bladder Cancer Panel Heteroclitic 9-Mers

| Gene | HLA Type | Sequence | SEQ ID NO | Representative Nucleic Acid SEQ ID NOS |
|---|---|---|---|---|
| MAGEA3 | B0702 | LPWTMNYPL | 814 | 2517-2534 |
| PRAME | A0201 | NMTHVLYPL | 815 | 2831 |

The in silico predicted binding affinity and in vitro binding affinity of the heteroclitic 9-mer peptides are provided in Table 77B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 77B are the percent expression of each gene in patients with bladder cancer (The Cancer Genome Atlas database), the HLA allele being tested, and whether the wild-type peptide corresponding to each heteroclitic peptide is known to be immunogenic. For a construct including each of the heteroclitic peptides in Table 77B, 100% of bladder cancer patients with HLA type A*02:01 express at least one of the TAA genes, 100% of bladder cancer patients with HLA type A*03:01 express at least one of the TAA genes, 100% of bladder cancer patients with HLA type A*24:02 express at least one of the TAA genes, and 100% of bladder cancer patients with HLA type B*07:02 express at least one of the TAA genes.

TABLE 77B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| NUF2 | 100 | A*02:01 | 2.79 | 160.0 | Yes |
| NUF2 | 100 | A*24:02 | 149.07 | 88.4 | unknown |
| KLHL7 | 100 | A*24:02 | 60.84 | 97.4 | Yes |
| RNF43 | 99 | B*07:02 | 161.95 | 65.4 | Yes |
| CEACAM5 | 93 | A*02:01 | 6.92 | 170.7 | Yes |
| CEACAM5 | 93 | A*03:01 | 9.69 | 85.4 | Yes |
| PRAME | 77 | A*02:01 | 11.72 | 139.4 | Yes |
| MAGE-A3 | 72 | B*07:02 | 12.52 | 112.2 | unknown |
| MAGE-A3 | 72 | A*24:02 | 28.11 | 92.8 | unknown |
| MAGE-A3 | 72 | A*03:01 | 9.40 | 86.9 | unknown |
| NY-ESO1 | 58 | A*02:01 | 4.61 | 212.9 | unknown |
| NY-ESO1 | 58 | B*07:02 | 3.32 | 109.7 | unknown |
| GAGE1 | 14 | B*07:02 | 2.58 | 58.5 | unknown |
| GAGE1 | 14 | A*03:01 | 60.49 | 93.1 | unknown |

[#]NetMHC4.0
[^]% relative to positive control peptide binding

Constructs were designed to encode a fusion polypeptide comprising tLLO fused to the hotspot peptides and one or more or all of the heteroclitic peptides, with the C-terminal heteroclitic peptide following a ubiquitin peptide. In some constructs, the ubiquitin was fused to the NYESO1_A0201 heteroclitic peptide. In some of the constructs, the ubiquitin was fused to the NUF2_A0201 heteroclitic peptide. The heteroclitic peptides were C-terminal to the hotspot peptides. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) Bladder HOT EVO2 EAAAK.G4S (A) (SEQ ID NO: 878; EAAAK=SEQ ID NO: 316; G4S=SEQ ID NO: 313); (2) Bladder HOT G4S (A) (SEQ ID NO: 879; G4S=SEQ ID NO: 313); (3) Bladder HOT EVO2 EAAAK-G4S mix (A) (SEQ ID NO: 880; EAAAK=SEQ ID NO: 316; G4S=SEQ ID NO: 313); (4) Bladder HOT EVO2 EAAAK.i20 (A) (SEQ ID NO: 881; EAAAK=SEQ ID NO: 316); (5) Bladder HOT EVO2 G4S.i20 (A) (SEQ ID NO: 882; G4S=SEQ ID NO: 313); (6) Bladder HOT EVO2 EAAAK.G4S (B) (SEQ ID NO: 888; EAAAK=SEQ ID NO: 316; G4S=SEQ ID NO: 313); (7) Bladder HOT EVO2 EAAAK.i20 (B) (SEQ ID NO: 889; EAAAK=SEQ ID NO: 316); (8) Bladder HOT EVO2 EAAAK.G4S NUF minigene (B) (SEQ ID NO: 890; EAAAK=SEQ ID NO: 316; G4S=SEQ ID NO: 313); and (9) Bladder HOT EVO2 EAAAK.i20 NUF minigene (B) (SEQ ID NO: 891; EAAAK=SEQ ID NO: 316). A breakdown of the amino acids positions of the individual components in each construct is provided in Tables 78-86. For the (B) constructs, additional heteroclitic epitopes were added to complement the original hotspot mutation peptides so that total patient coverage within a cancer type approaches 100%. Any patient will therefore likely express a tumor-associated antigen that we have designed heteroclitic peptides for to cover the most prevalent HLAs (HLA-A0201, HLA-A0301, HLA-A2402, and HLA-B0702). G4S (SEQ ID NO: 313), EAAAK (SEQ ID NO: 316), and i20 refer to inclusion of flexible linkers, rigid linkers, and immunoproteasome processing linkers, respectively.

TABLE 78

Positions of Components of Bladder HOT EVO2 EAAAK.G4S (A) Insert.

14-34: PIK3CA_E545K
40-60: FGFR3_S249C
66-86: TP53_R248Q
92-112: PIK3CA_E542K
118-138: RXRA_S427F
144-164: FBXW7_R505G
170-190: TP53_R280T
196-216: NFE2L2_E79K
222-242: FGFR3_R248C
248-268: TP53_K132N
274-294: TP53_R248W
300-320: TP53_R175H
326-346: TP53_R273C
352-360: NUF2_A0201
366-374: NUF2_A2402
380-388: KLHL7_A2402
394-402: MAGEA3_A2402
408-416: GAGE1_A0301
422-430: MAGEA3_A0301
436-444: NYESO1_B0702
450-458: MAGEA3_B0702
464-472: GAGE1_B0702
486-506: FLAG
507-526: Linker-SIINFEKL
533-607: Ubiquitin
608-616: NYESO1_A0201_MINI

TABLE 79

Positions of Components of Bladder HOT G4S (A) Insert.

14-34: PIK3CA_E545K
40-60: FGFR3_S249C
66-86: TP53_R248Q
92-112: PIK3CA_E542K
118-138: RXRA_S427F
144-164: FBXW7_R505G
170-190: TP53_R280T
196-216: NFE2L2_E79K
222-242: FGFR3_R248C
248-268: TP53_K132N
274-294: TP53_R248W
300-320: TP53_R175H
326-346: TP53_R273C
352-360: NUF2_A0201
366-374: NUF2_A2402
380-388: KLHL7_A2402

TABLE 79-continued

Positions of Components of Bladder HOT G4S (A) Insert.

394-402: MAGEA3__A2402
408-416: GAGE1__A0301
422-430: MAGEA3__A0301
436-444: NYESO1__B0702
450-458: MAGEA3__B0702
464-472: GAGE1__B0702
486-506: FLAG
507-526: Linker-SIINFEKL
533-607: Ubiquitin
608-616: NYESO1__A0201__MINI

TABLE 80

Positions of Components of Bladder HOT EVO2 EAAAK-G4S mix (A) Insert.

14-34: PIK3CA__E545K
40-60: FGFR3__S249C
66-86: TP53__R248Q
92-112: PIK3CA__E542K
118-138: RXRA__S427F
144-164: FBXW7__R505G
170-190: TP53__R280T
196-216: NFE2L2__E79K
222-242: FGFR3__R248C
248-268: TP53__K132N
274-294: TP53__R248W
300-320: TP53__R175H
326-346: TP53__R273C
352-360: NUF2__A0201
366-374: NUF2__A2402
380-388: KLHL7__A2402
394-402: MAGEA3__A2402
408-416: GAGE1__A0301
422-430: MAGEA3__A0301
436-444: NYESO1__B0702
450-458: MAGEA3__B0702
464-472: GAGE1__B0702
486-506: FLAG
507-526: Linker-SIINFEKL
533-607: Ubiquitin
608-616: NYESO1__A0201__MINI

TABLE 81

Positions of Components of Bladder HOT EVO2 EAAAK.i20 (A) Insert.

14-34: PIK3CA__E545K
40-60: FGFR3__S249C
66-86: TP53__R248Q
92-112: PIK3CA__E542K
118-138: RXRA__S427F
144-164: FBXW7__R505G
170-190: TP53__R280T
196-216: NFE2L2__E79K
222-242: FGFR3__R248C
248-268: TP53__K132N
274-294: TP53__R248W
300-320: TP53__R175H
326-346: TP53__R273C
359-367: NUF2__A0201
380-388: NUF2__A2402
401-409: KLHL7__A2402
422-430: MAGEA3__A2402
443-451: GAGE1__A0301
464-472: MAGEA3__A0301
485-493: NYESO1__B0702
506-514: MAGEA3__B0702
527-535: GAGE1__B0702
556-576: FLAG

TABLE 81-continued

Positions of Components of Bladder HOT EVO2 EAAAK.i20 (A) Insert.

577-596: Linker-SIINFEKL
603-677: Ubiquitin
678-686: NYESO1__A0201__MINI

TABLE 82

Positions of Components of Bladder HOT EVO2 G4S.i20 (A) Insert.

14-34: PIK3CA__E545K
40-60: FGFR3__S249C
66-86: TP53__R248Q
92-112: PIK3CA__E542K
118-138: RXRA__S427F
144-164: FBXW7__R505G
170-190: TP53__R280T
196-216: NFE2L2__E79K
222-242: FGFR3__R248C
248-268: TP53__K132N
274-294: TP53__R248W
300-320: TP53__R175H
326-346: TP53__R273C
359-367: NUF2__A0201
380-388: NUF2__A2402
401-409: KLHL7__A2402
422-430: MAGEA3__A2402
443-451: GAGE1__A0301
464-472: MAGEA3__A0301
485-493: NYESO1__B0702
506-514: MAGEA3__B0702
527-535: GAGE1__B0702
556-576: FLAG
577-596: Linker-SIINFEKL
603-677: Ubiquitin
678-686: NYESO1__A0201__MINI

TABLE 83

Positions of Components of Bladder HOT EVO2 EAAAK.G4S (B) Insert.

14-34: PIK3CA__E545K
40-60: FGFR3__S249C
66-86: TP53__R248Q
92-112: PIK3CA__E542K
118-138: RXRA__S427F
144-164: FBXW7__R505G
170-180: TP53__R280T
196-216: NFE2L2__E79K
222-242: FGFR3__R248C
248-268: TP53__K132N
274-294: TP53__R248W
300-320: TP53__R175H
326-346: TP53__R273C
352-360: NUF2__A0201
366-374: NUF2__A2402
380-388: KLHL7__A2402
394-402: MAGEA3__A2402
408-416: GAGE1__A0301
422-430: MAGEA3__A0301
436-444: NYESO1__B0702
450-458: MAGEA3__B0702
464-472: GAGE1__B0702
478-486: CEACAM5__A0301
492-500: CEACAM5__A0201
506-514: PRAME__A0201
520-528: RNF43__B0702
542-562: FLAG
563-582: Linker-SIINFEKL
589-663: Ubiquitin
664-672: NYESO1__A0201__MINI

TABLE 84

Positions of Components of Bladder HOT EVO2 EAAAK.i20 (B) Insert.

14-34: PIK3CA_E545K
40-60: FGFR3_S249C
66-86: TP53_R248Q
92-112: PIK3CA_E542K
118-138: RXRA_S427F
144-164: FBXW7_R505G
170-190: TP53_R280T
196-216: NFE2L2_E79K
222-242: FGFR3_R248C
248-268: TP53_K132N
274-294: TP53_R248W
300-320: TP53_R175H
326-346: TP53_R273C
359-367: NUF2_A0201
380-388: NUF2_A2402
401-409: KLHL7_A2402
422-430: MAGEA3_A2402
443-451: GAGE1_A0301
464-472: MAGEA3_A0301
485-493: NYESO1_B0702
506-514: MAGEA3_B0702
527-535: GAGE1_B0702
548-556: CEACAM5_A0301
569-577: CEACAM5_A0201
590-598: PRAME_A0201
611-619: RNF43_B0702
640-660: FLAG
661-680: Linker-SIINFEKL
687-761: Ubiquitin
762-770: NYESO1_A0201_MINI

TABLE 85

Positions of Components of Bladder HOT EVO2 EAAAK.G4S NUF minigene (B) Insert.

14-34: PIK3CA_E545K
40-60: FGFR3_S249C
66-86: TP53_R248Q
92-112: PIK3CA_E542K
118-138: RXRA_S427F
144-164: FBXW7_R505G
170-190: TP53_R280T
196-216: NFE2L2_E79K
222-242: FGFR3_R248C
248-268: TP53_K132N
274-294: TP53_R248W
300-320: TP53_R175H
326-346: TP53_R273C
352-360: NYESO1_A0201_
366-374: NUF2_A2402
380-388: KLHL7_A2402
394-402: MAGEA3_A2402
408-416: GAGE1_A0301
422-430: MAGEA3_A0301
436-444: NYESO1_B0702
450-458: MAGEA3_B0702
464-472: GAGE1_B0702
478-486: CEACAM5_A0301
492-500: CEACAM5_A0201
506-514: PRAME_A0201
520-528: RNF43_B0702
542-562: FLAG
563-582: Linker-SIINFEKL
589-663: Ubiquitin
664-672: NUF2_A0201_MINI

TABLE 86

Positions of Components of Bladder HOT EVO2 EAAAK.i20_NUF minigene (B) Insert.

Figure 14:
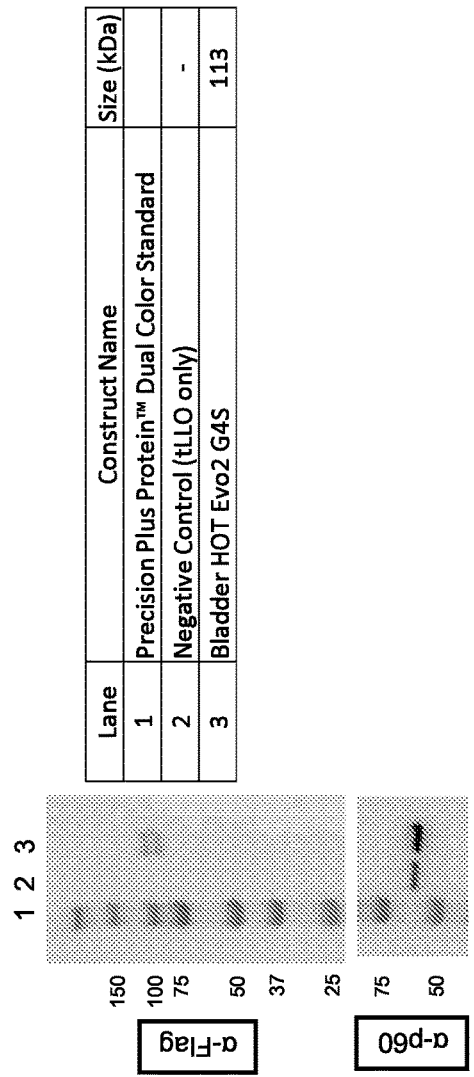
FIG. 14 shows Western blot data for different bladder cancer constructs. The upper left panel shows detection, using an anti-Flag antibody, of bladder cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 15:
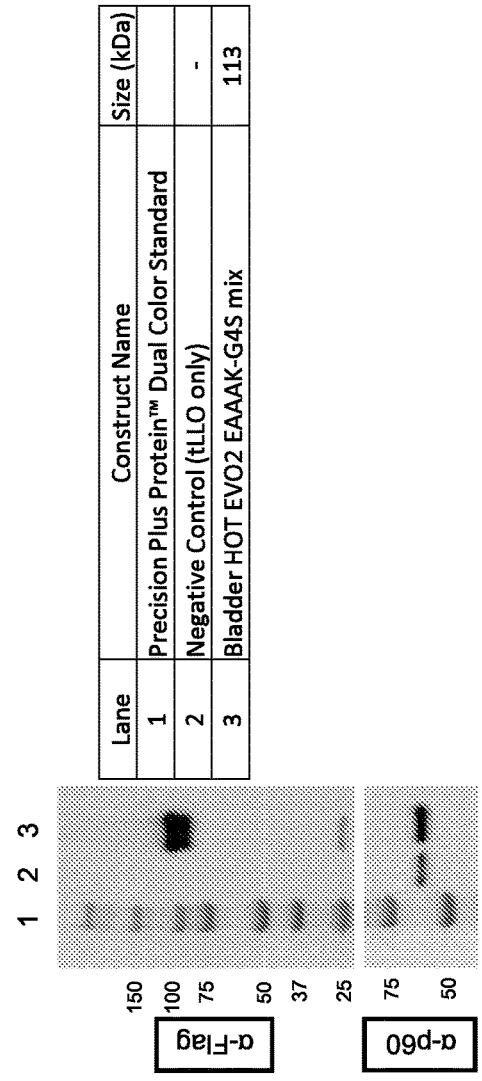
FIG. 15 shows Western blot data for different bladder cancer constructs. The upper left panel shows detection, using an anti-Flag antibody, of bladder cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 26:
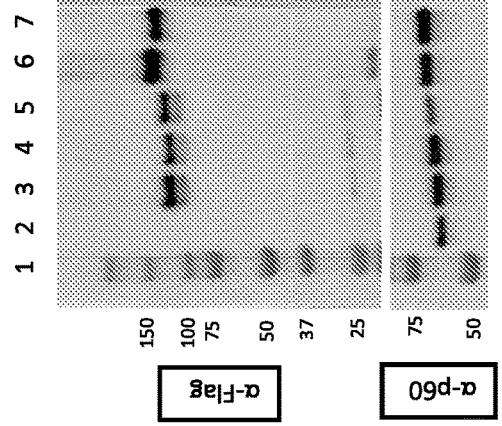
FIG. 26 shows Western blot data for different bladder cancer constructs. The upper left panel shows detection, using an anti-Flag antibody, of bladder cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.
Figure 31:
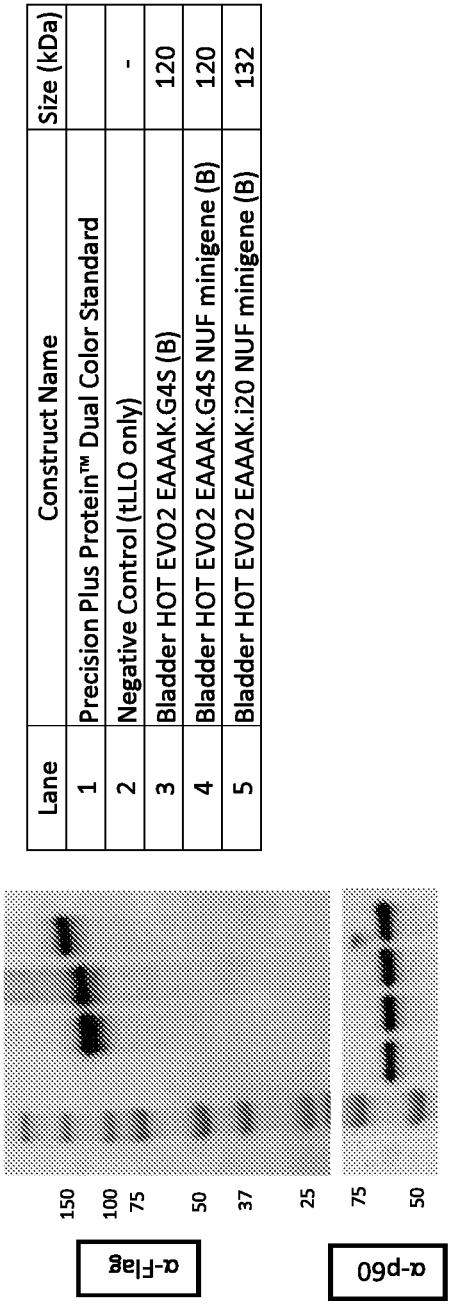
FIG. 31 shows Western blot data for different bladder cancer constructs. The upper left panel shows detection, using an anti-Flag antibody, of bladder cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.

14-34: PIK3CA_E545K
40-60: FGFR3_S249C
66-86: TP53_R248Q
92-112: PIK3CA_E542K
118-138: RXRA_S427F
144-164: FBXW7_R505G
170-190: TP53_R280T
196-216: NFE2L2_E79K
222-242: FGFR3_R248C
248-268: TP53_K132N
274-294: TP53_R248W
300-320: TP53_R175H
326-346: TP53_R273C
359-367: NYESO1_A0201_
380-388: NUF2_A2402
401-409: KLHL7_A2402
422-430: MAGEA3_A2402
443-451: GAGE1_A0301
464-472: MAGEA3_A0301
485-493: NYESO1_B0702
506-514: MAGEA3_B0702
527-535: GAGE1_B0702
548-556: CEACAM5_A0301
569-577: CEACAM5_A0201
590-598: PRAME_A0201
611-619: RNF43_B0702
640-660: FLAG
661-680: Linker-SIINFEKL
687-761: Ubiquitin
762-770: NUF2_A0201_MINI To assess the expression of tLLO-antigenic-peptide fusion proteins by Lmdda *Listeria* constructs, the DNA constructs were generated as described elsewhere herein and transformed into Lmdda. Each individual Lmdda construct was assayed by Western blot for tLLO fusion polypeptide expression using an anti-FLAG antibody. FIGS. 14 and 15 show expression and secretion of the tLLO fusion polypeptide into supernatant by Lmdda for various bladder cancer constructs. The constructs visualized on these Western blots all fall between 103-125 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing. FIG. 26 shows expression and secretion of the tLLO fusion polypeptide into supernatant by Lmdda for the Bladder HOT EVO2 EAAAK.G4S (EAAAK=SEQ ID NO: 316; G4S=SEQ ID NO: 313), Bladder HOT G4S (G4S=SEQ ID NO: 313), Bladder HOT EAAAK-G4S mix (EAAAK=SEQ ID NO: 316; G4S=SEQ ID NO: 313), Bladder HOT EVO2 EAAAK.i20 (EAAAK=SEQ ID NO: 316), and Bladder HOT EVO2 G4S.i20 (G4S=SEQ ID NO: 313) constructs. The constructs visualized on these Western blots fall between 103-125 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing. FIG. 31 shows expression and secretion of the tLLO fusion polypeptide into supernatant by Lmdda for the Bladder HOT EVO2 EAAAK.G4S (B) (EAAAK=SEQ ID NO: 316; G4S=SEQ ID NO: 313), Bladder HOT EVO2 EAAAK.G4S NUF minigene (B) (EAAAK=SEQ ID NO: 316; G4S=SEQ ID NO: 313), and Bladder HOT EVO2 EAAAK.i20 NUF minigene (B) (EAAAK=SEQ ID NO: 316) constructs. The constructs visualized on these Western blots fall between 103-135 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing.

Breast Cancer Hotspot/Heteroclitic/Minigene Constructs

A total of 14 hotspot mutations across 3 genes were selected as described in Example 4 and elsewhere herein for the breast cancer ADXS-HOT constructs. This panel of hotspot mutations covers 47% of all estrogen-receptor-positive (ER+) breast cancer patients (i.e., 47% of ER+breast cancer patients will have at least one of the hotspot mutations from the panel). For each recurrent cancer mutation included in the constructs, a peptide of 21 amino acids in length was designed as described in Example 4 and elsewhere herein. The peptides are shown in Table 87. The hotspot mutation in each is bolded and underlined.

A total of 11 peptides with heteroclitic mutations across 6 genes were selected for the breast cancer ADXS-HOT constructs. For each heteroclitic mutation, a peptide of 9 amino acids in length was designed as described in Example 4 and elsewhere herein. The peptides are shown in Table 88. The heteroclitic mutation in each is as described in Table 122.

TABLE 88

Exemplary Breast Cancer Panel Heteroclitic 9-Mers.
Breast Cancer Panel Heteroclitic 9-Mers

| Gene | HLA Type | Sequence | SEQ ID NO | Representative Nucleic Acid SEQ ID NOS |
|---|---|---|---|---|
| CEACAM5 | A0301 | HVFGYSWYK | 791 | 2535-2544 |
| CEACAM5 | B0702 | IPQVHTQVL | 793 | 2545-2554 |
| CEACAM5 | A2402 | IYPNASLLF | 796 | 2555-2564 |
| CEACAM5 | A0201 | ILIGVLVGV | 798 | 2565-2574 |
| STEAP1 | A0201 | LLLGTIHAV | 799 | 2575-2584 |

TABLE 87

Exemplary Breast Cancer Panel Hotspot Peptides.
Breast Cancer Panel Hotspot 21-Mers

| Gene | Hotspot Mutation | % Prevalence in Breast Cancer Patients | Sequence | SEQ ID NO | Representative Nucleic Acid SEQ ID NOS |
|---|---|---|---|---|---|
| PIK3CA | E545K | 9.6 | STRDPLSEITKQEKDFLWSHR | 437 | 1711-1720 |
| PIK3CA | E542K | 6.8 | KAISTRDPLSKITEQEKDFLW | 436 | 1721-1730 |
| PIK3CA | H1047R | 22.2 | EYFMKQMNDARHGGWTTKMDW | 447 | 1731-1740 |
| AKT1 | E17K | 4.6 | VKEGWLHKRGKYIKTWRPRYF | 585 | 1741-1750 |
| PIK3CA | H1047L | 2.2 | EYFMKQMNDALHGGWTTKMDW | 448 | 1751-1760 |
| PIK3CA | Q546K | <1.0 | TRDPLSEITEKEKDFLWSHRH | 442 | 1761-1770 |
| PIK3CA | E545A | <1.0 | STRDPLSEITAQEKDFLWSHR | 438 | 1771-1780 |
| PIK3CA | E545G | <1.0 | STRDPLSEITGQEKDFLWSHR | 439 | 1781-1790 |
| ESR1 | K303R | *associated with drug resistance | PSPLMIKRSKRNSLALSLTAD | 774 | 1791-1800 |
| ESR1 | D538G | *associated with drug resistance | MKCKNVVPLYGLLLEMLDAHR | 775 | 1801-1810 |
| ESR1 | Y537S | *associated with drug resistance | SMKCKNVVPLSDLLLEMLDAH | 776 | 1811-1820 |
| ESR1 | Y537N | *associated with drug resistance | SMKCKNVVPLNDLLLEMLDAH | 777 | 1821-1830 |
| ESR1 | Y537C | *associated with drug resistance | SMKCKNVVPLCDLLLEMLDAH | 778 | 1831-1840 |
| ESR1 | E380Q | *associated with drug resistance | LTLHDQVHLLQCAWLEILMIG | 779 | 1841-1850 |

TABLE 88-continued

Exemplary Breast Cancer Panel Heteroclitic 9-Mers.
Breast Cancer Panel Heteroclitic 9-Mers

| Gene | HLA Type | Sequence | SEQ ID NO | Representative Nucleic Acid SEQ ID NOS |
|---|---|---|---|---|
| STEAP1 | A2402 | KYKKFPWWL | 800 | 2585-2594 |
| RNF43 | B0702 | NPQPVWLCL | 801 | 2595-2604 |
| MAGEA3 | A2402 | IMPKAGLLF | 810 | 2605-2614 |
| MAGEA3 | A0301 | YMFPVIFSK | 812 | 2615-2624 |
| PRAME | A0201 | NMTHVLYPL | 815 | 2625-2634 | binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 88B are the percent expression of each gene in patients with breast cancer (The Cancer Genome Atlas database), the HLA allele being tested, and whether the wild-type peptide corresponding to each heteroclitic peptide is known to be immunogenic. For a construct including each of the heteroclitic peptides in Table 88B, 100% of breast cancer patients with HLA type A*02:01 express at least one of the TAA genes, 95% of breast cancer patients with HLA type A*03:01 express at least one of the TAA genes, 100% of breast cancer patients with HLA type A*24:02 express at least one of the TAA genes, and 100% of breast cancer patients with HLA type B*07:02 express at least one of the TAA genes.

TABLE 88B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| STEAP1 | 100 | A*02:01 | 5.77 | 188.4 | Yes |
| STEAP1 | 100 | A*24:02 | 47.48 | 104.7 | unknown |
| RNF43 | 100 | B*07:02 | 161.95 | 65.4 | Yes |
| CEACAM5 | 95 | A*02:01 | 6.92 | 170.7 | Yes |
| CEACAM5 | 95 | A*03:01 | 9.69 | 85.4 | Yes |
| CEACAM5 | 95 | A*24:02 | 6.22 | 77.2 | Yes |
| CEACAM5 | 95 | B*07:02 | 8.36 | 88.3 | Yes |
| PRAME | 92 | A*02:01 | 11.72 | 139.4 | Yes |
| TERT | 87 | A*02:01 | 7.04 | 123.3 | Yes |
| TERT | 87 | A*24:02 | 2197.84 | 142.3 | unknown |
| MAGE-A3 | 31 | A*03:01 | 9.40 | 85.4 | unknown |
| MAGE-A3 | 31 | A*24:02 | 28.11 | 92.8 | unknown |

[#]NetMHC4.0
[^]% relative to positive control peptide binding

TABLE 88-continued

Exemplary Breast Cancer Panel Heteroclitic 9-Mers.
Breast Cancer Panel Heteroclitic 9-Mers

| Gene | HLA Type | Sequence | SEQ ID NO | Representative Nucleic Acid SEQ ID NOS |
|---|---|---|---|---|
| hTERT | A0201_A2402 | IMAKFLHWL | 816 | 2635-2644 |

The in silico predicted binding affinity and in vitro binding affinity of the heteroclitic 9-mer peptides are provided in Table 88B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized Constructs were designed to encode a fusion polypeptide comprising tLLO fused to the hotspot peptides and one or more or all of the heteroclitic peptides, with the C-terminal heteroclitic peptide following a ubiquitin peptide. In some constructs, the ubiquitin was fused to the STEAP1_A0201 heteroclitic peptide. In some of the constructs, the ubiquitin was fused to the STEAP1_A2402 heteroclitic peptide. The heteroclitic peptides were C-terminal to the hotspot peptides. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) Breast HOT EVO2 EAAAK.G4S (A) (SEQ ID NO: 883; EAAAK=SEQ ID NO: 316; G4S=SEQ ID NO: 313); (2) Breast HOT G4S (A) (SEQ ID NO: 884; G4S=SEQ ID NO: 313); (3) Breast HOT EVO2 EAAAK-G4S mix (A) (SEQ ID NO: 885; EAAAK=SEQ ID NO: 316; G4S=SEQ ID NO: 313); (4) Breast HOT EVO2 EAAAK.i20 (A) (SEQ ID NO: 886; EAAAK=SEQ ID NO: 316); (5) Breast HOT EVO2 G4S.i20 (A) (SEQ ID NO: 887; G4S=SEQ ID NO: 313); and (6) Breast A24 HOT (SEQ ID NO: 907). A breakdown of the amino acids positions of the individual components in each construct is provided in Tables 89-94. For the A24 construct, the 9-mer in the minigene was replaced by an A24 9mer. A24 (HLA-A2402) is the HLA type commonly found in Asia. G4S (SEQ ID NO: 313), EAAAK (SEQ ID NO: 316), and i20 refer to inclusion of flexible linkers, rigid linkers, and immunoproteasome processing linkers, respectively.

TABLE 89

Positions of Components of Breast HOT EVO2 EAAAK.G4S (A) Insert.

14-34: PIK3CA__H1047R
40-60: PIK3CA__E545K
66-86: PIK3CA__E542K
92-112: AKT1__E17K
118-138: PIK3CA__H1047L
144-164: PIK3CA__Q546K
170-190: PIK3CA__E545A
196-216: PIK3CA__E545G
222-242: ESR1__K303R
248-268: ESR1__D538G
274-294: ESR1__Y537S
300-320: ESR1__Y537N
326-346: ESR1__Y537C
352-372: ESR1__E380Q
378-386: CEACAM5__A0201
392-400: PRAME__A0201
406-414: hTERT__A0201__A2402
420-428: CEACAM5__A0301
434-442: MAGEA3__A0301
448-456: STEAP1__A2402
462-470: CEACAM5__A2402
476-484: MAGEA3__A2402
490-498: CEACAM5__B0702
504-512: RNF43__B0702
526-546: FLAG
547-566: Linker-SIINFEKL
572-646: Ubiquitin
647-655: STEAP1__A0201__MINI

TABLE 90

Positions of Components of Breast HOT G4S (A) Insert.

14-34: PIK3CA__H1047R
40-60: PIK3CA__E545K
66-86: PIK3CA__E542K
92-112: AKT1__E17K
118-138: PIK3CA__H1047L
144-164: PIK3CA__Q546K
170-190: PIK3CA__E545A
196-216: PIK3CA__E545G
222-242: ESR1__K303R
248-268: ESR1__D538G
274-294: ESR1__Y537S
300-320: ESR1__Y537N
326-346: ESR1__Y537C
352-372: ESR1__E380Q
378-386: CEACAM5__A0201
392-400: PRAME__A0201
406-414: hTERT__A0201__A2402
420-428: CEACAM5__A0301
434-442: MAGEA3__A0301
448-456: STEAP1__A2402
462-470: CEACAM5__A2402
476-484: MAGEA3__A2402
490-498: CEACAM5__B0702
504-512: RNF43__B0702
526-546: FLAG
547-566: Linker-SIINFEKL
572-646: Ubiquitin
647-655: STEAP1__A0201__MINI

TABLE 91

Positions of Components of Breast HOT EVO2 EAAAK-G4S mix (A) Insert.

14-34: PIK3CA__H1047R
40-60: PIK3CA__E545K
66-86: PIK3CA__E542K
92-112: AKT1__E17K
118-138: PIK3CA__H1047L
144-164: PIK3CA__Q546K
170-190: PIK3CA__E545A
196-216: PIK3CA__E545G
222-242: ESR1__K303R
248-268: ESR1__D538G
274-294: ESR1__Y537S
300-320: ESR1__Y537N
326-346: ESR1__Y537C
352-372: ESR1__E380Q
378-386: CEACAM5__A0201
392-400: PRAME__A0201
406-414: hTERT__A0201__A2402
420-428: CEACAM5__A0301
434-442: MAGEA3__A0301
448-456: STEAP1__A2402
462-470: CEACAM5__A2402
476-484: MAGEA3__A2402
490-498: CEACAM5__B0702
504-512: RNF43__B0702
526-546: FLAG
576-566: Linker-SIINFEKL
567-641: Ubiquitin
642-650: STEAP1__A0201__MINI

TABLE 92

Positions of Components of Breast HOT EVO2 EAAAK.i20 (A) Insert.

14-34: PIK3CA__H1047R
40-60: PIK3CA__E545K
66-86: PIK3CA__E542K
92-112: AKT1__E17K
118-138: PIK3CA__H1047L
144-164: PIK3CA__Q546K
170-190: PIK3CA__E545A
196-216: PIK3CA__E545G
222-242: ESR1__K303R
248-268: ESR1__D538G
274-294: ESR1__Y537S
300-320: ESR1__Y537N
326-346: ESR1__Y537C
352-372: ESR1__E380Q
385-393: CEACAM5__A0201
406-414: PRAME__A0201
427-435: hTERT__A0201__A2402
448-456: CEACAM5__A0301
469-477: MAGEA3__A0301
490-498: STEAP1__A2402
511-519: CEACAM5__A2402
532-540: MAGEA3__A2402
553-561: CEACAM5__B0702
574-582: RNF43__B0702
603-623: FLAG
624-643: Linker-SIINFEKL
650-724: Ubiquitin
725-733: STEAP1__A0201__MINI

TABLE 93

Positions of Components of Breast HOT EVO2 G4S.i20 (A) Insert.

14-34: PIK3CA__H1047R
40-60: PIK3CA__E545K
66-86: PIK3CA__E542K
92-112: AKT1__E17K
118-138: PIK3CA__H1047L

TABLE 93-continued

Positions of Components of Breast HOT EVO2 G4S.i20 (A) Insert.

144-164: PIK3CA__Q546K
170-190: PIK3CA__E545A
196-216: PIK3CA__E545G
222-242: ESR1__K303R
248-268: ESR1__D538G
274-294: ESR1__Y537S
300-320: ESR1__Y537N
326-346: ESR1__Y537C
352-372: ESR1__E380Q
385-393: CEACAM5__A0201
406-414: PRAME__A0201
427-435: hTERT__A0201__A2402
448-456: CEACAM5__A0301
469-477: MAGEA3__A0301
490-498: STEAP1__A2402
511-519: CEACAM5__A2402
532-540: MAGEA3__A2402
553-561: CEACAM5__B0702
574-582: RNF43__B0702
603-623: FLAG
624-643: Linker-SIINFEKL
650-724: Ubiquitin
725-733: STEAP1__A0201__MINI

TABLE 94

Positions of Components of Breast A24 HOT Insert.

14-34: PIK3CA__H1047R
40-60: PIK3CA__E545K
66-86: PIK3CA__E542K
92-112: AKT1__E17K
118-138: PIK3CA__H1047L
144-164: PIK3CA__Q546K
170-190: PIK3CA__E545A
196-216: PIK3CA__E545G
222-242: ESR1__K303R
248-268: ESR1__D538G
274-294: ESR1__Y537S
300-320: ESR1__Y537N
326-346: ESR1__Y537C
352-372: ESR1__E380Q
385-393: CEACAM5__A0201
406-414: PRAME__A0201
427-435: hTERT__A0201__A2402
448-456: CEACAM5__A0301
469-477: MAGEA3__A0301
490-498: STEAP1__A0201

TABLE 94-continued

Positions of Components of Breast A24 HOT Insert.

Figure 16:
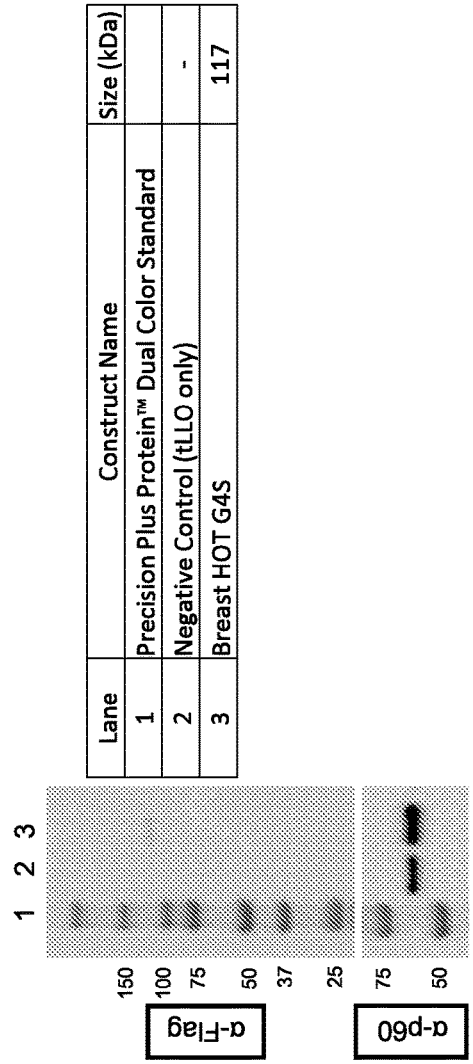
FIG. 16 shows Western blot data for different breast cancer constructs. The upper left panel shows detection, using an anti-Flag antibody, of breast cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.

511-519: CEACAM5__A2402
532-540: MAGEA3__A2402
553-561: CEACAM5__B0702
574-582: RNF43__B0702
603-623: FLAG
624-643: Linker-SIINFEKL
650-724: Ubiquitin
725-733: STEAP1__A2402 MINI To assess the expression of tLLO-antigenic-peptide fusion proteins by Lmdda *Listeria* constructs, the DNA constructs were generated as described elsewhere herein and transformed into Lmdda. Each individual Lmdda construct was assayed by Western blot for tLLO fusion polypeptide expression using an anti-FLAG antibody. FIG. 16 shows expression and secretion of the tLLO fusion polypeptide into supernatant by Lmdda for the Breast HOT G4S (G4S=SEQ ID NO: 313) construct. FIG. 23 shows expression and secretion of the tLLO fusion polypeptide into supernatant by Lmdda for the Breast HOT EVO2 EAAAK.G4S (EAAAK=SEQ ID NO: 316; G4S=SEQ ID NO: 313), Breast HOT G4S (G4S=SEQ ID NO: 313), Breast HOT EVO2 EAAAK-G4S mix (EAAAK=SEQ ID NO: 316; G4S=SEQ ID NO: 313), Breast HOT EVO2 EAAAK.i20 (EAAAK=SEQ ID NO: 316), and Breast HOT EVO2 G4s.i20 (G4S=SEQ ID NO: 313) constructs. The constructs visualized on these Western blots fall between 103-130 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing.

Uterine Cancer Hotspot/Heteroclitic/Minigene Constructs

A total of 16 hotspot mutations across 6 genes were selected as described in Example 4 and elsewhere herein for the uterine cancer ADXS-HOT constructs. This panel of hotspot mutations covers 64% of all uterine cancer patients (i.e., 64% of uterine cancer patients will have at least one of the hotspot mutations from the panel). For each recurrent cancer mutation included in the constructs, a peptide of 21 amino acids in length was designed as described in Example 4 and elsewhere herein. The peptides are shown in Table 95. The hotspot mutation in each is bolded and underlined.

TABLE 95

Exemplary Uterine Cancer Panel Hotspot 21-Mers.
Uterine Cancer Panel Hotspot 21-Mers

| Gene | Hotspot Mutation | % Prevalence in Uterine Cancer Patients | Sequence | SEQ ID NO |
|---|---|---|---|---|
| PTEN | R130G | 10.0 | AAIHCKAGKGGTGVMICAYLL | 471 |
| PTEN | R130Q | 7.0 | AAIHCKAGKGQTGVMICAYLL | 470 |
| KRAS | G12D | 6.0 | TEYKLVVVGADGVGKSALTIQ | 489 |
| KRAS | G12V | 5.0 | TEYKLVVVGAVGVGKSALTIQ | 491 |
| PIK3CA | H1047R | 5.0 | EYFMKQMNDARHGGWTTKMDW | 447 |
| PIK3CA | R88Q | 4.0 | EREEFFDETRQLCDLRLFQPF | 427 |

TABLE 95-continued

Exemplary Uterine Cancer Panel Hotspot 21-Mers.
Uterine Cancer Panel Hotspot 21-Mers

| Gene | Hotspot Mutation | % Prevalence in Uterine Cancer Patients | Sequence | SEQ ID NO |
|---|---|---|---|---|
| PIK3CA | E545K | 4.0 | STRDPLSEITKQEKDFLWSHR | 437 |
| PIK3CA | E542K | 4.0 | KAISTRDPLSKITEQEKDFLW | 436 |
| CTNNB1 | S37F | 3.0 | QQSYLDSGIHFGATTTAPSLS | 783 |
| KRAS | G13D | 3.0 | EYKLVVVGAGDVGKSALTIQL | 492 |
| CTNNB1 | S37C | 3.0 | QQSYLDSGIHCGATTTAPSLS | 784 |
| PIK3CA | H1047L | 2.4 | EYFMKQMNDALHGGWTTKMDW | 448 |
| PIK3CA | G118D | 2.4 | REEKILNREIDFAIGMPVCEF | 431 |
| KRAS | G12A | 2.0 | TEYKLVVVGAAGVGKSALTIQ | 487 |
| FBXW7 | R505C | 2.0 | HVLMGHVAAVCCVQYDGRRVV | 785 |
| TP53 | R248W | 2.0 | CNSSCMGGMNWRPILTIITLE | 559 |

A total of 14 peptides with heteroclitic mutations across 8 genes were selected for the uterine cancer ADXS-HOT constructs. For each heteroclitic mutation, a peptide of 9 amino acids in length was designed as described in Example 4 and elsewhere herein. The peptides are shown in Table 96. The heteroclitic mutation in each is as described in Table 122.

TABLE 96

Exemplary Uterine Cancer Panel Heteroclitic 9-Mers.
Uterine Cancer Panel Heteroclitic 9-Mers

| Gene | HLA Type | Sequence | SEQ ID NO |
|---|---|---|---|
| CEACAM5 | A0201 | ILMGVLVGV | 820 |
| CEACAM5 | A0301 | HVFGYSWYK | 791 |
| CEACAM5 | B0702 | IPQVHTQVL | 793 |
| CEACAM5 | A0201 | ILIGVLVGV | 798 |
| PRAME | A0201 | NMTHVLYPL | 815 |
| hTERT | A0201_A2402 | IMAKFLHWL | 816 |
| STEAP1 | A0201 | LLLGTIHAV | 799 |
| CEACAM5 | A2402 | IYPNASLLF | 796 |
| RNF43 | B0702 | NPQPVWLCL | 801 |
| NUF2 | A0201 | YLMPVNSEV | 807 |
| NUF2 | A2402 | VWGIRLEHF | 808 |
| KLHL7 | A2402 | VYILGGSQF | 809 |
| SART3 | A0201 | LMQAEAPRL | 803 |
| STEAP1 | A2402 | KYKKFPWWL | 800 |

The in silico predicted binding affinity and in vitro binding affinity of the heteroclitic 9-mer peptides are provided in Table 96B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 96B are the percent expression of each gene in patients with uterine cancer (The Cancer Genome Atlas (TCGA) database), the HLA allele being tested, and whether the wild-type peptide corresponding to each heteroclitic peptide is known to be immunogenic. For a construct including each of the heteroclitic peptides in Table 96B, 100% of uterine cancer patients with HLA type A*02:01 express at least one of the TAA genes, 83% of uterine cancer patients with HLA type A*03:01 express at least one of the TAA genes, 100% of uterine cancer patients with HLA type A*24:02 express at least one of the TAA genes, and 100% of uterine cancer patients with HLA type B*07:02 express at least one of the TAA genes.

TABLE 96B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| CEACAM5[1] | 84 | A*02:01 | 6.92 | 170.7 | Yes |
| CEACAM5[2] | 84 | A*02:01 | 3.47 | TBD | Yes |
| CEACAM5 | 84 | A*03:01 | 9.69 | 85.4 | Yes |
| CEACAM5 | 84 | B*07:02 | 8.36 | 88.3 | Yes |
| STEAP1 | 100 | A*02:01 | 5.77 | 188.4 | Yes |
| PRAME | 99 | A*02:01 | 11.72 | 139.4 | Yes |
| TERT | 92 | A*02:01 | 7.04 | 123.3 | Yes |
| TERT | 92 | A*24:02 | 2197.84 | 142.3 | unknown |
| STEAP1 | 100 | A*24:02 | 47.48 | 104.7 | unknown |
| CEACAM5 | 84 | A*24:02 | 6.22 | 77.2 | Yes |
| RNF43 | 100 | B*07:02 | 161.95 | 65.4 | Yes |
| NUF2 | 99 | A*02:01 | 2.79 | 160.0 | Yes |
| KLHL7 | 100 | A*24:02 | 60.84 | 97.4 | Yes |
| SART3 | 100 | A*02:01 | 235.57 | 160.0 | Yes |
| NUF2 | 99 | A*24:02 | 149.07 | 88.4 | Yes |

[#]NetMHC4.0
[^]% relative to positive control peptide binding
[1]SEQ ID NO: 798
[2]SEQ ID NO: 820

Constructs were designed to encode a fusion polypeptide comprising tLLO fused to the hotspot peptides and one or more or all of the heteroclitic peptides, with the C-terminal heteroclitic peptide following a ubiquitin peptide. In some constructs, the ubiquitin was fused to the STEAP1_A0201 heteroclitic peptide. In some of the constructs, the ubiquitin was fused to the STEAP_A2402 heteroclitic peptide. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) Uterine HOT EVO2 EAAAK.G4S (SEQ ID NO: 896; EAAAK=SEQ ID NO: 316; G4S=SEQ ID NO: 313); (2) Uterine HOT EVO2 EAAAK.i20 (SEQ ID NO: 897; EAAAK=SEQ ID NO: 316); and (3) Uterine A24 HOT (SEQ ID NO: 904). A breakdown of the amino acids positions of the individual components in each construct is provided in Tables 97-99. For the A24 construct, the 9-mer in the minigene was replaced by an A24 9mer. A24 (HLA-A2402) is the HLA type commonly found in Asia. G4S (SEQ ID NO: 313), EAAAK (SEQ ID NO: 316), and i20 refer to inclusion of flexible linkers, rigid linkers, and immunoproteasome processing linkers, respectively.

TABLE 97

Positions of Components of Uterine HOT EVO2 EAAAk.G4S Insert.

14-34: PTEN_R130G
40-60: PTEN_R130Q
66-86: KRAS_G12D
92-112: KRAS_G12V
118-138: PIK3CA_H1047R
144-164: PIK3CA_R88Q
170-190: PIK3CA_E545K
196-216: PIK3CA_E542K
222-242: CTNNB1_S37F
248-268: KRAS_G13D
274-294: CTNNB1_S37C
300-320: PIK3CA_H1047L
326-346: PIK3CA_G118D

TABLE 97-continued

Positions of Components of Uterine HOT EVO2 EAAAk.G4S Insert.

352-372: KRAS_G12A
378-398: FBXW7_R505C
404-424: TP53_R248W
430-438: CEACAM5_A0201
444-452: CEACAM5_A0301
458-466: CEACAM5_B0702
472-480: CEACAM5_A0201
486-494: PRAME_A0201
500-508: hTERT_A0201_A2402
514-522: STEAP1_A2402
528-536: CEACAM5_A2402
542-550: RNF43_B0702
556-564: NUF2_A0201
570-578: NUF2_A2402
584-592: KLHL7_A2402
598-606: SART3_A0201
620-640: FLAG
641-660: Linker-SIINFEKL
667-741: Ubiquitin
742-750: STEAP1_A0201_MINI

TABLE 98

Positions of Components of Uterine HOT EVO2 EAAAK.i20 Insert.

14-34: PTEN_R130G
40-60: PTEN_R130Q
66-86: KRAS_G12D
92-112: KRAS_G12V
118-138: PIK3CA_H1047R
144-164: PIK3CA_R88Q
170-190: PIK3CA_E545K
196-216: PIK3CA_E542K
222-242: CTNNB1_S37F
248-268: KRAS_G13D
274-294: CTNNB1_S37C
300-320: PIK3CA_H1047L
326-346: PIK3CA_G118D
352-372: KRAS_G12A
378-398: FBXW7_R505C
404-424: TP53_R248W
437-445: CEACAM5_A0201
458-466: CEACAM5_A0301

TABLE 98-continued

Positions of Components of Uterine HOT EVO2 EAAAK.i20 Insert.

479-487: CEACAM5__B0702
500-508: CEACAM5__A0201
521-529: PRAME__A0201
542-550: hTERT__A0201__A2402
563-571: STEAP1__A2402
584-592: CEACAM5__A2402
605-613: RNF43__B0702
626-634: NUF2__A0201
647-655: NUF2__A2402
668-676: KLHL7__A2402
689-697: SART3__A0201
718-738: FLAG
739-758: Linker-SIINFEKL
765-839: Ubiquitin
840-848: STEAP1__A0201__MINI

TABLE 99

Positions of Components of Uterine A24 HOT Insert.

14-34: PTEN__R130G
40-60: PTEN__R130Q
66-86: KRAS__G12D
92-112: KRAS__G12V
118-138: PIK3CA__H1047R
144-164: PIK3CA__R88Q
170-190: PIK3CA__E545K
196-216: PIK3CA__E542K
222-242: CTNNB1__S37F
248-268: KRAS__G13D

TABLE 99-continued

Positions of Components of Uterine A24 HOT Insert.

274-294: CTNNB1__S37C
300-320: PIK3CA__H1047L
326-346: PIK3CA__G118D

TABLE 99-continued

Positions of Components of Uterine A24 HOT Insert.

352-372: KRAS__G12A
378-398: FBXW7__R505C
404-424: TP53__R248W
437-445: CEACAM5__A0201
458-466: CEACAM5__A0301
479-487: CEACAM5__B0702
500-508: CEACAM5__A0201
521-529: PRAME__A0201
542-550: hTERT__A0201__A2402
563-571: STEAP1__A0201
584-592: CEACAM5__A2402
605-613: RNF43__B0702
626-634: NUF2__A0201
647-655: NUF2__A2402
668-676: KLHL7__A2402
689-697: SART3__A0201
718-738: FLAG
739-758: Linker-SIINFEKL
765-839: Ubiquitin
840-848: STEAP1__A2402 MINI Ovarian Cancer Hotspot/Heteroclitic/Minigene Constructs A total of 12 hotspot mutations across 1 gene were selected as described in Example 4 and elsewhere herein for the ovarian cancer ADXS-HOT constructs. This panel of hotspot mutations covers 25% of all ovarian cancer patients (i.e., 25% of ovarian cancer patients will have at least one of the hotspot mutations from the panel). For each recurrent cancer mutation included in the constructs, a peptide of 21 amino acids in length was designed as described in Example 4 and elsewhere herein. The peptides are shown in Table 100. The hotspot mutation in each is bolded and underlined.

TABLE 100

Exemplary Ovarian Cancer Panel Hotspot 21-Mers.
Ovarian Cancer Panel Hotspot 21-Mers

| Gene | Hotspot Mutation | % Prevalence in Ovarian Cancer Patients | Sequence | SEQ ID NO |
| --- | --- | --- | --- | --- |
| TP53 | R248Q | 2.8 | CNSSCMGGMNQRPILTIITLE | 560 |
| TP53 | R248W | 1.9 | CNSSCMGGMNWRPILTIITLE | 559 |
| TP53 | R175H | 2.5 | QSQHMTEVVRHCPHHERCSDS | 542 |
| TP53 | R273C | 2.2 | NLLGRNSFEVCVCACPGRDRR | 565 |
| TP53 | R282W | 1.6 | VRVCACPGRDWRTEEENLRKK | 569 |
| TP53 | R273H | 3.0 | NLLGRNSFEVHVCACPGRDRR | 563 |
| TP53 | Y220C | 3.0 | NTFRHSVVVPCEPPEVGSDCT | 552 |
| TP53 | I195T | 2.2 | SDGLAPPQHLTRVEGNLRVEY | 549 |
| TP53 | C176Y | 1.6 | SQHMTEVVRRYPHHERCSDSD | 545 |
| TP53 | H179R | 1.3 | MTEVVRRCPHRERCSDSDGLA | 546 |
| TP53 | S241F | 1.3 | TIHYNYMCNSFCMGGMNRRPI | 555 |
| TP53 | H193R | 0.9 | SDSDGLAPPQRLIRVEGNLRV | 548 |

A total of 14 peptides with heteroclitic mutations across 8 genes were selected for the ovarian cancer ADXS-HOT constructs. For each heteroclitic mutation, a peptide of 9 amino acids in length was designed as described in Example 4 and elsewhere herein. The peptides are shown in Table 101. The heteroclitic mutation in each is as described in Table 122.

TABLE 101

Exemplary Ovarian Cancer Panel Heteroclitic 9-Mers.
Ovarian Cancer Panel Heteroclitic 9-Mers

| Gene | HLA Type | Sequence | SEQ ID NO |
|---|---|---|---|
| CEACAM5 | A0301 | HVFGYSWYK | 791 |
| CEACAM5 | B0702 | IPQVHTQVL | 793 |
| CEACAM5 | A2402 | IYPNASLLF | 796 |
| CEACAM5 | A0201 | ILIGVLVGV | 798 |
| STEAP1 | A0201 | LLLGTIHAV | 799 |
| STEAP1 | A2402 | KYKKFPWWL | 800 |
| RNF43 | B0702 | NPQPVWLCL | 801 |
| SART3 | A0201 | LMQAEAPRL | 803 |
| NUF2 | A0201 | YLMPVNSEV | 807 |
| NUF2 | A2402 | VWGIRLEHF | 808 |
| KLHL7 | A2402 | VYILGGSQF | 809 |
| PRAME | A0201 | NMTHVLYPL | 815 |
| hTERT | A0201_A2402 | IMAKFLHWL | 816 |
| CEACAM5 | A0201 | ILMGVLVGV | 820 | is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 101B are the percent expression of each gene in patients with ovarian cancer (The Cancer Genome Atlas (TCGA) database), the HLA allele being tested, and whether the wild-type peptide corresponding to each heteroclitic peptide is known to be immunogenic. For a construct including each of the heteroclitic peptides in Table 101B, 100% of ovarian cancer patients with HLA type A*02:01 express at least one of the TAA genes, 83% of ovarian cancer patients with HLA type A*03:01 express at least one of the TAA genes, 100% of ovarian cancer patients with HLA type A*24:02 express at least one of the TAA genes, and 100% of ovarian cancer patients with HLA type B*07:02 express at least one of the TAA genes.

TABLE 101B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| CEACAM5[1] | 93 | A*02:01 | 6.92 | 170.7 | Yes |
| CEACAM5[2] | 93 | A*02:01 | 3.47 | TBD | Yes |
| CEACAM5 | 93 | A*03:01 | 9.69 | 85.4 | Yes |
| CEACAM5 | 93 | B*07:02 | 8.36 | 88.3 | Yes |
| STEAP1 | 100 | A*02:01 | 5.77 | 188.4 | Yes |
| PRAME | 100 | A*02:01 | 11.72 | 139.4 | Yes |
| TERT | 94 | A*02:01 | 7.04 | 123.3 | Yes |
| TERT | 94 | A*24:02 | 2197.84 | 142.3 | unknown |
| STEAP1 | 100 | A*24:02 | 47.48 | 104.7 | unknown |
| CEACAM5 | 93 | A*24:02 | 6.22 | 77.2 | Yes |
| RNF43 | 100 | B*07:02 | 161.95 | 65.4 | Yes |
| NUF2 | 100 | A*02:01 | 2.79 | 160.0 | Yes |
| KLHL7 | 100 | A*24:02 | 60.84 | 97.4 | Yes |
| SART3 | 100 | A*02:01 | 235.57 | 160.0 | Yes |
| NUF2 | 100 | A*24:02 | 149.07 | 88.4 | Yes |

[#]NetMHC4.0
[^]% relative to positive control peptide binding
[1]SEQ ID NO: 798
[2]SEQ ID NO: 820

The in silico predicted binding affinity and in vitro binding affinity of the heteroclitic 9-mer peptides are provided in Table 101B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength Constructs were designed to encode a fusion polypeptide comprising tLLO fused to the hotspot peptides and one or more or all of the heteroclitic peptides, with the C-terminal heteroclitic peptide following a ubiquitin peptide. The ubiquitin was fused to the STEAP1_A0201 heteroclitic peptide. FLAG tags and SIINFEKL (SEQ ID NO: 1007)tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) Ovarian HOT EVO2 EAAAK.G4S (C) (SEQ ID NO: 898; EAAAK=SEQ ID NO: 316; G4S=SEQ ID NO: 313); and (2) Ovarian HOT EVO2 EAAAK.i20 (C) (SEQ ID NO: 899; EAAAK=SEQ ID NO: 316). A breakdown of the amino acids positions of the individual components in each construct is provided in Tables 102-103. G4S (SEQ ID NO: 313), EAAAK (SEQ ID NO: 316), and i20 refer to inclusion of flexible linkers, rigid linkers, and immunoproteasome processing linkers, respectively.

TABLE 102

Positions of Components of Ovarian HOT EVO2 EAAAK.G4S (C) Insert.

14-34: TP53_Y220C
40-60: TP53_R273H
66-86: TP53_R248Q
92-112: TP53_R175H
118-138: TP53_I195T
144-164: TP53_R273C
170-190: TP53_R248W
196-216: TP53_C176Y
222-242: TP53_R282W
248-268: TP53_H179R
274-294: TP53_S241F
300-320: TP53_H193R
326-334: CEACAM5_A0201
340-348: CEACAM5_A0301
354-362: CEACAM5_B0702
368-376: CEACAM5_A0201
382-390: PRAME_A0201
396-404: hTERT_A0201_A2402
410-418: STEAP1_A2402
424-432: CEACAM5_A2402
438-446: RNF43_B0702
452-460: NUF2_A0201
466-474: NUF2_A2402
480-488: KLHL7_A2402
494-502: SART3_A0201
516-536: FLAG
537-556: Linker-SIINFEKL
563-637: Ubiquitin
638-646: STEAP1_A0201_MINI

TABLE 103

Positions of Components of Ovarian HOT EVO2 EAAAK.i20 (C) Insert.

14-34: TP53_Y220C
40-60: TP53_R273H
66-86: TP53_R248Q
92-112: TP53_R175H
118-138: TP53_I195T
144-164: TP53_R273C
170-190: TP53_R248W
196-216: TP53_C176Y
222-242: TP53_R282W
248-268: TP53_H179R
274-294: TP53_S241F
300-320: TP53_H193R
333-341: CEACAM5_A0201
354-362: CEACAM5_A0301
375-383: CEACAM5_B0702
396-404: CEACAM5_A0201
417-425: PRAME_A0201
438-446: hTERT_A0201_A2402
459-467: STEAP1_A2402
480-488: CEACAM5_A2402
501-509: RNF43_B0702
522-530: NUF2_A0201
543-551: NUF2_A2402
564-572: KLHL7_A2402
585-593: SART3_A0201
614-634: FLAG
635-654: Linker-SIINFEKL
661-735: Ubiquitin
736-744: STEAP1_A0201_MINI Low-Grade Glioma (LGG) Hotspot/Heteroclitic/Minigene Constructs A total of 11 hotspot mutations across 5 genes were selected as described in Example 4 and elsewhere herein for the low-grade glioma (LGG) ADXS-HOT constructs. This panel of hotspot mutations covers 80% of all low-grade glioma patients (i.e., 80% of low-grade glioma patients will have at least one of the hotspot mutations from the panel). For each recurrent cancer mutation included in the constructs, a peptide of 21 amino acids in length was designed as described in Example 4 and elsewhere herein. The peptides are shown in Table 104. The hotspot mutation in each is bolded and underlined.

TABLE 104

Exemplary LGG Panel Hotspot 21-Mers.
LGG Panel Hotspot 21-Mers

| Gene | Hotspot Mutation | % Prevalence in LGG Patients | Sequence | SEQ ID NO |
|---|---|---|---|---|
| TP53 | R273L | 1.1 | NLLGRNSFEVLVCACPGRDRR | 566 |
| TP53 | R273C | 11.0 | NLLGRNSFEVCVCACPGRDRR | 565 |
| TP53 | R273H | 3.0 | NLLGRNSFEVHVCACPGRDRR | 563 |
| PIK3CA | G118D | 1.4 | REEKILNREIDFAIGMPVCEF | 431 |
| IDH1 | R132C | 4.0 | SGWVKPIIIGCHAYGDQYRAT | 786 |
| IDH1 | R132G | 1.8 | SGWVKPIIIGGHAYGDQYRAT | 787 |
| IDH1 | R132H | 70.0 | SGWVKPIIIGHHAYGDQYRAT | 788 |
| IDH1 | R132S | 2.1 | SGWVKPIIIGSHAYGDQYRAT | 789 |
| IDH2 | R172K | 2.5 | PGWTKPITIGKHAHGDQYKAT | 790 |

TABLE 104-continued

Exemplary LGG Panel Hotspot 21-Mers.
LGG Panel Hotspot 21-Mers

| Gene | Hotspot Mutation | % Prevalence in LGG Patients | Sequence | SEQ ID NO |
|---|---|---|---|---|
| PIK3CA | E453K | 1.1 | LNLWPVPHGLKDLLNPIGVTG | 435 |
| EGFR | G598V | 1.4 | GPHCVKTCPAVVMGENNTLVW | 393 |

A total of 10 peptides with heteroclitic mutations across 8 genes were selected for the LGG ADXS-HOT constructs. For each heteroclitic mutation, a peptide of 9 amino acids in length was designed as described in Example 4 and elsewhere herein. The peptides are shown in Table 105. The heteroclitic mutation in each is as described in Table 122.

TABLE 105

Exemplary LGGPanel Heteroclitic 9-Mers.
LGG Panel Heteroclitic 9-Mers

| Gene | HLA Type | Sequence | SEQ ID NO |
|---|---|---|---|
| CEACAM5 | A0301 | HVFGYSWYK | 791 |
| MAGEA6 | A0301 | YLFPVIFSK | 792 |
| STEAP1 | A0201 | LLLGTIHAV | 799 |
| STEAP1 | A2402 | KYKKFPWWL | 800 |
| RNF43 | B0702 | NPQPVWLCL | 801 |
| SART3 | A0201 | LMQAEAPRL | 803 |
| NUF2 | A0201 | YLMPVNSEV | 807 |
| NUF2 | A2402 | VWGIRLEHF | 808 |
| KLHL7 | A2402 | VYILGGSQF | 809 |
| hTERT | A0201_A2402 | IMAKFLHWL | 816 |

The in silico predicted binding affinity and in vitro binding affinity of the heteroclitic 9-mer peptides are provided in concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 105B are the percent expression of each gene in patients with low-grade glioma (LGG) (The Cancer Genome Atlas (TCGA) database), the HLA allele being tested, and whether the wild-type peptide corresponding to each heteroclitic peptide is known to be immunogenic. For a construct including each of the heteroclitic peptides in Table 105B, 100% of LGG patients with HLA type A*02:01 express at least one of the TAA genes, 43% of LGG patients with HLA type A*03:01 express at least one of the TAA genes, 100% of LGG patients with HLA type A*24:02 express at least one of the TAA genes, and 100% of LGG patients with HLA type B*07:02 express at least one of the TAA genes.

TABLE 105B

Binding Affinities of Heteroclitic 9-Mers to HLA.

| TAA Gene | % Expression in TCGA | HLA Allele | In silico Predicted Binding Affinity IC50# | In vitro Binding Affinity^ | Wild-Type Peptide Immunogenic? |
|---|---|---|---|---|---|
| NUF2 | 100 | A*02:01 | 2.79 | 160.0 | Yes |
| MAGE-A6 | 43 | A*03:01 | 12.83 | 103.7 | unknown |
| CEACAM5 | 27 | A*03:01 | 9.69 | 85.4 | Yes |
| STEAP1 | 99 | A*02:01 | 5.77 | 188.4 | Yes |
| STEAP1 | 99 | A*24:02 | 47.48 | 104.7 | unknown |
| RNF43 | 100 | B*07:02 | 161.95 | 65.4 | Yes |
| hTERT | 100 | A*02:01 | 7.05 | 123.3 | Yes |
| hTERT | 100 | A*24:02 | 2197.85 | 142.3 | unknown |
| NUF2 | 100 | A*24:02 | 149.07 | 88.4 | unknown |
| KLHL7 | 100 | A*24:02 | 60.84 | 97.4 | Yes |
| SART3 | 100 | A*02:01 | 235.57 | 160.0 | Yes |

NetMHC4.0
^% relative to positive control peptide binding

Table 105B. The in silico predicted binding affinity is based on the NetMHC4.0 algorithm, which predicts peptide binding to MHC class I molecules in terms of 50% o inhibitory Constructs were designed to encode a fusion polypeptide comprising tLLO fused to the hotspot peptides and one or more or all of the heteroclitic peptides, with the C-terminal heteroclitic peptide following a ubiquitin peptide. The ubiquitin was fused to the NUF2_A0201 heteroclitic peptide. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) LGG HOT EVO2 EAAAK.G4S NUF minigene (C) (SEQ ID NO: 900; EAAAK=SEQ ID NO: 316; G4S=SEQ ID NO: 313); and (2) LGG HOT EVO2 EAAAK.i20_NUF minigene (C) (SEQ ID NO: 901; EAAAK=SEQ ID NO: 316). A breakdown of the amino acids positions of the individual components in each construct is provided in Tables 106-107. G4S (SEQ ID NO: 313), EAAAK (SEQ ID NO: 316), and i20 refer to inclusion of flexible linkers, rigid linkers, and immunoproteasome processing linkers, respectively.

TABLE 106

Positions of Components of LGG HOT EVO2 EAAAK.G4S NUF minigene (C) Insert.

14-34: IDH1_R132C
40-60: IDH1_R132G
66-86: IDH1_R132H
92-112: IDH1_R132S
118-138: IDH2_R172K
144-164: TP53_R273C
170-190: TP53_R273H
196-216: TP53_R273L
222-242: PIK3CA_G118D
248-268: PIK3CA_E453K
274-294: EGFR_G598V
300-308: CEACAM5_A0301
314-322: MAGEA6_A0301
328-336: STEAP1_A0201
342-350: hTERT_A0201_A2402
356-364: STEAP1_A2402
370-378: RNF43_B0702
384-392: NUF2_A2402
398-406: KLHL7_A2402
412-420: SART3_A0201
434-454: FLAG
455-474: Linker-SIINFEKL TABLE 106-continued Positions of Components of LGG HOT EVO2 EAAAK.G4S NUF minigene (C) Insert.

481-555: Ubiquitin
556-564: NUF2_A0201 MINI

TABLE 107

Positions of Components of LGG HOT EVO2 EAAAK.i20_NUF minigene (C) Insert.

14-34: IDH1_R132C
40-60: IDH1_R132G
66-86: IDH1_R132H
92-112: IDH1_R132S
118-138: IDH2_R172K
144-164: TP53_R273C
170-190: TP53_R273H
196-216: TP53_R273L
222-242: PIK3CA_G118D
248-268: PIK3CA_E453K
274-294: EGFR_G598V
307-315: CEACAM5_A0301
328-336: MAGEA6_A0301
349-357: STEAP1_A0201
370-378: hTERT_A0201_A2402
391-399: STEAP1_A2402
412-420: RNF43_B0702
433-441: NUF2_A2402
454-462: KLHL7_A2402
475-483: SART3_A0201
504-524: FLAG
525-544: Linker-SIINFEKL
551-625: Ubiquitin
626-634: NUF2_A0201 MINI Colorectal Cancer (CRC) Hotspot/Heteroclitic/Minigene Constructs A total of 12 hotspot mutations across 4 genes were selected as described in Example 4 and elsewhere herein for the colorectal cancer (CRC) ADXS-HOT constructs. This panel of hotspot mutations covers 58% of all microsatellite stable (MSS) colorectal cancer patients (i.e., 58% of MSS colorectal cancer patients will have at least one of the hotspot mutations from the panel). For each recurrent cancer mutation included in the constructs, a peptide of 21 amino acids in length was designed as described in Example 4 and elsewhere herein. The peptides are shown in Table 108. The hotspot mutation in each is bolded and underlined.

TABLE 108

Exemplary CRC Panel Hotspot 21-Mers.
CRC Panel Hotspot 21-Mers

| Gene | Hotspot Mutation | % Prevalence in MSS Colorectal Cancer Patients | Sequence | SEQ ID NO | Representative Nucleic Acid SEQ ID NOS |
|---|---|---|---|---|---|
| KRAS | G12C | 3.0 | TEYKLVVVGACGVGKSALTIQ | 486 | 2011-2014 |
| KRAS | G12D | 10.0 | TEYKLVVVGADGVGKSALTIQ | 489 | 2015-2018 |
| BRAF | V600E | 8.0 | VKIGDFGLATEKSRWSGSHQF | 377 | 2019-2022 |
| KRAS | G12V | 4.0 | TEYKLVVVGAVGVGKSALTIQ | 491 | 2023-2026 |
| PIK3CA | E545K | 3.0 | STRDPLSEITKQEKDFLWSHR | 437 | 2027-2030 |
| TP53 | R248W | 3.0 | CNSSCMGGMNWRPILTIITLE | 559 | 2031-2034 |
| TP53 | R175H | 9.0 | QSQHMTEVVRHCPHHERCSDS | 542 | 2035-2038 |
| TP53 | R273C | 3.0 | NLLGRNSFEVCVCACPGRDRR | 565 | 2039-2042 |

TABLE 108-continued

Exemplary CRC Panel Hotspot 21-Mers.
CRC Panel Hotspot 21-Mers

| Gene | Hotspot Mutation | % Prevalence in MSS Colorectal Cancer Patients | Sequence | SEQ ID NO | Representative Nucleic Acid SEQ ID NOS |
|---|---|---|---|---|---|
| PIK3CA | H1047R | 2.0 | EYFMKQMNDARHGGWTTKMDW | 447 | 2043-2046 |
| TP53 | R282W | 3.0 | VRVCACPGRDWRTEEENLRKK | 569 | 2047-2050 |
| TP53 | R273H | 2.0 | NLLGRNSFEVHVCACPGRDRR | 563 | 2051-2054 |
| KRAS | G13D | 8.0 | EYKLVVVGAGDVGKSALTIQL | 492 | 2055-2058 |

A total of 10 peptides with heteroclitic mutations across 8 genes were selected for the CRC ADXS-HOT constructs. For each heteroclitic mutation, a peptide of 9 amino acids in length was designed as described in Example 4 and elsewhere herein. The peptides are shown in Table 109. The heteroclitic mutation in each is as described in Table 122.

TABLE 109

Exemplary CRC Panel Heteroclitic 9-Mers.
CRC Panel Heteroclitic 9-Mers

| Gene | HLA Type | Sequence | SEQ ID NO | Representative Nucleic Acid SEQ ID NOS |
|---|---|---|---|---|
| CEACAM5 | A0301 | HVFGYSWYK | 791 | 2765-2768 |
| MAGEA6 | A0301 | YLFPVIFSK | 792 | 2769-2772 |
| CEACAM5 | B0702 | IPQVHTQVL | 793 | 2773-2776 |
| MAGEA4 | B0702 | MPSLREAAL | 794 | 2777-2780 |
| GAGE1 | B0702 | WPRPRRYVM | 795 | 2781-2784 |
| CEACAM5 | A2402 | IYPNASLLF | 796 | 2785-2788 |
| NYESO1 | A0201 | RLLEFYLAV | 797 | 2789-2792 |
| STEAP1 | A0201 | LLLGTIHAV | 799 | 2793-2796 |
| RNF43 | B0702 | NPQPVWLCL | 801 | 2797-2800 |
| MAGEA3 | A0201_A2402 | KVPEIVHFL | 817 | 2801-2804 |

The in silico predicted binding affinity and in vitro binding affinity of the heteroclitic 9-mer peptides are provided in Table 109B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 109B are the percent expression of each gene in patients with colorectal cancer (The Cancer Genome Atlas database), the HLA allele being tested, and whether the wild-type peptide corresponding to each heteroclitic peptide is known to be immunogenic. For a construct including each of the heteroclitic peptides in Table 109B, 100% of colorectal cancer patients with HLA type A*02:01 express at least one of the TAA genes, 98% of colorectal cancer patients with HLA type A*03:01 express at least one of the TAA genes, 100% of colorectal cancer patients with HLA type A*24:02 express at least one of the TAA genes, and 98% of colorectal cancer patients with HLA type B*07:02 express at least one of the TAA genes.

TABLE 109B

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| STEAP1 | 100 | A*02:01 | 5.77 | 188.4 | Yes |
| CEACAM5 | 100 | B*07:02 | 8.36 | 88.3 | Yes |
| CEACAM5 | 100 | A*03:01 | 9.69 | 85.4 | Yes |
| CEACAM5 | 100 | A*24:02 | 6.22 | 77.2 | Yes |
| RNF43 | 100 | B*07:02 | 161.95 | 65.4 | Yes |
| MAGE-A6 | 38 | A*03:01 | 12.83 | 103.7 | unknown |
| MAGE-A3 | 35 | A*02:01 | 50.31 | 168.7 | Yes |
| MAGE-A3 | 35 | A*24:02 | 2966 | 102.4 | unknown |

TABLE 109B-continued

Binding Affinities of Heteroclitic 9-Mers to HLA.

| TAA Gene | % Expression in TCGA | HLA Allele | In silico Predicted Binding Affinity IC50[#] | In vitro Binding Affinity[^] | Wild-Type Peptide Immunogenic? |
|---|---|---|---|---|---|
| MAGE-A4 | 25 | B*07:02 | 7.67 | 49.5 | unknown |
| NY-ESO1 | 21 | A*02:01 | 4.61 | 212.9 | unknown |
| GAGE1 | 3 | B*07:02 | 2.58 | 58.5 | unknown |

[#]NetMHC4.0
[^]% relative to positive control peptide binding

Constructs were designed to encode a fusion polypeptide comprising tLLO fused to the hotspot peptides and one or more or all of the heteroclitic peptides, with the C-terminal heteroclitic peptide following a ubiquitin peptide. The CEACAM5_B0702 was included twice. The ubiquitin was fused to the STEAP1_A0201 heteroclitic peptide. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) CRC MSS EVO2 EAAAK.G4S (C) (SEQ ID NO: 902; EAAAK=SEQ ID NO: 316; G4S=SEQ ID NO: 313); and (2) CRC MSS EVO2 EAAAK.i20 (C) (SEQ ID NO: 903; EAAAK=SEQ ID NO: 316). A breakdown of the amino acids positions of the individual components in each construct is provided in Tables 110-111. G4S (SEQ ID NO: 313), EAAAK (SEQ ID NO: 316), and i20 refer to inclusion of flexible linkers, rigid linkers, and immunoproteasome processing linkers, respectively.

TABLE 110

Positions of Components of CRC MSS EVO2 EAAAK.G4S (C) Insert.

14-34: BRAF_V600E
40-60: KRAS_G12D
66-86: KRAS_G12V
92-112: TP53_R175H
118-138: KRAS_G13D
144-164: PIK3CA_E545K
170-190: KRAS_G12C
196-216: PIK3CA_H1047R
222-242: TP53_R248W
248-268: TP53_R273C
274-294: TP53_R282W
300-320: TP53_R273H
326-334: MAGEA3_A0201_A2402
340-348: CEACAM5_A0301
354-362: MAGEA6_A0301
368-376: CEACAM5_B0702
382-390: MAGEA4_B0702
396-404: GAGE1_B0702
410-418: CEACAM5_A2402
424-432: NYESO1_A0201
438-446: CEACAM5_B0702
452-460: RNF43_B0702
474-494: FLAG
495-514: Linker-SIINFEKL
520-594: Ubiquitin
595-603: STEAP1_A0201_MINI

TABLE 111

Positions of Components of CRC MSS EVO2 EAAAK.i20 (C) Insert.

Figure 29:
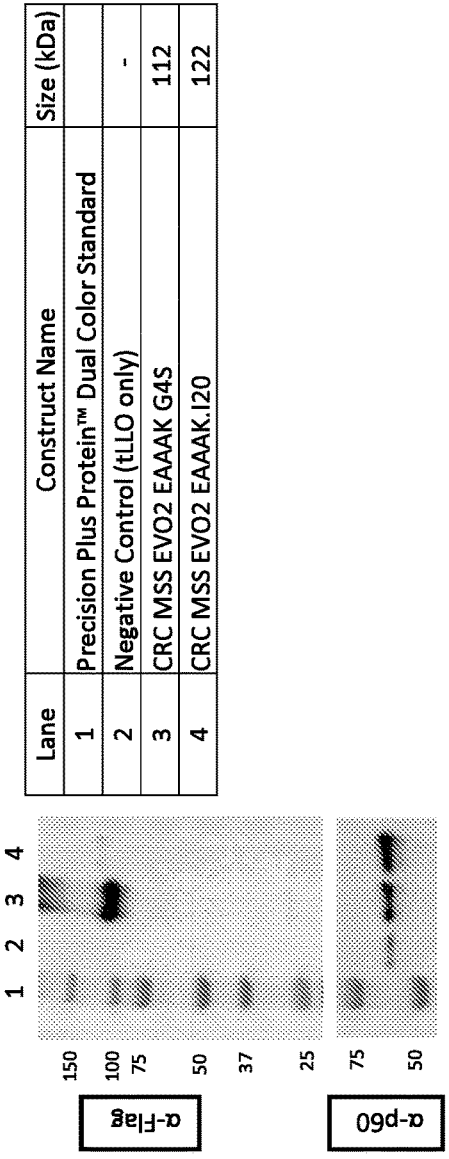
FIG. 29 shows Western blot data for different colorectal cancer constructs. The upper left panel shows detection, using an anti-Flag antibody, of colorectal cancer constructs expressed and secreted into supernatant by LmddA (Western blot). The lower left panel shows detection, using an anti-p60 antibody, of the loading control p60 protein expressed and secreted into supernatant by LmddA (Western blot). The table on the right shows the lane orders for the Western blots.

14-34: BRAF_V600E
40-60: KRAS_G12D
66-86: KRAS_G12V
92-112: TP53_R175H
118-138: KRAS_G13D
144-164: PIK3CA_E545K
170-190: KRAS_G12C
196-216: PIK3CA_H1047R
222-242: TP53_R248W
248-268: TP53_R273C
274-294: TP53_R282W
300-320: TP53_R273H
333-341: MAGEA3_A0201_A2402
354-362: CEACAM5_A0301
375-383: MAGEA6_A0301
396-404: CEACAM5_B0702
417-425: MAGEA4_B0702
438-446: GAGE1_B0702
459-467: CEACAM5_A2402
480-488: NYESO1_A0201
501-509: CEACAM5_B0702
522-530: RNF43_B0702
551-571: FLAG
572-591: Linker-SIINFEKL
598-672: Ubiquitin
673-681: STEAP1_A0201_MINI To assess the expression of tLLO-antigenic-peptide fusion proteins by Lmdda *Listeria* constructs, the DNA constructs were generated as described elsewhere herein and transformed into Lmdda. Each individual Lmdda construct was assayed by Western blot for tLLO fusion polypeptide expression using an anti-FLAG antibody. FIG. 29 shows expression and secretion of the tLLO fusion polypeptide into supernatant by Lmdda for the CRC MSS EVO2 EAAAK.G4S (EAAAK=SEQ ID NO: 316; G4S=SEQ ID NO: 313) and CRC MSS EVO2 EAAAK.i20 constructs (EAAAK=SEQ ID NO: 316). The constructs visualized on these Western blots fall between 103-125 kDa and are similarly sized to the majority of constructs found within this filing. While these sizes indicate fairly large proteins, the expression data shown demonstrate the ability of the LmddA strain to express and secrete the HOT constructs at levels that should be more than sufficient for antigen processing.

Head and Neck Cancer Hotspot/Heteroclitic/Minigene Constructs

A total of 17 hotspot mutations across 9 genes were selected as described in Example 4 and elsewhere herein for the head and neck cancer ADXS-HOT constructs. This panel of hotspot mutations covers 34% of all head and neck cancer patients (i.e., 34% of head and neck cancer patients will have at least one of the hotspot mutations from the panel). For each recurrent cancer mutation included in the constructs, a peptide of 21 amino acids in length was designed as described in Example 4 and elsewhere herein. However, the RGPD8_P1760A peptide was 16 amino acid in length because the hotspot mutation was near the C-terminus of the protein. The peptides are shown in Table 112. The hotspot mutation in each is bolded and underlined.

TABLE 112

Exemplary Head and Neck Cancer Panel Hotspot 21-Mers.
Head and Neck Cancer Panel Hotspot 21-Mers

| Gene | Hotspot Mutation | % Prevalence in Head and neck Cancer Patients | Sequence | SEQ ID NO |
|---|---|---|---|---|
| PIK3CA | E545K | 4.9 | STRDPLSEITKQEKDFLWSHR | 437 |
| CHEK2 | K373E | 2.2 | LIKITDFGHSEILGETSLMRT | 707 |
| RGPD8 | P1760A | 1.3 | AAVAQDEEENASRSSG | 714 |
| ANKRD36C | I634T | 1.5 | TSDEKDSVSNTATEIKEGQQS | 704 |
| TP53 | R248Q | 2.6 | CNSSCMGGMNQRPILTIITLE | 560 |
| PIK3CA | E542K | 3.3 | KAISTRDPLSKITEQEKDFLW | 436 |
| TP53 | R248W | 1.6 | CNSSCMGGMNWRPILTIITLE | 559 |
| TP53 | R175H | 2.5 | QSQHMTEVVRHCPHHERCSDS | 542 |
| PIK3CA | H1047R | 2.4 | EYFMKQMNDARHGGWTTKMDW | 447 |
| TP53 | R282W | 2.2 | VRVCACPGRDWRTEEENLRKK | 569 |
| TP53 | R273H | 1.5 | NLLGRNSFEVHVCACPGRDRR | 563 |
| TP53 | G245S | 1.5 | NYMCNSSCMGSMNRRPILTII | 558 |
| TP53 | Y220C | 1.8 | NTFRHSVVVPCEPPEVGSDCT | 552 |
| ZNF814 | D404E | 1.6 | SFSNHQRVHTEKKHYECGECG | 830 |
| KRTAP1-5 | I88T | 1.5 | TSCCQPSCCQTSSCGTGCGIG | 831 |
| KRTAP4-11 | L161V | 1.5 | ESSCCRPCCCVRPVCGGVSCH | 832 |
| HRAS | G13V | 1.3 | EYKLVVVGAGVVGKSALTIQL | 833 |

A total of 10 peptides with heteroclitic mutations across 6 genes were selected for the head and neck cancer ADXS-HOT constructs. For each heteroclitic mutation, a peptide of 9 amino acids in length was designed as described in Example 4 and elsewhere herein. The peptides are shown in Table 113. The heteroclitic mutation in each is as described in Table 122.

TABLE 113

Exemplary Hea and Neck Cancer Panel Heteroclitic 9-Mers.
Head and Neck Cancer Panel Heteroclitic 9-Mers

| Gene | HLA Type | Sequence | SEQ ID NO |
|---|---|---|---|
| CEACAM5 | A0301 | HVFGYSWYK | 791 |
| CEACAM5 | B0702 | IPQVHTQVL | 793 |
| MAGEA4 | B0702 | MPSLREAAL | 794 |
| CEACAM5 | A2402 | IYPNASLLF | 796 |
| CEACAM5 | A0201 | ILIGVLVGV | 798 |
| STEAP1 | A0201 | LLLGTIHAV | 799 |
| STEAP1 | A2402 | KYKKFPWWL | 800 |
| NYESO1 | B0702 | APRGPHGGM | 813 |

TABLE 113-continued

Exemplary Hea and Neck Cancer Panel Heteroclitic 9-Mers.
Head and Neck Cancer Panel Heteroclitic 9-Mers

| Gene | HLA Type | Sequence | SEQ ID NO |
|---|---|---|---|
| PRAME | A0201 | NMTHVLYPL | 815 |
| hTERT | A0201_A2402 | IMAKFLHWL | 816 |

The in silico predicted binding affinity and in vitro binding affinity of the heteroclitic 9-mer peptides are provided in of head and neck cancer patients with HLA type B*07:02 express at least one of the TAA genes.

TABLE 113B

Binding Affinities of Heteroclitic 9-Mers to HLA.

| TAA Gene | % Expression in TCGA | HLA Allele | In silico Predicted Binding Affinity IC50# | In vitro Binding Affinity^ | Wild-Type Peptide Immunogenic? |
|---|---|---|---|---|---|
| CEACAM5 | 100 | A*02:01 | 6.92 | 170.7 | Yes |
| CEACAM5 | 100 | B*07:02 | 8.36 | 88.3 | Yes |
| CEACAM5 | 100 | A*03:01 | 9.69 | 85.4 | Yes |
| CEACAM5 | 100 | A*24:02 | 6.22 | 77.2 | Yes |
| STEAP1 | 99 | A*02:01 | 5.77 | 188.4 | Yes |
| STEAP1 | 99 | A*24:02 | 47.48 | 104.7 | unknown |
| TERT | 94 | A*02:01 | 7.04 | 123.3 | Yes |
| TERT | 94 | A*24:02 | 2197.84 | 142.3 | unknown |
| PRAME | 91 | A*02:01 | 11.72 | 139.4 | Yes |
| MAGE-A4 | 78 | B*07:02 | 7.67 | 49.5 | unknown |
| NY-ESO1 | 44 | B*07:02 | 3.32 | 109.7 | unknown |

NetMHC4.0
^% relative to positive control peptide binding

Table 113B. The in silico predicted binding affinity is based on the NetMHC4.0 algorithm, which predicts peptide binding to MHC class I molecules in terms of 50% inhibitory concentration (IC50) values (nM); a lower number reflects stronger predicted binding affinity. The in vitro binding affinity was determined through a binding assay that determines the ability of each candidate peptide to bind to the indicated MHC class I alleles and stabilize the MHC-peptide complex by comparing the binding to that of a high affinity T cell epitope. Briefly, each peptide is incubated with its specific HLA molecule in an in vitro assay. Binding strength is compared against a known, immunogenic peptide for the same HLA molecule as a positive control with the positive control binding score set to 100%. The sequence-optimized binding score is normalized to the control peptide. That is, each peptide was given a score relative to the positive control peptide, which is a known T cell epitope with very strong binding properties. The score of the heteroclitic test peptide is reported quantitatively as a percentage of the signal generated by the positive control peptide. Peptides with scores greater than or equal to 45% of the positive control are considered binders. Also provided in Table 113B are the percent expression of each gene in patients with head and neck cancer (The Cancer Genome Atlas database), the HLA allele being tested, and whether the wild-type peptide corresponding to each heteroclitic peptide is known to be immunogenic. For a construct including each of the heteroclitic peptides in Table 113B, 100% of head and neck cancer patients with HLA type A*02:01 express at least one of the TAA genes, 100% of head and neck cancer patients with HLA type A*03:01 express at least one of the TAA genes, 100% of head and neck cancer patients with HLA type A*24:02 express at least one of the TAA genes, and 100%

Constructs were designed to encode a fusion polypeptide comprising tLLO fused to the hotspot peptides and one or more or all of the heteroclitic peptides, with the C-terminal heteroclitic peptide following a ubiquitin peptide. The ubiquitin was fused to the STEAP1_A0201 heteroclitic peptide. FLAG tags and SIINFEKL (SEQ ID NO: 1007) tags were also included upstream of the ubiquitin. The tLLO, hotspot peptide, heteroclitic peptide, and ubiquitin/heteroclitic peptide components of the fusion polypeptides were joined by various linkers selected from those in Table 37.

Exemplary fusion polypeptide insert sequences (i.e., the peptide sequence downstream of the tLLO) include the following: (1) Head & Neck HOT EVO2 EAAAK.G4S (SEQ ID NO: 918; EAAAK=SEQ ID NO: 316; G4S=SEQ ID NO: 313); and (2) Head & Neck HOT EVO2 EAAAK.i20 (SEQ ID NO: 919; EAAAK=SEQ ID NO: 316). A breakdown of the amino acids positions of the individual components in each construct is provided in Tables 114-115. G4S (SEQ ID NO: 313), EAAAK (SEQ ID NO: 316), and i20 refer to inclusion of flexible linkers, rigid linkers, and immunoproteasome processing linkers, respectively.

TABLE 114

Positions of Components of Head
& Neck HOT EVO2 EAAAK.G4S Insert.

14-34: PIK3CA_E545K
40-60: PIK3CA_E542K
66-86: TP53_R248Q
92-112: TP53_R175H
118-138: PIK3CA_H1047R
144-164: CHEK2_K373E

TABLE 114-continued

Positions of Components of Head
& Neck HOT EVO2 EAAAK.G4S Insert.

170-190: TP53_R282W
196-216: TP53_Y220C
222-242: TP53_R248W
248-268: ZNF814_D404E
274-294: ANKRD36C_I634T
300-320: KRTAP1-5_I88T
326-346: KRTAP4-11_L161V
352-372: TP53_G245S
378-398: TP53_R273H
404-424: HRAS_G13V
430-445: RGPD8_P1760A
451-459: CEACAM5_A0301
465-473: CEACAM5_B0702
479-487: MAGEA4_B0702
493-501: CEACAM5_A0201
507-515: PRAME_A0201
521-529: hTERT_A0201_A2402
535-543: STEAP1_A2402
549-557: CEACAM5_A2402
563-571: NYESO1_B0702
585-605: FLAG
606-625: Linker-SIINFEKL
632-706: Ubiquitin
707-715: STEAP1_A0201_MINI

TABLE 115

Positions of Components of Head
& Neck HOT EVO2 EAAAK.i20 Insert.

14-34: PIK3CA_E545K
40-60: PIK3CA_E542K
66-86: TP53_R248Q
92-112: TP53_R175H
118-138: PIK3CA_H1047R
144-164: CHEK2_K373E
170-190: TP53_R282W
196-216: TP53_Y220C
222-242: TP53_R248W
248-268: ZNF814_D404E
274-294: ANKRD36C_I634T
300-320: KRTAP1-5_I88T
326-346: KRTAP4-11_L161V
352-372: TP53_G245S
378-398: TP53_R273H
404-424: HRAS_G13V
430-445: RGPD8_P1760A
458-466: CEACAM5_A0301
479-487: CEACAM5_B0702
500-508: MAGEA4_B0702

TABLE 115-continued

Positions of Components of Head
& Neck HOT EVO2 EAAAK.i20 Insert.

521-529: CEACAM5_A0201
542-550: PRAME_A0201
563-571: hTERT_A0201_A2402
584-592: STEAP1_A2402
605-613: CEACAM5_A2402
626-634: NYESO1_B0702
655-675: FLAG
676-695: Linker-SIINFEKL
702-776: Ubiquitin
777-785: STEAP1_A0201_MINI dMMR Hotspot Constructs DNA mismatch repair is a biological mechanism that identifies and repairs genetic mismatches during DNA replication. Deficient DNA Mismatch Repair (dMMR) results in the inability to repair DNA mismatches arising during replication. Patients with dMMR generally develop microsatellite instability high (MSI-H) due to frequent errors during DNA replication that give rise to high mutation rates. These high mutation tumors are excellent targets for immunotherapy as each mutation can be presented by the MIHC system and recognized as foreign by a T cell. dMMR is associated with loss of four proteins: PMS2, MLH1, MSH6, and MSH2.

To design the dMMR panel, we selected all patients in TCGA across numerous tumor types. We filtered for patients that harbored a mutation in PMS2, MLH1, MSH6 and MSH2, as patients with mutations in those genes are more likely to be MSI. The frequency of all somatic mutations within this cohort were then calculated, and the top mutation with frequencies above 4.5% were selected.

A total of 28 hotspot mutations across 26 genes were selected as described in Example 4 and elsewhere herein for the DNA mismatch repair deficient (dMMR) ADXS-HOT constructs. This panel of hotspot mutations covers 54% of all DNA mismatch repair deficient cancer patients (i.e., 54% of DNA mismatch repair deficient cancer patients will have at least one of the hotspot mutations from the panel). For each recurrent missense cancer mutation included in the constructs, a peptide of 21 amino acids in length was designed as described in Example 4 and elsewhere herein. For each frameshift mutation included in the constructs, longer peptides were designed to include the predicted peptide sequence arising from the out-of-frame INDEL substitution. The peptides are shown in Table 116. The hotspot mutation in each is bolded and underlined.

TABLE 116

Exemplary dMMR Panel Hotspot Peptides.
dMMR Panel Hotspot Peptides

| Gene | Hotspot Mutation | Sequence | SEQ ID NO |
| --- | --- | --- | --- |
| KRAS | G12D | TEYKLVVVGADGVGKSALTIQ | 489 |
| BRAF | V600E | VKIGDFGLATEKSRWSGSHQF | 377 |
| PIK3CA | H1047R | EYFMKQMNDARHGGWTTKMDW | 447 |
| TRIM48 | Y192H | SHWKAFGDILHRSESVLLHMP | 834 |
| PTEN | R130N | AAIHCKAGKGNTGVMICAYLL | 835 |
| POLE | V411L | QCIHMDCLRWLKRDSYLPVGS | 836 |
| POLE | P286R | IETTKLPLKFRDAETDQIMMI | 837 |

TABLE 116-continued

Exemplary dMMR Panel Hotspot Peptides.
dMMR Panel Hotspot Peptides

| Gene | Hotspot Mutation | Sequence | SEQ ID NO |
|---|---|---|---|
| PIK3CA | R88N | EREEFFDETRNLCDLRLFQPF | 838 |
| PGM5 | I98V | IGRLIIGQNGVLSTPAVSCII | 839 |
| MBOAT2 | R43N | LFALLAAIWFNTYLHSSKTSS | 840 |
| KIAA2026 | R574C | GVKSNYEIRICRPCEIKKTDC | 841 |
| FBXW7 | R465C | HTLYGHTSTVCMHLHEKRVV | 842 |
| C12orf4 | R335N | LCGLVLLVDNNINSYSGIKRD | 843 |
| ZBTB20 | p.Pro692LeufsTer43 | ALHSASNGTPLQAHPQVPALAPQAWWPARRGP LTSAPSAQQSLTKSSSSTTT | 844 |
| XYLT2 | p.Gly529AlafsTer78 | DFHLYGSYPPARQPSRPTGRTPTTRLMAPVGSV MSCSLLTQPSPASACTMPPLLHPQWAPHSAGLS PGACRPACTCISMTTISRATW | 845 |
| WNT16 | p.Gly167AlafsTer17 | GSASEGWHWGAAPMMSSMACGSAESS | 846 |
| UBR5 | p.Glu2121LysfsTer28 | VMNMQNRQKKKGKNSPCCQKKLRVQNQGHLL MILLHN | 847 |
| TGFBR2 | p.Glu150GlyfsTer35 | DAASPKCIMKGLVRLSSCVPVALMSAMTTSSSQ KNITPAILTCC | 848 |
| SVIL | p.Met1863TrpfsTer44 | PCFLQCFQGGWWCTRGGGKRKKKMCKVSGGC TACVERCPWKGICWKWPVTVAA | 849 |
| RNF43 | p.Gly659ValfsTer41 | ARHPQRKRRGVPPSPPLALGPRIVIQLCTQLARFF PITPPVWHILGPRHTP | 850 |
| PLEKHA6 | p.Val328TyrfsTer172 | LQQWVNLRRGYPRLKTFGVPLGSILCLAGSLST MAPTPPSTPMIISTTRQECGRRASVPCRPMIGSA RPGPWRTSAMPSAMGVALPTSCESGRSPPATG GRMPPSGSQAPPGSQSIMMSWMPPLAPCAACP CSPAPTLCPAHPARAPTAVPAFTPLSAHPVPVLS GCHLAVRTSMLTLLPM | 851 |
| LARP4B | p.Thr163HisfsTer47 | QEDPREVLKKHWNSAYLGRTLLVTCILYHRWI VTSMCSRWLTSTTSRSSALMWT | 852 |
| FHOD3 | p.Ser336ValfsTer138 | DGDETTEPPPVGAGTGGGPACVPVAEASTGAW TAEGAAGTRCRASRAPCRPPPVPAPSQLPASSP TKCEICVKNTAILAITLITPQDPHLDPVCPPPPH HPSHPHRRPGWKGHHRVVFSHHPSGSTKSHW RERGGGRREKKGCRE | 853 |
| DOCK3 | p.Pro1852GlnfsTer45 | AFHHPLGDTPQPSLPGPCASLLSTLSQPPPQAPS QVWTAATLRCPAVPAAACPP | 854 |
| BMPR2 | p.Asn583ThrfsTer44 | SSTPLTIGEKTEIQLTMNDSKHKLESPALKQVSP ASPPTQQPQTPQDSRQVLA | 855 |
| ARID1A | p.Asp1850ThrfsTer33 | GLLHWRIGGGTPLSISRPTSRARQSCCLPGLTHP AHQPLGSM | 856 |

TABLE 116-continued

Exemplary dMMR Panel Hotspot Peptides.
dMMR Panel Hotspot Peptides

| Gene | Hotspot Mutation | Sequence | SEQ ID NO |
|---|---|---|---|
| ADAM28 | p.Asn75LysfsTer15 | GKIAVLYLKKKQEPPCTRLHGNIL | 857 |
| ACVR2A | p.Lys435GlufsTer19 | LEDMQEVVVHEACFKRLLAETCWNGNAL | 858 |

A construct was designed to encode a fusion polypeptide comprising tLLO fused to the hotspot peptides. A SIINFEKL (SEQ ID NO: 1007) tag was also included. The tLLO and hotspot peptide components of the fusion polypeptides were joined by various linkers selected from those in Table 37. The sequence of the fusion polypeptide insert (i.e., the peptide downstream of the tLLO) is set forth in SEQ ID NO: 917 (DNA Mismatch Repair HOT EVO2 EAAAK.G4S (EAAAK=SEQ ID NO: 316; G4S=SEQ ID NO: 313)). A breakdown of the amino acids positions of the individual components in each construct is provided in Table 117. G4S (SEQ ID NO: 313) and EAAAK (SEQ ID NO: 316) refer to inclusion of flexible linkers and rigid linkers, respectively.

TABLE 117

Positions of Components of DNA Mismatch
Repair HOT EVO2 EAAAK.G4S Insert.

14-34: TRIM48_Y192H
40-60: PTEN_R130N
66-86: POLE_V411L
92-112: POLE_P286R
118-138: PIK3CA_H1047R
144-164: PIK3CA_R88N
170-190: PGM5_I98V
196-216: MBOAT2_R43N
222-242: KRAS_G12D
248-268: KIAA2026_R574C
274-294: FBXW7_R465C
300-320: C12orf4_R335N
326-346: BRAF_V600E
352-403: ZBTB20_p.Pro692LeufsTer43
409-495: XYLT2_p.Gly529AlafsTer78
501-526: WNT16_p.Gly167AlafsTer17
532-568: UBR5_p.Glu2121LysfsTer28
574-617: TGFBR2_p.Glu150GlyfsTer35
623-675: SVIL_p.Met1863TrpfsTer44
681-730: RNF43_p.Gly659ValfsTer41
736-916: PLEKHA6_p.Val328TyrfsTer172
922-977: LARP4B_p.Thr163HisfsTer47

TABLE 117-continued

Positions of Components of DNA Mismatch
Repair HOT EVO2 EAAAK.G4S Insert.

983-1129: FHOD3_p.Ser336ValfsTer138
1135-1188: DOCK3_p.Pro1852GlnfsTer45
1194-1246: BMPR2_p.Asn583ThrfsTer44
1252-1293: ARID1A_p.Asp1850ThrfsTer33
1299-1322: ADAM28_p.Asn75LysfsTer15
1328-1355: ACVR2A_p.Lys435GlufsTer19
1361-1380: Linker-SIINFEKL Example 12. Proof of Concept: Generation of Immunity with Low-Expressing Lm Constructs This study evaluated the immune response for constructs with extremely low or below the limit of detection Western blot results in C57BL/6 mice after immunization with Lm constructs. This assay examined the generation of SIINFEKL (SEQ ID NO: 1007)-specific immunity in mice immunized with 10 different Lm SIINFEKL (SEQ ID NO: 1007)-tagged constructs. Each Lm construct had a SIINFEKL (SEQ ID NO: 1007) tag at the C-terminus of the fusion protein (tLLO+antigens). SIINFEKL (SEQ ID NO: 1007)-specific immune response was detected by ex vivo stimulation of splenocytes with SIINFEKL (SEQ ID NO: 1007) peptide and detection of IFNγ-positive cells with the ELISPOT assay. The details of immunization schedule and strains are given in Tables 118 and 119.

Treatment Schedule

TABLE 118

Immunization Schedule.

| Vaccine/ Group | Titer- CFU/mL | Mice/ Group | PRIME Dose 1 (IP/200 μL/ mouse) | BOOST Dose 2 (IP/200 μL/ mouse) | BOOST Dose 3 (IP/200 μL/ mouse) | Harvest |
|---|---|---|---|---|---|---|
| LmddA 274 | $5.9 \times 10^8$ | 5 | 6 APR. 2017 | 20 APR. 2017 | 5 MAY 2017 | 11 MAY 2017 |
| LmddA-il2 flag | $1 \times 10^9$ | 5 | 6 APR. 2017 | 20 APR. 2017 | 5 MAY 2017 | 11 MAY 2017 |
| 5319-35032 | $4.9 \times 10^8$ | 5 | 6 APR. 2017 | 20 APR. 2017 | 5 MAY 2017 | 11 MAY 2017 |
| 5319-35033 | $8.1 \times 10^8$ | 5 | 6 APR. 2017 | 20 APR. 2017 | 5 MAY 2017 | 11 MAY 2017 |
| 5301-34844 | $6 \times 10^8$ | 5 | 6 APR. 2017 | 20 APR. 2017 | 5 MAY 2017 | 11 MAY 2017 |
| 5316-34955 | $6.5 \times 10^8$ | 5 | 6 APR. 2017 | 20 APR. 2017 | 5 MAY 2017 | 11 MAY 2017 |
| 5316-34949 | $6 \times 10^8$ | 5 | 6 APR. 2017 | 20 APR. 2017 | 5 MAY 2017 | 11 MAY 2017 |
| 5316-34997 | $8.2 \times 10^8$ | 5 | 6 APR. 2017 | 20 APR. 2017 | 5 MAY 2017 | 11 MAY 2017 |
| 5317-35029 | $6.7 \times 10^8$ | 5 | 6 APR. 2017 | 20 APR. 2017 | 5 MAY 2017 | 11 MAY 2017 |
| 5366-35478 | $6.1 \times 10^8$ | 5 | 6 APR. 2017 | 20 APR. 2017 | 5 MAY 2017 | 11 MAY 2017 |
| 5366-35498 | $6 \times 10^8$ | 5 | 6 APR. 2017 | 20 APR. 2017 | 5 MAY 2017 | 11 MAY 2017 |

TABLE 119

Identification of Vaccine.

| Vaccine Number & Group | Vaccine Name | 25D Results | WB Results |
|---|---|---|---|
| 5319-35032 (GRP3) | Sample A | Neg. | Barely above background |
| 5319-35033 (GRP4) | Sample B | Neg. | Barely above background |
| 5301-34844 (GRP5) | Sample C | Neg. | Barely above background |
| 5316-34955 (GRP6) | Sample D | Neg. | Barely above background |
| 5316-34949 (GRP7) | Sample E | Neg. | Barely above background |
| 5316-34997 (GRP8) | Sample F | Neg. | Barely above background |
| 5317-35029 (GRP9) | Sample G | Neg. | Barely above background |
| 5366-35478 (GRP10) | Sample H | Neg. | Barely above background |
| 5366-35498 (GRP12) | Sample I | Neg. | Negative |

Vaccine Preparations

Vaccine preparation was as follows (all prepared with BHI media): (a) thawed 1 vial form −80° C. in 37° C. water bath; (b) spun at 14,000 rpm for 2 min and discarded supernatant; (c) washed 2 times with 1 mL PBS and discarded PBS; and (d) re-suspended to an appropriate final concentration of $5 \times 10^8$ CFU/mL.

TABLE 120

Materials.

| Description | Provider | Catalog Number | Expiration date |
|---|---|---|---|
| 2-Mercaptoethanol (2-ME) | Fisher Scientific | BP176-100 | Not Applicable |
| DMSO | Sigma | D2438-10ml | May 2016 |
| Water | Invitrogen | 10977-015 | Not Applicable |
| RPMI-1640 | Sigma | R8758 | January 2016 |
| HEPES 1M | Fisher Scientific | BP299-100 | Not Applicable |
| Non-essential amino acids NEAA (100X) | Sigma | M7145 | Not Applicable |
| L-Glutamine 200 mM (100X) | Corning (Cellgro) | 25-005-CL | May 2016 |
| Na-Pyruvate 100 mM | Sigma | S8636 | January 2016 |
| Pen/step 10,000 U/ml | Sigma | P7539 | September 2015 |
| RBC lysis buffer | Sigma | R7757 | June 2016 |
| 0.4% Trypan blue solution | Sigma | T8154 | Not Applicable |
| Bovine Serum Albumin (BSA) | Sigma | A7030-10G | Not Applicable |
| Fetal bovine serum (FBS) | Sigma | F0926 | March 2018 |
| PBS - Calcium and Magnesium | Hyclone (Thermo Scientific) | SH30256.01 | October 2016 |
| Cell strainer | BD Falcon | 1119157 | Not Applicable |
| Formaldehyde 16% methano-free, ultra-pure EM grade | Polysciences | 18814 | Not Applicable |
| HPV 16 E7 49-57 (PE conjugated) | ProImmune | F502H-2A-D Batch# LP/4849-29 F502H-2B-D Batch# OP/5853-03 | December 2015 |
| E7 peptide | ProImmune | P502H-OA-D | June 2016 |
| Anti-mouse CD8-FITC | BD Pharmingen | 553030 | February 2016 |
| Anti-mouse CD3-PerCP-cy5.5 | BD Pharmingen | 551163 | May 2017 |
| Anti-mouse CD62L-APC | BD Pharmingen | 553152 | October 2017 |
| Mouse IFNg ELISA kit | BD Biosciences | 558258 | February 2016 |

Preparing Isolated Splenocytes (1) Harvested spleens from experimental and controls using sterile forceps and scissors. Transported in 15 mL tubes containing complete RPMI to the lab.

(2) Poured the spleens into a sterile Petri dish.

(3) Disrupted the spleens in cRPM1 using the back of plunger from a 3 mL Syringe.

(4) Transferred cells in the medium to a 15 mL tube, for 1 or 2 spleens or 50 mL tubes if more than two spleens.

(5) Pelleted cells at 1,000 RPM for 5 min at RT.

(6) Discarded supernatant, re-suspended cells in the remaining wash buffer gently, and added 2 mL RBC lysis buffer per spleen to the cell pellet. Mixed cells gently with lysis buffer by tapping the tube and waited for 1 min.

(7) Immediately added 10 mL of c-RPMI medium to the cell suspension to deactivate lysis buffer.

(8) Spun cells at 1,000 for 5 min at RT.

(9) Passed the cells through a cell strainer and wash them one more time with 10 mL c-RPMI.

(10) Resuspended cell pellet in 25 mL of c-RPMI.

(11) Counted cells using hemocytometer and check the viability by PI staining. Each spleen yielded $1-2 \times 10^8$ cells.

(12) Divided the cells for pentamer staining and ELISpot.

ELISPOT Protocol

The ELISpot peptides used included peptide #1 (SIINFEKL—SEQ ID NO: 1007) and peptide #2 (PSA-9—irrelevant peptide control and background subtraction).

On Day 1, the CTL immunospot protocol for plate coating was followed.

Antigen solutions were then set up as follows: (a) created 1 mM OVA-8 (SIINFEKL (SEQ ID NO: 1007)): 1:10 dilution of 10 mM OVA-21 stock into IMDM. IE 5 µL:45 µL; (b) created 2 µM Antigen Solution: added 2 µL/mL of the 1 mM solution to the antigen solution, ~8 µL of 1 mM OVA-8 to 4 mL antigen solution; (c) created 1 mM PSA-9 (irrelevant peptide): 1:10 dilution of 10 mM PSA-9 stock into IMDM. IE 5 µL:45 µL; (d) created 2 µM Antigen Solution: added 2 µL/mL of the 1 mM solution to the antigen solution, ~8 µL of 1 mM PSA-9 to 4 mL antigen solution; (e) created 1×PMA/Iono: 1:100 dilution 100×PMA stock to antigen solution: ~4 µL to 396 µL antigen solution; and (f) added 100 µL of each antigen solution to the appropriate wells.

Splenocytes were prepared as follows: (a) washed ~$2 \times 10^6$ of each splenocyte. Resuspend in CTL test medium to concentration of $2 \times 10^6$/mL (~1 mL CTL medium); and (b) added 100 µL of each splenocyte to appropriate well.

The ELISPOT protocol was then followed per kit instructions (i.e., incubated at 37° C. overnight).

On Day2, the ELISPOT protocol was followed as provided below.

DAY 0 (Sterile Conditions). Prepared Capture Solution by diluting the Capture Antibody according to specific protocol. Many cytokines benefit from pre-wetting the PVDF membrane with 70% ethanol for 30 sec and washing with 150 μL of PBS three times before adding 80 μL of the Capture Solution into each well. Incubated plate overnight at 4° C. in a humidified chamber.

DAY 1 (Sterile Conditions). Prepared CTL-TEST™ Medium by adding 1% fresh L-glutamine. Prepared antigen/mitogen solutions at 2× final concentration in CTL-TEST™ Medium. Decanted plate with coating antibody from Day 0 and washed one time with 150 μL PBS. Plated antigen/mitogen solutions, 100 μL/well. After thawing PBMC or isolating white blood cells with density gradient, adjusted PBMC to desired concentration in CTL-TEST™ Medium, e.g., 3 million/mL corresponding to 300,000 cells/well (however, cell numbers can be adjusted according to expected spot counts since 100,000-800,000 cells/well will provide linear results). While processing PBMC and until plating, kept cells at 37° C. in humidified incubator, 5-9% $CO_2$. Plated PBMC, 100 μL/well using large orifice tips. Once completed, gently tapped the sides of the plate and immediately placed into a 37° C. humidified incubator, 5-9% $CO_2$. Incubated for 24-72 hours depending on your cytokine. Did not stack plates. Avoided shaking plates by carefully opening and shutting incubator door. Did not touch plates during incubation.

DAY2. Prepared Wash Solutions for the day: PBS, distilled water and Tween-PBS. Prepared Detection Solution by diluting Detection Antibody according to specific protocol. Washed plate two times with PBS and then two times with 0.05% Tween-PBS, 200 μL/well each time. Added 80 μL/well Detection Solution. Incubated at RT, 2h. Prepared Tertiary Solution by diluting the Tertiary Antibody according to specific protocol. Washed plate three times with 0.05% Tween-PBS, 200 μL/well. Added 80 μL/well of Strep-AP Solution. Incubated at RT, 30 min. Prepared Developer Solution according to your specific protocol. Washed plate two times with 0.05% Tween-PBS, and then two times with distilled water, 200 μL/well each time. Add Developer Solution, 80 μL/well. Incubated at RT, 10-20 min. Stopped reaction by gently rinsing membrane with tap water, decanted, and repeated three times. Removed protective underdrain of the plate and rinsed back of plate with tap water. Air dried plate for 2 hours face-down in running hood or on paper towels for 24 hours on bench top. Scanned and counted plate.

Results and Conclusions

Figure 20:
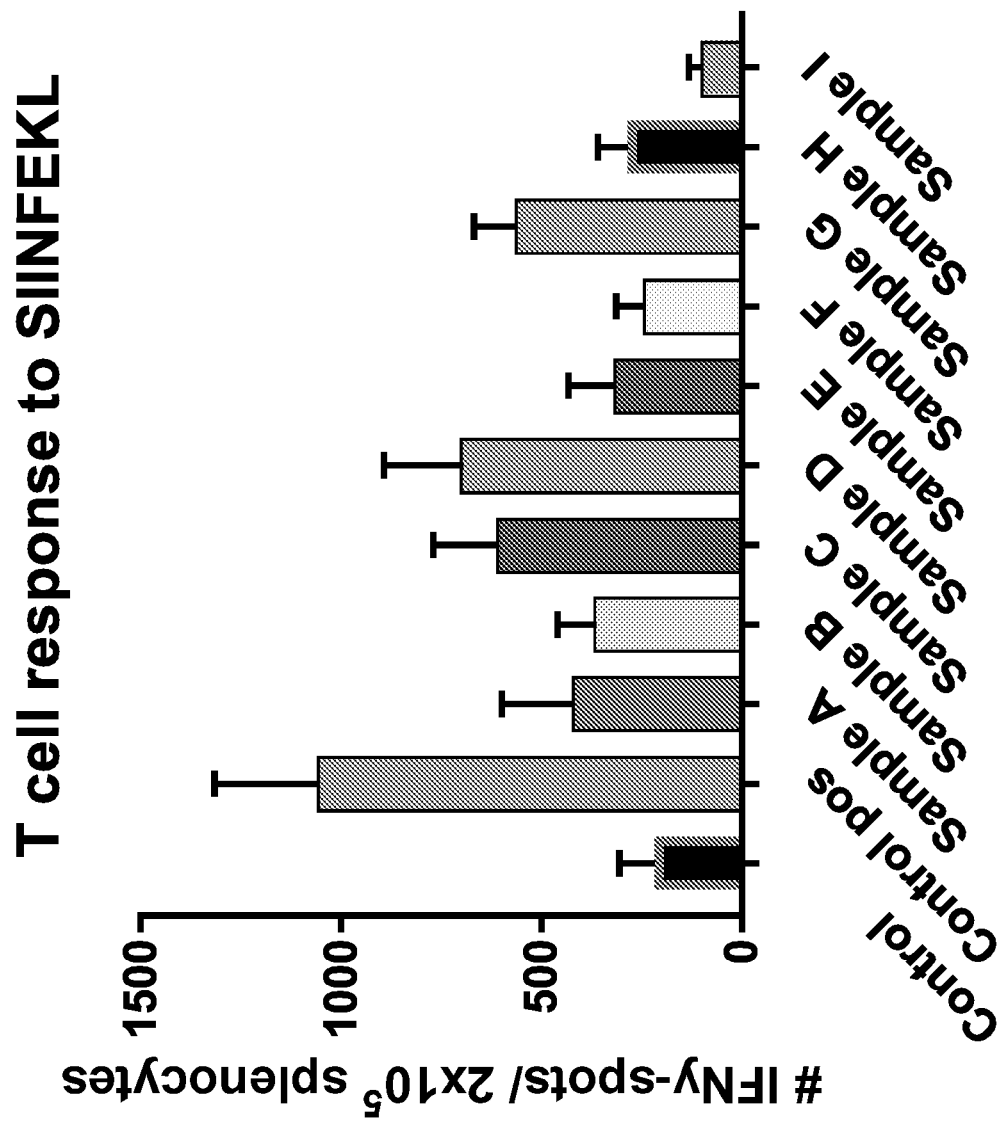
FIG. 20 shows IFN-γ spot-forming cells (SFC) per $2\times10^5$ splenocytes stimulated ex vivo with the minimal SIINFEKL peptide (SEQ ID NO: 1007). The splenocytes were from mice immunized with various low-expressing Lm constructs.

The 10 constructs with the lowest fusion protein expression levels to date (April 2017) were selected for immunization into mice. Even though the constructs were barely detectable or in some cases would have been considered "negative" for fusion protein expression by western blot, we were able to detect murine T cell responses targeting the SIINFEKL (SEQ ID NO: 1007) tag within the fusion protein. See FIG. 20. In FIG. 20, ex vivo splenocytes were stimulated with the minimal SIINFEKL (SEQ ID NO: 1007) peptide, which specifically binds MHC-I (H-2 $K^b$ $OVA_{257-264}$) in order to detect SIINFEKL (SEQ ID NO: 1007) specific $CD8^+$ T cells. Subsequent testing revealed that the first control in FIG. 20 was not a true negative control. Rather, it was a second positive control due to contamination with a construct that expressed SIINFEKL (SEQ ID NO: 1007). However, all of the samples exhibited a positive T cell response.

These data demonstrate that Lm constructs with extremely low levels of fusion protein expression (or possibly non-detectable by western blot) are still capable of eliciting a T cell response following immunization with the Lm construct. In addition, these data demonstrate that Lm constructs with fusion protein expression (even low levels) elicit T cell responses following immunization with the Lm construct.

Example 13. Inclusion of Linkers and Spacers in tLLO Fusion Proteins

This study examined whether flanking antigenic peptides with defined linker sequences improves expression of the tLLO-antigenic-peptide fusion proteins. Secretion of the tLLO-antigenic-peptide fusion protein was detected by Western blot using anti-FLAG antibody. The preclinical data generated in these studies demonstrate that the inclusion of defined linker sequences significantly improves the expression and secretion of the tLLO-antigenic-peptide fusion protein and drastically improves the ability to generate constructs at a much higher rate of success.

In designing fusion polypeptides with multiple 21-mers (e.g., 21-mers from cancer-associated proteins with 10 amino acids flanking either side of a hotspot mutation), the sequential order of the unique 21-mers can be randomly generated in order to minimize the likelihood that the junction of two proximal 21-mers may interfere with Lm expression and secretion. However, the random assembly method may not always be dependable enough to generate constructs that express and secrete the tLLO fusion protein, as determined by anti-FLAG Western blot, with a 100% rate of success. The more 21-mers added to a construct using the "beads on a string" method significantly increases the odds that two or more 21-mer sequences will interact with one another in a way that significantly reduces, or even eliminates, the expression and secretion of the tLLO fusion protein.

Here, we describe a new plasmid design strategy used to significantly improve the expression and secretion of Lm constructs. We found that the limitations associated with the random assembly design strategy can be significantly mitigated by joining unique 21-mers by defined amino acid sequences known as linkers. Linkers, also known as spacers, are short amino acid sequences ranging from 2 to greater than 25 residues generated in nature to separate domains within a protein. There are many different classes of linkers with specific characteristics; our study focused on linkers that were designed to add rigidity, flexibility, or enhance proteasomal cleavage. The table below describes suitable linkers that were evaluated in Lm constructs:

TABLE 121

Linkers.

| Linker | SEQ ID NO | Function |
|---|---|---|
| $(GGGGS)_{1-3}$ | 313 | Flexibility |
| VGKGGSGG | 314 | Flexibility |
| $(GGS)_n$, n = 1-3 | N/A | Flexibility |
| $(EAAAK)_n$, n = 1-3 | 316 | Rigidity |
| AAY | N/A | Immunoproteasome Processing |
| ADGSVKTLSKVL | 825 | Immunoproteasome Processing |

The data described in this report detail the construction of Lm constructs with a combination of rigid, flexible, and proteasomal linkers and demonstrates that expression and secretion are enhanced when linkers are present.

Materials and Methods

Construct Design. To generate sample constructs, target sequences were scored for hydropathy using the Kyte/Doolittle methodology with a window size of 21 amino acids (web.expasy.org/protscale/?_ga=1.215352275.536452039.1486395060), with all target sequences scoring greater than or equal to 1.6 being excluded from use as they are unlikely to be secretable by Listeria monocytogenes. All remaining target sequences were then reverse-translated into L. monocytogenes codon-optimized sequences using OPTIMIZER (genomes.urv.es/OPTIMIZER/). Sample construct inserts were designed by concatamerizing 20 target sequences and adding a FLAG (DYKDHDGDYKDHDIDYKDDDK (SEQ ID NO: 762)) SIINFEKL (SEQ ID NO: 1007) tag-encoding sequences to the 3' end to generate construct inserts. Individual insert suitability was then reconfirmed to contain no peaks at or above 1.6 by hydropathy as above using a 21-amino acid sliding window across the entirety of the insert sequence.

Western Blot Screen for tLLO Fusion Polypeptide Secretion. Single colonies from plates containing Lm constructs were used to inoculate an overnight culture in 6 mL of BHI in a dry shaking incubator at 37° C. The following day, 1:10 dilutions of the original overnight culture were resuspended in 9 mL of fresh BHI and grown in the dry shaking incubator at 37° C. until reaching an $OD_{600}$=0.6. Cells were pelleted by 2 minute centrifugation at 13000 RPM. Sample supernatants were collected and run on SDS-PAGE. Samples were prepared by diluting 75 µL of sample with 25 µL of 4×LDS Sample Buffer (Cat #161-0747), boiled at 98° C. for 10 minutes, placed on ice, and then centrifuged at max speed for 10 minutes at 4° C. 13 µL of the sample was run on 4-15% precast protein gel (BioRad Cat #4561086). Protein gels were transferred using the Trans-Blot Turbo transfer apparatus (Cat #170-4155) and PVDF Midi transfer packs (Bio-Rad #170-4157). Blots were incubated with anti-FLAG monoclonal Antibody (Sigma F1804) or Anti-LLO (Abcam ab200538) as primary and Goat Anti-mouse IgG-HRP conjugated (sc2005) as a secondary antibody. The blots were then incubated on iBind Flex (Invitrogen cat #1772866), washed, and then developed by Super Signal West Dura Extended Duration Substrate (ThermoFisher #34076); the images were developed on the Amersham Imager 600 (GE).

Results

Figure 21:
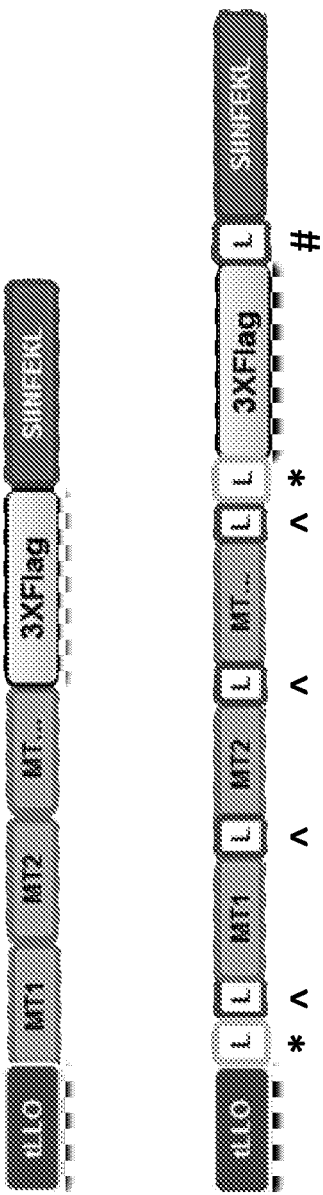
FIG. 21 shows a construct design schematic. The top panel shows the tLLO fusion protein design with the C-terminal 3×FLAG and SIINFEKL (SEQ ID NO: 1007) tag moieties but no linker sequences. The middle panel shows the tLLO fusion protein with C-terminal tags and flanking linker sequences. The bottom panel defines each component of the tLLO fusion protein, with 21mer flanking linkers (^), long spacers (*), and immunoproteasome spacers (#).

Peptides comprising mutations from the murine mc38 tumor cell line were designed, and individual 21-mers were scored for hydropathy as per Kyte and Doolittle. The 21-mers that passed the hydropathy filter cut off were arranged either sequentially as 15 "beads-on-a-string" with a SIINFEKL (SEQ ID NO: 1007) minigene and a FLAG-Tag moiety added at the C-terminus (FIG. 21) or with various permutations and combinations of linkers flanking each individual 21-mer (FIG. 21). The addition of these C-terminal moiety tags allows for the monitoring of expression, secretion, processing and presentation, and immunogenicity of the tLLO fusion protein. Longer and slightly charged spacers (FIG. 21, *) were used right after tLLO to provide additional separation between the TAA cassette and the N-terminus and C-terminus of the fusion protein as well as maintaining the net positive charge of the tLLO secretion signal. Flanking linkers (FIG. 21, ^) were used to separate individual 21-mers. Rigid, flexible, and proteasomal enhancing linkers were generated and tested in hundreds of Lm constructs. Finally, an immunoproteasome linker was placed between 3×FLAG and SIINFEKL (SEQ ID NO: 1007), which allows for more efficient proteasomal processing of the C-terminal SIINFEKL (SEQ ID NO: 1007) tag. The immunoproteasome linker was comprised of a 12 amino acid cleavage motif, 6 C-terminal followed by 6 N-terminal, that is preferentially cleaved by the 20S subunit of the immunoproteasome. See, e.g., Toes et al. (2001) J Exp. Med. 194(1):1-12, herein incorporated by reference in its entirety for all purposes. The inclusion of proteasomal enhancing linkers allow for the directed liberation of a desired amino acid sequence (e.g., SIINFEKL (SEQ ID NO: 1007)) with a higher frequency than would be expected by stochastic proteasomal C-terminal cleavage and N-terminal degradation alone (FIG. 21, #).

Figure 22:
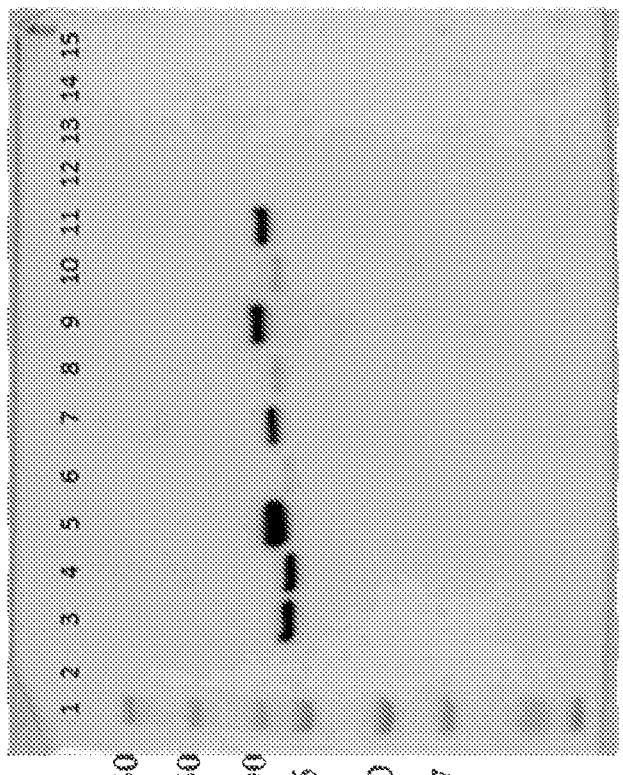
FIG. 22 shows expression and secretion of a Lm construct targeting 15 nonsynonymous mutations from the murine MC38 colorectal cancer cell line with or without various linker combinations. The left panel shows a representative anti-FLAG antibody Western blot of culture supernatant from ten unique constructs targeting the same 15 mutations. The right panel shows the construct design strategy and expected size (kDa) of each construct. The same base MT15 amino acid sequence was used in all constructs; the constructs differed by the absence or inclusion of various permutations of flanking linkers and long spacers that have either flexible, rigid, or preferential proteasomal cleavage enhancing properties.

In order to evaluate the effect linkers and spacers have on the expression and secretion of the tLLO fusion protein, we generated hundreds of Lm constructs, each with unique combinations of flexible, rigid, and proteasome-enhancing linkers and spacers. FIG. 22 depicts 10 such constructs that were assayed by Western blot to determine the relative effect of linkers on expression, secretion, and overall rate of success regarding Lm product generation. The culture supernatant from the MT15 construct that was designed using only the random assembly strategy (FIG. 22-Lane 2) did not yield detectible levels of tLLO fusion protein and ultimately failed the screening process. However, we could clearly detect the correct size tLLO fusion protein from a construct designed with the same randomly assembled MT15 construct (Lane 2), but with the inclusion of flexible long spacers and flexible linkers (Lane 3); this construct passed the overall screening process. In all cases, the inclusion of long spacers significantly improved the levels of detectable tLLO fusion protein compared to the base MT15 construct. Furthermore, the addition of flanking linkers to each corresponding long-spacer construct significantly enhanced tLLO fusion protein expression (data not shown) and secretion (e.g. Lane 4 vs. Lane 5). Additionally, adding flanking linkers removed the need for the brute-force random assembly design strategy. Constructs with significant differences in the levels of secreted tLLO fusion protein, resulting from only an alternate ordering of the 21-mers, showed no significant differences in tLLO fusion protein expression or secretion when designed with flanking linkers separating each unique 21-mer, regardless of 21-mer order (data not shown).

In conclusion, by incorporating spacers and linkers into the Lm construct, we can significantly improve the expression and secretion of the tLLO fusion protein. Additionally, the incorporation of linkers and spacers into Lm construct design significantly reduces the need for generating multiple randomly assembled constructs in order to increase the odds of producing a full Lm construct (e.g., that targets all desired hotspot mutations).

By adding linkers and spacers we can significantly enhance the expression and secretion of the tLLO fusion protein as well as the overall success rate of generating a construct that secretes a detectable level of tLLO fusion protein. From the hundreds of Lm constructs made with linkers and spacers, we have been able to detect tLLO fusion protein by Western blot in all cases. This is a significant improvement over the success rate of constructs designed without linkers and spacers. While we have identified effective linker and spacer combinations that yield significantly improved tLLO expression and secretion, the linkers identified in this study are not exhaustive. Collectively, these data demonstrate the feasibility of adding linkers and spacers to the Lm platform.

SEQUENCE LISTING

The patent contains a lengthy sequence listing. A copy of the sequence listing is available in electronic form from the USPTO web site (https://seqdata.uspto.gov/?pageRequest=docDetail&DocID=US11897927B2). An electronic copy of the sequence listing will also be available from the USPTO upon request and payment of the fee set forth in 37 CFR 1.19(b)(3).

We claim:

1. A recombinant *Listeria* strain comprising a nucleic acid comprising a first open reading frame encoding a fusion polypeptide comprising a PEST-containing peptide fused to two or more antigenic peptides,
    wherein at least one antigenic peptide is from a cancer-associated protein and comprises a recurrent cancer mutation,
    wherein at least one antigenic peptide is from a cancer-associated protein and comprises a heteroclitic mutation,
    wherein the PEST-containing peptide comprises a bacterial secretion signal sequence, and the fusion polypeptide further comprises a ubiquitin protein fused to a carboxy-terminal antigenic peptide,
    wherein the PEST-containing peptide, the two or more antigenic peptides, the ubiquitin, and the carboxy-terminal antigenic peptide are arranged in tandem from the amino-terminal end to the carboxy-terminal end of the fusion polypeptide, and
    wherein (i) the antigenic peptides comprise recurrent cancer mutations from proteins encoded by all of the following genes: SPOP, CHEK2, RGPD8, ANKRD36C, and AR; or (ii) the antigenic peptides comprise heteroclitic mutations in proteins encoded by all of the following genes: CEACAM5, MAGEA4, STEAP1, RNF43, SSX2, SART3, PAGE4, PSMA, and PSA.

2. The recombinant *Listeria* strain of claim 1, wherein the antigenic peptides comprise recurrent cancer mutations from proteins encoded by all of the following genes: SPOP, CHEK2, RGPD8, ANKRD36C, and AR.

3. The recombinant *Listeria* strain of claim 2, wherein the antigenic peptides comprise all of the following recurrent cancer mutations: SPOP_F133V, CHEK2_K373E, RGPD8_P1760A, ANKRD36C_1634T, ANKRD36C_D629Y, SPOP_W131G, ANKRD36C_D626N, SPOP_F133L, AR_T878A, AR_L702H, AR_W742C, AR_H875Y, and AR_F877L.

4. The recombinant *Listeria* strain of claim 3, wherein the antigenic peptides comprise all of the peptides set forth in SEQ ID NOS: 717, 707, 714, 704, 705, 715, 706, 716, and 763-768.

5. The recombinant *Listeria* strain of claim 1, wherein the antigenic peptides comprise heteroclitic mutations in proteins encoded by all of the following genes: CEACAM5, MAGEA4, STEAP1, RNF43, SSX2, SART3, PAGE4, PSMA, and PSA.

6. The recombinant *Listeria* strain of claim 5, wherein the antigenic peptides comprise all of the peptides set forth in SEQ ID NOS: 793, 794, and 799-806.

7. The recombinant *Listeria* strain of claim 4, wherein the antigenic peptides comprise all of the peptides set forth in SEQ ID NOS: 717, 707, 714, 704, 705, 715, 706, 716, 763-768, 793, 794, and 799-806.

8. The recombinant *Listeria* strain of claim 7, wherein one or more of the antigenic peptides comprising a recurrent cancer mutation are preceded by the linker set forth in SEQ ID NO: 316, and wherein one or more of the antigenic peptides comprising a heteroclitic mutation are preceded by the linker set forth in any one of SEQ ID NOS: 821-829.

9. The recombinant *Listeria* strain of claim 8, wherein the fusion polypeptide comprises the sequence set forth in SEQ ID NO: 893.

10. The recombinant *Listeria* strain of claim 1, wherein the carboxy-terminal antigenic peptide is from a cancer-associated protein and comprises a heteroclitic mutation.

11. The recombinant *Listeria* strain of claim 1, wherein the carboxy-terminal antigenic peptide is about 7-11, 8-10, or 9 amino acids in length.

12. The recombinant *Listeria* strain of e4aim-2claim 1, wherein the carboxy-terminal antigenic peptide binds to one or more of the following HLA types: HLA-A*02:01, HLA-A*03:01, HLA-A*24:02, and HLA-B*07:02.

13. The recombinant *Listeria* strain of claim 1, wherein the carboxy-terminal antigenic peptide is from a protein encoded by one of the following genes: STEAP1, CEACAM5, NYESO1, and NUF2.

14. The recombinant *Listeria* strain of claim 13, wherein the carboxy-terminal antigenic peptide is selected from the peptides set forth in SEQ ID NOS: 796, 797, 798, 799, 800, and 807.

15. The recombinant *Listeria* strain of claim 1, wherein each antigenic peptide is a fragment of a cancer-associated protein and is about 7-200 amino acids in length.

16. The recombinant *Listeria* strain of claim 1, wherein the fusion polypeptide comprises at least about 5, 6, 7, 8, 9, 10, 11, 12, 13, 14, 15, 16, 17, 18, 19, 20, 21, 22, 23, 24, or 25 antigenic peptides or comprises between about 5-50, 10-40, or 20-30 antigenic peptides.

17. The recombinant *Listeria* strain of claim 1, wherein the fusion polypeptide comprises at least about 2, 3, 4, 5, 6, 7, 8, 9, or 10 antigenic peptides comprising a recurrent cancer mutation or between about 5-30 or 10-20 antigenic peptides comprising a recurrent cancer mutation, and/or
    wherein the fusion polypeptide comprises at least about 2, 3, 4, 5, 6, 7, 8, 9, or 10 antigenic peptides comprising a heteroclitic mutation or between about 5-30 or 10-20 antigenic peptides comprising a heteroclitic mutation.

18. The recombinant *Listeria* strain of claim 17, wherein the antigenic peptides comprising a recurrent cancer mutation are in tandem, and the antigenic peptides comprising a heteroclitic mutation are in tandem.

19. The recombinant *Listeria* strain of claim 17, wherein the antigenic peptides comprising a recurrent cancer mutation and the antigenic peptides comprising a heteroclitic mutation are intermixed within the fusion polypeptide.

20. The recombinant *Listeria* strain of claim 1, wherein the two or more antigenic peptides are linked to each other via peptide linkers.

21. The recombinant *Listeria* strain of claim 20, wherein the peptide linkers comprise flexibility linkers and/or rigidity linkers and/or immunoproteasome processing linkers, or wherein one or more of the linkers set forth in SEQ ID NOS: 313-316, 319, and 821-829 are used to link the two or more antigenic peptides.

22. The recombinant *Listeria* strain of claim 21, wherein the peptide linker upstream of one or more of the antigenic peptides comprising a heteroclitic mutation is an immunoproteasome processing linker or is selected from the linkers set forth in SEQ ID NOS: 821-829.

23. The recombinant *Listeria* strain of claim 1, wherein no region of the fusion polypeptide scores above a cutoff of around 1.6 when scored for hydropathy by a Kyte and Doolittle hydropathy index with a sliding 21 amino acid window.

24. The recombinant *Listeria* strain of claim 1, wherein at least two of the antigenic peptides comprise different recurrent cancer mutations and are fragments of the same cancer-associated protein.

25. The recombinant *Listeria* strain of claim 1, wherein the recurrent cancer mutations in at least two of the antigenic peptides are from the same cancer-associated protein and do not occur naturally together.

26. The recombinant *Listeria* strain of claim 1, wherein at least two of the antigenic peptides are overlapping fragments of the same cancer-associated protein.

27. The recombinant *Listeria* strain of claim 26, wherein the recurrent cancer mutations in at least two of the antigenic peptides are from the same cancer-associated protein and occur at the same amino acid residue of the cancer-associated protein.

28. The recombinant *Listeria* strain of claim 27, wherein two of the antigenic peptides comprise the same recurrent cancer mutation.

29. The recombinant *Listeria* strain of claim 1, wherein each antigenic peptide comprising a recurrent cancer mutation comprises a different recurrent cancer mutation.

30. The recombinant *Listeria* strain of claim 1, wherein each recurrent cancer mutation in the fusion polypeptide is a somatic frameshift mutation or a somatic missense mutation.

31. The recombinant *Listeria* strain of claim 30, wherein each recurrent cancer mutation in the fusion polypeptide is a somatic missense mutation.

32. The recombinant *Listeria* strain of claim 1, wherein one or more or all of the antigenic peptides comprising a recurrent cancer mutation have an equal number of amino acids flanking each side of the recurrent cancer mutation.

33. The recombinant *Listeria* strain of claim 32, wherein the number of flanking amino acids on each side of the recurrent cancer mutation is at least 10 amino acids.

34. The recombinant *Listeria* strain of claim 1, wherein the antigenic peptides comprise the 2, 3, 4, 5, 6, 7, 8, 9, or 10 most common recurrent cancer mutations or recurrent somatic missense cancer mutations from a particular type of cancer.

35. The recombinant *Listeria* strain of claim 1, wherein at least about 5%, 10%, 15%, 20%, 25%, 30%, 35%, 40%, 35%, 50%, 60%, 70%, 80%, or 90% of patients with a particular type of cancer have a recurrent cancer mutation that is included in the combination of antigenic peptides in the fusion polypeptide.

36. The recombinant *Listeria* strain of claim 1, wherein the antigenic peptides comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, or 30 different recurrent cancer mutations or recurrent somatic missense cancer mutations from a particular type of cancer, or wherein the antigenic peptides comprise about 2-80, 10-60, 10-50, 10-40, or 10-30 different recurrent cancer mutations or recurrent somatic missense cancer mutations from a particular type of cancer.

37. The recombinant *Listeria* strain of claim 34, wherein the particular type of cancer is non-small cell lung cancer, prostate cancer, pancreatic cancer, bladder cancer, breast cancer, uterine cancer, ovarian cancer, low-grade glioma, colorectal cancer, or head and neck cancer.

38. The recombinant *Listeria* strain of claim 1, wherein the antigenic peptides are from two or more cancer-associated proteins.

39. The recombinant *Listeria* strain of claim 38, wherein the two or more cancer-associated proteins are at least about 2, 3, 4, 5, 6, 7, 8, 9, or 10 cancer-associated proteins, or wherein the two or more cancer-associated proteins are about 2-30, 2-25, 2-20, 2-15, or 2-10 cancer-associated proteins.

40. The recombinant *Listeria* strain of claim 1, wherein the antigenic peptides comprise recurrent cancer mutations from proteins encoded by one or more of the following genes: ACVR2A, ADAM28, AKT1, ANKRD36C, AR, ARID1A, BMPR2, BRAF, CHEK2, C12orf4, CTNNB1, DOCK3, EGFR, ESR1, FBXW7, FGFR3, FHOD3, GNAS, HRAS, IDH1, IDH2, KIAA2026, KRAS\, KRTAP1-5, KRTAP4-11, LARP4B, MBOAT2, NFE2L2, PGM5, PIK3CA, PLEKHA6, POLE, PTEN, RGPD8, RNF43, RXRA, SMAD4, SPOP, SVIL, TGFBR2, TP53, TRIM48, UBR5, U2AF1, WNT16, XYLT2, ZBTB20, and ZNF814.

41. The recombinant *Listeria* strain of claim 40, wherein:
 (a) the antigenic peptides comprise recurrent cancer mutations from proteins encoded by one or more or all of the following genes: KRAS\, EGFR, U2AF1, BRAF, PIK3CA, and TP53;
 (b) the antigenic peptides comprise recurrent cancer mutations from proteins encoded by one or more or all of the following genes: SPOP, CHEK2, RGPD8, ANKRD36C, and AR;
 (c) the antigenic peptides comprise recurrent cancer mutations from proteins encoded by one or more or all of the following genes: KRAS\, U2AF1, TP53, SMAD4, and GNAS;
 (d) the antigenic peptides comprise recurrent cancer mutations from proteins encoded by one or more or all of the following genes: PIK3CA, FGFR3, TP53, RXRA, FBXW7, and NFE2L2;
 (e) the antigenic peptides comprise recurrent cancer mutations from proteins encoded by one or more or all of the following genes: PIK3CA, AKT1, and ESR1;
 (f) the antigenic peptides comprise recurrent cancer mutations from proteins encoded by one or more or all of the following genes: PTEN, KRAS\, PIK3CA, CTNNB1, FBXW7, and TP53;
 (g) the antigenic peptides comprise recurrent cancer mutations from proteins encoded by one or more or all of the following genes: TP53;

(h) the antigenic peptides comprise recurrent cancer mutations from proteins encoded by one or more or all of the following genes: TP53, PIK3CA, IDH1, IDH2, and EGFR;
(i) the antigenic peptides comprise recurrent cancer mutations from proteins encoded by one or more or all of the following genes: KRAS\, BRAF, PIK3CA, and TP53; or
(j) the antigenic peptides comprise recurrent cancer mutations from proteins encoded by one or more or all of the following genes: PIK3CA, CHEK2, RGPD8, ANKRD36C, TP53, ZNF814, KRTAP1-5, KRTAP4-11, and HRAS.

42. The recombinant *Listeria* strain of claim 41, wherein:
(a) the antigenic peptides comprise one or more or all of the following recurrent cancer mutations: KRAS\_G12C, EGFR_L858R, KRAS\_G12D, U2AF1_S34F, BRAF_V600E, KRAS\_G12V, PIK3CA_E545K, TP53_R158L, KRAS\_G12A, EGFR_L861Q, and TP53_R273L;
(b) the antigenic peptides comprise one or more or all of the following recurrent cancer mutations: SPOP_F133V, CHEK2_K373E, RGPD8_P1760A, ANKRD36C_I634T, ANKRD36C_D629Y, SPOP_W131G, ANKRD36C_D626N, SPOP_F133L, AR_T878A, AR_L702H, AR_W742C, AR_H875Y, and AR_F877L;
(c) the antigenic peptides comprise one or more or all of the following recurrent cancer mutations: KRAS\_G12C, KRAS\_G12D, U2AF1_S34F, KRAS\_G12V, TP53_R248Q, TP53_R248W, TP53_R175H, TP53_R273C, KRAS\_G12R, KRAS\_Q61H, TP53_R282W, TP53_R273H, TP53_G245S, SMAD4_R361C, GNAS_R201C, and GNAS_R201H;
(d) the antigenic peptides comprise one or more or all of the following recurrent cancer mutations: PIK3CA_E545K, FGFR3_S249C, TP53_R248Q, PIK3CA_E542K, RXRA_S427F, FBXW7_R505G, TP53_R280T, NFE2L2_E79K, FGFR3_R248C, TP53_K132N, TP53_R248W, TP53_R175H, and TP53_R273C;
(e) the antigenic peptides comprise one or more or all of the following recurrent cancer mutations: PIK3CA_E545K, PIK3CA_E542K, PIK3CA_H1047R, AKT1_E17K, PIK3CA_H1047L, PIK3CA_Q546K, PIK3CA_E545A, PIK3CA_E545G, ESR1_K303R, ESR1_D538G, ESR1_Y537S, ESR1_Y537N, ESR1_Y537C, and ESR1_E380Q;
(f) the antigenic peptides comprise one or more or all of the following recurrent cancer mutations: PTEN_R130G, PTEN_R130Q, KRAS\_G12D, KRAS\_G12V, PIK3CA_H1047R; PIK3CA\R88Q, PIK3CA_E545K, PIK3CA_E542K, CTNNB1_S37F, KRAS\_G13D, CTNNB1_S37C, PIK3CA_H1047L, PIK3CA_G118D, KRAS\_G12A, FBXW7_R505C, and TP53_R248W;
(g) the antigenic peptides comprise one or more or all of the following recurrent cancer mutations: TP53_R248Q, TP53_R248W, TP53_R175H, TP53_R273C, TP53_R282W, TP53_R273H, TP53_Y220C, TP53_I195T, TP53_C176Y, TP53_H179R, TP53_S241F, and TP53_H193R;
(h) the antigenic peptides comprise one or more or all of the following recurrent cancer mutations: TP53_R273L, TP53_R273C, TP53_R273H, PIK3CA_G118D, IDH1_R132C, IDH1_R132G, IDH1_R132H, IDH1_R132S, IDH2_R172K, PIK3CA_E453K, and EGFR\G598V;
(i) the antigenic peptides comprise one or more or all of the following recurrent cancer mutations: KRAS\_G12C, KRAS\_G12D, BRAF_V600E, KRAS\_G12V, PIK3CA_E545K, TP53_R248W, TP53_R175H, TP53_R273C, PIK3CA_H1047R, TP53_R282W, TP53_R273H, and KRAS\_G13D; or
(j) the antigenic peptides comprise one or more or all of the following recurrent cancer mutations: PIK3CA_E545K, CHEK2_K373E, RGPD8_P1760A, ANKRD36C_I634T, TP53 R248Q, PIK3CA_E542K, TP53_R248W, TP53_R175H, PIK3CA_H1047R, TP53_R282W, TP53_R273H, TP53_G245S, TP53_Y220C, ZNF814_D404E, KRTAP1-5_I88T, KRTAP4-11_L161V, and HRAS_G13V.

43. The recombinant *Listeria* strain of claim 42 wherein:
(a) the antigenic peptides comprise one or more or all of the peptides set forth in SEQ ID NOS: 486, 405, 489, 643, 377, 491, 437, 631, 487, 406, and 566;
(b) the antigenic peptides comprise one or more or all of the peptides set forth in SEQ ID NOS: 717, 707, 714, 704, 705, 715, 706, 716, and 763-768;
(c) the antigenic peptides comprise one or more or all of the peptides set forth in SEQ ID NOS: 486, 489, 643, 491, 560, 559, 542, 565, 490, 498, 569, 563, 558, and 780-782;
(d) the antigenic peptides comprise one or more or all of the peptides set forth in SEQ ID NOS: 437, 769, 560, 436, 770, 771, 642, 772, 773, 535, 559, 542, and 565;
(e) the antigenic peptides comprise one or more or all of the peptides set forth in SEQ ID NOS: 437, 436, 447, 585, 448, 442, 438, 439, and 774-779;
(f) the antigenic peptides comprise one or more or all of the peptides set forth in SEQ ID NOS: 471, 470, 489, 491, 447, 427, 437, 436, 783, 492, 784, 448, 431, 487, 785 and 559;
(g) the antigenic peptides comprise one or more or all of the peptides set forth in SEQ ID NOS: 560, 559, 542, 565, 569, 563, 552, 549, 545, 546, 555, and 548;
(h) the antigenic peptides comprise one or more or all of the peptides set forth in SEQ ID NOS: 566, 565, 563, 431, 786-790, 435, and 393;
(i) the antigenic peptides comprise one or more or all of the peptides set forth in SEQ ID NOS: 486, 489, 377, 491, 437, 559, 542, 565, 447, 569, 563, and 492; or
(j) the antigenic peptides comprise one or more or all of the peptides set forth in SEQ ID NOS: 437, 707, 714, 704, 560, 436, 559, 542, 447, 569, 563, 558, 552, and 830-833.

44. The recombinant *Listeria* strain of claim 1, wherein each antigenic peptide comprising a heteroclitic mutation is about 7-11, 8-10, or 9 amino acids in length.

45. The recombinant *Listeria* strain of claim 1, wherein the antigenic peptides comprising a heteroclitic mutation bind to one or more or all of the following HLA types: HLA-A*02:01, HLA-A*03:01, HLA-A*24:02, and HLA-B*07:02.

46. The recombinant *Listeria* strain of claim 1, wherein the antigenic peptides comprise heteroclitic mutations in proteins encoded by one or more of the following genes: CEACAM5, GAGE1, hTERT, KLHL7, MAGEA3, MAGEA4, MAGEA6, NUF2, NYESO1, PAGE4, PRAME, PSA, PSMA, RNF43, SART3, SSX2, STEAP1, and SURVIVIN.

47. The recombinant *Listeria* strain of claim/5, wherein:
(a) the antigenic peptides comprise heteroclitic mutations in proteins encoded by one or more or all of the following genes: CEACAM5, MAGEA6, MAGEA4, GAGE1, NYESO1, STEAP1, and RNF43;
(b) the antigenic peptides comprise heteroclitic mutations in proteins encoded by one or more or all of the following genes: CEACAM5, MAGEA4, STEAP1, RNF43, SSX2, SART3, PAGE4, PSMA, and PSA;
(c) the antigenic peptides comprise heteroclitic mutations in proteins encoded by one or more or all of the following genes: CEACAM5, STEAP1, MAGEA3, PRAME, hTERT, and SURVIVIN;
(d) the antigenic peptides comprise heteroclitic mutations in proteins encoded by one or more or all of the following genes: CEACAM5, GAGE1, NYESO1, RNF43, NUF2, KLHL7, MAGEA3, and PRAME;
(e) the antigenic peptides comprise heteroclitic mutations in proteins encoded by one or more or all of the following genes: CEACAM5, STEAP1, RNF43, MAGEA3, PRAME, and hTERT;
(f) the antigenic peptides comprise heteroclitic mutations in proteins encoded by one or more or all of the following genes: CEACAM5, PRAME, hTERT, STEAP1, RNF43, NUF2, KLHL7, and SART3;
(g) the antigenic peptides comprise heteroclitic mutations in proteins encoded by one or more or all of the following genes: CEACAM5, STEAP1, RNF43, SART3, NUF2, KLHL7, PRAME, and hTERT;
(h) the antigenic peptides comprise heteroclitic mutations in proteins encoded by one or more or all of the following genes: CEACAM5, MAGEA6, STEAP1, RNF43, SART3, NUF2, KLHL7, and hTERT;
(i) the antigenic peptides comprise heteroclitic mutations in proteins encoded by one or more or all of the following genes: CEACAM5, MAGEA6, MAGEA4, GAGE1, NYESO1, STEAP1, RNF43, and MAGEA3; or
(j) the antigenic peptides comprise heteroclitic mutations in proteins encoded by one or more or all of the following genes: CEACAM5, MAGEA4, STEAP1, NYESO1, PRAME, and hTERT.

48. The recombinant *Listeria* strain of claim 47, wherein:
(a) the antigenic peptides comprise one or more or all of the peptides set forth in SEQ ID NOS: 791-801;
(b) the antigenic peptides comprise one or more or all of the peptides set forth in SEQ ID NOS: 793, 794, and 799-806;
(c) the antigenic peptides comprise one or more or all of the peptides set forth in SEQ ID NOS: 791, 793, 796, 798-800, 812, and 815-819;
(d) the antigenic peptides comprise one or more or all of the peptides set forth in SEQ ID NOS: 791, 795, 797, 798, 801, and 807-815;
(e) the antigenic peptides comprise one or more or all of the peptides set forth in SEQ ID NOS: 791, 793, 796, 798-801, 810, 812, 815, and 816;
(f) the antigenic peptides comprise one or more or all of the peptides set forth in SEQ ID NOS: 820, 791, 793, 798, 815, 816, 799, 796, 801, 807-809, 803, and 800;
(g) the antigenic peptides comprise one or more or all of the peptides set forth in SEQ ID NOS: 791, 793, 796, 798-801, 803, 807-809, 815, 816, and 820;
(h) the antigenic peptides comprise one or more or all of the peptides set forth in SEQ ID NOS: 791, 792, 799-801, 803, 807-809, and 816;
(i) the antigenic peptides comprise one or more or all of the peptides set forth in SEQ ID NOS: 791-797, 799, 801, and 817; or
(j) the antigenic peptides comprise one or more or all of the peptides set forth in SEQ ID NOS: 791, 793, 794, 796, 798-800, 813, 815, and 816.

49. The recombinant *Listeria* strain of claim 1, wherein:
(a) the antigenic peptides comprise one or more or all of the peptides set forth in SEQ ID NOS: 486, 405, 489, 643, 377, 491, 437, 631, 487, 406, 566, and 791-801;
(b) the antigenic peptides comprise one or more or all of the peptides set forth in SEQ ID NOS: 717, 707, 714, 704, 705, 715, 706, 716, 763-768, 793, 794, and 799-806;
(c) the antigenic peptides comprise one or more or all of the peptides set forth in SEQ ID NOS: 486, 489, 643, 491, 560, 559, 542, 565, 490, 498, 569, 563, 558, 780-782, 791, 793, 796, 798-800, 812, and 815-819;
(d) the antigenic peptides comprise one or more or all of the peptides set forth in SEQ ID NOS: 437, 769, 560, 436, 770, 771, 642, 772, 773, 535, 559, 542, 565, 791, 795, 797, 798, 801, and 807-815;
(e) the antigenic peptides comprise one or more or all of the peptides set forth in SEQ ID NOS: 437, 436, 447, 585, 448, 442, 438, 439, 774-779, 791, 793, 796, 798-801, 810, 812, 815, and 816;
(f) the antigenic peptides comprise one or more or all of the peptides set forth in SEQ ID NOS: 471, 470, 489, 491, 447, 427, 437, 436, 783, 492, 784, 448, 431, 487, 785, 559, 820, 791, 793, 798, 815, 816, 799, 796, 801, 807-809, 803, and 800;
(g) the antigenic peptides comprise one or more or all of the peptides set forth in SEQ ID NOS: 560, 559, 542, 565, 569, 563, 552, 549, 545, 546, 555, 548, 791, 793, 796, 798-801, 803, 807-809, 815, 816, and 820;
(h) the antigenic peptides comprise one or more or all of the peptides set forth in SEQ ID NOS: 566, 565, 563, 431, 786-790, 435, 393, 791, 792, 799-801, 803, 807-809, and 816;
(i) the antigenic peptides comprise one or more or all of the peptides set forth in SEQ ID NOS: 486, 489, 377, 491, 437, 559, 542, 565, 447, 569, 563, 492, 791-797, 799, 801, and 817; or
(j) the antigenic peptides comprise one or more or all of the peptides set forth in SEQ ID NOS: 437, 707, 714, 704, 560, 436, 559, 542, 447, 569, 563, 558, 552, 830-833, 791, 793, 794, 796, 798-800, 813, 815, and 816.

50. The recombinant *Listeria* strain of claim 49, wherein:
(a) the fusion polypeptide comprises the sequence set forth in any one of SEQ ID NOS: 859, 860, 861, 862, 863, 864, 865, 894, 895, and 905;
(b) the fusion polypeptide comprises the sequence set forth in any one of SEQ ID NOS: 871, 872 873, 874, 875, 876, 877, 892, 893, and 906;
(c) the fusion polypeptide comprises the sequence set forth in any one of SEQ ID NOS: 866, 867, 868, 869, 870, and 908;
(d) the fusion polypeptide comprises the sequence set forth in any one of SEQ ID NOS: 878, 879, 880, 881, 882, 888, 889, 890, and 891;
(e) the fusion polypeptide comprises the sequence set forth in any one of SEQ ID NOS: 883, 884, 885, 886, 887, and 907;
(f) the fusion polypeptide comprises the sequence set forth in any one of SEQ ID NOS: 896, 897, and 904;

(g) the fusion polypeptide comprises the sequence set forth in any one of SEQ ID NOS: 898 and 899;
(h) the fusion polypeptide comprises the sequence set forth in any one of SEQ ID NOS: 900 and 901;
(i) the fusion polypeptide comprises the sequence set forth in any one of SEQ ID NOS: 902 and 903; or
(j) the fusion polypeptide comprises the sequence set forth in any one of SEQ ID NOS: 918 and 919.

51. The recombinant *Listeria* strain of claim 1, wherein the fusion polypeptide has a molecular weight of no more than about 150 kDa or no more than about 125 kDa.

52. The recombinant *Listeria* strain of claim 1, wherein the fusion polypeptide further comprises one or more peptide tags N-terminal and/or C-terminal to the combination of the two or more antigenic peptides, wherein the one or more peptide tags comprise one or both of the following: FLAG tag and SIINFEKL (SEQ ID NO: 1007) tag.

53. The recombinant *Listeria* strain of claim 1, wherein the PEST-containing peptide is on the N-terminal end of the fusion polypeptide.

54. The recombinant *Listeria* strain of claim 53, wherein the PEST-containing peptide is an N-terminal fragment of LLO.

55. The recombinant *Listeria* strain of claim 54, wherein the N-terminal fragment of LLO has the sequence set forth in SEQ ID NO: 336.

56. The recombinant *Listeria* strain of claim 1, wherein the nucleic acid is in an episomal plasmid.

57. The recombinant *Listeria* strain of claim 1, wherein the nucleic acid does not confer antibiotic resistance upon the recombinant *Listeria* strain.

58. The recombinant *Listeria* strain of claim 1, wherein the recombinant *Listeria* strain is an attenuated, auxotrophic *Listeria* strain.

59. The recombinant *Listeria* strain of claim 58, wherein the attenuated, auxotrophic *Listeria* strain comprises a mutation in one or more endogenous genes that inactivates the one or more endogenous genes.

60. The recombinant *Listeria* strain of claim 59, wherein the one or more endogenous genes comprise act4, dal, and dat.

61. The recombinant *Listeria* strain of claim 1, wherein the nucleic acid comprises a second open reading frame encoding a metabolic enzyme.

62. The recombinant *Listeria* strain of claim 61, wherein the metabolic enzyme is an alanine racemase enzyme or a D-amino acid aminotransferase enzyme.

63. The recombinant *Listeria* strain of claim 1, wherein the fusion polypeptide is expressed from an hly promoter.

64. The recombinant *Listeria* strain of claim 1, wherein the recombinant *Listeria* strain is a recombinant *Listeria monocytogenes* strain.

65. The recombinant *Listeria* strain of claim 1, wherein the recombinant *Listeria* strain is an attenuated *Listeria monocytogenes* strain comprising a deletion of or inactivating mutation in actA, dal, and dat, wherein the nucleic acid is in an episomal plasmid and comprises a second open reading frame encoding an alanine racemase enzyme or a D-amino acid aminotransferase enzyme, and wherein the PEST-containing peptide is an N-terminal fragment of LLO.

66. An immunogenic composition comprising the recombinant *Listeria* strain of claim 1.

67. The immunogenic composition of claim 66, wherein the immunogenic composition comprises a combination of two or more recombinant *Listeria* strains, wherein each recombinant *Listeria* strain comprises a different set of antigenic peptides or the same set of antigenic peptides in a different order.

68. The immunogenic composition of claim 67, wherein each recombinant *Listeria* strain comprises a different set of antigenic peptides.

69. The immunogenic composition of claim 68, wherein the combination of recombinant *Listeria* strains comprises about 5-10, 10-15, 15-20, 20-25, 25-30, 30-35, 35-40, 40-45, 45-50, 50-60, 60-70, 70-80, 80-90, 90-100, 100-120, 120-140, 140-160, 160-180, 180-200, 200-220, 220-240, 240-260, 260-280, or 280-300 different antigenic peptides.

70. The immunogenic composition of claim 66, wherein the immunogenic composition further comprises an adjuvant.

71. The immunogenic composition of claim 70, wherein the adjuvant comprises a granulocyte/macrophage colony-stimulating factor (GM-CSF) protein, a nucleotide molecule encoding a GM-CSF protein, saponin QS21, monophosphoryl lipid A, an unmethylated CpG-containing oligonucleotide, or a detoxified listeriolysin O protein.

72. A method of inducing an immune response against a tumor or cancer in a subject, comprising administering to the subject the recombinant *Listeria* strain of claim 1.

73. A cell bank comprising one or more recombinant *Listeria* strains as in claim 1.

74. The cell bank of claim 73, wherein the cell bank is a frozen cell bank or a lyophilized cell bank.

* * * * *